United States Patent [19]
Inouye et al.

[11] Patent Number: 6,162,627
[45] Date of Patent: Dec. 19, 2000

[54] METHODS OF IDENTIFYING INHIBITORS OF SENSOR HISTIDINE KINASES THROUGH RATIONAL DRUG DESIGN

[75] Inventors: Masayori Inouye, Piscataway, N.J.; Heiyoung Park, Cambridge, Mass.; Mitsuhiko Ikura, North York, Canada

[73] Assignees: University of Medicine and Dentistry of New Jersey, Piscataway, N.J.; Ontario Cancer Institute, Ontario, Canada

[21] Appl. No.: 09/158,843

[22] Filed: Sep. 23, 1998

Related U.S. Application Data

[60] Provisional application No. 60/078,769, Mar. 19, 1998.

[51] Int. Cl.$^7$ .............................. C12N 9/12; C12N 1/20; C12N 15/00; C12N 5/00; C07K 1/00
[52] U.S. Cl. ...................... 435/194; 530/350; 530/324; 435/252.3; 435/320.1; 435/325
[58] Field of Search ............................... 435/194, 320.1, 435/252.3, 325; 530/350, 324

[56] References Cited

PUBLICATIONS

Alex et al, 1996, Proc Natl Acad Sci USA, 99:3416–21.
Alexandrov et al., 1992, J Mol Biol 225:5–9.
Altschul et al, 1997, Nucleic Acids Res, 25:3389–402.
Altschul et al., 1990, J Mol Biol, 215:403–10.
Appleby et al., 1996, Cell. 86:845–8.
Bagby et al, 1995, Cell, 82:857–67.
Bagby et al., 1994, Biochem, 33:2409–21.
Barrett et al., 1998, Proc Natl Acad Sci USA, 95:5317–22.
Baumgartner et al., 1994, J Bacteriol, 176:1157–63.
Chang et al., 1993, Science, 262:539–44.
Delgado et al., 1993 Mol Microbiol. 10:1037–47.
Dutta et al, 1996, J Biol Chem, 271:1424–9.
Egger et al., 1997, Gen Cell, 2:167–84.
Gardina et al., 1996, Science, 274:425–6.
Gill et al., 1989, Analytical Biochem. 182:319–26.
Hidaka et al., 1997, FEBS Lett, 400:238–42.
Holdgate et al., 1997, Biochemistry, 36:9663–73.
Igo et al., 1989, Gen Dev, 3:1725–34.
Kraulis, 1991, J. Appl. Cryst. 24:946–959.
Munoz–Dorado et al., 1993, J Cell Biochem, 51:29–33.
Ota et al., 1993, Science, 262:566–9.
Pan et al., 1993, Proc Natl. Acad Sci USA, 90:9939–43.
Park et al., 1997, J Bacteriol, 179:4382–90.
Parkinson et al., 1992, An Rev. Gen, 26:71–112.
Prodromou et al., 1997, Cell, 90:65–76.
Roberts et al., 1994, J Biol Chem, 269:8728–33.
Sicheri et al., 1997, Nature, 385:602–9.
Soncini et al., 1996, J Bacteriol. 178:6796–801.
Stock et al., 1989, Microbiol Rev, 53:450–90.
Swanson et al., 1993, Mol Microbiol, 8:435–41.
Swanson et al., 1993, Biochem, 32:7623–9.
Surette et al., 1996, J Biol Chem, 271:939–45.
Tatsuno et al., 1996, Science, 274:423–5.
Uhl et al., 1996, EMBO J, 15:1028–36.
Utsumi et al., 1989, Science, 245:1246–9.
Wigley et al., 1991, Nature, 351:624–9.
Yang et al., 1993, J Mol Biol 232:493–8.
Yang et al., 1991, Proc Natl Acad Sci USA, 88:11057–61.
Yang et al., 1993, J Mol Biol, 231:335–42.
Yoshida et al., 1993, Biochemistry 32:2162–66.
Comeau et al., J. bacteriol., 164(2), 578–584, Aug. 1985.
Roberts et al., J.B.C., 269(12), 8728–8733, Mar. 1994.

*Primary Examiner*—Rebecca E. Prouty
*Assistant Examiner*—M. Monshipouri
*Attorney, Agent, or Firm*—Klauber & Jackson

[57] ABSTRACT

The present invention provides N-terminal truncated transmembrane sensor histidine kinases that retain their ability to be autophosphorylated and/or their related histidine kinase activity. The N-terminal truncated transmembrane sensor histidine kinases are useful for obtaining detailed three-dimensional structural data of the catalytic portion of the protein. The three-dimensional structural data is included as part of the invention. In addition, the present invention provides methodology for related structure based rational drug design using the three-dimensional data. Nucleotide and amino acid sequences of the N-terminal truncated transmembrane sensor histidine kinases are also provided.

28 Claims, 15 Drawing Sheets

(6 of 15 Drawing Sheet(s) Filed in Color)

EnvZ catalytic domain | Hsp90 ATP-binding domain

FIG. 11

```
              290       300       310       320       330       340       350
EnvZ          TGQEMPMEMADLNAVLGEVIAAESGYEREIETALVPGSIEVKMRPLSIKRAVANMVVNAARYGN
                        *   *                    *    **   **       *
HSP90   ASETFEFQAEITQLMSLIINTV                  YSNKEIFLRELISNASDALDKIRYKSLSDPKQLETEP
        10        20                            30        40        50        60
GYRB    SNSYDSSSIKVLKGLDAVRKRPGMYIGDTDDGT         GLHHMVFEVVDNAIDEALAGHC
        10        20        30                  40        50

360       370       380           390                400       410
EnvZ      GW         EPNF         DGPGIA              HLFQPPVRGDSARTI         SGTGLGLAIV      NH
           *  *               *                                    *                       *  *  **  *
HSP90   DLF       PE   QK       SGIGMT           LGT   IAKS             GADVSMIGQFGVGFYSLFLV
               70        80        90                 100       110        120       130
GYRB    K        A   DN       DGRGIPTGIHPEEGVS        V   LHAGGKFDDNSYKVSG       GLHGVG        LS
         60        70        80        90              100       110          120

420                  430       440      450
EnvZ      NGM     TSER          GGL    PVPVT    RAQGTTKEG
             * *                    * ***
HSP90               SNDDEQYIWESNAGGSFT VTLDEVNERIGR          KDDQL   EYLEEKRIKEVIKRHSEFV AYPIQLVVTKEVEKE
               140       150       160       170       180        190       200       210
GYRB            EGKIHRQIYEHGVPQAPLAVTGE TEKT      SLETFTNVTEFEYEILAKRLRELSFLNSGVSIRLRDKRDGKEDHFH
         130       140       150       160       170       180       190       200       210
```

EnvZ His Kinase

Src Tyr Kinase

PKA Ser/Thr Kinase

SEQUENCE LISTING

<160> NUMBER OF SEQ ID NOS: 14

<210> SEQ ID NO 1
<211> LENGTH: 1353
<212> TYPE: DNA
<213> ORGANISM: Escherichia coli
<220> FEATURE:
<221> NAME/KEY: CDS
<222> LOCATION: (1)..(1353)

```
<400> SEQUENCE: 1 atg agg cga ttg cgc ttc tcg cca cga agt tca ttt gcc cgt acg tta      48
Met Arg Arg Leu Arg Phe Ser Pro Arg Ser Ser Phe Ala Arg Thr Leu
 1               5                  10                  15 ttg ctc atc gtc acc ttg ctc ttc gcc agc ctg gtg acg act tat ctg      96
Leu Leu Ile Val Thr Leu Leu Phe Ala Ser Leu Val Thr Thr Tyr Leu
            20                  25                  30 gtg gtg ctg aac ttc gcg att ttg ccg agc ctc cag cag ttt aat aaa     144
Val Val Leu Asn Phe Ala Ile Leu Pro Ser Leu Gln Gln Phe Asn Lys
        35                  40                  45 gtc ctc gcg tac gaa gtg cgt atg ttg atg acc gac aaa ctg caa ctg     192
Val Leu Ala Tyr Glu Val Arg Met Leu Met Thr Asp Lys Leu Gln Leu
    50                  55                  60 gag gac ggc acg cag ttg gtt gtg cct ccc gct ttc cgt cgg gag atc     240
Glu Asp Gly Thr Gln Leu Val Val Pro Pro Ala Phe Arg Arg Glu Ile
 65                  70                  75                  80 tac cgt gag ctg ggg atc tct ctc tac tcc aac gag gct gcc gaa gag     288
Tyr Arg Glu Leu Gly Ile Ser Leu Tyr Ser Asn Glu Ala Ala Glu Glu
                 85                  90                  95 gca ggt ctg cgt tgg gcg caa cac tat gaa ttc tta agc cat cag atg     336
Ala Gly Leu Arg Trp Ala Gln His Tyr Glu Phe Leu Ser His Gln Met
            100                 105                 110 gcg cag caa ctg ggc ggc ccg acg gaa gtg cgc gtt gag gtc aac aaa     384
Ala Gln Gln Leu Gly Gly Pro Thr Glu Val Arg Val Glu Val Asn Lys
        115                 120                 125 agt tcg cct gtc gtc tgg ctg aaa acc tgg ctg tcg ccc aat atc tgg     432
Ser Ser Pro Val Val Trp Leu Lys Thr Trp Leu Ser Pro Asn Ile Trp
    130                 135                 140 gta cgc gtg ccg ctg acc gaa att cat cag ggc gat ttc tct ccg ctg     480
Val Arg Val Pro Leu Thr Glu Ile His Gln Gly Asp Phe Ser Pro Leu
145                 150                 155                 160 ttc cgc tat acg ctg gcg att atg cta ttg gcg ata ggc ggg gcg tgg     528
Phe Arg Tyr Thr Leu Ala Ile Met Leu Leu Ala Ile Gly Gly Ala Trp
                165                 170                 175 ctg ttt att cgt atc cag aac cga ccg ttg gtc gat ctc gaa cac gca     576
Leu Phe Ile Arg Ile Gln Asn Arg Pro Leu Val Asp Leu Glu His Ala
            180                 185                 190 gcc ttg cag gtt ggt aaa ggg att att ccg ccg ccg ctg cgt gag tat     624
Ala Leu Gln Val Gly Lys Gly Ile Ile Pro Pro Pro Leu Arg Glu Tyr
        195                 200                 205 ggc gct tcg gag gtg cgt tcc gtt acc cgt gcc ttt aac cat atg gcg     672
Gly Ala Ser Glu Val Arg Ser Val Thr Arg Ala Phe Asn His Met Ala
    210                 215                 220 gct ggt gtt aag caa ctg gcg gat gac cgc acg ctg ctg atg gcg ggg     720
Ala Gly Val Lys Gln Leu Ala Asp Asp Arg Thr Leu Leu Met Ala Gly
225                 230                 235                 240 gta agt cac gac ttg cgc acg ccg ctg acg cgt att cgc ctg gcg act     768
Val Ser His Asp Leu Arg Thr Pro Leu Thr Arg Ile Arg Leu Ala Thr
                245                 250                 255 gag atg atg agc gag cag gat ggc tat ctg gca gaa tcg atc aat aaa     816
Glu Met Met Ser Glu Gln Asp Gly Tyr Leu Ala Glu Ser Ile Asn Lys
            260                 265                 270 gat atc gaa gag tgc aac gcc atc att gag cag ttt atc gac tac ctg     864
Asp Ile Glu Glu Cys Asn Ala Ile Ile Glu Gln Phe Ile Asp Tyr Leu
        275                 280                 285 cgc acc ggg cag gag atg ccg atg gaa atg gcg gat ctt aat gca gta     912
Arg Thr Gly Gln Glu Met Pro Met Glu Met Ala Asp Leu Asn Ala Val
    290                 295                 300 ctc ggt gag gtg att gct gcc gaa agt ggc tat gag cgg gaa att gaa     960
```

```
Leu Gly Glu Val Ile Ala Ala Glu Ser Gly Tyr Glu Arg Glu Ile Glu
305                 310                 315                 320 acc gcg ctt tac ccc ggc agc att gaa gtg aaa atg cac ccg ctg tcg    1008
Thr Ala Leu Tyr Pro Gly Ser Ile Glu Val Lys Met His Pro Leu Ser
                325                 330                 335 atc aaa cgc gcg gtg gcg aat atg gtg gtc aac gcc gcc cgt tat ggc    1056
Ile Lys Arg Ala Val Ala Asn Met Val Val Asn Ala Ala Arg Tyr Gly
            340                 345                 350 aat ggc tgg atc aaa gtc agc agc gga acg gag ccg aat cgc gcc tgg    1104
Asn Gly Trp Ile Lys Val Ser Ser Gly Thr Glu Pro Asn Arg Ala Trp
        355                 360                 365 ttc cag gtg gaa gat gac ggt ccg gga att gcg ccg gaa caa cgt aag    1152
Phe Gln Val Glu Asp Asp Gly Pro Gly Ile Ala Pro Glu Gln Arg Lys
    370                 375                 380 cac ctg ttc cag ccg ttt gtc cgc ggc gac agt gcg cgc acc att agc    1200
His Leu Phe Gln Pro Phe Val Arg Gly Asp Ser Ala Arg Thr Ile Ser
385                 390                 395                 400 ggc acg gga tta ggg ctg gca att gtg cag cgt atc gtg gat aac cat    1248
Gly Thr Gly Leu Gly Leu Ala Ile Val Gln Arg Ile Val Asp Asn His
                405                 410                 415 aac ggg atg ctg gag ctt ggc acc agc gag cgg ggc ggg ctt tcc att    1296
Asn Gly Met Leu Glu Leu Gly Thr Ser Glu Arg Gly Gly Leu Ser Ile
            420                 425                 430 cgc gcc tgg ctg cca gtg ccg gta acg cgg gcg cag ggc acg aca aaa    1344
Arg Ala Trp Leu Pro Val Pro Val Thr Arg Ala Gln Gly Thr Thr Lys
        435                 440                 445 gaa ggg taa                                                         1353
Glu Gly
    450

<210> SEQ ID NO 2
<211> LENGTH: 450
<212> TYPE: PRT
<213> ORGANISM: Escherichia coli

<400> SEQUENCE: 2

Met Arg Arg Leu Arg Phe Ser Pro Arg Ser Ser Phe Ala Arg Thr Leu
  1               5                  10                  15

Leu Leu Ile Val Thr Leu Leu Phe Ala Ser Leu Val Thr Thr Tyr Leu
             20                  25                  30

Val Val Leu Asn Phe Ala Ile Leu Pro Ser Leu Gln Gln Phe Asn Lys
         35                  40                  45

Val Leu Ala Tyr Glu Val Arg Met Leu Met Thr Asp Lys Leu Gln Leu
     50                  55                  60

Glu Asp Gly Thr Gln Leu Val Val Pro Ala Phe Arg Arg Glu Ile
 65                  70                  75                  80

Tyr Arg Glu Leu Gly Ile Ser Leu Tyr Ser Asn Glu Ala Ala Glu Glu
                 85                  90                  95

Ala Gly Leu Arg Trp Ala Gln His Tyr Glu Phe Leu Ser His Gln Met
            100                 105                 110

Ala Gln Gln Leu Gly Gly Pro Thr Glu Val Arg Val Glu Val Asn Lys
        115                 120                 125

Ser Ser Pro Val Val Trp Leu Lys Thr Trp Leu Ser Pro Asn Ile Trp
    130                 135                 140

Val Arg Val Pro Leu Thr Glu Ile His Gln Gly Asp Phe Ser Pro Leu
145                 150                 155                 160

Phe Arg Tyr Thr Leu Ala Ile Met Leu Leu Ala Ile Gly Gly Ala Trp
                165                 170                 175
```

```
Leu Phe Ile Arg Ile Gln Asn Arg Pro Leu Val Asp Leu Glu His Ala
            180                 185                 190

Ala Leu Gln Val Gly Lys Gly Ile Ile Pro Pro Leu Arg Glu Tyr
        195                 200                 205

Gly Ala Ser Glu Val Arg Ser Val Thr Arg Ala Phe Asn His Met Ala
        210                 215                 220

Ala Gly Val Lys Gln Leu Ala Asp Asp Arg Thr Leu Leu Met Ala Gly
225                 230                 235                 240

Val Ser His Asp Leu Arg Thr Pro Leu Thr Arg Ile Arg Leu Ala Thr
                245                 250                 255

Glu Met Met Ser Glu Gln Asp Gly Tyr Leu Ala Glu Ser Ile Asn Lys
            260                 265                 270

Asp Ile Glu Glu Cys Asn Ala Ile Ile Glu Gln Phe Ile Asp Tyr Leu
        275                 280                 285

Arg Thr Gly Gln Glu Met Pro Met Glu Met Ala Asp Leu Asn Ala Val
        290                 295                 300

Leu Gly Glu Val Ile Ala Ala Glu Ser Gly Tyr Glu Arg Glu Ile Glu
305                 310                 315                 320

Thr Ala Leu Tyr Pro Gly Ser Ile Glu Val Lys Met His Pro Leu Ser
                325                 330                 335

Ile Lys Arg Ala Val Ala Asn Met Val Val Asn Ala Ala Arg Tyr Gly
            340                 345                 350

Asn Gly Trp Ile Lys Val Ser Ser Gly Thr Glu Pro Asn Arg Ala Trp
        355                 360                 365

Phe Gln Val Glu Asp Asp Gly Pro Gly Ile Ala Pro Glu Gln Arg Lys
    370                 375                 380

His Leu Phe Gln Pro Phe Val Arg Gly Asp Ser Ala Arg Thr Ile Ser
385                 390                 395                 400

Gly Thr Gly Leu Gly Leu Ala Ile Val Gln Arg Ile Val Asp Asn His
                405                 410                 415

Asn Gly Met Leu Glu Leu Gly Thr Ser Glu Arg Gly Gly Leu Ser Ile
            420                 425                 430

Arg Ala Trp Leu Pro Val Pro Val Thr Arg Ala Gln Gly Thr Thr Lys
        435                 440                 445

Glu Gly
    450

<210> SEQ ID NO 3
<211> LENGTH: 813
<212> TYPE: DNA
<213> ORGANISM: Escherichia coli
<220> FEATURE:
<221> NAME/KEY: CDS
<222> LOCATION: (1)..(813)

<400> SEQUENCE: 3 cgt atc cag aac cga ccg ttg gtc gat ctc gaa cac gca gcc ttg cag      48
Arg Ile Gln Asn Arg Pro Leu Val Asp Leu Glu His Ala Ala Leu Gln
  1               5                  10                  15 gtt ggt aaa ggg att att ccg ccg ctg cgt gag tat ggc gct tcg          96
Val Gly Lys Gly Ile Ile Pro Pro Leu Arg Glu Tyr Gly Ala Ser
             20                  25                  30 gag gtg cgt tcc gtt acc cgt gcc ttt aac cat atg gcg gct ggt gtt    144
Glu Val Arg Ser Val Thr Arg Ala Phe Asn His Met Ala Ala Gly Val
         35                  40                  45 aag caa ctg gcg gat gac cgc acg ctg ctg atg gcg ggg gta agt cac    192
```

-continued

```
Lys Gln Leu Ala Asp Asp Arg Thr Leu Leu Met Ala Gly Val Ser His
 50                  55                  60 gac ttg cgc acg ccg ctg acg cgt att cgc ctg gcg act gag atg atg      240
Asp Leu Arg Thr Pro Leu Thr Arg Ile Arg Leu Ala Thr Glu Met Met
 65                  70                  75                  80 agc gag cag gat ggc tat ctg gca gaa tcg atc aat aaa gat atc gaa      288
Ser Glu Gln Asp Gly Tyr Leu Ala Glu Ser Ile Asn Lys Asp Ile Glu
                 85                  90                  95 gag tgc aac gcc atc att gag cag ttt atc gac tac ctg cgc acc ggg      336
Glu Cys Asn Ala Ile Ile Glu Gln Phe Ile Asp Tyr Leu Arg Thr Gly
            100                 105                 110 cag gag atg ccg atg gaa atg gcg gat ctt aat gca gta ctc ggt gag      384
Gln Glu Met Pro Met Glu Met Ala Asp Leu Asn Ala Val Leu Gly Glu
        115                 120                 125 gtg att gct gcc gaa agt ggc tat gag cgg gaa att gaa acc gcg ctt      432
Val Ile Ala Ala Glu Ser Gly Tyr Glu Arg Glu Ile Glu Thr Ala Leu
    130                 135                 140 tac ccc ggc agc att gaa gtg aaa atg cac ccg ctg tcg atc aaa cgc      480
Tyr Pro Gly Ser Ile Glu Val Lys Met His Pro Leu Ser Ile Lys Arg
145                 150                 155                 160 gcg gtg gcg aat atg gtg gtc aac gcc gcc cgt tat ggc aat ggc tgg      528
Ala Val Ala Asn Met Val Val Asn Ala Ala Arg Tyr Gly Asn Gly Trp
                165                 170                 175 atc aaa gtc agc agc gga acg gag ccg aat cgc gcc tgg ttc cag gtg      576
Ile Lys Val Ser Ser Gly Thr Glu Pro Asn Arg Ala Trp Phe Gln Val
            180                 185                 190 gaa gat gac ggt ccg gga att gcg ccg gaa caa cgt aag cac ctg ttc      624
Glu Asp Asp Gly Pro Gly Ile Ala Pro Glu Gln Arg Lys His Leu Phe
        195                 200                 205 cag ccg ttt gtc cgc ggc gac agt gcg cgc acc att agc ggc acg gga      672
Gln Pro Phe Val Arg Gly Asp Ser Ala Arg Thr Ile Ser Gly Thr Gly
    210                 215                 220 tta ggg ctg gca att gtg cag cgt atc gtg gat aac cat aac ggg atg      720
Leu Gly Leu Ala Ile Val Gln Arg Ile Val Asp Asn His Asn Gly Met
225                 230                 235                 240 ctg gag ctt ggc acc agc gag cgg ggc ggg ctt tcc att cgc gcc tgg      768
Leu Glu Leu Gly Thr Ser Glu Arg Gly Gly Leu Ser Ile Arg Ala Trp
                245                 250                 255 ctg cca gtg ccg gta acg cgg gcg cag ggc acg aca aaa gaa ggg          813
Leu Pro Val Pro Val Thr Arg Ala Gln Gly Thr Thr Lys Glu Gly
            260                 265                 270
```

<210> SEQ ID NO 4
<211> LENGTH: 271
<212> TYPE: PRT
<213> ORGANISM: Escherichia coli

<400> SEQUENCE: 4

```
Arg Ile Gln Asn Arg Pro Leu Val Asp Leu Glu His Ala Ala Leu Gln
  1               5                  10                  15

Val Gly Lys Gly Ile Ile Pro Pro Leu Arg Glu Tyr Gly Ala Ser
                 20                  25                  30

Glu Val Arg Ser Val Thr Arg Ala Phe Asn His Met Ala Ala Gly Val
             35                  40                  45

Lys Gln Leu Ala Asp Asp Arg Thr Leu Leu Met Ala Gly Val Ser His
         50                  55                  60

Asp Leu Arg Thr Pro Leu Thr Arg Ile Arg Leu Ala Thr Glu Met Met
 65                  70                  75                  80

Ser Glu Gln Asp Gly Tyr Leu Ala Glu Ser Ile Asn Lys Asp Ile Glu
```

```
                    85                  90                  95
Glu Cys Asn Ala Ile Ile Glu Gln Phe Ile Asp Tyr Leu Arg Thr Gly
                100                 105                 110

Gln Glu Met Pro Met Glu Met Ala Asp Leu Asn Ala Val Leu Gly Glu
            115                 120                 125

Val Ile Ala Ala Glu Ser Gly Tyr Glu Arg Glu Ile Glu Thr Ala Leu
130                 135                 140

Tyr Pro Gly Ser Ile Glu Val Lys Met His Pro Leu Ser Ile Lys Arg
145                 150                 155                 160

Ala Val Ala Asn Met Val Val Asn Ala Arg Tyr Gly Asn Gly Trp
                165                 170                 175

Ile Lys Val Ser Ser Gly Thr Glu Pro Asn Arg Ala Trp Phe Gln Val
            180                 185                 190

Glu Asp Asp Gly Pro Gly Ile Ala Pro Glu Gln Arg Lys His Leu Phe
        195                 200                 205

Gln Pro Phe Val Arg Gly Asp Ser Ala Arg Thr Ile Ser Gly Thr Gly
    210                 215                 220

Leu Gly Leu Ala Ile Val Gln Arg Ile Val Asp Asn His Asn Gly Met
225                 230                 235                 240

Leu Glu Leu Gly Thr Ser Glu Arg Gly Gly Leu Ser Ile Arg Ala Trp
                245                 250                 255

Leu Pro Val Pro Val Thr Arg Ala Gln Gly Thr Thr Lys Glu Gly
            260                 265                 270

<210> SEQ ID NO 5
<211> LENGTH: 813
<212> TYPE: DNA
<213> ORGANISM: Escherichia coli
<220> FEATURE:
<221> NAME/KEY: CDS
<222> LOCATION: (1)..(813)

<400> SEQUENCE: 5 cgt atc cag aac cga ccg ttg gtc gat ctc gaa cac gca gcc ttg cag      48
Arg Ile Gln Asn Arg Pro Leu Val Asp Leu Glu His Ala Ala Leu Gln
  1               5                  10                  15 gtt ggt aaa ggg att att ccg ccg ctg cgt gag tat ggc gct tcg           96
Val Gly Lys Gly Ile Ile Pro Pro Leu Arg Glu Tyr Gly Ala Ser
             20                  25                  30 gag gtg cgt tcc gtt acc cgt gcc ttt aac cat atg gcg gct ggt gtt     144
Glu Val Arg Ser Val Thr Arg Ala Phe Asn His Met Ala Ala Gly Val
         35                  40                  45 aag caa ctg gcg gat gac cgc acg ctg ctg atg gcg ggg gta agt gtc     192
Lys Gln Leu Ala Asp Asp Arg Thr Leu Leu Met Ala Gly Val Ser Val
     50                  55                  60 gac ttg cgc acg ccg ctg acg cgt att cgc ctg gcg act gag atg atg     240
Asp Leu Arg Thr Pro Leu Thr Arg Ile Arg Leu Ala Thr Glu Met Met
 65                  70                  75                  80 agc gag cag gat ggc tat ctg gca gaa tcg atc aat aaa gat atc gaa     288
Ser Glu Gln Asp Gly Tyr Leu Ala Glu Ser Ile Asn Lys Asp Ile Glu
                 85                  90                  95 gag tgc aac gcc atc att gag cag ttt atc gac tac ctg cgc acc ggg     336
Glu Cys Asn Ala Ile Ile Glu Gln Phe Ile Asp Tyr Leu Arg Thr Gly
                100                 105                 110 cag gag atg ccg atg gaa atg gcg gat ctt aat gca gta ctc ggt gag     384
Gln Glu Met Pro Met Glu Met Ala Asp Leu Asn Ala Val Leu Gly Glu
            115                 120                 125 gtg att gct gcc gaa agt ggc tat gag cgg gaa att gaa acc gcg ctt     432
```

-continued

```
                Val Ile Ala Ala Glu Ser Gly Tyr Glu Arg Glu Ile Glu Thr Ala Leu
                                130                 135                 140 tac ccc ggc agc att gaa gtg aaa atg cac ccg ctg tcg atc aaa cgc              480
Tyr Pro Gly Ser Ile Glu Val Lys Met His Pro Leu Ser Ile Lys Arg
145                 150                 155                 160 gcg gtg gcg aat atg gtg gtc aac gcc gcc cgt tat ggc aat ggc tgg              528
Ala Val Ala Asn Met Val Val Asn Ala Ala Arg Tyr Gly Asn Gly Trp
                165                 170                 175 atc aaa gtc agc agc gga acg gag ccg aat cgc gcc tgg ttc cag gtg              576
Ile Lys Val Ser Ser Gly Thr Glu Pro Asn Arg Ala Trp Phe Gln Val
            180                 185                 190 gaa gat gac ggt ccg gga att gcg ccg gaa caa cgt aag cac ctg ttc              624
Glu Asp Asp Gly Pro Gly Ile Ala Pro Glu Gln Arg Lys His Leu Phe
        195                 200                 205 cag ccg ttt gtc cgc ggc gac agt gcg cgc acc att agc ggc acg gga              672
Gln Pro Phe Val Arg Gly Asp Ser Ala Arg Thr Ile Ser Gly Thr Gly
    210                 215                 220 tta ggg ctg gca att gtg cag cgt atc gtg gat aac cat aac ggg atg              720
Leu Gly Leu Ala Ile Val Gln Arg Ile Val Asp Asn His Asn Gly Met
225                 230                 235                 240 ctg gag ctt ggc acc agc gag cgg ggc ggg ctt tcc att cgc gcc tgg              768
Leu Glu Leu Gly Thr Ser Glu Arg Gly Gly Leu Ser Ile Arg Ala Trp
                245                 250                 255 ctg cca gtg ccg gta acg cgg gcg cag ggc acg aca aaa gaa ggg                  813
Leu Pro Val Pro Val Thr Arg Ala Gln Gly Thr Thr Lys Glu Gly
                260                 265                 270
```

<210> SEQ ID NO 6
<211> LENGTH: 271
<212> TYPE: PRT
<213> ORGANISM: Escherichia coli

<400> SEQUENCE: 6

```
Arg Ile Gln Asn Arg Pro Leu Val Asp Leu Glu His Ala Ala Leu Gln
  1               5                  10                  15

Val Gly Lys Gly Ile Ile Pro Pro Leu Arg Glu Tyr Gly Ala Ser
             20                  25                  30

Glu Val Arg Ser Val Thr Arg Ala Phe Asn His Met Ala Ala Gly Val
         35                  40                  45

Lys Gln Leu Ala Asp Asp Arg Thr Leu Leu Met Ala Gly Val Ser Val
     50                  55                  60

Asp Leu Arg Thr Pro Leu Thr Arg Ile Arg Leu Ala Thr Glu Met Met
 65                  70                  75                  80

Ser Glu Gln Asp Gly Tyr Leu Ala Glu Ser Ile Asn Lys Asp Ile Glu
                 85                  90                  95

Glu Cys Asn Ala Ile Ile Glu Gln Phe Ile Asp Tyr Leu Arg Thr Gly
            100                 105                 110

Gln Glu Met Pro Met Glu Met Ala Asp Leu Asn Ala Val Leu Gly Glu
        115                 120                 125

Val Ile Ala Ala Glu Ser Gly Tyr Glu Arg Glu Ile Glu Thr Ala Leu
    130                 135                 140

Tyr Pro Gly Ser Ile Glu Val Lys Met His Pro Leu Ser Ile Lys Arg
145                 150                 155                 160

Ala Val Ala Asn Met Val Val Asn Ala Ala Arg Tyr Gly Asn Gly Trp
                165                 170                 175

Ile Lys Val Ser Ser Gly Thr Glu Pro Asn Arg Ala Trp Phe Gln Val
            180                 185                 190
```

```
Glu Asp Asp Gly Pro Gly Ile Ala Pro Glu Gln Arg Lys His Leu Phe
            195                 200                 205

Gln Pro Phe Val Arg Gly Asp Ser Ala Arg Thr Ile Ser Gly Thr Gly
            210                 215                 220

Leu Gly Leu Ala Ile Val Gln Arg Ile Val Asp Asn His Asn Gly Met
225                 230                 235                 240

Leu Glu Leu Gly Thr Ser Glu Arg Gly Gly Leu Ser Ile Arg Ala Trp
                245                 250                 255

Leu Pro Val Pro Val Thr Arg Ala Gln Gly Thr Thr Lys Glu Gly
            260                 265                 270

<210> SEQ ID NO 7
<211> LENGTH: 684
<212> TYPE: DNA
<213> ORGANISM: Escherichia coli
<220> FEATURE:
<221> NAME/KEY: CDS
<222> LOCATION: (1)..(684)

<400> SEQUENCE: 7
```

| | |
|---|---|
| atg gcg gct ggt gtt aag caa ctg gcg gat gac cgc acg ctg ctg atg<br>Met Ala Ala Gly Val Lys Gln Leu Ala Asp Asp Arg Thr Leu Leu Met<br>1               5                   10                  15 | 48 |
| gcg ggg gta agt cac gac ttg cgc acg ccg ctg acg cgt att cgc ctg<br>Ala Gly Val Ser His Asp Leu Arg Thr Pro Leu Thr Arg Ile Arg Leu<br>                20                  25                  30 | 96 |
| gcg act gag atg atg agc gag cag gat ggc tat ctg gca gaa tcg atc<br>Ala Thr Glu Met Met Ser Glu Gln Asp Gly Tyr Leu Ala Glu Ser Ile<br>            35                  40                  45 | 144 |
| aat aaa gat atc gaa gag tgc aac gcc atc att gag cag ttt atc gac<br>Asn Lys Asp Ile Glu Glu Cys Asn Ala Ile Ile Glu Gln Phe Ile Asp<br>50                  55                  60 | 192 |
| tac ctg cgc acc ggg cag gag atg ccg atg gaa atg gcg gat ctt aat<br>Tyr Leu Arg Thr Gly Gln Glu Met Pro Met Glu Met Ala Asp Leu Asn<br>65                  70                  75                  80 | 240 |
| gca gta ctc ggt gag gtg att gct gcc gaa agt ggc tat gag cgg gaa<br>Ala Val Leu Gly Glu Val Ile Ala Ala Glu Ser Gly Tyr Glu Arg Glu<br>                85                  90                  95 | 288 |
| att gaa acc gcg ctt tac ccc ggc agc att gaa gtg aaa atg cac ccg<br>Ile Glu Thr Ala Leu Tyr Pro Gly Ser Ile Glu Val Lys Met His Pro<br>            100                 105                 110 | 336 |
| ctg tcg atc aaa cgc gcg gtg gcg aat atg gtg gtc aac gcc gcc cgt<br>Leu Ser Ile Lys Arg Ala Val Ala Asn Met Val Val Asn Ala Ala Arg<br>        115                 120                 125 | 384 |
| tat ggc aat ggc tgg atc aaa gtc agc agc gga acg gag ccg aat cgc<br>Tyr Gly Asn Gly Trp Ile Lys Val Ser Ser Gly Thr Glu Pro Asn Arg<br>    130                 135                 140 | 432 |
| gcc tgg ttc cag gtg gaa gat gac ggt ccg gga att gcg ccg gaa caa<br>Ala Trp Phe Gln Val Glu Asp Asp Gly Pro Gly Ile Ala Pro Glu Gln<br>145                 150                 155                 160 | 480 |
| cgt aag cac ctg ttc cag ccg ttt gtc cgc ggc gac agt gcg cgc acc<br>Arg Lys His Leu Phe Gln Pro Phe Val Arg Gly Asp Ser Ala Arg Thr<br>                165                 170                 175 | 528 |
| att agc ggc acg gga tta ggg ctg gca att gtg cag cgt atc gtg gat<br>Ile Ser Gly Thr Gly Leu Gly Leu Ala Ile Val Gln Arg Ile Val Asp<br>            180                 185                 190 | 576 |
| aac cat aac ggg atg ctg gag ctt ggc acc agc gag cgg ggc ggg ctt<br>Asn His Asn Gly Met Leu Glu Leu Gly Thr Ser Glu Arg Gly Gly Leu<br>        195                 200                 205 | 624 |
| tcc att cgc gcc tgg ctg cca gtg ccg gta acg cgg gcg cag ggc acg | 672 |

```
Ser Ile Arg Ala Trp Leu Pro Val Pro Val Thr Arg Ala Gln Gly Thr
        210                 215                 220 aca aaa gaa ggg                                                           684
Thr Lys Glu Gly
225
```

<210> SEQ ID NO 8
<211> LENGTH: 228
<212> TYPE: PRT
<213> ORGANISM: Escherichia coli

<400> SEQUENCE: 8

```
Met Ala Ala Gly Val Lys Gln Leu Ala Asp Asp Arg Thr Leu Leu Met
 1               5                  10                  15

Ala Gly Val Ser His Asp Leu Arg Thr Pro Leu Thr Arg Ile Arg Leu
            20                  25                  30

Ala Thr Glu Met Met Ser Glu Gln Asp Gly Tyr Leu Ala Glu Ser Ile
        35                  40                  45

Asn Lys Asp Ile Glu Glu Cys Asn Ala Ile Ile Glu Gln Phe Ile Asp
    50                  55                  60

Tyr Leu Arg Thr Gly Gln Glu Met Pro Met Glu Met Ala Asp Leu Asn
 65                 70                  75                  80

Ala Val Leu Gly Glu Val Ile Ala Ala Glu Ser Gly Tyr Glu Arg Glu
                85                  90                  95

Ile Glu Thr Ala Leu Tyr Pro Gly Ser Ile Glu Val Lys Met His Pro
            100                 105                 110

Leu Ser Ile Lys Arg Ala Val Ala Asn Met Val Val Asn Ala Ala Arg
        115                 120                 125

Tyr Gly Asn Gly Trp Ile Lys Val Ser Ser Gly Thr Glu Pro Asn Arg
    130                 135                 140

Ala Trp Phe Gln Val Glu Asp Asp Gly Pro Gly Ile Ala Pro Glu Gln
145                 150                 155                 160

Arg Lys His Leu Phe Gln Pro Phe Val Arg Gly Asp Ser Ala Arg Thr
                165                 170                 175

Ile Ser Gly Thr Gly Leu Gly Leu Ala Ile Val Gln Arg Ile Val Asp
            180                 185                 190

Asn His Asn Gly Met Leu Glu Leu Gly Thr Ser Glu Arg Gly Gly Leu
        195                 200                 205

Ser Ile Arg Ala Trp Leu Pro Val Pro Val Thr Arg Ala Gln Gly Thr
    210                 215                 220

Thr Lys Glu Gly
225
```

<210> SEQ ID NO 9
<211> LENGTH: 525
<212> TYPE: DNA
<213> ORGANISM: Escherichia coli
<220> FEATURE:
<221> NAME/KEY: CDS
<222> LOCATION: (1)..(525)

<400> SEQUENCE: 9

```
atg gcg gct ggt gtt aag caa ctg gcg gat gac cgc acg ctg ctg atg      48
Met Ala Ala Gly Val Lys Gln Leu Ala Asp Asp Arg Thr Leu Leu Met
 1               5                  10                  15 gcg ggg gta agt cac gac ttg cgc acg ccg ctg acg cgt att cgc ctg      96
Ala Gly Val Ser His Asp Leu Arg Thr Pro Leu Thr Arg Ile Arg Leu
            20                  25                  30
```

```
gcg act gag atg atg agc gag cag gat ggc tat ctg gca gaa tcg atc    144
Ala Thr Glu Met Met Ser Glu Gln Asp Gly Tyr Leu Ala Glu Ser Ile
         35                  40                  45 aat aaa gat atc gaa gag tgc aac gcc atc att gag cag ttt atc gac    192
Asn Lys Asp Ile Glu Glu Cys Asn Ala Ile Ile Glu Gln Phe Ile Asp
 50                  55                  60 tac ctg cgc acc ggg cag gag atg ccg atg gaa atg gcg gat ctt aat    240
Tyr Leu Arg Thr Gly Gln Glu Met Pro Met Glu Met Ala Asp Leu Asn
 65                  70                  75                  80 gca gta ctc ggt gag gtg att gct gcc gaa agt ggc tat gag cgg gaa    288
Ala Val Leu Gly Glu Val Ile Ala Ala Glu Ser Gly Tyr Glu Arg Glu
                 85                  90                  95 att gaa acc gcg ctt tac ccc ggc agc att gaa gtg aaa atg cac ccg    336
Ile Glu Thr Ala Leu Tyr Pro Gly Ser Ile Glu Val Lys Met His Pro
            100                 105                 110 ctg tcg atc aaa cgc gcg gtg gcg aat atg gtg gtc aac gcc gcc cgt    384
Leu Ser Ile Lys Arg Ala Val Ala Asn Met Val Val Asn Ala Ala Arg
        115                 120                 125 tat ggc aat ggc tgg atc aaa gtc agc agc gga acg gag ccg aat cgc    432
Tyr Gly Asn Gly Trp Ile Lys Val Ser Ser Gly Thr Glu Pro Asn Arg
    130                 135                 140 gcc tgg ttc cag gtg gaa gat gac ggt ccg gga att gcg ccg gaa caa    480
Ala Trp Phe Gln Val Glu Asp Asp Gly Pro Gly Ile Ala Pro Glu Gln
145                 150                 155                 160 cgt aag cac ctg ttc cag ccg ttt gtc cgc ggc gac agt gcg cgc        525
Arg Lys His Leu Phe Gln Pro Phe Val Arg Gly Asp Ser Ala Arg
                165                 170                 175

<210> SEQ ID NO 10
<211> LENGTH: 175
<212> TYPE: PRT
<213> ORGANISM: Escherichia coli

<400> SEQUENCE: 10

Met Ala Ala Gly Val Lys Gln Leu Ala Asp Asp Arg Thr Leu Leu Met
 1               5                  10                  15

Ala Gly Val Ser His Asp Leu Arg Thr Pro Leu Thr Arg Ile Arg Leu
            20                  25                  30

Ala Thr Glu Met Met Ser Glu Gln Asp Gly Tyr Leu Ala Glu Ser Ile
        35                  40                  45

Asn Lys Asp Ile Glu Glu Cys Asn Ala Ile Ile Glu Gln Phe Ile Asp
 50                  55                  60

Tyr Leu Arg Thr Gly Gln Glu Met Pro Met Glu Met Ala Asp Leu Asn
 65                  70                  75                  80

Ala Val Leu Gly Glu Val Ile Ala Ala Glu Ser Gly Tyr Glu Arg Glu
                 85                  90                  95

Ile Glu Thr Ala Leu Tyr Pro Gly Ser Ile Glu Val Lys Met His Pro
            100                 105                 110

Leu Ser Ile Lys Arg Ala Val Ala Asn Met Val Val Asn Ala Ala Arg
        115                 120                 125

Tyr Gly Asn Gly Trp Ile Lys Val Ser Ser Gly Thr Glu Pro Asn Arg
    130                 135                 140

Ala Trp Phe Gln Val Glu Asp Asp Gly Pro Gly Ile Ala Pro Glu Gln
145                 150                 155                 160

Arg Lys His Leu Phe Gln Pro Phe Val Arg Gly Asp Ser Ala Arg
                165                 170                 175

<210> SEQ ID NO 11
```

-continued

```
<211> LENGTH: 201
<212> TYPE: DNA
<213> ORGANISM: Escherichia coli
<220> FEATURE:
<221> NAME/KEY: CDS
<222> LOCATION: (1)..(201)

<400> SEQUENCE: 11 atg gcg gct ggt gtt aag caa ctg gcg gat gac cgc acg ctg ctg atg      48
Met Ala Ala Gly Val Lys Gln Leu Ala Asp Asp Arg Thr Leu Leu Met
 1               5                  10                  15 gcg ggg gta agt cac gac ttg cgc acg ccg ctg acg cgt att cgc ctg      96
Ala Gly Val Ser His Asp Leu Arg Thr Pro Leu Thr Arg Ile Arg Leu
             20                  25                  30 gcg act gag atg atg agc gag cag gat ggc tat ctg gca gaa tcg atc     144
Ala Thr Glu Met Met Ser Glu Gln Asp Gly Tyr Leu Ala Glu Ser Ile
         35                  40                  45 aat aaa gat atc gaa gag tgc aac gcc atc att gag cag ttt atc gac     192
Asn Lys Asp Ile Glu Glu Cys Asn Ala Ile Ile Glu Gln Phe Ile Asp
     50                  55                  60 tac ctg cgc                                                         201
Tyr Leu Arg
 65

<210> SEQ ID NO 12
<211> LENGTH: 67
<212> TYPE: PRT
<213> ORGANISM: Escherichia coli

<400> SEQUENCE: 12

Met Ala Ala Gly Val Lys Gln Leu Ala Asp Asp Arg Thr Leu Leu Met
 1               5                  10                  15

Ala Gly Val Ser His Asp Leu Arg Thr Pro Leu Thr Arg Ile Arg Leu
             20                  25                  30

Ala Thr Glu Met Met Ser Glu Gln Asp Gly Tyr Leu Ala Glu Ser Ile
         35                  40                  45

Asn Lys Asp Ile Glu Glu Cys Asn Ala Ile Ile Glu Gln Phe Ile Asp
     50                  55                  60

Tyr Leu Arg
 65

<210> SEQ ID NO 13
<211> LENGTH: 483
<212> TYPE: DNA
<213> ORGANISM: Escherichia coli
<220> FEATURE:
<221> NAME/KEY: CDS
<222> LOCATION: (1)..(483)

<400> SEQUENCE: 13 acc ggg cag gag atg ccg atg gaa atg gcg gat ctt aat gca gta ctc      48
Thr Gly Gln Glu Met Pro Met Glu Met Ala Asp Leu Asn Ala Val Leu
 1               5                  10                  15 ggt gag gtg att gct gcc gaa agt ggc tat gag cgg gaa att gaa acc      96
Gly Glu Val Ile Ala Ala Glu Ser Gly Tyr Glu Arg Glu Ile Glu Thr
             20                  25                  30 gcg ctt tac ccc ggc agc att gaa gtg aaa atg cac ccg ctg tcg atc     144
Ala Leu Tyr Pro Gly Ser Ile Glu Val Lys Met His Pro Leu Ser Ile
         35                  40                  45 aaa cgc gcg gtg gcg aat atg gtg gtc aac gcc gcc cgt tat ggc aat     192
Lys Arg Ala Val Ala Asn Met Val Val Asn Ala Ala Arg Tyr Gly Asn
     50                  55                  60
```

-continued

```
ggc tgg atc aaa gtc agc agc gga acg gag ccg aat cgc gcc tgg ttc     240
Gly Trp Ile Lys Val Ser Ser Gly Thr Glu Pro Asn Arg Ala Trp Phe
 65              70                  75                  80 cag gtg gaa gat gac ggt ccg gga att gcg ccg gaa caa cgt aag cac     288
Gln Val Glu Asp Asp Gly Pro Gly Ile Ala Pro Glu Gln Arg Lys His
                 85                  90                  95 ctg ttc cag ccg ttt gtc cgc ggc gac agt gcg cgc acc att agc ggc     336
Leu Phe Gln Pro Phe Val Arg Gly Asp Ser Ala Arg Thr Ile Ser Gly
            100                 105                 110 acg gga tta ggg ctg gca att gtg cag cgt atc gtg gat aac cat aac     384
Thr Gly Leu Gly Leu Ala Ile Val Gln Arg Ile Val Asp Asn His Asn
        115                 120                 125 ggg atg ctg gag ctt ggc acc agc gag cgg ggc ggg ctt tcc att cgc     432
Gly Met Leu Glu Leu Gly Thr Ser Glu Arg Gly Gly Leu Ser Ile Arg
    130                 135                 140 gcc tgg ctg cca gtg ccg gta acg cgg gcg cag ggc acg aca aaa gaa     480
Ala Trp Leu Pro Val Pro Val Thr Arg Ala Gln Gly Thr Thr Lys Glu
145                 150                 155                 160 ggg                                                                  483
Gly
```

<210> SEQ ID NO 14
<211> LENGTH: 161
<212> TYPE: PRT
<213> ORGANISM: Escherichia coli

<400> SEQUENCE: 14

```
Thr Gly Gln Glu Met Pro Met Glu Met Ala Asp Leu Asn Ala Val Leu
 1               5                  10                  15

Gly Glu Val Ile Ala Ala Glu Ser Gly Tyr Glu Arg Glu Ile Glu Thr
                20                  25                  30

Ala Leu Tyr Pro Gly Ser Ile Glu Val Lys Met His Pro Leu Ser Ile
            35                  40                  45

Lys Arg Ala Val Ala Asn Met Val Val Asn Ala Ala Arg Tyr Gly Asn
        50                  55                  60

Gly Trp Ile Lys Val Ser Ser Gly Thr Glu Pro Asn Arg Ala Trp Phe
 65                  70                  75                  80

Gln Val Glu Asp Asp Gly Pro Gly Ile Ala Pro Glu Gln Arg Lys His
                 85                  90                  95

Leu Phe Gln Pro Phe Val Arg Gly Asp Ser Ala Arg Thr Ile Ser Gly
            100                 105                 110

Thr Gly Leu Gly Leu Ala Ile Val Gln Arg Ile Val Asp Asn His Asn
        115                 120                 125

Gly Met Leu Glu Leu Gly Thr Ser Glu Arg Gly Gly Leu Ser Ile Arg
    130                 135                 140

Ala Trp Leu Pro Val Pro Val Thr Arg Ala Gln Gly Thr Thr Lys Glu
145                 150                 155                 160

Gly
```

METHODS OF IDENTIFYING INHIBITORS OF SENSOR HISTIDINE KINASES THROUGH RATIONAL DRUG DESIGN

CROSS-REFERENCE TO RELATED APPLICATIONS

The present Application is a non-provisional application claiming the priority of copending provisional U.S. Ser. No. 60/078,769 filed on Mar. 19, 1998. Applicants claim the benefits of this Application under 35 U.S.C. §119(e).

GOVERNMENTAL SUPPORT

The research leading to the present invention was supported, at least in part, by a grant from the National Institutes of Health, Grant No. GM 19043. Accordingly, the Government may have certain rights in the invention.

FIELD OF THE INVENTION

The present invention relates to N-terminal truncated transmembrane sensor histidine kinases that retain their ability to be autophosphorylated and/or their related histidine kinase activity. The N-terminal truncated transmembrane sensor histidine kinases are used for obtaining detailed three-dimensional structural data of the catalytic portion of the protein. In addition, methodology for related structure based rational drug design using the three-dimensional data are disclosed. Nucleotide and amino acid sequences of the N-terminal truncated transmembrane sensor histidine kinases are also provided.

BACKGROUND OF THE INVENTION

Bacteria are particularly susceptible to acute environmental changes which require rapid adaptation for survival. These environmental changes include nutritional deficiencies, exposure to a chemical toxin, and changes in osmolarity. In order to cope with such environmental stresses, bacteria have developed a sophisticated signaling system which enables the cell to respond swiftly to any given environmental alteration. The most common signaling system in bacteria is the histidyl-aspartyl (His-Asp) phosphorelay signal transduction system. Recently His-Asp phosphorelay systems also have been identified in eukaryotic cells [Egger et al, *Genes to Cells*, 2:167–184 (1997); Appleby et al., *Cell*, 86:845–848 (1996); Inouye, *Cell*, 85:13–14 (1996); Parkinson and Kofoid, *Ann. Rev. Gen.*, 26:71–112 (1992); Stock et al., *Microbiol Rev.*, 53:450–490 (1989)].

There are two key participants in the His-Asp phosphorelay signal transduction system: (1) a sensor histidine kinase, which is generally a transmembrane protein; and (2) a response regulator which mediates changes in gene expression and/or cellular locomotion. The sensor histidine kinase responds to a particular environmental parameter by activating the response regulator. The activated response regulator then serves as a mediator of the signal to effect the cellular response to the environmental parameter. Thus, for each particular type of environmental challenge, a corresponding bacterial sensor histidine kinase exists that initiates the appropriate cellular response. Recently 23–28 open reading frames were identified in the *Escherichia coli* genome as encoding putative sensory kinases, whereas 32 open reading frames were identified as encoding putative response regulators [Mizuno, *DNA Research.*, 4:161–168 (1997)].

The transmembrane sensor histidine kinase (TSHK) of the His-Asp phosphorelay signal transduction system contains a specific histidine that is autophosphorylated using ATP as the co-substrate. The TSHK can then transfer the phosphoryl group to a specific aspartyl residue of the response regulator. This phosphoryl transfer activates the response regulator and thereby mediates the signal. Unlike the analogous eukaryotic signal transduction pathways that employ either tyrosine (e.g., STATs) or threonine and/or serine (e.g., Smads) and in which the flow of the phosphoryl group is irreversible, the His-Asp pathway is based on a reversible phosphoryl transfer between histidine and aspartic acid residues.

Bacterial infections remain among the most common and deadly causes of human disease. For example, evidence of a virulent strain of *E. coli* in ground beef resulted in a recall of approximately $15 million worth of that food product. Such virulent strains can cause severe diarrhea, a condition which kills a million more people (3 million) each year worldwide than malaria. [D. Leff, *BIOWORLD TODAY*, 9:1,3 (1998)].

Although, there was initial optimism in the middle of this century that diseases caused by bacteria would be quickly eradicated, it has become evident that the so-called "miracle drugs" are not sufficient to accomplish this task. Indeed, antibiotic resistant pathogenic strains of bacteria have become common-place, and bacterial resistance to the new variations of these drugs appears to be outpacing the ability of scientists to develop effective chemical analogs of the existing drugs (See, Stuart B. Levy, *The Challenge of Antibiotic Resistance*, in *Scientific American*, 46–53 (March, 1998)). Therefore, new approaches to drug development are necessary to combat the ever-increasing number of antibiotic-resistant pathogens.

Classical penicillin-type antibiotics effect a single class of proteins known as autolysins. Thus, the development of new drugs which effect an alternative bacterial target protein would be desirable. Such a target protein ideally would be indispensable for bacterial survival. A protein involved in the His-Asp pathway such as a sensor histidine kinase would thus be a prime candidate for such drug development.

Therefore, there is a need to develop methods for identifying drugs that interfere with transmembrane sensor histidine kinase activity. Unfortunately, such identification has heretofore relied on serendipity and/or systematic screening of large numbers of natural and synthetic compounds. One superior method for drug screening relies on structure based rational drug design. In such cases, a three dimensional structure of the protein or peptide is determined and potential agonists and/or antagonists are designed with the aid of computer modeling [Bugg et al., *Scientific American*, December: 92–98 (1993); West et al., *TIPS*, 16:67–74 (1995); Dunbrack et al., *Folding & Design*, 2:27–42 (1997)]. Unfortunately, with the notable exception of certain sensors involved in chemotaxis, bacterial sensors tend to be transmembrane proteins having multiple domains and have heretofor not been amenable to three-dimensional structural analysis. This is due to the intrinsic difficulty in preparing high quality TSHK crystals required for X-ray crystallographic analysis and the fact that the multidomain TSHK is too large for NMR three-dimensional analysis. Therefore, there is essentially no detailed structural information for TSHKs.

Therefore, there is a need for obtaining a form of the transmembrane sensor histidine kinase that is amenable for NMR analysis and/or X-ray crystallographic analysis. In addition, there is a need for determining the three-dimensional structure of such a TSHK form. Furthermore, there is a need for developing procedures of structure based rational drug design using such three-dimensional information. Finally, there is a need to employ such procedures to develop new anti-bacterial drugs.

The citation of any reference herein should not be construed as an admission that such reference is available as "Prior Art" to the instant application.

SUMMARY OF THE INVENTION

The present invention provides detailed three-dimensional structural information for transmembrane sensor histidine kinases (TSHK), proteins that play a crucial role in the signal transduction pathways of prokaryotes. The present invention further provides methods of using this structural information in the rational design of drugs for use in the treatment and/or prevention of bacterial infections.

One aspect of the present invention includes a nucleic acid encoding an N-terminal truncated transmembrane sensor histidine kinase ($N_t$TSHK) that comprises an amino acid sequence that is substantially homologous to that of SEQ ID NO:12, and contains a histidine that can be phosphorylated by a protein histidine kinase. In a preferred embodiment of this type, the protein histidine kinase is a transmembrane sensor histidine kinase (TSHK). In another embodiment, the protein histidine kinase is a fragment of the TSHK having protein histidine kinase activity.

In a particular embodiment of this aspect of the invention the nucleic acid encodes a $N_t$TSHK that comprises the amino acid sequence of SEQ ID NO:12. In a related embodiment of this type the nucleic acid encodes a $N_t$TSHK that comprises the amino acid sequence of SEQ ID NO:12 with a conservative amino acid substitution. In a preferred embodiment of this type the nucleic acid encodes a $N_t$TSHK that consists of the amino acid sequence of SEQ ID NO:12 with a conservative amino acid substitution. In a related embodiment, the nucleic acid encodes a $N_t$TSHK that consists of an amino acid sequence of SEQ ID NO:12. In a preferred embodiment the nucleic acid encoding the $N_t$TSHK comprises the coding sequence of SEQ ID NO:11.

A related aspect of the present invention includes a nucleic acid encoding an N-terminal truncated transmembrane sensor histidine kinase that comprises an amino acid sequence that is substantially homologous to that of SEQ ID NO:10 and contains a histidine that can be phosphorylated by a protein histidine kinase. In a preferred embodiment of this type, the protein histidine kinase is a transmembrane sensor histidine kinase. In another embodiment, the protein histidine kinase is a fragment of a TSHK that has protein histidine kinase activity.

One embodiment of this aspect of the invention is a nucleic acid that encodes an $N_t$TSHK that comprises the amino acid sequence of SEQ ID NO:10. In a related embodiment of this type, the nucleic acid encodes an $N_t$TSHK that comprises the amino acid of SEQ ID NO:10 with a conservative amino acid substitution. In a preferred embodiment of this type the nucleic acid encodes a $N_t$TSHK that consists of the amino acid sequence of SEQ ID NO:10 with a conservative amino acid substitution. In a particular embodiment of this type, the nucleic acid encodes a $N_t$TSHK that consists of the amino acid sequence of SEQ ID NO:10. In a preferred embodiment, the nucleic acid encoding the $N_t$TSHK comprises the coding sequence of SEQ ID NO:9.

Another related aspect of the present invention includes a nucleic acid encoding an N-terminal truncated transmembrane sensor histidine kinase that comprises an amino acid sequence that is substantially homologous to that of SEQ ID NO:8, and contains a histidine that can phosphorylated by a protein histidine kinase. In a preferred embodiment of this type, the protein histidine kinase is a transmembrane sensor histidine kinase. In another embodiment, the protein histidine kinase is a fragment of a TSHK that has protein histidine kinase activity.

In another embodiment of this aspect of the invention is a nucleic acid that encodes a $N_t$TSHK that comprises the amino acid sequence of SEQ ID NO:8. In a related embodiment of this type, the nucleic acid encodes an $N_t$TSHK that comprises the amino acid sequence of SEQ ID NO:8 with a conservative amino acid substitution. In a preferred embodiment of this type the nucleic acid encodes a $N_t$TSHK that consists of the amino acid sequence of SEQ ID NO:8. In a related embodiment of this type the nucleic acid encodes a $N_t$TSHK that consists of the amino acid sequence of SEQ ID NO:8 with a conservative amino acid substitution. In a preferred embodiment, the nucleic acid encodes a $N_t$TSHK comprising the coding sequence of SEQ ID NO:7.

Yet another related aspect of the present invention includes a nucleic acid encoding a N-terminal truncated transmembrane sensor histidine kinase that comprises an amino acid sequence that is substantially homologous to that of SEQ ID NO:4, and contains a histidine that can be phosphorylated by a protein histidine kinase. In a preferred embodiment of this type the protein histidine kinase is a transmembrane sensor histidine kinase. In another embodiment, the protein histidine kinase is a fragment of a TSHK that has protein histidine kinase activity.

In another embodiment of this aspect of the invention, the nucleic acid encodes a $N_t$TSHK that comprises the amino acid sequence of SEQ ID NO:4. In a related embodiment of this type the nucleic acid encodes a $N_t$TSHK that comprises the amino acid sequence of SEQ ID NO:4 with a conservative amino acid substitution. In a preferred embodiment of this type the nucleic acid encodes a $N_t$TSHK that consists of the amino acid sequence of SEQ ID NO:4. In a related embodiment the nucleic acid encodes a $N_t$TSHK that consists of the amino acid sequence of SEQ ID NO:4 with a conservative amino acid substitution. In a preferred embodiment, the nucleic acid encodes a $N_t$TSHK comprising the coding sequence of SEQ ID NO:3.

Another aspect of the invention provides a nucleic acid encoding an N-terminal truncated transmembrane sensor histidine kinase that comprises an amino acid sequence that is substantially homologous to SEQ ID NO:14, wherein the $N_t$TSHK is capable of phosphorylating the corresponding TSHK. In a preferred embodiment of this type the $N_t$TSHK lacks the autophosphorylatable histidine of the TSHK.

In a particular embodiment of this aspect of the invention, the nucleic acid encodes a $N_t$TSHK that comprises the amino acid sequence of SEQ ID NO:14. In a related embodiment of this type, the nucleic acid encodes a $N_t$TSHK which comprises the amino acid sequence of SEQ ID NO:14 with a conservative amino acid substitution. In a preferred embodiment of this type the nucleic acid encodes a $N_t$TSHK that consists of the amino acid sequence of SEQ ID NO:14. In a related embodiment, the nucleic acid encodes a $N_t$TSHK that consists of the amino acid sequence of SEQ ID NO:14 with a conservative amino acid substitution. In a preferred embodiment, the nucleic acid encoding the $N_t$TSHK comprises the coding sequence of SEQ ID NO:13.

A related aspect of the present invention includes a nucleic acid including an N-terminal truncated transmembrane sensor histidine kinase that comprises an amino acid sequence that is substantially homologous to that of SEQ ID NO:6, wherein the $N_t$TSHK is capable of phosphorylating the corresponding TSHK. In a preferred embodiment of this type the N,TSHK lacks the autophosphorylatable histidine of the TSHK. In a particular embodiment of this aspect of the invention, the nucleic acid encodes a N,TSHK that comprises the amino acid sequence of SEQ ID NO:6. In a related embodiment of this type, the nucleic acid encodes a N,TSHK that comprises the amino acid sequence of SEQ ID NO:6 with a conservative amino acid substitution. In a preferred embodiment, the nucleic acid encodes a N,TSHK which consists of the amino acid sequence of SEQ ID NO:6. In another such embodiment, the nucleic acid encodes a N,TSHK which consists of the amino acid sequence of SEQ ID NO:6 with a conservative amino acid substitution. In a preferred embodiment, the nucleic acid encoding the N,T-SHK comprises the coding sequence of SEQ ID NO:5.

The present invention also provides a nucleic acid encoding a N,TSHK that further comprises a heterologous nucleotide sequence. In one such embodiment, the nucleic acid encodes a N,TSHK that comprises an amino acid sequence that is substantially homologous to that of SEQ ID NO:12 and a heterologous nucleotide sequence. In another such embodiment the nucleic acid encodes the amino acid sequence of SEQ ID NO:12 with a conservative substitution and a heterologous nucleotide sequence. In a preferred embodiment of this type the nucleic acid encodes the amino acid sequence of SEQ ID NO:12 with a heterologous nucleotide sequence. In a more preferred embodiment of this type, the nucleic acid comprises the nucleotide sequence of SEQ ID NO:11 with a heterologous nucleotide sequence.

The present invention also provides a nucleic acid that encodes a N,TSHK that comprises an amino acid sequenced that is substantially homologous to that of SEQ ID NO:10, and a heterologous nucleotide sequence. In another such embodiment, the nucleic acid encodes a N,TSHK having the amino acid sequence of SEQ ID NO:10 with a conservative substitution and a heterologous nucleotide sequence. In a preferred embodiment of this type, the nucleic acid encodes a N,TSHK having the amino acid sequence of SEQ ID NO:10 and a heterologous nucleotide sequence. In a more preferred embodiment of this type, the nucleic acid comprises the nucleotide sequence of SEQ ID NO:9 with a heterologous nucleotide sequence.

The present invention further provides a nucleic acid that encodes a N,TSHK that comprises an amino acid sequence that is substantially homologous to that of SEQ ID NO:8, and a heterologous nucleotide sequence. Another embodiment of this type the nucleic acid encodes a N,TSHK having the amino acid sequence of SEQ ID NO:8 with a conservative substitution, and a heterologous nucleotide sequence. In a preferred embodiment of this type, the nucleic acid encodes a N,TSHK having the amino acid sequence of SEQ ID NO:8 and a heterologous nucleotide sequence. In a more preferred embodiment of this type, the nucleic acid comprises the nucleotide sequence of SEQ ID NO:7 with a heterologous nucleotide sequence.

The present invention also provides a nucleic acid that encodes a N,TSHK that comprises a nucleic acid sequence that is substantially homologous to that of SEQ ID NO:4, and a heterologous nucleotide sequence. In another embodiment of this type the nucleic acid encodes a N,TSHK having the amino acid sequence of SEQ ID NO:4 with a conservative substitution, and a heterologous nucleotide sequence. In a preferred embodiment of this type the nucleic acid encodes a N,TSHK having the amino acid sequence of SEQ ID NO:4 and a heterologous nucleotide sequence. In a more preferred embodiment of this type, the nucleic acid comprises the nucleotide sequence of SEQ ID NO:3 with a heterologous nucleotide sequence.

The present invention further provides a nucleic acid encoding an N-terminal truncated transmembrane sensor histidine kinase (N,TSHK) fragment that is capable of phosphorylating a transmembrane sensor histidine kinase (TSHK) but lacks the autophosphorylatable histidine of the TSHK, comprising a catalytic core that has a single globular fold that contains four glycines analagous to G375, G403, G405, and G429 of SEQ ID NO:2. In a preferred embodiment of this type, the single globular fold further contains two asparagines analogous to N343 and N347 of SEQ ID NO:2. In a more preferred embodiment the single fold comprises an α/β sandwich fold with one layer consisting of a five stranded β-sheet and the other layer comprising three helices wherein the two layers enclose an extensive hydrophobic core, augmented by a small anti-parallel β-sheet which seals the sandwich at one end.

In one such particular embodiment the nucleic acid encodes an N,TSHK that contains amino acids 380 to 417 of SEQ ID NO:2. In another such embodiment the nucleic acid encodes an N,TSHK that contains amino acids 380 to 417 of SEQ ID NO:2 with a conservative amino acid substitution. In yet another such particular embodiment the nucleic acid encodes an N,TSHK that contains amino acids 366 to 425 of SEQ ID NO:2. In still another such embodiment the nucleic acid encodes an N,TSHK that contains amino acids 366 to 425 of SEQ ID NO:2 with a conservative amino acid substitution. In yet another such particular embodiment the nucleic acid encodes an N,TSHK that contains amino acids 334 to 437 of SEQ ID NO:2. In still another such embodiment the nucleic acid encodes an N,TSHK that contains amino acids 334 to 437 of SEQ ID NO:2 with a conservative amino acid substitution.

Additionally, the present invention also provides a nucleic acid that encodes a N,TSHK that comprises an amino acid sequence that is substantially homologous to that of SEQ ID NO:14, and a heterologous nucleotide sequence. In another embodiment of this type, the nucleic acid encodes a N,T-SHK having the amino acid sequence of SEQ ID NO:14 with a conservative substitution, and a heterologous nucleotide sequence. In a preferred embodiment of this type the nucleic acid encodes a N,TSHK having a the amino acid sequence of SEQ ID NO:14 and a heterologous nucleotide sequence. In a more preferred embodiment of this type, the nucleic acid comprises the nucleotide sequence of SEQ ID NO:13 with a heterologous nucleotide sequence.

The present invention also provides a nucleic acid that encodes a N,TSHK that comprises an amino acid sequence that is substantially homologous to that of SEQ ID NO:6, and a heterologous nucleotide sequence. In another embodiment of this type, the nucleic acid encodes a N,TSHK having the amino acid sequence of SEQ ID NO:6 with a conservative substitution, and a heterologous nucleotide sequence. In a preferred embodiment of this type, the nucleic acid encodes a N,TSHK having the amino acid sequence of SEQ ID NO:6 and a heterologous nucleotide sequence. In a more preferred embodiment of this type, the nucleic acid comprises the nucleotide sequence of SEQ ID NO:5 with a heterologous nucleotide sequence.

The present invention further provides all of the nucleic acids of the present invention in isolated form, and/or operatively linked to an expression control sequence. Similarly, any of the nucleic acids of the present invention operatively linked to an expression control sequence can be used to transform or transfect a unicellular host.

The present invention also provides methods of expressing a N,TSHK of the present invention that is contained in the unicellular host. One such method comprises culturing the unicellular host in an appropriate cell culture medium under conditions that provide for the expression of the $N_tTSHK$ by the cell. In addition, the present invention includes methods that further comprise the step of purifying the $N_tTSHK$. The purified form of the $N_tTSHK$ is also included as part of the present invention.

In addition, the N-terminal truncated transmembrane sensor histidine kinases are part of the present invention. Thus, the present invention provides a $N_tTSHK$ comprising an amino acid sequence substantially homologous to that of SEQ ID NO:12 which contains a histidine that can be phosphorylated by a protein histidine kinase. In one such embodiment, the protein histidine kinase is a transmembrane sensor histidine kinase. In another such embodiment, the protein histidine kinase is a fragment of the TSHK having protein histidine kinase activity. In one particular embodiment of this type, the $N_tTSHK$ comprises the amino acid sequence of SEQ ID NO:12 with a conservative amino acid substitution. In another embodiment the $N_tTSHK$ comprises the amino acid sequence of SEQ ID NO:12. In still another embodiment of this type the $N_tTSHK$ consists of the amino acid sequence of SEQ ID NO:12 with a conservative amino acid substitution. In a more preferred embodiment of this type the $N_tTSHK$ consists of the amino acid sequence of SEQ ID NO:12.

In a related aspect, the present invention provides a $N_tTSHK$ that comprises an amino acid sequence substantially homologous to that of SEQ ID NO:10, which contains a histidine that can be phosphorylated by a protein histidine kinase. In one such embodiment, the protein histidine kinase is a TSHK. In another such embodiment the protein histidine kinase is a fragment of the TSHK having protein histidine kinase activity.

In a particular embodiment of this aspect of the invention, the $N_tTSHK$ comprises the amino acid sequence of SEQ ID NO:10 with a conservative amino acid substitution. In another embodiment the $N_tTSHK$ comprises the amino acid sequence of SEQ ID NO:10. In still another embodiment of this type, the $N_tTSHK$ consists of the amino acid sequence of SEQ ID NO:10 with a conservative amino acid substitution. In a preferred embodiment of this type the $N_tTSHK$ consists of the amino acid sequence of SEQ ID NO:10.

In another related aspect of the present invention, the $N_tTSHK$ comprises an amino acid sequence substantially homologous to that of SEQ ID NO:8, and contains a histidine that can be phosphorylated by a protein histidine kinase. In one such embodiment, the protein histidine kinase is a TSHK. In another such embodiment, the protein histidine kinase is a fragment of the TSHK, having protein histidine kinase activity.

In a particular embodiment of this type, the $N_tTSHK$ comprises the amino acid sequence of SEQ ID NO:8 with a conservative amino acid substitution. In another embodiment the $N_tTSHK$ comprises the amino acid sequence of SEQ ID NO:8. In still another embodiment of this type the $N_tTSHK$ consists of the amino acid sequence of SEQ ID NO:8 with a conservative amino acid substitution. In a preferred embodiment of this type the $N_tTSHK$ consists of the amino acid sequence of SEQ ID NO:8.

In another related aspect, the present invention provides a $N_tTSHK$ comprising an amino acid sequence substantially homologous to that of SEQ ID NO:4, and contains a histidine that can be phosphorylated by a protein histidine kinase. In one such embodiment, the protein histidine kinase is a TSHK. In another such embodiment the protein histidine kinase is a fragment of a TSHK, having protein histidine kinase activity.

In one particular embodiment of this aspect of the invention, the $N_tTSHK$ comprises the amino acid sequence of SEQ ID NO:4 with a conservative amino acid substitution. In another embodiment, the $N_tTSHK$ comprises the amino acid sequence of SEQ ID NO:4. In still another embodiment of this type the $N_tTSHK$ consists of the amino acid sequence of SEQ ID NO:4 with a conservative amino acid substitution. In a preferred embodiment of this type the $N_tTSHK$ consists of the amino acid sequence of SEQ ID NO:4.

Another aspect of the present invention provides a $N_tTSHK$ that comprises an amino acid sequence that is substantially homologous to SEQ ID NO:14, wherein the $N_tTSHK$ is capable of phosphorylating a TSHK. In a preferred embodiment of this type, the $N_tTSHK$ lacks the autophosphorylatable histidine of the TSHK. In a particular embodiment of this type, the $N_tTSHK$ comprises the amino acid sequence of SEQ ID NO:14 with a conservative amino acid substitution. In another such embodiment the $N_tTSHK$ comprises the amino acid sequence of SEQ ID NO:14. In still another embodiment of this type, the $N_tTSHK$ consists of the amino acid sequence of SEQ ID NO:14. In a preferred embodiment of this type, the $N_tTSHK$ consists of the amino acid sequence of SEQ ID NO:14.

The present invention also provides a $N_tTSHK$ that comprises an amino acid sequence that is substantially homologous to SEQ ID NO:6, wherein the $N_tTSHK$ is capable of phosphorylating a TSHK. In a preferred embodiment of this type, the $N_tTSHK$ lacks the autophosphorylatable histidine of the TSHK.

In a particular embodiment of this type, the $N_tTSHK$ comprises the amino acid sequence of SEQ ID NO:6 with a conservative amino acid substitution. In another such embodiment, the $N_tTSHK$ comprises the amino acid sequence of SEQ ID NO:6. In a related embodiment of this type, the $N_tTSHK$ consists of the amino acid sequence of SEQ ID NO:6 with a conservative amino acid substitution. In a preferred embodiment of this type, the $N_tTSHK$ consists of the amino acid sequence of SEQ ID NO:6.

The present invention further provides an N-terminal truncated transmembrane sensor histidine kinase ($N_tTSHK$) fragment that is capable of phosphorylating a transmembrane sensor histidine kinase (TSHK) but lacks the autophosphorylatable histidine of the TSHK, comprising a catalytic core that has a single globular fold that contains four glycines analagous to G375, G403, G405, and G429 of SEQ ID NO:2. In a preferred embodiment of this type, the single globular fold further contains two asparagines analogous to N343 and N347 of SEQ ID NO:2. In a more preferred embodiment the single fold comprises an α/β sandwich fold with one layer consisting of a five stranded β-sheet and the other layer comprising three helices wherein the two layers enclose an extensive hydrophobic core, augmented by a small anti-parallel β-sheet which seals the sandwich at one end.

In one such particular embodiment the $N_tTSHK$ contains amino acids 380 to 417 of SEQ ID NO:2. In another such embodiment the $N_tTSHK$ contains amino acids 380 to 417 of SEQ ID NO:2 with a conservative amino acid substitution. In yet another such particular embodiment the $N_tTSHK$ contains amino acids 366 to 425 of SEQ ID NO:2. In still another such embodiment the $N_tTSHK$ contains amino acids 366 to 425 of SEQ ID NO:2 with a conservative amino acid substitution. In yet another such particular embodiment the N$_t$TSHK contains amino acids 334 to 437 of SEQ ID NO:2. In still another such embodiment the N$_t$TSHK contains amino acids 334 to 437 of SEQ ID NO:2 with a conservative amino acid substitution.

The present invention also provides fusion proteins/peptides and chimeric proteins/peptides comprising the N$_t$TSHKs of the present invention. All of the isolated N$_t$TSHKs of the present invention, and all of the recombinant N$_t$TSHKs of the present invention may be parts of these fusion and chimeric proteins/peptides. In one such embodiment, a fusion protein comprises a N$_t$TSHK of the present invention and the green fluorescent protein. In another such embodiment, the fusion protein comprises a N$_t$TSHK of the present invention together with a FLAGG tag. In a preferred embodiment of the present invention, the fusion protein comprises SEQ ID NO:12 containing six histidines (H6) at its N-terminus.

The present invention further provides methods of using an N$_t$TSHK in a drug screening assay. Any of the N$_t$TSHKs, and/or fusion proteins/peptides of the present invention may be used in such methods. One such method comprises selecting a potential drug by performing structure based rational drug design with the determined three-dimensional structure of a N$_t$TSHK. The selecting is preferably performed in conjunction with computer modeling. In a preferred embodiment the N$_t$TSHK used in the three-dimensional structural analysis has the amino acid sequence of SEQ ID NO:14. In another preferred embodiment the N$_t$TSHK used in the three-dimensional structural analysis has the amino acid sequence of SEQ ID NO:12.

The selected potential drug can then be contacted with a polypeptide that comprises a N$_t$TSHK. The binding of the selected potential drug with the polypeptide is detected, and a potential drug is selected as a drug if it binds to the polypeptide. In one preferred embodiment, the N$_t$TSHK has the amino acid sequence of SEQ ID NO:14. In another preferred embodiment, the N$_t$TSHK has the amino acid sequence of SEQ ID NO:12.

The polypeptide comprising the N$_t$TSHK can also be labeled. In another such embodiment, the polypeptide comprising the N$_t$TSHK can be bound to a solid support.

In an alternative embodiment, a potential drug can be identified using the three-dimensional structure determined for an N$_t$TSHK and then the potential drug can be contacted with a polypeptide comprising the N$_t$TSHK in the presence of a protein histidine kinase, under conditions in which in the absence of a potential drug the protein histidine kinase phosphorylates the N$_t$TSHK. The phosphorylation state of the N$_t$TSHK is then determined.

A drug is selected when a change in the phosphorylation state of the N$_t$TSHK is determined in the presence of the potential drug relative to in its absence. When the change in phosphorylation state of the N$_t$TSHK is determined to be increased in the presence of the potential drug relative to in its absence, the potential drug is selected as an agonist of the corresponding TSHK. Alteratively, when the change in the phosphorylation state of the N$_t$TSHK determined in the presence of the potential drug is determined to be decreased, relative to in its absence, the potential drug is selected as an inhibitor of the corresponding TSHK.

In one particular embodiment of this type, the polypeptide comprises a N$_t$TSHK having the amino acid sequence of SEQ ID NO:4. In another such embodiment, the polypeptide comprises a N$_t$TSHK having the amino acid sequence of SEQ ID NO:8. In still another such embodiment, the polypeptide comprises a N$_t$TSHK having the amino acid sequence of SEQ ID NO:10. In a preferred embodiment of this type, the polypeptide comprises a N$_t$TSHK having the amino acid sequence of SEQ ID NO:12.

In still another embodiment, a potential drug can be identified using the three-dimensional structure determined for an N$_t$TSHK of the present invention and then the potential drug can be contacted with a polypeptide comprising a N$_t$TSHK in the presence of a protein histidine kinase substrate, wherein in the absence of the potential drug, the protein histidine kinase substrate is phosphorylated by the N$_t$TSHK. The phosphorylation state of the protein histidine kinase substrate is then determined, wherein a drug is selected when a change in the phosphorylation state of the protein histidine kinase substrate is determined in the presence of the potential drug relative to in its absence. When the change in phosphorylation state of the protein histidine kinase substrate determined in the presence of the potential drug, relative to in its absence increases, the potential drug is selected as a stimulator of the TSHK. When the change in phosphorylation state of the protein histidine kinase substrate decreases in the presence of the potential drug, relative to in its absence, the potential drug is selected as an inhibitor of the TSHK. In one embodiment of this type, the polypeptide comprises a N$_t$TSHK that has the amino acid sequence of SEQ ID NO:14. In a preferred embodiment of this type the polypeptide comprises N$_t$TSHK that has the amino acid sequence of SEQ ID NO:6.

The present invention further provides assays for testing potential drugs that are selected/identified by the three-dimensional structural analysis of an N$_t$TSHK of the present invention, for the ability of the potential drug to modulate the signal transduction mediated by the TSHK and its corresponding response regulator. For example, a cell can be constructed to contain a reporter gene (such as a gene encoding green fluorescent protein, or β-galactosidase) under the transcriptional control of the TSHK. The TSHK can be activated and thereby stimulate the transcription of the reporter gene. The potential drug can be added and the change in the amount of transcription of the reporter gene can be determined. A potential drug causing an increase in transcription is selected as an agonist of the TSHK, whereas a potential drug causing a decrease is selected as an antagonist of the TSHK. Controls can be performed to confirm that the potential drug is acting on the TSHK directly. In one such control, a cell is constructed to be lacking a functional TSHK. In this case, the response regulator is activated artificially. The transcription of the reporter gene is monitored in such cells in the presence or absence of the selected drug. A selected drug is identified as acting directly on the TSHK when it has no effect on the transcription of the reporter gene in a cell lacking functional TSHK.

As anyone having skill in the art of drug development would readily understand, the potential drugs selected by the above methodologies can be refined by re-testing in appropriate drug assays, including those disclosed herein. Chemical analogues of such potential drugs can be obtained (either through chemical synthesis or drug libraries) and be analogously tested. Therefore methods comprising successive iterations of the steps of the individual drug assays, as exemplified herein, using either repetitive or different binding studies, phosphorylation studies, or transcription activation studies or other such studies are envisioned in the present invention. In addition, potential drugs may be identified first by rapid throughput drug screening, as described below, prior to performing computer modeling on a potential drug using the three-dimensional structure of an N$_t$TSHK.

Any of the drug assays of the present invention can further comprise a step of contacting the potential drug and the N$_t$TSHK, wherein a binding complex forms between the potential drug and the N$_t$TSHK. The three-dimensional structure of the binding complex can then be determined by NMR. A drug can then be selected by performing structure based rational drug design with the three-dimensional structure determined for the binding complex. The selection is preferably performed in conjunction with computer modeling. Such a drug can be further tested as described above.

The present invention further comprises all of the potential, selected, and putative drugs as well as the drugs identified by methods of the present invention.

The present invention further provides specific antibodies that react with an N$_t$TSHK of the present invention but does not cross react with the corresponding TSHK. The antibodies are raised against the N$_t$TSHK of the present invention. Such antibodies include but are not limited to polyclonal, monoclonal, chimeric, single chain, fab fragments and a fab expression library. These antibodies may also be labeled. Also included is an immortal cell line that produces a monoclonal antibody that reacts with a N$_t$TSHK of the present invention but not its corresponding TSHK.

Accordingly, it is a principal object of the present invention to provide detailed structural information regarding the catalytic site of a transmembrane sensor histidine kinase (TSHK).

It is a further object of the present invention to provide structural characteristics and properties of N-terminal truncated TSHKs (N$_t$TSHKs) which are amenable for detailed NMR structural analysis and which (1) retain their ability to be autophosphorylated, and/or (2) transfer a phosphoryl group from the autophosphorylated phosphoryl histidine to an aspartyl group of their corresponding response regulators and/or (3) function as a protein histidine kinase.

It is a further object of the present invention to provide methodologies for exploiting such structural information in order to develop potential anti-bacterial drugs through structure based rational drug design.

It is a further object of the present invention to provide structural characteristics and properties of N$_t$TSHKs which can be used to form X-ray quality crystals and which (1) retain their ability to be autophosphorylated, and/or (2) transfer a phosphoryl group from the autophosphorylated phosphoryl histidine to an aspartyl group of their corresponding response regulators and/or (3) function as a protein histidine kinase.

It is a further object of the present invention to provide nucleic acid and amino acid sequences for the N$_t$TSHKs of the present invention.

It is a further object of the present invention to provide a method of producing the N$_t$TSHKs of the present invention, including by proteolysis and through recombinant technology.

It is a further object of the present invention to provide a method of selecting an appropriate N$_t$TSHK for use in structure based rational drug design of TSHK inhibitors.

It is a further object of the present invention to provide a method of screening drug libraries for agents that interfere with TSHK-response regulator activity by interfering with the binding of the TSHK to the response regulator.

It is a further object of the present invention to provide a method of screening drug libraries for agents that interfere with TSHK autophosphorylation by interfering with the binding of the interaction of sub-domain A and sub-domain B of the TSHK.

It is a further object of the present invention to provide an antibody specific for an N$_t$TSHK of the present invention that binds to the N$_t$TSHK fragment but does not bind to the corresponding full-length TSHK.

It is a further object of the present invention to provide drugs obtained by the methodology of the present invention for treating and/or preventing bacterial inflammations and infections.

These and other aspects of the present invention will be better appreciated by reference to the following drawings and Detailed Description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1a shows the serial deletions of EnvZ(C) proteins. The N- and C-terminal amino acid residue numbers of each EnvZ(C) fragment are shown above ends of the bar. Solid bars represent the EnvZ sequence. The transmembrane regions, TM1 and TM2, are indicated by shaded boxes. The open bars at the left hand side of the bars indicate the six-histidine residues [Met-(His)6] at the N-terminal end. Conserved motifs among all of the histidine kinases, H243, N347, F387, two glycine-rich regions G1 (residues 373–377) and G2 (residues 403–405) are shown on the top of the full-length EnvZ. The activities of autophosphorylation and phosphorylation by EnvZ(C)H1 of each protein are indicated by + or − (no activity) or ND (not determined). FIGS. 1b and 1c show the purified EnvZ (C) fragments (3 µg each) which were incubated with 0.2 µCi of [γ-$^{32}$P]ATP in a 20-µl reaction mixture consisting of 50 mM Tris-HCl (pH 8.0), 50 mM KCl, 5 mM CaCl$_2$, 5% glycerol, and 1 mM PMSF (buffer A) for 10 minutes at room temperature. The autophosphorylation reaction was stopped by adding 5×SDS gel loading buffer. The reaction mixture was subjected to SDS-PAGE using a 16% Tricine gel (Novex), followed by Coomassie brilliant blue staining in FIG. 1B and autoradiography in FIG. 1C. Lane 1, protein molecular weight markers; lane 2, H6-EnvZ(C)wt; lane 3, H6-EnvZ(C)H1; lane 4, H6-EnvZ(C)ΔL; lane 5, H6-EnvZ (C)ΔG2; lane 6, H6-EnvZ(C)(223–289); lane 7, EnvZ(C) (223–289) and lane 8, EnvZ(C)(290–450).

FIG. 2a shows the results of the kinase assay using the EnvZ(C) fragments. The purified protein H6-EnvZ (C)ΔL [0.13 µM in the upper panel with H6-EnvZ(C)ΔG2 or 0.26 µM in the lower panel with H6-EnvZ(C)(223–289)] was autophosphorylated with 0.2 µCi of [γ-$^{32}$P]ATP at room temperature for 15 min as a control (lane 1). For trans-autophosphorylation of H6-EnvZ(C)ΔG2 [or H6-EnvZ(C) (223–289)] by H6-EnvZ(C)H1, equimolar concentrations of each protein (1.3 µM each) were mixed and incubated with 0.2 µCi of [γ-$^{32}$P]ATP for 15 minutes (lane 2) and 25 minutes (lane 7) at room temperature. For the phosphotransfer reaction to OmpR, H6-EnvZ(C)ΔG2 [or H6-EnvZ(C)(223–289)] and H6-EnvZ(C)H1 were mixed and the mixture was first incubated for 15 minutes (lane 2). After incubation, OmpR was added to the mixture. The molar ratio of H6-EnvZ(C)H1 and OmpR was 1:1: 1 (1.3 µM each). The phosphotransfer reaction was stopped by adding 5×SDS gel loading buffer at 15 seconds (lane 3), 1 minute (lane 4), 5 minutes (lane 5), and 10 minutes (lane 6). The samples were then subjected to SDS-PAGE analysis followed by autoradiography. The position of each protein is indicated by an arrow. FIG. 2b shows the results of the phosphatase assay of the EnvZ(C) fragments. The phosphorylated OmpR in 2.6 μM of total OmpR protein [Pan et al., *Proc. Natl. Acad. Sci. USA*, 90:9939–9943 (1993)] was incubated at room temperature with the following proteins; 2.6 μM of BSA, H-6EnvZ(C) H1, H6-EnvZ(C)wt, H6-EnvZ(C)ΔL, H6-EnvZ(C)ΔG2, H6-EnvZ(C)(223–289) and EnvZ(C)(290–450) as indicated at the right hand side. The reaction was carried out in the presence of 1 mM ADP. The reaction times are indicated at the bottom of the figures. The reaction was stopped by adding 5×SDS gel loading buffer and analyzed by SDS-PAGE, followed by autoradiography.

In FIG. 4a the purified proteins were mixed at room temperature for 30 minutes (lanes 1, 2 and 3) or 60 minutes (lanes 4, 5 and 6) in 20 μl of buffer I [50 mM Na-Phosphate (pH 9.0), 0.3M NaCl, and 5% glycerol], 10 μl of Ni-NTA resin (50% v/v, Qiagen) equilibrated with buffer I was added, followed by further incubation for 30 minutes on ice. After washing three times with buffer II [50 mM Na-phosphate (pH 6.0), 0.3M NaCl, and 5% glycerol], proteins bound to Ni-NTA resin were eluted by 0.2M imidazole in buffer II. Proteins thus eluted were subjected to 20% SDS-PAGE and the gel was stained by silver staining. Lane 1, EnvZ(C)(223–289) ($2.5 \times 10^{-5}$M); lane 2, H6-EnvZ(C) (223–289) and EnvZ(C) (223–289) ($2.5 \times 10^{-5}$M each); lane 3, H6-EnvZ(C)wt and EnvZ(C)(223–289) ($2.5 \times 10^{-5}$M each); lane 4, 0 mpR ($6.1 \times 10^{-6}$M); lane 5, 0 mpR ($6.1 \times 10^{-6}$M) and H6-EnvZ(C) (223–289) ($2.5 \times 10^{-5}$M); and lane 6, 0 mpR ($6.1 \times 10^{-6}$M) and H6-EnvZ(C)wt ($2.5 \times 10^{-5}$M). FIG. 4b shows the gel filtration profiles of EnvZ(C)(223–289) and EnvZ(C) (290–450). The migrations of EnvZ(C)(223–289) and EnvZ (C)(290–450) were analyzed by using a TSK-GEL column (TosoHaas) equipped with HPLC system (model 110B, Beckman). The standard proteins are indicated as closed circles; bovine serum albumin (66,000 Da), ovalbumin (43,000 Da), carbonic anhydrase (29,000 Da), cytochrome C (12,400 Da), and CspA (7,400 Da). The proteins of EnvZ (C)(223–289) and EnvZ(C)(290–450) are indicated by open circles and arrows. The Y-axis represents the molecular weight (Da) in a log scale. The X-axis represents the ratio of the elution volume of sample (Ve) to the void volume (Vo).

FIG. 11 shows the structural alignment of the amino acid sequence of the EnvZ catalytic domain and the ATP-binding domains of Hsp90 and DNA Gyrase B [Wigley et al., *Nature*, 351:624–629 (1991); Holdgate et al., *Biochemistry*, 36:9663–9673 (1997)] searched by the SSAP program [Orengo et al., *Proteins*, 14:139–167 (1992)]. The colour coding for the secondary structure elements is the same as in FIG. 10. Helices and strands of each structure are indicated as double and zigzag lines, respectively, under the sequences. Asterisks denote the conserved hydrophobic amino acid resides and the residues that are conserved among all three sequences are shown in bold.

FIG. 12A is the EnvZ histidine kinase. FIG. 12B is the src tyrosine kinase (PDB; lad5) [Sicheri et al., *Nature*, 385:602–609 (1997)]. FIG. 12C is the cyclic AMP-dependent serine/threonine kinase (PDB; latp) [Zheng et al., *Biochemistry*, 32:2154–2161 (1993)]. ATP in FIG. 12C or its analogue, AMP-PNP, in FIGS. 12A and 12B is shown as a stick model, and the helices and strands are colored in yellow and in green, respectively. The models were generated using MOLSCRIPT [Kraulis, *J. Appl. Crystallogr.*, 24:946–950 (1991)] and Raster3D [Merritt and Murphy, *Acta Crystallogr.*, D50:869–873 (1994)].

DETAILED DESCRIPTION OF THE INVENTION

The present invention provides detailed structural information regarding a transmembrane sensor histidine kinase (TSHK), a protein that plays a crucial role in signal transduction pathways of prokaryotes. More particularly, the present invention provides structural information regarding the cytoplasmic kinase domain of EnvZ, a transmembrane osmosensor of *Escherichia coli*. This cytoplasmic kinase domain is shown to contain two distinct functional sub-domains; sub-domain A [EnvZ(C)(223–289) containing 67 residues (SEQ ID NO:12)] and sub-domain B [EnvZ(C) (290–450) containing 161 residues (SEQ ID NO:14)], each of which are a N$_t$TSHK of the present invention.

The three-dimensional structures of the two subdomains, determined by NMR spectroscopy, are also provided. Sub-domain A is shown, herein, to have a high helical content and to contain the autophosphorylation site, H243, i.e., the autophosphorylatable substrate site. Consistently sub-domain A is also shown to contain the recognition site for OmpR, the cognate response regulator of EnvZ, which is phosphorylated by the TSHK following the autophosphorylation.

Figure 5:
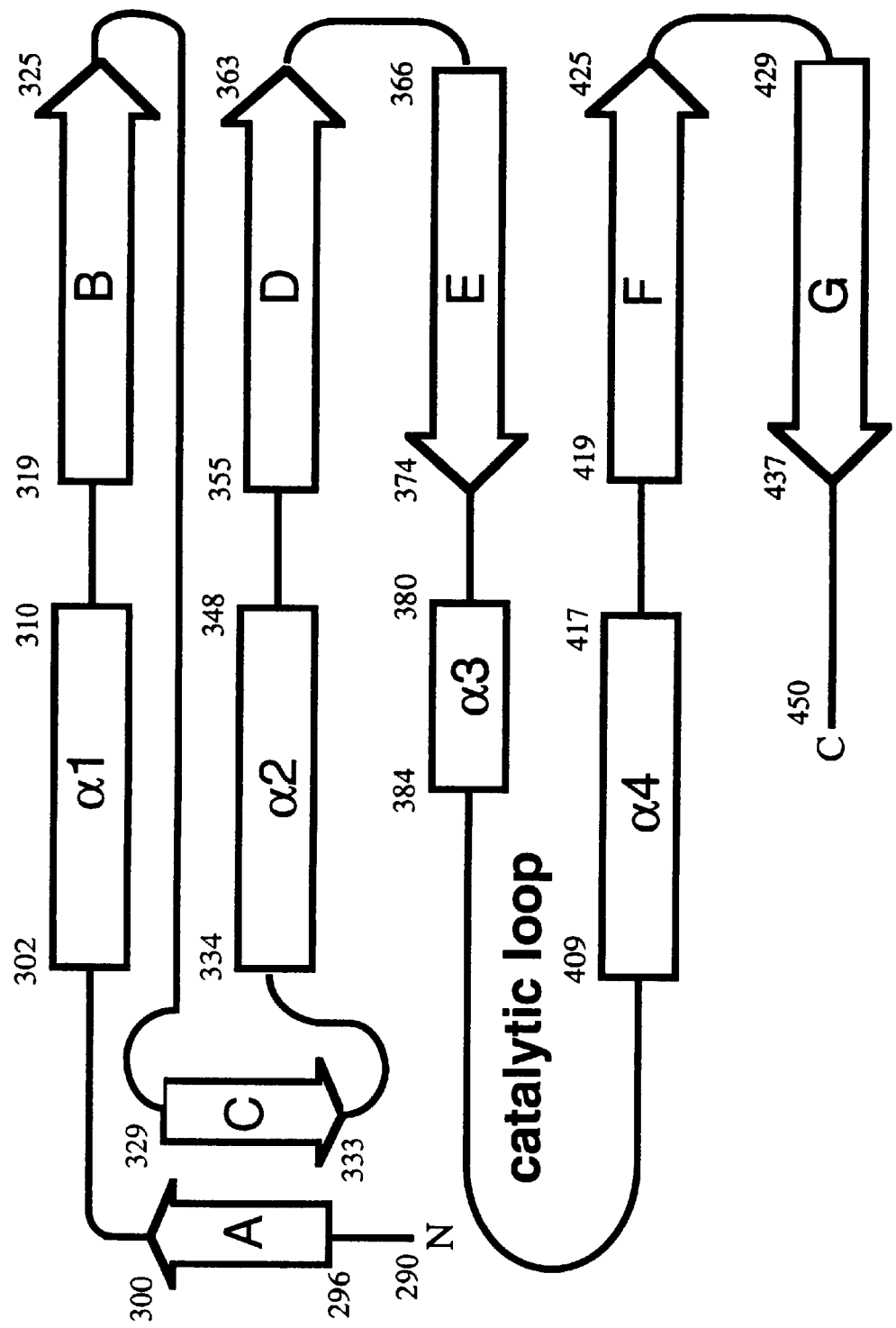
FIG. 5 depicts a the secondary structure of the N$_t$TSHK, sub-domain B [EnvZ(C)(290–450) containing 161 residues (SEQ ID NO:14)].

Sub-domain B is shown to contain the catalytic kinase activity. The overall fold of this histidine kinase catalytic domain differs significantly from the known structures of protein serine/threonine and tyrosine kinases. The EnvZ histidine kinase domain comprises a single globular fold of 161 residues that has all the functionalities of a protein kinase. A striking feature in this fold is the presence of a long polypeptide segment that extends away from the rest of the molecule (See Example 2, FIG. 5). This segment consists of a short α-helix α3 (380–384) followed by a long loop (385–409) that appears to be a random coil that is highly mobile in solution relative to the overall tumbling motion of the molecule. This characteristic loop, together with helix α3, provides a nucleotide binding site where the phosphorylation catalysis takes place, and is thereby referred to as "catalytic loop" (FIG. 5). The disclosed structure of the *E. coli* EnvZ histidine kinase catalytic domain of the present invention provides a vital foundation for rational design of effective antibiotics specifically blocking the histidine kinases *E. coli* as well as in other microbial species.

The present invention further discloses that whereas sub-domain A forms a stable dimer, sub-domain B exists as a monomer. The present invention also discloses that when the individual sub-domains A and B are mixed together, the kinase activity of sub-domain B acts to phosphorylate sub-domain A at His243 in the presence of ATP. The phosphorylated sub-domain A is then capable to transfer its phosphoryl group to OmpR.

By providing a two-sub-domain structure of the cytoplasmic histidine kinase domain of a TSHK, the present invention further provides insight into the structural arrangement of the TSHK, and its corresponding transphosphorylation mechanism. The structural information provided by the present invention further allows new means for designing drug screens for agents that interfere with the signal transduction function of this important bacterial pathway. Thus, by identifying the specific structural sub-domains involved in both the autophosphorylation of TSHK, and in the subsequent phosphoryl transfer between TSHK and OmpR, the present invention allows specific protein sites to be targeted in novel drug assays. The present invention, therefore, provides new methodologies for identifying potential drugs, which can be used for treating bacterial infections.

The present invention is partially based on the need to identify new classes of anti-bacterial drugs which are necessary to replace standard antibiotics, due to the increasing number of antibiotic-resistant bacterial strains. These drugs would ideally target enzyme systems required for bacterial survival, such as the proteins involved in the His-Asp phosphorelay signal transduction system, and more particularly a transmembrane sensor histidine kinase.

Structure based rational drug design is the most efficient method of such drug development. However, to date, little information is known regarding the structure of the catalytic domain(s) of TSHKs. Proteolytic digestions, as described below, allow initial insight into the structural analysis. However, obtaining detailed structural information requires an extensive NMR or X-ray crystallographic analysis. In the former case, TSHK exists as a dimer having a molecular weight (25.8 kDa per monomer) which is beyond the present capabilities of NMR analysis. In the latter case, transmembrane proteins such as a TSHK are particularly difficult to crystallize, and therefore not surprisingly, it has not been possible to grow TSHK crystals of X-ray crystallographic quality.

The present invention overcomes the difficulties described above, by providing N-terminal truncated TSHK fragments (N$_t$TSHKs) that retain the structure of the individual sub-domains of the catalytic sites of a TSHK. Such N$_t$TSHKs are amenable to NMR structural analysis, and in addition, can be used to grow X-ray quality crystals. By determining and then exploiting the detailed structural information of these sub-domains (exemplified by NMR analysis below) the present invention provides novel methods for developing new anti-bacterial drugs through structure based rational drug design.

In addition the present invention provides spatial coordinates for sub-domain A (Table 1) and sub-domain B (Table 2) and a chemical shift table (Table 3) for the $^1$H-$^{15}$N HSQC spectrum of sub-domain B. Furthermore, the coordinates (data set) of Table 1, Table 2 and the chemical shifts of Table 3 in a computer readable form are also part of the present invention.

In addition, methods of using these coordinates and chemical shifts (including such computer readable forms) in the drug assays disclosed below, are fully contemplated by the present invention. More particularly, such coordinates can be used to identify potential ligands or drugs which will bind to a N$_t$TSHK of the present invention.

Therefore, if appearing herein, the following terms shall have the definitions set out below.

As used herein the term "transmembrane sensor histidine kinase", "transmembrane sensor kinase", "TSHK", "transmembrane histidine kinase sensor" and any variants not specifically listed, may be used herein interchangeably, and as used throughout the present Application and Claims refer to proteinaceous material including single or multiple proteins (including dimers and the like). Accordingly, proteins displaying substantially equivalent activity are likewise contemplated. In addition, these terms are intended to include within their scope proteins specifically recited herein as well as all substantially homologous analogs and allelic variations. A TSHK minimally contains a putative periplasmic receptor domain, a transmembrane domain, and a cytoplasmic histidine kinase domain. One example of a TSHK is *E. coli* EnvZ, a transmembrane osmosensor having an amino acid sequence of SEQ ID NO:2.

Unless otherwise stated, the use of the term "TSHK" indicates a full-length transmembrane histidine kinase sensor as opposed to an "N-terminal truncated TSHK fragment" which is defined below.

As used herein an "N-terminal truncated TSHK fragment," an "N-terminal fragment of a TSHK", "$N_t$TSHK" and any analogous variants not specifically listed, may be used herein interchangeably, and as used throughout the present Application and Claims and refer to a TSHK fragment that minimally contains at least a portion of a TSHK cytoplasmic domain, but is missing at least a portion of the N-terminal transmembrane domain of the TSHK. Preferably all of the N-terminal transmembrane domain(s) of the TSHK are deleted. Examples of N-terminal truncated TSHK fragments include peptides having SEQ ID NOs:2, 4, 6, 8, 10, 12 and 14. As disclosed herein, these fragments can be produced by a number of means including by proteolytic digestion of a TSHK, chemical synthesis and more preferably by recombinant DNA techniques.

Accordingly as used herein an "isolated nucleic acid encoding an N-terminal truncated TSHK fragment" is meant to include a purified nucleic acid, as well as a recombinant nucleic acid.

A "polypeptide" comprising an "N-terminal truncated TSHK fragment" as used herein can be the "$N_t$TSHK" alone, or a larger chimeric or fusion peptide/protein which contains a "$N_t$TSHK".

As used herein, and unless otherwise specified, the terms "agent", "potential drug", "test compound" and the like are used interchangeably, and refer to chemicals which potentially have a use as an inhibitor or activator of a TSHK, or preferably as a drug in the treatment or prevention of a disease caused by bacteria. Therefore, such "agents", "potential drugs", and "test compounds" may be used, as described herein, in drug assays and drug screens and the like.

General Techniques for Constructing Nucleic Acids That Express N-terminal Truncated Fragments of Transmembrane Sensor Histidine Kinases $N_t$TSHKs)

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis (M. J. Gait ed.* 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [*R. I. Freshney, ed.* (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (ie., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)]. Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

Two DNA sequences are "substantially homologous" when at least about 60% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. Likewise, two polypeptide sequences are "substantially homologous" when at least about 60% (preferably at least about 80%, and most preferably at least about 90 or 95%) of the amino acids are either identical or contain conservative changes, as defined herein, over the defined length of the polypeptide sequences, e.g., preferably without gaps.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein, an amino acid residue in a $N_t$TSHK is said to be "analogous" to an amino acid residue of a TSHK amino acid sequence, when the amino acid residue in the $N_t$TSHK is contained in a domain that corresponds to a domain of the TSHK, and the amino acid residue of the $N_t$TSHK and the analogous amino acid of the TSHK play the essentially the same role in the three diminsional configuration of their respective domains.

A gene encoding a TSHK, whether genomic DNA or cDNA, can be isolated from any source, particularly from a prokaryotic cell. Methods for obtaining the TSHK gene are well known in the art, as exemplified above [see, e.g., Sambrook et al., 1989, supra].

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins or peptides. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed (the H6 sequence described in Example 1, below). In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing genes encoding analogs and derivatives of the $N_t$TSHK of the present invention, including modified $N_t$TSHKs, that have the same or homologous functional activity as the individual $N_t$TSHKs, and homologs thereof. The production and use of derivatives and analogs related to the $N_t$TSHKs are within the scope of the present invention.

As exemplified below any of a number of cells (preferably prokaryotic cells) can be used to express wild-type TSHK, mutant TSHK and/or N-terminal truncated TSHK fragments. E. coli B BL21-DE3 (F-ompTrBmB) was used in Example 1, below. Once expressed the TSHK or $N_t$TSHK can be purified by standard methodology, see, e.g. Park et al., [*J. Bacteriol.,* 179:4382–4390 (1997)]. Similarly the construction of plasmids containing nucleotide sequences encoding a TSHK or an $N_t$TSHK can be performed by standard methodology [Park et al., *J. Bacteriol.,* 179:4382–4390 (1997)]. For example, pET11a-EnvZ(C)ΔL, which contains the EnvZ sequence encoding residues Met223 to Gly450 of SEQ ID NO:2, was constructed by the digestion of pET11a-EnvZ(C) with a restriction enzyme, NdeI, followed by self-ligation in Example 1. In this case a linker, 5'TATGCACCATCACCATCACCA3' (SEQ ID NO:15)
3'ACGTGGTAGTGGTAGTGGTAT5' (SEQ ID NO:16)

was inserted at an NdeI site of pET11a-EnvZ(C)ΔL, generating pPH006 which encodes H6-EnvZ(C)ΔL. Confirmation of the nucleotide sequence by sequencing can be performed using Sequenase (USB).

As further exemplified below, a restriction fragment obtained from the construct, pPH006, can be used for site-directed mutagenesis, e.g., to create a stop codon at either Thr397, or Thr290 of SEQ ID NO:2, using 5'AGTGCGCGCTGAATTAGCGG3' (SEQ ID NO:17), and 5'TACCTGCGCTAAGGGCAGGAG3' (SEQ ID NO:18) oligomers, respectively; or to change a particular amino acid residue. In the former case, nucleotide fragments containing the stop codons can then be subcloned back into the construct, pPH006. In the latter procedure, PCR can be used as described in Example 1, in the construction of plasmid pET11a-EnvZ(C)(290–450) containing the EnvZ sequence from Thr290 to Gly450 of SEQ ID NO:2. In this case PCR was carried out with primer 7109 (5'CGCATATGACCGGGCAGGAG3' (SEQ ID NO:19)) that contained an NdeI site to substitute Arg289 (CGC) with Met (ATG), and primer 4163 (5'TCGGATCCCGTTATTTAC3' (SEQ ID NO:20)) containing a BamHI site downstream of Gly450 codon. pET11a-EnvZ(C)ΔL was used as the template. The 507-bp PCR fragment thus obtained was digested with NdeI and BamHI and subcloned into the pET11a-EnvZ(C)ΔL vector cut with NdeI and BamHI. The sequence of PCR product can be confirmed by DNA sequencing [Park et al., *J. Bacteriol,* 179:4382–4390 (1997)].

In another such embodiment, the highly conserved HIS243 of *E. Coli* EnvZ can be replaced by a leucine or a valine (as described in Example 1, below).

Due to the degeneracy of nucleotide coding sequences, other DNA sequences which encode substantially the same amino acid sequence as a nucleic acid encoding an $N_t$TSHK of the present invention may be used in the practice of the present invention. These include but are not limited to allelic genes, homologous genes from other species, which are altered by the substitution of different codons that encode the same amino acid residue within the sequence, thus producing a silent change. Likewise, the $N_t$TSHKs of the invention include, but are not limited to, those containing, as a primary amino acid sequence, analogous portions of the amino acid sequence of a TSHK including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained;

(e) Ile for Leu or for Val or vice versa as roughly equivalent hydrophobic amino acids; and (f) Phe for Tyr or vice versa as roughly equivalent aromatic amino acids.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

All of the $N_t$TSHKs of the present invention can be modified by being placed in a fusion or chimeric peptide or protein, or labeled e.g., to have an N-terminal FLAG-tag, or H6 tag as described in detail below. In a particular embodiment the $N_t$TSHK can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The genes encoding $N_t$TSHKs and analogs thereof can be produced by various methods known in the art. The manipulations which result in their production can occur at the gene or protein level [Sambrook et al., 1989, supra]. The nucleotide sequence can be cleaved at appropriate sites with restriction endonuclease(s), followed by further enzymatic modification if desired, isolated, and ligated in vitro. In the production of the gene encoding a derivative or analog of an $N_t$TSHK care should be taken to ensure that the modified gene remains within the same translational reading frame as the TSHK gene, uninterrupted by translational stop signals, in the gene region where the desired activity is encoded.

Additionally, the $N_t$TSHK-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson et al., *J. Biol. Chem.,* 253:6551 (1978); Zoller and Smith, *DNA,* 3:479–488 (1984); Oliphant et al., *Gene,* 44:177 (1986); Hutchinson et al., *Proc. Natl. Acad. Sci. U.S.A.,* 83:710 (1986)], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification,* H. Erlich, ed., Stockton Press, Chapter 6, pp. 61–70].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini (as exemplified in Example 1, below); these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2$\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of N-terminal Truncated TSHK Fragments

The nucleotide sequence coding for an $N_t$TSHK or analogs thereof, including a chimeric protein, thereof, can be inserted into an appropriate expression vector, i.e., a vector which contains the necessary elements for the transcription and translation of the inserted protein-coding sequence, as exemplified below. Such elements are termed herein a "promoter." Thus, the nucleic acid encoding an $N_t$TSHK or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector.

Potential host-vector systems include but are not limited to prokaryotic cell systems such as bacteria transformed with bacteriophage, DNA, plasmid DNA as exemplified below, or cosmid DNA; insect cell systems infected with virus (e.g., baculovirus); microorganisms such as yeast containing yeast vectors. The expression elements of vectors vary in their strengths and specificities. Depending on the host-vector system utilized, any one of a number of suitable transcription and translation elements may be used.

A recombinant $N_t$TSHK of the invention, may be expressed chromosomally, after integration of the coding sequence by recombination. In this regard, any of a number of amplification systems may be used to achieve high levels of stable gene expression [See Sambrook et al., 1989, supra].

The cell into which the recombinant vector comprising the nucleic acid encoding the $N_t$TSHK is cultured in an appropriate cell culture medium under conditions that provide for expression of the protein or peptide by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of an $N_t$TSHK may be controlled by any promoter/enhancer element known in the art, but these regulatory elements must be functional in the host selected for expression.

Expression vectors containing a nucleic acid encoding an $N_t$TSHK of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding the N,TSHK is inserted within the "selection marker" gene sequence of the vector, recombinants containing the insert can be identified by the absence of the selection maker gene function. In the fourth approach, recombinant expression vectors can be identified by assaying for the activity, biochemical, or immunological characteristics of the gene product expressed by the recombinant, provided that the expressed protein assumes a functionally active conformation, e.g. protein histidine kinase activity or ability to be a substrate for a protein histidine kinase.

A wide variety of host/expression vector combinations may be employed in expressing the DNA sequences of this invention which are well known in the field.

Once a particular recombinant DNA molecule is identified and isolated, several methods known in the art may be used to propagate it. Once a suitable host system and growth conditions are established, recombinant expression vectors can be propagated and prepared in quantity. Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990].

Synthetic Polypeptides

The term "polypeptide" is used in its broadest sense to refer to a compound of two or more subunit amino acids, amino acid analogs, or peptidomimetics. The subunits are linked by peptide bonds. The N,TSHKs of the present invention may be chemically synthesized.

In addition, potential drugs or agents that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149–2154 (1963)], or the base-labile $N^\alpha$-amino protected 9-fluorenylmethoxycarbonyl (Fmoc) amino acids first described by Carpino and Han [*J. Org. Chem.*, 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young [Solid Phase Synthesis, Second Edition, Pierce Chemical Co., Rockford, Ill. (1984)] and Fields and Noble [*Int. J. Pept Protein Res.*, 35:161–214 (1990)], or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, *Life Sciences*, 31:189–199 (1982); Hruby et al., *Biochem J.*, 268:249–262 (1990)]; the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson [*Biophys. Biochem. Res. Commun.*, 94:1128–1132 (1980)]. A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, in The Peptides: Analysis, Synthesis, Biology, Vol. 3, Gross and Meienhofer, eds., Academic Press: New York, pp.137–167 (1981); Ponsanti et al., *Tetrahedron*, 46:8255–8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate [Kazmierski et al., *J. Am. Chem. Soc.*, 113:2275–2283 (1991)]; (2S,3S)-methyl-phenylalanine, (2S,3R)-methyl-phenylalanine, (2R,3S)-methyl-phenylalanine and (2R,3R)-methyl-phenylalanine (Kazmierski and Hruby, *Tetrahedron Lett.* (1991)]; 2-aminotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al., *J. Takeda Res. Labs.*, 43:53–76 (1989)]; β-carboline (D and L) [Kazmierski, Ph.D. Thesis, University of Arizona (1988)]; HIC (histidine isoquinoline carboxylic acid) [Zechel et al., *Int. J. Pep. Protein Res.*, 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog [Kemp et al., *J. Org. Chem.*, 50:5834–5838 (1985)]; β-sheet inducing analogs [Kemp et al., *Tetrahedron Lett.*, 29:5081–5082 (1988); β-turn inducing analogs [Kemp et al., *Tetrahedron Lett.*, 29:5057–5060 (1988)]; -helix inducing analogs (Kemp et al., *Tetrahedron Lett.*, 29:4935–4938 (1988)]; γ-turn inducing analogs [Kemp et al., *J. Org. Chem.*, 54:109:115 (1989)]; and analogs provided by the following references: Nagai and Sato, *Tetrahedron Lett.*, 26:647–650 (1985); DiMaio et al., *J. Chem. Soc. Perkin Trans.*, p. 1687 (1989); also a Gly-Ala turn analog [Kahn et al., *Tetrahedron Lett.*, 30:2317 (1989)]; amide bond isostere [Jones et al., *Tetrahedron Lett.*, 29:3853–3856 (1988)]; tretrazol [Zabrocki et al., *J. Am. Chem. Soc.*, 110:5875–5880 (1988)]; DTC [Samanen et al., *Int. J. Protein Pep. Res.*, 35:501:509 (1990)]; and analogs taught in Olson et al., *J. Am. Chem. Sci*, 112:323–333 (1990) and Garvey et al., *J. Org. Chem.*, 56:436 (1990). Conformationally restricted mimetics of beta turns and beta bulges, and peptides containing them, are described in U.S. Pat. No. 5,440,013, issued Aug. 8, 1995 to Kahn.

Nuclear Magnetic Resonance Analysis of the Catalytic Core Domain of EnvZ

The catalytic core domain of EnvZ assumes an α/β sandwich fold: one layer consists of a five-stranded β-sheet (strand B, residues 319–323; D, 356–363; E, 366–373; F, 419–425; G, 429–436) and the other layer comprises three helices (α1, 301–311; α2, 334–343; α4, 410–414) in a topology. The two layers enclose an extensive hydrophobic core, augmented by a small anti-parallel β-sheet (strand A, 297–299; C, 330–332) which seals the sandwich at one end. The hydrophobic core consists of the following residues: L301, L305, I309 in helix α1; I319, T321, L323 in strand B; V330, M332 in strand C; I337, V341 in helix α2; I356, V358 in strand D; A367, F369, V371 in strand E; V409, V413 in helix α4; L420 in strand F; I432, A434, L436 in strand G. The sequence conservation of these structurally critical residues are indicative that the histidine kinase domain of other proteins adapt the α/β sandwich fold observed in EnvZ.

The overall fold of the histidine kinase catalytic domain differs significantly from the known structures of protein serine/threonine and tyrosine kinases. The EnvZ histidine kinase domain comprises a single globular fold of 161 residues that has all the functionalities of a protein kinase. Indeed, the present invention provides the identification of this unique and charcteristic globular fold of histidine kinases.

A striking feature in this fold is the presence of a long polypeptide segment that extends away from the rest of the molecule (See Example 2, FIG. 5). This segment consists of a short α-helix α3 (380–384) followed by a long loop (385–409) that appears to be a random coil that is highly mobile in solution relative to the overall tumbling motion of the molecule. This characteristic loop, together with helix α3, provides a nucleotide binding site where the phosphorylation catalysis takes place, and is thereby referred to as "catalytic loop" (FIG. 5).

When the corresponding structure was determined in the presence of a nonhydrolysable analog of ATP (AMPPNP) and $Mg^{2+}$ a number of intermolecular NOE interactions between the protein and the adenosine moiety of AMPPNP can be identified. The AMPPNP molecule is mainly surrounded by part of the catalytic loop and helix α3, and also contacts with strand F and helix α4. The AMPPNP adenine is placed in a pocket made of conserved residues such as N343, V346, N347, I378, F387, and I408. In addition to those residues, highly conserved are residues (V345, A348, I356, V371, D373, G375, P376, G377, F390, G401, G403, L404, G405, L406, A407, V409, G418, G429, L438) that also cluster around the AMPPNP binding site. The degree of conservation is even greater than that of the hydrophobic core of the α/β sandwich fold, suggesting that the nucleotide binding site is the most important part of the molecule and that members of the histidine kinase family share a similar nucleotide binding site made of a long loop and a short α-helix. Most remarkably, four glycines (G375, G403, G405, G429) and two asparagines (N343 and N347) in the catalytic core are absolutely conserved and strategically located in the structure, indicating their structural and functional significance. Importantly, the glycine-rich regions, G1 (D373–G377) and G2 (G401–G405), are essential for the kinase activity. G403 and G405, located within G2, are in close spatial proximity to the triphosphate chain of AMPPNP. G375 in G1 and G429 allow a sharp kink between strand E and helix α3 and between strands F and G, respectively, adjacent to the AMPPNP binding site. N343 and N347 in helix α2 clamp the adenine ring of AMPPNP in the binding pocket.

The triphosphate chain and part of the ribose ring are surface exposed, with the terminal phosphate group most accessible to solvent, consistent with its potential to transfer the γ-phosphate to H243 in domain A. It is apparent that the residues in the catalytic loop are the candidates for being active participants in catalysis. For example, R383 and/or K384 could be involved in direct interaction with the triphosphate chain by electrostatic attraction, and E381 might be involved in $Mg^{2+}$ coordination and charge compensation upon binding to domain A.

Protein-Structure Based Design of Agonists and Antagonists of TSHKs and $N_t$TSHKs Once the three-dimensional structure of an $N_t$TSHK is determined, a potential drug or agent (antagonist or agonist) can be examined through the use of computer modeling using a docking program such as GRAM, DOCK, or AUTODOCK [Dunbrack et al., 1997, supra]. This procedure can include computer fitting of potential agents to the $N_t$TSHK to ascertain how well the shape and the chemical structure of the potential ligand will complement or interfere with the dimerization of sub-domain A, or the interaction between sub-domain A and sub-domain B [Bugg et al., *Scientific American, December*:92–98 (1993); West et al., *TIPS*, 16:67–74 (1995)]. Computer programs can also be employed to estimate the attraction, repulsion, and steric hindrance of the agent to the dimer-dimer binding site, for example. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with related mammalian proteins (particularly mammalian transmembrane sensor histidine kinases). This will minimize potential side-effects due to unwanted interactions with other proteins.

Initially a potential drug could be obtained by screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)] or a chemical library. An agent selected in this manner could be then be systematically modified by computer modeling programs until one or more promising potential drugs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1: 109–128 (1993)].

Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structural analysis disclosed herein and computer modeling, a large number of these compounds can be rapidly screened on the computer monitor screen, and a few likely candidates can be determined without the laborious synthesis of untold numbers of compounds.

Once a potential drug (agonist or antagonist) is identified it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential drug may be synthesized de novo. As mentioned above, the de novo synthesis of one or even a relatively small group of specific compounds is reasonable in the art of drug design.

The potential drug can then be tested in any standard binding assay (including in high throughput binding assays) for its ability to bind to a TSHK or fragment thereof, including a $N_t$TSHK. Alternatively the potential drug can be tested for: (1) its ability to modulate (either inhibit or stimulate) the histidine kinase activity of a TSHK or $N_t$TSHK; (2) its ability to effect (either positively or negatively) the autophosphorylation of the TSHK or $N_t$TSHK; or (3) its ability to effect the phosphoryl transfer from the TSHK or $N_t$TSHK to its corresponding response regulator. When a suitable potential drug is identified, a second NMR structural analysis can optionally be performed on the binding complex formed between the $N_t$TSHK and the potential drug. Computer programs that can be used to aid in solving the three-dimensional structure of the $N_t$TSHKs and binding complexes thereof include QUANTA, CHARMM, INSIGHT, SYBYL, MACROMODE, and ICM, MOLMOL, RASMOL, AND GRASP [Kraulis, *J. Appl Crystallogr.* 24:946–950 (1991)]. Most if not all of these programs and others as well can be also obtained from the WorldWideWeb through the internet.

Using the approach described herein and equipped with the structural analysis disclosed herein, the three-dimensional structures of other transmembrane sensor histidine kinases can also be readily obtained and analyzed. Such analysis will, in turn, allow corresponding drug screening methodology to be performed using the three-dimensional structures of such related TSHK proteins and $N_t$TSHKs.

For all of the drug screening assays described herein further refinements to the structure of the drug will generally be necessary and can be made by the successive iterations of any and/or all of the steps provided by the particular drug screening assay, including further structural analysis by NMR, for example.

Phage libraries for Drug Screening.

Phage libraries have been constructed which when infected into host *E. coli* produce random peptide sequences of approximately 10 to 15 amino acids [Parmley and Smith, Gene 73:305–318 (1988), Scott and Smith, Science 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive $N_t$TSHK (e.g., preferably an $N_t$TSHK having an amino acid sequence comprising SEQ ID NO:14 or SEQ ID NO:12). After a specified incubation period, the filters can be thoroughly washed and developed for autoradiography. Plagues containing the phage that bind to the radioactive $N_t$TSHK can then be identified. These phages can be further cloned and then retested for their ability to bind to the $N_t$TSHK as before. Once the phage has been purified, the binding sequence contained within the phage can be determined by standard DNA sequencing techniques. Once the DNA sequence is known, synthetic peptides can be generated which are encoded by these sequences.

These peptides can be tested, for example, for their ability to e.g. (1) interfere with the dimerization of sub-domain A and/or (2) interfere with phosphorylation of the autophosphorylatable histidine of a TSHK or an $N_t$TSHK and/or (3) interfere with the kinase activity of a TSHK or an $N_t$TSHK; and/or (4) interfere with the phosphoryl transfer of a histidyl phosphate to an aspartyl residue of a response regulator or fragment thereof (e.g. OmpR).

The effective peptide(s) can be synthesized in large quantities for use in in vivo models and eventually in humans to aid in the fight against diseases caused by bacteria. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine*, 10:175–178 (1990)].

Assays for Drug Screening Assays

The drug screening assays of the present invention may use any of a number of means for determining the interaction between an agent or drug and a TSHK or an $N_t$TSHK.

In one such assay, a drug can be specifically designed to bind to a N$_t$TSHK of the present invention through NMR based methodology. [Shuker et al., *Science* 274:1531–1534 (1996) hereby incorporated by reference herein in its entirety.] In one such embodiment, a library of low molecular weight compounds is screened to identify a binding partner for the N$_t$TSHK. Any such chemical library can be used including those discussed herein.

The assay begins with contacting a compound with a $^{15}$N-labeled N$_t$TSHK. Binding of the compound with the N$_t$TSHK can be determined by monitoring the $^{15}$N- or $^1$H-amide chemical shift changes in two dimensional $^{15}$N-heteronuclear single-quantum correlation ($^{15}$N-HSQC) spectra upon the addition of the compound to the $^{15}$N-labeled N$_t$TSHK. Since these spectra can be rapidly obtained, it is feasible to screen a large number of compounds [Shuker et al., *Science* 274:1531–1534 (1996)]. A compound is identified as a potential ligand if it binds to the N$_t$TSHK. In a further embodiment, the potential ligand can then be used as a model structure, and analogs to the compound can be obtained (e.g, from the vast chemical libraries commercially available, or alternatively through de novo synthesis). The analogs are then screened for their ability to bind the N$_t$TSHK to obtain a ligand. An analog of the potential ligand is chosen as a ligand when it binds to the N$_t$TSHK with a higher binding affinity than the potential ligand. In a preferred embodiment of this type the analogs are screened by monitoring the $^{15}$N- or $^1$H-amide chemical shift changes in two dimensional $^{15}$N-heteronuclear single-quantum correlation ($^{15}$N-HSQC) spectra upon the addition of the analog to the $^{15}$N-labeled N$_t$TSHK as described above.

In another further embodiment, compounds are screened for binding to two nearby sites on an N$_t$TSHK. In this case, a compound that binds a first site of the N$_t$TSHK does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by NMR spectroscopy or X-ray crystallography. On the basis of this structural information, a linked compound is synthesized in which the ligand for the first site and the ligand for the second site are linked. In a preferred embodiment of this type the two ligands are covalently linked. This linked compound is tested to determine if it has a higher binding affinity for the N$_t$TSHK than either of the two individual ligands. A linked compound is selected as a ligand when it has a higher binding affinity for the N$_t$TSHK than either of the two ligand. In a preferred embodiment the affinity of the linked compound with the N$_t$TSHK is determined monitoring the $^{15}$N- or $^1$H-amide chemical shift changes in two dimensional $^{15}$N-heteronuclear single-quantum correlation ($^{15}$N-HSQC) spectra upon the addition of the linked compound to the $^{15}$N-labeled N$_t$TSHK as described above.

Any of the N$_t$THSKs of the invention may be used in this NMR drug screening procedure. In addition, a larger linked compound can be constructed in an analogous manner, e.g., linking three ligands which bind to three nearby sites on the N$_t$TSHK to form a multilinked compound that has an even higher affinity for the N$_t$TSHK than linked compound.

In another assay, a TSHK or N$_t$TSHK is placed on or coated onto a solid support. Methods for placing the peptides or proteins on the solid support are well known in the art and include such things as linking biotin to the protein and linking avidin to the solid support. An agent is allowed to equilibrate with the TSHK or N$_t$TSHK to test for binding. Generally, the solid support is washed and agents that are retained are selected as potential drugs. In a particular embodiment of this type, the N$_t$TSHK comprises the amino acid sequence of SEQ ID NO:12. In another embodiment, the $N_t$TSHK comprises the amino acid sequence of SEQ ID NO:14.

The agent may be labeled. For example, in one embodiment radiolabeled agents are used to measure the binding of the agent. In another embodiment the agents have fluorescent markers. In yet another embodiment, a Biocore chip (Pharmacia) coated with the TSHK or the $N_t$TSHK is used and the change in surface conductivity can be measured.

In yet another embodiment, the affect of a prospective drug (a test compound or agent) on a TSHK or $N_t$TSHK is assayed in a living cell that contains or can be induced to contain a TSHK or $N_t$TSHK, and OmpR. This cell also contains or can be constructed to contain a reporter gene, such as the heterologous gene for luciferase, green fluorescent protein, chloramphenicol acetyl transferase or β-galactosidase, operably linked to a promoter that is activated through the histidy-aspartyl (His-Asp) phosphorelay signal transduction system.

The prospective drug is tested under conditions in which the TSHK or $N_t$TSHK has been activated. In one such embodiment, the expression of the TSHK, or $N_t$TSHK is constitutive. The amount (and/or activity) of reporter produced in the absence and presence of prospective drug is determined and compared. Prospective drugs which reduce the amount (and/or activity) of reporter produced are candidate antagonists of the N-terminal interaction, whereas prospective drugs which increase the amount (and/or activity) of reporter produced are candidate agonists.

Cells that naturally encode a TSHK may be used, or alternatively a cell that is transfected with a plasmid encoding the TSHK or an $N_t$TSHK can be used. The cells can also be modified to contain one or more reporter genes, a heterologous gene encoding a reporter such as luciferase, green fluorescent protein or derivative thereof, chloramphenicol acetyl transferase, β-galactosidase, etc. Such reporter genes can be operably linked to promoters comprising a binding site for a transcription factor under the control of the His-Asp phosphorelay pathway. Assays for detecting the reporter genes products are readily available in the literature. For example, luciferase assays can be performed according to the manufacturer's protocol (Promega), and β-galactosidase assays can be performed as described by Ausubel et al. [in *Current Protocols in Molecular Biology,* J. Wiley & Sons, Inc. (1994)]. The preparation of such plasmid containing reporter genes is now routine in the art, and many appropriate plasmids are now commercially available which can be readily modified for such assays. The transmembrane sensor histidine kinase may also be activated by an antibody. Alternatively, a permantively activated $N_t$T-SHK can be constitutively expressed.

Labels

Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

The kinase activity of a TSHK or fragment thereof can be determined by many appropriate means including with the aid of an antibody against phospho-histidine or $^{32}$P. Thus the autophosphorylation of the TSHK histidine, and the phosphotransfer to OmpR, and Phospho-OmpR phosphatase activity can be readily determined [Yang, et al., *Proc. Natl. Acad Sci. USA,* 88,11057–11061 (1991); and Park et al., *J. Bacteriol.,* 179:4382–4390 (1997), each of which are hereby incorporated by reference in their entireties herein].

General Protein Purification Procedures

The purification of the N-terminal truncated TSHK fragments of the present invention can be performed by any conventional method. One such method employs linking a small peptide to the N$_t$TSHK. The small peptide can be FLAG or H6 for example. In Example 1, below N$_t$TSHKs are prepared containing H6, and are purified using Ni-NTA resin. Similarly an $N_t$TSHK can be constructed as a fusion protein containing a fusion partner which is a protein that binds with specificity to a particular affinity resin. Such a fusion partner can be joined in-frame to the $N_t$TSHK. Preferably the fusion protein also contains a cleavage site for a specific protease, e.g., thrombin or Factor Xa, which is placed at the juncture of the fusion partner and the $N_t$TSHK. After the fusion protein is bound to the affinity resin, and purified, the protease is added to release the $N_t$TSHK from the fusion partner and resin.

Alternatively, classical means of purifying a TSHK or $N_t$TSHK can be performed. Thus, initial steps for purifying the $N_t$TSHKs of the present invention can include salting in or salting out, such as in ammonium sulfate fractionations; solvent exclusion fractionations, e.g., an ethanol precipitation; detergent extractions to free membrane bound proteins using such detergents as TRITON X-100, TWEEN-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer; affinity-binding, using, e.g. immuno-binding, using an antibody to an $N_t$TSHK bound to an activated support. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Materials to perform all of these techniques are available from a variety of sources such as Sigma Chemical Company in St. Louis, Mo.

Antibodies to the N-terminal Truncated TSHK Fragments

According to the present invention, the N-terminal truncated TSHK fragment as produced by a recombinant source, or through chemical synthesis, or through the modification of a TSHK isolated from natural sources; and derivatives or analogs thereof, including fusion proteins, may be used as an immunogen to generate antibodies that specifically recognize the $N_t$TSHKs and not TSHK itself. Such antibodies include but are not limited to polyclonal, monoclonal, chimeric, single chain, Fab fragments, and a Fab expression library. The antibodies of the invention may be cross reactive, that is, they may recognize the $N_t$TSHKs derived from a different natural TSHK. Polyclonal antibodies have greater likelihood of cross reactivity. Alternatively, an antibody of the invention may be specific for a single form of an $N_t$TSHK, such as the $N_t$TSHK having an amino acid sequence of SEQ ID NO:12 or SEQ ID NO:14.

Various procedures known in the art may be used for the production of polyclonal antibodies to the N$_t$TSHK or derivative or analog thereof. For the production of antibody, various host animals can be immunized by injection with the N$_t$TSHK, or a derivative (e.g., or fusion protein) thereof, including but not limited to rabbits, mice, rats, sheep, goats, etc. In one embodiment, the $N_t$TSHK can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum.*

For preparation of monoclonal antibodies directed toward the $N_t$TSHK of the present invention, or analog, or derivative thereof, any technique that provides for the production of antibody molecules by continuous cell lines in culture may be used. These include but are not limited to the hybridoma technique originally developed by Kohler and Milstein [*Nature,* 256:495–497 (1975)], as well as the trioma technique, the human B-cell hybridoma technique [Kozbor et al., *Immunology Today,* 4:72 (1983); Cote et al., *Proc. Natl. Acad. Sci. U.S.A.,* 80:2026–2030 (1983)], and the EBV-hybridoma technique to produce human monoclonal antibodies [Cole et al., in *Monoclonal Antibodies and Cancer Therapy,* Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604–608 (1984); Takeda et al., *Nature,* 314:452–454 (1985)] by splicing the genes from a mouse antibody molecule specific for an $N_t$TSHK together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce $N_t$TSHK-specific single chain antibodies. An additional embodiment of the invention utilizes the techniques described for the construction of Fab expression libraries [Huse et al., *Science,* 246:1275–1281 (1989)] to allow rapid and easy identification of monoclonal Fab fragments with the desired specificity for an $N_t$TSHK, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the $N_t$TSHK and not TSHK, one may assay generated hybridomas for a product which binds to the $N_t$TSHK containing such epitope and choose those which do not cross-react with TSHK. For selection of an antibody specific to the fragment from a particular source, one can select on the basis of positive binding with the $N_t$TSHK expressed by or isolated from that specific source.

The foregoing antibodies can be used in methods known in the art relating to the localization and activity of the $N_t$TSHK, e.g., for Western blotting, imaging the fragment in situ, measuring levels thereof in appropriate physiological samples, etc. using any of the detection techniques mentioned herein or known in the art.

In a specific embodiment, antibodies that agonize or antagonize the activity of $N_t$TSHK can be generated. Such antibodies can be tested using the assays described infra for identifying agents or potential drugs.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Two-Doamin Reconstitution of a Functional Protein Histidine Kinase

Introduction

*Escherichia coli* possess a large number of transmembrane sensors for cellular adaption to various environmental stresses. With the notable exception of certain sensors that are involved in chemotaxis, most bacterial sensors are transmembrane histidine kinase sensors that contain a cytoplasmic signaling domain having histidine kinase activity. Such transmembrane sensor histidine kinases are part of a histidyl-aspartyl (His-Asp) phosphorelay signal transduction pathway, which recently has been reported also to exist in eukaryotic cells [Egger et al., *Genes to Cells,* 2:167–184 (1997); Appelby et al., *Cell,* 86:845–848 (1996); Inouye, *Cell,* 85:13–14 (1996); Parkinson and Kofoid, *Ann. Rev. Gen.,* 26:71–112 (1992); Stock et al., *Microbiol. Rev.,* 53:45–490 (1989)].

Autophosphorylation of sensor histidine kinases, which is an obligatory step for the phosphorylation of their corresponding response regulators, occurs through a bimolecular transphosphorylation reaction. This has been surmised on the basis of complementation experiments with two defective mutants of EnvZ, a transmembrane osmosensor of *E. coli* and Taz1, a hybrid sensor between Tar and EnvZ [Yang et al., *Proc. Natl. Acad. Sci. USA*, 88:11057–11061 (1991) and Yang et al., *J. Mol. Biol.*, 231:335–342 (1993)]. Tar is a chemosensor for aspartate which may be able to transduce a signal within a single cytoplasmic domain [Gardina et al., *Science*, 274:425426 (1996) and Tatsuno et al., *Science*, 274:423–425 (1996)]. In the case of Taz1, asymmetric binding of its ligand, aspartate, at the interphase of two Taz1 receptor domains in a dimer has been shown to modulate the function of the cytoplasmic signaling domain in the dimer [Yang et al., *J. Mol. Biol.*, 232:493–498 (1993); Milburn et al., *Science*, 254:1342–1347 (1991) and Jin et al., *J. Mol. Biol.*, 232:484–492 (1993)]. Autophosphorylation of other histidine kinases also has been shown to occur by a transphosphorylation reaction [Uhl et al., *EMBO J.*, 15:1028–1036 (1996); Pan et al., *Proc. Natl. Acad. Sci USA*, 90:9939–9943 (1993); Ninfa et al., *J. Bacteriol*, 175:7024–7032 (1993); Swanson et al., *Mol. Microbiol*, 8:435–441 (1993); Swanson et al., *Biochem.*, 32:7623–7629 (1993) and Surette et al., *J. Biol. Chem.*, 271:939–945 (1996)].

EnvZ, a transmembrane histidine kinase osmosensor of *E. coli* interacts with the response regulator, OmpR. OmpR functions as a transcription factor for the outer membrane porin genes, ompC and ompF [Aiba et al., *J. Biol. Chem.*, 64:8563–8567 (1989) and Delgado et al., *Mol. Microbiol.*, 10:1037–1047 (1993)]. EnvZ consists of the periplasmic putative receptor domain from residue 48 to 162, which is anchored in the cytoplasmic membrane with two transmembrane domains (TM1, residue 16 to 47; and TM2, residue 163 to 179) [Forst et al., *J. Biol. Chem.*, 262:16433–16438 (1987)]. The second membrane segment is connected to the cytoplasmic signaling domain (residue 180 to 450),which is the portion of the EnvZ polypeptide that contains the histidine kinase activity. This domain undergoes autophosphorylation at His243 with ATP [Roberts et al., *J. Biol. Chem.*, 269:8728–8733 (1994)]. The phosphate group is subsequently transferred to Asp55 of OmpR.

The EnvZ signaling domain performs dual enzymatic functions, one as a kinase for OmpR and the other as a phosphatase for phosphorylated OmpR. The ratio of kinase and phosphatase activities is believed to control the level of phosphorylated OmpR [Igo et al., *Gen. And Dev.*, 3:1725–1734 (1989); Tokishita et al., *J. Biochem.*, 108:488493 (1990) and Park et al., *J. Bacteriol.*, 179:4382–4390 (1997)]. However, the precise regulatory mechanism for controlling the functional activity of EnvZ is yet to be elucidated.

As presented herein, the cytoplasmic signaling domain of EnvZ can be further divided into two distinct sub-domains, sub-domain A (67 residues) and sub-domain B (161 residues). These subdomains complement their respective abilities to phosphorylate OmpR. Furthermore, the two-domain structure of the histidine kinase disclosed herein provides crucial information in the determination of the structural arrangement of the transmembrane histidine kinase sensors that are involved in the unique His-Asp pathway.

Materials and Methods

Strains and Plasmids: *E. coli* B BL21-DE3 (F-ompTrBmB) was used for the expression and purification of wild-type and mutant EnvZ(C) proteins [Park et al., *J. Bacteriol.*, 179:4382–4390 (1997)]. Construction of plasmid pET11a-EnvZ(C) was described as elsewhere [Park et al., *J. Bacteriol.*, 179:43824390 (1997)]. pET11a-EnvZ(C)ΔL which contains the EnvZ sequence encoding residues Met223 to Gly450 was constructed by the digestion of pET11a-EnvZ(C) with NdeI followed by self-ligation. A linker, 5'TATGCACCATCACCATCACCA3' (SEQ ID NO:15)
3'ACGTGGTAGTGGTAGTGGTAT5' (SEQ ID NO:16)

was inserted at the NdeI site of pET11a-EnvZ(C)ΔL, generating pPH006 which encodes H6-EnvZ(C)ΔL. The construct was confirmed by DNA sequencing (Sequenase, USB). The 1.4-kb XbaI—EcoRI fragment from pPH006 was used for site-directed mutagenesis to create a stop codon at either Thr397, or Thr290. For this purpose, 5'AGTGCGCGCTGAATTAGCGG3' (SEQ ID NO:17), and 5'TACCTGCGCTAAGGGCAGGAG3' (SEQ ID NO:18) oligomers were used, respectively. After confirming the mutations by DNA sequencing, the 1.4-kb XbaI—EcoR1 fragments containing the mutations were subcloned back into pPH006. Thus the plasmid designated pPH007 for Thr398 (ACC)→(TGA) which encodes H6-EnvZ(C)ΔG2, and pPH009 for Thr290 (ACC)→(TAA) which encodes H6-EnvZ(C)(223–289), respectively. pET11a-EnvZ(C) (223–289) was obtained by digestion of pPH009 with NdeI followed by self-ligation. For the construction of plasmid pET11a-EnvZ(C)(290–450) containing the EnvZ sequence from Thr290 to Gly450, PCR was carried out with primer 7109 (5'CGCATATGACCGGGCAGGAG3' (SEQ ID NO:19)) that contained an NdeI site to substitute Arg289 (CGC) with Met (ATG), and primer 4163 (5'TCGGATCCCGTTTATTTAC3' (SEQ ID NO:20)) containing a BamHI site downstream of Gly450 codon. pET11a-EnvZ(C)ΔL was used as the template. The 507-bp PCR fragment thus obtained was digested with NdeI and BamHI and subcloned into the pET11a-EnvZ(C)ΔL vector cut with NdeI and BamHI. The sequence of PCR product was confirmed by DNA sequencing as previously described [Park et al., *J. Bacteriol*, 179:43824390 (1997)].

Biochemical Assays of EnvZ and EnvZ(C) Constructs: Autophosphorylation, phosphotransfer to OmpR, and Phospho-OmpR phosphatase activity were determined essentially in the same way as was carried out previously [Yang, et al., *Proc. Natl. Acad. Sci. USA*, 88,11057–11061 (1991) and Park et al., *J. Bacteriol.*, 179:4382–4390 (1997), each of which are hereby incorporated by reference in their entireties herein]. The phosphorylated OmpR was prepared as follows. The membrane fraction containing EnvZ-T247R (Kinase+/Phosphatase) was first phosphorylated with 50 μCi [$\gamma$-$^{32}$P]ATP in 200 μl of buffer A for 20 minutes at room temperature. The reaction mixture was centrifuged at 393, 000×g for 14 minutes at 4° C. using a Beckman TL100 ultracentrifuge.

The membrane pellet was washed five times with 200 μl of buffer A, sonicated, and then re-suspended in the same buffer. Purified OmpR protein was incubated with the membrane fraction containing phosphorylated EnvZ-T247R for 20 minutes at room temperature in order to allow phosphotransfer to OmpR. After incubation, the reaction mixture was centrifuged at 393,000×g for 14 minutes at 4° C. to remove the membrane containing EnvZ-T247R. The supernatant containing phospho-OmpR was then applied onto a G-50 gel filtration column in order to remove residual [$\gamma$-$^{32}$P]ATP and inorganic phosphate [$^{32}$Pi]. Each fraction was analyzed by thin-layer chromatography to confirm that the phospho-OmpR preparation was not contaminated with [$\gamma$-$^{32}$P]ATP or inorganic phosphate [$^{32}$Pi]. The fractions containing only phospho-OmpR were pooled and total OmpR protein concentration was measured by the Bio-Rad protein concentration assay. During the preparation, protein solutions were kept on ice.

Binding Assay on Ni-NTA Resin: Purified proteins, EnvZ (C)(223–289) plus either H6-EnvZ(C)wt or H6-EnvZ(C) (223–289) were mixed in 20 μl of buffer I [50 mM sodium-phosphate buffer (pH7.8), 0.3M NaCl, 5% glycerol] at room temperature for 30 minutes, and 10 μl of Ni-NTA resin (50% v/v) was added to the protein mixture followed by a 30 minute incubation on ice. After washing three times with buffer II [50 mM sodium-phosphate buffer (pH 6.0), 0.3M NaCl, 5% glycerol] using ultrafree-MC centrifugal filters (Millipore Corp.), proteins bound to Ni-NTA resin were eluted with 0.2M imidazole/buffer II. The binding experiments between OmpR and either H6-EnvZ(C)wt or H6-EnvZ(C)(223–289) were carried out as described previously [Hidaka et al., FEBS LETT., 400:238–242 (1997), hereby incorporated by reference in its entirety herein]. The proteins eluted with 0.2M imidazole/buffer II in each binding assay were subjected to 20% SDS-PAGE followed by silver staining [Sambrook et al., Molecular Cloning: A Laboratory Manual, 18.56–18.57 (1989)].

Circular Dichroism Spectral Analysis: The CD spectrum was obtained using a Aviv Model 62DS spectropolarimeter at 25° C. Far-UV CD spectra (200 nm–250 nm) of EnvZ (C)(223–289) and Env(C)(290–450) in sodium phosphate buffer [50 MM sodium phosphate (pH 7.4), 0.3M KCl, and 1 mM PMSF] was measured in a cuvette with a 1-cm path length. Protein concentrations of EnvZ(C)(223–289) and Env(C)(289450) were 0.338 mg/ml and 0.118 mg/ml, respectively. These values were determined by Absorbance readings at 280 nm and calculated based on protein molar extinction coefficients which are 2680 for EnvZ(C) (223–289) and 20910 for EnvZ(C)(290–450) [Gill et al., Analytical Biochem., 182:319–326 (1989)].

Analytical Size Exclusion Chromatography and Light Scattering: Gel filtration chromatography of the purified EnvZ(C)(223–289) or EnvZ(C)(290–450) protein was accomplished by HPLC (model 110B, Beckman) using a TSK-GEL column (TosoHaas). Protein samples and standard marker proteins were loaded in an equal volume (0.2 ml) to the column pre-equilibrated with buffer [20 mM Tris-HCl (pH 8.0), 350 mM ammonium acetate, 200 mM NaCl, 2 mM DTT, 10% glycerol, 100 mM sodium azide, and 1 mM PMSF] at a flow rate of 0.5 ml/min. The absorbance of the fractions were monitored at 280 nm, and fractions at each peak were pooled. The void volume of the column was determined using blue dextran 2000. For light scattering experiment, EnvZ(C)(223–289) (6.5 mg/l) and EnvZ(C) (290–450) (4.5 mg/l) proteins were analyzed with a DanaPro-901 dynamic light scattering instrument, and the molecular weights of each protein were determined by using the AutoPro software.

Results

Figure 1A:
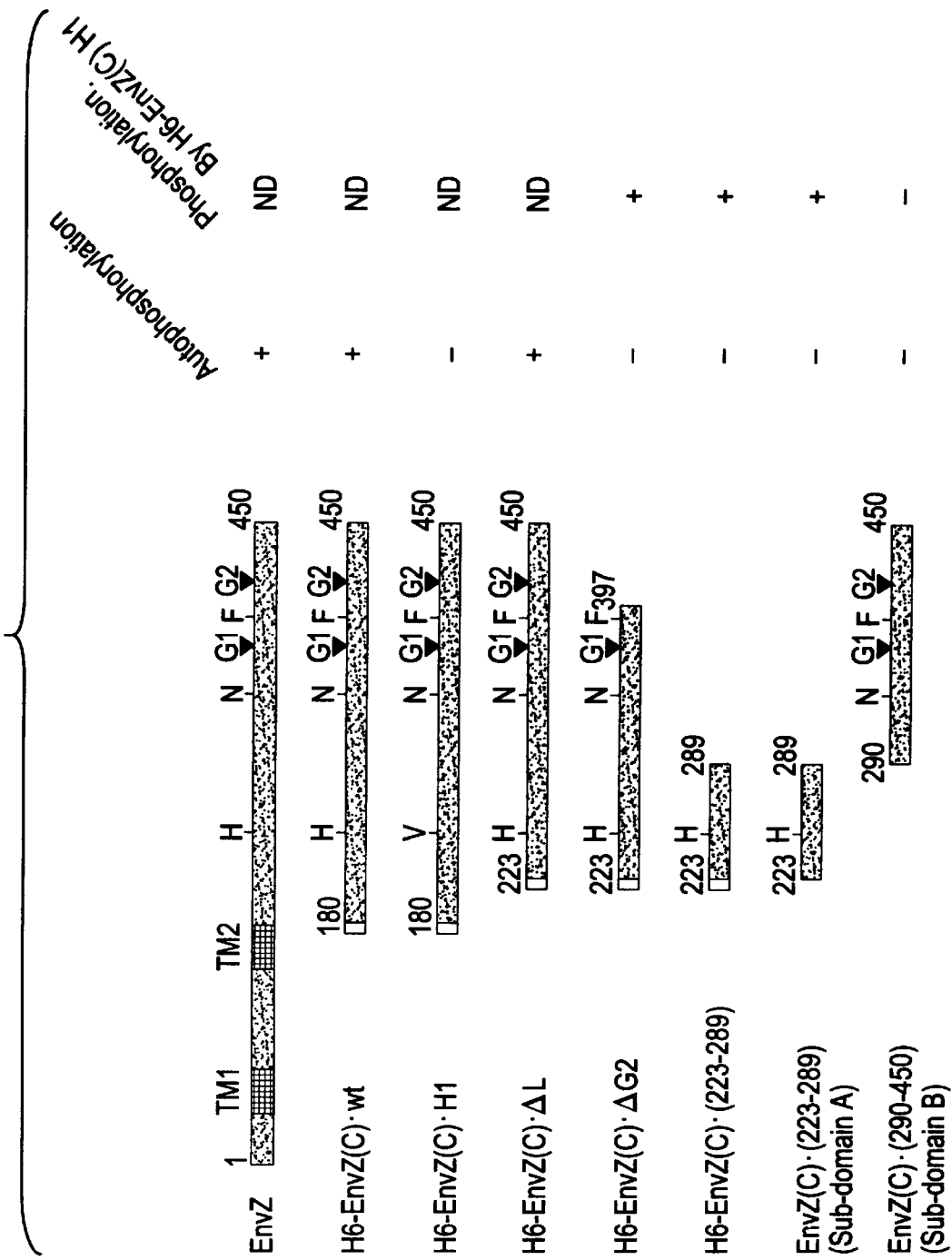
FIGS. 1a–1c shows the purification and autophosphorylation of various EnvZ(C) fragments.

The kinase activity of the cytoplasmic domain of EnvZ was initially analyzed (residue 180 to 450). This domain retained the kinase activity even when it was detached from TM2 (FIG. 1A). The cytoplasmic domain was further truncated by deleting the so-called linker region between residue 180 to 222, resulting in EnvZ(C)ΔL (FIG. 1A). This truncated domain still retained both the kinase and phosphatase activities of the holoprotein (FIG. 1C, lane 3 and FIG. 2B, respectively) [Park et al., J. Bacteriol. 179:4382–4390 (1997)]. The resulting 228-residue EnvZ fragment has been shown to contain all of the features that are highly conserved in the histidine kinases [Egger et al., Genes to Cells, 2:167–184 (1997); Appleby et al., Cell, 86:845–848 (1996); Inouye et al., Cell, 85:13–14 (1996); Parkinson et al., Ann. Rev. Gen., 26:71–112 (1992); and Stock et al., Microbiol. Rev., 53:450490 (1989)], His243 (autophosphorylation site), Asn347, Phe387, and the two Gly-rich boxes, G1 (DXGXG; 373 to 377) and G2 (GXG; 403 to 405) (See FIG. 1A).

Figure 1B:
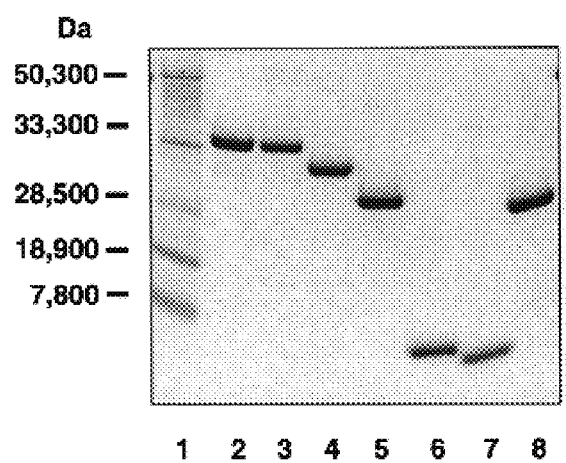
Figure 2A:
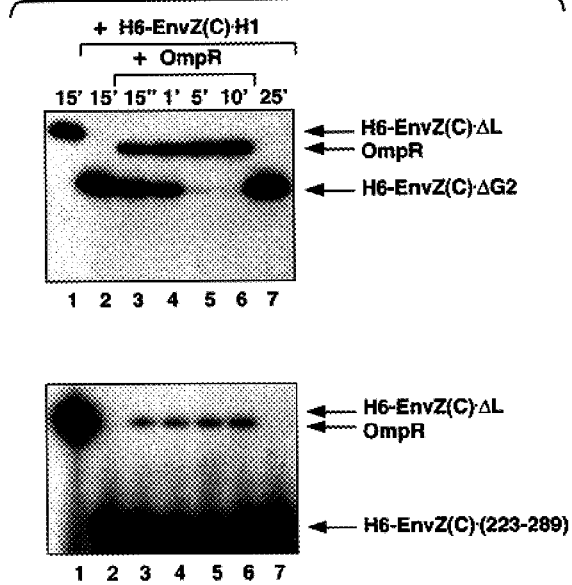
FIGS. 2a–2b shows the enzymatic assay of various EnvZ (C) fragments.

In order to further dissect structural domains of H6-EnvZ (C)ΔL [6 histidine residues were tagged at the N-terminal end of EnvZ(C)ΔL], the smallest kinase, a limited tryptic digestion was carried out. The mass spectrometer analysis of the tryptic fragments revealed that there are two major cleavage sites, one at Arg289 and the other at Arg397. The latter site is located between the G1 and G2 boxes. Thus, two N-terminal fragments, one from residue 223 to 397 [H6-EnvZ(C)ΔG2] and the other from residue 223 to 289 [H6-EnvZ(C)(223–289) or EnvZ(C)(223–289)] were generated (See FIGS. 1A and 1B). As evident from the enzymatic assays, it was determined that not only H6-EnvZ(C)ΔG2 but also H6-EnvZ(C)(223–289), which consists of only 67 residues, were transphosphorylated by H6-EnvZ(C)H1 (FIG. 2A; lanes 2 and 7).

Figure 2B:
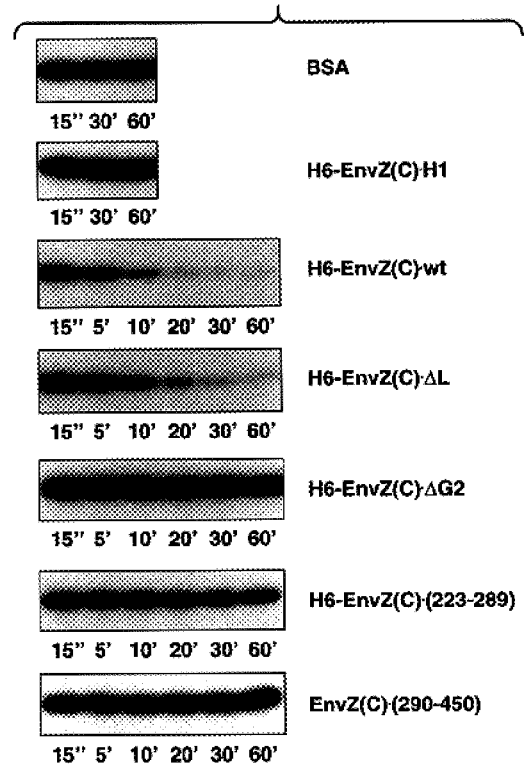

H6-EnvZ(C)H1, an EnvZ truncated fragment in which the autophosphorylation site of His 243 is replaced with Val, is known to transphosphorylate EnvZ fragments deficient in kinase activity, even though it is obviously unable to phosphorylate itself [Yang et al., Proc. Natl Acad. Sci. USA, 88:11057–11061 (1991) and Yang et al., J. Mol. Biol., 231:335–342 (1993)]. Furthermore, such N-terminal fragments of H6-EnvZ(C)H1 were able to phosphorylate OmpR (FIG. 2A, lanes 3 to 6). Interestingly these fragments no longer possess the corresponding phosphatase activity (FIG. 2B). A further attempt to obtain a shorter fragment having kinase activity, such as the fragment from Met223 to Lys272, proved unsuccessful.

Figure 1C:
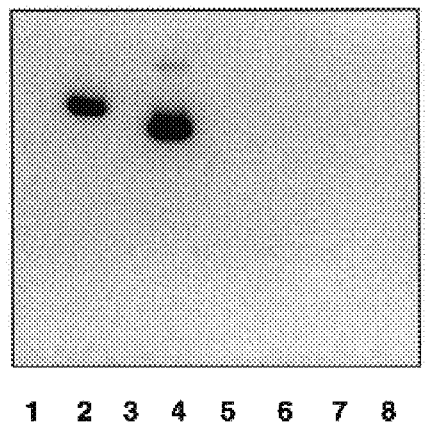
Figure 3A:
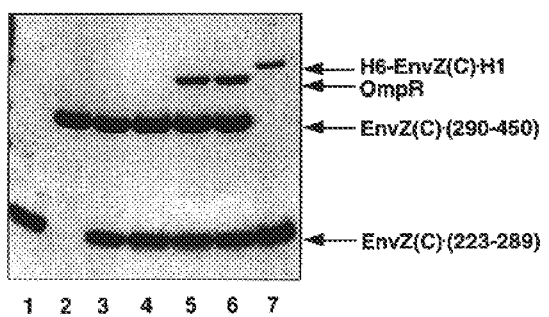
FIGS. 3a–3b shows the recovery of kinase activity by complementation between EnvZ(C)(223–289) and EnvZ(C) (290–450). EnvZ(C)(223–289) (lane 1) or EnvZ(C) (290–450) (lane 2) ($1.2 \times 10^{-5}$M) was incubated with 0.5 μCi of [$\gamma$-$^{32}$P]ATP for 20 minutes. For trans-autophosphorylation of EnvZ(C)(223–289) ($1.2 \times 10^{-5}$M) by EnvZ(C)(290–450) ($1.2 \times 10^{-5}$M), two proteins were incubated with 0.5 μCi of [$\gamma$-$^{32}$P]ATP for 5 minutes (lane 3) and 20 minutes (lane 4). For the phosphotransfer reaction to OmpR, EnvZ(C) (223–289) ($1.2 \times 10^{-5}$M) was first trans-autophosphorylated by EnvZ(C)(290–450) ($1.2 \times 10^{-5}$M) with 0.5 μCi of [$\gamma$-$^{32}$P] ATP for 5 minutes (lane 3), then OmpR ($2.4 \times 10^{-6}$M) was added into the transautophosphorylation mixture and the mixture was incubated for another 15 seconds (lane 5) and 15 minutes (lane 6). Lane 7 shows trans-autophosphorylation of EnvZ(C)(223–289) ($1.2 \times 10^{-5}$M) by H6-EnvZ(C)H1 ($2.4 \times 10^{-6}$M) with 0.5 μCi of [$\gamma$-$^{32}$P]ATP for 5 minutes. All reactions were conducted at room temperature in 20 μl of buffer A and stopped by adding 5×SDS gel loading buffer. Samples were then subjected to SDS-PAGE using a 16% Tricine gel (Novex), followed by staining with Coomassie brilliant blue FIG. 3A and autoradiography FIG. 3B.
Figure 3B:
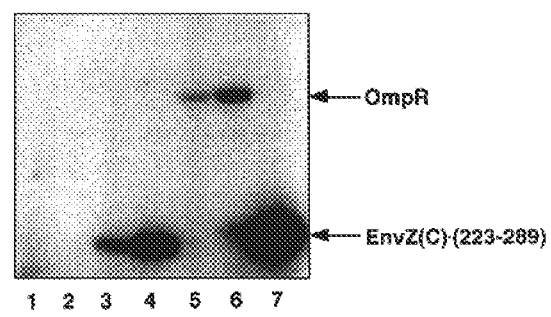

These results indicate that EnvZ(C)ΔL can be divided into two sub-domains, A and B, severed at Arg 289: EnvZ(C) (223–289), subdomain A, and EnvZ(C)(290450), subdomain B. Both sub-domains can be expressed as stable soluble proteins (FIG. 1B, lanes 7 and 8, respectively). Although sub-domain B had neither autophosphorylation activity (FIG. 1C, lane 8) nor phosphatase activity (FIG. 2B), it was able to phosphorylate sub-domain A when sub-domains A and B were mixed in the presence of ATP (FIGS. 3A and 3B, lanes 3 and 4). Furthermore, when the response regulator, OmpR, was added to the mixture, it was phosphorylated in a time-dependent manner (FIGS. 3A and 3B, lanes 5 and 6). In comparison with the transphosphorylation of sub-domain A with H6-EnvZ(C)H1 (FIGS. 3A and 3B, lane 7), the phosphorylation activity was approximately 5% with sub-domain B.

Figure 4A:
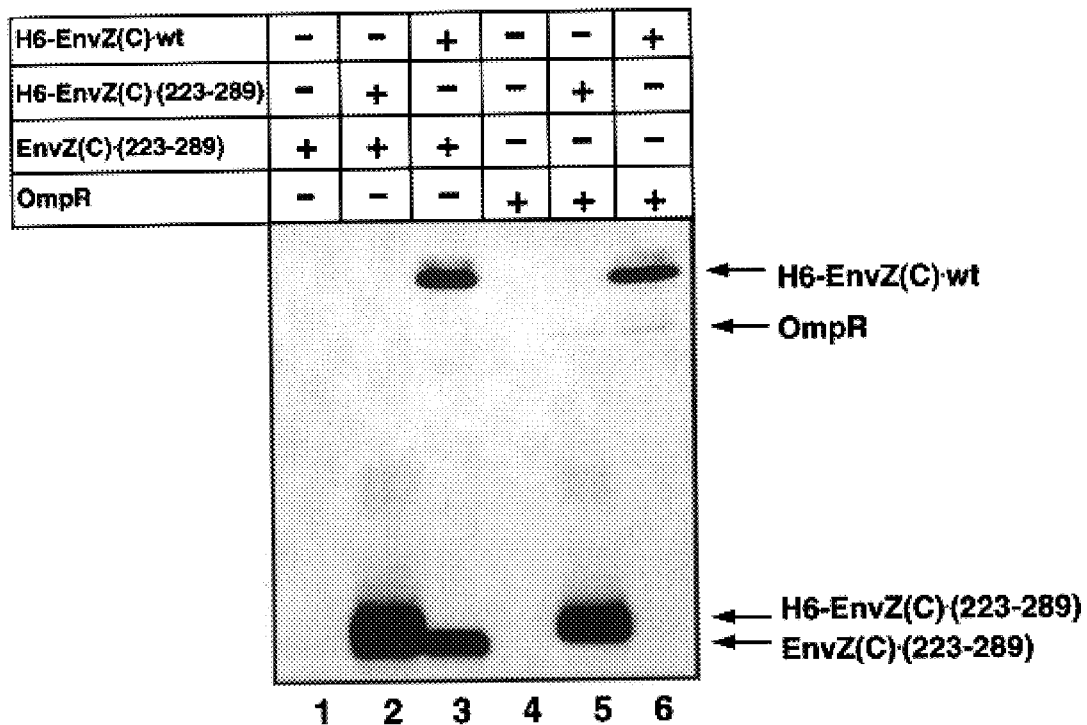
FIGS. 4a–4b shows the analysis of the dimerization of EnvZ(C)(223–289) and its interaction with OmpR.

Circular dichroism analysis of sub-domain A showed a high α-helical content (55%), while sub-domain B had both α-helix (29%) and β-sheet (26%). With Ni-NTA resin chromatography sub-domain A was found to be a dimer [Hidaka et al., FEBS Lett. 400:238–242 (1997)]. Sub-domain A binds to the resin only when it contains a His-tag, i.e., [H6-EnvZ (C)(223–289)] (compare lane 1 and lane 2 in FIG. 4A). Sub-domain A also binds to H6-EnvZ(C)wt (lane 3) as anticipated from FIG. 2A. Since it has been demonstrated that EnvZ(C) is a dimeric protein [Roberts et al., J. Biol. Chem., 269:8728–8733 (1994) and Hidaka et al., FEBS Lett., 400:238–242 (1997)], the present results indicate that the region required for the dimer formation resides in the 67-residue of sub-domain A. This domain further contains the region required for OmpR interaction, since the response regulator, OmpR, was trapped on the resin only in the presence of His-tagged sub-domain A (compare land 4 and 5 in FIG. 4A). Note that the amount of OmpR bound to the resin in lane 5 is comparable to that found with H6-EnvZ (C)wt shown in lane 6. Consistent with this finding, when purified phosphorylated sub-domain A was mixed with OmpR, the phosphoryl group could be efficiently transferred to OmpR in the absence of sub-domain B.

Figure 4B:
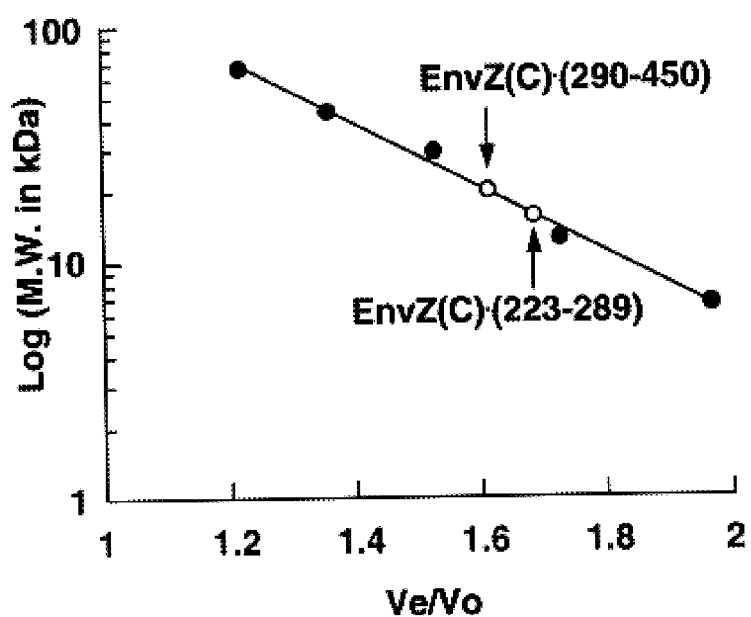

The conclusion that sub-domain A forms a dimer was further confirmed by size exclusion chromatography. The molecular weight of sub-domain A was determined to be about 19.9 kDa by gel filtration (FIG. 4B). In addition, light scattering data showed it to be about 20 kDa. These results are fully consistent with sub-domain A (calculated molecular weight, 7.6 kDa) being a dimer in solution. In direct contrast, the molecular weight of sub-domain B (calculated molecular weight, 17.6 kDa) was determined to be 21.6 kDa (FIG. 4b) and 26.5 kDa by gel filtration and light scattering respectively, indicating that sub-domain B exists as a monomer in solution.

Discussion

Identification of the dimerization domain together with the fact that autophosphorylation occurs via transphosphorylation between two kinase molecules indicates that signal transduction by histidine kinases is carried out through obligatory bimolecular transphosphorylation reaction within a dimer. The two EnvZ signaling domains in a dimer apparently assemble symmetrically in such a way as to allow the autophosphorylation domain (sub-domain A) of one kinase from the dimer to interact with the catalytic domain (sub-domain B) of the other kinase. Thus, sub-domain A serves as the substrate for sub-domain B kinase activity.

Despite having a number of similarities, transmembrane signal transduction by histidine kinases cannot be carried out through a single cytoplasmic signaling domain, [Utsumi et al., Science, 245:1246–1249 (1989) and Baumgartner et al., J. Bacteriol., 176:1157–1163 (1994)], as is apparently true for methyl accepting chemotaxis receptors (MCPs) [Gardina et al., Science, 274:425–426 (1996) and Tatsuno et al., Science, 274:423–425 (1996)].

Previously it has been suggested that the kinase activity of the transmembrane sensor histidine kinase is independent of ligand concentration, whereas the corresponding phosphatase activity is inhibited by an increase in the ligand concentration [Jin et al., J. Mol. Biol., 232:484492 (1993)]. An explanation for this phenomena within the context of the results disclosed herein, may be that such high ligand concentrations stimulate the interaction of sub-domain A with sub-domain B to directly inhibit the phosphatase activity, or alternatively, to inhibit the binding of phospho-OmpR to the sub-domain A-B complex. Indeed, as disclosed herein, the phosphatase activity appears to be very sensitive to the structural arrangement of the signaling domain, since the phosphatase activity could not be detected in the complementation experiment with sub-domains A and B.

Example 2

A Novel Protein Kinase Fold in *Escherichia Coli* Osmosensor ENVZ

Introduction

The His-Asp phosphorelay signal transduction system (so-called two-component system) plays a major role in cellular adaptation to growth conditions and environmental changes in prokaryotes [Egger et al., Genes to Cells, 2:167–184 (1997); Wurgler-Murphy and Saito, Trends. in Biochem. Sci., 22:172–176 (1997)]. In this system, protein histidine kinases function as sensors or as signal transducers. There are 100 examples of His-Asp phosphorelay or two-component systems in bacteria, and 17 such systems have been biochemically characterized in E. coli [Egger et al., Genes to Cells, 2:167–184 (1997)]. In the gram-negative bacterium Salmonella typhimurium, the PhoP/PhoQ two-component system appears to be essential for virulence in host organisms [Soncini and Groisman, J. Bacteriol., 178:6796–6801 (1996)]. Since all two-component systems contain a conserved histidine kinase domain and the His-Asp phosphorelay system has never been found in mammalian cells, histidine kinases are excellent targets for antimicrobial action [Dziejman and Mekalanos, In *Two-Component Signal Transduction*, Eds. J. A. Hock and T. J. Silhavy, ASM Press, Washington, D.C., pp. 25–52 (1995)].

In spite of their importance in cellular functions and as a possible target for antibiotics, the three-dimensional structure of protein histidine kinases has remained unknown. *E. coli* osmosensor EnvZ is a transmembrane receptor of which cytoplasmic signalling domain is a histidine kinase. As disclosed above (Example 1) this domain can be dissected into two functional subdomains A and B; subdomain A (67 residues) contains the essential histidine residue for autophosphorylation and transphosphorylation, and subdomain B (161 residues) contains all the other highly conserved residues. In the presence of ATP, subdomain B exhibits kinase activity to phosphorylate subdomain A. The phosphoryl group is subsequently transferred to OmpR, the response regulator for EnvZ. As disclosed herein, using heteronuclear multidimensional NMR spectroscopy the solution structure of subdomain B, the catalytic domain of EnvZ is determined. The structure as described herein reveals a novel protein kinase fold distinct from the previously known protein kinase fold found in eukaryotic protein serine/threonine and tyrosine kinases.

Methods

Sample preparation: Recombinant EnvZ with uniformly $^{15}$N- and $^{13}$C-labelled protein was expressed in overproducing *E. coli* strain pET11a/BL21(DE3) grown in M9 minimal medium and purified as described elsewhere [Park et al., Proc. Natl. Acad. Sci. USA, 95:6728–6732 (1998)]. NMR samples contained 1.0 to 1.5 mM uniformly $^{15}$N- or $^{13}$C/$^{15}$N-labelled, or unlabelled protein in either 95% $H_2O$/5% $^2H_2O$ or 99.996% $^2H_2O$ containing 20 mM sodium phosphate, 50 mM KCl, 0.5 mM AEBSF, 50 $\mu$M sodium azide and 5 mM $MgCl_2$ (pH 7.0) with 5 mM unlabelled or $^{15}$N/$^{13}$C-labelled AMP-PNP (AMPPNP).

NMR Spectroscopy and Structure Calculations: NMR spectra were recorded at 25° C. using Varian Unity Plus 500, Unity 600 and Bruker DMX750 spectrometers, each equipped with a pulsed-field gradient triple resonance probe as analyzed as described in Bagby et al., [Cell 82:857–867 (1995)] hereby incorporated by reference in its entirety. Sequential resonance assignments of backbone $^1H$, $^{15}N$, and $^{13}C$ atoms were assigned by analyzing four triple resonance experiments (HB)CBCA(CO)NNH, HNCACB, (HB)CBCACO(CA)HA and HNCO. For similar procedures see Bagby et al. [Biochemistry, 33:2409–2421 (1994a)], except with enhanced sensitivity [Muhandiram and Kay, J. Magn. Reson., 103:203–216 (1994)] and minimal $H_2O$ saturation [Kay et al., J. Magn. Reson., 109:129–133 (1994)]. Side chain $^1H$ and $^{13}C$ assignments were made using HCCH-TOCSY [Bax et al., J. Magn. Reson., 87:620–627 (1990)]

experiments with mixing times of 8 ms and 16 ms in solution and were not included in structure calculations and $^{13}$C-edited NOESY-HMQC spectra. Nuclear Overhauser effect (NOE) cross peaks in two-dimensional $^1$H-$^1$H NOE spectroscopy (NOESY), three-dimensional $^{15}$N-edited NOESY-HSQC [Zhang et al., *J. Biomol. NMR,* 4:845–858 (1994)] and three-dimensional simultaneous acquisition $^{15}$N/$^{13}$C-edited NOE [Pascal et al., *J. Magn. Reson.,* 103:197–201 (1994)] spectra were obtained with 100 ms NOE mixing times [Park et al., *Proc. Natl. Acad. Sci USA,* 95:6728–6732 (1998)]. $^3$JNHα coupling constants were measured from $^1$H/$^{15}$N HMQC-J spectrum, and slow-exchanging amide protons were identified by recording a series of gradient-enhanced $^1$H-$^{15}$N HSQC spectra at different time points immediately after the H$_2$O buffer was changed to a $^2$H$_2$O buffer. Standard pseudo-atom distance corrections [Wüthrich et al., *J. Mol. Biol.,* 169:949–961 (1983)] were incorporated to account for center averaging. An additional 0.5 Å was added to the upper limits for distances involving methyl groups [Wagner et al., *J. Mol. Biol.,* 196:611–639 (1987); Clore et al., *Biochemistry,* 26:8012–8023 (1987)].

Structure Calculation: The structures can be calculated using a restained molecular dynamics simulated annealing protocol [Nilges et al., *In computational Aspects of the Study of Biological Macromolecules by Nuclear Magnetic Resonance Spectroscopy,* J. C. Hoch, F. M. Poulsen, and C. Redfield, eds., New York: Plenum Press, pp.451–455 (1991)] within X-PLOR [Brünger, *X-PLOR Manual, Version 3.1,* New Haven, Conn.: Department of Molecular Biophysics and Biochemistry, Yale University (1993)] using the previously described strategy [Bagby et al., *Structure,* 2:107–122 (1994b)]. Structural coordinates are reported in Tables 1 and 2. Structure calculations employed 1782 inter-proton restraints (comprising 556 intraresidue, 440 sequential, 260 short-range, 507 long-range, 13 protein-ATP analogue, and 10 intra-analogue) obtained from heteronuclear three-dimensional nuclear Overhauser effect (NOE) spectra. In addition to the NOE-derived distance restraints, 92 distance restraints for 46 hydrogen bonds and 122 dihedral angle restraints were included in the structure calculation. The average rmsd values from idealized geometry for bonds, angles and impropers are 0.005 Å, 0.61° and 0.39°, respectively. The total and Lennard-Jones potential energies are 516±70 and −134±29 kcal mol$^{-1}$, respectively (calculated with the use of square-well potentials for the experimental distance empirical energy term with a force constant of 50 kcal mol$^{-1}$ Å$^{-2}$). None of the structures has violations greater than 0:40 Å (for distance restraints) and 3.0° (for dihedral angle restraints).

UV-crosslinking assay: Purified proteins were each incubated in crosslinking buffer (20 mM Tris pH 7.8, 50 mM KCl and 5% glycerol) containing radioactive ATP, [α$^{32}$P] ATP (800 Ci/mmole, 10 mCi/ml) or [γ$^{32}$P] ATP (3000 Ci/mmole, 10 mCi/ml) in a final volume of 25 μL and incubated at 4° C. for 15 min. Proteins were crosslinked by UV irradiation at 254 nm at a height of 4.5 cm for 5 min on ice using a UV lamp (Model UVG45, 115 Volts, 60 Hz, 0.16 Amps, UVP Inc. California). Crosslinked protein was visualized through autoradiography after 17.5% SDS-PAGE. For competion experiments, non-radioactive ATP was added in the reaction mixture.

*Escherichia coli* osmosensor EnvZ is an integral membrane receptor of 450 residues, posessing a histidine kinase activity in the cytoplasmic region [Egger et al, *Genes to Cells,* 2:167–184 (1997)]. In Example 1 above, it has been demonstrated that the cytoplasmic contains two functional domains, A and B. In Example 1 it is furier shown that domain A (residues 223–289) nestles the conserved histidine residue (H243), the site of autophosphorylation and transphosphorylation, whereas domain B (290–450) encloses all the other highly conserved regions (G1, G2, F and N boxes) and exhibits catalytic activity to phosphorylate H243. The phosphoryl group is subsequently transferred to an aspartate in OmpR, the response regulator for EnvZ. In the present example, the NMR-derived structure of domain B, the catalytic core of EnvZ histidine kinase is defined. The structure reveals a novel protein kinase fold distinct from the previously known protein kinase fold found in eukaryotic protein serine/threonine and tyrosine kinases, as described herein.

Results

Figure 8A:
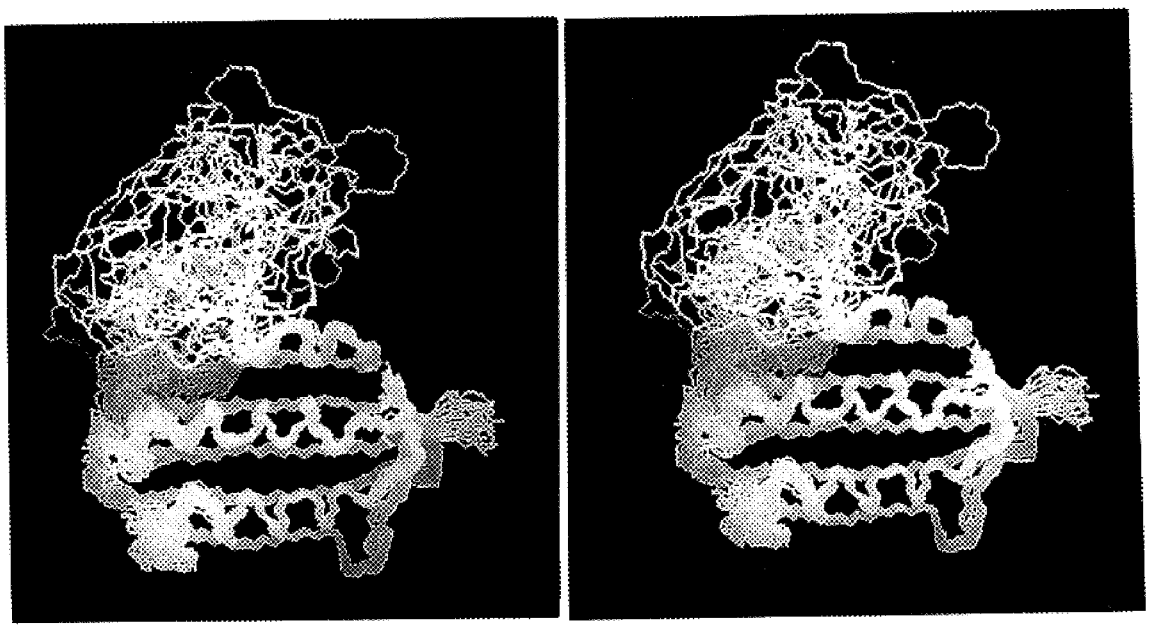
FIG. 8A shows the stereoview of a best fit superposition of the backbone (N, Cα, and C') atoms of the 25 NMR-derived structures of the EnvZ catalytic domain, generated using Insight II (Molecular Simulations Inc., San Diego, Calif.). The main chain atoms of the 25 structures are superimposed against the energy-minimized average structure using residues 297–299, 301–311, 319–323, 330–332, 334–343, 356–362, 367–373, 420–423 and 431–436 (root-mean-square deviation [rmsd] of 0.57±0.12 Å for backbone atoms and 0.94±0.08 Å for all heavy atoms). The central loop region is less well-defined due to its flexibility. The N-terminal 5 and C-terminal 10 residues, which are also not well-defined due to the lack of a large number of experimental distance and dihedral angle restraints, are omitted in the figure.

The catalytic core domain of EnvZ (FIGS. 5, 8A and 8B) assumes an α/β sandwich fold: one layer consists of a five-stranded β-sheet (strand B, residues 319–323; D, 356–363; E, 366–373; F, 419–425; G, 429–436) and the other layer comprises three helices (α1, 301–311; α2, 334–343; α4, 410–414) in a topology shown in FIG. 5. Two adjacent parallel β strands, B and D connected by helix α2, display an unusual "left-handed" connectivity [Brandon et al. *Introduction to Protein Structure,* Garland Publishing, N.Y. (1991)]. The two layers enclose an extensive hydrophobic core, augmented by a small anti-parallel β-sheet (strand A, 297–299; C, 330–332) which seals the sandwich at one end. The hydrophobic core consists of the following residues: L301, L305, I309 in helix α1; I319, T321, L323 in strand B; V330, M332 in strand C; I337, V341 in helix α2; I356, V358 in strand D; A367, F369, V371 in strand E; V409, V413 in helix α4; L420 in strand F; I432, A434, L436 in strand G. The sequence conservation of these structurally critical hydrophobic residues (FIG. 6) suggest that the histidine kinase domain of other proteins adapts the α/β sandwich fold observed in EnvZ.

The overall fold of the histidine kinase catalytic domain differs significantly from the known structures of protein serine/threonine and tyrosine kinases [Taylor and Radzio-Andzelm, In *Protein Kinases,* Ed. J. R. Woodgett, 1–29 (1994)]. The EnvZ histidine kinase domain comprises a single globular fold of 161 residues that has all the functionalities of a protein kinase. In contrast, the catalytic core of serine/threonine and tyrosine kinases consists of two lobes: a smaller lobe of approximately 90 residues primarily responsible for ATP binding and a larger lobe of about 170 residues responsible for catalysis and substrate/inhibitor binding. The histidine kinase fold is unrelated to the serine/threonine and tyrosine kinase fold, and is also distinct from the folds found in other bacterial kinases such as pyruvate and adenylate kinases [Mattevi et al., *Structure,* 3:729–741 (1995); Berry et al., *Protein: Struct. Function, and Genetics,* 19:183–198 (1994)] and in the sugar phosphotransferase system [Liao et al., *Structure,* 4:861–872 (1996); Garrett et al., *Biochemistry,* 36:2517–2530 (1997); Herzberg and Klevit, *Curr. Opin. Struct. Biol.,* 4:814–822 (1994)]. Finally, a search of folds in the Protein Data Bank using the SARF algorithm [Alexandrov et al., *J. Mol. Biol.,* 225:5–9 (1992)] indicates that the histidine kinase fold is uniquely novel.

Figure 8B:
FIG. 8B depicts a schematic ribbon drawing of the energy-minimized average structure of the EnvZ catalytic domain. The ATP analogue (AMP-PNP) is shown as a stick model, and the helices (in magenta) and strands (in yellow) are labelled. The backbone heavy atoms of glycines in G1 and G2 boxes (in blue), and side-chain heavy atoms of N347 (in pink), D373 (in blue), I378, L386, and F387 (in green) are also shown as a stick model. The N-terminal 5 and C-terminal 10 residues are omitted as in FIG. 8A. The model was generated using QUANTA (Molecular Simulations Inc., San Diego, Calif.).

A striking feature in this fold is the presence of a long polypeptide segment that extends away from the rest of the molecule (FIG. 5 and FIG. 8B). This segment consists of a short α-helix α3 (380–384) followed by a long loop (385–409) designated as the central loop. Almost no medium- or long-range NOEs were detected for the residues in this loop, and the chemical shifts and backbone coupling constants ($^3J_{NH\alpha}$) are nearly the same with those in a random coil. Furthermore, $^1H$-$^{15}N$ heteronuclear NOE measurements showed small NOE values (0.49±0.10) for the residues in this loop than the values (0.75±0.12) of the structurally well defined region, suggesting that this region is highly mobile in solution relative to the overall tumbling motion of the molecule. This characteristic loop, together with helix α3, provides a nucleotide binding site where the phosphorylation catalysis takes place, and is thereby referred to as 'catalytic loop'.

Figure 7:
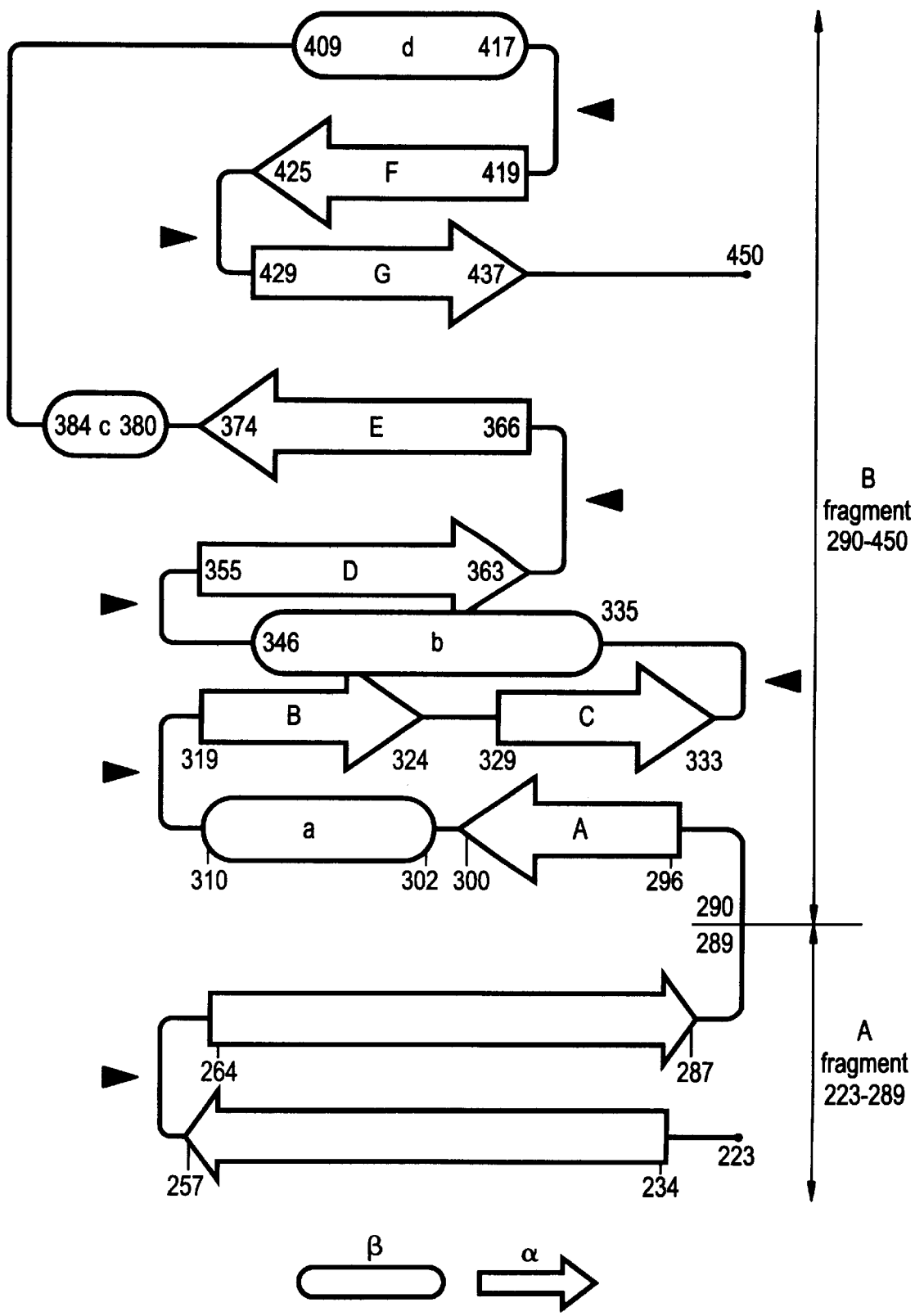
FIG. 7 depicts the secondary structure of the N$_t$TSHK, containing both sub-domain A and sub-domain B (SEQ ID NO:8). The arrowheads indicate regions in which the protein can be fragmented while still maintaining the structural integrity of its structural domains.

FIG. 7 shows that the two functional features of the catalytic domain, i.e., the autophosphorylatable histidine and the catalytic kinase domain can be contained by N,T-SHKs with overlapping sequences, e.g., the domain comprising the autophosphorylatable histidine can consist of amino acids 223 to 340 of SEQ ID NO:2 and the kinase domain can consist of amino acids 330 to 450 of SEQ ID NO:2.

Figure 6:
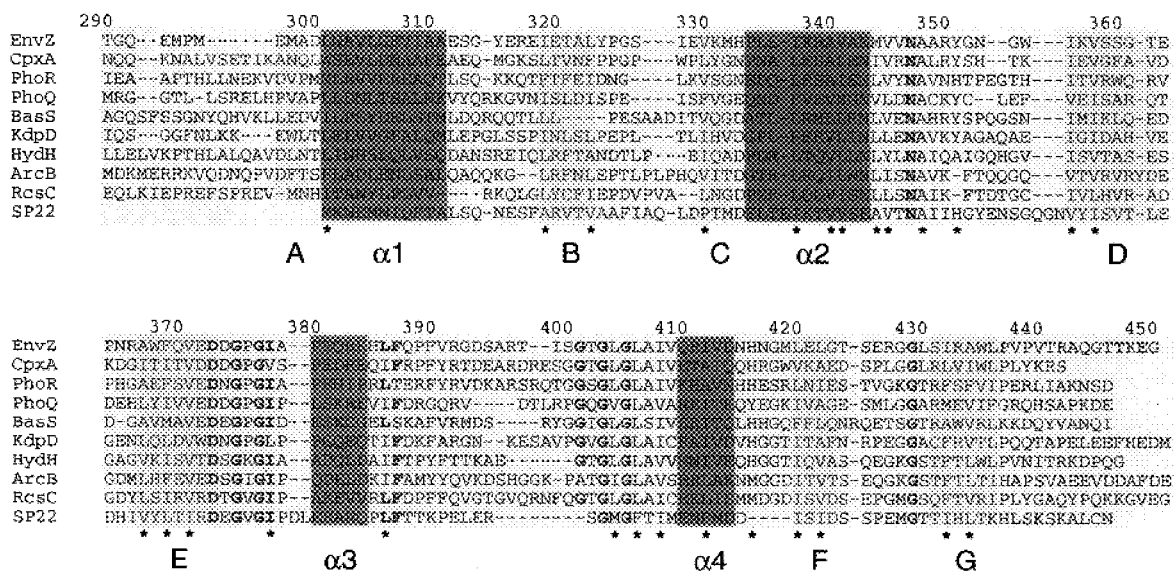
FIG. 6 depicts the sequence alignment of the EnvZ catalytic domain with other members of the histidine kinase family. The accession number of the SWISS-PROT database for the sequences are P02933 (EnvZ), P08336 (CpxA), P08400 (PhoR), P23837 (PhoQ), P30844 (BasS), P21865 (KdpD), P14377 (HydH), P22763 (ArcB), P14376 (RcsC), and P10728 (SpoIIAB; labelled as SP22 in the figure). Secondary structural elements are shown by boxes colored as in FIG. 8B below, with their notation indicated below the boxes. Asterisks denote the conserved hydrophobic amino acid residues. The residues that are found to be important in the ATP binding are shown in bold.
Figure 9A:
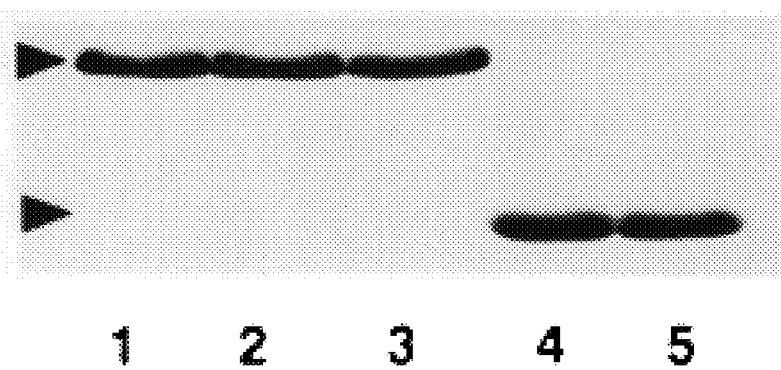
FIGS. 9a–9b show the identification of ATP-binding domain in EnvZ and the involvement of N347 in ATP-binding. UV-crosslinked protein (as described in Methods) was visualized through autoradiography (FIG. 9a) after 17.5% SDS-PAGE. An identical amount of each protein was used as shown by the CMB stained SDS-PAGE (FIG. 9b). The crosslinked proteins are as follows: EnvZ(223–450) with 10 μCi [$\alpha^{32}$P] ATP (lane 1); EnvZ(223–450) with 10 μCi [$\alpha^{32}$P] ATP and 500 μM non-radioactive ATP (lane 2); EnvZ·N347D(223–450) with 10 μCi [$\alpha^{32}$P] ATP (lane 3); EnvZ(290–450) with 50 μCi [$\gamma^{32}$P] ATP (lane 4); EnvZ (290–450) with 50 μCi [$\gamma^{32}$P] ATP and 1 mM non-radioactive ATP (lane 5).
Figure 9B:
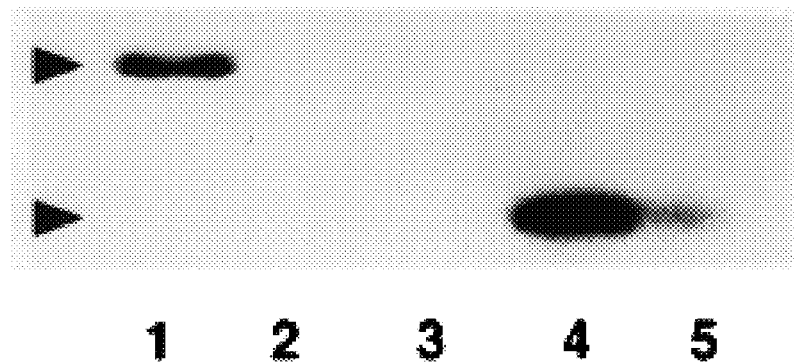

As is true for eukaryotic protein kinases, the catalytic reaction of histidine kinases requires the presence of ATP and $Mg^{2+}$ [Stock et al., In *Two-component signal transduction*, eds Hock, J. A. & Silhavy, T. J, 25–51, ASM Press, Washington (1995)]. Indeed, non-radioactive ATP competes with [$\alpha^{32}P$] ATP for the cytoplasmic domain of EnvZ (223–450) (FIG. 9, lanes 1 and 2). This ATP binding function is retained in domain B (lane 4) and again non-radioactive ATP competes with the binding of [$\gamma^{32}P$]-ATP to domain B (lane 5). The present structure contains a nonhydrolysable analog of ATP, AMP-PNP (β, γ-imidoadenosine-5'-triphosphate) whose location in the structure has been determined on the basis of a dozen intermolecular NOEs observed between I378/L386/L422 side chain protons and the adenosine H2, H8, H1', H4' and H5' protons. The AMP-PNP molecule is mainly surrounded by helix α3 and part of the central loop, and also contacts with strands F and G. The AMP-PNP adenine ring is in close spatial proximity to N347, D373, I378, L386, and F387 (FIG. 8B), which are conserved in other members of the histidine kinase family (FIG. 6).

The triphosphate chain is exposed to the protein surface, consistent with the potential to transfer the γ-phosphate to H243 in domain A. In addition, five glycines (G375, G377, G403, G405, G429) and an asparagine (N347) in the catalytic core are absolutely conserved and strategically located in the structure (FIG. 8B), indicating their structural and functional significance. Previous mutagenesis studies [Yang and Inouye, *J. Mol. Biol.*, 231:335–342 (1993)] demonstrated that the glycine-rich regions, G1 (D373–G377) and G2 (G401–G405), are essential for kinase activity. The present structure shows that G375 and G429 allow a sharp kink between strand E and helix α3 and between strands F and G, respectively, adjacent to the AMP-PNP binding site.

Figure 10:
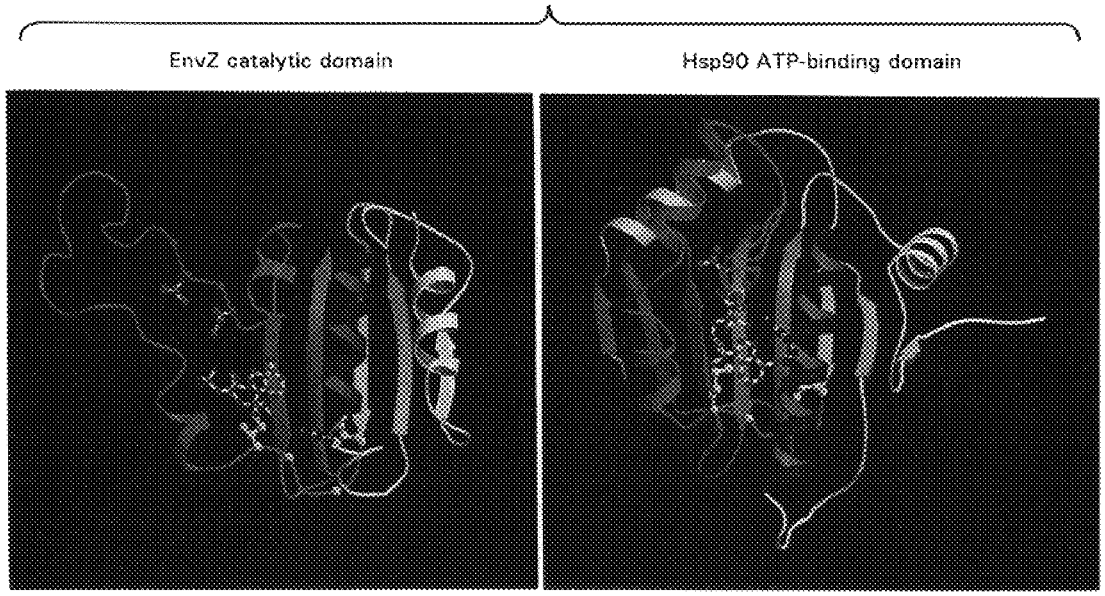
FIG. 10 shows that EnvZ and Hsp90 share a similar fold in their ATP-binding regions. Ribbon representation of EnvZ catalytic domain and the ATP-binding domain of Hsp90 molecular chaperone (PDB: 1amw) [Prodromou et al., *Cell*, 90:65–76 (1997)]. For the EnvZ catalytic domain, strands D and E are shown in light blue, strands F and G in purple, helix α2 in dark blue, and the central loop including helices α3 and α4 in green. Heavy atoms (except N, C, and O) of N347 (in blue), D373, G375, G377, I378 (in yellow), G403, L404, G405, and L406 (in purple) are shown as ball-and-stick models. The corresponding secondary structural elements and specific residues of Hsp90 are colored the same as EnvZ. AMP-PNP (ADP in Hsp90) is also shown as a ball-and-stick model in red. The model was generated using MOLSCRIPT [Kraulis, *J Appl. Crystallogr.*, 24:946–950 (1991)) and Raster3D [Merritt and Murphy, *Acta Crystallogr.*, D50:869–873 (1994)].

High deviation of the central loop in the NMR-derived structure, due to high mobility, precludes close examination of the residues that could be involved in the catalysis. However, an indication of how the mechanism may operate can be extracted from the structures of yeast Hsp90 [Prodromou et al., *Cell*, 90:65–75 (1997)] and *E. coli* DNA gyrase B [Wigley et al., *Nature*, 351:624–629 (1991)]. While the structure of EnvZ domain B was being determined, detailed ψ-BLAST searches [Altschul et al., *Nucleic Acids Res.*, 25:3389–3402 (1997)] suggested a similarity between these proteins. Hsp90 is already known to be surprisingly similar to DNA gyrase B [Prodromou et al., *Cell*, 90:65–75 (1997)], and both proteins bind ATP requisite to their functions. Structural similarities with EnvZ domain B are more restricted (FIGS. 10 and 11), involving helix α2, four strands (D, E, F, and G) and the central loop (385–409). Together they enclose N347, and G1 (DxGxGφ) motif (373–378), and the G2 (GφGφ) motif (403–406) (φ-hydrophobic) which are conserved in all three proteins and are close to the ATP binding site of Hsp90 (Protein Data Bank codes 1amw and 1aml).

In detail, the Hsp90-ADP complex shows its N37 (corresponding to N347 in EnvZ) binding directly to β phosphate and $Mg^{2+}$ as well as indirectly to the adenine base [Prodromou et al. *Cell,* 90:65–75 (1997)]. Interestingly, the EnvZ mutant protein N347D results in a phenotype in which ATP-dependent autokinase activity is lost, but phosphorelay ability between the mutant protein and phosphorylated OmpR is retained [Dutta et al., *J. Biol. Chem.*, 271:1424–1429 (1996)]. The importance of N347 is demonstrated in FIG. 9 (lane 3), where ATP binding to EnvZ (223–450) is abolished in the N347D mutant. The decrease ATP affinity of N347D provides compelling evidence that this conserved asparagine plays a critical role in ATP-dependent autophosphorylation activity of EnvZ. In the structures of both Hsp90 and DNA gyrase, the only highly conserved charged residue, aspartate in the DxGxGφ motif (D79 and D73 in Hsp90 and DNA gyrase respectively) interacts with the N6 atom in the adenine base. The corresponding residue in EnvZ, D373, is also close to the N6 atom of AMP-PNP in the present structure (FIG. 8b).

Despite the clear similarity between EnvZ, Hsp90 and DNA gyrase B, EnvZ initially appears to be the outlier of the trio, mainly because of the left-handed βαβ connection between strands B and D. Cases of clear left-handed connectivity are quite rare despite the present availability of more than 1,000 non-homologous structures. It is therefore all the more surprising that one such case is found in the carboxy-terminal, DNA-binding domain of *E. coli* DNA gyrase. The similarity of the ATP-binding domain, coupled with the presence of a left-handed βαβ connection in both proteins supports an evolutionary link between the two protein families.

Figure 12A:
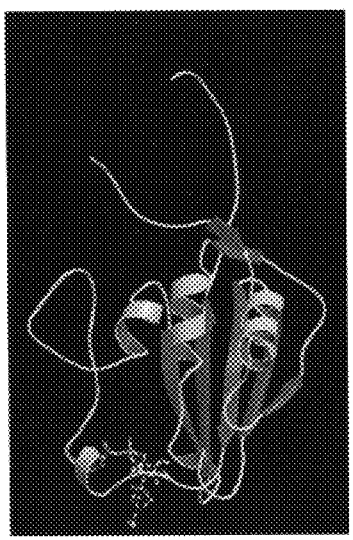
FIGS. 12A–12C shows the catalytic core fold of EnvZ histidine kinase is distinct from the previously known protein kinase fold.
Figure 12B:
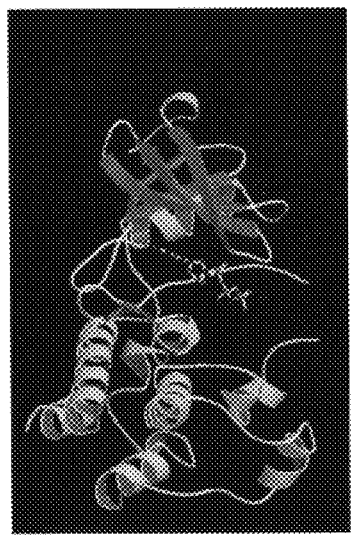
Figure 12C:
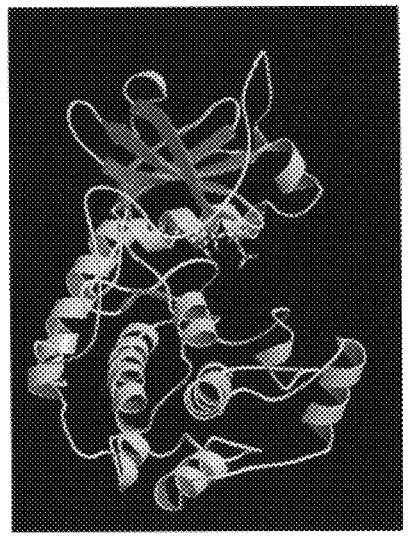
Figure 13:
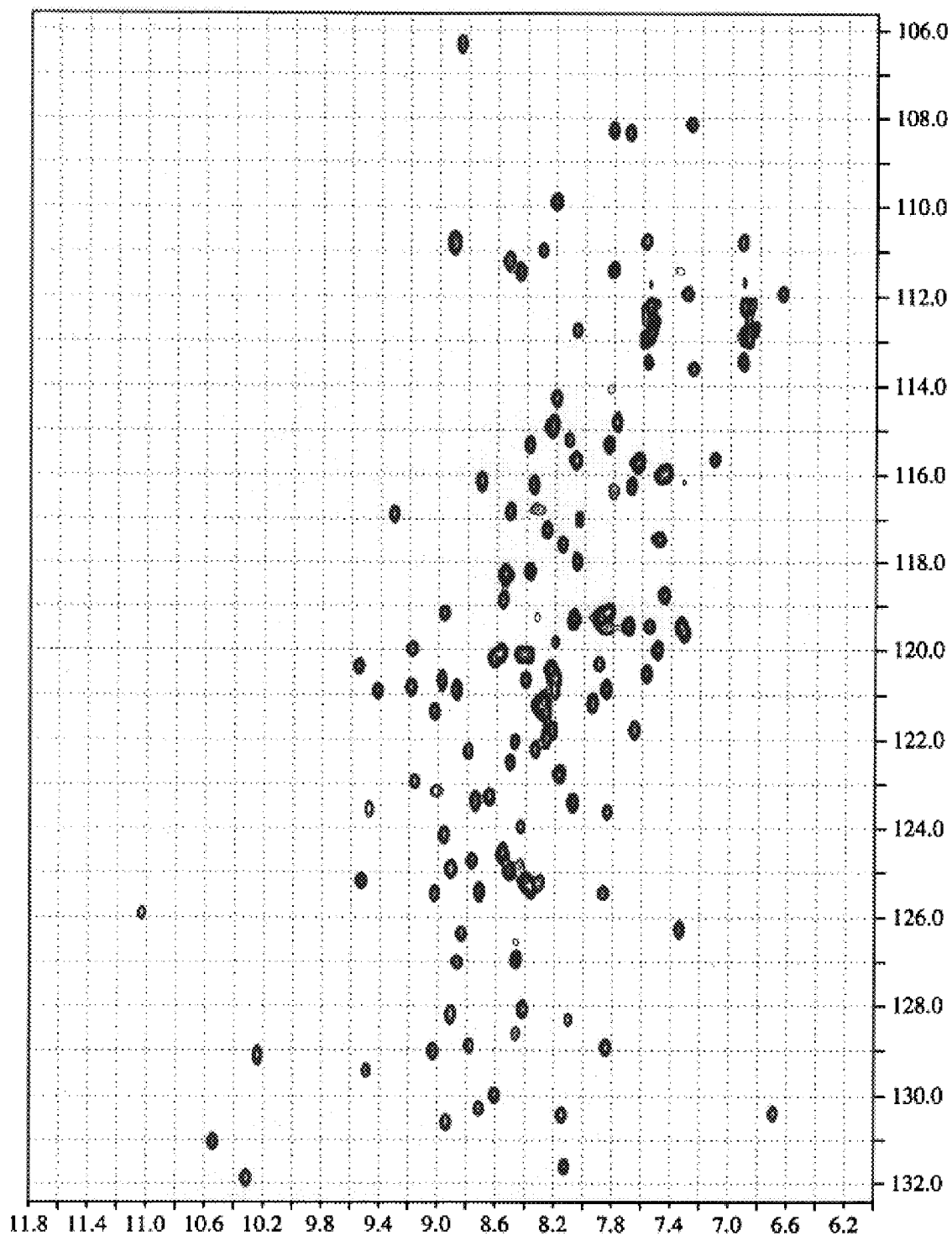
FIG. 13 shows the H-$^{15}$N HSQC spectrum of the EnvZ B domain. Chemical shift data corresponding to this spectrum is included in Table 3.

The overall fold of the histidine kinase catalytic domain differs significantly from the known structures of protein serine/threonine and tyrosine kinases [Taylor and Radzio-Andzelm, in *Protein Kinases*, ed Woodgett, J. R., 1–29, IRL Press, Oxford (1994)] (FIG. 12). The EnvZ catalytic domain comprises a single globular fold of 161 residues that has all the functions of a protein kinase. In contrast, the catalytic core of serine/threonine and tyrosine kinases consists of two lobes: a smaller lobe of approximately 90 residues primarily responsible for ATP binding and a larger lobe of about 170 residues responsible for catalysis and substrate/inhibitor binding. The histidine kinase fold is unrelated to the serine/threonine and tyrosine kinase fold, and is also distinct from the folds found in other bacterial kinases such as pyruvate and adenylate kinases [Mattevi et al., *Structure*, 3:729–741 (1995); Berry et al., *Proteins*, 19:183–198 (1994)] and in the sugar phosphotransferase system [Herzberg and Klevit, *Curr. Opin. Struct. Biol.*, 4:814–822 (1994); Liao et al., *Structure*, 4:861–872 (1996); Garrett et al., *Biochemistry*, 36:2517–2530 (1997)].

Over 300 gene sequences can be identified as members of the histidine kinase family by a ψ-BLAST search with an E-value of 0.001 [Altschul et al., *Nucleic Acids Res.*, 25:3389–3402 (1997)]. The simplest example of such a sequence identified was found in *Bacillus subtilis*, SpoIIAB (an anti-sigma factor), which encodes only the catalytic core of histidine kinase and is implicated in transcription regulation [Min et al., *Cell*, 27:735–742 (1993)]. On the *E. coli* chromosome, 32 histidine kinases have been identified

[Mizuno, *DNA Res.*, 4:161–168 (1997)], and 17 of them have been biochemically characterized [Egger et al., *Genes to Cells*, 2:167–184 (1997)]. Sln1, an osmosensor in yeast [Ota and Varshavsky, *Science*, 262:566–569 (1993)], has its sequence conserved in all regions corresponding to secondary structural elements of EnvZ, and contains a 120-residue insertion between strands D and E of the EnvZ structure. This long insertion suggests that additional structural elements have been added to the catalytic core of eukaryotic members of the histidine kinase family, presumably owing to additional function(s).

There are at least 100 examples of His-Asp phosphorelay in bacteria, and some are implicated in bacterial virulence [Egger et al., *Genes to Cells*, 2:167–184 (1997)]. For example, a life-threatening bacterium *Salmonella typhimurium* possesses the PhoP/PhoQ phosphorelay system which appears to be essential for its virulence in host organisms [Soncini and Groisman, *J. Bacteriol.*, 178:6796–6801 (1996)]. Since all these phosphorelay systems contain a conserved histidine kinase domain which has not been found in mammalian cells, histidine kinases are excellent targets for antimicrobial action [Dziejman and Mekalanos, In *Two-component signal transduction*, eds. Hock, J. A. & Silhavy, T. J., 305–317, ASM Press, Washington (1995)]. A family of hydrophobic tyramines has already been identified as potent histidine kinase inhibitors which showed $IC_{50}$=2–600 $\mu$M [Barrett et al., *Proc. Natl. Acad. Sci. USA*, 95:5317–5322 (1998)]. The present structure of the *E. coli* EnvZ histidine kinase catalytic domain will provide a vital foundation for rational design of more effective antibiotics specifically blocking multiple histidine kinases in this and other microbial species.

TABLE 1

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| | | | | | | | | | |
|---|---|---|---|---|---|---|---|---|---|
| ATOM | 1 | CA | MET | 223 | 14.751 | −8.953 | −18.178 | 1.00 | 0.00 | A |
| ATOM | 2 | HA | MET | 223 | 14.048 | −9.180 | −18.962 | 1.00 | 0.00 | A |
| ATOM | 3 | CB | MET | 223 | 14.254 | −9.526 | −16.849 | 1.00 | 0.00 | A |
| ATOM | 4 | HB1 | MET | 223 | 13.304 | −9.081 | −16.597 | 1.00 | 0.00 | A |
| ATOM | 5 | HB2 | MET | 223 | 14.973 | −9.307 | −16.072 | 1.00 | 0.00 | A |
| ATOM | 6 | CG | MET | 223 | 14.088 | −11.040 | −16.979 | 1.00 | 0.00 | A |
| ATOM | 7 | HG1 | MET | 223 | 15.038 | −11.484 | −17.234 | 1.00 | 0.00 | A |
| ATOM | 8 | HG2 | MET | 223 | 13.370 | −11.257 | −17.755 | 1.00 | 0.00 | A |
| ATOM | 9 | SD | MET | 223 | 13.505 | −11.724 | −15.408 | 1.00 | 0.00 | A |
| ATOM | 10 | CE | MET | 223 | 15.048 | −11.521 | −14.485 | 1.00 | 0.00 | A |
| ATOM | 11 | HE1 | MET | 223 | 15.435 | −10.523 | −14.648 | 1.00 | 0.00 | A |
| ATOM | 12 | HE2 | MET | 223 | 15.769 | −12.243 | −14.826 | 1.00 | 0.00 | A |
| ATOM | 13 | HE3 | MET | 223 | 14.859 | −11.672 | −13.431 | 1.00 | 0.00 | A |
| ATOM | 14 | C | MET | 223 | 14.961 | −7.440 | −18.068 | 1.00 | 0.00 | A |
| ATOM | 15 | O | MET | 223 | 16.076 | −6.960 | −18.026 | 1.00 | 0.00 | A |
| ATOM | 16 | N | MET | 223 | 16.058 | −9.638 | −18.434 | 1.00 | 0.00 | A |
| ATOM | 17 | HT1 | MET | 223 | 15.892 | −10.504 | −18.985 | 1.00 | 0.00 | A |
| ATOM | 18 | HT2 | MET | 223 | 16.507 | −9.884 | −17.528 | 1.00 | 0.00 | A |
| ATOM | 19 | HT3 | MET | 223 | 16.683 | −9.002 | −18.969 | 1.00 | 0.00 | A |
| ATOM | 20 | N | ALA | 224 | 13.896 | −6.684 | −18.021 | 1.00 | 0.00 | A |
| ATOM | 21 | HN | ALA | 224 | 13.004 | −7.090 | −18.058 | 1.00 | 0.00 | A |
| ATOM | 22 | CA | ALA | 224 | 14.037 | −5.204 | −17.912 | 1.00 | 0.00 | A |
| ATOM | 23 | HA | ALA | 224 | 14.617 | −4.943 | −17.044 | 1.00 | 0.00 | A |
| ATOM | 24 | CB | ALA | 224 | 14.783 | −4.786 | −19.180 | 1.00 | 0.00 | A |
| ATOM | 25 | HB1 | ALA | 224 | 15.598 | −4.128 | −18.918 | 1.00 | 0.00 | A |
| ATOM | 26 | HB2 | ALA | 224 | 14.104 | −4.271 | −19.845 | 1.00 | 0.00 | A |
| ATOM | 27 | HB3 | ALA | 224 | 15.173 | −5.663 | −19.674 | 1.00 | 0.00 | A |
| ATOM | 28 | C | ALA | 224 | 12.658 | −4.540 | −17.854 | 1.00 | 0.00 | A |
| ATOM | 29 | O | ALA | 224 | 11.661 | −5.115 | −18.245 | 1.00 | 0.00 | A |
| ATOM | 30 | N | ALA | 225 | 12.597 | −3.332 | −17.369 | 1.00 | 0.00 | A |
| ATOM | 31 | HN | ALA | 225 | 13.413 | −2.890 | −17.058 | 1.00 | 0.00 | A |
| ATOM | 32 | CA | ALA | 225 | 11.289 | −2.622 | −17.281 | 1.00 | 0.00 | A |
| ATOM | 33 | HA | ALA | 225 | 10.817 | −2.576 | −18.248 | 1.00 | 0.00 | A |
| ATOM | 34 | CB | ALA | 225 | 10.445 | −3.461 | −16.325 | 1.00 | 0.00 | A |
| ATOM | 35 | HB1 | ALA | 225 | 9.424 | −3.490 | −16.677 | 1.00 | 0.00 | A |
| ATOM | 36 | HB2 | ALA | 225 | 10.474 | −3.021 | −15.339 | 1.00 | 0.00 | A |
| ATOM | 37 | HB3 | ALA | 225 | 10.840 | −4.466 | −16.283 | 1.00 | 0.00 | A |
| ATOM | 38 | C | ALA | 225 | 11.502 | −1.219 | −16.719 | 1.00 | 0.00 | A |
| ATOM | 39 | O | ALA | 225 | 10.955 | −0.858 | −15.697 | 1.00 | 0.00 | A |
| ATOM | 40 | N | GLY | 226 | 12.297 | −0.425 | −17.381 | 1.00 | 0.00 | A |
| ATOM | 41 | HN | GLY | 226 | 12.724 | −0.738 | −18.206 | 1.00 | 0.00 | A |
| ATOM | 42 | CA | GLY | 226 | 12.553 | 0.957 | −16.891 | 1.00 | 0.00 | A |
| ATOM | 43 | HA1 | GLY | 226 | 13.373 | 1.386 | −17.443 | 1.00 | 0.00 | A |
| ATOM | 44 | HA2 | GLY | 226 | 12.807 | 0.924 | −15.840 | 1.00 | 0.00 | A |
| ATOM | 45 | C | GLY | 226 | 11.306 | 1.821 | −17.085 | 1.00 | 0.00 | A |
| ATOM | 46 | O | GLY | 226 | 10.941 | 2.592 | −16.225 | 1.00 | 0.00 | A |
| ATOM | 47 | N | VAL | 227 | 10.658 | 1.707 | −18.215 | 1.00 | 0.00 | A |
| ATOM | 48 | HN | VAL | 227 | 10.974 | 1.081 | −18.899 | 1.00 | 0.00 | A |
| ATOM | 49 | CA | VAL | 227 | 9.432 | 2.527 | −18.463 | 1.00 | 0.00 | A |
| ATOM | 50 | HA | VAL | 227 | 9.616 | 3.561 | −18.223 | 1.00 | 0.00 | A |
| ATOM | 51 | CB | VAL | 227 | 9.154 | 2.382 | −19.957 | 1.00 | 0.00 | A |
| ATOM | 52 | HB | VAL | 227 | 9.009 | 1.339 | −20.196 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 53 | CG1 | VAL | 227 | 7.894 | 3.169 | −20.322 | 1.00 | 0.00 | A |
|---|---|---|---|---|---|---|---|---|---|---|
| ATOM | 54 | HG11 | VAL | 227 | 7.345 | 2.636 | −21.083 | 1.00 | 0.00 | A |
| ATOM | 55 | HG12 | VAL | 227 | 8.172 | 4.144 | −20.695 | 1.00 | 0.00 | A |
| ATOM | 56 | HG13 | VAL | 227 | 7.274 | 3.283 | −19.444 | 1.00 | 0.00 | A |
| ATOM | 57 | CG2 | VAL | 227 | 10.343 | 2.930 | −20.751 | 1.00 | 0.00 | A |
| ATOM | 58 | HG21 | VAL | 227 | 10.331 | 4.010 | −20.720 | 1.00 | 0.00 | A |
| ATOM | 59 | HG22 | VAL | 227 | 10.274 | 2.598 | −21.775 | 1.00 | 0.00 | A |
| ATOM | 60 | HG23 | VAL | 227 | 11.263 | 2.567 | −20.316 | 1.00 | 0.00 | A |
| ATOM | 61 | C | VAL | 227 | 8.254 | 1.992 | −17.644 | 1.00 | 0.00 | A |
| ATOM | 62 | O | VAL | 227 | 7.407 | 1.281 | −18.148 | 1.00 | 0.00 | A |
| ATOM | 63 | N | LYS | 228 | 8.191 | 2.331 | −16.387 | 1.00 | 0.00 | A |
| ATOM | 64 | HN | LYS | 228 | 8.869 | 2.918 | −16.003 | 1.00 | 0.00 | A |
| ATOM | 65 | CA | LYS | 228 | 7.069 | 1.841 | −15.540 | 1.00 | 0.00 | A |
| ATOM | 66 | HA | LYS | 228 | 6.902 | 0.793 | −15.706 | 1.00 | 0.00 | A |
| ATOM | 67 | CB | LYS | 228 | 7.535 | 2.081 | −14.102 | 1.00 | 0.00 | A |
| ATOM | 68 | HB1 | LYS | 228 | 6.827 | 1.643 | −13.419 | 1.00 | 0.00 | A |
| ATOM | 69 | HB2 | LYS | 228 | 7.610 | 3.143 | −13.917 | 1.00 | 0.00 | A |
| ATOM | 70 | CG | LYS | 228 | 8.903 | 1.422 | −13.894 | 1.00 | 0.00 | A |
| ATOM | 71 | HG1 | LYS | 228 | 9.613 | 1.836 | −14.593 | 1.00 | 0.00 | A |
| ATOM | 72 | HG2 | LYS | 228 | 8.818 | 0.357 | −14.054 | 1.00 | 0.00 | A |
| ATOM | 73 | CD | LYS | 228 | 9.387 | 1.684 | −12.464 | 1.00 | 0.00 | A |
| ATOM | 74 | HD1 | LYS | 228 | 8.685 | 1.261 | −11.762 | 1.00 | 0.00 | A |
| ATOM | 75 | HD2 | LYS | 228 | 9.464 | 2.751 | −12.300 | 1.00 | 0.00 | A |
| ATOM | 76 | CE | LYS | 228 | 10.761 | 1.036 | −12.261 | 1.00 | 0.00 | A |
| ATOM | 77 | HE1 | LYS | 228 | 10.706 | −0.025 | −12.441 | 1.00 | 0.00 | A |
| ATOM | 78 | HE2 | LYS | 228 | 11.124 | 1.233 | −11.261 | 1.00 | 0.00 | A |
| ATOM | 79 | NZ | LYS | 228 | 11.643 | 1.682 | −13.274 | 1.00 | 0.00 | A |
| ATOM | 80 | HZ1 | LYS | 228 | 11.510 | 1.220 | −14.194 | 1.00 | 0.00 | A |
| ATOM | 81 | HZ2 | LYS | 228 | 12.637 | 1.587 | −12.977 | 1.00 | 0.00 | A |
| ATOM | 82 | HZ3 | LYS | 228 | 11.399 | 2.689 | −13.355 | 1.00 | 0.00 | A |
| ATOM | 83 | C | LYS | 228 | 5.800 | 2.646 | −15.862 | 1.00 | 0.00 | A |
| ATOM | 84 | O | LYS | 228 | 4.777 | 2.097 | −16.217 | 1.00 | 0.00 | A |
| ATOM | 85 | N | GLN | 229 | 5.867 | 3.942 | −15.737 | 1.00 | 0.00 | A |
| ATOM | 86 | HN | GLN | 229 | 6.697 | 4.352 | −15.447 | 1.00 | 0.00 | A |
| ATOM | 87 | CA | GLN | 229 | 4.671 | 4.794 | −16.037 | 1.00 | 0.00 | A |
| ATOM | 88 | HA | GLN | 229 | 4.211 | 4.466 | −16.956 | 1.00 | 0.00 | A |
| ATOM | 89 | CB | GLN | 229 | 3.682 | 4.596 | −14.866 | 1.00 | 0.00 | A |
| ATOM | 90 | HB1 | GLN | 229 | 3.470 | 3.542 | −14.756 | 1.00 | 0.00 | A |
| ATOM | 91 | HB2 | GLN | 229 | 2.762 | 5.121 | −15.086 | 1.00 | 0.00 | A |
| ATOM | 92 | CG | GLN | 229 | 4.267 | 5.134 | −13.544 | 1.00 | 0.00 | A |
| ATOM | 93 | HG1 | GLN | 229 | 3.488 | 5.164 | −12.791 | 1.00 | 0.00 | A |
| ATOM | 94 | HG2 | GLN | 229 | 4.652 | 6.130 | −13.700 | 1.00 | 0.00 | A |
| ATOM | 95 | CD | GLN | 229 | 5.393 | 4.228 | −13.065 | 1.00 | 0.00 | A |
| ATOM | 96 | OE1 | GLN | 229 | 5.274 | 3.025 | −13.122 | 1.00 | 0.00 | A |
| ATOM | 97 | NE2 | GLN | 229 | 6.481 | 4.756 | −12.570 | 1.00 | 0.00 | A |
| ATOM | 98 | HE21 | GLN | 229 | 6.568 | 5.729 | −12.507 | 1.00 | 0.00 | A |
| ATOM | 99 | HE22 | GLN | 229 | 7.209 | 4.180 | −12.263 | 1.00 | 0.00 | A |
| ATOM | 100 | C | GLN | 229 | 5.077 | 6.278 | −16.157 | 1.00 | 0.00 | A |
| ATOM | 101 | O | GLN | 229 | 4.438 | 7.149 | −15.599 | 1.00 | 0.00 | A |
| ATOM | 102 | N | LEU | 230 | 6.140 | 6.574 | −16.883 | 1.00 | 0.00 | A |
| ATOM | 103 | HN | LEU | 230 | 6.643 | 5.866 | −17.325 | 1.00 | 0.00 | A |
| ATOM | 104 | CA | LEU | 230 | 6.570 | 8.004 | −17.029 | 1.00 | 0.00 | A |
| ATOM | 105 | HA | LEU | 230 | 5.867 | 8.649 | −16.541 | 1.00 | 0.00 | A |
| ATOM | 106 | CB | LEU | 230 | 7.948 | 8.124 | −16.347 | 1.00 | 0.00 | A |
| ATOM | 107 | HB1 | LEU | 230 | 8.338 | 9.119 | −16.504 | 1.00 | 0.00 | A |
| ATOM | 108 | HB2 | LEU | 230 | 8.625 | 7.404 | −16.785 | 1.00 | 0.00 | A |
| ATOM | 109 | CG | LEU | 230 | 7.836 | 7.857 | −14.842 | 1.00 | 0.00 | A |
| ATOM | 110 | HG | LEU | 230 | 7.001 | 8.413 | −14.440 | 1.00 | 0.00 | A |
| ATOM | 111 | CD1 | LEU | 230 | 7.620 | 6.372 | −14.597 | 1.00 | 0.00 | A |
| ATOM | 112 | HD11 | LEU | 230 | 8.252 | 6.045 | −13.785 | 1.00 | 0.00 | A |
| ATOM | 113 | HD12 | LEU | 230 | 7.873 | 5.824 | −15.492 | 1.00 | 0.00 | A |
| ATOM | 114 | HD13 | LEU | 230 | 6.590 | 6.196 | −14.344 | 1.00 | 0.00 | A |
| ATOM | 115 | CD2 | LEU | 230 | 9.126 | 8.301 | −14.149 | 1.00 | 0.00 | A |
| ATOM | 116 | HD21 | LEU | 230 | 9.899 | 7.567 | −14.324 | 1.00 | 0.00 | A |
| ATOM | 117 | HD22 | LEU | 230 | 8.952 | 8.392 | −13.088 | 1.00 | 0.00 | A |
| ATOM | 118 | HD23 | LEU | 230 | 9.438 | 9.255 | −14.547 | 1.00 | 0.00 | A |
| ATOM | 119 | C | LEU | 230 | 6.702 | 8.392 | −18.512 | 1.00 | 0.00 | A |
| ATOM | 120 | O | LEU | 230 | 7.579 | 9.150 | −18.881 | 1.00 | 0.00 | A |
| ATOM | 121 | N | ALA | 231 | 5.849 | 7.891 | −19.365 | 1.00 | 0.00 | A |
| ATOM | 122 | HN | ALA | 231 | 5.155 | 7.278 | −19.062 | 1.00 | 0.00 | A |
| ATOM | 123 | CA | ALA | 231 | 5.966 | 8.263 | −20.818 | 1.00 | 0.00 | A |
| ATOM | 124 | HA | ALA | 231 | 6.172 | 9.303 | −20.910 | 1.00 | 0.00 | A |
| ATOM | 125 | CB | ALA | 231 | 7.154 | 7.452 | −21.336 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 126 | HB1  | ALA | 231 | 7.875  | 8.117  | −21.788 | 1.00 | 0.00 | A |
| ---- | --- | ---- | --- | --- | ------ | ------ | ------- | ---- | ---- | - |
| ATOM | 127 | HB2  | ALA | 231 | 6.809  | 6.740  | −22.072 | 1.00 | 0.00 | A |
| ATOM | 128 | HB3  | ALA | 231 | 7.615  | 6.923  | −20.514 | 1.00 | 0.00 | A |
| ATOM | 129 | C    | ALA | 231 | 4.696  | 7.910  | −21.607 | 1.00 | 0.00 | A |
| ATOM | 130 | O    | ALA | 231 | 4.703  | 7.894  | −22.820 | 1.00 | 0.00 | A |
| ATOM | 131 | N    | ASP | 232 | 3.613  | 7.671  | −20.931 | 1.00 | 0.00 | A |
| ATOM | 132 | HN   | ASP | 232 | 3.630  | 7.745  | −19.963 | 1.00 | 0.00 | A |
| ATOM | 133 | CA   | ASP | 232 | 2.328  | 7.319  | −21.634 | 1.00 | 0.00 | A |
| ATOM | 134 | HA   | ASP | 232 | 2.211  | 7.904  | −22.500 | 1.00 | 0.00 | A |
| ATOM | 135 | CB   | ASP | 232 | 2.427  | 5.824  | −22.000 | 1.00 | 0.00 | A |
| ATOM | 136 | HB1  | ASP | 232 | 1.498  | 5.505  | −22.447 | 1.00 | 0.00 | A |
| ATOM | 137 | HB2  | ASP | 232 | 2.606  | 5.250  | −21.103 | 1.00 | 0.00 | A |
| ATOM | 138 | CG   | ASP | 232 | 3.570  | 5.586  | −22.987 | 1.00 | 0.00 | A |
| ATOM | 139 | OD1  | ASP | 232 | 4.695  | 5.446  | −22.538 | 1.00 | 0.00 | A |
| ATOM | 140 | OD2  | ASP | 232 | 3.301  | 5.553  | −24.177 | 1.00 | 0.00 | A |
| ATOM | 141 | C    | ASP | 232 | 1.158  | 7.535  | −20.705 | 1.00 | 0.00 | A |
| ATOM | 142 | O    | ASP | 232 | 0.117  | 8.022  | −21.088 | 1.00 | 0.00 | A |
| ATOM | 143 | N    | ASP | 233 | 1.323  | 7.162  | −19.499 | 1.00 | 0.00 | A |
| ATOM | 144 | HN   | ASP | 233 | 2.170  | 6.774  | −19.242 | 1.00 | 0.00 | A |
| ATOM | 145 | CA   | ASP | 233 | 0.233  | 7.329  | −18.498 | 1.00 | 0.00 | A |
| ATOM | 146 | HA   | ASP | 233 | −0.686 | 6.906  | −18.867 | 1.00 | 0.00 | A |
| ATOM | 147 | CB   | ASP | 233 | 0.705  | 6.558  | −17.262 | 1.00 | 0.00 | A |
| ATOM | 148 | HB1  | ASP | 233 | −0.038 | 6.637  | −16.483 | 1.00 | 0.00 | A |
| ATOM | 149 | HB2  | ASP | 233 | 1.640  | 6.972  | −16.913 | 1.00 | 0.00 | A |
| ATOM | 150 | CG   | ASP | 233 | 0.902  | 5.064  | −17.625 | 1.00 | 0.00 | A |
| ATOM | 151 | OD1  | ASP | 233 | 1.742  | 4.808  | −18.466 | 1.00 | 0.00 | A |
| ATOM | 152 | OD2  | ASP | 233 | 0.210  | 4.255  | −17.055 | 1.00 | 0.00 | A |
| ATOM | 153 | C    | ASP | 233 | 0.045  | 6.611  | −16.170 | 1.00 | 0.00 | A |
| ATOM | 154 | O    | ASP | 233 | −0.995 | 9.226  | −17.712 | 1.00 | 0.00 | A |
| ATOM | 155 | N    | ARG | 234 | 1.042  | 9.612  | −18.406 | 1.00 | 0.00 | A |
| ATOM | 156 | HN   | ARG | 234 | 1.871  | 9.262  | −18.783 | 1.00 | 0.00 | A |
| ATOM | 157 | CA   | ARG | 234 | 0.905  | 11.068 | −18.101 | 1.00 | 0.00 | A |
| ATOM | 158 | HA   | ARG | 234 | 0.487  | 11.193 | −17.115 | 1.00 | 0.00 | A |
| ATOM | 159 | CB   | ARG | 234 | 2.330  | 11.639 | −18.128 | 1.00 | 0.00 | A |
| ATOM | 160 | HB1  | ARG | 234 | 2.933  | 11.117 | −17.405 | 1.00 | 0.00 | A |
| ATOM | 161 | HB2  | ARG | 234 | 2.296  | 12.687 | −17.872 | 1.00 | 0.00 | A |
| ATOM | 162 | CG   | ARG | 234 | 2.956  | 11.480 | −19.515 | 1.00 | 0.00 | A |
| ATOM | 163 | HG1  | ARG | 234 | 2.406  | 12.073 | −20.229 | 1.00 | 0.00 | A |
| ATOM | 164 | HG2  | ARG | 234 | 2.930  | 10.440 | −19.812 | 1.00 | 0.00 | A |
| ATOM | 165 | CD   | ARG | 234 | 4.407  | 11.970 | −19.465 | 1.00 | 0.00 | A |
| ATOM | 166 | HD1  | ARG | 234 | 4.974  | 11.392 | −18.754 | 1.00 | 0.00 | A |
| ATOM | 167 | HD2  | ARG | 234 | 4.437  | 13.020 | −19.208 | 1.00 | 0.00 | A |
| ATOM | 168 | NE   | ARG | 234 | 4.940  | 11.756 | −20.837 | 1.00 | 0.00 | A |
| ATOM | 169 | HE   | ARG | 234 | 4.375  | 11.346 | −21.524 | 1.00 | 0.00 | A |
| ATOM | 170 | CZ   | ARG | 234 | 6.165  | 12.114 | −21.124 | 1.00 | 0.00 | A |
| ATOM | 171 | NH1  | ARG | 234 | 6.801  | 11.536 | −22.106 | 1.00 | 0.00 | A |
| ATOM | 172 | HH11 | ARG | 234 | 6.353  | 10.818 | −22.638 | 1.00 | 0.00 | A |
| ATOM | 173 | HH12 | ARG | 234 | 7.737  | 11.811 | −22.327 | 1.00 | 0.00 | A |
| ATOM | 174 | NH2  | ARG | 234 | 6.753  | 13.051 | −20.428 | 1.00 | 0.00 | A |
| ATOM | 175 | HH21 | ARG | 234 | 6.267  | 13.494 | −19.675 | 1.00 | 0.00 | A |
| ATOM | 176 | HH22 | ARG | 234 | 7.689  | 13.325 | −20.649 | 1.00 | 0.00 | A |
| ATOM | 177 | C    | ARG | 234 | 0.002  | 11.753 | −19.136 | 1.00 | 0.00 | A |
| ATOM | 178 | O    | ARG | 234 | −0.910 | 12.451 | −18.788 | 1.00 | 0.00 | A |
| ATOM | 179 | N    | THR | 235 | 0.240  | 11.548 | −20.399 | 1.00 | 0.00 | A |
| ATOM | 180 | HN   | THR | 235 | 0.963  | 10.952 | −20.672 | 1.00 | 0.00 | A |
| ATOM | 181 | CA   | THR | 235 | −0.619 | 12.199 | −21.437 | 1.00 | 0.00 | A |
| ATOM | 182 | HA   | THR | 235 | −0.842 | 13.214 | −21.169 | 1.00 | 0.00 | A |
| ATOM | 183 | CB   | THR | 235 | 0.217  | 12.146 | −22.720 | 1.00 | 0.00 | A |
| ATOM | 184 | HB   | THR | 235 | 0.490  | 11.115 | −22.930 | 1.00 | 0.00 | A |
| ATOM | 185 | OG1  | THR | 235 | 1.396  | 12.918 | −22.544 | 1.00 | 0.00 | A |
| ATOM | 186 | HG1  | THR | 235 | 2.086  | 12.336 | −22.219 | 1.00 | 0.00 | A |
| ATOM | 187 | CG2  | THR | 235 | −0.593 | 12.700 | −23.893 | 1.00 | 0.00 | A |
| ATOM | 188 | HG21 | THR | 235 | 0.037  | 13.339 | −24.495 | 1.00 | 0.00 | A |
| ATOM | 189 | HG22 | THR | 235 | −1.430 | 13.270 | −23.518 | 1.00 | 0.00 | A |
| ATOM | 190 | HG23 | THR | 235 | −0.957 | 11.882 | −24.497 | 1.00 | 0.00 | A |
| ATOM | 191 | C    | THR | 235 | −1.902 | 11.414 | −21.595 | 1.00 | 0.00 | A |
| ATOM | 192 | O    | THR | 235 | −2.913 | 11.922 | −22.036 | 1.00 | 0.00 | A |
| ATOM | 193 | N    | LEU | 236 | −1.864 | 10.182 | −21.238 | 1.00 | 0.00 | A |
| ATOM | 194 | HN   | LEU | 236 | −1.031 | 9.803  | −20.885 | 1.00 | 0.00 | A |
| ATOM | 195 | CA   | LEU | 236 | −3.065 | 9.338  | −21.354 | 1.00 | 0.00 | A |
| ATOM | 196 | HA   | LEU | 236 | −3.460 | 9.366  | −22.323 | 1.00 | 0.00 | A |
| ATOM | 197 | CB   | LEU | 236 | −2.582 | 7.948  | −21.039 | 1.00 | 0.00 | A |
| ATOM | 198 | HB1  | LEU | 236 | −2.095 | 7.941  | −20.076 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 199 | HB2  | LEU | 236 | −1.890  | 7.621  | −21.802 | 1.00 | 0.00 | A |
|------|-----|------|-----|-----|---------|--------|---------|------|------|---|
| ATOM | 200 | CG   | LEU | 236 | −3.774  | 7.036  | −21.006 | 1.00 | 0.00 | A |
| ATOM | 201 | HG   | LEU | 236 | −4.529  | 7.491  | −20.365 | 1.00 | 0.00 | A |
| ATOM | 202 | CD1  | LEU | 236 | −4.342  | 6.876  | −22.421 | 1.00 | 0.00 | A |
| ATOM | 203 | HD11 | LEU | 236 | −5.259  | 6.306  | −22.379 | 1.00 | 0.00 | A |
| ATOM | 204 | HD12 | LEU | 236 | −3.625  | 6.358  | −23.041 | 1.00 | 0.00 | A |
| ATOM | 205 | HD13 | LEU | 236 | −4.542  | 7.850  | −22.841 | 1.00 | 0.00 | A |
| ATOM | 206 | CD2  | LEU | 236 | −3.356  | 5.684  | −20.449 | 1.00 | 0.00 | A |
| ATOM | 207 | HD21 | LEU | 236 | −2.510  | 5.311  | −21.012 | 1.00 | 0.00 | A |
| ATOM | 208 | HD22 | LEU | 236 | −4.177  | 4.992  | −20.531 | 1.00 | 0.00 | A |
| ATOM | 209 | HD23 | LEU | 236 | −3.076  | 5.794  | −19.413 | 1.00 | 0.00 | A |
| ATOM | 210 | C    | LEU | 236 | −4.124  | 9.753  | −20.366 | 1.00 | 0.00 | A |
| ATOM | 211 | O    | LEU | 236 | −5.280  | 9.907  | −20.710 | 1.00 | 0.00 | A |
| ATOM | 212 | N    | LEU | 237 | −3.763  | 9.938  | −19.148 | 1.00 | 0.00 | A |
| ATOM | 213 | HN   | LEU | 237 | −2.829  | 9.814  | −18.882 | 1.00 | 0.00 | A |
| ATOM | 214 | CA   | LEU | 237 | −4.777  | 10.340 | −18.152 | 1.00 | 0.00 | A |
| ATOM | 215 | HA   | LEU | 237 | −5.699  | 9.852  | −18.376 | 1.00 | 0.00 | A |
| ATOM | 216 | CB   | LEU | 237 | −4.237  | 9.816  | −16.840 | 1.00 | 0.00 | A |
| ATOM | 217 | HB1  | LEU | 237 | −4.991  | 9.883  | −16.079 | 1.00 | 0.00 | A |
| ATOM | 218 | HB2  | LEU | 237 | −3.370  | 10.396 | −16.547 | 1.00 | 0.00 | A |
| ATOM | 219 | CG   | LEU | 237 | −3.831  | 8.329  | −17.036 | 1.00 | 0.00 | A |
| ATOM | 220 | HG   | LEU | 237 | −2.899  | 8.292  | −17.578 | 1.00 | 0.00 | A |
| ATOM | 221 | CD1  | LEU | 237 | −3.629  | 7.689  | −15.695 | 1.00 | 0.00 | A |
| ATOM | 222 | HD11 | LEU | 237 | −4.544  | 7.749  | −15.133 | 1.00 | 0.00 | A |
| ATOM | 223 | HD12 | LEU | 237 | −2.845  | 8.207  | −15.172 | 1.00 | 0.00 | A |
| ATOM | 224 | HD13 | LEU | 237 | −3.355  | 6.658  | −15.832 | 1.00 | 0.00 | A |
| ATOM | 225 | CD2  | LEU | 237 | −4.916  | 7.551  | −17.840 | 1.00 | 0.00 | A |
| ATOM | 226 | HD21 | LEU | 237 | −4.529  | 6.585  | −18.124 | 1.00 | 0.00 | A |
| ATOM | 227 | HD22 | LEU | 237 | −5.173  | 8.100  | −18.733 | 1.00 | 0.00 | A |
| ATOM | 228 | HD23 | LEU | 237 | −5.795  | 7.423  | −17.237 | 1.00 | 0.00 | A |
| ATOM | 229 | C    | LEU | 237 | −4.999  | 11.838 | −18.181 | 1.00 | 0.00 | A |
| ATOM | 230 | O    | LEU | 237 | −5.506  | 12.438 | −17.264 | 1.00 | 0.00 | A |
| ATOM | 231 | N    | MET | 238 | −4.571  | 12.430 | −19.211 | 1.00 | 0.00 | A |
| ATOM | 232 | HN   | MET | 238 | −4.251  | 11.912 | −19.935 | 1.00 | 0.00 | A |
| ATOM | 233 | CA   | MET | 238 | −4.732  | 13.873 | −19.368 | 1.00 | 0.00 | A |
| ATOM | 234 | HA   | MET | 238 | −4.947  | 14.314 | −18.418 | 1.00 | 0.00 | A |
| ATOM | 235 | CB   | MET | 238 | −3.435  | 14.420 | −19.954 | 1.00 | 0.00 | A |
| ATOM | 236 | HB1  | MET | 238 | −3.634  | 15.339 | −20.481 | 1.00 | 0.00 | A |
| ATOM | 237 | HB2  | MET | 238 | −3.011  | 13.694 | −20.635 | 1.00 | 0.00 | A |
| ATOM | 238 | CG   | MET | 238 | −2.452  | 14.691 | −18.815 | 1.00 | 0.00 | A |
| ATOM | 239 | HG1  | MET | 238 | −2.346  | 13.809 | −18.212 | 1.00 | 0.00 | A |
| ATOM | 240 | HG2  | MET | 238 | −2.834  | 15.495 | −18.203 | 1.00 | 0.00 | A |
| ATOM | 241 | SD   | MET | 238 | −0.846  | 15.171 | −19.497 | 1.00 | 0.00 | A |
| ATOM | 242 | CE   | MET | 238 | −0.091  | 15.713 | −17.944 | 1.00 | 0.00 | A |
| ATOM | 243 | HE1  | MET | 238 | −0.170  | 14.921 | −17.211 | 1.00 | 0.00 | A |
| ATOM | 244 | HE2  | MET | 238 | −0.603  | 16.588 | −17.581 | 1.00 | 0.00 | A |
| ATOM | 245 | HE3  | MET | 238 |  0.951  | 15.951 | −18.115 | 1.00 | 0.00 | A |
| ATOM | 246 | C    | MET | 238 | −5.890  | 14.022 | −20.292 | 1.00 | 0.00 | A |
| ATOM | 247 | O    | MET | 238 | −6.738  | 14.851 | −20.136 | 1.00 | 0.00 | A |
| ATOM | 248 | N    | ALA | 239 | −5.842  | 13.245 | −21.340 | 1.00 | 0.00 | A |
| ATOM | 249 | HN   | ALA | 239 | −5.075  | 12.653 | −21.457 | 1.00 | 0.00 | A |
| ATOM | 250 | CA   | ALA | 239 | −6.897  | 13.242 | −22.354 | 1.00 | 0.00 | A |
| ATOM | 251 | HA   | ALA | 239 | −7.398  | 14.192 | −22.399 | 1.00 | 0.00 | A |
| ATOM | 252 | CB   | ALA | 239 | −6.172  | 12.942 | −23.667 | 1.00 | 0.00 | A |
| ATOM | 253 | HB1  | ALA | 239 | −6.206  | 11.878 | −23.860 | 1.00 | 0.00 | A |
| ATOM | 254 | HB2  | ALA | 239 | −5.141  | 13.259 | −23.590 | 1.00 | 0.00 | A |
| ATOM | 255 | HB3  | ALA | 239 | −6.652  | 13.470 | −24.474 | 1.00 | 0.00 | A |
| ATOM | 256 | C    | ALA | 239 | −7.869  | 12.109 | −22.006 | 1.00 | 0.00 | A |
| ATOM | 257 | O    | ALA | 239 | −8.592  | 11.615 | −22.850 | 1.00 | 0.00 | A |
| ATOM | 258 | N    | GLY | 240 | −7.888  | 11.685 | −20.752 | 1.00 | 0.00 | A |
| ATOM | 259 | HN   | GLY | 240 | −7.332  | 12.118 | −20.063 | 1.00 | 0.00 | A |
| ATOM | 260 | CA   | GLY | 240 | −8.784  | 10.603 | −20.349 | 1.00 | 0.00 | A |
| ATOM | 261 | HA1  | GLY | 240 | −8.276  | 9.652  | −20.454 | 1.00 | 0.00 | A |
| ATOM | 262 | HA2  | GLY | 240 | −9.673  | 10.614 | −20.951 | 1.00 | 0.00 | A |
| ATOM | 263 | C    | GLY | 240 | −9.132  | 10.811 | −18.909 | 1.00 | 0.00 | A |
| ATOM | 264 | O    | GLY | 240 | −10.263 | 10.672 | −18.503 | 1.00 | 0.00 | A |
| ATOM | 265 | N    | VAL | 241 | −8.163  | 11.088 | −18.099 | 1.00 | 0.00 | A |
| ATOM | 266 | HN   | VAL | 241 | −7.243  | 11.192 | −18.425 | 1.00 | 0.00 | A |
| ATOM | 267 | CA   | VAL | 241 | −8.479  | 11.294 | −16.704 | 1.00 | 0.00 | A |
| ATOM | 268 | HA   | VAL | 241 | −9.389  | 10.821 | −16.523 | 1.00 | 0.00 | A |
| ATOM | 269 | CB   | VAL | 241 | −7.368  | 10.580 | −15.915 | 1.00 | 0.00 | A |
| ATOM | 270 | HB   | VAL | 241 | −6.440  | 11.081 | −16.057 | 1.00 | 0.00 | A |
| ATOM | 271 | CG1  | VAL | 241 | −7.709  | 10.549 | −14.436 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 272 | HG11 | VAL | 241 | −7.103  | 9.793  | −13.948 | 1.00 | 0.00 | A |
|------|-----|------|-----|-----|---------|--------|---------|------|------|---|
| ATOM | 273 | HG12 | VAL | 241 | −8.753  | 10.302 | −14.315 | 1.00 | 0.00 | A |
| ATOM | 274 | HG13 | VAL | 241 | −7.509  | 11.507 | −14.001 | 1.00 | 0.00 | A |
| ATOM | 275 | CG2  | VAL | 241 | −7.260  | 9.133  | −16.408 | 1.00 | 0.00 | A |
| ATOM | 276 | HG21 | VAL | 241 | −6.419  | 8.653  | −15.933 | 1.00 | 0.00 | A |
| ATOM | 277 | HG22 | VAL | 241 | −7.130  | 9.121  | −17.475 | 1.00 | 0.00 | A |
| ATOM | 278 | HG23 | VAL | 241 | −8.165  | 8.599  | −16.153 | 1.00 | 0.00 | A |
| ATOM | 279 | C    | VAL | 241 | −8.619  | 12.823 | −16.402 | 1.00 | 0.00 | A |
| ATOM | 280 | O    | VAL | 241 | −9.328  | 13.229 | −15.502 | 1.00 | 0.00 | A |
| ATOM | 281 | N    | SER | 242 | −7.906  | 13.661 | −17.126 | 1.00 | 0.00 | A |
| ATOM | 282 | HN   | SER | 242 | −7.329  | 13.321 | −17.836 | 1.00 | 0.00 | A |
| ATOM | 283 | CA   | SER | 242 | −8.000  | 15.149 | −16.883 | 1.00 | 0.00 | A |
| ATOM | 284 | HA   | SER | 242 | −8.303  | 15.337 | −15.866 | 1.00 | 0.00 | A |
| ATOM | 285 | CB   | SER | 242 | −6.589  | 15.678 | −17.100 | 1.00 | 0.00 | A |
| ATOM | 286 | HB1  | SER | 242 | −6.304  | 15.516 | −18.128 | 1.00 | 0.00 | A |
| ATOM | 287 | HB2  | SER | 242 | −5.903  | 15.164 | −16.453 | 1.00 | 0.00 | A |
| ATOM | 288 | CG   | SER | 242 | −6.559  | 17.070 | −16.807 | 1.00 | 0.00 | A |
| ATOM | 289 | HG   | SER | 242 | −6.529  | 17.547 | −17.640 | 1.00 | 0.00 | A |
| ATOM | 290 | C    | SER | 242 | −8.984  | 15.849 | −17.872 | 1.00 | 0.00 | A |
| ATOM | 291 | O    | SER | 242 | −9.673  | 16.775 | −17.525 | 1.00 | 0.00 | A |
| ATOM | 292 | N    | HIS | 243 | −9.019  | 15.418 | −19.106 | 1.00 | 0.00 | A |
| ATOM | 293 | HN   | HIS | 243 | −8.497  | 14.648 | −19.358 | 1.00 | 0.00 | A |
| ATOM | 294 | CA   | HIS | 243 | −9.942  | 16.057 | −20.115 | 1.00 | 0.00 | A |
| ATOM | 295 | HA   | HIS | 243 | −10.092 | 17.088 | −19.868 | 1.00 | 0.00 | A |
| ATOM | 296 | CB   | HIS | 243 | −9.188  | 15.954 | −21.447 | 1.00 | 0.00 | A |
| ATOM | 297 | HB1  | HIS | 243 | −9.033  | 14.913 | −21.691 | 1.00 | 0.00 | A |
| ATOM | 298 | HB2  | HIS | 243 | −8.231  | 16.447 | −21.356 | 1.00 | 0.00 | A |
| ATOM | 299 | CG   | HIS | 243 | −9.986  | 16.612 | −22.546 | 1.00 | 0.00 | A |
| ATOM | 300 | ND1  | HIS | 243 | −11.262 | 16.191 | −22.902 | 1.00 | 0.00 | A |
| ATOM | 301 | HD1  | HIS | 243 | −11.751 | 15.438 | −22.517 | 1.00 | 0.00 | A |
| ATOM | 302 | CD2  | HIS | 243 | −9.705  | 17.678 | −23.365 | 1.00 | 0.00 | A |
| ATOM | 303 | HD2  | HIS | 243 | −8.789  | 18.249 | −23.348 | 1.00 | 0.00 | A |
| ATOM | 304 | CE1  | HIS | 243 | −11.692 | 16.995 | −23.893 | 1.00 | 0.00 | A |
| ATOM | 305 | HE1  | HIS | 243 | −12.654 | 16.901 | −24.375 | 1.00 | 0.00 | A |
| ATOM | 306 | NE2  | HIS | 243 | −10.781 | 17.917 | −24.212 | 1.00 | 0.00 | A |
| ATOM | 307 | C    | HIS | 243 | −11.278 | 15.319 | −20.180 | 1.00 | 0.00 | A |
| ATOM | 308 | O    | HIS | 243 | −12.308 | 15.866 | −20.506 | 1.00 | 0.00 | A |
| ATOM | 309 | N    | ASP | 244 | −11.256 | 14.084 | −19.927 | 1.00 | 0.00 | A |
| ATOM | 310 | HN   | ASP | 244 | −10.464 | 13.687 | −19.609 | 1.00 | 0.00 | A |
| ATOM | 311 | CA   | ASP | 244 | −12.484 | 13.310 | −19.968 | 1.00 | 0.00 | A |
| ATOM | 312 | HA   | ASP | 244 | −13.209 | 13.797 | −20.600 | 1.00 | 0.00 | A |
| ATOM | 313 | CB   | ASP | 244 | −12.110 | 11.951 | −20.552 | 1.00 | 0.00 | A |
| ATOM | 314 | HB1  | ASP | 244 | −11.375 | 11.493 | −19.943 | 1.00 | 0.00 | A |
| ATOM | 315 | HB2  | ASP | 244 | −11.717 | 12.084 | −21.548 | 1.00 | 0.00 | A |
| ATOM | 316 | CG   | ASP | 244 | −13.348 | 11.057 | −20.612 | 1.00 | 0.00 | A |
| ATOM | 317 | OD1  | ASP | 244 | −14.342 | 11.488 | −21.174 | 1.00 | 0.00 | A |
| ATOM | 318 | OD2  | ASP | 244 | −13.277 | 9.953  | −20.099 | 1.00 | 0.00 | A |
| ATOM | 319 | C    | ASP | 244 | −13.000 | 13.210 | −18.564 | 1.00 | 0.00 | A |
| ATOM | 320 | O    | ASP | 244 | −14.182 | 13.274 | −18.329 | 1.00 | 0.00 | A |
| ATOM | 321 | N    | LEU | 245 | −12.104 | 13.028 | −17.599 | 1.00 | 0.00 | A |
| ATOM | 322 | HN   | LEU | 245 | −11.081 | 12.942 | −17.830 | 1.00 | 0.00 | A |
| ATOM | 323 | CA   | LEU | 245 | −12.586 | 12.923 | −16.167 | 1.00 | 0.00 | A |
| ATOM | 324 | HA   | LEU | 245 | −13.587 | 12.520 | −16.163 | 1.00 | 0.00 | A |
| ATOM | 325 | CB   | LEU | 245 | −11.657 | 11.921 | −15.505 | 1.00 | 0.00 | A |
| ATOM | 326 | HB1  | LEU | 245 | −11.443 | 12.230 | −14.496 | 1.00 | 0.00 | A |
| ATOM | 327 | HB2  | LEU | 245 | −10.759 | 11.871 | −16.063 | 1.00 | 0.00 | A |
| ATOM | 328 | CG   | LEU | 245 | −12.311 | 10.537 | −15.489 | 1.00 | 0.00 | A |
| ATOM | 329 | HG   | LEU | 245 | −11.638 | 9.828  | −15.026 | 1.00 | 0.00 | A |
| ATOM | 330 | CD1  | LEU | 245 | −13.610 | 10.602 | −14.685 | 1.00 | 0.00 | A |
| ATOM | 331 | HD11 | LEU | 245 | −14.445 | 10.368 | −15.328 | 1.00 | 0.00 | A |
| ATOM | 332 | HD12 | LEU | 245 | −13.734 | 11.596 | −14.282 | 1.00 | 0.00 | A |
| ATOM | 333 | HD13 | LEU | 245 | −13.568 | 9.889  | −13.875 | 1.00 | 0.00 | A |
| ATOM | 334 | CD2  | LEU | 245 | −12.620 | 10.090 | −16.923 | 1.00 | 0.00 | A |
| ATOM | 335 | HD21 | LEU | 245 | −12.209 | 10.799 | −17.618 | 1.00 | 0.00 | A |
| ATOM | 336 | HD22 | LEU | 245 | −13.688 | 10.032 | −17.060 | 1.00 | 0.00 | A |
| ATOM | 337 | HD23 | LEU | 245 | −12.182 | 9.118  | −17.098 | 1.00 | 0.00 | A |
| ATOM | 338 | C    | LEU | 245 | −12.589 | 14.290 | −15.405 | 1.00 | 0.00 | A |
| ATOM | 339 | O    | LEU | 245 | −13.467 | 14.539 | −14.604 | 1.00 | 0.00 | A |
| ATOM | 340 | N    | ARG | 246 | −11.632 | 15.172 | −15.633 | 1.00 | 0.00 | A |
| ATOM | 341 | HN   | ARG | 246 | −10.959 | 15.003 | −16.315 | 1.00 | 0.00 | A |
| ATOM | 342 | CA   | ARG | 246 | −11.651 | 16.497 | −14.875 | 1.00 | 0.00 | A |
| ATOM | 343 | HA   | ARG | 246 | −12.190 | 16.368 | −13.961 | 1.00 | 0.00 | A |
| ATOM | 344 | CB   | ARG | 246 | −10.189 | 16.856 | −14.573 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 345 | HB1 | ARG | 246 | −9.640 | 16.934 | −15.483 | 1.00 | 0.00 | A |
|---|---|---|---|---|---|---|---|---|---|---|
| ATOM | 346 | HB2 | ARG | 246 | −9.751 | 16.088 | −13.953 | 1.00 | 0.00 | A |
| ATOM | 347 | CG | ARG | 246 | −10.141 | 18.198 | −13.831 | 1.00 | 0.00 | A |
| ATOM | 348 | HG1 | ARG | 246 | −10.676 | 18.111 | −12.899 | 1.00 | 0.00 | A |
| ATOM | 349 | HG2 | ARG | 246 | −10.603 | 18.960 | −14.442 | 1.00 | 0.00 | A |
| ATOM | 350 | CD | ARG | 246 | −8.684 | 18.585 | −13.546 | 1.00 | 0.00 | A |
| ATOM | 351 | HD1 | ARG | 246 | −8.182 | 17.793 | −13.017 | 1.00 | 0.00 | A |
| ATOM | 352 | HD2 | ARG | 246 | −8.646 | 19.504 | −12.975 | 1.00 | 0.00 | A |
| ATOM | 353 | NE | ARG | 246 | −8.058 | 18.780 | −14.886 | 1.00 | 0.00 | A |
| ATOM | 354 | HE | ARG | 246 | −8.503 | 18.442 | −15.689 | 1.00 | 0.00 | A |
| ATOM | 355 | CZ | ARG | 246 | −6.914 | 19.407 | −14.988 | 1.00 | 0.00 | A |
| ATOM | 356 | NH1 | ARG | 246 | −6.111 | 19.475 | −13.960 | 1.00 | 0.00 | A |
| ATOM | 357 | HH11 | ARG | 246 | 6.368 | 19.047 | −13.094 | 1.00 | 0.00 | A |
| ATOM | 358 | HH12 | ARG | 246 | −5.238 | 19.959 | −14.039 | 1.00 | 0.00 | A |
| ATOM | 359 | NH2 | ARG | 246 | −6.572 | 19.961 | −16.120 | 1.00 | 0.00 | A |
| ATOM | 360 | HH21 | ARG | 246 | −7.183 | 19.905 | −16.908 | 1.00 | 0.00 | A |
| ATOM | 361 | HH22 | ARG | 246 | −5.698 | 20.442 | −16.197 | 1.00 | 0.00 | A |
| ATOM | 362 | C | ARG | 246 | −12.345 | 17.582 | −15.651 | 1.00 | 0.00 | A |
| ATOM | 363 | O | ARG | 246 | −12.963 | 18.455 | −15.072 | 1.00 | 0.00 | A |
| ATOM | 364 | N | THR | 247 | −12.270 | 17.569 | −16.942 | 1.00 | 0.00 | A |
| ATOM | 365 | HN | THR | 247 | −11.786 | 16.863 | −17.410 | 1.00 | 0.00 | A |
| ATOM | 366 | CA | THR | 247 | −12.958 | 18.629 | −17.684 | 1.00 | 0.00 | A |
| ATOM | 367 | HA | THR | 247 | −13.029 | 19.495 | −17.059 | 1.00 | 0.00 | A |
| ATOM | 368 | CB | THR | 247 | −12.090 | 18.966 | −18.869 | 1.00 | 0.00 | A |
| ATOM | 369 | HB | THR | 247 | −12.531 | 19.769 | −19.397 | 1.00 | 0.00 | A |
| ATOM | 370 | OG1 | THR | 247 | −11.989 | 17.868 | −19.707 | 1.00 | 0.00 | A |
| ATOM | 371 | HG1 | THR | 247 | −12.415 | 18.090 | −20.538 | 1.00 | 0.00 | A |
| ATOM | 372 | CG2 | THR | 247 | −10.700 | 19.383 | −18.390 | 1.00 | 0.00 | A |
| ATOM | 373 | HG21 | THR | 247 | −10.637 | 19.262 | −17.319 | 1.00 | 0.00 | A |
| ATOM | 374 | HG22 | THR | 247 | −10.527 | 20.416 | −18.646 | 1.00 | 0.00 | A |
| ATOM | 375 | HG23 | THR | 247 | −9.954 | 18.765 | −18.867 | 1.00 | 0.00 | A |
| ATOM | 376 | C | THR | 247 | −14.406 | 18.197 | −18.146 | 1.00 | 0.00 | A |
| ATOM | 377 | O | THR | 247 | −15.032 | 18.942 | −18.874 | 1.00 | 0.00 | A |
| ATOM | 378 | N | PRO | 248 | −14.922 | 17.000 | −17.718 | 1.00 | 0.00 | A |
| ATOM | 379 | CA | PRO | 248 | −16.261 | 16.610 | −18.148 | 1.00 | 0.00 | A |
| ATOM | 380 | HA | PRO | 248 | −16.348 | 16.708 | −19.206 | 1.00 | 0.00 | A |
| ATOM | 381 | CB | PRO | 248 | −16.394 | 15.154 | −17.736 | 1.00 | 0.00 | A |
| ATOM | 382 | HB1 | PRO | 248 | −16.106 | 14.506 | −18.547 | 1.00 | 0.00 | A |
| ATOM | 383 | HB2 | PRO | 248 | −17.408 | 14.943 | −17.422 | 1.00 | 0.00 | A |
| ATOM | 384 | CG | PRO | 248 | −15.456 | 14.999 | −16.605 | 1.00 | 0.00 | A |
| ATOM | 385 | HG1 | PRO | 248 | −15.034 | 14.016 | −16.600 | 1.00 | 0.00 | A |
| ATOM | 386 | HG2 | PRO | 248 | −15.978 | 15.180 | −15.672 | 1.00 | 0.00 | A |
| ATOM | 387 | CD | PRO | 248 | −14.368 | 16.026 | −16.792 | 1.00 | 0.00 | A |
| ATOM | 388 | HD1 | PRO | 248 | −13.474 | 15.582 | −17.209 | 1.00 | 0.00 | A |
| ATOM | 389 | HD2 | PRO | 248 | −14.166 | 16.486 | −15.858 | 1.00 | 0.00 | A |
| ATOM | 390 | C | PRO | 248 | −17.270 | 17.494 | −17.371 | 1.00 | 0.00 | A |
| ATOM | 391 | O | PRO | 248 | −18.483 | 17.497 | −17.611 | 1.00 | 0.00 | A |
| ATOM | 392 | N | LEU | 249 | −16.751 | 18.235 | −16.400 | 1.00 | 0.00 | A |
| ATOM | 393 | HN | LEU | 249 | −15.803 | 18.184 | −16.206 | 1.00 | 0.00 | A |
| ATOM | 394 | CA | LEU | 249 | −17.590 | 19.117 | −15.589 | 1.00 | 0.00 | A |
| ATOM | 395 | HA | LEU | 249 | −18.359 | 18.548 | −15.065 | 1.00 | 0.00 | A |
| ATOM | 396 | CB | LEU | 249 | −16.612 | 19.740 | −14.565 | 1.00 | 0.00 | A |
| ATOM | 397 | HB1 | LEU | 249 | −15.857 | 18.989 | −14.296 | 1.00 | 0.00 | A |
| ATOM | 398 | HB2 | LEU | 249 | −17.148 | 20.026 | −13.682 | 1.00 | 0.00 | A |
| ATOM | 399 | CG | LEU | 249 | −15.900 | 20.960 | −15.167 | 1.00 | 0.00 | A |
| ATOM | 400 | HG | LEU | 249 | −16.634 | 21.654 | −15.550 | 1.00 | 0.00 | A |
| ATOM | 401 | CD1 | LEU | 249 | −15.055 | 21.643 | −14.097 | 1.00 | 0.00 | A |
| ATOM | 402 | HD11 | LEU | 249 | −14.018 | 21.374 | −14.233 | 1.00 | 0.00 | A |
| ATOM | 403 | HD12 | LEU | 249 | −15.386 | 21.323 | −13.121 | 1.00 | 0.00 | A |
| ATOM | 404 | HD13 | LEU | 249 | −15.163 | 22.715 | −14.182 | 1.00 | 0.00 | A |
| ATOM | 405 | CD2 | LEU | 249 | −14.994 | 20.505 | −16.289 | 1.00 | 0.00 | A |
| ATOM | 406 | HD21 | LEU | 249 | −14.557 | 19.559 | −16.023 | 1.00 | 0.00 | A |
| ATOM | 407 | HD22 | LEU | 249 | −14.211 | 21.234 | −16.439 | 1.00 | 0.00 | A |
| ATOM | 408 | HD23 | LEU | 249 | −15.563 | 20.397 | −17.196 | 1.00 | 0.00 | A |
| ATOM | 409 | C | LEU | 249 | −18.244 | 20.168 | −16.514 | 1.00 | 0.00 | A |
| ATOM | 410 | O | LEU | 249 | −19.057 | 20.934 | −16.086 | 1.00 | 0.00 | A |
| ATOM | 411 | N | THR | 250 | −17.807 | 20.257 | −17.774 | 1.00 | 0.00 | A |
| ATOM | 412 | HN | THR | 250 | −17.085 | 19.710 | −18.074 | 1.00 | 0.00 | A |
| ATOM | 413 | CA | THR | 250 | −18.410 | 21.239 | −18.705 | 1.00 | 0.00 | A |
| ATOM | 414 | HA | THR | 250 | −18.484 | 22.204 | −18.257 | 1.00 | 0.00 | A |
| ATOM | 415 | CB | THR | 250 | −17.505 | 21.277 | −19.940 | 1.00 | 0.00 | A |
| ATOM | 416 | HB | THR | 250 | −16.481 | 21.425 | −19.639 | 1.00 | 0.00 | A |
| ATOM | 417 | OG1 | THR | 250 | −17.917 | 22.340 | −20.790 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 418 | HG1 | THR | 250 | −17.370 | 22.320 | −21.576 | 1.00 | 0.00 | A |
|------|-----|-----|-----|-----|---------|--------|---------|------|------|---|
| ATOM | 419 | CG2 | THR | 250 | −17.626 | 19.961 | −20.694 | 1.00 | 0.00 | A |
| ATOM | 420 | HG21 | THR | 250 | −18.648 | 19.844 | −21.043 | 1.00 | 0.00 | A |
| ATOM | 421 | HG22 | THR | 250 | −17.380 | 19.146 | −20.031 | 1.00 | 0.00 | . A |
| ATOM | 422 | HG23 | THR | 250 | −16.960 | 19.964 | −21.531 | 1.00 | 0.00 | A |
| ATOM | 423 | C | THR | 250 | −19.778 | 20.672 | −19.055 | 1.00 | 0.00 | A |
| ATOM | 424 | O | THR | 250 | −20.750 | 21.359 | −19.209 | 1.00 | 0.00 | A |
| ATOM | 425 | N | ARG | 251 | −19.831 | 19.371 | −19.207 | 1.00 | 0.00 | A |
| ATOM | 426 | HN | ARG | 251 | −19.026 | 18.845 | −19.107 | 1.00 | 0.00 | A |
| ATOM | 427 | CA | ARG | 251 | −21.108 | 18.712 | −19.538 | 1.00 | 0.00 | A |
| ATOM | 428 | HA | ARG | 251 | −21.457 | 19.009 | −20.514 | 1.00 | 0.00 | A |
| ATOM | 429 | CB | ARG | 251 | −20.796 | 17.211 | −19.495 | 1.00 | 0.00 | A |
| ATOM | 430 | HB1 | ARG | 251 | −21.694 | 16.647 | −19.664 | 1.00 | 0.00 | A |
| ATOM | 431 | HB2 | ARG | 251 | −20.382 | 16.957 | −18.527 | 1.00 | 0.00 | A |
| ATOM | 432 | CG | ARG | 251 | −19.772 | 16.879 | −20.583 | 1.00 | 0.00 | A |
| ATOM | 433 | HG1 | ARG | 251 | −18.859 | 17.421 | −20.395 | 1.00 | 0.00 | A |
| ATOM | 434 | HG2 | ARG | 251 | −20.169 | 17.163 | −21.548 | 1.00 | 0.00 | A |
| ATOM | 435 | CD | ARG | 251 | −19.480 | 15.375 | −20.573 | 1.00 | 0.00 | A |
| ATOM | 436 | HD1 | ARG | 251 | −20.381 | 14.816 | −20.762 | 1.00 | 0.00 | A |
| ATOM | 437 | HD2 | ARG | 251 | −19.045 | 15.084 | −19.625 | 1.00 | 0.00 | A |
| ATOM | 438 | NE | ARG | 251 | −18.505 | 15.165 | −21.680 | 1.00 | 0.00 | A |
| ATOM | 439 | HE | ARG | 251 | −18.062 | 15.934 | −22.094 | 1.00 | 0.00 | A |
| ATOM | 440 | CZ | ARG | 251 | −18.242 | 13.958 | −22.098 | 1.00 | 0.00 | A |
| ATOM | 441 | NH1 | ARG | 251 | −19.072 | 13.352 | −22.903 | 1.00 | 0.00 | A |
| ATOM | 442 | HH11 | ARG | 251 | −19.909 | 13.814 | −23.199 | 1.00 | 0.00 | A |
| ATOM | 443 | HH12 | ARG | 251 | −18.871 | 12.426 | −23.225 | 1.00 | 0.00 | A |
| ATOM | 444 | NH2 | ARG | 251 | −17.151 | 13.356 | −21.712 | 1.00 | 0.00 | A |
| ATOM | 445 | HH21 | ARG | 251 | −16.516 | 13.821 | −21.095 | 1.00 | 0.00 | A |
| ATOM | 446 | HH22 | ARG | 251 | −16.950 | 12.431 | −22.033 | 1.00 | 0.00 | A |
| ATOM | 447 | C | ARG | 251 | −22.078 | 19.130 | −18.454 | 1.00 | 0.00 | A |
| ATOM | 448 | O | ARG | 251 | −23.175 | 19.581 | −18.715 | 1.00 | 0.00 | A |
| ATOM | 449 | N | ILE | 252 | −21.671 | 18.974 | −17.221 | 1.00 | 0.00 | A |
| ATOM | 450 | HN | ILE | 252 | −20.786 | 18.577 | −17.044 | 1.00 | 0.00 | A |
| ATOM | 451 | CA | ILE | 252 | −22.568 | 19.377 | −16.091 | 1.00 | 0.00 | A |
| ATOM | 452 | HA | ILE | 252 | −23.571 | 19.017 | −16.247 | 1.00 | 0.00 | A |
| ATOM | 453 | CB | ILE | 252 | −21.987 | 18.805 | −14.841 | 1.00 | 0.00 | A |
| ATOM | 454 | HB | ILE | 252 | −22.540 | 19.150 | −13.975 | 1.00 | 0.00 | A |
| ATOM | 455 | CG1 | ILE | 252 | −20.567 | 19.249 | −14.708 | 1.00 | 0.00 | A |
| ATOM | 456 | HG11 | ILE | 252 | −20.521 | 20.323 | −14.709 | 1.00 | 0.00 | A |
| ATOM | 457 | HG12 | ILE | 252 | −19.991 | 18.861 | −15.528 | 1.00 | 0.00 | A |
| ATOM | 458 | CG2 | ILE | 252 | −22.058 | 17.331 | −14.915 | 1.00 | 0.00 | A |
| ATOM | 459 | HG21 | ILE | 252 | −22.981 | 17.050 | −15.397 | 1.00 | 0.00 | A |
| ATOM | 460 | HG22 | ILE | 252 | −22.028 | 16.929 | −13.920 | 1.00 | 0.00 | A |
| ATOM | 461 | HG23 | ILE | 252 | −21.228 | 16.969 | −15.487 | 1.00 | 0.00 | A |
| ATOM | 462 | CD1 | ILE | 252 | −20.031 | 18.722 | −13.404 | 1.00 | 0.00 | A |
| ATOM | 463 | HD11 | ILE | 252 | −20.684 | 19.031 | −12.602 | 1.00 | 0.00 | A |
| ATOM | 464 | HD12 | ILE | 252 | −19.043 | 19.109 | −13.240 | 1.00 | 0.00 | A |
| ATOM | 465 | HD13 | ILE | 252 | −19.999 | 17.643 | −13.444 | 1.00 | 0.00 | A |
| ATOM | 466 | C | ILE | 252 | −22.543 | 20.864 | −16.001 | 1.00 | 0.00 | A |
| ATOM | 467 | O | ILE | 252 | −23.405 | 21.468 | −15.470 | 1.00 | 0.00 | A |
| ATOM | 468 | N | ARG | 253 | −21.517 | 21.478 | −16.498 | 1.00 | 0.00 | A |
| ATOM | 469 | HN | ARG | 253 | −20.831 | 20.986 | −16.946 | 1.00 | 0.00 | A |
| ATOM | 470 | CA | ARG | 253 | −21.469 | 22.952 | −16.427 | 1.00 | 0.00 | A |
| ATOM | 471 | HA | ARG | 253 | −21.372 | 23.289 | −15.405 | 1.00 | 0.00 | A |
| ATOM | 472 | CB | ARG | 253 | −20.274 | 23.370 | −17.257 | 1.00 | 0.00 | A |
| ATOM | 473 | HB1 | ARG | 253 | −20.418 | 23.074 | −18.268 | 1.00 | 0.00 | A |
| ATOM | 474 | HB2 | ARG | 253 | −19.393 | 22.900 | −16.863 | 1.00 | 0.00 | A |
| ATOM | 475 | CG | ARG | 253 | −20.097 | 24.864 | −17.204 | 1.00 | 0.00 | A |
| ATOM | 476 | HG1 | ARG | 253 | −21.026 | 25.339 | −17.459 | 1.00 | 0.00 | A |
| ATOM | 477 | HG2 | ARG | 253 | −19.333 | 25.155 | −17.908 | 1.00 | 0.00 | A |
| ATOM | 478 | CD | ARG | 253 | −19.682 | 25.274 | −15.797 | 1.00 | 0.00 | A |
| ATOM | 479 | HD1 | ARG | 253 | −18.744 | 24.809 | −15.534 | 1.00 | 0.00 | A |
| ATOM | 480 | HD2 | ARG | 253 | −20.452 | 25.001 | −15.087 | 1.00 | 0.00 | A |
| ATOM | 481 | NE | ARG | 253 | −19.521 | 26.756 | −15.858 | 1.00 | 0.00 | A |
| ATOM | 482 | HE | ARG | 253 | −20.080 | 27.332 | −15.295 | 1.00 | 0.00 | A |
| ATOM | 483 | CZ | ARG | 253 | −18.636 | 27.288 | −16.663 | 1.00 | 0.00 | A |
| ATOM | 484 | NH1 | ARG | 253 | −19.004 | 28.191 | −17.532 | 1.00 | 0.00 | A |
| ATOM | 485 | HH11 | ARG | 253 | −19.961 | 28.476 | −17.583 | 1.00 | 0.00 | A |
| ATOM | 486 | HH12 | ARG | 253 | −18.327 | 28.597 | −18.148 | 1.00 | 0.00 | A |
| ATOM | 487 | NH2 | ARG | 253 | −17.386 | 26.919 | −16.596 | 1.00 | 0.00 | A |
| ATOM | 488 | HH21 | ARG | 253 | −17.102 | 26.230 | −15.928 | 1.00 | 0.00 | A |
| ATOM | 489 | HH22 | ARG | 253 | −16.710 | 27.327 | −17.212 | 1.00 | 0.00 | A |
| ATOM | 490 | C | ARG | 253 | −22.764 | 23.421 | −17.037 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 491 | O    | ARG | 253 | −23.306 | 24.419 | −16.673 | 1.00 | 0.00 | A |
| ---- | --- | ---- | --- | --- | ------- | ------ | ------- | ---- | ---- | - |
| ATOM | 492 | N    | LEU | 254 | −23.270 | 22.620 | −17.971 | 1.00 | 0.00 | A |
| ATOM | 493 | HN   | LEU | 254 | −22.790 | 21.807 | −18.223 | 1.00 | 0.00 | A |
| ATOM | 494 | CA   | LEU | 254 | −24.521 | 22.935 | −18.645 | 1.00 | 0.00 | A |
| ATOM | 495 | HA   | LEU | 254 | −24.651 | 23.984 | −18.704 | 1.00 | 0.00 | A |
| ATOM | 496 | CB   | LEU | 254 | −24.391 | 22.325 | −20.048 | 1.00 | 0.00 | A |
| ATOM | 497 | HB1  | LEU | 254 | −25.251 | 22.598 | −20.639 | 1.00 | 0.00 | A |
| ATOM | 498 | HB2  | LEU | 254 | −24.340 | 21.249 | −19.964 | 1.00 | 0.00 | A |
| ATOM | 499 | CG   | LEU | 254 | −23.112 | 22.849 | −20.735 | 1.00 | 0.00 | A |
| ATOM | 500 | HG   | LEU | 254 | −22.233 | 22.429 | −20.244 | 1.00 | 0.00 | A |
| ATOM | 501 | CD1  | LEU | 254 | −23.111 | 22.414 | −22.199 | 1.00 | 0.00 | A |
| ATOM | 502 | HD11 | LEU | 254 | −22.358 | 22.970 | −22.738 | 1.00 | 0.00 | A |
| ATOM | 503 | HD12 | LEU | 254 | −24.081 | 22.607 | −22.632 | 1.00 | 0.00 | A |
| ATOM | 504 | HD13 | LEU | 254 | −22.891 | 21.358 | −22.260 | 1.00 | 0.00 | A |
| ATOM | 505 | CD2  | LEU | 254 | −23.067 | 24.382 | −20.653 | 1.00 | 0.00 | A |
| ATOM | 506 | HD21 | LEU | 254 | −22.350 | 24.760 | −21.369 | 1.00 | 0.00 | A |
| ATOM | 507 | HD22 | LEU | 254 | −22.772 | 24.681 | −19.657 | 1.00 | 0.00 | A |
| ATOM | 508 | HD23 | LEU | 254 | −24.043 | 24.786 | −20.875 | 1.00 | 0.00 | A |
| ATOM | 509 | C    | LEU | 254 | −25.673 | 22.286 | −17.845 | 1.00 | 0.00 | A |
| ATOM | 510 | O    | LEU | 254 | −26.726 | 22.866 | −17.674 | 1.00 | 0.00 | A |
| ATOM | 511 | N    | ALA | 255 | −25.470 | 21.065 | −17.349 | 1.00 | 0.00 | A |
| ATOM | 512 | HN   | ALA | 255 | −24.594 | 20.619 | −17.471 | 1.00 | 0.00 | A |
| ATOM | 513 | CA   | ALA | 255 | −26.555 | 20.382 | −16.553 | 1.00 | 0.00 | A |
| ATOM | 514 | HA   | ALA | 255 | −27.464 | 20.275 | −17.107 | 1.00 | 0.00 | A |
| ATOM | 515 | CB   | ALA | 255 | −25.980 | 19.008 | −16.184 | 1.00 | 0.00 | A |
| ATOM | 516 | HB1  | ALA | 255 | −25.322 | 18.670 | −16.971 | 1.00 | 0.00 | A |
| ATOM | 517 | HB2  | ALA | 255 | −26.788 | 18.301 | −16.060 | 1.00 | 0.00 | A |
| ATOM | 518 | HB3  | ALA | 255 | −25.425 | 19.086 | −15.261 | 1.00 | 0.00 | A |
| ATOM | 519 | C    | ALA | 255 | −26.768 | 21.217 | −15.326 | 1.00 | 0.00 | A |
| ATOM | 520 | O    | ALA | 255 | −27.836 | 21.693 | −15.044 | 1.00 | 0.00 | A |
| ATOM | 521 | N    | THR | 256 | −25.732 | 21.387 | −14.609 | 1.00 | 0.00 | A |
| ATOM | 522 | HN   | THR | 256 | −24.944 | 20.963 | −14.864 | 1.00 | 0.00 | A |
| ATOM | 523 | CA   | THR | 256 | −25.766 | 22.183 | −13.379 | 1.00 | 0.00 | A |
| ATOM | 524 | HA   | THR | 256 | −26.521 | 21.830 | −12.706 | 1.00 | 0.00 | A |
| ATOM | 525 | CB   | THR | 256 | −24.393 | 22.054 | −12.745 | 1.00 | 0.00 | A |
| ATOM | 526 | HB   | THR | 256 | −24.440 | 22.464 | −11.777 | 1.00 | 0.00 | A |
| ATOM | 527 | OG1  | THR | 256 | −23.451 | 22.778 | −13.515 | 1.00 | 0.00 | A |
| ATOM | 528 | HG1  | THR | 256 | −23.332 | 23.638 | −13.105 | 1.00 | 0.00 | A |
| ATOM | 529 | CG2  | THR | 256 | −23.944 | 20.588 | −12.652 | 1.00 | 0.00 | A |
| ATOM | 530 | HG21 | THR | 256 | −24.402 | 20.011 | −13.430 | 1.00 | 0.00 | A |
| ATOM | 531 | HG22 | THR | 256 | −24.227 | 20.187 | −11.699 | 1.00 | 0.00 | A |
| ATOM | 532 | HG23 | THR | 256 | −22.869 | 20.541 | −12.753 | 1.00 | 0.00 | A |
| ATOM | 533 | C    | THR | 256 | −25.996 | 23.641 | −13.732 | 1.00 | 0.00 | A |
| ATOM | 534 | O    | THR | 256 | −26.331 | 24.428 | −12.890 | 1.00 | 0.00 | A |
| ATOM | 535 | N    | GLU | 257 | −25.752 | 24.034 | −14.965 | 1.00 | 0.00 | A |
| ATOM | 536 | HN   | GLU | 257 | −25.408 | 23.372 | −15.664 | 1.00 | 0.00 | A |
| ATOM | 537 | CA   | GLU | 257 | −25.985 | 25.490 | −15.318 | 1.00 | 0.00 | A |
| ATOM | 538 | HA   | GLU | 257 | −25.395 | 26.141 | −14.700 | 1.00 | 0.00 | A |
| ATOM | 539 | CB   | GLU | 257 | −25.606 | 25.625 | −16.772 | 1.00 | 0.00 | A |
| ATOM | 540 | HB1  | GLU | 257 | −26.481 | 25.888 | −17.342 | 1.00 | 0.00 | A |
| ATOM | 541 | HB2  | GLU | 257 | −25.231 | 24.691 | −17.122 | 1.00 | 0.00 | A |
| ATOM | 542 | CG   | GLU | 257 | −24.550 | 26.726 | −16.931 | 1.00 | 0.00 | A |
| ATOM | 543 | HG1  | GLU | 257 | −23.684 | 26.486 | −16.336 | 1.00 | 0.00 | A |
| ATOM | 544 | HG2  | GLU | 257 | −24.963 | 27.667 | −16.598 | 1.00 | 0.00 | A |
| ATOM | 545 | CD   | GLU | 257 | −24.143 | 26.842 | −18.401 | 1.00 | 0.00 | A |
| ATOM | 546 | OE1  | GLU | 257 | −23.307 | 27.678 | −18.700 | 1.00 | 0.00 | A |
| ATOM | 547 | OE2  | GLU | 257 | −24.674 | 26.093 | −19.203 | 1.00 | 0.00 | A |
| ATOM | 548 | C    | GLU | 257 | −27.450 | 25.776 | −15.180 | 1.00 | 0.00 | A |
| ATOM | 549 | O    | GLU | 257 | −27.892 | 26.576 | −14.388 | 1.00 | 0.00 | A |
| ATOM | 550 | N    | MET | 258 | −28.183 | 25.136 | −15.995 | 1.00 | 0.00 | A |
| ATOM | 551 | HN   | MET | 258 | −27.755 | 24.523 | −16.633 | 1.00 | 0.00 | A |
| ATOM | 552 | CA   | MET | 258 | −29.643 | 25.281 | −16.009 | 1.00 | 0.00 | A |
| ATOM | 553 | HA   | MET | 258 | −29.943 | 26.306 | −16.177 | 1.00 | 0.00 | A |
| ATOM | 554 | CB   | MET | 258 | −30.024 | 24.390 | −17.196 | 1.00 | 0.00 | A |
| ATOM | 555 | HB1  | MET | 258 | −29.321 | 23.564 | −17.253 | 1.00 | 0.00 | A |
| ATOM | 556 | HB2  | MET | 258 | −29.961 | 24.966 | −18.104 | 1.00 | 0.00 | A |
| ATOM | 557 | CG   | MET | 258 | −31.424 | 23.839 | −17.042 | 1.00 | 0.00 | A |
| ATOM | 558 | HG1  | MET | 258 | −31.481 | 23.295 | −16.107 | 1.00 | 0.00 | A |
| ATOM | 559 | HG2  | MET | 258 | −31.628 | 23.169 | −17.859 | 1.00 | 0.00 | A |
| ATOM | 560 | SD   | MET | 258 | −32.626 | 25.194 | −17.036 | 1.00 | 0.00 | A |
| ATOM | 561 | CE   | MET | 258 | −33.589 | 24.650 | −18.467 | 1.00 | 0.00 | A |
| ATOM | 562 | HE1  | MET | 258 | −33.112 | 24.998 | −19.374 | 1.00 | 0.00 | A |
| ATOM | 563 | HE2  | MET | 258 | −34.584 | 25.057 | −18.409 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 564 | HE3 | MET | 258 | −33.643 | 23.569 | −18.474 | 1.00 | 0.00 | A |
|---|---|---|---|---|---|---|---|---|---|---|
| ATOM | 565 | C | MET | 258 | −30.203 | 24.758 | −14.699 | 1.00 | 0.00 | A |
| ATOM | 566 | O | MET | 258 | −31.234 | 25.192 | −14.224 | 1.00 | 0.00 | A |
| ATOM | 567 | N | MET | 259 | −29.528 | 23.837 | −14.121 | 1.00 | 0.00 | A |
| ATOM | 568 | HN | MET | 259 | −28.701 | 23.545 | −14.497 | 1.00 | 0.00 | A |
| ATOM | 569 | CA | MET | 259 | −29.989 | 23.277 | −12.862 | 1.00 | 0.00 | A |
| ATOM | 570 | HA | MET | 259 | −31.027 | 23.270 | −12.839 | 1.00 | 0.00 | A |
| ATOM | 571 | CB | MET | 259 | −29.457 | 21.854 | −12.827 | 1.00 | 0.00 | A |
| ATOM | 572 | HB1 | MET | 259 | −29.690 | 21.404 | −11.875 | 1.00 | 0.00 | A |
| ATOM | 573 | HB2 | MET | 259 | −28.391 | 21.865 | −12.970 | 1.00 | 0.00 | A |
| ATOM | 574 | CG | MET | 259 | −30.122 | 21.047 | −13.946 | 1.00 | 0.00 | A |
| ATOM | 575 | HG1 | MET | 259 | −29.967 | 21.544 | −14.891 | 1.00 | 0.00 | A |
| ATOM | 576 | HG2 | MET | 259 | −31.181 | 20.970 | −13.752 | 1.00 | 0.00 | A |
| ATOM | 577 | SD | MET | 259 | −29.406 | 19.388 | −14.011 | 1.00 | 0.00 | A |
| ATOM | 578 | CE | MET | 259 | −29.573 | 19.146 | −15.794 | 1.00 | 0.00 | A |
| ATOM | 579 | HE1 | MET | 259 | −29.769 | 20.100 | −16.264 | 1.00 | 0.00 | A |
| ATOM | 580 | HE2 | MET | 259 | −30.389 | 18.473 | −15.993 | 1.00 | 0.00 | A |
| ATOM | 581 | HE3 | MET | 259 | −28.657 | 18.726 | −16.188 | 1.00 | 0.00 | A |
| ATOM | 582 | C | MET | 259 | −29.469 | 24.098 | −11.730 | 1.00 | 0.00 | A |
| ATOM | 583 | O | MET | 259 | −29.908 | 23.968 | −10.639 | 1.00 | 0.00 | A |
| ATOM | 584 | N | SER | 260 | −28.553 | 24.989 | −11.995 | 1.00 | 0.00 | A |
| ATOM | 585 | HN | SER | 260 | −28.269 | 25.122 | −12.902 | 1.00 | 0.00 | A |
| ATOM | 586 | CA | SER | 260 | −28.002 | 25.839 | −10.892 | 1.00 | 0.00 | A |
| ATOM | 587 | HA | SER | 260 | −27.409 | 25.257 | −10.209 | 1.00 | 0.00 | A |
| ATOM | 588 | CB | SER | 260 | −27.162 | 26.920 | −11.566 | 1.00 | 0.00 | A |
| ATOM | 589 | HB1 | SER | 260 | −26.420 | 26.457 | −12.203 | 1.00 | 0.00 | A |
| ATOM | 590 | HB2 | SER | 260 | −26.668 | 27.511 | −10.817 | 1.00 | 0.00 | A |
| ATOM | 591 | OG | SER | 260 | −28.012 | 27.759 | −12.339 | 1.00 | 0.00 | A |
| ATOM | 592 | HG | SER | 260 | −28.322 | 28.470 | −11.772 | 1.00 | 0.00 | A |
| ATOM | 593 | C | SER | 260 | −29.183 | 26.456 | −10.210 | 1.00 | 0.00 | A |
| ATOM | 594 | O | SER | 260 | −29.233 | 26.626 | −9.008 | 1.00 | 0.00 | A |
| ATOM | 595 | N | GLU | 261 | −30.147 | 26.793 | −11.005 | 1.00 | 0.00 | A |
| ATOM | 596 | HN | GLU | 261 | −30.056 | 26.641 | −11.969 | 1.00 | 0.00 | A |
| ATOM | 597 | CA | GLU | 261 | −31.360 | 27.396 | −10.491 | 1.00 | 0.00 | A |
| ATOM | 598 | HA | GLU | 261 | −31.180 | 27.836 | −9.528 | 1.00 | 0.00 | A |
| ATOM | 599 | CB | GLU | 261 | −31.753 | 28.438 | −11.557 | 1.00 | 0.00 | A |
| ATOM | 600 | HB1 | GLU | 261 | −32.056 | 27.919 | −12.464 | 1.00 | 0.00 | A |
| ATOM | 601 | HB2 | GLU | 261 | −30.896 | 29.061 | −11.780 | 1.00 | 0.00 | A |
| ATOM | 602 | CG | GLU | 261 | −32.915 | 29.316 | −11.062 | 1.00 | 0.00 | A |
| ATOM | 603 | HG1 | GLU | 261 | −33.138 | 30.068 | −11.806 | 1.00 | 0.00 | A |
| ATOM | 604 | HG2 | GLU | 261 | −32.631 | 29.800 | −10.139 | 1.00 | 0.00 | A |
| ATOM | 605 | CD | GLU | 261 | −34.159 | 28.459 | −10.826 | 1.00 | 0.00 | A |
| ATOM | 606 | OE1 | GLU | 261 | −34.448 | 28.176 | −9.676 | 1.00 | 0.00 | A |
| ATOM | 607 | OE2 | GLU | 261 | −34.800 | 28.097 | −11.799 | 1.00 | 0.00 | A |
| ATOM | 608 | C | GLU | 261 | −32.362 | 26.286 | −10.381 | 1.00 | 0.00 | A |
| ATOM | 609 | O | GLU | 261 | −33.107 | 26.206 | −9.430 | 1.00 | 0.00 | A |
| ATOM | 610 | N | GLN | 262 | −32.418 | 25.437 | −11.376 | 1.00 | 0.00 | A |
| ATOM | 611 | HN | GLN | 262 | −31.832 | 25.548 | −12.154 | 1.00 | 0.00 | A |
| ATOM | 612 | CA | GLN | 262 | −33.369 | 24.324 | −11.318 | 1.00 | 0.00 | A |
| ATOM | 613 | HA | GLN | 262 | −34.253 | 24.630 | −10.864 | 1.00 | 0.00 | A |
| ATOM | 614 | CB | GLN | 262 | −33.627 | 23.884 | −12.768 | 1.00 | 0.00 | A |
| ATOM | 615 | HB1 | GLN | 262 | −32.717 | 23.564 | −13.220 | 1.00 | 0.00 | A |
| ATOM | 616 | HB2 | GLN | 262 | −34.032 | 24.714 | −13.327 | 1.00 | 0.00 | A |
| ATOM | 617 | CG | GLN | 262 | −34.632 | 22.729 | −12.776 | 1.00 | 0.00 | A |
| ATOM | 618 | HG1 | GLN | 262 | −35.550 | 23.047 | −12.305 | 1.00 | 0.00 | A |
| ATOM | 619 | HG2 | GLN | 262 | −34.220 | 21.888 | −12.236 | 1.00 | 0.00 | A |
| ATOM | 620 | CD | GLN | 262 | −34.920 | 22.316 | −14.219 | 1.00 | 0.00 | A |
| ATOM | 621 | OE1 | GLN | 262 | −34.048 | 21.825 | −14.908 | 1.00 | 0.00 | A |
| ATOM | 622 | NE2 | GLN | 262 | −36.116 | 22.497 | −14.709 | 1.00 | 0.00 | A |
| ATOM | 623 | HE21 | GLN | 262 | −36.818 | 22.894 | −14.152 | 1.00 | 0.00 | A |
| ATOM | 624 | HE22 | GLN | 262 | −36.311 | 22.236 | −15.633 | 1.00 | 0.00 | A |
| ATOM | 625 | C | GLN | 262 | −32.683 | 23.249 | −10.493 | 1.00 | 0.00 | A |
| ATOM | 626 | O | GLN | 262 | −32.178 | 22.276 | −11.010 | 1.00 | 0.00 | A |
| ATOM | 627 | N | ASP | 263 | −32.648 | 23.453 | −9.185 | 1.00 | 0.00 | A |
| ATOM | 628 | HN | ASP | 263 | −33.069 | 24.244 | −8.815 | 1.00 | 0.00 | A |
| ATOM | 629 | CA | ASP | 263 | −31.999 | 22.486 | −8.267 | 1.00 | 0.00 | A |
| ATOM | 630 | HA | ASP | 263 | −32.186 | 22.758 | −7.243 | 1.00 | 0.00 | A |
| ATOM | 631 | CB | ASP | 263 | −32.608 | 21.107 | −8.573 | 1.00 | 0.00 | A |
| ATOM | 632 | HB1 | ASP | 263 | −32.326 | 20.795 | −9.561 | 1.00 | 0.00 | A |
| ATOM | 633 | HB2 | ASP | 263 | −33.684 | 21.165 | −8.505 | 1.00 | 0.00 | A |
| ATOM | 634 | CG | ASP | 263 | −32.087 | 20.090 | −7.558 | 1.00 | 0.00 | A |
| ATOM | 635 | OD1 | ASP | 263 | −31.513 | 20.511 | −6.578 | 1.00 | 0.00 | A |
| ATOM | 636 | OD2 | ASP | 263 | −32.280 | 18.909 | −7.777 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 637 | C | ASP | 263 | −30.499 | 22.517 | −8.550 | 1.00 | 0.00 | A |
|---|---|---|---|---|---|---|---|---|---|---|
| ATOM | 638 | O | ASP | 263 | −29.942 | 21.568 | −9.063 | 1.00 | 0.00 | A |
| ATOM | 639 | N | GLY | 264 | −29.845 | 23.666 | −8.288 | 1.00 | 0.00 | A |
| ATOM | 640 | HN | GLY | 264 | −30.361 | 24.493 | −8.011 | 1.00 | 0.00 | A |
| ATOM | 641 | CA | GLY | 264 | −28.361 | 23.775 | −8.542 | 1.00 | 0.00 | A |
| ATOM | 642 | HA1 | GLY | 264 | −28.080 | 24.818 | −8.493 | 1.00 | 0.00 | A |
| ATOM | 643 | HA2 | GLY | 264 | −28.148 | 23.402 | −9.533 | 1.00 | 0.00 | A |
| ATOM | 644 | C | GLY | 264 | −27.507 | 22.982 | −7.517 | 1.00 | 0.00 | A |
| ATOM | 645 | O | GLY | 264 | −26.522 | 23.489 | −7.013 | 1.00 | 0.00 | A |
| ATOM | 646 | N | TYR | 265 | −27.861 | 21.764 | −7.200 | 1.00 | 0.00 | A |
| ATOM | 647 | HN | TYR | 265 | −28.643 | 21.369 | −7.584 | 1.00 | 0.00 | A |
| ATOM | 648 | CA | TYR | 265 | −27.053 | 20.992 | −6.227 | 1.00 | 0.00 | A |
| ATOM | 649 | HA | TYR | 265 | −26.591 | 21.661 | −5.518 | 1.00 | 0.00 | A |
| ATOM | 650 | CB | TYR | 265 | −28.034 | 20.071 | −5.502 | 1.00 | 0.00 | A |
| ATOM | 651 | HB1 | TYR | 265 | −27.486 | 19.374 | −4.885 | 1.00 | 0.00 | A |
| ATOM | 652 | HB2 | TYR | 265 | −28.620 | 19.524 | −6.230 | 1.00 | 0.00 | A |
| ATOM | 653 | CG | TYR | 265 | −28.953 | 20.902 | −4.628 | 1.00 | 0.00 | A |
| ATOM | 654 | CD1 | TYR | 265 | −29.792 | 21.896 | −5.200 | 1.00 | 0.00 | A |
| ATOM | 655 | HD1 | TYR | 265 | −29.804 | 22.050 | −6.260 | 1.00 | 0.00 | A |
| ATOM | 656 | CD2 | TYR | 265 | −28.953 | 20.703 | −3.230 | 1.00 | 0.00 | A |
| ATOM | 657 | HD2 | TYR | 265 | −28.315 | 19.948 | −2.793 | 1.00 | 0.00 | A |
| ATOM | 658 | CE1 | TYR | 265 | −30.623 | 22.678 | −4.374 | 1.00 | 0.00 | A |
| ATOM | 659 | HE1 | TYR | 265 | −31.260 | 23.433 | −4.813 | 1.00 | 0.00 | A |
| ATOM | 660 | CE2 | TYR | 265 | −29.790 | 21.485 | −2.404 | 1.00 | 0.00 | A |
| ATOM | 661 | HE2 | TYR | 265 | −29.789 | 21.331 | −1.340 | 1.00 | 0.00 | A |
| ATOM | 662 | CZ | TYR | 265 | −30.625 | 22.472 | −2.973 | 1.00 | 0.00 | A |
| ATOM | 663 | OH | TYR | 265 | −31.438 | 23.237 | −2.164 | 1.00 | 0.00 | A |
| ATOM | 664 | HH | TYR | 265 | −30.995 | 23.348 | −1.318 | 1.00 | 0.00 | A |
| ATOM | 665 | C | TYR | 265 | −25.977 | 20.185 | −6.966 | 1.00 | 0.00 | A |
| ATOM | 666 | O | TYR | 265 | −25.113 | 19.585 | −6.358 | 1.00 | 0.00 | A |
| ATOM | 667 | N | LEU | 266 | −26.019 | 20.166 | −8.284 | 1.00 | 0.00 | A |
| ATOM | 668 | HN | LEU | 266 | −26.623 | 20.725 | −8.757 | 1.00 | 0.00 | A |
| ATOM | 669 | CA | LEU | 266 | −25.015 | 19.413 | −9.028 | 1.00 | 0.00 | A |
| ATOM | 670 | HA | LEU | 266 | −24.627 | 18.616 | −8.408 | 1.00 | 0.00 | A |
| ATOM | 671 | CB | LEU | 266 | −25.701 | 18.805 | −10.297 | 1.00 | 0.00 | A |
| ATOM | 672 | HB1 | LEU | 266 | −26.366 | 18.010 | −9.987 | 1.00 | 0.00 | A |
| ATOM | 673 | HB2 | LEU | 266 | −24.946 | 18.394 | −10.935 | 1.00 | 0.00 | A |
| ATOM | 674 | CG | LEU | 266 | −26.507 | 19.841 | −11.107 | 1.00 | 0.00 | A |
| ATOM | 675 | HG | LEU | 266 | −25.989 | 20.790 | −11.124 | 1.00 | 0.00 | A |
| ATOM | 676 | CD1 | LEU | 266 | −26.679 | 19.302 | −12.528 | 1.00 | 0.00 | A |
| ATOM | 677 | HD11 | LEU | 266 | −26.920 | 20.102 | −13.198 | 1.00 | 0.00 | A |
| ATOM | 678 | HD12 | LEU | 266 | −27.472 | 18.589 | −12.536 | 1.00 | 0.00 | A |
| ATOM | 679 | HD13 | LEU | 266 | −25.766 | 18.824 | −12.848 | 1.00 | 0.00 | A |
| ATOM | 680 | CD2 | LEU | 266 | −27.910 | 20.007 | −10.503 | 1.00 | 0.00 | A |
| ATOM | 681 | HD21 | LEU | 266 | −28.652 | 19.896 | −11.283 | 1.00 | 0.00 | A |
| ATOM | 682 | HD22 | LEU | 266 | −28.000 | 20.987 | −10.061 | 1.00 | 0.00 | A |
| ATOM | 683 | HD23 | LEU | 266 | −28.069 | 19.253 | −9.746 | 1.00 | 0.00 | A |
| ATOM | 684 | C | LEU | 266 | −23.907 | 20.377 | −9.361 | 1.00 | 0.00 | A |
| ATOM | 685 | O | LEU | 266 | −22.770 | 20.015 | −9.498 | 1.00 | 0.00 | A |
| ATOM | 686 | N | ALA | 267 | −24.241 | 21.627 | −9.499 | 1.00 | 0.00 | A |
| ATOM | 697 | HN | ALA | 267 | −25.173 | 21.904 | −9.394 | 1.00 | 0.00 | A |
| ATOM | 688 | CA | ALA | 267 | −23.209 | 22.621 | −9.817 | 1.00 | 0.00 | A |
| ATOM | 689 | HA | ALA | 267 | −22.663 | 22.339 | −10.703 | 1.00 | 0.00 | A |
| ATOM | 690 | CB | ALA | 267 | −23.961 | 23.942 | −10.039 | 1.00 | 0.00 | A |
| ATOM | 691 | HB1 | ALA | 267 | −23.577 | 24.432 | −10.923 | 1.00 | 0.00 | A |
| ATOM | 692 | HB2 | ALA | 267 | −23.822 | 24.585 | −9.183 | 1.00 | 0.00 | A |
| ATOM | 693 | HB3 | ALA | 267 | −25.014 | 23.740 | −10.170 | 1.00 | 0.00 | A |
| ATOM | 694 | C | ALA | 267 | −22.291 | 22.735 | −8.633 | 1.00 | 0.00 | A |
| ATOM | 695 | O | ALA | 267 | −21.140 | 23.058 | −8.758 | 1.00 | 0.00 | A |
| ATOM | 696 | N | GLU | 268 | −22.788 | 22.455 | −7.465 | 1.00 | 0.00 | A |
| ATOM | 697 | HN | GLU | 268 | −23.725 | 22.182 | −7.374 | 1.00 | 0.00 | A |
| ATOM | 698 | CA | GLU | 268 | −21.924 | 22.557 | −6.286 | 1.00 | 0.00 | A |
| ATOM | 699 | HA | GLU | 268 | −21.129 | 23.183 | −6.512 | 1.00 | 0.00 | A |
| ATOM | 700 | CB | GLU | 268 | −22.794 | 23.174 | −5.189 | 1.00 | 0.00 | A |
| ATOM | 701 | HB1 | GLU | 268 | −22.212 | 23.278 | −4.285 | 1.00 | 0.00 | A |
| ATOM | 702 | HB2 | GLU | 268 | −23.642 | 22.531 | −4.998 | 1.00 | 0.00 | A |
| ATOM | 703 | CG | GLU | 268 | −23.289 | 24.554 | −5.635 | 1.00 | 0.00 | A |
| ATOM | 704 | HG1 | GLU | 268 | −23.949 | 24.960 | −4.883 | 1.00 | 0.00 | A |
| ATOM | 705 | HG2 | GLU | 268 | −23.825 | 24.458 | −6.569 | 1.00 | 0.00 | A |
| ATOM | 706 | CD | GLU | 268 | −22.097 | 25.495 | −5.827 | 1.00 | 0.00 | A |
| ATOM | 707 | OE1 | GLU | 268 | −22.315 | 26.610 | −6.270 | 1.00 | 0.00 | A |
| ATOM | 708 | OE2 | GLU | 268 | −20.988 | 25.087 | −5.522 | 1.00 | 0.00 | A |
| ATOM | 709 | C | GLU | 268 | −21.388 | 21.206 | −5.868 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 710 | O | GLU | 268 | −20.204 | 21.035 | −5.697 | 1.00 | 0.00 | A |
| ATOM | 711 | N | SER | 269 | −22.223 | 20.252 | −5.681 | 1.00 | 0.00 | A |
| ATOM | 712 | HN | SER | 269 | −23.184 | 20.398 | −5.805 | 1.00 | 0.00 | A |
| ATOM | 713 | CA | SER | 269 | −21.711 | 18.931 | −5.275 | 1.00 | 0.00 | A |
| ATOM | 714 | HA | SER | 269 | −21.224 | 18.990 | −4.315 | 1.00 | 0.00 | A |
| ATOM | 715 | CB | SER | 269 | −22.945 | 18.036 | −5.187 | 1.00 | 0.00 | A |
| ATOM | 716 | HB1 | SER | 269 | −22.641 | 17.030 | −4.921 | 1.00 | 0.00 | A |
| ATOM | 717 | HB2 | SER | 269 | −23.445 | 18.017 | −6.138 | 1.00 | 0.00 | A |
| ATOM | 718 | OG | SER | 269 | −23.833 | 18.554 | −4.203 | 1.00 | 0.00 | A |
| ATOM | 719 | HG | SER | 269 | −23.310 | 18.828 | −3.447 | 1.00 | 0.00 | A |
| ATOM | 720 | C | SER | 269 | −20.742 | 18.414 | −6.344 | 1.00 | 0.00 | A |
| ATOM | 721 | O | SER | 269 | −19.795 | 17.702 | −6.056 | 1.00 | 0.00 | A |
| ATOM | 722 | N | ILE | 270 | −20.940 | 18.805 | −7.576 | 1.00 | 0.00 | A |
| ATOM | 723 | HN | ILE | 270 | −21.646 | 19.469 | −7.779 | 1.00 | 0.00 | A |
| ATOM | 724 | CA | ILE | 270 | −20.017 | 18.316 | −8.650 | 1.00 | 0.00 | A |
| ATOM | 725 | HA | ILE | 270 | −19.617 | 17.357 | −8.363 | 1.00 | 0.00 | A |
| ATOM | 726 | CB | ILE | 270 | −20.868 | 18.143 | −9.911 | 1.00 | 0.00 | A |
| ATOM | 727 | HB | ILE | 270 | −21.103 | 19.109 | −10.338 | 1.00 | 0.00 | A |
| ATOM | 728 | CG1 | ILE | 270 | −22.152 | 17.388 | −9.558 | 1.00 | 0.00 | A |
| ATOM | 729 | HG11 | ILE | 270 | −22.740 | 17.974 | −8.870 | 1.00 | 0.00 | A |
| ATOM | 730 | HG12 | ILE | 270 | −21.896 | 16.444 | −9.097 | 1.00 | 0.00 | A |
| ATOM | 731 | CG2 | ILE | 270 | −20.086 | 17.302 | −10.925 | 1.00 | 0.00 | A |
| ATOM | 732 | HG21 | ILE | 270 | −20.728 | 17.055 | −11.759 | 1.00 | 0.00 | A |
| ATOM | 733 | HG22 | ILE | 270 | −19.749 | 16.389 | −10.451 | 1.00 | 0.00 | A |
| ATOM | 734 | HG23 | ILE | 270 | −19.235 | 17.859 | −11.279 | 1.00 | 0.00 | A |
| ATOM | 735 | CD1 | ILE | 270 | −22.959 | 17.134 | −10.827 | 1.00 | 0.00 | A |
| ATOM | 736 | HD11 | ILE | 270 | −22.475 | 16.369 | −11.415 | 1.00 | 0.00 | A |
| ATOM | 737 | HD12 | ILE | 270 | −23.023 | 18.046 | −11.403 | 1.00 | 0.00 | A |
| ATOM | 738 | HD13 | ILE | 270 | −23.953 | 16.806 | −10.561 | 1.00 | 0.00 | A |
| ATOM | 739 | C | ILE | 270 | −18.861 | 19.296 | −8.874 | 1.00 | 0.00 | A |
| ATOM | 740 | O | ILE | 270 | −17.723 | 18.906 | −8.848 | 1.00 | 0.00 | A |
| ATOM | 741 | N | ASN | 271 | −19.130 | 20.571 | −9.110 | 1.00 | 0.00 | A |
| ATOM | 742 | HN | ASN | 271 | −20.053 | 20.889 | −9.145 | 1.00 | 0.00 | A |
| ATOM | 743 | CA | ASN | 271 | −17.994 | 21.523 | −9.326 | 1.00 | 0.00 | A |
| ATOM | 744 | HA | ASN | 271 | −17.508 | 21.322 | −10.269 | 1.00 | 0.00 | A |
| ATOM | 745 | CB | ASN | 271 | −18.618 | 22.912 | −9.338 | 1.00 | 0.00 | A |
| ATOM | 746 | HB1 | ASN | 271 | −18.966 | 23.159 | −8.349 | 1.00 | 0.00 | A |
| ATOM | 747 | HB2 | ASN | 271 | −19.450 | 22.920 | −10.028 | 1.00 | 0.00 | A |
| ATOM | 748 | CG | ASN | 271 | −17.585 | 23.939 | −9.787 | 1.00 | 0.00 | A |
| ATOM | 749 | OD1 | ASN | 271 | −16.665 | 24.256 | −9.060 | 1.00 | 0.00 | A |
| ATOM | 750 | ND2 | ASN | 271 | −17.701 | 24.475 | −10.974 | 1.00 | 0.00 | A |
| ATOM | 751 | HD21 | ASN | 271 | −18.446 | 24.213 | −11.560 | 1.00 | 0.00 | A |
| ATOM | 752 | HD22 | ASN | 271 | −17.049 | 25.137 | −11.278 | 1.00 | 0.00 | A |
| ATOM | 753 | C | ASN | 271 | −17.008 | 21.348 | −8.171 | 1.00 | 0.00 | A |
| ATOM | 754 | O | ASN | 271 | −15.811 | 21.482 | −8.324 | 1.00 | 0.00 | A |
| ATOM | 755 | N | LYS | 272 | −17.509 | 21.066 | −7.000 | 1.00 | 0.00 | A |
| ATOM | 756 | HN | LYS | 272 | −18.472 | 20.979 | −6.887 | 1.00 | 0.00 | A |
| ATOM | 757 | CA | LYS | 272 | −16.598 | 20.876 | −5.852 | 1.00 | 0.00 | A |
| ATOM | 758 | HA | LYS | 272 | −15.874 | 21.672 | −5.807 | 1.00 | 0.00 | A |
| ATOM | 759 | CB | LYS | 272 | −17.474 | 20.867 | −4.599 | 1.00 | 0.00 | A |
| ATOM | 760 | HB1 | LYS | 272 | −16.868 | 20.624 | −3.739 | 1.00 | 0.00 | A |
| ATOM | 761 | HB2 | LYS | 272 | −18.258 | 20.130 | −4.708 | 1.00 | 0.00 | A |
| ATOM | 762 | CG | LYS | 272 | −18.093 | 22.253 | −4.407 | 1.00 | 0.00 | A |
| ATOM | 763 | HG1 | LYS | 272 | −18.708 | 22.496 | −5.258 | 1.00 | 0.00 | A |
| ATOM | 764 | HG2 | LYS | 272 | −17.306 | 22.987 | −4.312 | 1.00 | 0.00 | A |
| ATOM | 765 | CD | LYS | 272 | −18.950 | 22.262 | −3.143 | 1.00 | 0.00 | A |
| ATOM | 766 | HD1 | LYS | 272 | −19.723 | 21.515 | −3.229 | 1.00 | 0.00 | A |
| ATOM | 767 | HD2 | LYS | 272 | −19.400 | 23.235 | −3.022 | 1.00 | 0.00 | A |
| ATOM | 768 | CE | LYS | 272 | −18.074 | 21.947 | −1.928 | 1.00 | 0.00 | A |
| ATOM | 769 | HE1 | LYS | 272 | −17.284 | 22.675 | −1.834 | 1.00 | 0.00 | A |
| ATOM | 770 | HE2 | LYS | 272 | −17.661 | 20.949 | −2.012 | 1.00 | 0.00 | A |
| ATOM | 771 | NZ | LYS | 272 | −18.992 | 22.034 | −0.759 | 1.00 | 0.00 | A |
| ATOM | 772 | HZ1 | LYS | 272 | −18.560 | 21.559 | 0.058 | 1.00 | 0.00 | A |
| ATOM | 773 | HZ2 | LYS | 272 | −19.895 | 21.572 | −0.993 | 1.00 | 0.00 | A |
| ATOM | 774 | HZ3 | LYS | 272 | −19.162 | 23.032 | −0.525 | 1.00 | 0.00 | A |
| ATOM | 775 | C | LYS | 272 | −15.913 | 19.542 | −6.075 | 1.00 | 0.00 | A |
| ATOM | 776 | O | LYS | 272 | −14.750 | 19.367 | −5.784 | 1.00 | 0.00 | A |
| ATOM | 777 | N | ASP | 273 | −16.654 | 18.581 | −6.591 | 1.00 | 0.00 | A |
| ATOM | 778 | HN | ASP | 273 | −17.600 | 18.745 | −6.786 | 1.00 | 0.00 | A |
| ATOM | 779 | CA | ASP | 273 | −16.066 | 17.243 | −6.855 | 1.00 | 0.00 | A |
| ATOM | 780 | HA | ASP | 273 | −15.648 | 16.824 | −5.954 | 1.00 | 0.00 | A |
| ATOM | 781 | CB | ASP | 273 | −17.228 | 16.387 | −7.362 | 1.00 | 0.00 | A |
| ATOM | 782 | HB1 | ASP | 273 | −17.643 | 16.833 | −8.252 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 783 | HB2 | ASP | 273 | −17.990 | 16.329 | −6.599 | 1.00 | 0.00 | A |
| ATOM | 784 | CG | ASP | 273 | −16.726 | 14.979 | −7.688 | 1.00 | 0.00 | A |
| ATOM | 785 | OD1 | ASP | 273 | −16.247 | 14.317 | −6.781 | 1.00 | 0.00 | A |
| ATOM | 786 | OD2 | ASP | 273 | −16.832 | 14.585 | −8.837 | 1.00 | 0.00 | A |
| ATOM | 787 | C | ASP | 273 | −14.984 | 17.408 | −7.938 | 1.00 | 0.00 | A |
| ATOM | 788 | O | ASP | 273 | −14.189 | 16.535 | −8.170 | 1.00 | 0.00 | A |
| ATOM | 789 | N | ILE | 274 | −15.002 | 18.541 | −8.622 | 1.00 | 0.00 | A |
| ATOM | 790 | HN | ILE | 274 | −15.651 | 19.191 | −8.421 | 1.00 | 0.00 | A |
| ATOM | 791 | CA | ILE | 274 | −14.016 | 18.834 | −9.687 | 1.00 | 0.00 | A |
| ATOM | 792 | HA | ILE | 274 | −13.738 | 17.939 | −10.203 | 1.00 | 0.00 | A |
| ATOM | 793 | CB | ILE | 274 | −14.728 | 19.797 | −10.633 | 1.00 | 0.00 | A |
| ATOM | 794 | HB | ILE | 274 | −15.102 | 20.632 | −10.074 | 1.00 | 0.00 | A |
| ATOM | 795 | CG1 | ILE | 274 | −15.896 | 19.077 | −11.314 | 1.00 | 0.00 | A |
| ATOM | 796 | HG11 | ILE | 274 | −16.402 | 19.758 | −11.972 | 1.00 | 0.00 | A |
| ATOM | 797 | HG12 | ILE | 274 | −16.581 | 18.725 | −10.570 | 1.00 | 0.00 | A |
| ATOM | 798 | CG2 | ILE | 274 | −13.753 | 20.299 | −11.681 | 1.00 | 0.00 | A |
| ATOM | 799 | HG21 | ILE | 274 | −14.080 | 19.984 | −12.660 | 1.00 | 0.00 | A |
| ATOM | 800 | HG22 | ILE | 274 | −12.773 | 19.895 | −11.479 | 1.00 | 0.00 | A |
| ATOM | 801 | HG23 | ILE | 274 | −13.713 | 21.378 | −11.644 | 1.00 | 0.00 | A |
| ATOM | 802 | CD1 | ILE | 274 | −15.379 | 17.891 | −12.117 | 1.00 | 0.00 | A |
| ATOM | 803 | HD11 | ILE | 274 | −14.405 | 18.120 | −12.514 | 1.00 | 0.00 | A |
| ATOM | 804 | HD12 | ILE | 274 | −16.060 | 17.685 | −12.929 | 1.00 | 0.00 | A |
| ATOM | 805 | HD13 | ILE | 274 | −15.313 | 17.025 | −11.475 | 1.00 | 0.00 | A |
| ATOM | 806 | C | ILE | 274 | −12.810 | 19.505 | −9.012 | 1.00 | 0.00 | A |
| ATOM | 807 | O | ILE | 274 | −11.711 | 19.491 | −9.508 | 1.00 | 0.00 | A |
| ATOM | 808 | N | GLU | 275 | −13.077 | 20.148 | −7.887 | 1.00 | 0.00 | A |
| ATOM | 809 | HN | GLU | 275 | −13.944 | 20.174 | −7.595 | 1.00 | 0.00 | A |
| ATOM | 810 | CA | GLU | 275 | −12.038 | 20.847 | −7.092 | 1.00 | 0.00 | A |
| ATOM | 811 | HA | GLU | 275 | −11.413 | 21.463 | −7.720 | 1.00 | 0.00 | A |
| ATOM | 812 | CB | GLU | 275 | −12.804 | 21.697 | −6.074 | 1.00 | 0.00 | A |
| ATOM | 813 | HB1 | GLU | 275 | −13.400 | 21.055 | −5.443 | 1.00 | 0.00 | A |
| ATOM | 814 | HB2 | GLU | 275 | −13.451 | 22.390 | −6.598 | 1.00 | 0.00 | A |
| ATOM | 815 | CG | GLU | 275 | −11.812 | 22.477 | −5.211 | 1.00 | 0.00 | A |
| ATOM | 816 | HG1 | GLU | 275 | −11.152 | 21.787 | −4.708 | 1.00 | 0.00 | A |
| ATOM | 817 | HG2 | GLU | 275 | −12.351 | 23.059 | −4.479 | 1.00 | 0.00 | A |
| ATOM | 818 | CD | GLU | 275 | −10.988 | 23.407 | −6.098 | 1.00 | 0.00 | A |
| ATOM | 819 | OE1 | GLU | 275 | −11.578 | 24.275 | −6.720 | 1.00 | 0.00 | A |
| ATOM | 820 | OE2 | GLU | 275 | −9.782 | 23.237 | −6.142 | 1.00 | 0.00 | A |
| ATOM | 821 | C | GLU | 275 | −11.239 | 19.767 | −6.408 | 1.00 | 0.00 | A |
| ATOM | 822 | O | GLU | 275 | −10.072 | 19.911 | −6.134 | 1.00 | 0.00 | A |
| ATOM | 823 | N | GLU | 276 | −11.893 | 18.675 | −6.067 | 1.00 | 0.00 | A |
| ATOM | 824 | HN | GLU | 276 | −12.825 | 18.569 | −6.288 | 1.00 | 0.00 | A |
| ATOM | 825 | CA | GLU | 276 | −11.179 | 17.588 | −5.421 | 1.00 | 0.00 | A |
| ATOM | 826 | HA | GLU | 276 | −10.499 | 17.940 | −4.658 | 1.00 | 0.00 | A |
| ATOM | 827 | CB | GLU | 276 | −12.234 | 16.634 | −4.876 | 1.00 | 0.00 | A |
| ATOM | 828 | HB1 | GLU | 276 | −11.752 | 15.812 | −4.370 | 1.00 | 0.00 | A |
| ATOM | 829 | HB2 | GLU | 276 | −12.836 | 16.255 | −5.691 | 1.00 | 0.00 | A |
| ATOM | 830 | CG | GLU | 276 | −13.111 | 17.384 | −3.899 | 1.00 | 0.00 | A |
| ATOM | 831 | HG1 | GLU | 276 | −13.553 | 18.229 | −4.400 | 1.00 | 0.00 | A |
| ATOM | 832 | HG2 | GLU | 276 | −12.508 | 17.726 | −3.075 | 1.00 | 0.00 | A |
| ATOM | 833 | CD | GLU | 276 | −14.215 | 16.462 | −3.379 | 1.00 | 0.00 | A |
| ATOM | 834 | OE1 | GLU | 276 | −14.945 | 16.882 | −2.495 | 1.00 | 0.00 | A |
| ATOM | 835 | OE2 | GLU | 276 | −14.317 | 15.353 | −3.877 | 1.00 | 0.00 | A |
| ATOM | 836 | C | GLU | 276 | −10.482 | 17.020 | −6.578 | 1.00 | 0.00 | A |
| ATOM | 837 | O | GLU | 276 | −9.292 | 16.957 | −6.635 | 1.00 | 0.00 | A |
| ATOM | 838 | N | CYS | 277 | −11.283 | 16.730 | −7.600 | 1.00 | 0.00 | A |
| ATOM | 839 | HN | CYS | 277 | −12.235 | 16.903 | −7.514 | 1.00 | 0.00 | A |
| ATOM | 840 | CA | CYS | 277 | −10.765 | 16.166 | −8.850 | 1.00 | 0.00 | A |
| ATOM | 841 | HA | CYS | 277 | −10.496 | 15.162 | −8.748 | 1.00 | 0.00 | A |
| ATOM | 842 | CB | CYS | 277 | −11.901 | 16.306 | −9.840 | 1.00 | 0.00 | A |
| ATOM | 843 | HB1 | CYS | 277 | −12.152 | 17.340 | −9.930 | 1.00 | 0.00 | A |
| ATOM | 844 | HB2 | CYS | 277 | −12.754 | 15.753 | −9.491 | 1.00 | 0.00 | A |
| ATOM | 845 | SG | CYS | 277 | −11.395 | 15.671 | −11.453 | 1.00 | 0.00 | A |
| ATOM | 846 | HG1 | CYS | 277 | −10.731 | 16.264 | −11.810 | 1.00 | 0.00 | A |
| ATOM | 847 | C | CYS | 277 | −9.611 | 17.040 | −9.286 | 1.00 | 0.00 | A |
| ATOM | 848 | O | CYS | 277 | −8.688 | 16.608 | −9.960 | 1.00 | 0.00 | A |
| ATOM | 849 | N | ASN | 278 | −9.641 | 18.286 | −8.855 | 1.00 | 0.00 | A |
| ATOM | 850 | HN | ASN | 278 | −10.346 | 18.587 | −8.275 | 1.00 | 0.00 | A |
| ATOM | 851 | CA | ASN | 278 | −8.596 | 19.189 | −9.217 | 1.00 | 0.00 | A |
| ATOM | 852 | HA | ASN | 278 | −8.434 | 19.118 | −10.237 | 1.00 | 0.00 | A |
| ATOM | 853 | CB | ASN | 278 | −9.101 | 20.597 | −8.888 | 1.00 | 0.00 | A |
| ATOM | 854 | HB1 | ASN | 278 | −9.272 | 20.685 | −7.840 | 1.00 | 0.00 | A |
| ATOM | 855 | HB2 | ASN | 278 | −10.018 | 20.787 | −9.422 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 856 | CG | ASN | 278 | −8.044 | 21.620 | −9.313 | 1.00 | 0.00 | A |
|---|---|---|---|---|---|---|---|---|---|---|
| ATOM | 857 | OD1 | ASN | 278 | −7.668 | 21.678 | −10.467 | 1.00 | 0.00 | A |
| ATOM | 858 | ND2 | ASN | 278 | −7.544 | 22.434 | −8.423 | 1.00 | 0.00 | A |
| ATOM | 859 | HD21 | ASN | 278 | −7.846 | 22.388 | −7.491 | 1.00 | 0.00 | A |
| ATOM | 860 | HD22 | ASN | 278 | −6.867 | 23.092 | −8.687 | 1.00 | 0.00 | A |
| ATOM | 861 | C | ASN | 278 | −7.337 | 18.878 | −8.406 | 1.00 | 0.00 | A |
| ATOM | 862 | O | ASN | 278 | −6.270 | 18.794 | −8.927 | 1.00 | 0.00 | A |
| ATOM | 863 | N | ALA | 279 | −7.491 | 18.681 | −7.117 | 1.00 | 0.00 | A |
| ATOM | 864 | HN | ALA | 279 | −8.373 | 18.765 | −6.724 | 1.00 | 0.00 | A |
| ATOM | 865 | CA | ALA | 279 | −6.314 | 18.375 | −6.230 | 1.00 | 0.00 | A |
| ATOM | 866 | HA | ALA | 279 | −5.519 | 19.048 | −6.465 | 1.00 | 0.00 | A |
| ATOM | 867 | CB | ALA | 279 | −6.814 | 18.683 | −4.824 | 1.00 | 0.00 | A |
| ATOM | 868 | HB1 | ALA | 279 | −7.620 | 18.009 | −4.574 | 1.00 | 0.00 | A |
| ATOM | 869 | HB2 | ALA | 279 | −7.171 | 19.702 | −4.784 | 1.00 | 0.00 | A |
| ATOM | 870 | HB3 | ALA | 279 | −6.006 | 18.556 | −4.119 | 1.00 | 0.00 | A |
| ATOM | 871 | C | ALA | 279 | −5.786 | 16.902 | −6.288 | 1.00 | 0.00 | A |
| ATOM | 872 | O | ALA | 279 | −4.765 | 16.630 | −5.745 | 1.00 | 0.00 | A |
| ATOM | 873 | N | ILE | 280 | −6.430 | 15.972 | −6.941 | 1.00 | 0.00 | A |
| ATOM | 874 | HN | ILE | 280 | −7.150 | 16.204 | −7.498 | 1.00 | 0.00 | A |
| ATOM | 875 | CA | ILE | 280 | −5.846 | 14.551 | −6.949 | 1.00 | 0.00 | A |
| ATOM | 876 | HA | ILE | 280 | −5.049 | 14.511 | −6.309 | 1.00 | 0.00 | A |
| ATOM | 877 | CB | ILE | 280 | −6.876 | 13.457 | −6.556 | 1.00 | 0.00 | A |
| ATOM | 878 | HB | ILE | 280 | −6.383 | 12.533 | −6.607 | 1.00 | 0.00 | A |
| ATOM | 879 | CG1 | ILE | 280 | −8.044 | 13.408 | −7.504 | 1.00 | 0.00 | A |
| ATOM | 880 | HG11 | ILE | 280 | −8.702 | 12.601 | −7.227 | 1.00 | 0.00 | A |
| ATOM | 881 | HG12 | ILE | 280 | −7.693 | 13.262 | −8.497 | 1.00 | 0.00 | A |
| ATOM | 882 | CG2 | ILE | 280 | −7.369 | 13.647 | −5.147 | 1.00 | 0.00 | A |
| ATOM | 883 | HG21 | ILE | 280 | −8.443 | 13.752 | −5.158 | 1.00 | 0.00 | A |
| ATOM | 884 | HG22 | ILE | 280 | −6.919 | 14.528 | −4.729 | 1.00 | 0.00 | A |
| ATOM | 885 | HG23 | ILE | 280 | −7.097 | 12.783 | −4.558 | 1.00 | 0.00 | A |
| ATOM | 886 | CD1 | ILE | 280 | −8.767 | 14.657 | −7.424 | 1.00 | 0.00 | A |
| ATOM | 887 | HD11 | ILE | 280 | −9.802 | 14.458 | −7.345 | 1.00 | 0.00 | A |
| ATOM | 888 | HD12 | ILE | 280 | −8.571 | 15.234 | −8.303 | 1.00 | 0.00 | A |
| ATOM | 889 | HD13 | ILE | 280 | −8.441 | 15.195 | −6.566 | 1.00 | 0.00 | A |
| ATOM | 890 | C | ILE | 280 | −5.374 | 14.280 | −8.260 | 1.00 | 0.00 | A |
| ATOM | 891 | O | ILE | 280 | −4.382 | 13.661 | −8.446 | 1.00 | 0.00 | A |
| ATOM | 892 | N | ILE | 281 | −6.079 | 14.700 | −9.190 | 1.00 | 0.00 | A |
| ATOM | 893 | HN | ILE | 281 | −6.902 | 15.184 | −9.008 | 1.00 | 0.00 | A |
| ATOM | 894 | CA | ILE | 281 | −5.666 | 14.469 | −10.525 | 1.00 | 0.00 | A |
| ATOM | 895 | HA | ILE | 281 | −5.359 | 13.476 | −10.650 | 1.00 | 0.00 | A |
| ATOM | 896 | CB | ILE | 281 | −6.868 | 14.741 | −11.345 | 1.00 | 0.00 | A |
| ATOM | 897 | HB | ILE | 281 | −7.146 | 15.782 | −11.238 | 1.00 | 0.00 | A |
| ATOM | 898 | CGA | ILE | 281 | −7.972 | 13.848 | −10.784 | 1.00 | 0.00 | A |
| ATOM | 899 | HG11 | ILE | 281 | −8.351 | 14.301 | −9.873 | 1.00 | 0.00 | A |
| ATOM | 900 | HG12 | ILE | 281 | −7.550 | 12.877 | −10.538 | 1.00 | 0.00 | A |
| ATOM | 901 | CG2 | ILE | 281 | −6.574 | 14.413 | −12.819 | 1.00 | 0.00 | A |
| ATOM | 902 | HG21 | ILE | 281 | −5.551 | 14.674 | −13.047 | 1.00 | 0.00 | A |
| ATOM | 903 | HG22 | ILE | 281 | −7.241 | 14.978 | −13.454 | 1.00 | 0.00 | A |
| ATOM | 904 | HG23 | ILE | 281 | −6.724 | 13.358 | −12.988 | 1.00 | 0.00 | A |
| ATOM | 905 | CD1 | ILE | 281 | −9.100 | 13.698 | −11.783 | 1.00 | 0.00 | A |
| ATOM | 906 | HD11 | ILE | 281 | −8.864 | 12.897 | −12.467 | 1.00 | 0.00 | A |
| ATOM | 907 | HD12 | ILE | 281 | −9.217 | 14.622 | −12.331 | 1.00 | 0.00 | A |
| ATOM | 908 | HD13 | ILE | 281 | −10.010 | 13.470 | −11.260 | 1.00 | 0.00 | A |
| ATOM | 909 | C | ILE | 281 | −4.567 | 15.399 | −10.793 | 1.00 | 0.00 | A |
| ATOM | 910 | O | ILE | 281 | −3.644 | 15.104 | −11.523 | 1.00 | 0.00 | A |
| ATOM | 911 | N | GLU | 282 | −4.591 | 16.536 | −10.171 | 1.00 | 0.00 | A |
| ATOM | 912 | HN | GLU | 282 | −5.315 | 16.769 | −9.550 | 1.00 | 0.00 | A |
| ATOM | 913 | CA | GLU | 282 | −3.529 | 17.429 | −10.433 | 1.00 | 0.00 | A |
| ATOM | 914 | HA | GLU | 282 | −3.220 | 17.233 | −11.383 | 1.00 | 0.00 | A |
| ATOM | 915 | CB | GLU | 282 | −4.080 | 18.841 | −10.342 | 1.00 | 0.00 | A |
| ATOM | 916 | HB1 | GLU | 282 | −4.289 | 19.075 | −9.314 | 1.00 | 0.00 | A |
| ATOM | 917 | HB2 | GLU | 282 | −4.984 | 18.921 | −10.928 | 1.00 | 0.00 | A |
| ATOM | 918 | CG | GLU | 282 | −3.032 | 19.824 | −10.867 | 1.00 | 0.00 | A |
| ATOM | 919 | HG1 | GLU | 282 | −2.798 | 19.587 | −11.894 | 1.00 | 0.00 | A |
| ATOM | 920 | HG2 | GLU | 282 | −2.137 | 19.750 | −10.267 | 1.00 | 0.00 | A |
| ATOM | 921 | CD | GLU | 282 | −3.582 | 21.247 | −10.787 | 1.00 | 0.00 | A |
| ATOM | 922 | OE1 | GLU | 282 | −4.652 | 21.479 | −11.325 | 1.00 | 0.00 | A |
| ATOM | 923 | OE2 | GLU | 282 | −2.924 | 22.082 | −10.191 | 1.00 | 0.00 | A |
| ATOM | 924 | C | GLU | 282 | −2.378 | 17.238 | −9.453 | 1.00 | 0.00 | A |
| ATOM | 925 | O | GLU | 282 | −1.267 | 16.917 | −9.845 | 1.00 | 0.00 | A |
| ATOM | 926 | N | GLN | 283 | −2.629 | 17.375 | −8.178 | 1.00 | 0.00 | A |
| ATOM | 927 | HN | GLN | 283 | −3.546 | 17.552 | −7.857 | 1.00 | 0.00 | A |
| ATOM | 928 | CA | GLN | 283 | −1.541 | 17.207 | −7.207 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 929 | HA | GLN | 283 | −0.650 | 17.683 | −7.577 | 1.00 | 0.00 | A |
|---|---|---|---|---|---|---|---|---|---|---|
| ATOM | 930 | CB | GLN | 283 | −2.025 | 17.947 | −5.971 | 1.00 | 0.00 | A |
| ATOM | 931 | HB1 | GLN | 283 | −2.958 | 17.548 | −5.656 | 1.00 | 0.00 | A |
| ATOM | 932 | HB2 | GLN | 283 | −2.139 | 18.996 | −6.198 | 1.00 | 0.00 | A |
| ATOM | 933 | CG | GLN | 283 | −1.016 | 17.777 | −4.878 | 1.00 | 0.00 | A |
| ATOM | 934 | HG1 | GLN | 283 | −0.062 | 18.111 | −5.229 | 1.00 | 0.00 | A |
| ATOM | 935 | HG2 | GLN | 283 | −0.965 | 16.732 | −4.613 | 1.00 | 0.00 | A |
| ATOM | 936 | CD | GLN | 283 | −1.433 | 18.598 | −3.659 | 1.00 | 0.00 | A |
| ATOM | 937 | OE1 | GLN | 283 | −1.660 | 19.788 | −3.761 | 1.00 | 0.00 | A |
| ATOM | 938 | NE2 | GLN | 283 | −1.542 | 18.011 | −2.503 | 1.00 | 0.00 | A |
| ATOM | 939 | HE21 | GLN | 283 | −1.357 | 17.053 | −2.422 | 1.00 | 0.00 | A |
| ATOM | 940 | HE22 | GLN | 283 | −1.812 | 18.526 | −1.717 | 1.00 | 0.00 | A |
| ATOM | 941 | C | GLN | 283 | −1.248 | 15.738 | −6.903 | 1.00 | 0.00 | A |
| ATOM | 942 | O | GLN | 283 | −0.229 | 15.428 | −6.315 | 1.00 | 0.00 | A |
| ATOM | 943 | N | PHE | 284 | −2.099 | 14.818 | −7.277 | 1.00 | 0.00 | A |
| ATOM | 944 | HN | PHE | 284 | −2.934 | 15.056 | −7.764 | 1.00 | 0.00 | A |
| ATOM | 945 | CA | PHE | 284 | −1.774 | 13.400 | −6.962 | 1.00 | 0.00 | A |
| ATOM | 946 | HA | PHE | 284 | −0.860 | 13.365 | −6.395 | 1.00 | 0.00 | A |
| ATOM | 947 | CB | PHE | 284 | −2.922 | 12.845 | −6.094 | 1.00 | 0.00 | A |
| ATOM | 948 | HB1 | PHE | 284 | −2.814 | 11.774 | −6.005 | 1.00 | 0.00 | A |
| ATOM | 949 | HB2 | PHE | 284 | −3.859 | 13.066 | −6.551 | 1.00 | 0.00 | A |
| ATOM | 950 | CG | PHE | 284 | −2.879 | 13.465 | −4.717 | 1.00 | 0.00 | A |
| ATOM | 951 | CD1 | PHE | 284 | −2.999 | 14.859 | −4.561 | 1.00 | 0.00 | A |
| ATOM | 952 | HD1 | PHE | 284 | −3.110 | 15.483 | −5.419 | 1.00 | 0.00 | A |
| ATOM | 953 | CD2 | PHE | 284 | −2.725 | 12.638 | −3.579 | 1.00 | 0.00 | A |
| ATOM | 954 | HD2 | PHE | 284 | −2.633 | 11.569 | −3.698 | 1.00 | 0.00 | A |
| ATOM | 955 | CE1 | PHE | 284 | −2.964 | 15.436 | −3.271 | 1.00 | 0.00 | A |
| ATOM | 956 | HE1 | PHE | 284 | −3.059 | 16.503 | −3.156 | 1.00 | 0.00 | A |
| ATOM | 957 | CE2 | PHE | 284 | −2.690 | 13.216 | −2.284 | 1.00 | 0.00 | A |
| ATOM | 958 | HE2 | PHE | 284 | −2.569 | 12.591 | −1.413 | 1.00 | 0.00 | A |
| ATOM | 959 | CZ | PHE | 284 | −2.810 | 14.614 | −2.133 | 1.00 | 0.00 | A |
| ATOM | 960 | HZ | PHE | 284 | −2.784 | 15.055 | −1.148 | 1.00 | 0.00 | A |
| ATOM | 961 | C | PHE | 284 | −1.607 | 12.574 | −8.228 | 1.00 | 0.00 | A |
| ATOM | 962 | O | PHE | 284 | −0.976 | 11.570 | −8.199 | 1.00 | 0.00 | A |
| ATOM | 963 | N | ILE | 285 | −2.183 | 12.965 | −9.337 | 1.00 | 0.00 | A |
| ATOM | 964 | HN | ILE | 285 | −2.664 | 13.824 | −9.387 | 1.00 | 0.00 | A |
| ATOM | 965 | CA | ILE | 285 | −2.010 | 12.149 | −10.558 | 1.00 | 0.00 | A |
| ATOM | 966 | HA | ILE | 285 | −1.779 | 11.137 | −10.284 | 1.00 | 0.00 | A |
| ATOM | 967 | CB | ILE | 285 | −3.366 | 12.195 | −11.255 | 1.00 | 0.00 | A |
| ATOM | 968 | HB | ILE | 285 | −3.665 | 13.221 | −11.376 | 1.00 | 0.00 | A |
| ATOM | 969 | CG1 | ILE | 285 | −4.425 | 11.436 | −10.389 | 1.00 | 0.00 | A |
| ATOM | 970 | HG11 | ILE | 285 | −5.418 | 11.597 | −10.800 | 1.00 | 0.00 | A |
| ATOM | 971 | HG12 | ILE | 285 | −4.403 | 11.812 | −9.373 | 1.00 | 0.00 | A |
| ATOM | 972 | CG2 | ILE | 285 | −3.254 | 11.533 | −12.630 | 1.00 | 0.00 | A |
| ATOM | 973 | HG21 | ILE | 285 | −2.354 | 10.937 | −12.670 | 1.00 | 0.00 | A |
| ATOM | 974 | HG22 | ILE | 285 | −3.214 | 12.296 | −13.394 | 1.00 | 0.00 | A |
| ATOM | 975 | HG23 | ILE | 285 | −4.113 | 10.900 | −12.797 | 1.00 | 0.00 | A |
| ATOM | 976 | CD1 | ILE | 285 | −4.117 | 9.935 | −10.377 | 1.00 | 0.00 | A |
| ATOM | 977 | HD11 | ILE | 285 | −3.052 | 9.782 | −10.437 | 1.00 | 0.00 | A |
| ATOM | 978 | HD12 | ILE | 285 | −4.595 | 9.464 | −11.221 | 1.00 | 0.00 | A |
| ATOM | 979 | HD13 | ILE | 285 | −4.491 | 9.499 | −9.463 | 1.00 | 0.00 | A |
| ATOM | 980 | C | ILE | 285 | −0.877 | 12.719 | −11.430 | 1.00 | 0.00 | A |
| ATOM | 981 | O | ILE | 285 | −0.363 | 12.051 | −12.305 | 1.00 | 0.00 | A |
| ATOM | 982 | N | ASP | 286 | −0.482 | 13.954 | −11.197 | 1.00 | 0.00 | A |
| ATOM | 983 | HN | ASP | 286 | −0.916 | 14.490 | −10.486 | 1.00 | 0.00 | A |
| ATOM | 984 | CA | ASP | 286 | 0.616 | 14.558 | −12.019 | 1.00 | 0.00 | A |
| ATOM | 985 | HA | ASP | 286 | 0.304 | 14.640 | −13.045 | 1.00 | 0.00 | A |
| ATOM | 986 | CB | ASP | 286 | 0.823 | 15.955 | −11.440 | 1.00 | 0.00 | A |
| ATOM | 987 | HB1 | ASP | 286 | 1.050 | 15.881 | −10.388 | 1.00 | 0.00 | A |
| ATOM | 988 | HB2 | ASP | 286 | −0.077 | 16.537 | −11.578 | 1.00 | 0.00 | A |
| ATOM | 989 | CG | ASP | 286 | 1.985 | 16.636 | −12.165 | 1.00 | 0.00 | A |
| ATOM | 990 | OD1 | ASP | 286 | 3.115 | 16.251 | −11.918 | 1.00 | 0.00 | A |
| ATOM | 991 | OD2 | ASP | 286 | 1.725 | 17.525 | −12.959 | 1.00 | 0.00 | A |
| ATOM | 992 | C | ASP | 286 | 1.927 | 13.748 | −11.932 | 1.00 | 0.00 | A |
| ATOM | 993 | O | ASP | 286 | 2.838 | 13.974 | −12.700 | 1.00 | 0.00 | A |
| ATOM | 994 | N | TYR | 287 | 2.050 | 12.821 | −11.015 | 1.00 | 0.00 | A |
| ATOM | 995 | HN | TYR | 287 | 1.321 | 12.647 | −10.380 | 1.00 | 0.00 | A |
| ATOM | 996 | CA | TYR | 287 | 3.337 | 12.040 | −10.945 | 1.00 | 0.00 | A |
| ATOM | 997 | HA | TYR | 287 | 4.159 | 12.723 | −10.794 | 1.00 | 0.00 | A |
| ATOM | 998 | CB | TYR | 287 | 3.225 | 11.098 | −9.722 | 1.00 | 0.00 | A |
| ATOM | 999 | HB1 | TYR | 287 | 3.097 | 11.697 | −8.831 | 1.00 | 0.00 | A |
| ATOM | 1000 | HB2 | TYR | 287 | 4.138 | 10.530 | −9.632 | 1.00 | 0.00 | A |
| ATOM | 1001 | CG | TYR | 287 | 2.051 | 10.130 | −9.842 | 1.00 | 0.00 | A |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1002 | CD1 | TYR | 287 | 1.957 | 9.200 | −10.916 | 1.00 | 0.00 | A |
|---|---|---|---|---|---|---|---|---|---|---|
| ATOM | 1003 | HD1 | TYR | 287 | 2.719 | 9.163 | −11.674 | 1.00 | 0.00 | A |
| ATOM | 1004 | CD2 | TYR | 287 | 1.049 | 10.155 | −8.856 | 1.00 | 0.00 | A |
| ATOM | 1005 | HD2 | TYR | 287 | 1.116 | 10.860 | −8.043 | 1.00 | 0.00 | A |
| ATOM | 1006 | CE1 | TYR | 287 | 0.850 | 8.306 | −10.980 | 1.00 | 0.00 | A |
| ATOM | 1007 | HE1 | TYR | 287 | 0.771 | 7.598 | −11.789 | 1.00 | 0.00 | A |
| ATOM | 1008 | CE2 | TYR | 287 | −0.051 | 9.267 | −8.927 | 1.00 | 0.00 | A |
| ATOM | 1009 | HE2 | TYR | 287 | −0.820 | 9.298 | −8.165 | 1.00 | 0.00 | A |
| ATOM | 1010 | CZ | TYR | 287 | −0.150 | 8.347 | −9.982 | 1.00 | 0.00 | A |
| ATOM | 1011 | OH | TYR | 287 | −1.226 | 7.483 | −10.040 | 1.00 | 0.00 | A |
| ATOM | 1012 | HH | TYR | 287 | −2.031 | 8.008 | −10.045 | 1.00 | 0.00 | A |
| ATOM | 1013 | C | TYR | 287 | 3.560 | 11.262 | −12.240 | 1.00 | 0.00 | A |
| ATOM | 1014 | O | TYR | 287 | 4.666 | 10.868 | −12.555 | 1.00 | 0.00 | A |
| ATOM | 1015 | N | LEU | 288 | 2.525 | 11.039 | −12.994 | 1.00 | 0.00 | A |
| ATOM | 1016 | HN | LEU | 288 | 1.643 | 11.365 | −12.723 | 1.00 | 0.00 | A |
| ATOM | 1017 | CA | LEU | 288 | 2.680 | 10.284 | −14.273 | 1.00 | 0.00 | A |
| ATOM | 1018 | HA | LEU | 288 | 2.933 | 9.284 | −14.072 | 1.00 | 0.00 | A |
| ATOM | 1019 | CB | LEU | 288 | 1.306 | 10.359 | −14.940 | 1.00 | 0.00 | A |
| ATOM | 1020 | HB1 | LEU | 288 | 1.358 | 9.918 | −15.923 | 1.00 | 0.00 | A |
| ATOM | 1021 | HB2 | LEU | 288 | 1.002 | 11.394 | −15.023 | 1.00 | 0.00 | A |
| ATOM | 1022 | CG | LEU | 28 | 0.292 | 9.593 | −14.093 | 1.00 | 0.00 | A |
| ATOM | 1023 | HG | LEU | 288 | 0.321 | 9.956 | −13.077 | 1.00 | 0.00 | A |
| ATOM | 1024 | CD1 | LEU | 288 | −1.112 | 9.784 | −14.666 | 1.00 | 0.00 | A |
| ATOM | 1025 | HD11 | LEU | 288 | −1.208 | 9.216 | −15.577 | 1.00 | 0.00 | A |
| ATOM | 1026 | HD12 | LEU | 288 | −1.278 | 10.830 | −14.873 | 1.00 | 0.00 | A |
| ATOM | 1027 | HD13 | LEU | 288 | −1.841 | 9.439 | −13.948 | 1.00 | 0.00 | A |
| ATOM | 1028 | CD2 | LEU | 288 | 0.645 | 8.107 | −14.119 | 1.00 | 0.00 | A |
| ATOM | 1029 | HD21 | LEU | 288 | −0.126 | 7.548 | −13.616 | 1.00 | 0.00 | A |
| ATOM | 1030 | HD22 | LEU | 288 | 1.588 | 7.953 | −13.617 | | | |
| ATOM | 1031 | HD23 | LEU | 288 | 0.723 | 7.772 | −15.143 | 1.00 | 0.00 | A |
| ATOM | 1032 | C | LEU | 288 | 3.744 | 10.925 | −15.152 | 1.00 | 0.00 | A |
| ATOM | 1033 | O | LEU | 288 | 4.327 | 10.293 | −16.010 | 1.00 | 0.00 | A |
| ATOM | 1034 | N | ARG | 289 | 4.006 | 12.158 | −14.932 | 1.00 | 0.00 | A |
| ATOM | 1035 | HN | ARG | 289 | 3.538 | 12.620 | −14.222 | 1.00 | 0.00 | A |
| ATOM | 1036 | CA | ARG | 289 | 5.037 | 12.868 | −15.749 | 1.00 | 0.00 | A |
| ATOM | 1037 | HA | ARG | 289 | 4.731 | 12.912 | −16.780 | 1.00 | 0.00 | A |
| ATOM | 1038 | CB | ARG | 289 | 5.105 | 14.278 | −15.174 | 1.00 | 0.00 | A |
| ATOM | 1039 | HB1 | ARG | 289 | 5.860 | 14.845 | −15.697 | 1.00 | 0.00 | A |
| ATOM | 1040 | HB2 | ARG | 289 | 5.352 | 14.228 | −14.123 | 1.00 | 0.00 | A |
| ATOM | 1041 | CG | ARG | 289 | 3.750 | 14.960 | −15.349 | 1.00 | 0.00 | A |
| ATOM | 1042 | HG1 | ARG | 289 | 3.000 | 14.419 | −14.793 | 1.00 | 0.00 | A |
| ATOM | 1043 | HG2 | ARG | 289 | 3.485 | 14.971 | −16.397 | 1.00 | 0.00 | A |
| ATOM | 1044 | CD | ARG | 289 | 3.832 | 16.392 | −14.829 | 1.00 | 0.00 | A |
| ATOM | 1045 | HD1 | ARG | 289 | 4.148 | 16.399 | −13.800 | 1.00 | 0.00 | A |
| ATOM | 1046 | HD2 | ARG | 289 | 2.876 | 16.885 | −14.936 | 1.00 | 0.00 | A |
| ATOM | 1047 | NE | ARG | 289 | 4.859 | 17.051 | −15.681 | 1.00 | 0.00 | A |
| ATOM | 1048 | HE | ARG | 289 | 5.221 | 16.583 | −16.462 | 1.00 | 0.00 | A |
| ATOM | 1049 | CZ | ARG | 289 | 5.274 | 18.252 | −15.388 | 1.00 | 0.00 | A |
| ATOM | 1050 | NH1 | ARG | 289 | 4.726 | 19.289 | −15.958 | 1.00 | 0.00 | A |
| ATOM | 1051 | HH11 | ARG | 289 | 3.986 | 19.164 | −16.619 | 1.00 | 0.00 | A |
| ATOM | 1052 | HH12 | ARG | 289 | 5.045 | 20.210 | −15.732 | 1.00 | 0.00 | A |
| ATOM | 1053 | NH2 | ARG | 289 | 6.240 | 18.414 | −14.525 | 1.00 | 0.00 | A |
| ATOM | 1054 | HH21 | ARG | 289 | 6.660 | 17.619 | −14.088 | 1.00 | 0.00 | A |
| ATOM | 1055 | HH22 | ARG | 289 | 6.559 | 19.335 | −14.299 | 1.00 | 0.00 | A |
| ATOM | 1056 | C | ARG | 289 | 6.395 | 12.169 | −15.623 | 1.00 | 0.00 | A |
| ATOM | 1057 | OT1 | ARG | 289 | 6.732 | 11.410 | −16.516 | 1.00 | 0.00 | A |
| ATOM | 1058 | OT2 | ARG | 289 | 7.073 | 12.407 | −14.636 | 1.00 | 0.00 | A |
| ATOM | 1059 | CA | MET | 223 | 20.757 | 7.576 | −2.089 | 1.00 | 0.00 | B |
| ATOM | 1060 | HA | MET | 223 | 20.343 | 8.263 | −1.370 | 1.00 | 0.00 | B |
| ATOM | 1061 | CB | MET | 223 | 20.920 | 8.270 | −3.443 | 1.00 | 0.00 | B |
| ATOM | 1062 | HB1 | MET | 223 | 19.956 | 8.600 | −3.798 | 1.00 | 0.00 | B |
| ATOM | 1063 | HB2 | MET | 223 | 21.349 | 7.578 | −4.154 | 1.00 | 0.00 | B |
| ATOM | 1064 | CG | MET | 223 | 21.843 | 9.478 | −3.285 | 1.00 | 0.00 | B |
| ATOM | 1065 | HG1 | MET | 223 | 22.807 | 9.149 | −2.927 | 1.00 | 0.00 | B |
| ATOM | 1066 | HG2 | MET | 223 | 21.414 | 10.169 | −2.577 | 1.00 | 0.00 | B |
| ATOM | 1067 | SD | MET | 223 | 22.045 | 10.302 | −4.885 | 1.00 | 0.00 | B |
| ATOM | 1068 | CE | MET | 223 | 23.085 | 9.041 | −5.660 | 1.00 | 0.00 | B |
| ATOM | 1069 | HE1 | MET | 223 | 22.652 | 8.064 | −5.490 | 1.00 | 0.00 | B |
| ATOM | 1070 | HE2 | MET | 223 | 24.072 | 9.074 | −5.230 | 1.00 | 0.00 | B |
| ATOM | 1071 | HE3 | MET | 223 | 23.150 | 9.233 | −6.723 | 1.00 | 0.00 | B |
| ATOM | 1072 | C | MET | 223 | 19.863 | 6.340 | −2.224 | 1.00 | 0.00 | B |
| ATOM | 1073 | O | MET | 223 | 20.328 | 5.218 | −2.171 | 1.00 | 0.00 | B |
| ATOM | 1074 | N | MET | 223 | 22.142 | 7.172 | −1.689 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1075 | HT1  | MET | 223 | 22.577 | 7.934 | −1.131 | 1.00 | 0.00 | B |
|------|------|------|-----|-----|--------|-------|--------|------|------|---|
| ATOM | 1076 | HT2  | MET | 223 | 22.714 | 6.994 | −2.540 | 1.00 | 0.00 | B |
| ATOM | 1077 | HT3  | MET | 223 | 22.097 | 6.306 | −1.115 | 1.00 | 0.00 | B |
| ATOM | 1078 | N    | ALA | 224 | 18.583 | 6.535 | −2.394 | 1.00 | 0.00 | B |
| ATOM | 1079 | HN   | ALA | 224 | 18.226 | 7.447 | −2.432 | 1.00 | 0.00 | B |
| ATOM | 1080 | CA   | ALA | 224 |        |       |        |      |      |   |
| ATOM | 1081 | HA   | ALA | 224 | 17.972 | 4.740 | −3.348 | 1.00 | 0.00 | B |
| ATOM | 1082 | CB   | ALA | 224 | 17.789 | 4.610 | −1.210 | 1.00 | 0.00 | B |
| ATOM | 1083 | HB1  | ALA | 224 | 17.936 | 3.560 | −1.412 | 1.00 | 0.00 | B |
| ATOM | 1084 | HB2  | ALA | 224 | 16.888 | 4.743 | −0.629 | 1.00 | 0.00 | B |
| ATOM | 1085 | HB3  | ALA | 224 | 18.635 | 4.991 | −0.657 | 1.00 | 0.00 | B |
| ATOM | 1086 | C    | ALA | 224 | 16.223 | 5.849 | −2.742 | 1.00 | 0.00 | B |
| ATOM | 1087 | O    | ALA | 224 | 15.878 | 6.973 | −2.432 | 1.00 | 0.00 | B |
| ATOM | 1088 | N    | ALA | 225 | 15.382 | 5.002 | −3.265 | 1.00 | 0.00 | B |
| ATOM | 1089 | HN   | ALA | 225 | 15.684 | 4.102 | −3.509 | 1.00 | 0.00 | B |
| ATOM | 1090 | CA   | ALA | 225 | 13.964 | 5.398 | −3.500 | 1.00 | 0.00 | B |
| ATOM | 1091 | HA   | ALA | 225 | 13.510 | 5.737 | −2.584 | 1.00 | 0.00 | B |
| ATOM | 1092 | CB   | ALA | 225 | 14.032 | 6.542 | −4.508 | 1.00 | 0.00 | B |
| ATOM | 1093 | HB1  | ALA | 225 | 13.294 | 7.289 | −4.256 | 1.00 | 0.00 | B |
| ATOM | 1094 | HB2  | ALA | 225 | 13.835 | 6.160 | −5.499 | 1.00 | 0.00 | B |
| ATOM | 1095 | HB3  | ALA | 225 | 15.016 | 6.986 | −4.482 | 1.00 | 0.00 | B |
| ATOM | 1096 | C    | ALA | 225 | 13.190 | 4.217 | −4.080 | 1.00 | 0.00 | B |
| ATOM | 1097 | O    | ALA | 225 | 12.640 | 4.290 | −5.160 | 1.00 | 0.00 | B |
| ATOM | 1098 | N    | GLY | 226 | 13.145 | 3.126 | −3.368 | 1.00 | 0.00 | B |
| ATOM | 1099 | HN   | GLY | 226 | 13.593 | 3.092 | −2.497 | 1.00 | 0.00 | B |
| ATOM | 1100 | CA   | GLY | 226 | 12.409 | 1.933 | −3.871 | 1.00 | 0.00 | B |
| ATOM | 1101 | HA1  | GLY | 226 | 12.646 | 1.081 | −3.254 | 1.00 | 0.00 | B |
| ATOM | 1102 | HA2  | GLY | 226 | 12.707 | 1.732 | −4.891 | 1.00 | 0.00 | B |
| ATOM | 1103 | C    | GLY | 226 | 10.902 | 2.188 | −3.822 | 1.00 | 0.00 | B |
| ATOM | 1104 | O    | GLY | 226 | 10.182 | 1.850 | −4.736 | 1.00 | 0.00 | B |
| ATOM | 1105 | N    | VAL | 227 | 10.419 | 2.773 | −2.758 | 1.00 | 0.00 | B |
| ATOM | 1106 | HN   | VAL | 227 | 11.018 | 3.034 | −2.029 | 1.00 | 0.00 | B |
| ATOM | 1107 | CA   | VAL | 227 | 8.951  | 3.048 | −2.653 | 1.00 | 0.00 | B |
| ATOM | 1108 | HA   | VAL | 227 | 8.385  | 2.167 | −2.904 | 1.00 | 0.00 | B |
| ATOM | 1109 | CB   | VAL | 227 | 8.721  | 3.414 | −1.189 | 1.00 | 0.00 | B |
| ATOM | 1110 | HB   | VAL | 227 | 9.323  | 4.275 | −0.935 | 1.00 | 0.00 | B |
| ATOM | 1111 | CG1  | VAL | 227 | 7.243  | 3.742 | −0.971 | 1.00 | 0.00 | B |
| ATOM | 1112 | HG11 | VAL | 227 | 7.155  | 4.542 | −0.251 | 1.00 | 0.00 | B |
| ATOM | 1113 | HG12 | VAL | 227 | 6.730  | 2.867 | −0.601 | 1.00 | 0.00 | B |
| ATOM | 1114 | HG13 | VAL | 227 | 6.801  | 4.051 | −1.907 | 1.00 | 0.00 | B |
| ATOM | 1115 | CG2  | VAL | 227 | 9.117  | 2.232 | −0.301 | 1.00 | 0.00 | B |
| ATOM | 1116 | HG21 | VAL | 227 | 8.360  | 1.465 | −0.363 | 1.00 | 0.00 | B |
| ATOM | 1117 | HG22 | VAL | 227 | 9.207  | 2.566 | 0.722  | 1.00 | 0.00 | B |
| ATOM | 1118 | HG23 | VAL | 227 | 10.064 | 1.832 | −0.634 | 1.00 | 0.00 | B |
| ATOM | 1119 | C    | VAL | 227 | 8.558  | 4.213 | −3.566 | 1.00 | 0.00 | B |
| ATOM | 1120 | O    | VAL | 227 | 8.404  | 5.335 | −3.125 | 1.00 | 0.00 | B |
| ATOM | 1121 | N    | LYS | 228 | 8.390  | 3.955 | −4.833 | 1.00 | 0.00 | B |
| ATOM | 1122 | HN   | LYS | 228 | 8.499  | 3.044 | −5.165 | 1.00 | 0.00 | B |
| ATOM | 1123 | CA   | LYS | 228 | 8.008  | 5.047 | −5.769 | 1.00 | 0.00 | B |
| ATOM | 1124 | HA   | LYS | 228 | 8.603  | 5.923 | −5.590 | 1.00 | 0.00 | B |
| ATOM | 1125 | CB   | LYS | 228 | 8.301  | 4.485 | −7.161 | 1.00 | 0.00 | B |
| ATOM | 1126 | HB1  | LYS | 228 | 8.162  | 5.259 | −7.897 | 1.00 | 0.00 | B |
| ATOM | 1127 | HB2  | LYS | 228 | 7.632  | 3.662 | −7.369 | 1.00 | 0.00 | B |
| ATOM | 1128 | CG   | LYS | 228 | 9.753  | 3.997 | −7.218 | 1.00 | 0.00 | B |
| ATOM | 1129 | HG1  | LYS | 228 | 9.908  | 3.239 | −6.466 | 1.00 | 0.00 | B |
| ATOM | 1130 | HG2  | LYS | 228 | 10.419 | 4.829 | −7.035 | 1.00 | 0.00 | B |
| ATOM | 1131 | CD   | LYS | 228 | 10.043 | 3.406 | −8.601 | 1.00 | 0.00 | B |
| ATOM | 1132 | HD1  | LYS | 228 | 9.900  | 4.165 | −9.356 | 1.00 | 0.00 | B |
| ATOM | 1133 | HD2  | LYS | 228 | 9.370  | 2.580 | −8.787 | 1.00 | 0.00 | B |
| ATOM | 1134 | CE   | LYS | 228 | 11.491 | 2.907 | −8.651 | 1.00 | 0.00 | B |
| ATOM | 1135 | HE1  | LYS | 228 | 12.174 | 3.714 | −8.446 | 1.00 | 0.00 | B |
| ATOM | 1136 | HE2  | LYS | 228 | 11.703 | 2.466 | −9.618 | 1.00 | 0.00 | B |
| ATOM | 1137 | NZ   | LYS | 228 | 11.580 | 1.878 | −7.578 | 1.00 | 0.00 | B |
| ATOM | 1138 | HZ1  | LYS | 228 | 11.724 | 2.344 | −6.661 | 1.00 | 0.00 | B |
| ATOM | 1139 | HZ2  | LYS | 228 | 12.380 | 1.241 | −7.774 | 1.00 | 0.00 | B |
| ATOM | 1140 | HZ3  | LYS | 228 | 10.698 | 1.329 | −7.550 | 1.00 | 0.00 | B |
| ATOM | 1141 | C    | LYS | 228 | 6.514  | 5.366 | −5.595 | 1.00 | 0.00 | B |
| ATOM | 1142 | O    | LYS | 228 | 6.135  | 6.487 | −5.323 | 1.00 | 0.00 | B |
| ATOM | 1143 | N    | GLN | 229 | 5.672  | 4.384 | −5.750 | 1.00 | 0.00 | B |
| ATOM | 1144 | HN   | GLN | 229 | 6.003  | 3.499 | −5.970 | 1.00 | 0.00 | B |
| ATOM | 1145 | CA   | GLN | 229 | 4.199  | 4.618 | −5.591 | 1.00 | 0.00 | B |
| ATOM | 1146 | HA   | GLN | 229 | 4.017  | 5.216 | −4.712 | 1.00 | 0.00 | B |
| ATOM | 1147 | CB   | GLN | 229 | 3.736  | 5.393 | −6.846 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1148 | HB1  | GLN | 229 | 4.329  | 6.291  | −6.945 | 1.00 | 0.00 | B |
|------|------|------|-----|-----|--------|--------|--------|------|------|---|
| ATOM | 1149 | HB2  | GLN | 229 | 2.697  | 5.666  | −6.731 | 1.00 | 0.00 | B |
| ATOM | 1150 | CG   | GLN | 229 | 3.898  | 4.539  | −8.120 | 1.00 | 0.00 | B |
| ATOM | 1151 | HG1  | GLN | 229 | 3.390  | 5.024  | −8.946 | 1.00 | 0.00 | B |
| ATOM | 1152 | HG2  | GLN | 229 | 3.464  | 3.564  | −7.957 | 1.00 | 0.00 | B |
| ATOM | 1153 | CD   | GLN | 229 | 5.373  | 4.385  | −8.462 | 1.00 | 0.00 | B |
| ATOM | 1154 | OE1  | GLN | 229 | 6.120  | 5.333  | −8.383 | 1.00 | 0.00 | B |
| ATOM | 1155 | NE2  | GLN | 229 | 5.825  | 3.226  | −8.864 | 1.00 | 0.00 | B |
| ATOM | 1156 | HE21 | GLN | 229 | 5.215  | 2.466  | −8.947 | 1.00 | 0.00 | B |
| ATOM | 1157 | HE22 | GLN | 229 | 6.773  | 3.120  | −9.085 | 1.00 | 0.00 | B |
| ATOM | 1158 | C    | GLN | 229 | 3.445  | 3.277  | −5.476 | 1.00 | 0.00 | B |
| ATOM | 1159 | O    | GLN | 229 | 2.433  | 3.070  | −6.118 | 1.00 | 0.00 | B |
| ATOM | 1160 | N    | LEU | 230 | 3.931  | 2.359  | −4.659 | 1.00 | 0.00 | B |
| ATOM | 1161 | HN   | LEU | 230 | 4.743  | 2.537  | −4.151 | 1.00 | 0.00 | B |
| ATOM | 1162 | CA   | LEU | 230 | 3.229  | 1.040  | −4.515 | 1.00 | 0.00 | B |
| ATOM | 1163 | HA   | LEU | 230 | 2.324  | 1.044  | −5.086 | 1.00 | 0.00 | B |
| ATOM | 1164 | CB   | LEU | 230 | 4.189  | −0.034 | −5.064 | 1.00 | 0.00 | B |
| ATOM | 1165 | HB1  | LEU | 230 | 3.760  | −1.012 | −4.899 | 1.00 | 0.00 | B |
| ATOM | 1166 | HB2  | LEU | 230 | 5.133  | 0.032  | −4.541 | 1.00 | 0.00 | B |
| ATOM | 1167 | CG   | LEU | 230 | 4.430  | 0.165  | −6.565 | 1.00 | 0.00 | B |
| ATOM | 1168 | HG   | LEU | 230 | 3.484  | 0.327  | −7.062 | 1.00 | 0.00 | B |
| ATOM | 1169 | CD1  | LEU | 230 | 5.330  | 1.370  | −6.785 | 1.00 | 0.00 | B |
| ATOM | 1170 | HD11 | LEU | 230 | 6.081  | 1.128  | −7.523 | 1.00 | 0.00 | B |
| ATOM | 1171 | HD12 | LEU | 230 | 5.812  | 1.629  | −5.855 | 1.00 | 0.00 | B |
| ATOM | 1172 | HD13 | LEU | 230 | 4.742  | 2.201  | −7.132 | 1.00 | 0.00 | B |
| ATOM | 1173 | CD2  | LEU | 230 | 5.102  | −1.082 | −7.142 | 1.00 | 0.00 | B |
| ATOM | 1174 | HD21 | LEU | 230 | 6.147  | −1.085 | −6.872 | 1.00 | 0.00 | B |
| ATOM | 1175 | HD22 | LEU | 230 | 5.009  | −1.076 | −8.218 | 1.00 | 0.00 | B |
| ATOM | 1176 | HD23 | LEU | 230 | 4.624  | −1.965 | −6.744 | 1.00 | 0.00 | B |
| ATOM | 1177 | C    | LEU | 230 | 2.922  | 0.739  | −3.038 | 1.00 | 0.00 | B |
| ATOM | 1178 | O    | LEU | 230 | 2.986  | −0.396 | −2.608 | 1.00 | 0.00 | B |
| ATOM | 1179 | N    | ALA | 231 | 2.586  | 1.731  | −2.257 | 1.00 | 0.00 | B |
| ATOM | 1180 | HN   | ALA | 231 | 2.546  | 2.639  | −2.607 | 1.00 | 0.00 | B |
| ATOM | 1181 | CA   | ALA | 231 | 2.281  | 1.450  | −0.810 | 1.00 | 0.00 | B |
| ATOM | 1182 | HA   | ALA | 231 | 1.694  | 0.565  | −0.729 | 1.00 | 0.00 | B |
| ATOM | 1183 | CB   | ALA | 231 | 3.645  | 1.231  | −0.157 | 1.00 | 0.00 | B |
| ATOM | 1184 | HB1  | ALA | 231 | 3.656  | 0.274  | 0.342  | 1.00 | 0.00 | B |
| ATOM | 1185 | HB2  | ALA | 231 | 3.829  | 2.016  | −0.562 | 1.00 | 0.00 | B |
| ATOM | 1186 | HB3  | ALA | 231 | 4.415  | 1.251  | −0.915 | 1.00 | 0.00 | B |
| ATOM | 1187 | C    | ALA | 231 | 1.551  | 2.622  | −0.138 | 1.00 | 0.00 | B |
| ATOM | 1188 | O    | ALA | 231 | 1.458  | 2.685  | 1.071  | 1.00 | 0.00 | B |
| ATOM | 1189 | N    | ASP | 232 | 1.006  | 3.515  | −0.909 | 1.00 | 0.00 | B |
| ATOM | 1190 | HN   | ASP | 232 | 1.052  | 3.405  | −1.871 | 1.00 | 0.00 | B |
| ATOM | 1191 | CA   | ASP | 232 | 0.273  | 4.694  | −0.322 | 1.00 | 0.00 | B |
| ATOM | 1192 | HA   | ASP | 232 | −0.296 | 4.395  | 0.511  | 1.00 | 0.00 | B |
| ATOM | 1193 | CB   | ASP | 232 | 1.350  | 5.714  | 0.095  | 1.00 | 0.00 | B |
| ATOM | 1194 | HB1  | ASP | 232 | 0.870  | 6.610  | 0.460  | 1.00 | 0.00 | B |
| ATOM | 1195 | HB2  | ASP | 232 | 1.958  | 5.960  | −0.763 | 1.00 | 0.00 | B |
| ATOM | 1196 | CG   | ASP | 232 | 2.241  | 5.137  | 1.194  | 1.00 | 0.00 | B |
| ATOM | 1197 | OD1  | ASP | 232 | 3.182  | 4.435  | 0.859  | 1.00 | 0.00 | B |
| ATOM | 1198 | OD2  | ASP | 232 | 1.967  | 5.403  | 2.353  | 1.00 | 0.00 | B |
| ATOM | 1199 | C    | ASP | 232 | −0.628 | 5.309  | −1.365 | 1.00 | 0.00 | B |
| ATOM | 1200 | O    | ASP | 232 | −1.743 | 5.700  | −1.098 | 1.00 | 0.00 | B |
| ATOM | 1201 | N    | ASP | 233 | −0.144 | 5.405  | −2.539 | 1.00 | 0.00 | B |
| ATOM | 1202 | HN   | ASP | 233 | 0.753  | 5.084  | −2.701 | 1.00 | 0.00 | B |
| ATOM | 1203 | CA   | ASP | 233 | −0.948 | 5.997  | −3.645 | 1.00 | 0.00 | B |
| ATOM | 1204 | HA   | ASP | 233 | −1.341 | 6.956  | −3.353 | 1.00 | 0.00 | B |
| ATOM | 1205 | CB   | ASP | 233 | 0.036  | 6.166  | −4.806 | 1.00 | 0.00 | B |
| ATOM | 1206 | HB1  | ASP | 233 | −0.479 | 6.588  | −5.655 | 1.00 | 0.00 | B |
| ATOM | 1207 | HB2  | ASP | 233 | 0.445  | 5.202  | −5.075 | 1.00 | 0.00 | B |
| ATOM | 1208 | CG   | ASP | 233 | 1.170  | 7.103  | −4.383 | 1.00 | 0.00 | B |
| ATOM | 1209 | OD1  | ASP | 233 | 1.885  | 6.756  | −3.457 | 1.00 | 0.00 | B |
| ATOM | 1210 | OD2  | ASP | 233 | 1.304  | 8.152  | −4.993 | 1.00 | 0.00 | B |
| ATOM | 1211 | C    | ASP | 233 | −2.084 | 5.050  | −4.032 | 1.00 | 0.00 | B |
| ATOM | 1212 | O    | ASP | 233 | −3.074 | 5.453  | −4.601 | 1.00 | 0.00 | B |
| ATOM | 1213 | N    | ARG | 234 | −1.952 | 3.793  | −3.724 | 1.00 | 0.00 | B |
| ATOM | 1214 | HN   | ARG | 234 | −1.151 | 3.486  | −3.260 | 1.00 | 0.00 | B |
| ATOM | 1215 | CA   | ARG | 234 | −3.035 | 2.829  | −4.083 | 1.00 | 0.00 | B |
| ATOM | 1216 | HA   | ARG | 234 | −3.332 | 2.984  | −5.108 | 1.00 | 0.00 | B |
| ATOM | 1217 | CB   | ARG | 234 | −2.419 | 1.430  | −3.936 | 1.00 | 0.00 | B |
| ATOM | 1218 | HB1  | ARG | 234 | −1.562 | 1.352  | −4.582 | 1.00 | 0.00 | B |
| ATOM | 1219 | HB2  | ARG | 234 | −3.150 | 0.690  | −4.224 | 1.00 | 0.00 | B |
| ATOM | 1220 | CG   | ARG | 234 | −1.986 | 1.173  | −2.491 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1221 | HG1  | ARG | 234 | −2.855 | 1.163  | −1.851 | 1.00 | 0.00 | B |
|------|------|------|-----|-----|--------|--------|--------|------|------|---|
| ATOM | 1222 | HG2  | ARG | 234 | −1.308 | 1.951  | −2.168 | 1.00 | 0.00 | B |
| ATOM | 1223 | CD   | ARG | 234 | −1.289 | −0.189 | −2.414 | 1.00 | 0.00 | B |
| ATOM | 1224 | HD1  | ARG | 234 | −0.420 | −0.201 | −3.051 | 1.00 | 0.00 | B |
| ATOM | 1225 | HD2  | ARG | 234 | −1.976 | −0.976 | −2.697 | 1.00 | 0.00 | B |
| ATOM | 1226 | NE   | ARG | 234 | −0.883 | −0.342 | −0.992 | 1.00 | 0.00 | B |
| ATOM | 1227 | HE   | ARG | 234 | −1.061 | 0.376  | −0.352 | 1.00 | 0.00 | B |
| ATOM | 1228 | CZ   | ARG | 234 | −0.285 | −1.437 | −0.599 | 1.00 | 0.00 | B |
| ATOM | 1229 | NH1  | ARG | 234 | 0.483  | −1.419 | 0.456  | 1.00 | 0.00 | B |
| ATOM | 1230 | HH11 | ARG | 234 | 0.615  | −0.567 | 0.963  | 1.00 | 0.00 | B |
| ATOM | 1231 | HH12 | ARG | 234 | 0.939  | −2.257 | 0.757  | 1.00 | 0.00 | B |
| ATOM | 1232 | HN2  | ARG | 234 | −0.456 | −2.550 | −1.262 | 1.00 | 0.00 | B |
| ATOM | 1233 | HH21 | ARG | 234 | −1.044 | −2.565 | −2.071 | 1.00 | 0.00 | B |
| ATOM | 1234 | HH22 | ARG | 234 | 0.001  | −3.388 | −0.961 | 1.00 | 0.00 | B |
| ATOM | 1235 | C    | ARG | 234 | −4.247 | 3.013  | −3.161 | 1.00 | 0.00 | B |
| ATOM | 1236 | O    | ARG | 234 | −5.352 | 3.130  | −3.616 | 1.00 | 0.00 | B |
| ATOM | 1237 | N    | THR | 235 | −4.048 | 3.053  | −1.875 | 1.00 | 0.00 | B |
| ATOM | 1238 | HN   | THR | 235 | −3.142 | 2.991  | −1.516 | 1.00 | 0.00 | B |
| ATOM | 1239 | CA   | THR | 235 | −5.206 | 3.231  | −0.944 | 1.00 | 0.00 | B |
| ATOM | 1240 | HA   | THR | 235 | −6.047 | 2.644  | −1.263 | 1.00 | 0.00 | B |
| ATOM | 1241 | CB   | THR | 235 | −4.688 | 2.747  | 0.414  | 1.00 | 0.00 | B |
| ATOM | 1242 | HB   | THR | 235 | −3.795 | 3.306  | 0.680  | 1.00 | 0.00 | B |
| ATOM | 1243 | OG1  | THR | 235 | −4.370 | 1.365  | 0.331  | 1.00 | 0.00 | B |
| ATOM | 1244 | HG1  | THR | 235 | −3.445 | 1.289  | 0.091  | 1.00 | 0.00 | B |
| ATOM | 1245 | CG2  | THR | 235 | −5.756 | 2.967  | 1.488  | 1.00 | 0.00 | B |
| ATOM | 1246 | HG21 | THR | 235 | −5.805 | 2.098  | 2.129  | 1.00 | 0.00 | B |
| ATOM | 1247 | HG22 | THR | 235 | −6.715 | 3.121  | 1.017  | 1.00 | 0.00 | B |
| ATOM | 1248 | HG23 | THR | 235 | −5.500 | 3.835  | 2.077  | 1.00 | 0.00 | B |
| ATOM | 1249 | C    | THR | 235 | −5.587 | 4.693  | −0.888 | 1.00 | 0.00 | B |
| ATOM | 1250 | O    | THR | 235 | −6.702 | 5.052  | −0.561 | 1.00 | 0.00 | B |
| ATOM | 1251 | N    | LEU | 236 | −4.763 | 5.534  | −1.203 | 1.00 | 0.00 | B |
| ATOM | 1252 | HN   | LEU | 236 | −3.783 | 5.210  | −1.463 | 1.00 | 0.00 | B |
| ATOM | 1253 | CA   | LEU | 236 | −4.950 | 6.979  | −1.179 | 1.00 | 0.00 | B |
| ATOM | 1254 | HA   | LEU | 236 | −5.337 | 7.279  | −0.254 | 1.00 | 0.00 | B |
| ATOM | 1255 | CB   | LEU | 236 | −3.612 | 7.626  | −1.406 | 1.00 | 0.00 | B |
| ATOM | 1256 | HB1  | LEU | 236 | −3.173 | 7.249  | −2.317 | 1.00 | 0.00 | B |
| ATOM | 1257 | HB2  | LEU | 236 | −2.958 | 7.416  | −0.570 | 1.00 | 0.00 | B |
| ATOM | 1258 | CG   | LEU | 236 | −3.823 | 9.108  | −1.526 | 1.00 | 0.00 | B |
| ATOM | 1259 | HG   | LEU | 236 | −4.620 | 9.278  | −2.251 | 1.00 | 0.00 | B |
| ATOM | 1260 | CD1  | LEU | 236 | −4.242 | 9.683  | −0.168 | 1.00 | 0.00 | B |
| ATOM | 1261 | HD11 | LEU | 236 | −4.496 | 10.727 | −0.282 | 1.00 | 0.00 | B |
| ATOM | 1262 | HD12 | LEU | 236 | −3.427 | 9.585  | 0.532  | 1.00 | 0.00 | B |
| ATOM | 1263 | HD13 | LEU | 236 | −5.101 | 9.142  | 0.202  | 1.00 | 0.00 | B |
| ATOM | 1264 | CD2  | LEU | 236 | −2.533 | 9.759  | −1.999 | 1.00 | 0.00 | B |
| ATOM | 1265 | HD21 | LEU | 236 | −1.723 | 9.464  | −1.349 | 1.00 | 0.00 | B |
| ATOM | 1266 | HD22 | LEU | 236 | −2.644 | 10.823 | −1.973 | 1.00 | 0.00 | B |
| ATOM | 1267 | HD23 | LEU | 236 | −2.318 | 9.442  | −3.009 | 1.00 | 0.00 | B |
| ATOM | 1268 | C    | LEU | 236 | −5.906 | 7.372  | −2.277 | 1.00 | 0.00 | B |
| ATOM | 1269 | O    | LEU | 236 | −6.867 | 8.081  | −2.050 | 1.00 | 0.00 | B |
| ATOM | 1270 | N    | LEU | 237 | −5.669 | 6.932  | −3.458 | 1.00 | 0.00 | B |
| ATOM | 1271 | HN   | LEU | 237 | −4.892 | 6.359  | −3.629 | 1.00 | 0.00 | B |
| ATOM | 1272 | CA   | LEU | 237 | −6.582 | 7.302  | −4.559 | 1.00 | 0.00 | B |
| ATOM | 1273 | HA   | LEU | 237 | −6.919 | 8.303  | −4.411 | 1.00 | 0.00 | B |
| ATOM | 1274 | CB   | LEU | 237 | −5.715 | 7.241  | −5.797 | 1.00 | 0.00 | B |
| ATOM | 1275 | HB1  | LEU | 237 | −6.231 | 7.681  | −6.628 | 1.00 | 0.00 | B |
| ATOM | 1276 | HB2  | LEU | 237 | −5.476 | 6.211  | −6.022 | 1.00 | 0.00 | B |
| ATOM | 1277 | CG   | LEU | 237 | −4.409 | 8.036  | −5.520 | 1.00 | 0.00 | B |
| ATOM | 1278 | HG   | LEU | 237 | −3.768 | 7.440  | −4.889 | 1.00 | 0.00 | B |
| ATOM | 1279 | CD1  | LEU | 237 | −3.699 | 8.292  | −6.816 | 1.00 | 0.00 | B |
| ATOM | 1280 | HD11 | LEU | 237 | −4.343 | 8.859  | −7.466 | 1.00 | 0.00 | B |
| ATOM | 1281 | HD12 | LEU | 237 | −3.455 | 7.352  | −7.275 | 1.00 | 0.00 | B |
| ATOM | 1282 | HD13 | LEU | 237 | −2.798 | 8.848  | −6.623 | 1.00 | 0.00 | B |
| ATOM | 1283 | CD2  | LEU | 237 | −4.712 | 9.385  | −4.802 | 1.00 | 0.00 | B |
| ATOM | 1284 | HD21 | LEU | 237 | −3.790 | 9.823  | −4.454 | 1.00 | 0.00 | B |
| ATOM | 1285 | HD22 | LEU | 237 | −5.357 | 9.212  | −3.954 | 1.00 | 0.00 | B |
| ATOM | 1286 | HD23 | LEU | 237 | −5.195 | 10.059 | −5.483 | 1.00 | 0.00 | B |
| ATOM | 1287 | C    | LEU | 237 | −7.784 | 6.383  | −4.595 | 1.00 | 0.00 | B |
| ATOM | 1288 | O    | LEU | 237 | −8.482 | 6.261  | −5.573 | 1.00 | 0.00 | B |
| ATOM | 1289 | N    | MET | 238 | −7.984 | 5.708  | −3.547 | 1.00 | 0.00 | B |
| ATOM | 1290 | HN   | MET | 238 | −7.460 | 5.892  | −2.781 | 1.00 | 0.00 | B |
| ATOM | 1291 | CA   | MET | 238 | −9.116 | 4.793  | −3.447 | 1.00 | 0.00 | B |
| ATOM | 1292 | HA   | MET | 238 | −9.492 | 4.580  | −4.427 | 1.00 | 0.00 | B |
| ATOM | 1293 | CB   | MET | 238 | −8.625 | 3.526  | −2.756 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1294 | HB1 | MET | 238 | −9.455 | 3.030 | −2.277 | 1.00 | 0.00 | B |
|------|------|-----|-----|-----|--------|-------|--------|------|------|---|
| ATOM | 1295 | HB2 | MET | 238 | −7.879 | 3.783 | −2.016 | 1.00 | 0.00 | B |
| ATOM | 1296 | CG | MET | 238 | −8.013 | 2.595 | −3.802 | 1.00 | 0.00 | B |
| ATOM | 1297 | HG1 | MET | 238 | −7.270 | 3.126 | −4.366 | 1.00 | 0.00 | B |
| ATOM | 1298 | HG2 | MET | 238 | −8.789 | 2.254 | −4.472 | 1.00 | 0.00 | B |
| ATOM | 1299 | SD | MET | 238 | −7.262 | 1.166 | −2.982 | 1.00 | 0.00 | B |
| ATOM | 1300 | CE | MET | 238 | −6.963 | 0.181 | −4.471 | 1.00 | 0.00 | B |
| ATOM | 1301 | HE1 | MET | 238 | −6.403 | 0.770 | −5.185 | 1.00 | 0.00 | B |
| ATOM | 1302 | HE2 | MET | 238 | −7.904 | −0.108 | −4.907 | 1.00 | 0.00 | B |
| ATOM | 1303 | HE3 | MET | 238 | −6.402 | −0.706 | −4.208 | 1.00 | 0.00 | B |
| ATOM | 1304 | C | MET | 238 | −10.129 | 5.534 | −2.645 | 1.00 | 0.00 | B |
| ATOM | 1305 | O | MET | 238 | −11.297 | 5.521 | −2.905 | 1.00 | 0.00 | B |
| ATOM | 1306 | N | ALA | 239 | −9.647 | 6.106 | −1.574 | 1.00 | 0.00 | B |
| ATOM | 1307 | HN | ALA | 239 | −8.699 | 6.003 | −1.367 | 1.00 | 0.00 | B |
| ATOM | 1308 | CA | ALA | 239 | −10.488 | 6.888 | −0.667 | 1.00 | 0.00 | B |
| ATOM | 1309 | HA | ALA | 239 | −11.509 | 6.557 | −0.698 | 1.00 | 0.00 | B |
| ATOM | 1310 | CB | ALA | 239 | −9.880 | 6.660 | 0.718 | 1.00 | 0.00 | B |
| ATOM | 1311 | HB1 | ALA | 239 | −9.179 | 7.456 | 0.938 | 1.00 | 0.00 | B |
| ATOM | 1312 | HB2 | ALA | 239 | −9.359 | 5.712 | 0.731 | 1.00 | 0.00 | B |
| ATOM | 1313 | HB3 | ALA | 239 | −10.661 | 6.652 | 1.459 | 1.00 | 0.00 | B |
| ATOM | 1314 | C | ALA | 239 | −10.360 | 8.361 | −1.074 | 1.00 | 0.00 | B |
| ATOM | 1315 | O | ALA | 239 | −10.608 | 9.256 | −0.291 | 1.00 | 0.00 | B |
| ATOM | 1316 | N | GLY | 240 | −9.967 | 8.620 | −2.311 | 1.00 | 0.00 | B |
| ATOM | 1317 | HN | GLY | 240 | −9.811 | 7.890 | −2.956 | 1.00 | 0.00 | B |
| ATOM | 1318 | CA | GLY | 240 | −9.817 | 10.000 | −2.767 | 1.00 | 0.00 | B |
| ATOM | 1319 | HA1 | GLY | 240 | −8.801 | 10.334 | −2.586 | 1.00 | 0.00 | B |
| ATOM | 1320 | HA2 | GLY | 240 | −10.510 | 10.638 | −2.254 | 1.00 | 0.00 | B |
| ATOM | 1321 | C | GLY | 240 | −10.080 | 10.026 | −4.239 | 1.00 | 0.00 | B |
| ATOM | 1322 | O | GLY | 240 | −10.754 | 10.893 | −4.748 | 1.00 | 0.00 | B |
| ATOM | 1323 | N | VAL | 241 | −9.510 | 9.116 | −4.960 | 1.00 | 0.00 | B |
| ATOM | 1324 | HN | VAL | 241 | −8.957 | 8.417 | −4.550 | 1.00 | 0.00 | B |
| ATOM | 1325 | CA | VAL | 241 | −9.755 | 9.124 | −6.383 | 1.00 | 0.00 | B |
| ATOM | 1326 | HA | VAL | 241 | −10.058 | 10.087 | −6.638 | 1.00 | 0.00 | B |
| ATOM | 1327 | CB | VAL | 241 | −8.397 | 8.827 | −7.042 | 1.00 | 0.00 | B |
| ATOM | 1328 | HB | VAL | 241 | −8.097 | 7.829 | −6.827 | 1.00 | 0.00 | B |
| ATOM | 1329 | CG1 | VAL | 241 | −8.491 | 9.018 | −8.545 | 1.00 | 0.00 | B |
| ATOM | 1330 | HG11 | VAL | 241 | −7.493 | 9.117 | −8.953 | 1.00 | 0.00 | B |
| ATOM | 1331 | HG12 | VAL | 241 | −9.056 | 9.915 | −8.756 | 1.00 | 0.00 | B |
| ATOM | 1332 | HG13 | VAL | 241 | −8.980 | 8.171 | −8.985 | 1.00 | 0.00 | B |
| ATOM | 1333 | CG2 | VAL | 241 | −7.355 | 9.813 | −6.500 | 1.00 | 0.00 | B |
| ATOM | 1334 | HG21 | VAL | 241 | −6.380 | 9.551 | −6.876 | 1.00 | 0.00 | B |
| ATOM | 1335 | HG22 | VAL | 241 | −7.350 | 9.781 | −5.424 | 1.00 | 0.00 | B |
| ATOM | 1336 | HG23 | VAL | 241 | −7.606 | 10.813 | −6.824 | 1.00 | 0.00 | B |
| ATOM | 1337 | C | VAL | 241 | −10.891 | 8.110 | −6.742 | 1.00 | 0.00 | B |
| ATOM | 1338 | O | VAL | 241 | −11.599 | 8.269 | −7.718 | 1.00 | 0.00 | B |
| ATOM | 1339 | N | SER | 242 | −11.031 | 7.046 | −5.978 | 1.00 | 0.00 | B |
| ATOM | 1340 | HN | SER | 242 | −10.447 | 6.922 | −5.205 | 1.00 | 0.00 | B |
| ATOM | 1341 | CA | SER | 242 | −12.111 | 6.033 | −6.272 | 1.00 | 0.00 | B |
| ATOM | 1342 | HA | SER | 242 | −12.368 | 6.062 | −7.319 | 1.00 | 0.00 | B |
| ATOM | 1343 | CB | SER | 242 | −11.493 | 4.683 | −5.936 | 1.00 | 0.00 | B |
| ATOM | 1344 | HB1 | SER | 242 | −11.269 | 4.649 | −4.881 | 1.00 | 0.00 | B |
| ATOM | 1345 | HB2 | SER | 242 | −10.589 | 4.545 | −6.498 | 1.00 | 0.00 | B |
| ATOM | 1346 | OG | SER | 242 | −12.415 | 3.650 | −6.265 | 1.00 | 0.00 | B |
| ATOM | 1347 | HG | SER | 242 | −12.800 | 3.325 | −5.448 | 1.00 | 0.00 | B |
| ATOM | 1348 | C | SER | 242 | −13.388 | 6.260 | −5.403 | 1.00 | 0.00 | B |
| ATOM | 1349 | O | SER | 242 | −14.493 | 6.058 | −5.843 | 1.00 | 0.00 | B |
| ATOM | 1350 | N | HIS | 243 | −13.224 | 6.651 | −4.166 | 1.00 | 0.00 | B |
| ATOM | 1351 | HN | HIS | 243 | −12.339 | 6.853 | −3.843 | 1.00 | 0.00 | B |
| ATOM | 1352 | CA | HIS | 243 | −14.416 | 6.880 | −3.270 | 1.00 | 0.00 | B |
| ATOM | 1353 | HA | HIS | 243 | −15.219 | 6.234 | −3.560 | 1.00 | 0.00 | B |
| ATOM | 1354 | CB | HIS | 243 | −13.926 | 6.492 | −1.869 | 1.00 | 0.00 | B |
| ATOM | 1355 | HB1 | HIS | 243 | −13.113 | 7.143 | −1.582 | 1.00 | 0.00 | B |
| ATOM | 1356 | HB2 | HIS | 243 | −13.579 | 5.469 | −1.882 | 1.00 | 0.00 | B |
| ATOM | 1357 | CG | HIS | 243 | −15.051 | 6.625 | −0.872 | 1.00 | 0.00 | B |
| ATOM | 1358 | ND1 | HIS | 243 | −15.698 | 7.831 | −0.629 | 1.00 | 0.00 | B |
| ATOM | 1359 | HD1 | HIS | 243 | −15.489 | 8.694 | −1.036 | 1.00 | 0.00 | B |
| ATOM | 1360 | CD2 | HIS | 243 | −15.665 | 5.704 | −0.061 | 1.00 | 0.00 | B |
| ATOM | 1361 | HD2 | HIS | 243 | −15.408 | 4.656 | −0.007 | 1.00 | 0.00 | B |
| ATOM | 1362 | CE1 | HIS | 243 | −16.653 | 7.599 | 0.293 | 1.00 | 0.00 | B |
| ATOM | 1363 | HE1 | HIS | 243 | −17.317 | 8.357 | 0.682 | 1.00 | 0.00 | B |
| ATOM | 1364 | NE2 | HIS | 243 | −16.675 | 6.318 | 0.671 | 1.00 | 0.00 | B |
| ATOM | 1365 | C | HIS | 243 | −14.861 | 8.342 | −3.313 | 1.00 | 0.00 | B |
| ATOM | 1366 | O | HIS | 243 | −16.004 | 8.680 | −3.103 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1367 | N    | ASP | 244 | −13.962 | 9.201  | −3.527  | 1.00 | 0.00 | B |
|------|------|------|-----|-----|---------|--------|---------|------|------|---|
| ATOM | 1368 | HN   | ASP | 244 | −13.094 | 8.919  | −3.755  | 1.00 | 0.00 | B |
| ATOM | 1369 | CA   | ASP | 244 | −14.303 | 10.612 | −3.582  | 1.00 | 0.00 | B |
| ATOM | 1370 | HA   | ASP | 244 | −15.215 | 10.795 | −3.037  | 1.00 | 0.00 | B |
| ATOM | 1371 | CB   | ASP | 244 | −13.142 | 11.356 | −2.925  | 1.00 | 0.00 | B |
| ATOM | 1372 | HB1  | ASP | 244 | −12.245 | 11.146 | −3.446  | 1.00 | 0.00 | B |
| ATOM | 1373 | HB2  | ASP | 244 | −13.044 | 11.032 | −1.900  | 1.00 | 0.00 | B |
| ATOM | 1374 | CG   | ASP | 244 | −13.411 | 12.861 | −2.959  | 1.00 | 0.00 | B |
| ATOM | 1375 | OD1  | ASP | 244 | −14.468 | 13.265 | −2.505  | 1.00 | 0.00 | B |
| ATOM | 1376 | OD2  | ASP | 244 | −12.551 | 13.584 | −3.434  | 1.00 | 0.00 | B |
| ATOM | 1377 | C    | ASP | 244 | −14.475 | 10.976 | −5.026  | 1.00 | 0.00 | B |
| ATOM | 1378 | O    | ASP | 244 | −15.340 | 11.741 | −5.375  | 1.00 | 0.00 | B |
| ATOM | 1379 | N    | LEU | 245 | −13.623 | 10.440 | −5.894  | 1.00 | 0.00 | B |
| ATOM | 1380 | HN   | LEU | 245 | −12.856 | 9.801  | −5.564  | 1.00 | 0.00 | B |
| ATOM | 1381 | CA   | LEU | 245 | −13.766 | 10.783 | −7.362  | 1.00 | 0.00 | B |
| ATOM | 1382 | HA   | LEU | 245 | −14.200 | 11.768 | −7.451  | 1.00 | 0.00 | B |
| ATOM | 1383 | CB   | LEU | 245 | −12.348 | 10.826 | −7.902  | 1.00 | 0.00 | B |
| ATOM | 1384 | HB1  | LEU | 245 | −12.320 | 10.409 | −8.895  | 1.00 | 0.00 | B |
| ATOM | 1385 | HB2  | LEU | 245 | −11.723 | 10.264 | −7.259  | 1.00 | 0.00 | B |
| ATOM | 1386 | CG   | LEU | 245 | −11.849 | 12.273 | −7.940  | 1.00 | 0.00 | B |
| ATOM | 1387 | HG   | LEU | 245 | −10.835 | 12.292 | −8.315  | 1.00 | 0.00 | B |
| ATOM | 1388 | CD1  | LEU | 245 | −12.749 | 13.092 | −8.867  | 1.00 | 0.00 | B |
| ATOM | 1389 | HD11 | LEU | 245 | −13.238 | 13.870 | −8.301  | 1.00 | 0.00 | B |
| ATOM | 1390 | HD12 | LEU | 245 | −13.493 | 12.446 | −9.310  | 1.00 | 0.00 | B |
| ATOM | 1391 | HD13 | LEU | 245 | −12.150 | 13.538 | −9.649  | 1.00 | 0.00 | B |
| ATOM | 1392 | CD2  | LEU | 245 | −11.886 | 12.875 | −6.531  | 1.00 | 0.00 | B |
| ATOM | 1393 | HD21 | LEU | 245 | −12.150 | 12.112 | −5.820  | 1.00 | 0.00 | B |
| ATOM | 1394 | HD22 | LEU | 245 | −12.619 | 13.666 | −6.496  | 1.00 | 0.00 | B |
| ATOM | 1395 | HD23 | LEU | 245 | −10.913 | 13.275 | −6.286  | 1.00 | 0.00 | B |
| ATOM | 1396 | C    | LEU | 245 | −14.650 | 9.770  | −8.160  | 1.00 | 0.00 | B |
| ATOM | 1397 | O    | LEU | 245 | −15.378 | 10.164 | −9.050  | 1.00 | 0.00 | B |
| ATOM | 1398 | N    | ARG | 246 | −14.603 | 8.483  | −7.866  | 1.00 | 0.00 | B |
| ATOM | 1399 | HN   | ARG | 246 | −14.067 | 8.168  | −7.118  | 1.00 | 0.00 | B |
| ATOM | 1400 | CA   | ARG | 246 | −15.470 | 7.510  | −8.661  | 1.00 | 0.00 | B |
| ATOM | 1401 | HA   | ARG | 246 | −15.683 | 7.934  | −9.618  | 1.00 | 0.00 | B |
| ATOM | 1402 | CB   | ARG | 246 | −14.653 | 6.221  | −8.831  | 1.00 | 0.00 | B |
| ATOM | 1403 | HB1  | ARG | 246 | −14.397 | 5.826  | −7.875  | 1.00 | 0.00 | B |
| ATOM | 1404 | HB2  | ARG | 246 | −13.751 | 6.439  | −9.383  | 1.00 | 0.00 | B |
| ATOM | 1405 | CG   | ARG | 246 | −15.485 | 5.192  | −9.603  | 1.00 | 0.00 | B |
| ATOM | 1406 | HG1  | ARG | 246 | −15.723 | 5.583  | −10.579 | 1.00 | 0.00 | B |
| ATOM | 1407 | HG2  | ARG | 246 | −16.400 | 4.994  | −9.062  | 1.00 | 0.00 | B |
| ATOM | 1408 | CD   | ARG | 246 | −14.692 | 3.888  | −9.758  | 1.00 | 0.00 | B |
| ATOM | 1409 | HD1  | ARG | 246 | −13.735 | 4.083  | −10.213 | 1.00 | 0.00 | B |
| ATOM | 1410 | HD2  | ARG | 246 | −15.254 | 3.175  | −10.349 | 1.00 | 0.00 | B |
| ATOM | 1411 | NE   | ARG | 246 | −14.501 | 3.375  | −8.370  | 1.00 | 0.00 | B |
| ATOM | 1412 | HE   | ARG | 246 | −14.655 | 3.965  | −7.604  | 1.00 | 0.00 | B |
| ATOM | 1413 | CZ   | ARG | 246 | −14.132 | 2.135  | −8.177  | 1.00 | 0.00 | B |
| ATOM | 1414 | NH1  | ARG | 246 | −13.514 | 1.480  | −9.124  | 1.00 | 0.00 | B |
| ATOM | 1415 | HH11 | ARG | 246 | −13.322 | 1.926  | −9.998  | 1.00 | 0.00 | B |
| ATOM | 1416 | HH12 | ARG | 246 | −13.236 | 0.530  | −8.977  | 1.00 | 0.00 | B |
| ATOM | 1417 | NH2  | ARG | 246 | −14.375 | 1.553  | −7.034  | 1.00 | 0.00 | B |
| ATOM | 1418 | HH21 | ARG | 246 | −14.841 | 2.053  | −6.307  | 1.00 | 0.00 | B |
| ATOM | 1419 | HH22 | ARG | 246 | −14.093 | 0.604  | −6.887  | 1.00 | 0.00 | B |
| ATOM | 1420 | C    | ARG | 246 | −16.790 | 7.249  | −7.987  | 1.00 | 0.00 | B |
| ATOM | 1421 | O    | ARG | 246 | −17.786 | 7.024  | −8.648  | 1.00 | 0.00 | B |
| ATOM | 1422 | N    | THR | 247 | −16.844 | 7.267  | −6.695  | 1.00 | 0.00 | B |
| ATOM | 1423 | HN   | THR | 247 | −16.049 | 7.459  | −6.162  | 1.00 | 0.00 | B |
| ATOM | 1424 | CA   | THR | 247 | −18.138 | 7.018  | −6.054  | 1.00 | 0.00 | B |
| ATOM | 1425 | HA   | THR | 247 | −18.735 | 6.417  | −6.708  | 1.00 | 0.00 | B |
| ATOM | 1426 | CB   | THR | 247 | −17.859 | 6.228  | −4.802  | 1.00 | 0.00 | B |
| ATOM | 1427 | HB   | THR | 247 | −18.781 | 5.983  | −4.342  | 1.00 | 0.00 | B |
| ATOM | 1428 | OG1  | THR | 247 | −17.098 | 6.984  | −3.926  | 1.00 | 0.00 | B |
| ATOM | 1429 | HG1  | THR | 247 | −17.631 | 7.159  | −3.146  | 1.00 | 0.00 | B |
| ATOM | 1430 | CG2  | THR | 247 | −17.116 | 4.940  | −5.157  | 1.00 | 0.00 | B |
| ATOM | 1431 | HG21 | THR | 247 | −16.891 | 4.934  | −6.213  | 1.00 | 0.00 | B |
| ATOM | 1432 | HG22 | THR | 247 | −17.737 | 4.089  | −4.916  | 1.00 | 0.00 | B |
| ATOM | 1433 | HG23 | THR | 247 | −16.198 | 4.888  | −4.592  | 1.00 | 0.00 | B |
| ATOM | 1434 | C    | THR | 247 | −18.910 | 8.356  | −5.721  | 1.00 | 0.00 | B |
| ATOM | 1435 | O    | THR | 247 | −19.939 | 8.291  | −5.080  | 1.00 | 0.00 | B |
| ATOM | 1436 | N    | PRO | 248 | −18.406 | 9.554  | −6.162  | 1.00 | 0.00 | B |
| ATOM | 1437 | CA   | PRO | 248 | −19.127 | 10.784 | −5.853  | 1.00 | 0.00 | B |
| ATOM | 1438 | HA   | PRO | 248 | −19.351 | 10.823 | −4.812  | 1.00 | 0.00 | B |
| ATOM | 1439 | CB   | PRO | 248 | −18.172 | 11.901 | −6.233  | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1440 | HB1  | PRO | 248 | −17.589 | 12.205 | −5.379  | 1.00 | 0.00 | B |
|------|------|------|-----|-----|---------|--------|---------|------|------|---|
| ATOM | 1441 | HB2  | PRO | 248 | −18.720 | 12.743 | −6.637  | 1.00 | 0.00 | B |
| ATOM | 1442 | CG   | PRO | 248 | −17.295 | 11.309 | −7.263  | 1.00 | 0.00 | B |
| ATOM | 1443 | HG1  | PRO | 248 | −16.310 | 11.721 | −7.199  | 1.00 | 0.00 | B |
| ATOM | 1444 | HG2  | PRO | 248 | −17.710 | 11.498 | −8.246  | 1.00 | 0.00 | B |
| ATOM | 1445 | CD   | PRO | 248 | −17.251 | 9.825  | −7.002  | 1.00 | 0.00 | B |
| ATOM | 1446 | HD1  | PRO | 248 | −16.343 | 9.541  | −6.488  | 1.00 | 0.00 | B |
| ATOM | 1447 | HD2  | PRO | 248 | −17.344 | 9.311  | −7.926  | 1.00 | 0.00 | B |
| ATOM | 1448 | C    | PRO | 248 | −20.392 | 10.815 | −6.749  | 1.00 | 0.00 | B |
| ATOM | 1449 | O    | PRO | 248 | −21.280 | 11.667 | −6.627  | 1.00 | 0.00 | B |
| ATOM | 1450 | N    | LEU | 249 | −20.451 | 9.878  | −7.686  | 1.00 | 0.00 | B |
| ATOM | 1451 | HN   | LEU | 249 | −19.723 | 9.247  | −7.786  | 1.00 | 0.00 | B |
| ATOM | 1452 | CA   | LEU | 249 | −21.590 | 9.790  | −8.599  | 1.00 | 0.00 | B |
| ATOM | 1453 | HA   | LEU | 249 | −21.696 | 10.708 | −9.178  | 1.00 | 0.00 | B |
| ATOM | 1454 | CB   | LEU | 249 | −21.236 | 8.616  | −9.543  | 1.00 | 0.00 | B |
| ATOM | 1455 | HB1  | LEU | 249 | −20.151 | 8.618  | −9.715  | 1.00 | 0.00 | B |
| ATOM | 1456 | HB2  | LEU | 249 | −21.738 | 8.742  | −10.480 | 1.00 | 0.00 | B |
| ATOM | 1457 | CG   | LEU | 249 | −21.631 | 7.273  | −8.910  | 1.00 | 0.00 | B |
| ATOM | 1458 | HG   | LEU | 249 | −22.671 | 7.303  | −8.620  | 1.00 | 0.00 | B |
| ATOM | 1459 | CD1  | LEU | 249 | −21.409 | 6.147  | −9.913  | 1.00 | 0.00 | B |
| ATOM | 1460 | HD11 | LEU | 249 | −20.495 | 5.625  | −9.671  | 1.00 | 0.00 | B |
| ATOM | 1461 | HD12 | LEU | 249 | −21.335 | 6.560  | −10.907 | 1.00 | 0.00 | B |
| ATOM | 1462 | HD13 | LEU | 249 | −22.239 | 5.457  | −9.870  | 1.00 | 0.00 | B |
| ATOM | 1463 | CD2  | LEU | 249 | −20.769 | 7.022  | −7.693  | 1.00 | 0.00 | B |
| ATOM | 1464 | HD21 | LEU | 249 | −19.776 | 7.386  | −7.888  | 1.00 | 0.00 | B |
| ATOM | 1465 | HD22 | LEU | 249 | −20.732 | 5.962  | −7.490  | 1.00 | 0.00 | B |
| ATOM | 1466 | HD23 | LEU | 249 | −21.181 | 7.537  | −6.842  | 1.00 | 0.00 | B |
| ATOM | 1467 | C    | LEU | 249 | −22.870 | 9.533  | −7.773  | 1.00 | 0.00 | B |
| ATOM | 1468 | O    | LEU | 249 | −23.945 | 9.529  | −8.299  | 1.00 | 0.00 | B |
| ATOM | 1469 | N    | THR | 250 | −22.734 | 9.225  | −6.480  | 1.00 | 0.00 | B |
| ATOM | 1470 | HN   | THR | 250 | −21.865 | 9.129  | −6.095  | 1.00 | 0.00 | B |
| ATOM | 1471 | CA   | THR | 250 | −23.930 | 8.982  | −5.640  | 1.00 | 0.00 | B |
| ATOM | 1472 | HA   | THR | 250 | −24.614 | 8.320  | −6.121  | 1.00 | 0.00 | B |
| ATOM | 1473 | CB   | THR | 250 | −23.421 | 8.383  | −4.325  | 1.00 | 0.00 | B |
| ATOM | 1474 | HB   | THR | 250 | −22.769 | 7.551  | −4.530  | 1.00 | 0.00 | B |
| ATOM | 1475 | OG1  | THR | 250 | −24.531 | 7.947  | −3.550  | 1.00 | 0.00 | B |
| ATOM | 1476 | HG1  | THR | 250 | −24.198 | 7.616  | −2.715  | 1.00 | 0.00 | B |
| ATOM | 1477 | CG2  | THR | 250 | −22.660 | 9.447  | −3.548  | 1.00 | 0.00 | B |
| ATOM | 1478 | HG21 | THR | 250 | −23.338 | 10.257 | −3.296  | 1.00 | 0.00 | B |
| ATOM | 1479 | HG22 | THR | 250 | −21.859 | 9.829  | −4.160  | 1.00 | 0.00 | B |
| ATOM | 1480 | HG23 | THR | 250 | −22.262 | 9.020  | −2.652  | 1.00 | 0.00 | B |
| ATOM | 1481 | C    | THR | 250 | −24.542 | 10.356 | −5.408  | 1.00 | 0.00 | B |
| ATOM | 1482 | O    | THR | 250 | −25.726 | 10.545 | −5.367  | 1.00 | 0.00 | B |
| ATOM | 1483 | N    | ARG | 251 | −23.688 | 11.333 | −5.224  | 1.00 | 0.00 | B |
| ATOM | 1484 | HN   | ARG | 251 | −22.739 | 11.146 | −5.230  | 1.00 | 0.00 | B |
| ATOM | 1485 | CA   | ARG | 251 | −24.168 | 12.708 | −4.998  | 1.00 | 0.00 | B |
| ATOM | 1486 | HA   | ARG | 251 | −24.711 | 12.783 | −4.069  | 1.00 | 0.00 | B |
| ATOM | 1487 | CB   | ARG | 251 | −22.898 | 13.566 | −4.967  | 1.00 | 0.00 | B |
| ATOM | 1488 | HB1  | ARG | 251 | −23.160 | 14.603 | −4.868  | 1.00 | 0.00 | B |
| ATOM | 1489 | HB2  | ARG | 251 | −22.340 | 13.415 | −5.883  | 1.00 | 0.00 | B |
| ATOM | 1490 | CG   | ARG | 251 | −22.034 | 13.144 | −3.776  | 1.00 | 0.00 | B |
| ATOM | 1491 | HG1  | ARG | 251 | −21.745 | 12.111 | −3.890  | 1.00 | 0.00 | B |
| ATOM | 1492 | HG2  | ARG | 251 | −22.601 | 13.260 | −2.863  | 1.00 | 0.00 | B |
| ATOM | 1493 | CD   | ARG | 251 | −20.779 | 14.020 | −3.714  | 1.00 | 0.00 | B |
| ATOM | 1494 | HD1  | ARG | 251 | −21.048 | 15.056 | −3.596  | 1.00 | 0.00 | B |
| ATOM | 1495 | HD2  | ARG | 251 | −20.182 | 13.882 | −4.607  | 1.00 | 0.00 | B |
| ATOM | 1496 | NE   | ARG | 251 | −20.037 | 13.544 | −2.513  | 1.00 | 0.00 | B |
| ATOM | 1497 | HE   | ARG | 251 | −20.294 | 12.704 | −2.080  | 1.00 | 0.00 | B |
| ATOM | 1498 | CZ   | ARG | 251 | −19.288 | 15.295 | −1.298  | 1.00 | 0.00 | B |
| ATOM | 1499 | NH1  | ARG | 251 | −19.288 | 15.295 | −1.298  | 1.00 | 0.00 | B |
| ATOM | 1500 | HH11 | ARG | 251 | −20.232 | 15.559 | −1.097  | 1.00 | 0.00 | B |
| ATOM | 1501 | HH12 | ARG | 251 | −18.530 | 15.835 | −0.931  | 1.00 | 0.00 | B |
| ATOM | 1502 | NH2  | ARG | 251 | −17.816 | 13.902 | −2.298  | 1.00 | 0.00 | B |
| ATOM | 1503 | HH21 | ARG | 251 | −17.631 | 13.098 | −2.864  | 1.00 | 0.00 | B |
| ATOM | 1504 | HH22 | ARG | 251 | −17.057 | 14.442 | −1.932  | 1.00 | 0.00 | B |
| ATOM | 1505 | C    | ARG | 251 | −25.054 | 13.033 | −6.182  | 1.00 | 0.00 | B |
| ATOM | 1506 | O    | ARG | 251 | −26.172 | 13.483 | −6.041  | 1.00 | 0.00 | B |
| ATOM | 1507 | N    | ILE | 252 | −24.545 | 12.804 | −7.365  | 1.00 | 0.00 | B |
| ATOM | 1508 | HN   | ILE | 252 | −23.622 | 12.466 | −7.445  | 1.00 | 0.00 | B |
| ATOM | 1509 | CA   | ILE | 252 | −25.364 | 13.086 | −8.587  | 1.00 | 0.00 | B |
| ATOM | 1510 | HA   | ILE | 252 | −25.841 | 14.050 | −8.518  | 1.00 | 0.00 | B |
| ATOM | 1511 | CB   | ILE | 252 | −24.440 | 13.034 | −9.759  | 1.00 | 0.00 | B |
| ATOM | 1512 | HB   | ILE | 252 | −24.996 | 13.131 | −10.683 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1513 | CG1  | ILE | 252 | −23.725 | 11.723 | −9.767  | 1.00 | 0.00 | B |
|------|------|------|-----|-----|---------|--------|---------|------|------|---|
| ATOM | 1514 | HG11 | ILE | 252 | −24.440 | 10.920 | −9.793  | 1.00 | 0.00 | B |
| ATOM | 1515 | HG12 | ILE | 252 | −23.118 | 11.639 | −8.884  | 1.00 | 0.00 | B |
| ATOM | 1516 | CG2  | ILE | 252 | −23.471 | 14.146 | −9.649  | 1.00 | 0.00 | B |
| ATOM | 1517 | HG21 | ILE | 252 | −23.977 | 15.011 | −9.251  | 1.00 | 0.00 | B |
| ATOM | 1518 | HG22 | ILE | 252 | −23.081 | 14.366 | −10.623 | 1.00 | 0.00 | B |
| ATOM | 1519 | HG23 | ILE | 252 | −22.678 | 13.855 | −8.989  | 1.00 | 0.00 | B |
| ATOM | 1520 | CD1  | ILE | 252 | −22.860 | 11.668 | −10.997 | 1.00 | 0.00 | B |
| ATOM | 1521 | HD11 | ILE | 252 | −23.469 | 11.863 | −11.867 | 1.00 | 0.00 | B |
| ATOM | 1522 | HD12 | ILE | 252 | −22.412 | 10.696 | −11.076 | 1.00 | 0.00 | B |
| ATOM | 1523 | HD13 | ILE | 252 | −22.091 | 12.422 | −10.923 | 1.00 | 0.00 | B |
| ATOM | 1524 | C    | ILE | 252 | −26.372 | 11.998 | −8.718  | 1.00 | 0.00 | B |
| ATOM | 1525 | O    | ILE | 252 | −27.360 | 12.139 | −9.346  | 1.00 | 0.00 | B |
| ATOM | 1526 | N    | ARG | 253 | −26.113 | 10.867 | −8.142  | 1.00 | 0.00 | B |
| ATOM | 1527 | HN   | ARG | 253 | −25.322 | 10.765 | −7.616  | 1.00 | 0.00 | B |
| ATOM | 1528 | CA   | ARG | 253 | −27.098 | 9.772  | −8.251  | 1.00 | 0.00 | B |
| ATOM | 1529 | HA   | ARG | 253 | −27.172 | 9.416  | −9.269  | 1.00 | 0.00 | B |
| ATOM | 1530 | CB   | ARG | 253 | −26.611 | 8.681  | −7.322  | 1.00 | 0.00 | B |
| ATOM | 1531 | HB1  | ARG | 253 | −26.599 | 9.040  | −6.322  | 1.00 | 0.00 | B |
| ATOM | 1532 | HB2  | ARG | 253 | −25.621 | 8.388  | −7.616  | 1.00 | 0.00 | B |
| ATOM | 1533 | CG   | ARG | 253 | −27.521 | 7.483  | −7.402  | 1.00 | 0.00 | B |
| ATOM | 1534 | HG1  | ARG | 253 | −28.537 | 7.799  | −7.251  | 1.00 | 0.00 | B |
| ATOM | 1535 | HG2  | ARG | 253 | −27.242 | 6.777  | −6.636  | 1.00 | 0.00 | B |
| ATOM | 1536 | CD   | ARG | 253 | −27.384 | 6.836  | −8.773  | 1.00 | 0.00 | B |
| ATOM | 1537 | HD1  | ARG | 253 | −26.369 | 6.505  | −8.931  | 1.00 | 0.00 | B |
| ATOM | 1538 | HD2  | ARG | 253 | −27.679 | 7.535  | −9.546  | 1.00 | 0.00 | B |
| ATOM | 1539 | NE   | ARG | 253 | −28.306 | 5.664  | −8.741  | 1.00 | 0.00 | B |
| ATOM | 1540 | HE   | ARG | 253 | −29.055 | 5.612  | −9.371  | 1.00 | 0.00 | B |
| ATOM | 1541 | CZ   | ARG | 253 | −28.118 | 4.704  | −7.870  | 1.00 | 0.00 | B |
| ATOM | 1542 | NH1  | ARG | 253 | −29.086 | 4.352  | −7.066  | 1.00 | 0.00 | B |
| ATOM | 1543 | HH11 | ARG | 253 | −29.971 | 4.815  | −7.116  | 1.00 | 0.00 | B |
| ATOM | 1544 | HH12 | ARG | 253 | −28.942 | 3.619  | −6.401  | 1.00 | 0.00 | B |
| ATOM | 1545 | NH2  | ARG | 253 | −26.964 | 4.096  | −7.805  | 1.00 | 0.00 | B |
| ATOM | 1546 | HH21 | ARG | 253 | −26.224 | 4.363  | −8.421  | 1.00 | 0.00 | B |
| ATOM | 1547 | HH22 | ARG | 253 | −26.821 | 3.363  | −7.139  | 1.00 | 0.00 | B |
| ATOM | 1548 | C    | ARG | 253 | −28.401 | 10.365 | −7.782  | 1.00 | 0.00 | B |
| ATOM | 1549 | O    | ARG | 253 | −29.450 | 10.008 | −8.226  | 1.00 | 0.00 | B |
| ATOM | 1550 | N    | LEU | 254 | −28.288 | 11.333 | −6.878  | 1.00 | 0.00 | B |
| ATOM | 1551 | HN   | LEU | 254 | −27.403 | 11.596 | −6.559  | 1.00 | 0.00 | B |
| ATOM | 1552 | CA   | LEU | 254 | −29.459 | 12.009 | −6.338  | 1.00 | 0.00 | B |
| ATOM | 1553 | HA   | LEU | 254 | −30.287 | 11.349 | −6.323  | 1.00 | 0.00 | B |
| ATOM | 1554 | CB   | LEU | 254 | −29.068 | 12.421 | −4.913  | 1.00 | 0.00 | B |
| ATOM | 1555 | HB1  | LEU | 254 | −29.924 | 12.850 | −4.415  | 1.00 | 0.00 | B |
| ATOM | 1556 | HB2  | LEU | 254 | −28.275 | 13.154 | −4.959  | 1.00 | 0.00 | B |
| ATOM | 1557 | CG   | LEU | 254 | −28.582 | 11.188 | −4.120  | 1.00 | 0.00 | B |
| ATOM | 1558 | HG   | LEU | 254 | −27.620 | 10.856 | −4.512  | 1.00 | 0.00 | B |
| ATOM | 1559 | CD1  | LEU | 254 | −28.409 | 11.567 | −2.651  | 1.00 | 0.00 | B |
| ATOM | 1560 | HD11 | LEU | 254 | −28.308 | 10.671 | −2.058  | 1.00 | 0.00 | B |
| ATOM | 1561 | HD12 | LEU | 254 | −29.273 | 12.123 | −2.319  | 1.00 | 0.00 | B |
| ATOM | 1562 | HD13 | LEU | 254 | −27.524 | 12.175 | −2.539  | 1.00 | 0.00 | B |
| ATOM | 1563 | CD2  | LEU | 254 | −29.610 | 10.052 | −4.242  | 1.00 | 0.00 | B |
| ATOM | 1564 | HD21 | LEU | 254 | −29.427 | 9.316  | −3.472  | 1.00 | 0.00 | B |
| ATOM | 1565 | HD22 | LEU | 254 | −29.519 | 9.588  | −5.213  | 1.00 | 0.00 | B |
| ATOM | 1566 | HD23 | LEU | 254 | −30.606 | 10.452 | −4.127  | 1.00 | 0.00 | B |
| ATOM | 1567 | C    | LEU | 254 | −29.756 | 13.238 | −7.226  | 1.00 | 0.00 | B |
| ATOM | 1568 | O    | LEU | 254 | −30.895 | 13.546 | −7.515  | 1.00 | 0.00 | B |
| ATOM | 1569 | N    | ALA | 255 | −28.718 | 13.949 | −7.665  | 1.00 | 0.00 | B |
| ATOM | 1570 | HN   | ALA | 255 | −27.795 | 13.666 | −7.446  | 1.00 | 0.00 | B |
| ATOM | 1571 | CA   | ALA | 255 | −28.946 | 15.156 | −8.541  | 1.00 | 0.00 | B |
| ATOM | 1572 | HA   | ALA | 255 | −29.570 | 15.890 | −8.072  | 1.00 | 0.00 | B |
| ATOM | 1573 | CB   | ALA | 255 | −27.547 | 15.726 | −8.813  | 1.00 | 0.00 | B |
| ATOM | 1574 | HB1  | ALA | 255 | −26.913 | 15.548 | −7.957  | 1.00 | 0.00 | B |
| ATOM | 1575 | HB2  | ALA | 255 | −27.619 | 16.789 | −8.993  | 1.00 | 0.00 | B |
| ATOM | 1576 | HB3  | ALA | 255 | −27.123 | 15.243 | −9.681  | 1.00 | 0.00 | B |
| ATOM | 1577 | C    | ALA | 255 | −29.569 | 14.648 | −9.807  | 1.00 | 0.00 | B |
| ATOM | 1578 | O    | ALA | 255 | −30.635 | 15.037 | −10.204 | 1.00 | 0.00 | B |
| ATOM | 1579 | N    | THR | 256 | −28.884 | 13.774 | −10.425 | 1.00 | 0.00 | B |
| ATOM | 1580 | HN   | THR | 256 | −28.050 | 13.543 | −10.084 | 1.00 | 0.00 | B |
| ATOM | 1581 | CA   | THR | 256 | −29.353 | 13.170 | −11.675 | 1.00 | 0.00 | B |
| ATOM | 1582 | HA   | THR | 256 | −29.584 | 13.917 | −12.407 | 1.00 | 0.00 | B |
| ATOM | 1583 | CB   | THR | 256 | −28.228 | 12.279 | −12.170 | 1.00 | 0.00 | B |
| ATOM | 1584 | HB   | THR | 256 | −28.460 | 11.973 | −13.150 | 1.00 | 0.00 | B |
| ATOM | 1585 | OG1  | THR | 256 | −28.129 | 11.140 | −11.334 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1586 | HG1 | THR | 256 | −28.606 | 10.421 | −11.756 | 1.00 | 0.00 | B |
|---|---|---|---|---|---|---|---|---|---|---|
| ATOM | 1587 | CG2 | THR | 256 | −26.880 | 13.014 | −12.177 | 1.00 | 0.00 | B |
| ATOM | 1588 | HG21 | THR | 256 | −26.874 | 13.782 | −11.429 | 1.00 | 0.00 | B |
| ATOM | 1589 | HG22 | THR | 256 | −26.717 | 13.454 | −13.141 | 1.00 | 0.00 | B |
| ATOM | 1590 | HG23 | THR | 256 | −26.090 | 12.305 | −11.972 | 1.00 | 0.00 | B |
| ATOM | 1591 | C | THR | 256 | −30.562 | 12.300 | −11.389 | 1.00 | 0.00 | B |
| ATOM | 1592 | O | THR | 256 | −31.274 | 11.929 | −12.282 | 1.00 | 0.00 | B |
| ATOM | 1593 | N | GLU | 257 | −30.772 | 11.905 | −10.149 | 1.00 | 0.00 | B |
| ATOM | 1594 | HN | GLU | 257 | −30.129 | 12.174 | −9.402 | 1.00 | 0.00 | B |
| ATOM | 1595 | CA | GLU | 257 | −31.983 | 11.039 | −9.864 | 1.00 | 0.00 | B |
| ATOM | 1596 | HA | GLU | 257 | −31.961 | 10.133 | −10.441 | 1.00 | 0.00 | B |
| ATOM | 1597 | CB | GLU | 257 | −31.937 | 10.746 | −8.384 | 1.00 | 0.00 | B |
| ATOM | 1598 | HB1 | GLU | 257 | −32.794 | 11.191 | −7.909 | 1.00 | 0.00 | B |
| ATOM | 1599 | HB2 | GLU | 257 | −31.051 | 11.171 | −7.973 | 1.00 | 0.00 | B |
| ATOM | 1600 | CG | GLU | 257 | −31.965 | 9.229 | −8.157 | 1.00 | 0.00 | B |
| ATOM | 1601 | HG1 | GLU | 257 | −31.128 | 8.771 | −8.658 | 1.00 | 0.00 | B |
| ATOM | 1602 | HG2 | GLU | 257 | −32.884 | 8.825 | −8.555 | 1.00 | 0.00 | B |
| ATOM | 1603 | CD | GLU | 257 | −31.887 | 8.931 | −6.658 | 1.00 | 0.00 | B |
| ATOM | 1604 | OE1 | GLU | 257 | −31.900 | 7.764 | −6.304 | 1.00 | 0.00 | B |
| ATOM | 1605 | OE2 | GLU | 257 | −31.816 | 9.875 | −5.890 | 1.00 | 0.00 | B |
| ATOM | 1606 | C | GLU | 257 | −33.214 | 11.845 | −10.150 | 1.00 | 0.00 | B |
| ATOM | 1607 | O | GLU | 257 | −34.015 | 11.542 | −11.004 | 1.00 | 0.00 | B |
| ATOM | 1608 | N | MET | 258 | −33.364 | 12.852 | −9.392 | 1.00 | 0.00 | B |
| ATOM | 1609 | HN | MET | 258 | −32.690 | 13.023 | −8.697 | 1.00 | 0.00 | B |
| ATOM | 1610 | CA | MET | 258 | −34.506 | 13.763 | −9.522 | 1.00 | 0.00 | B |
| ATOM | 1611 | HA | MET | 258 | −35.448 | 13.244 | −9.414 | 1.00 | 0.00 | B |
| ATOM | 1612 | CB | MET | 258 | −34.263 | 14.721 | −8.352 | 1.00 | 0.00 | B |
| ATOM | 1613 | HB1 | MET | 258 | −33.192 | 14.828 | −8.204 | 1.00 | 0.00 | B |
| ATOM | 1614 | HB2 | MET | 258 | −34.701 | 14.308 | −7.460 | 1.00 | 0.00 | B |
| ATOM | 1615 | CG | MET | 258 | −34.864 | 16.083 | −8.625 | 1.00 | 0.00 | B |
| ATOM | 1616 | HG1 | MET | 258 | −34.442 | 16.470 | −9.545 | 1.00 | 0.00 | B |
| ATOM | 1617 | HG2 | MET | 258 | −34.616 | 16.743 | −7.812 | 1.00 | 0.00 | B |
| ATOM | 1618 | SD | MET | 258 | −36.662 | 15.945 | −8.786 | 1.00 | 0.00 | B |
| ATOM | 1619 | CE | MET | 258 | −37.098 | 17.072 | −7.439 | 1.00 | 0.00 | B |
| ATOM | 1620 | HE1 | MET | 258 | −37.082 | 16.533 | −6.501 | 1.00 | 0.00 | B |
| ATOM | 1621 | HE2 | MET | 258 | −38.085 | 17.469 | −7.605 | 1.00 | 0.00 | B |
| ATOM | 1622 | HE3 | MET | 258 | −36.386 | 17.886 | −7.405 | 1.00 | 0.00 | B |
| ATOM | 1623 | C | MET | 258 | −34.424 | 14.466 | −10.864 | 1.00 | 0.00 | B |
| ATOM | 1624 | O | MET | 258 | −35.418 | 14.849 | −11.449 | 1.00 | 0.00 | B |
| ATOM | 1625 | N | MET | 259 | −33.250 | 14.632 | −11.349 | 1.00 | 0.00 | B |
| ATOM | 1626 | HN | MET | 259 | −32.492 | 14.283 | −10.886 | 1.00 | 0.00 | B |
| ATOM | 1627 | CA | MET | 259 | −33.076 | 15.295 | −12.629 | 1.00 | 0.00 | B |
| ATOM | 1628 | HA | MET | 259 | −33.810 | 16.021 | −12.751 | 1.00 | 0.00 | B |
| ATOM | 1629 | CB | MET | 259 | −31.704 | 15.945 | −12.571 | 1.00 | 0.00 | B |
| ATOM | 1630 | HB1 | MET | 259 | −31.472 | 16.386 | −13.527 | 1.00 | 0.00 | B |
| ATOM | 1631 | HB2 | MET | 259 | −30.965 | 15.203 | −12.326 | 1.00 | 0.00 | B |
| ATOM | 1632 | CG | MET | 259 | −31.717 | 17.038 | −11.498 | 1.00 | 0.00 | B |
| ATOM | 1633 | HG1 | MET | 259 | −32.037 | 16.617 | −10.558 | 1.00 | 0.00 | B |
| ATOM | 1634 | HG2 | MET | 259 | −32.400 | 17.820 | −11.790 | 1.00 | 0.00 | B |
| ATOM | 1635 | SD | MET | 259 | −30.059 | 17.732 | −11.316 | 1.00 | 0.00 | B |
| ATOM | 1636 | CE | MET | 259 | −30.168 | 18.107 | −9.551 | 1.00 | 0.00 | B |
| ATOM | 1637 | HE1 | MET | 259 | −31.016 | 17.585 | −9.127 | 1.00 | 0.00 | B |
| ATOM | 1638 | HE2 | MET | 259 | −30.297 | 19.167 | −9.414 | 1.00 | 0.00 | B |
| ATOM | 1639 | HE3 | MET | 259 | −29.259 | 17.788 | −9.058 | 1.00 | 0.00 | B |
| ATOM | 1640 | C | MET | 259 | −33.176 | 14.293 | −13.729 | 1.00 | 0.00 | B |
| ATOM | 1641 | O | MET | 259 | −33.302 | 14.640 | −14.853 | 1.00 | 0.00 | B |
| ATOM | 1642 | N | SER | 260 | −33.167 | 13.029 | −13.403 | 1.00 | 0.00 | B |
| ATOM | 1643 | HN | SER | 260 | −33.139 | 12.778 | −12.477 | 1.00 | 0.00 | B |
| ATOM | 1644 | CA | SER | 260 | −33.268 | 11.985 | −14.472 | 1.00 | 0.00 | B |
| ATOM | 1645 | HA | SER | 260 | −32.379 | 11.959 | −15.077 | 1.00 | 0.00 | B |
| ATOM | 1646 | CB | SER | 260 | −33.482 | 10.657 | −13.752 | 1.00 | 0.00 | B |
| ATOM | 1647 | HB1 | SER | 260 | −32.688 | 10.502 | −13.033 | 1.00 | 0.00 | B |
| ATOM | 1648 | HB2 | SER | 260 | −33.474 | 9.855 | −14.466 | 1.00 | 0.00 | B |
| ATOM | 1649 | OG | SER | 260 | −34.741 | 10.682 | −13.089 | 1.00 | 0.00 | B |
| ATOM | 1650 | HG | SER | 260 | −35.405 | 10.360 | −13.703 | 1.00 | 0.00 | B |
| ATOM | 1651 | C | SER | 260 | −34.477 | 12.332 | −15.282 | 1.00 | 0.00 | B |
| ATOM | 1652 | O | SER | 260 | −34.523 | 12.189 | −16.488 | 1.00 | 0.00 | B |
| ATOM | 1653 | N | GLU | 261 | −35.470 | 12.796 | −14.593 | 1.00 | 0.00 | B |
| ATOM | 1654 | HN | GLU | 261 | −35.385 | 12.887 | −13.622 | 1.00 | 0.00 | B |
| ATOM | 1655 | CA | GLU | 261 | −36.708 | 13.183 | −15.239 | 1.00 | 0.00 | B |
| ATOM | 1656 | HA | GLU | 261 | −36.800 | 12.698 | −16.193 | 1.00 | 0.00 | B |
| ATOM | 1657 | CB | GLU | 261 | −37.808 | 12.757 | −14.247 | 1.00 | 0.00 | B |
| ATOM | 1658 | HB1 | GLU | 261 | −37.745 | 13.383 | −13.359 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1659 | HB2  | GLU | 261 | −37.651 | 11.725 | −13.960 | 1.00 | 0.00 | B |
|------|------|------|-----|-----|---------|--------|---------|------|------|---|
| ATOM | 1660 | CG   | GLU | 261 | −39.203 | 12.913 | −14.878 | 1.00 | 0.00 | B |
| ATOM | 1661 | HG1  | GLU | 261 | −39.952 | 12.562 | −14.180 | 1.00 | 0.00 | B |
| ATOM | 1662 | HG2  | GLU | 261 | −39.255 | 12.325 | −15.783 | 1.00 | 0.00 | B |
| ATOM | 1663 | CD   | GLU | 261 | −39.472 | 14.381 | −15.208 | 1.00 | 0.00 | B |
| ATOM | 1664 | OE1  | GLU | 261 | −39.377 | 14.732 | −16.371 | 1.00 | 0.00 | B |
| ATOM | 1665 | OE2  | GLU | 261 | −39.764 | 15.131 | −14.290 | 1.00 | 0.00 | B |
| ATOM | 1666 | C    | GLU | 261 | −36.640 | 14.671 | −15.414 | 1.00 | 0.00 | B |
| ATOM | 1667 | O    | GLU | 261 | −37.030 | 15.202 | −16.429 | 1.00 | 0.00 | B |
| ATOM | 1668 | N    | GLN | 262 | −36.178 | 15.365 | −14.403 | 1.00 | 0.00 | B |
| ATOM | 1669 | HN   | GLN | 262 | −35.907 | 14.914 | −13.577 | 1.00 | 0.00 | B |
| ATOM | 1670 | CA   | GLN | 262 | −36.076 | 16.822 | −14.521 | 1.00 | 0.00 | B |
| ATOM | 1671 | HA   | GLN | 262 | −36.878 | 17.195 | −15.067 | 1.00 | 0.00 | B |
| ATOM | 1672 | CB   | GLN | 262 | −36.083 | 17.384 | −13.090 | 1.00 | 0.00 | B |
| ATOM | 1673 | HB1  | GLN | 262 | −35.252 | 17.002 | −12.544 | 1.00 | 0.00 | B |
| ATOM | 1674 | HB2  | GLN | 262 | −36.999 | 17.096 | −12.597 | 1.00 | 0.00 | B |
| ATOM | 1675 | CG   | GLN | 262 | −35.996 | 18.911 | −13.145 | 1.00 | 0.00 | B |
| ATOM | 1676 | HG1  | GLN | 262 | −36.829 | 19.299 | −13.712 | 1.00 | 0.00 | B |
| ATOM | 1677 | HG2  | GLN | 262 | −35.070 | 19.203 | −13.620 | 1.00 | 0.00 | B |
| ATOM | 1678 | CD   | GLN | 262 | −36.043 | 19.474 | −11.726 | 1.00 | 0.00 | B |
| ATOM | 1679 | OE1  | GLN | 262 | −35.142 | 19.253 | −10.942 | 1.00 | 0.00 | B |
| ATOM | 1680 | NE2  | GLN | 262 | −37.064 | 20.198 | −11.360 | 1.00 | 0.00 | B |
| ATOM | 1681 | HE21 | GLN | 262 | −37.791 | 20.375 | −11.992 | 1.00 | 0.00 | B |
| ATOM | 1682 | HE22 | GLN | 262 | −37.104 | 20.564 | −10.451 | 1.00 | 0.00 | B |
| ATOM | 1683 | C    | GLN | 262 | −34.765 | 17.078 | −15.245 | 1.00 | 0.00 | B |
| ATOM | 1684 | O    | GLN | 262 | −33.775 | 17.450 | −14.653 | 1.00 | 0.00 | B |
| ATOM | 1685 | N    | ASP | 263 | −34.766 | 16.846 | −16.548 | 1.00 | 0.00 | B |
| ATOM | 1686 | HN   | ASP | 263 | −35.582 | 16.554 | −16.980 | 1.00 | 0.00 | B |
| ATOM | 1687 | CA   | ASP | 263 | −33.548 | 17.047 | −17.371 | 1.00 | 0.00 | B |
| ATOM | 1688 | HA   | ASP | 263 | −33.779 | 16.934 | −18.417 | 1.00 | 0.00 | B |
| ATOM | 1689 | CB   | ASP | 263 | −33.050 | 18.473 | −17.086 | 1.00 | 0.00 | B |
| ATOM | 1690 | HB1  | ASP | 263 | −32.718 | 18.547 | −16.066 | 1.00 | 0.00 | B |
| ATOM | 1691 | HB2  | ASP | 263 | −33.851 | 19.177 | −17.258 | 1.00 | 0.00 | B |
| ATOM | 1692 | CG   | ASP | 263 | −31.881 | 18.794 | −18.017 | 1.00 | 0.00 | B |
| ATOM | 1693 | OD1  | ASP | 263 | −31.676 | 18.046 | −18.947 | 1.00 | 0.00 | B |
| ATOM | 1694 | OD2  | ASP | 263 | −31.220 | 19.788 | −17.786 | 1.00 | 0.00 | B |
| ATOM | 1695 | C    | ASP | 263 | −32.526 | 15.995 | −16.946 | 1.00 | 0.00 | B |
| ATOM | 1696 | O    | ASP | 263 | −31.514 | 16.313 | −16.354 | 1.00 | 0.00 | B |
| ATOM | 1697 | N    | GLY | 264 | −32.836 | 14.705 | −17.176 | 1.00 | 0.00 | B |
| ATOM | 1698 | HN   | GLY | 264 | −33.755 | 14.456 | −17.527 | 1.00 | 0.00 | B |
| ATOM | 1699 | CA   | GLY | 264 | −31.877 | 13.606 | −16.784 | 1.00 | 0.00 | B |
| ATOM | 1700 | HA1  | GLY | 264 | −32.399 | 12.661 | −16.836 | 1.00 | 0.00 | B |
| ATOM | 1701 | HA2  | GLY | 264 | −31.555 | 13.772 | −15.767 | 1.00 | 0.00 | B |
| ATOM | 1702 | C    | GLY | 264 | −30.625 | 13.534 | −17.699 | 1.00 | 0.00 | B |
| ATOM | 1703 | O    | GLY | 264 | −30.231 | 12.463 | −18.120 | 1.00 | 0.00 | B |
| ATOM | 1704 | N    | TYR | 265 | −30.001 | 14.640 | −18.012 | 1.00 | 0.00 | B |
| ATOM | 1705 | HN   | TYR | 265 | −30.318 | 15.485 | −17.694 | 1.00 | 0.00 | B |
| ATOM | 1706 | CA   | TYR | 265 | −28.801 | 14.587 | −18.881 | 1.00 | 0.00 | B |
| ATOM | 1707 | HA   | TYR | 265 | −28.874 | 13.753 | −19.561 | 1.00 | 0.00 | B |
| ATOM | 1708 | CB   | TYR | 265 | −28.794 | 15.896 | −19.670 | 1.00 | 0.00 | B |
| ATOM | 1709 | HB1  | TYR | 265 | −27.863 | 15.987 | −20.210 | 1.00 | 0.00 | B |
| ATOM | 1710 | HB2  | TYR | 265 | −28.898 | 16.729 | −18.986 | 1.00 | 0.00 | B |
| ATOM | 1711 | CG   | TYR | 265 | −29.950 | 15.898 | −20.652 | 1.00 | 0.00 | B |
| ATOM | 1712 | CD1  | TYR | 265 | −31.290 | 15.793 | −20.194 | 1.00 | 0.00 | B |
| ATOM | 1713 | HD1  | TYR | 265 | −31.501 | 15.740 | −19.144 | 1.00 | 0.00 | B |
| ATOM | 1714 | CD2  | TYR | 265 | −29.686 | 15.977 | −22.036 | 1.00 | 0.00 | B |
| ATOM | 1715 | HD2  | TYR | 265 | −28.667 | 16.054 | −22.388 | 1.00 | 0.00 | B |
| ATOM | 1716 | CE1  | TYR | 265 | −32.353 | 15.773 | −21.118 | 1.00 | 0.00 | B |
| ATOM | 1717 | HE1  | TYR | 265 | −33.372 | 15.694 | −20.763 | 1.00 | 0.00 | B |
| ATOM | 1718 | CE2  | TYR | 265 | −30.753 | 15.958 | −22.962 | 1.00 | 0.00 | B |
| ATOM | 1719 | HE2  | TYR | 265 | −30.550 | 16.020 | −24.017 | 1.00 | 0.00 | B |
| ATOM | 1720 | CZ   | TYR | 265 | −32.086 | 15.856 | −22.505 | 1.00 | 0.00 | B |
| ATOM | 1721 | OH   | TYR | 265 | −33.126 | 15.835 | −23.411 | 1.00 | 0.00 | B |
| ATOM | 1722 | HH   | TYR | 265 | −32.812 | 15.409 | −24.213 | 1.00 | 0.00 | B |
| ATOM | 1723 | C    | TYR | 265 | −27.539 | 14.453 | −18.018 | 1.00 | 0.00 | B |
| ATOM | 1724 | O    | TYR | 265 | −26.451 | 14.255 | −18.523 | 1.00 | 0.00 | B |
| ATOM | 1725 | N    | LEU | 266 | −27.673 | 14.557 | −16.710 | 1.00 | 0.00 | B |
| ATOM | 1726 | HN   | LEU | 266 | −28.536 | 14.597 | −16.314 | 1.00 | 0.00 | B |
| ATOM | 1727 | CA   | LEU | 266 | −26.500 | 14.434 | −15.852 | 1.00 | 0.00 | B |
| ATOM | 1728 | HA   | LEU | 266 | −25.615 | 14.707 | −16.408 | 1.00 | 0.00 | B |
| ATOM | 1729 | CB   | LEU | 266 | −26.680 | 15.406 | −14.637 | 1.00 | 0.00 | B |
| ATOM | 1730 | HB1  | LEU | 266 | −26.573 | 16.424 | −14.987 | 1.00 | 0.00 | B |
| ATOM | 1731 | HB2  | LEU | 266 | −25.913 | 15.206 | −13.919 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1732 | CG | LEU | 266 | −28.047 | 15.260 | −13.940 | 1.00 | 0.00 | B |
| --- | --- | --- | --- | --- | --- | --- | --- | --- | --- | --- |
| ATOM | 1733 | HG | LEU | 266 | −28.340 | 14.220 | −13.900 | 1.00 | 0.00 | B |
| ATOM | 1734 | CD1 | LEU | 266 | −27.921 | 15.832 | −12.526 | 1.00 | 0.00 | B |
| ATOM | 1735 | HD11 | LEU | 266 | −28.710 | 15.458 | −11.907 | 1.00 | 0.00 | B |
| ATOM | 1736 | HD12 | LEU | 266 | −27.989 | 16.895 | −12.574 | 1.00 | 0.00 | B |
| ATOM | 1737 | HD13 | LEU | 266 | −26.967 | 15.553 | −12.106 | 1.00 | 0.00 | B |
| ATOM | 1738 | CD2 | LEU | 266 | −29.109 | 16.089 | −14.680 | 1.00 | 0.00 | B |
| ATOM | 1739 | HD21 | LEU | 266 | −29.629 | 16.721 | −13.973 | 1.00 | 0.00 | B |
| ATOM | 1740 | HD22 | LEU | 266 | −29.815 | 15.428 | −15.156 | 1.00 | 0.00 | B |
| ATOM | 1741 | HD23 | LEU | 266 | −28.630 | 16.705 | −15.427 | 1.00 | 0.00 | B |
| ATOM | 1742 | C | LEU | 266 | −26.412 | 12.987 | −15.441 | 1.00 | 0.00 | B |
| ATOM | 1743 | O | LEU | 266 | −25.362 | 12.463 | −15.185 | 1.00 | 0.00 | B |
| ATOM | 1744 | N | ALA | 267 | −27.532 | 12.329 | −15.373 | 1.00 | 0.00 | B |
| ATOM | 1745 | HN | ALA | 267 | −28.380 | 12.773 | −15.575 | 1.00 | 0.00 | B |
| ATOM | 1746 | CA | ALA | 267 | −27.517 | 10.913 | −14.985 | 1.00 | 0.00 | B |
| ATOM | 1747 | HA | ALA | 267 | −17.011 | 10.777 | −14.043 | 1.00 | 0.00 | B |
| ATOM | 1748 | CB | ALA | 267 | −28.992 | 10.498 | −14.875 | 1.00 | 0.00 | B |
| ATOM | 1749 | HB1 | ALA | 267 | −29.138 | 9.920 | −13.974 | 1.00 | 0.00 | B |
| ATOM | 1750 | HB2 | ALA | 267 | −29.264 | 9.900 | −15.733 | 1.00 | 0.00 | B |
| ATOM | 1751 | HB3 | ALA | 267 | −29.614 | 11.381 | −14.841 | 1.00 | 0.00 | B |
| ATOM | 1752 | C | ALA | 267 | −26.836 | 10.139 | −16.079 | 1.00 | 0.00 | B |
| ATOM | 1753 | O | ALA | 267 | −26.251 | 9.113 | −15.853 | 1.00 | 0.00 | B |
| ATOM | 1754 | N | GLU | 268 | −26.892 | 10.631 | −17.281 | 1.00 | 0.00 | B |
| ATOM | 1755 | HN | GLU | 268 | −27.360 | 11.474 | −17.453 | 1.00 | 0.00 | B |
| ATOM | 1756 | CA | GLU | 268 | −26.241 | 9.903 | −18.373 | 1.00 | 0.00 | B |
| ATOM | 1757 | HA | GLU | 268 | −26.131 | 8.912 | −18.090 | 1.00 | 0.00 | B |
| ATOM | 1758 | CB | GLU | 268 | −27.192 | 10.013 | −19.567 | 1.00 | 0.00 | B |
| ATOM | 1759 | HB1 | GLU | 268 | −26.769 | 9.492 | −20.413 | 1.00 | 0.00 | B |
| ATOM | 1760 | HB2 | GLU | 268 | −27.332 | 11.055 | −19.819 | 1.00 | 0.00 | B |
| ATOM | 1761 | CG | GLU | 268 | −28.545 | 9.388 | −19.210 | 1.00 | 0.00 | B |
| ATOM | 1762 | HG1 | GLU | 268 | −29.230 | 9.520 | −20.034 | 1.00 | 0.00 | B |
| ATOM | 1763 | HG2 | GLU | 268 | −28.944 | 9.873 | −18.330 | 1.00 | 0.00 | B |
| ATOM | 1764 | CD | GLU | 268 | −28.368 | 7.894 | −18.932 | 1.00 | 0.00 | B |
| ATOM | 1765 | OE1 | GLU | 268 | −29.340 | 7.265 | −18.544 | 1.00 | 0.00 | B |
| ATOM | 1766 | OE2 | GLU | 268 | −27.267 | 7.401 | −19.117 | 1.00 | 0.00 | B |
| ATOM | 1767 | C | GLU | 268 | −24.882 | 10.481 | −18.698 | 1.00 | 0.00 | B |
| ATOM | 1768 | O | GLU | 268 | −23.903 | 9.772 | −18.749 | 1.00 | 0.00 | B |
| ATOM | 1769 | N | SER | 269 | −24.796 | 11.736 | −18.937 | 1.00 | 0.00 | B |
| ATOM | 1770 | HN | SER | 269 | −25.594 | 12.305 | −18.910 | 1.00 | 0.00 | B |
| ATOM | 1771 | CA | SER | 269 | −23.476 | 12.309 | −19.253 | 1.00 | 0.00 | B |
| ATOM | 1772 | HA | SER | 269 | −23.084 | 11.884 | −20.162 | 1.00 | 0.00 | B |
| ATOM | 1773 | CB | SER | 269 | −23.724 | 13.805 | −19.433 | 1.00 | 0.00 | B |
| ATOM | 1774 | HB1 | SER | 269 | −22.784 | 14.303 | −19.639 | 1.00 | 0.00 | B |
| ATOM | 1775 | HB2 | SER | 269 | −24.152 | 14.211 | −18.534 | 1.00 | 0.00 | B |
| ATOM | 1776 | OG | SER | 269 | −24.629 | 14.005 | −20.513 | 1.00 | 0.00 | B |
| ATOM | 1777 | HG | SER | 269 | −24.380 | 13.410 | −21.223 | 1.00 | 0.00 | B |
| ATOM | 1778 | C | SER | 269 | −22.521 | 12.056 | −18.081 | 1.00 | 0.00 | B |
| ATOM | 1779 | O | SER | 269 | −21.325 | 11.896 | −18.256 | 1.00 | 0.00 | B |
| ATOM | 1780 | N | ILE | 270 | −23.045 | 11.970 | −16.886 | 1.00 | 0.00 | B |
| ATOM | 1781 | HN | ILE | 270 | −24.027 | 11.994 | −16.771 | 1.00 | 0.00 | B |
| ATOM | 1782 | CA | ILE | 270 | −22.143 | 11.730 | −15.714 | 1.00 | 0.00 | B |
| ATOM | 1783 | HA | ILE | 270 | −21.164 | 12.127 | −15.933 | 1.00 | 0.00 | B |
| ATOM | 1784 | CB | ILE | 270 | −22.741 | 12.504 | −14.536 | 1.00 | 0.00 | B |
| ATOM | 1785 | HB | ILE | 270 | −23.618 | 11.994 | −14.162 | 1.00 | 0.00 | B |
| ATOM | 1786 | CG1 | ILE | 270 | −23.099 | 13.922 | −14.990 | 1.00 | 0.00 | B |
| ATOM | 1787 | HG11 | ILE | 270 | −23.865 | 13.877 | −15.747 | 1.00 | 0.00 | B |
| ATOM | 1788 | HG12 | ILE | 270 | −22.219 | 14.400 | −15.396 | 1.00 | 0.00 | B |
| ATOM | 1789 | CG2 | ILE | 270 | −21.689 | 12.612 | −13.427 | 1.00 | 0.00 | B |
| ATOM | 1790 | HG21 | ILE | 270 | −22.050 | 13.275 | −12.653 | 1.00 | 0.00 | B |
| ATOM | 1791 | HG22 | ILE | 270 | −20.771 | 13.011 | −13.840 | 1.00 | 0.00 | B |
| ATOM | 1792 | HG23 | ILE | 270 | −21.502 | 11.638 | −13.009 | 1.00 | 0.00 | B |
| ATOM | 1793 | CD1 | ILE | 270 | −23.611 | 14.724 | −13.797 | 1.00 | 0.00 | B |
| ATOM | 1794 | HD11 | ILE | 270 | −22.786 | 14.963 | −13.143 | 1.00 | 0.00 | B |
| ATOM | 1795 | HD12 | ILE | 270 | −24.343 | 14.140 | −13.257 | 1.00 | 0.00 | B |
| ATOM | 1796 | HD13 | ILE | 270 | −24.067 | 15.637 | −14.148 | 1.00 | 0.00 | B |
| ATOM | 1797 | C | ILE | 270 | −22.021 | 10.234 | −15.408 | 1.00 | 0.00 | B |
| ATOM | 1798 | O | ILE | 270 | −20.936 | 9.721 | −15.312 | 1.00 | 0.00 | B |
| ATOM | 1799 | N | ASN | 271 | −23.120 | 9.517 | −15.236 | 1.00 | 0.00 | B |
| ATOM | 1800 | HN | ASN | 271 | −24.003 | 9.932 | −15.300 | 1.00 | 0.00 | B |
| ATOM | 1801 | CA | ASN | 271 | −22.993 | 8.054 | −14.939 | 1.00 | 0.00 | B |
| ATOM | 1802 | HA | ASN | 271 | −22.590 | 7.904 | −13.948 | 1.00 | 0.00 | B |
| ATOM | 1803 | CB | ASN | 271 | −24.405 | 7.492 | −15.028 | 1.00 | 0.00 | B |
| ATOM | 1804 | HB1 | ASN | 271 | −24.737 | 7.512 | −16.053 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1805 | HB2  | ASN | 271 | −25.066 | 8.095  | −14.422 | 1.00 | 0.00 | B |
|------|------|------|-----|-----|---------|--------|---------|------|------|---|
| ATOM | 1806 | CG   | ASN | 271 | −24.424 | 6.058  | −14.513 | 1.00 | 0.00 | B |
| ATOM | 1807 | OD1  | ASN | 271 | −23.924 | 5.157  | −15.155 | 1.00 | 0.00 | B |
| ATOM | 1808 | ND2  | ASN | 271 | −24.986 | 5.809  | −13.358 | 1.00 | 0.00 | B |
| ATOM | 1809 | HD21 | ASN | 271 | −25.387 | 6.542  | −12.838 | 1.00 | 0.00 | B |
| ATOM | 1810 | HD22 | ASN | 271 | −25.009 | 4.895  | −13.012 | 1.00 | 0.00 | B |
| ATOM | 1811 | C    | ASN | 271 | −22.066 | 7.441  | −15.989 | 1.00 | 0.00 | B |
| ATOM | 1812 | O    | ASN | 271 | −21.320 | 6.520  | −15.725 | 1.00 | 0.00 | B |
| ATOM | 1813 | N    | LYS | 272 | −22.122 | 7.937  | −17.194 | 1.00 | 0.00 | B |
| ATOM | 1814 | HN   | LYS | 272 | −22.737 | 8.664  | −17.397 | 1.00 | 0.00 | B |
| ATOM | 1815 | CA   | LYS | 272 | −21.237 | 7.387  | −18.243 | 1.00 | 0.00 | B |
| ATOM | 1816 | HA   | LYS | 272 | −21.271 | 6.311  | −18.241 | 1.00 | 0.00 | B |
| ATOM | 1817 | CB   | LYS | 272 | −21.743 | 7.944  | −19.574 | 1.00 | 0.00 | B |
| ATOM | 1818 | HB1  | LYS | 272 | −21.066 | 7.657  | −20.364 | 1.00 | 0.00 | B |
| ATOM | 1819 | HB2  | LYS | 272 | −21.799 | 9.023  | −19.519 | 1.00 | 0.00 | B |
| ATOM | 1820 | CG   | LYS | 272 | −23.133 | 7.371  | −19.864 | 1.00 | 0.00 | B |
| ATOM | 1821 | HG1  | LYS | 272 | −23.815 | 7.663  | −19.083 | 1.00 | 0.00 | B |
| ATOM | 1822 | HG2  | LYS | 272 | −23.074 | 6.293  | −19.905 | 1.00 | 0.00 | B |
| ATOM | 1823 | CD   | LYS | 272 | −23.636 | 7.902  | −21.205 | 1.00 | 0.00 | B |
| ATOM | 1824 | HD1  | LYS | 272 | −23.674 | 8.979  | −21.171 | 1.00 | 0.00 | B |
| ATOM | 1825 | HD2  | LYS | 272 | −24.623 | 7.511  | −21.397 | 1.00 | 0.00 | B |
| ATOM | 1826 | CE   | LYS | 272 | −22.683 | 7.463  | −22.320 | 1.00 | 0.00 | B |
| ATOM | 1827 | HE1  | LYS | 272 | −22.620 | 6.387  | −22.358 | 1.00 | 0.00 | B |
| ATOM | 1828 | HE2  | LYS | 272 | −21.702 | 7.896  | −22.167 | 1.00 | 0.00 | B |
| ATOM | 1829 | NZ   | LYS | 272 | −23.293 | 7.984  | −23.574 | 1.00 | 0.00 | B |
| ATOM | 1830 | HZ1  | LYS | 272 | −22.582 | 7.987  | −24.332 | 1.00 | 0.00 | B |
| ATOM | 1831 | HZ2  | LYS | 272 | −23.637 | 8.954  | −23.415 | 1.00 | 0.00 | B |
| ATOM | 1832 | HZ3  | LYS | 272 | −24.088 | 7.375  | −23.852 | 1.00 | 0.00 | B |
| ATOM | 1833 | C    | LYS | 272 | −19.841 | 7.878  | −17.915 | 1.00 | 0.00 | B |
| ATOM | 1834 | O    | LYS | 272 | −18.864 | 7.183  | −18.089 | 1.00 | 0.00 | B |
| ATOM | 1835 | N    | ASP | 273 | −19.745 | 9.107  | −17.445 | 1.00 | 0.00 | B |
| ATOM | 1836 | HN   | ASP | 273 | −20.552 | 9.657  | −17.348 | 1.00 | 0.00 | B |
| ATOM | 1837 | CA   | ASP | 273 | −18.420 | 9.671  | −17.087 | 1.00 | 0.00 | B |
| ATOM | 1838 | HA   | ASP | 273 | −17.750 | 9.640  | −17.931 | 1.00 | 0.00 | B |
| ATOM | 1839 | CB   | ASP | 273 | −18.697 | 11.116 | −16.670 | 1.00 | 0.00 | B |
| ATOM | 1840 | HB1  | ASP | 273 | −19.383 | 11.126 | −15.838 | 1.00 | 0.00 | B |
| ATOM | 1841 | HB2  | ASP | 273 | −19.132 | 11.651 | −17.501 | 1.00 | 0.00 | B |
| ATOM | 1842 | CG   | ASP | 273 | −17.389 | 11.793 | −16.257 | 1.00 | 0.00 | B |
| ATOM | 1843 | OD1  | ASP | 273 | −16.505 | 11.893 | −17.093 | 1.00 | 0.00 | B |
| ATOM | 1844 | OD2  | ASP | 273 | −17.294 | 12.203 | −15.112 | 1.00 | 0.00 | B |
| ATOM | 1845 | OD2  | ASP | 273 | −17.861 | 8.851  | −15.910 | 1.00 | 0.00 | B |
| ATOM | 1846 | O    | ASP | 273 | −16.708 | 8.936  | −15.577 | 1.00 | 0.00 | B |
| ATOM | 1847 | N    | ILE | 274 | −18.723 | 8.082  | −15.265 | 1.00 | 0.00 | B |
| ATOM | 1848 | HN   | ILE | 274 | −19.620 | 8.058  | −15.546 | 1.00 | 0.00 | B |
| ATOM | 1849 | CA   | ILE | 274 | −18.320 | 7.236  | −14.119 | 1.00 | 0.00 | B |
| ATOM | 1850 | HA   | ILE | 274 | −17.544 | 7.708  | −13.553 | 1.00 | 0.00 | B |
| ATOM | 1851 | CB   | ILE | 274 | −19.582 | 7.083  | −13.274 | 1.00 | 0.00 | B |
| ATOM | 1852 | HB   | ILE | 274 | −20.380 | 6.718  | −13.890 | 1.00 | 0.00 | B |
| ATOM | 1853 | CG1  | ILE | 274 | −19.974 | 8.443  | −12.688 | 1.00 | 0.00 | B |
| ATOM | 1854 | HG11 | ILE | 274 | −20.867 | 8.336  | −12.102 | 1.00 | 0.00 | B |
| ATOM | 1855 | HG12 | ILE | 274 | −20.150 | 9.137  | −13.484 | 1.00 | 0.00 | B |
| ATOM | 1856 | CG2  | ILE | 274 | −19.330 | 6.094  | −12.152 | 1.00 | 0.00 | B |
| ATOM | 1857 | HG21 | ILE | 274 | −19.432 | 6.593  | −11.200 | 1.00 | 0.00 | B |
| ATOM | 1858 | HG22 | ILE | 274 | −18.333 | 5.693  | −12.247 | 1.00 | 0.00 | B |
| ATOM | 1859 | HG23 | ILE | 274 | −20.049 | 5.291  | −12.216 | 1.00 | 0.00 | B |
| ATOM | 1860 | CD1  | ILE | 274 | −18.851 | 8.973  | −11.805 | 1.00 | 0.00 | B |
| ATOM | 1861 | HD11 | ILE | 274 | −18.353 | 8.150  | −11.323 | 1.00 | 0.00 | B |
| ATOM | 1862 | HD12 | ILE | 274 | −19.266 | 9.631  | −11.057 | 1.00 | 0.00 | B |
| ATOM | 1863 | HD13 | ILE | 274 | −18.144 | 9.518  | −12.412 | 1.00 | 0.00 | B |
| ATOM | 1864 | C    | ILE | 274 | −17.867 | 5.885  | −14.693 | 1.00 | 0.00 | B |
| ATOM | 1865 | O    | ILE | 274 | −17.118 | 5.155  | −14.093 | 1.00 | 0.00 | B |
| ATOM | 1866 | N    | GLU | 275 | −18.404 | 5.557  | −15.857 | 1.00 | 0.00 | B |
| ATOM | 1867 | HN   | GLU | 275 | −19.013 | 6.127  | −16.232 | 1.00 | 0.00 | B |
| ATOM | 1868 | CA   | GLU | 275 | −18.080 | 4.297  | −16.569 | 1.00 | 0.00 | B |
| ATOM | 1869 | HA   | GLU | 275 | −18.118 | 3.449  | −15.902 | 1.00 | 0.00 | B |
| ATOM | 1870 | CB   | GLU | 275 | −19.126 | 4.172  | −17.680 | 1.00 | 0.00 | B |
| ATOM | 1871 | HB1  | GLU | 275 | −19.046 | 5.017  | −18.347 | 1.00 | 0.00 | B |
| ATOM | 1872 | HB2  | GLU | 275 | −20.115 | 4.148  | −17.242 | 1.00 | 0.00 | B |
| ATOM | 1873 | CG   | GLU | 275 | −18.884 | 2.883  | −18.465 | 1.00 | 0.00 | B |
| ATOM | 1874 | HG1  | GLU | 275 | −17.888 | 2.896  | −18.882 | 1.00 | 0.00 | B |
| ATOM | 1875 | HG2  | GLU | 275 | −19.608 | 2.805  | −19.263 | 1.00 | 0.00 | B |
| ATOM | 1876 | CD   | GLU | 275 | −19.024 | 1.684  | −17.531 | 1.00 | 0.00 | B |
| ATOM | 1877 | OE1  | GLU | 275 | −20.103 | 1.500  | −16.994 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1878 | OE2 | GLU | 275 | −18.049 | 0.969 | −17.366 | 1.00 | 0.00 | B |
|---|---|---|---|---|---|---|---|---|---|---|
| ATOM | 1879 | C | GLU | 275 | −16.697 | 4.485 | −17.140 | 1.00 | 0.00 | B |
| ATOM | 1880 | O | GLU | 275 | −15.942 | 3.558 | −17.305 | 1.00 | 0.00 | B |
| ATOM | 1881 | N | GLU | 276 | −16.372 | 5.707 | −17.511 | 1.00 | 0.00 | B |
| ATOM | 1882 | HN | GLU | 276 | −16.983 | 6.440 | −17.379 | 1.00 | 0.00 | B |
| ATOM | 1883 | CA | GLU | 276 | −15.049 | 5.960 | −18.053 | 1.00 | 0.00 | B |
| ATOM | 1884 | HA | GLU | 276 | −14.741 | 5.200 | −18.757 | 1.00 | 0.00 | B |
| ATOM | 1885 | CB | GLU | 276 | −15.088 | 7.353 | −18.670 | 1.00 | 0.00 | B |
| ATOM | 1886 | HB1 | GLU | 276 | −14.128 | 7.584 | −19.104 | 1.00 | 0.00 | B |
| ATOM | 1887 | HB2 | GLU | 276 | −15.326 | 8.081 | −17.906 | 1.00 | 0.00 | B |
| ATOM | 1888 | CG | GLU | 276 | −16.149 | 7.379 | −19.749 | 1.00 | 0.00 | B |
| ATOM | 1889 | HG1 | GLU | 276 | −17.096 | 7.102 | −19.316 | 1.00 | 0.00 | B |
| ATOM | 1890 | HG2 | GLU | 276 | −15.882 | 6.677 | −20.520 | 1.00 | 0.00 | B |
| ATOM | 1891 | CD | GLU | 276 | −16.251 | 8.784 | −20.345 | 1.00 | 0.00 | B |
| ATOM | 1892 | OE1 | GLU | 276 | −16.979 | 8.946 | −21.309 | 1.00 | 0.00 | B |
| ATOM | 1893 | OE2 | GLU | 276 | −15.606 | 9.675 | −19.823 | 1.00 | 0.00 | B |
| ATOM | 1894 | C | GLU | 276 | −14.261 | 5.938 | −16.819 | 1.00 | 0.00 | B |
| ATOM | 1895 | O | GLU | 276 | −13.373 | 5.160 | −16.646 | 1.00 | 0.00 | B |
| ATOM | 1896 | N | CYS | 277 | −14.721 | 6.750 | −15.870 | 1.00 | 0.00 | B |
| ATOM | 1897 | HN | CYS | 277 | −15.512 | 7.283 | −16.053 | 1.00 | 0.00 | B |
| ATOM | 1898 | CA | CYS | 277 | −14.071 | 6.852 | −14.560 | 1.00 | 0.00 | B |
| ATOM | 1899 | HA | CYS | 277 | −13.172 | 7.381 | −14.606 | 1.00 | 0.00 | B |
| ATOM | 1900 | CB | CYS | 277 | −15.067 | 7.587 | −13.689 | 1.00 | 0.00 | B |
| ATOM | 1901 | HB1 | CYS | 277 | −15.973 | 7.023 | −13.654 | 1.00 | 0.00 | B |
| ATOM | 1902 | HB2 | CYS | 277 | −15.258 | 8.560 | −14.102 | 1.00 | 0.00 | B |
| ATOM | 1903 | SG | CYS | 277 | −14.409 | 7.766 | −12.017 | 1.00 | 0.00 | B |
| ATOM | 1904 | HG1 | CYS | 277 | −14.380 | 6.895 | −11.615 | 1.00 | 0.00 | B |
| ATOM | 1905 | C | CYS | 277 | −13.896 | 5.444 | −14.041 | 1.00 | 0.00 | B |
| ATOM | 1906 | O | CYS | 277 | −12.998 | 5.143 | −13.268 | 1.00 | 0.00 | B |
| ATOM | 1907 | N | ASN | 278 | −14.746 | 4.550 | −14.509 | 1.00 | 0.00 | B |
| ATOM | 1908 | HN | ASN | 278 | −15.406 | 4.797 | −15.162 | 1.00 | 0.00 | B |
| ATOM | 1909 | CA | ASN | 278 | −14.662 | 3.192 | −14.075 | 1.00 | 0.00 | B |
| ATOM | 1910 | HA | ASN | 278 | −14.588 | 3.179 | −13.042 | 1.00 | 0.00 | B |
| ATOM | 1911 | CB | ASN | 278 | −15.973 | 2.518 | −14.491 | 1.00 | 0.00 | B |
| ATOM | 1912 | HB1 | ASN | 278 | −16.061 | 2.524 | −15.553 | 1.00 | 0.00 | B |
| ATOM | 1913 | HB2 | ASN | 278 | −16.806 | 3.045 | −14.054 | 1.00 | 0.00 | B |
| ATOM | 1914 | CG | ASN | 278 | −15.969 | 1.069 | −13.996 | 1.00 | 0.00 | B |
| ATOM | 1915 | OD1 | ASN | 278 | −15.844 | 0.820 | −12.814 | 1.00 | 0.00 | B |
| ATOM | 1916 | ND2 | ASN | 278 | −16.100 | 0.096 | −14.857 | 1.00 | 0.00 | B |
| ATOM | 1917 | HD21 | ASN | 278 | −16.200 | 0.296 | −15.812 | 1.00 | 0.00 | B |
| ATOM | 1918 | HD22 | ASN | 278 | −16.099 | −0.834 | −14.549 | 1.00 | 0.00 | B |
| ATOM | 1919 | C | ASN | 278 | −13.476 | 2.503 | −14.751 | 1.00 | 0.00 | B |
| ATOM | 1920 | O | ASN | 278 | −12.704 | 1.845 | −14.127 | 1.00 | 0.00 | B |
| ATOM | 1921 | N | ALA | 279 | −13.333 | 2.692 | −16.043 | 1.00 | 0.00 | B |
| ATOM | 1922 | HN | ALA | 279 | −13.985 | 3.226 | −16.521 | 1.00 | 0.00 | B |
| ATOM | 1923 | CA | ALA | 279 | −12.203 | 2.053 | −16.802 | 1.00 | 0.00 | B |
| ATOM | 1924 | HA | ALA | 279 | −12.126 | 1.028 | −16.511 | 1.00 | 0.00 | B |
| ATOM | 1925 | CB | ALA | 279 | −12.648 | 2.114 | −18.258 | 1.00 | 0.00 | B |
| ATOM | 1926 | HB1 | ALA | 279 | −12.730 | 3.145 | −18.566 | 1.00 | 0.00 | B |
| ATOM | 1927 | HB2 | ALA | 279 | −13.608 | 1.628 | −18.362 | 1.00 | 0.00 | B |
| ATOM | 1928 | HB3 | ALA | 279 | −11.921 | 1.611 | −18.878 | 1.00 | 0.00 | B |
| ATOM | 1929 | C | ALA | 279 | −10.807 | 2.745 | −16.651 | 1.00 | 0.00 | B |
| ATOM | 1930 | O | ALA | 279 | −9.841 | 2.204 | −17.085 | 1.00 | 0.00 | B |
| ATOM | 1931 | N | ILE | 280 | −10.677 | 3.890 | −16.036 | 1.00 | 0.00 | B |
| ATOM | 1932 | HN | ILE | 280 | −11.402 | 4.251 | −15.558 | 1.00 | 0.00 | B |
| ATOM | 1933 | CA | ILE | 280 | −9.273 | 4.504 | −15.931 | 1.00 | 0.00 | B |
| ATOM | 1934 | HA | ILE | 280 | −8.620 | 3.950 | −16.490 | 1.00 | 0.00 | B |
| ATOM | 1935 | CB | ILE | 280 | −9.210 | 5.987 | −16.390 | 1.00 | 0.00 | B |
| ATOM | 1936 | HB | ILE | 280 | −8.220 | 6.309 | −16.264 | 1.00 | 0.00 | B |
| ATOM | 1937 | CG1 | ILE | 280 | −10.092 | 6.877 | −15.557 | 1.00 | 0.00 | B |
| ATOM | 1938 | HG11 | ILE | 280 | −9.976 | 7.902 | −15.872 | 1.00 | 0.00 | B |
| ATOM | 1939 | HG12 | ILE | 280 | −9.830 | 6.785 | −14.531 | 1.00 | 0.00 | B |
| ATOM | 1940 | CG2 | ILE | 280 | −9.568 | 6.128 | −17.844 | 1.00 | 0.00 | B |
| ATOM | 1941 | HG21 | ILE | 280 | −10.408 | 6.801 | −17.939 | 1.00 | 0.00 | B |
| ATOM | 1942 | HG22 | ILE | 280 | −9.823 | 5.165 | −18.242 | 1.00 | 0.00 | B |
| ATOM | 1943 | HG23 | ILE | 280 | −8.720 | 6.533 | −18.378 | 1.00 | 0.00 | B |
| ATOM | 1944 | CD1 | ILE | 280 | −11.470 | 6.481 | −15.742 | 1.00 | 0.00 | B |
| ATOM | 1945 | HD11 | ILE | 280 | −12.061 | 7.339 | −15.915 | 1.00 | 0.00 | B |
| ATOM | 1946 | HD12 | ILE | 280 | −11.810 | 5.971 | −14.866 | 1.00 | 0.00 | B |
| ATOM | 1947 | HD13 | ILE | 280 | −11.535 | 5.828 | −16.581 | 1.00 | 0.00 | B |
| ATOM | 1948 | C | ILE | 280 | −8.865 | 4.432 | −14.573 | 1.00 | 0.00 | B |
| ATOM | 1949 | O | ILE | 280 | −7.743 | 4.195 | −14.274 | 1.00 | 0.00 | B |
| ATOM | 1950 | N | ILE | 281 | −9.743 | 4.663 | −13.728 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 1951 | HN   | ILE | 281 | −10.650 | 4.879  | −14.002 | 1.00 | 0.00 | B |
|------|------|------|-----|-----|---------|--------|---------|------|------|---|
| ATOM | 1952 | CA   | ILE | 281 | −9.407  | 4.604  | −12.353 | 1.00 | 0.00 | B |
| ATOM | 1953 | HA   | ILE | 281 | −8.507  | 5.109  | −12.170 | 1.00 | 0.00 | B |
| ATOM | 1954 | CB   | ILE | 281 | −10.526 | 5.282  | −11.662 | 1.00 | 0.00 | B |
| ATOM | 1955 | HB   | ILE | 281 | −11.439 | 4.723  | −11.825 | 1.00 | 0.00 | B |
| ATOM | 1956 | CG1  | ILE | 281 | −10.641 | 6.664  | −12.300 | 1.00 | 0.00 | B |
| ATOM | 1957 | HG11 | ILE | 281 | −11.146 | 6.560  | −13.256 | 1.00 | 0.00 | B |
| ATOM | 1958 | HG12 | ILE | 281 | −9.643  | 7.055  | −12.476 | 1.00 | 0.00 | B |
| ATOM | 1959 | CG2  | ILE | 281 | −10.221 | 5.381  | −10.157 | 1.00 | 0.00 | B |
| ATOM | 1960 | HG21 | ILE | 281 | −9.693  | 4.494  | −9.838  | 1.00 | 0.00 | B |
| ATOM | 1961 | HG22 | ILE | 281 | −11.145 | 5.468  | −9.606  | 1.00 | 0.00 | B |
| ATOM | 1962 | HG23 | ILE | 281 | −9.608  | 6.251  | −9.972  | 1.00 | 0.00 | B |
| ATOM | 1963 | CD1  | ILE | 281 | −11.430 | 7.602  | −11.410 | 1.00 | 0.00 | B |
| ATOM | 1964 | HD11 | ILE | 281 | −10.765 | 8.044  | −10.683 | 1.00 | 0.00 | B |
| ATOM | 1965 | HD12 | ILE | 281 | −12.205 | 7.045  | −10.903 | 1.00 | 0.00 | B |
| ATOM | 1966 | HD13 | ILE | 281 | −11.873 | 8.374  | −12.012 | 1.00 | 0.00 | B |
| ATOM | 1967 | C    | ILE | 281 | −9.295  | 3.185  | −12.008 | 1.00 | 0.00 | B |
| ATOM | 1968 | O    | ILE | 281 | −8.497  | 2.789  | −11.184 | 1.00 | 0.00 | B |
| ATOM | 1969 | N    | GLU | 282 | −10.047 | 2.357  | −12.662 | 1.00 | 0.00 | B |
| ATOM | 1970 | HN   | GLU | 282 | −10.670 | 2.664  | −13.357 | 1.00 | 0.00 | B |
| ATOM | 1971 | CA   | GLU | 282 | −9.935  | 0.990  | −12.325 | 1.00 | 0.00 | B |
| ATOM | 1972 | HA   | GLU | 282 | −9.663  | 0.960  | −11.344 | 1.00 | 0.00 | B |
| ATOM | 1973 | CB   | GLU | 282 | −11.302 | 0.356  | −12.510 | 1.00 | 0.00 | B |
| ATOM | 1974 | HB1  | GLU | 282 | −11.522 | 0.286  | −13.559 | 1.00 | 0.00 | B |
| ATOM | 1975 | HB2  | GLU | 282 | −12.055 | 0.954  | −12.017 | 1.00 | 0.00 | B |
| ATOM | 1976 | CG   | GLU | 282 | −11.287 | −1.053 | −11.915 | 1.00 | 0.00 | B |
| ATOM | 1977 | HG1  | GLU | 282 | −11.047 | −0.998 | −10.864 | 1.00 | 0.00 | B |
| ATOM | 1978 | HG2  | GLU | 282 | −10.544 | −1.650 | −12.423 | 1.00 | 0.00 | B |
| ATOM | 1979 | CD   | GLU | 282 | −12.662 | −1.695 | −12.089 | 1.00 | 0.00 | B |
| ATOM | 1980 | OE1  | GLU | 282 | −13.634 | −1.094 | −11.663 | 1.00 | 0.00 | B |
| ATOM | 1981 | OE2  | GLU | 282 | −12.721 | −2.780 | −12.643 | 1.00 | 0.00 | B |
| ATOM | 1982 | C    | GLU | 282 | −8.894  | 0.282  | −13.183 | 1.00 | 0.00 | B |
| ATOM | 1983 | O    | GLU | 282 | −7.915  | −0.240 | −12.677 | 1.00 | 0.00 | B |
| ATOM | 1984 | N    | GLU | 283 | −9.055  | 0.299  | −14.480 | 1.00 | 0.00 | B |
| ATOM | 1985 | HN   | GLN | 283 | −9.803  | 0.795  | −14.892 | 1.00 | 0.00 | B |
| ATOM | 1986 | CA   | GLN | 283 | −8.077  | −0.381 | −15.337 | 1.00 | 0.00 | B |
| ATOM | 1987 | HA   | GLN | 283 | −7.805  | −1.325 | −14.897 | 1.00 | 0.00 | B |
| ATOM | 1988 | CB   | GLN | 283 | −8.826  | −0.634 | −16.634 | 1.00 | 0.00 | B |
| ATOM | 1989 | HB1  | GLN | 283 | −9.184  | 0.287  | −17.026 | 1.00 | 0.00 | B |
| ATOM | 1990 | HB2  | GLN | 283 | −9.657  | −1.297 | −16.450 | 1.00 | 0.00 | B |
| ATOM | 1991 | CG   | GLN | 283 | −7.891  | −1.263 | −17.620 | 1.00 | 0.00 | B |
| ATOM | 1992 | HG1  | GLN | 283 | −7.474  | −2.150 | −17.188 | 1.00 | 0.00 | B |
| ATOM | 1993 | HG2  | GLN | 283 | −7.103  | −0.561 | −17.848 | 1.00 | 0.00 | B |
| ATOM | 1994 | CD   | GLN | 283 | −8.650  | −1.619 | −18.896 | 1.00 | 0.00 | B |
| ATOM | 1995 | OE1  | GLN | 283 | −9.648  | −2.310 | −18.851 | 1.00 | 0.00 | B |
| ATOM | 1996 | NE2  | GLN | 283 | −8.216  | −1.175 | −20.039 | 1.00 | 0.00 | B |
| ATOM | 1997 | HE21 | GLN | 283 | −7.410  | −0.620 | −20.074 | 1.00 | 0.00 | B |
| ATOM | 1998 | HE22 | GLN | 283 | −8.697  | −1.393 | −20.863 | 1.00 | 0.00 | B |
| ATOM | 1999 | C    | GLN | 283 | −6.818  | 0.455  | −15.568 | 1.00 | 0.00 | B |
| ATOM | 2000 | O    | GLN | 283 | −5.824  | −0.058 | −16.046 | 1.00 | 0.00 | B |
| ATOM | 2001 | N    | PHE | 284 | −6.819  | 1.724  | −15.251 | 1.00 | 0.00 | B |
| ATOM | 2002 | HN   | PHE | 284 | −7.622  | 2.156  | −14.853 | 1.00 | 0.00 | B |
| ATOM | 2003 | CA   | PHE | 284 | −5.571  | 2.501  | −15.492 | 1.00 | 0.00 | B |
| ATOM | 2004 | HA   | PHE | 284 | −4.844  | 1.865  | −15.968 | 1.00 | 0.00 | B |
| ATOM | 2005 | CB   | PHE | 284 | −5.925  | 3.657  | −16.450 | 1.00 | 0.00 | B |
| ATOM | 2006 | HB1  | PHE | 284 | −5.095  | 4.346  | −16.497 | 1.00 | 0.00 | B |
| ATOM | 2007 | HB2  | PHE | 284 | −6.788  | 4.172  | −16.093 | 1.00 | 0.00 | B |
| ATOM | 2008 | CG   | PHE | 284 | −6.202  | 3.120  | −17.835 | 1.00 | 0.00 | B |
| ATOM | 2009 | CD1  | PHE | 284 | −7.244  | 2.194  | −18.042 | 1.00 | 0.00 | B |
| ATOM | 2010 | HD1  | PHE | 284 | −7.834  | 1.864  | −17.217 | 1.00 | 0.00 | B |
| ATOM | 2011 | CD2  | PHE | 284 | −5.415  | 3.552  | −18.929 | 1.00 | 0.00 | B |
| ATOM | 2012 | HD2  | PHE | 284 | −4.615  | 4.261  | −18.773 | 1.00 | 0.00 | B |
| ATOM | 2013 | CE1  | PHE | 284 | −7.506  | 1.697  | −19.339 | 1.00 | 0.00 | B |
| ATOM | 2014 | HE1  | PHE | 284 | −8.306  | 0.990  | −19.493 | 1.00 | 0.00 | B |
| ATOM | 2015 | CE2  | PHE | 284 | −5.675  | 3.054  | −20.229 | 1.00 | 0.00 | B |
| ATOM | 2016 | HE2  | PHE | 284 | −5.075  | 3.381  | −21.064 | 1.00 | 0.00 | B |
| ATOM | 2017 | CZ   | PHE | 284 | −6.721  | 2.126  | −20.432 | 1.00 | 0.00 | B |
| ATOM | 2018 | HZ   | PHE | 284 | −6.922  | 1.746  | −21.422 | 1.00 | 0.00 | B |
| ATOM | 2019 | C    | PHE | 284 | −4.991  | 3.036  | −14.192 | 1.00 | 0.00 | B |
| ATOM | 2020 | O    | PHE | 284 | −3.840  | 3.317  | −14.131 | 1.00 | 0.00 | B |
| ATOM | 2021 | N    | ILE | 285 | −5.772  | 3.207  | −13.156 | 1.00 | 0.00 | B |
| ATOM | 2022 | HN   | ILE | 285 | −6.717  | 2.928  | −13.178 | 1.00 | 0.00 | B |
| ATOM | 2023 | CA   | ILE | 285 | −5.190  | 3.729  | −11.901 | 1.00 | 0.00 | B |

TABLE 1-continued

Coordinates determined by NMR for sub-domain A
[EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 2024 | HA   | ILE | 285 | -4.297 | 4.282  | -12.122 | 1.00 | 0.00 | B |
|------|------|------|-----|-----|--------|--------|---------|------|------|---|
| ATOM | 2025 | CB   | ILE | 285 | -6.251 | 4.671  | -11.339 | 1.00 | 0.00 | B |
| ATOM | 2026 | HB   | ILE | 285 | -7.189 | 4.148  | -11.278 | 1.00 | 0.00 | B |
| ATOM | 2027 | CG1  | ILE | 285 | -6.400 | 5.912  | -12.280 | 1.00 | 0.00 | B |
| ATOM | 2028 | HG11 | ILE | 285 | -7.256 | 6.505  | -11.972 | 1.00 | 0.00 | B |
| ATOM | 2029 | HG12 | ILE | 285 | -6.554 | 5.579  | -13.300 | 1.00 | 0.00 | B |
| ATOM | 2030 | CG2  | ILE | 285 | -5.833 | 5.131  | -9.941  | 1.00 | 0.00 | B |
| ATOM | 2031 | HG21 | ILE | 285 | -4.780 | 4.936  | -9.798  | 1.00 | 0.00 | B |
| ATOM | 2032 | HG22 | ILE | 285 | -6.404 | 4.592  | -9.199  | 1.00 | 0.00 | B |
| ATOM | 2033 | HG23 | ILE | 285 | -6.019 | 6.191  | -9.839  | 1.00 | 0.00 | B |
| ATOM | 2034 | CD1  | ILE | 285 | -5.134 | 6.773  | -12.219 | 1.00 | 0.00 | B |
| ATOM | 2035 | HD11 | ILE | 285 | -4.275 | 6.146  | -12.052 | 1.00 | 0.00 | B |
| ATOM | 2036 | HD12 | ILE | 285 | -5.222 | 7.483  | -11.411 | 1.00 | 0.00 | B |
| ATOM | 2037 | HD13 | ILE | 285 | -5.016 | 7.304  | -13.152 | 1.00 | 0.00 | B |
| ATOM | 2038 | C    | ILE | 285 | -4.858 | 2.574  | -10.940 | 1.00 | 0.00 | B |
| ATOM | 2039 | O    | ILE | 285 | -4.106 | 2.735  | -10.001 | 1.00 | 0.00 | B |
| ATOM | 2040 | N    | ASP | 286 | -5.415 | 1.402  | -11.171 | 1.00 | 0.00 | B |
| ATOM | 2041 | HN   | ASP | 286 | -6.033 | 1.286  | -11.936 | 1.00 | 0.00 | B |
| ATOM | 2042 | CA   | ASP | 286 | -5.126 | 0.244  | -10.264 | 1.00 | 0.00 | B |
| ATOM | 2043 | HA   | ASP | 286 | -5.497 | 0.450  | -9.275  | 1.00 | 0.00 | B |
| ATOM | 2044 | CB   | ASP | 286 | -5.899 | -0.930 | -10.860 | 1.00 | 0.00 | B |
| ATOM | 2045 | HB1  | ASP | 286 | -5.593 | -1.083 | -11.883 | 1.00 | 0.00 | B |
| ATOM | 2046 | HB2  | ASP | 286 | -6.957 | -0.715 | -10.827 | 1.00 | 0.00 | B |
| ATOM | 2047 | CG   | ASP | 286 | -5.609 | -2.192 | -10.048 | 1.00 | 0.00 | B |
| ATOM | 2048 | OD1  | ASP | 286 | -4.514 | -2.713 | -10.172 | 1.00 | 0.00 | B |
| ATOM | 2049 | OD2  | ASP | 286 | -6.485 | -2.613 | -9.308  | 1.00 | 0.00 | B |
| ATOM | 2050 | C    | ASP | 286 | -3.620 | -0.090 | -10.200 | 1.00 | 0.00 | B |
| ATOM | 2051 | O    | ASP | 286 | -3.197 | -0.850 | -9.355  | 1.00 | 0.00 | B |
| ATOM | 2052 | N    | TYR | 287 | -2.806 | 0.447  | -11.074 | 1.00 | 0.00 | B |
| ATOM | 2053 | HN   | TYR | 287 | -3.147 | 1.048  | -11.772 | 1.00 | 0.00 | B |
| ATOM | 2054 | CA   | TYR | 287 | -1.339 | 0.109  | -10.997 | 1.00 | 0.00 | B |
| ATOM | 2055 | HA   | TYR | 287 | -1.215 | -0.958 | -11.088 | 1.00 | 0.00 | B |
| ATOM | 2056 | CB   | TYR | 287 | -0.652 | 0.807  | -12.197 | 1.00 | 0.00 | B |
| ATOM | 2057 | HB1  | TYR | 287 | -1.082 | 0.425  | -13.114 | 1.00 | 0.00 | B |
| ATOM | 2058 | HB2  | TYR | 287 | 0.401  | 0.576  | -12.182 | 1.00 | 0.00 | B |
| ATOM | 2059 | CG   | TYR | 287 | -0.828 | 2.323  | -12.163 | 1.00 | 0.00 | B |
| ATOM | 2060 | CD1  | TYR | 287 | -0.344 | 3.107  | -11.076 | 1.00 | 0.00 | B |
| ATOM | 2061 | HD1  | TYR | 287 | 0.158  | 2.639  | -10.247 | 1.00 | 0.00 | B |
| ATOM | 2062 | CD2  | TYR | 287 | -1.472 | 2.956  | -13.241 | 1.00 | 0.00 | B |
| ATOM | 2063 | HD2  | TYR | 287 | -1.842 | 2.365  | -14.064 | 1.00 | 0.00 | B |
| ATOM | 2064 | CE1  | TYR | 287 | -0.520 | 4.521  | -11.094 | 1.00 | 0.00 | B |
| ATOM | 2065 | HE1  | TYR | 287 | -0.159 | 5.123  | -10.277 | 1.00 | 0.00 | B |
| ATOM | 2066 | CE2  | TYR | 287 | -1.646 | 4.362  | -13.250 | 1.00 | 0.00 | B |
| ATOM | 2067 | HE2  | TYR | 287 | -2.151 | 4.842  | -14.084 | 1.00 | 0.00 | B |
| ATOM | 2068 | CZ   | TYR | 287 | -1.171 | 5.139  | -12.182 | 1.00 | 0.00 | B |
| ATOM | 2069 | OH   | TYR | 287 | -1.342 | 6.508  | -12.201 | 1.00 | 0.00 | B |
| ATOM | 2070 | HH   | TYR | 287 | -2.280 | 6.691  | -12.293 | 1.00 | 0.00 | B |
| ATOM | 2071 | C    | TYR | 287 | -0.753 | 0.573  | -9.665  | 1.00 | 0.00 | B |
| ATOM | 2072 | O    | TYR | 287 | 0.280  | 0.102  | -9.233  | 1.00 | 0.00 | B |
| ATOM | 2073 | N    | LEU | 288 | -1.404 | 1.488  | -9.008  | 1.00 | 0.00 | B |
| ATOM | 2074 | HN   | LEU | 288 | -2.235 | 1.854  | -9.372  | 1.00 | 0.00 | B |
| ATOM | 2075 | CA   | LEU | 288 | -0.882 | 1.981  | -7.698  | 1.00 | 0.00 | B |
| ATOM | 2076 | HA   | LEU | 288 | 0.012  | 2.513  | -7.844  | 1.00 | 0.00 | B |
| ATOM | 2077 | CB   | LEU | 288 | -1.973 | 2.912  | -7.169  | 1.00 | 0.00 | B |
| ATOM | 2078 | HB1  | LEU | 288 | -1.717 | 3.239  | -6.173  | 1.00 | 0.00 | B |
| ATOM | 2079 | HB2  | LEU | 288 | -2.918 | 2.384  | -7.146  | 1.00 | 0.00 | B |
| ATOM | 2080 | CG   | LEU | 288 | -2.088 | 4.128  | -8.088  | 1.00 | 0.00 | B |
| ATOM | 2081 | HG   | LEU | 288 | -2.229 | 3.800  | -9.106  | 1.00 | 0.00 | B |
| ATOM | 2082 | CD1  | LEU | 288 | -3.271 | 4.993  | -7.659  | 1.00 | 0.00 | B |
| ATOM | 2083 | HD11 | LEU | 288 | -3.026 | 5.509  | -6.745  | 1.00 | 0.00 | B |
| ATOM | 2084 | HD12 | LEU | 288 | -4.137 | 4.368  | -7.498  | 1.00 | 0.00 | B |
| ATOM | 2085 | HD13 | LEU | 288 | -3.487 | 5.715  | -8.432  | 1.00 | 0.00 | B |
| ATOM | 2086 | CD2  | LEU | 288 | -0.804 | 4.951  | -7.986  | 1.00 | 0.00 | B |
| ATOM | 2087 | HD21 | LEU | 288 | -0.920 | 5.867  | -8.547  | 1.00 | 0.00 | B |
| ATOM | 2088 | HD22 | LEU | 288 | 0.020  | 4.382  | -8.390  | 1.00 | 0.00 | B |
| ATOM | 2089 | HD23 | LEU | 288 | -0.607 | 5.185  | -6.949  | 1.00 | 0.00 | B |
| ATOM | 2090 | C    | LEU | 288 | -0.648 | 0.822  | -6.740  | 1.00 | 0.00 | B |
| ATOM | 2091 | O    | LEU | 288 | 0.130  | 0.910  | -5.812  | 1.00 | 0.00 | B |
| ATOM | 2092 | N    | ARG | 289 | -1.300 | -0.256 | -6.969  | 1.00 | 0.00 | B |
| ATOM | 2093 | HN   | ARG | 289 | -1.893 | -0.295 | -7.734  | 1.00 | 0.00 | B |
| ATOM | 2094 | CA   | ARG | 289 | -1.133 | -1.444 | -6.078  | 1.00 | 0.00 | B |
| ATOM | 2095 | HA   | ARG | 289 | -1.473 | -1.214 | -5.084  | 1.00 | 0.00 | B |
| ATOM | 2096 | CB   | ARG | 289 | -2.015 | -2.529 | -6.684  | 1.00 | 0.00 | B |

TABLE 1-continued

Coordinates determined by NMR for sub-domain A [EnvZ(C)(223–289), SEQ ID NO: 12]

REMARK envZ final structure, seed 726891, noe 1084.93, tot 2773.89 REMARK
DATE: 10-Feb-98 13:57:38 created by user:

| ATOM | 2097 | HB1 | ARG | 289 | −1.918 | −3.436 | −6.107 | 1.00 | 0.00 | B |
|---|---|---|---|---|---|---|---|---|---|---|
| ATOM | 2098 | HB2 | ARG | 289 | −1.710 | −2.714 | −7.705 | 1.00 | 0.00 | B |
| ATOM | 2099 | CG | ARG | 289 | −3.470 | −2.068 | −6.661 | 1.00 | 0.00 | B |
| ATOM | 2100 | HG1 | ARG | 289 | −3.578 | −1.185 | −7.270 | 1.00 | 0.00 | B |
| ATOM | 2101 | HG2 | ARG | 289 | −3.761 | −1.843 | −5.644 | 1.00 | 0.00 | B |
| ATOM | 2102 | CD | ARG | 289 | −4.361 | −3.177 | −7.212 | 1.00 | 0.00 | B |
| ATOM | 2103 | HD1 | ARG | 289 | −4.050 | −3.449 | −8.205 | 1.00 | 0.00 | B |
| ATOM | 2104 | HD2 | ARG | 289 | −5.396 | −2.861 | −7.211 | 1.00 | 0.00 | B |
| ATOM | 2105 | NE | ARG | 289 | −4.165 | −4.324 | −6.284 | 1.00 | 0.00 | B |
| ATOM | 2106 | HE | ARG | 289 | −3.651 | −4.205 | −5.459 | 1.00 | 0.00 | B |
| ATOM | 2107 | CZ | ARG | 289 | −4.678 | −5.488 | −6.570 | 1.00 | 0.00 | B |
| ATOM | 2108 | NH1 | ARG | 289 | −5.842 | −5.825 | −6.087 | 1.00 | 0.00 | B |
| ATOM | 2109 | HH11 | ARG | 289 | −6.341 | −5.191 | −5.497 | 1.00 | 0.00 | B |
| ATOM | 2110 | HH12 | ARG | 289 | −6.236 | −6.718 | −6.308 | 1.00 | 0.00 | B |
| ATOM | 2111 | NH2 | ARG | 289 | −4.026 | −6.316 | −7.341 | 1.00 | 0.00 | B |
| ATOM | 2112 | HH21 | ARG | 289 | −3.134 | −6.057 | −7.712 | 1.00 | 0.00 | B |
| ATOM | 2113 | HH22 | ARG | 289 | −4.420 | −7.209 | −7.562 | 1.00 | 0.00 | B |
| ATOM | 2114 | C | ARG | 289 | 0.332 | −1.892 | −6.052 | 1.00 | 0.00 | B |
| ATOM | 2115 | OT1 | ARG | 289 | 1.021 | −1.540 | −5.109 | 1.00 | 0.00 | B |
| ATOM | 2116 | OT2 | ARG | 289 | 0.738 | −2.579 | −6.975 | 1.00 | 0.00 | B |
| END | | | | | | | | | | |

TABLE 2

Coordinates determined by NMR for sub-domain B [EnvZ(C)(290–450), SEQ ID NO: 14]; a representative structure.

REMARK final envZ structures
REMARK DATE:18-Feb-98 13:12:56                                created by user:

| ATOM | 1 | CA | THR | 290 | 13.696 | −20.007 | 11.535 | 1.00 | 0.00 |
|---|---|---|---|---|---|---|---|---|---|
| ATOM | 2 | HA | THR | 290 | 12.665 | −19.951 | 11.842 | 1.00 | 0.00 |
| ATOM | 3 | CB | THR | 290 | 14.180 | −18.628 | 11.081 | 1.00 | 0.00 |
| ATOM | 4 | HB | THR | 290 | 13.750 | −18.395 | 10.121 | 1.00 | 0.00 |
| ATOM | 5 | OG1 | THR | 290 | 15.598 | −18.633 | 10.977 | 1.00 | 0.00 |
| ATOM | 6 | HG1 | THR | 290 | 15.839 | −19.184 | 10.228 | 1.00 | 0.00 |
| ATOM | 7 | CG2 | THR | 290 | 13.744 | −17.573 | 12.098 | 1.00 | 0.00 |
| ATOM | 8 | HG21 | THR | 290 | 14.505 | −16.810 | 12.173 | 1.00 | 0.00 |
| ATOM | 9 | HG22 | THR | 290 | 13.604 | −18.038 | 13.062 | 1.00 | 0.00 |
| ATOM | 10 | HG23 | THR | 290 | 12.815 | −17.124 | 11.776 | 1.00 | 0.00 |
| ATOM | 11 | C | THR | 290 | 13.862 | −21.033 | 10.411 | 1.00 | 0.00 |
| ATOM | 12 | O | THR | 290 | 14.757 | −21.855 | 10.433 | 1.00 | 0.00 |
| ATOM | 13 | N | THR | 290 | 14.564 | −20.365 | 12.694 | 1.00 | 0.00 |
| ATOM | 14 | HT1 | THR | 290 | 14.206 | −19.898 | 13.552 | 1.00 | 0.00 |
| ATOM | 15 | HT2 | THR | 290 | 15.537 | −20.052 | 12.510 | 1.00 | 0.00 |
| ATOM | 16 | HT3 | THR | 290 | 14.551 | −21.396 | 12.830 | 1.00 | 0.00 |
| ATOM | 17 | N | GLY | 291 | 13.008 | −20.989 | 9.430 | 1.00 | 0.00 |
| ATOM | 18 | HN | GLY | 291 | 12.295 | −20.317 | 9.433 | 1.00 | 0.00 |
| ATOM | 19 | CA | GLY | 291 | 13.111 | −21.958 | 8.304 | 1.00 | 0.00 |
| ATOM | 20 | HA1 | GLY | 291 | 13.566 | −22.871 | 8.654 | 1.00 | 0.00 |
| ATOM | 21 | HA2 | GLY | 291 | 13.716 | −21.530 | 7.515 | 1.00 | 0.00 |
| ATOM | 22 | C | GLY | 291 | 11.711 | −22.262 | 7.771 | 1.00 | 0.00 |
| ATOM | 23 | O | GLY | 291 | 11.539 | −22.650 | 6.633 | 1.00 | 0.00 |
| ATOM | 24 | N | GLN | 292 | 10.710 | −22.087 | 8.588 | 1.00 | 0.00 |
| ATOM | 25 | HN | GLN | 292 | 10.872 | −21.774 | 9.502 | 1.00 | 0.00 |
| ATOM | 26 | CA | GLN | 292 | 9.318 | −22.364 | 8.134 | 1.00 | 0.00 |
| ATOM | 27 | HA | GLN | 292 | 9.322 | −23.028 | 7.287 | 1.00 | 0.00 |
| ATOM | 28 | CB | GLN | 292 | 8.645 | −23.042 | 9.327 | 1.00 | 0.00 |
| ATOM | 29 | HB1 | GLN | 292 | 7.595 | −23.175 | 9.121 | 1.00 | 0.00 |
| ATOM | 30 | HB2 | GLN | 292 | 8.767 | −22.426 | 10.207 | 1.00 | 0.00 |
| ATOM | 31 | CG | GLN | 292 | 9.293 | −24.407 | 9.565 | 1.00 | 0.00 |
| ATOM | 32 | HG1 | GLN | 292 | 10.356 | −24.335 | 9.391 | 1.00 | 0.00 |
| ATOM | 33 | HG2 | GLN | 292 | 8.864 | −25.131 | 8.887 | 1.00 | 0.00 |
| ATOM | 34 | CD | GLN | 292 | 9.044 | −24.848 | 11.008 | 1.00 | 0.00 |
| ATOM | 35 | OE1 | GLN | 292 | 8.609 | −25.957 | 11.249 | 1.00 | 0.00 |
| ATOM | 36 | NE2 | GLN | 292 | 9.304 | −24.022 | 11.985 | 1.00 | 0.00 |
| ATOM | 37 | HE21 | GLN | 292 | 9.654 | −23.127 | 11.791 | 1.00 | 0.00 |
| ATOM | 38 | HE22 | GLN | 292 | 9.151 | −24.297 | 12.913 | 1.00 | 0.00 |
| ATOM | 39 | C | GLN | 292 | 8.610 | −21.052 | 7.786 | 1.00 | 0.00 |
| ATOM | 40 | O | GLN | 292 | 8.870 | −20.021 | 8.374 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 41  | N   | GLU | 293 | 7.718  | −21.081 | 6.835  | 1.00 | 0.00 |
|------|-----|-----|-----|-----|--------|---------|--------|------|------|
| ATOM | 42  | HN  | GLU | 293 | 7.521  | −21.921 | 6.371  | 1.00 | 0.00 |
| ATOM | 43  | CA  | GLU | 293 | 6.998  | −19.831 | 6.455  | 1.00 | 0.00 |
| ATOM | 44  | HA  | GLU | 293 | 7.223  | −19.041 | 7.152  | 1.00 | 0.00 |
| ATOM | 45  | CB  | GLU | 293 | 7.536  | −19.473 | 5.070  | 1.00 | 0.00 |
| ATOM | 46  | HB1 | GLU | 293 | 7.471  | −20.335 | 4.425  | 1.00 | 0.00 |
| ATOM | 47  | HB2 | GLU | 293 | 8.569  | −19.164 | 5.155  | 1.00 | 0.00 |
| ATOM | 48  | CG  | GLU | 293 | 6.708  | −18.331 | 4.479  | 1.00 | 0.00 |
| ATOM | 49  | HG1 | GLU | 293 | 7.357  | −17.502 | 4.241  | 1.00 | 0.00 |
| ATOM | 50  | HG2 | GLU | 293 | 5.968  | −18.013 | 5.199  | 1.00 | 0.00 |
| ATOM | 51  | CD  | GLU | 293 | 6.011  | −18.811 | 3.205  | 1.00 | 0.00 |
| ATOM | 52  | OE1 | GLU | 293 | 4.793  | −18.881 | 3.211  | 1.00 | 0.00 |
| ATOM | 53  | OE2 | GLU | 293 | 6.706  | −19.101 | 2.245  | 1.00 | 0.00 |
| ATOM | 54  | C   | GLU | 293 | 5.486  | −20.081 | 6.399  | 1.00 | 0.00 |
| ATOM | 55  | O   | GLU | 293 | 4.864  | −19.946 | 5.364  | 1.00 | 0.00 |
| ATOM | 56  | N   | MET | 294 | 4.892  | −20.445 | 7.505  | 1.00 | 0.00 |
| ATOM | 57  | HN  | MET | 294 | 5.413  | −20.550 | 8.328  | 1.00 | 0.00 |
| ATOM | 58  | CA  | MET | 294 | 3.419  | −20.703 | 7.514  | 1.00 | 0.00 |
| ATOM | 59  | HA  | MET | 294 | 2.989  | −20.471 | 6.549  | 1.00 | 0.00 |
| ATOM | 60  | CB  | MET | 294 | 3.278  | −22.197 | 7.812  | 1.00 | 0.00 |
| ATOM | 61  | HB1 | MET | 294 | 2.239  | −22.481 | 7.749  | 1.00 | 0.00 |
| ATOM | 62  | HB2 | MET | 294 | 3.649  | −22.401 | 8.807  | 1.00 | 0.00 |
| ATOM | 63  | CG  | MET | 294 | 4.088  | −23.002 | 6.790  | 1.00 | 0.00 |
| ATOM | 64  | HG1 | MET | 294 | 4.730  | −23.699 | 7.309  | 1.00 | 0.00 |
| ATOM | 65  | HG2 | MET | 294 | 4.690  | −22.329 | 6.198  | 1.00 | 0.00 |
| ATOM | 66  | SD  | MET | 294 | 2.958  | −23.913 | 5.706  | 1.00 | 0.00 |
| ATOM | 67  | CE  | MET | 294 | 3.153  | −25.536 | 6.482  | 1.00 | 0.00 |
| ATOM | 68  | HE1 | MET | 294 | 2.837  | −26.306 | 5.790  | 1.00 | 0.00 |
| ATOM | 69  | HE2 | MET | 294 | 2.549  | −25.585 | 7.372  | 1.00 | 0.00 |
| ATOM | 70  | HE3 | MET | 294 | 4.192  | −25.685 | 6.746  | 1.00 | 0.00 |
| ATOM | 71  | C   | MET | 294 | 2.748  | −19.863 | 8.603  | 1.00 | 0.00 |
| ATOM | 72  | O   | MET | 294 | 2.768  | −20.210 | 9.768  | 1.00 | 0.00 |
| ATOM | 73  | N   | PRO | 295 | 2.171  | −18.784 | 8.169  | 1.00 | 0.00 |
| ATOM | 74  | CA  | PRO | 295 | 1.477  | −17.860 | 9.086  | 1.00 | 0.00 |
| ATOM | 75  | HA  | PRO | 295 | 2.049  | −17.707 | 9.983  | 1.00 | 0.00 |
| ATOM | 76  | CB  | PRO | 295 | 1.399  | −16.571 | 8.290  | 1.00 | 0.00 |
| ATOM | 77  | HB1 | PRO | 295 | 2.242  | −15.939 | 8.515  | 1.00 | 0.00 |
| ATOM | 78  | HB2 | PRO | 295 | 0.472  | −16.055 | 8.502  | 1.00 | 0.00 |
| ATOM | 79  | CG  | PRO | 295 | 1.447  | −16.994 | 6.846  | 1.00 | 0.00 |
| ATOM | 80  | HG1 | PRO | 295 | 2.007  | −16.280 | 6.271  | 1.00 | 0.00 |
| ATOM | 81  | HG2 | PRO | 295 | 0.444  | −17.080 | 6.456  | 1.00 | 0.00 |
| ATOM | 82  | CD  | PRO | 295 | 2.128  | −18.331 | 6.784  | 1.00 | 0.00 |
| ATOM | 83  | HD1 | PRO | 295 | 3.127  | −18.228 | 6.395  | 1.00 | 0.00 |
| ATOM | 84  | HD2 | PRO | 295 | 1.551  | −19.018 | 6.176  | 1.00 | 0.00 |
| ATOM | 85  | C   | PRO | 295 | 0.071  | −18.369 | 9.419  | 1.00 | 0.00 |
| ATOM | 86  | O   | PRO | 295 | −0.900 | −17.964 | 8.817  | 1.00 | 0.00 |
| ATOM | 87  | N   | MET | 296 | −0.044 | −19.239 | 10.379 | 1.00 | 0.00 |
| ATOM | 88  | HN  | MET | 296 | 0.742  | −19.531 | 10.866 | 1.00 | 0.00 |
| ATOM | 89  | CA  | MET | 296 | −1.375 | −19.771 | 10.752 | 1.00 | 0.00 |
| ATOM | 90  | HA  | MET | 296 | −2.155 | −19.128 | 10.370 | 1.00 | 0.00 |
| ATOM | 91  | CB  | MET | 296 | −1.464 | −21.126 | 10.102 | 1.00 | 0.00 |
| ATOM | 92  | HB1 | MET | 296 | −2.402 | −21.589 | 10.355 | 1.00 | 0.00 |
| ATOM | 93  | HB2 | MET | 296 | −0.645 | −21.745 | 10.441 | 1.00 | 0.00 |
| ATOM | 94  | CG  | MET | 296 | −1.380 | −20.931 | 8.601  | 1.00 | 0.00 |
| ATOM | 95  | HG1 | MET | 296 | −0.395 | −21.194 | 8.263  | 1.00 | 0.00 |
| ATOM | 96  | HG2 | MET | 296 | −1.574 | −19.892 | 8.372  | 1.00 | 0.00 |
| ATOM | 97  | SD  | MET | 296 | −2.607 | −21.962 | 7.768  | 1.00 | 0.00 |
| ATOM | 98  | CE  | MET | 296 | −3.050 | −20.768 | 6.480  | 1.00 | 0.00 |
| ATOM | 99  | HE1 | MET | 296 | −3.390 | −19.851 | 6.943  | 1.00 | 0.00 |
| ATOM | 100 | HE2 | MET | 296 | −3.837 | −21.171 | 5.868  | 1.00 | 0.00 |
| ATOM | 101 | HE3 | MET | 296 | −2.183 | −20.566 | 5.865  | 1.00 | 0.00 |
| ATOM | 102 | C   | MET | 296 | −1.462 | −19.864 | 12.261 | 1.00 | 0.00 |
| ATOM | 103 | O   | MET | 296 | −0.980 | −20.788 | 12.884 | 1.00 | 0.00 |
| ATOM | 104 | N   | GLU | 297 | −2.074 | −18.904 | 12.827 | 1.00 | 0.00 |
| ATOM | 105 | HN  | GLU | 297 | −2.452 | −18.215 | 12.269 | 1.00 | 0.00 |
| ATOM | 106 | CA  | GLU | 297 | −2.240 | −18.849 | 14.315 | 1.00 | 0.00 |
| ATOM | 107 | HA  | GLU | 297 | −1.652 | −19.615 | 14.791 | 1.00 | 0.00 |
| ATOM | 108 | CB  | GLU | 297 | −1.725 | −17.467 | 14.725 | 1.00 | 0.00 |
| ATOM | 109 | HB1 | GLU | 297 | −0.677 | −17.387 | 14.480 | 1.00 | 0.00 |
| ATOM | 110 | HB2 | GLU | 297 | −1.856 | −17.336 | 15.790 | 1.00 | 0.00 |
| ATOM | 111 | CG  | GLU | 297 | −2.505 | −16.383 | 13.977 | 1.00 | 0.00 |
| ATOM | 112 | HG1 | GLU | 297 | −3.560 | −16.495 | 14.178 | 1.00 | 0.00 |
| ATOM | 113 | HG2 | GLU | 297 | −2.328 | −16.478 | 12.916 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56         created by user:

| | | | | | | | |
|---|---|---|---|---|---|---|---|
| ATOM | 114 CD | GLU | 297 | −2.043 | −15.005 | 14.449 | 1.00 0.00 |
| ATOM | 115 OE1 | GLU | 297 | −1.414 | −14.938 | 15.493 | 1.00 0.00 |
| ATOM | 116 OE2 | GLU | 297 | −2.323 | −14.039 | 13.759 | 1.00 0.00 |
| ATOM | 117 C | GLU | 297 | −3.708 | −19.004 | 14.688 | 1.00 0.00 |
| ATOM | 118 O | GLU | 297 | −4.556 | −19.130 | 13.839 | 1.00 0.00 |
| ATOM | 119 N | MET | 298 | −4.017 | −18.944 | 15.951 | 1.00 0.00 |
| ATOM | 120 HN | MET | 298 | −3.316 | −18.811 | 16.619 | 1.00 0.00 |
| ATOM | 121 CA | MET | 298 | −5.440 | −19.093 | 16.376 | 1.00 0.00 |
| ATOM | 122 HA | MET | 298 | −5.940 | −19.823 | 15.766 | 1.00 0.00 |
| ATOM | 123 CB | MET | 298 | −5.367 | −19.587 | 17.824 | 1.00 0.00 |
| ATOM | 124 HB1 | MET | 298 | −6.351 | −19.883 | 18.154 | 1.00 0.00 |
| ATOM | 125 HB2 | MET | 298 | −4.999 | −18.792 | 18.457 | 1.00 0.00 |
| ATOM | 126 CG | MET | 298 | −4.420 | −20.787 | 17.910 | 1.00 0.00 |
| ATOM | 127 HG1 | MET | 298 | −3.647 | −20.585 | 18.636 | 1.00 0.00 |
| ATOM | 128 HG2 | MET | 298 | −3.971 | −20.961 | 16.944 | 1.00 0.00 |
| ATOM | 129 SD | MET | 298 | −5.353 | −22.252 | 18.414 | 1.00 0.00 |
| ATOM | 130 CE | MET | 298 | −6.752 | −22.016 | 17.294 | 1.00 0.00 |
| ATOM | 131 HE1 | MET | 298 | −7.472 | −21.350 | 17.753 | 1.00 0.00 |
| ATOM | 132 HE2 | MET | 298 | −7.220 | −22.964 | 17.095 | 1.00 0.00 |
| ATOM | 133 HE3 | MET | 298 | −6.399 | −21.587 | 16.364 | 1.00 0.00 |
| ATOM | 134 C | MET | 298 | −6.170 | −17.749 | 16.310 | 1.00 0.00 |
| ATOM | 135 O | MET | 298 | −6.057 | −16.915 | 17.187 | 1.00 0.00 |
| ATOM | 136 N | ALA | 299 | −6.922 | −17.546 | 15.260 | 1.00 0.00 |
| ATOM | 137 HN | ALA | 299 | −6.980 | −18.231 | 14.572 | 1.00 0.00 |
| ATOM | 138 CA | ALA | 299 | −7.675 | −16.277 | 15.096 | 1.00 0.00 |
| ATOM | 139 HA | ALA | 299 | −7.429 | −15.585 | 15.877 | 1.00 0.00 |
| ATOM | 140 CB | ALA | 299 | −7.220 | −15.731 | 13.745 | 1.00 0.00 |
| ATOM | 141 HB1 | ALA | 299 | −7.621 | −14.740 | 13.604 | 1.00 0.00 |
| ATOM | 142 HB2 | ALA | 299 | −7.580 | −16.380 | 12.956 | 1.00 0.00 |
| ATOM | 143 HB3 | ALA | 299 | −6.143 | −15.694 | 13.716 | 1.00 0.00 |
| ATOM | 144 C | ALA | 299 | −9.181 | −16.554 | 15.065 | 1.00 0.00 |
| ATOM | 145 O | ALA | 299 | −9.614 | −17.644 | 14.745 | 1.00 0.00 |
| ATOM | 146 N | ASP | 300 | −9.981 | −15.579 | 15.393 | 1.00 0.00 |
| ATOM | 147 HN | ASP | 300 | −9.613 | −14.710 | 15.650 | 1.00 0.00 |
| ATOM | 148 CA | ASP | 300 | −11.456 | −15.788 | 15.380 | 1.00 0.00 |
| ATOM | 149 HA | ASP | 300 | −11.708 | −16.745 | 15.793 | 1.00 0.00 |
| ATOM | 150 CB | ASP | 300 | −12.024 | −14.672 | 16.255 | 1.00 0.00 |
| ATOM | 151 HB1 | ASP | 300 | −13.081 | −14.567 | 16.064 | 1.00 0.00 |
| ATOM | 152 HB2 | ASP | 300 | −11.522 | −13.743 | 16.026 | 1.00 0.00 |
| ATOM | 153 CG | ASP | 300 | −11.808 | −15.022 | 17.727 | 1.00 0.00 |
| ATOM | 154 OD1 | ASP | 300 | −12.102 | −14.184 | 18.564 | 1.00 0.00 |
| ATOM | 155 OD2 | ASP | 300 | −11.352 | −16.121 | 17.992 | 1.00 0.00 |
| ATOM | 156 C | ASP | 300 | −11.977 | −15.669 | 13.951 | 1.00 0.00 |
| ATOM | 157 O | ASP | 300 | −11.860 | −14.634 | 13.326 | 1.00 0.00 |
| ATOM | 158 N | LEU | 301 | −12.542 | −16.717 | 13.419 | 1.00 0.00 |
| ATOM | 159 HN | LEU | 301 | −12.622 | −17.549 | 13.931 | 1.00 0.00 |
| ATOM | 160 CA | LEU | 301 | −13.061 | −16.637 | 12.029 | 1.00 0.00 |
| ATOM | 161 HA | LEU | 301 | −12.266 | −16.388 | 11.354 | 1.00 0.00 |
| ATOM | 162 CB | LEU | 301 | −13.613 | −18.033 | 11.711 | 1.00 0.00 |
| ATOM | 163 HB1 | LEU | 301 | −14.514 | −17.939 | 11.123 | 1.00 0.00 |
| ATOM | 164 HB2 | LEU | 301 | −13.839 | −18.549 | 12.634 | 1.00 0.00 |
| ATOM | 165 CG | LEU | 301 | −12.571 | −18.839 | 10.917 | 1.00 0.00 |
| ATOM | 166 HG | LEU | 301 | −11.759 | −19.120 | 11.573 | 1.00 0.00 |
| ATOM | 167 CD1 | LEU | 301 | −13.223 | −20.099 | 10.348 | 1.00 0.00 |
| ATOM | 168 HD11 | LEU | 301 | −12.476 | −20.870 | 10.236 | 1.00 0.00 |
| ATOM | 169 HD12 | LEU | 301 | −13.657 | −19.875 | 9.384 | 1.00 0.00 |
| ATOM | 170 HD13 | LEU | 301 | −13.995 | −20.440 | 11.020 | 1.00 0.00 |
| ATOM | 171 CD2 | LEU | 301 | −12.030 | −17.994 | 9.762 | 1.00 0.00 |
| ATOM | 172 HD21 | LEU | 301 | −12.795 | −17.310 | 9.428 | 1.00 0.00 |
| ATOM | 173 HD22 | LEU | 301 | −11.743 | −18.640 | 8.947 | 1.00 0.00 |
| ATOM | 174 HD23 | LEU | 301 | −11.169 | −17.434 | 10.099 | 1.00 0.00 |
| ATOM | 175 C | LEU | 301 | −14.163 | −15.583 | 11.952 | 1.00 0.00 |
| ATOM | 176 O | LEU | 301 | −14.428 | −15.025 | 10.909 | 1.00 0.00 |
| ATOM | 177 N | ASN | 302 | −14.806 | −15.300 | 13.048 | 1.00 0.00 |
| ATOM | 178 HN | ASN | 302 | −14.574 | −15.755 | 13.888 | 1.00 0.00 |
| ATOM | 179 CA | ASN | 302 | −15.887 | −14.278 | 13.021 | 1.00 0.00 |
| ATOM | 180 HA | ASN | 302 | −16.465 | −14.369 | 12.118 | 1.00 0.00 |
| ATOM | 181 CB | ASN | 302 | −16.757 | −14.577 | 14.240 | 1.00 0.00 |
| ATOM | 182 HB1 | ASN | 302 | −16.267 | −14.215 | 15.131 | 1.00 0.00 |
| ATOM | 183 HB2 | ASN | 302 | −16.912 | −15.644 | 14.321 | 1.00 0.00 |
| ATOM | 184 CG | ASN | 302 | −18.103 | −13.876 | 14.083 | 1.00 0.00 |
| ATOM | 185 OD1 | ASN | 302 | −18.248 | −12.995 | 13.259 | 1.00 0.00 |
| ATOM | 186 ND2 | ASN | 302 | −19.105 | −14.233 | 14.838 | 1.00 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                              created by user:

| | | | | | | | | |
|---|---|---|---|---|---|---|---|---|
| ATOM | 187 | HD21 | ASN | 302 | −18.990 | −14.946 | 15.501 | 1.00 0.00 |
| ATOM | 188 | HD22 | ASN | 302 | −19.975 | −13.792 | 14.739 | 1.00 0.00 |
| ATOM | 189 | C | ASN | 302 | −15.271 | −12.886 | 13.123 | 1.00 0.00 |
| ATOM | 190 | O | ASN | 302 | −15.877 | −11.892 | 12.769 | 1.00 0.00 |
| ATOM | 191 | N | ALA | 303 | −14.064 | −12.813 | 13.602 | 1.00 0.00 |
| ATOM | 192 | HN | ALA | 303 | −13.599 | −13.627 | 13.866 | 1.00 0.00 |
| ATOM | 193 | CA | ALA | 303 | −13.387 | −11.497 | 13.735 | 1.00 0.00 |
| ATOM | 194 | HA | ALA | 303 | −14.077 | −10.749 | 14.078 | 1.00 0.00 |
| ATOM | 195 | CB | ALA | 303 | −12.287 | −11.719 | 14.774 | 1.00 0.00 |
| ATOM | 196 | HB1 | ALA | 303 | −11.901 | −10.765 | 15.099 | 1.00 0.00 |
| ATOM | 197 | HB2 | ALA | 303 | −11.489 | −12.300 | 14.335 | 1.00 0.00 |
| ATOM | 198 | HB3 | ALA | 303 | −12.695 | −12.250 | 15.622 | 1.00 0.00 |
| ATOM | 199 | C | ALA | 303 | −12.788 | −11.102 | 12.390 | 1.00 0.00 |
| ATOM | 200 | O | ALA | 303 | −12.851 | −9.961 | 11.978 | 1.00 0.00 |
| ATOM | 201 | N | VAL | 304 | −12.206 | −12.044 | 11.701 | 1.00 0.00 |
| ATOM | 202 | HN | VAL | 304 | −12.167 | −12.956 | 12.057 | 1.00 0.00 |
| ATOM | 203 | CA | VAL | 304 | −11.602 | −11.735 | 10.377 | 1.00 0.00 |
| ATOM | 204 | HA | VAL | 304 | −10.924 | −10.900 | 10.456 | 1.00 0.00 |
| ATOM | 205 | CB | VAL | 304 | −10.838 | −12.998 | 9.979 | 1.00 0.00 |
| ATOM | 206 | HB | VAL | 304 | −11.529 | −13.828 | 9.903 | 1.00 0.00 |
| ATOM | 207 | CG1 | VAL | 304 | −10.155 | −12.779 | 8.630 | 1.00 0.00 |
| ATOM | 208 | HG11 | VAL | 304 | −9.337 | −12.085 | 8.751 | 1.00 0.00 |
| ATOM | 209 | HG12 | VAL | 304 | −10.868 | −12.376 | 7.927 | 1.00 0.00 |
| ATOM | 210 | HG13 | VAL | 304 | −9.776 | −13.721 | 8.261 | 1.00 0.00 |
| ATOM | 211 | CG2 | VAL | 304 | −9.778 | −13.309 | 11.039 | 1.00 0.00 |
| ATOM | 212 | HG21 | VAL | 304 | −9.387 | −14.303 | 10.877 | 1.00 0.00 |
| ATOM | 213 | HG22 | VAL | 304 | −10.222 | −13.252 | 12.021 | 1.00 0.00 |
| ATOM | 214 | HG23 | VAL | 304 | −8.975 | −12.590 | 10.965 | 1.00 0.00 |
| ATOM | 215 | C | VAL | 304 | −12.712 | −11.434 | 9.370 | 1.00 0.00 |
| ATOM | 216 | O | VAL | 304 | −12.606 | −10.528 | 8.561 | 1.00 0.00 |
| ATOM | 217 | N | LEU | 305 | −13.783 | −12.186 | 9.410 | 1.00 0.00 |
| ATOM | 218 | HN | LEU | 305 | −13.858 | −12.912 | 10.074 | 1.00 0.00 |
| ATOM | 219 | CA | LEU | 305 | −14.891 | −11.935 | 8.454 | 1.00 0.00 |
| ATOM | 220 | HA | LEU | 305 | −14.514 | −11.880 | 7.446 | 1.00 0.00 |
| ATOM | 221 | CB | LEU | 305 | −15.821 | −13.133 | 8.601 | 1.00 0.00 |
| ATOM | 222 | HB1 | LEU | 305 | −16.681 | −13.004 | 7.961 | 1.00 0.00 |
| ATOM | 223 | HB2 | LEU | 305 | −16.143 | −13.219 | 9.630 | 1.00 0.00 |
| ATOM | 224 | CG | LEU | 305 | −15.068 | −14.397 | 8.190 | 1.00 0.00 |
| ATOM | 225 | HG | LEU | 305 | −14.273 | −14.586 | 8.897 | 1.00 0.00 |
| ATOM | 226 | CD1 | LEU | 305 | −16.029 | −15.588 | 8.169 | 1.00 0.00 |
| ATOM | 227 | HD11 | LEU | 305 | −15.747 | −16.263 | 7.373 | 1.00 0.00 |
| ATOM | 228 | HD12 | LEU | 305 | −17.036 | −15.235 | 8.003 | 1.00 0.00 |
| ATOM | 229 | HD13 | LEU | 305 | −15.981 | −16.107 | 9.114 | 1.00 0.00 |
| ATOM | 230 | CD2 | LEU | 305 | −14.470 | −14.196 | 6.798 | 1.00 0.00 |
| ATOM | 231 | HD21 | LEU | 305 | −14.146 | −15.147 | 6.404 | 1.00 0.00 |
| ATOM | 232 | HD22 | LEU | 305 | −13.624 | −13.526 | 6.864 | 1.00 0.00 |
| ATOM | 233 | HD23 | LEU | 305 | −15.215 | −13.770 | 6.145 | 1.00 0.00 |
| ATOM | 234 | C | LEU | 305 | −15.596 | −10.637 | 8.834 | 1.00 0.00 |
| ATOM | 235 | O | LEU | 305 | −16.113 | −9.929 | 7.993 | 1.00 0.00 |
| ATOM | 236 | N | GLY | 306 | −15.622 | −10.318 | 10.100 | 1.00 0.00 |
| ATOM | 237 | HN | GLY | 306 | −15.204 | −10.907 | 10.764 | 1.00 0.00 |
| ATOM | 238 | CA | GLY | 306 | −16.290 | −9.066 | 10.533 | 1.00 0.00 |
| ATOM | 239 | HA1 | GLY | 306 | −16.286 | −9.004 | 11.609 | 1.00 0.00 |
| ATOM | 240 | HA2 | GLY | 306 | −17.308 | −9.051 | 10.168 | 1.00 0.00 |
| ATOM | 241 | C | GLY | 306 | −15.517 | −7.884 | 9.955 | 1.00 0.00 |
| ATOM | 242 | O | GLY | 306 | −16.029 | −6.788 | 9.834 | 1.00 0.00 |
| ATOM | 243 | N | GLU | 307 | −14.280 | −8.106 | 9.589 | 1.00 0.00 |
| ATOM | 244 | HN | GLU | 307 | −13.896 | −9.001 | 9.681 | 1.00 0.00 |
| ATOM | 245 | CA | GLU | 307 | −13.462 | −7.007 | 9.017 | 1.00 0.00 |
| ATOM | 246 | HA | GLU | 307 | −13.719 | −6.071 | 9.473 | 1.00 0.00 |
| ATOM | 247 | CB | GLU | 307 | −12.012 | −7.373 | 9.342 | 1.00 0.00 |
| ATOM | 248 | HB1 | GLU | 307 | −11.350 | −6.856 | 8.665 | 1.00 0.00 |
| ATOM | 249 | HB2 | GLU | 307 | −11.878 | −8.439 | 9.233 | 1.00 0.00 |
| ATOM | 250 | CG | GLU | 307 | −11.689 | −6.961 | 10.781 | 1.00 0.00 |
| ATOM | 251 | HG1 | GLU | 307 | −11.788 | −7.816 | 11.432 | 1.00 0.00 |
| ATOM | 252 | HG2 | GLU | 307 | −12.375 | −6.186 | 11.097 | 1.00 0.00 |
| ATOM | 253 | CD | GLU | 307 | −10.254 | −6.433 | 10.852 | 1.00 0.00 |
| ATOM | 254 | OE1 | GLU | 307 | −9.392 | −7.032 | 10.231 | 1.00 0.00 |
| ATOM | 255 | OE2 | GLU | 307 | −10.043 | −5.439 | 11.527 | 1.00 0.00 |
| ATOM | 256 | C | GLU | 307 | −13.682 | −6.947 | 7.509 | 1.00 0.00 |
| ATOM | 257 | O | GLU | 307 | −13.649 | −5.895 | 6.905 | 1.00 0.00 |
| ATOM | 258 | N | VAL | 308 | −13.905 | −8.077 | 6.896 | 1.00 0.00 |
| ATOM | 259 | HN | VAL | 308 | −13.928 | −8.916 | 7.405 | 1.00 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| | | | | | | | | |
|---|---|---|---|---|---|---|---|---|
| ATOM | 260 | CA   | VAL | 308 | −14.131 | −8.095  | 5.424 | 1.00 | 0.00 |
| ATOM | 261 | HA   | VAL | 308 | −13.418 | −7.464  | 4.923 | 1.00 | 0.00 |
| ATOM | 262 | CB   | VAL | 308 | −13.934 | −9.549  | 5.014 | 1.00 | 0.00 |
| ATOM | 263 | HB   | VAL | 308 | −14.685 | −10.163 | 5.490 | 1.00 | 0.00 |
| ATOM | 264 | CG1  | VAL | 308 | −14.058 | −9.674  | 3.498 | 1.00 | 0.00 |
| ATOM | 265 | HG11 | VAL | 308 | −13.923 | −8.704  | 3.046 | 1.00 | 0.00 |
| ATOM | 266 | HG12 | VAL | 308 | −15.036 | −10.056 | 3.248 | 1.00 | 0.00 |
| ATOM | 267 | HG13 | VAL | 308 | −13.302 | −10.351 | 3.131 | 1.00 | 0.00 |
| ATOM | 268 | CG2  | VAL | 308 | −12.547 | −10.009 | 5.449 | 1.00 | 0.00 |
| ATOM | 269 | HG21 | VAL | 308 | −12.398 | −11.034 | 5.150 | 1.00 | 0.00 |
| ATOM | 270 | HG22 | VAL | 308 | −12.464 | −9.930  | 6.523 | 1.00 | 0.00 |
| ATOM | 271 | HG23 | VAL | 308 | −11.800 | −9.384  | 4.983 | 1.00 | 0.00 |
| ATOM | 272 | C    | VAL | 308 | −15.556 | −7.640  | 5.138 | 1.00 | 0.00 |
| ATOM | 273 | O    | VAL | 308 | −15.882 | −7.200  | 4.053 | 1.00 | 0.00 |
| ATOM | 274 | N    | ILE | 309 | −16.402 | −7.743  | 6.120 | 1.00 | 0.00 |
| ATOM | 275 | HN   | ILE | 309 | −16.102 | −8.088  | 6.983 | 1.00 | 0.00 |
| ATOM | 276 | CA   | ILE | 309 | −17.813 | −7.329  | 5.955 | 1.00 | 0.00 |
| ATOM | 277 | HA   | ILE | 309 | −18.192 | −7.619  | 4.991 | 1.00 | 0.00 |
| ATOM | 278 | CB   | ILE | 309 | −18.547 | −8.090  | 7.072 | 1.00 | 0.00 |
| ATOM | 279 | HB   | ILE | 309 | −17.838 | −8.359  | 7.842 | 1.00 | 0.00 |
| ATOM | 280 | CG1  | ILE | 309 | −19.157 | −9.361  | 6.481 | 1.00 | 0.00 |
| ATOM | 281 | HG11 | ILE | 309 | −18.716 | −9.554  | 5.515 | 1.00 | 0.00 |
| ATOM | 282 | HG12 | ILE | 309 | −20.219 | −9.232  | 6.368 | 1.00 | 0.00 |
| ATOM | 283 | CG2  | ILE | 309 | −19.655 | −7.216  | 7.690 | 1.00 | 0.00 |
| ATOM | 284 | HG21 | ILE | 309 | −19.241 | −6.258  | 7.975 | 1.00 | 0.00 |
| ATOM | 285 | HG22 | ILE | 309 | −20.051 | −7.703  | 8.563 | 1.00 | 0.00 |
| ATOM | 286 | HG23 | ILE | 309 | −20.442 | −7.068  | 6.968 | 1.00 | 0.00 |
| ATOM | 287 | CD1  | ILE | 309 | −18.874 | −10.546 | 7.409 | 1.00 | 0.00 |
| ATOM | 288 | HD11 | ILE | 309 | −18.248 | −10.222 | 8.227 | 1.00 | 0.00 |
| ATOM | 289 | HD12 | ILE | 309 | −18.369 | −11.322 | 6.855 | 1.00 | 0.00 |
| ATOM | 290 | HD13 | ILE | 309 | −19.805 | −10.930 | 7.799 | 1.00 | 0.00 |
| ATOM | 291 | C    | ILE | 309 | −17.900 | −5.821  | 6.157 | 1.00 | 0.00 |
| ATOM | 292 | O    | ILE | 309 | −18.489 | −5.099  | 5.376 | 1.00 | 0.00 |
| ATOM | 293 | N    | ALA | 310 | −17.317 | −5.358  | 7.216 | 1.00 | 0.00 |
| ATOM | 294 | HN   | ALA | 310 | −16.848 | −5.974  | 7.820 | 1.00 | 0.00 |
| ATOM | 295 | CA   | ALA | 310 | −17.337 | −3.908  | 7.514 | 1.00 | 0.00 |
| ATOM | 296 | HA   | ALA | 310 | −18.307 | −3.498  | 7.312 | 1.00 | 0.00 |
| ATOM | 297 | CB   | ALA | 310 | −17.014 | −3.801  | 9.004 | 1.00 | 0.00 |
| ATOM | 298 | HB1  | ALA | 310 | −16.284 | −4.552  | 9.269 | 1.00 | 0.00 |
| ATOM | 299 | HB2  | ALA | 310 | −17.915 | −3.955  | 9.580 | 1.00 | 0.00 |
| ATOM | 300 | HB3  | ALA | 310 | −16.615 | −2.821  | 9.217 | 1.00 | 0.00 |
| ATOM | 301 | C    | ALA | 310 | −16.272 | −3.212  | 6.677 | 1.00 | 0.00 |
| ATOM | 302 | O    | ALA | 310 | −16.282 | −2.008  | 6.509 | 1.00 | 0.00 |
| ATOM | 303 | N    | ALA | 311 | −15.349 | −3.974  | 6.152 | 1.00 | 0.00 |
| ATOM | 304 | HN   | ALA | 311 | −15.405 | −4.934  | 6.262 | 1.00 | 0.00 |
| ATOM | 305 | CA   | ALA | 311 | −14.264 | −3.386  | 5.318 | 1.00 | 0.00 |
| ATOM | 306 | HA   | ALA | 311 | −13.491 | −2.959  | 5.931 | 1.00 | 0.00 |
| ATOM | 307 | CB   | ALA | 311 | −13.719 | −4.555  | 4.501 | 1.00 | 0.00 |
| ATOM | 308 | HB1  | ALA | 311 | −14.520 | −5.252  | 4.294 | 1.00 | 0.00 |
| ATOM | 309 | HB2  | ALA | 311 | −12.943 | −5.054  | 5.058 | 1.00 | 0.00 |
| ATOM | 310 | HB3  | ALA | 311 | −13.315 | −4.187  | 3.568 | 1.00 | 0.00 |
| ATOM | 311 | C    | ALA | 311 | −14.866 | −2.356  | 4.407 | 1.00 | 0.00 |
| ATOM | 312 | O    | ALA | 311 | −14.524 | −1.191  | 4.433 | 1.00 | 0.00 |
| ATOM | 313 | N    | GLU | 312 | −15.763 | −2.785  | 3.602 | 1.00 | 0.00 |
| ATOM | 314 | HN   | GLU | 312 | −16.008 | −3.735  | 3.611 | 1.00 | 0.00 |
| ATOM | 315 | CA   | GLU | 312 | −16.422 | −1.869  | 2.670 | 1.00 | 0.00 |
| ATOM | 316 | HA   | GLU | 312 | −16.567 | −0.921  | 3.133 | 1.00 | 0.00 |
| ATOM | 317 | CB   | GLU | 312 | −15.475 | −1.747  | 1.476 | 1.00 | 0.00 |
| ATOM | 318 | HB1  | GLU | 312 | −15.583 | −2.612  | 0.840 | 1.00 | 0.00 |
| ATOM | 319 | HB2  | GLU | 312 | −14.454 | −1.685  | 1.831 | 1.00 | 0.00 |
| ATOM | 320 | CG   | GLU | 312 | −15.817 | −0.486  | 0.680 | 1.00 | 0.00 |
| ATOM | 321 | HG1  | GLU | 312 | −16.183 | 0.276   | 1.352 | 1.00 | 0.00 |
| ATOM | 322 | HG2  | GLU | 312 | −16.579 | −0.718  | −0.051 | 1.00 | 0.00 |
| ATOM | 323 | CD   | GLU | 312 | −14.564 | 0.027   | −0.033 | 1.00 | 0.00 |
| ATOM | 324 | OE1  | GLU | 312 | −14.599 | 0.133   | −1.248 | 1.00 | 0.00 |
| ATOM | 325 | OE2  | GLU | 312 | −13.591 | 0.306   | 0.649 | 1.00 | 0.00 |
| ATOM | 326 | C    | GLU | 312 | −17.750 | −2.471  | 2.258 | 1.00 | 0.00 |
| ATOM | 327 | O    | GLU | 312 | −18.292 | −2.166  | 1.213 | 1.00 | 0.00 |
| ATOM | 328 | N    | SER | 313 | −18.282 | −3.328  | 3.085 | 1.00 | 0.00 |
| ATOM | 329 | HN   | SER | 313 | −17.817 | −3.548  | 3.927 | 1.00 | 0.00 |
| ATOM | 330 | CA   | SER | 313 | −19.584 | −3.970  | 2.764 | 1.00 | 0.00 |
| ATOM | 331 | HA   | SER | 313 | −19.741 | −4.835  | 3.385 | 1.00 | 0.00 |
| ATOM | 332 | CB   | SER | 313 | −20.635 | −2.905  | 3.071 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56          created by user:

| ATOM | 333 | HB1  | SER | 313 | −20.233 | −2.200 | 3.792  | 1.00 | 0.00 |
|------|-----|------|-----|-----|---------|--------|--------|------|------|
| ATOM | 334 | HB2  | SER | 313 | −21.511 | −3.372 | 3.483  | 1.00 | 0.00 |
| ATOM | 335 | OG   | SER | 313 | −20.985 | −2.227 | 1.871  | 1.00 | 0.00 |
| ATOM | 336 | HG   | SER | 313 | −21.176 | −1.312 | 2.091  | 1.00 | 0.00 |
| ATOM | 337 | C    | SER | 313 | −19.617 | 4.359  | 1.285  | 1.00 | 0.00 |
| ATOM | 338 | O    | SER | 313 | −20.608 | −4.181 | 0.606  | 1.00 | 0.00 |
| ATOM | 339 | N    | GLY | 314 | −18.534 | −4.891 | 0.780  | 1.00 | 0.00 |
| ATOM | 340 | HN   | GLY | 314 | −17.742 | −5.029 | 1.348  | 1.00 | 0.00 |
| ATOM | 341 | CA   | GLY | 314 | −18.500 | −5.292 | −0.653 | 1.00 | 0.00 |
| ATOM | 342 | HA1  | GLY | 314 | −19.258 | −6.036 | −0.838 | 1.00 | 0.00 |
| ATOM | 343 | HA2  | GLY | 314 | −17.526 | −5.700 | −0.891 | 1.00 | 0.00 |
| ATOM | 344 | C    | GLY | 314 | −18.769 | −4.068 | −1.527 | 1.00 | 0.00 |
| ATOM | 345 | O    | GLY | 314 | −18.348 | −2.970 | −1.222 | 1.00 | 0.00 |
| ATOM | 346 | N    | TYR | 315 | −19.469 | −4.245 | −2.608 | 1.00 | 0.00 |
| ATOM | 347 | HN   | TYR | 315 | −19.802 | −5.138 | −2.835 | 1.00 | 0.00 |
| ATOM | 348 | CA   | TYR | 315 | −19.764 | −3.090 | −3.501 | 1.00 | 0.00 |
| ATOM | 349 | HA   | TYR | 315 | −19.094 | −2.272 | −3.297 | 1.00 | 0.00 |
| ATOM | 350 | CB   | TYR | 315 | −19.532 | −3.618 | −4.912 | 1.00 | 0.00 |
| ATOM | 351 | HB1  | TYR | 315 | −19.966 | −2.935 | −5.626 | 1.00 | 0.00 |
| ATOM | 352 | HB2  | TYR | 315 | −20.001 | −4.588 | −5.013 | 1.00 | 0.00 |
| ATOM | 353 | CG   | TYR | 315 | −18.049 | −3.744 | −5.173 | 1.00 | 0.00 |
| ATOM | 354 | CD1  | TYR | 315 | −17.433 | −5.002 | −5.126 | 1.00 | 0.00 |
| ATOM | 355 | HD1  | TYR | 315 | −18.018 | −5.881 | −4.901 | 1.00 | 0.00 |
| ATOM | 356 | CD2  | TYR | 315 | −17.290 | −2.605 | −5.466 | 1.00 | 0.00 |
| ATOM | 357 | HD2  | TYR | 315 | −17.763 | −1.635 | −5.503 | 1.00 | 0.00 |
| ATOM | 358 | CE1  | TYR | 315 | −16.059 | −5.120 | −5.371 | 1.00 | 0.00 |
| ATOM | 359 | HE1  | TYR | 315 | −15.584 | −6.090 | −5.335 | 1.00 | 0.00 |
| ATOM | 360 | CE2  | TYR | 315 | −15.916 | −2.723 | −5.709 | 1.00 | 0.00 |
| ATOM | 361 | HE2  | TYR | 315 | −15.330 | −1.843 | −5.934 | 1.00 | 0.00 |
| ATOM | 362 | CZ   | TYR | 315 | −15.300 | −3.979 | −5.662 | 1.00 | 0.00 |
| ATOM | 363 | OH   | TYR | 315 | −13.947 | −4.094 | −5.906 | 1.00 | 0.00 |
| ATOM | 364 | HH   | TYR | 315 | −13.565 | −3.214 | −5.882 | 1.00 | 0.00 |
| ATOM | 365 | C    | TYR | 315 | −21.218 | −2.652 | −3.331 | 1.00 | 0.00 |
| ATOM | 366 | O    | TYR | 315 | −22.048 | −2.899 | −4.181 | 1.00 | 0.00 |
| ATOM | 367 | N    | GLU | 316 | −21.537 | −1.998 | −2.250 | 1.00 | 0.00 |
| ATOM | 368 | HN   | GLU | 316 | −20.858 | −1.794 | −1.578 | 1.00 | 0.00 |
| ATOM | 369 | CA   | GLU | 316 | −22.941 | −1.557 | −2.049 | 1.00 | 0.00 |
| ATOM | 370 | HA   | GLU | 316 | −23.061 | −1.093 | −1.087 | 1.00 | 0.00 |
| ATOM | 371 | CB   | GLU | 316 | −23.191 | −0.551 | −3.155 | 1.00 | 0.00 |
| ATOM | 372 | HB1  | GLU | 316 | −24.248 | −0.375 | −3.244 | 1.00 | 0.00 |
| ATOM | 373 | HB2  | GLU | 316 | −22.809 | −0.946 | −4.086 | 1.00 | 0.00 |
| ATOM | 374 | CG   | GLU | 316 | −22.478 | 0.764  | −2.828 | 1.00 | 0.00 |
| ATOM | 375 | HG1  | GLU | 316 | −21.531 | 0.553  | −2.356 | 1.00 | 0.00 |
| ATOM | 376 | HG2  | GLU | 316 | −23.093 | 1.351  | −2.159 | 1.00 | 0.00 |
| ATOM | 377 | CD   | GLU | 316 | −22.237 | 1.546  | −4.120 | 1.00 | 0.00 |
| ATOM | 378 | OE1  | GLU | 316 | −21.112 | 1.964  | −4.334 | 1.00 | 0.00 |
| ATOM | 379 | OE2  | GLU | 316 | −23.182 | 1.713  | −4.874 | 1.00 | 0.00 |
| ATOM | 380 | C    | GLU | 316 | −23.875 | −2.752 | −2.194 | 1.00 | 0.00 |
| ATOM | 381 | O    | GLU | 316 | −25.000 | −2.634 | −2.638 | 1.00 | 0.00 |
| ATOM | 382 | N    | ARG | 317 | −23.405 | −3.901 | −1.829 | 1.00 | 0.00 |
| ATOM | 383 | HN   | ARG | 317 | −22.535 | −3.972 | −1.515 | 1.00 | 0.00 |
| ATOM | 384 | CA   | ARG | 317 | −24.190 | −5.091 | −1.920 | 1.00 | 0.00 |
| ATOM | 385 | HA   | ARG | 317 | −24.829 | −5.046 | −2.762 | 1.00 | 0.00 |
| ATOM | 386 | CB   | ARG | 317 | −23.170 | −6.210 | −2.098 | 1.00 | 0.00 |
| ATOM | 387 | HB1  | ARG | 317 | −23.435 | −7.045 | −1.469 | 1.00 | 0.00 |
| ATOM | 388 | HB2  | ARG | 317 | −22.186 | −5.848 | −1.822 | 1.00 | 0.00 |
| ATOM | 389 | CG   | ARG | 317 | −23.159 | −6.656 | −3.555 | 1.00 | 0.00 |
| ATOM | 390 | HG1  | ARG | 317 | −24.112 | −7.096 | −3.802 | 1.00 | 0.00 |
| ATOM | 391 | HG2  | ARG | 317 | −22.376 | −7.384 | −3.700 | 1.00 | 0.00 |
| ATOM | 392 | CD   | ARG | 317 | −22.910 | −5.449 | −4.459 | 1.00 | 0.00 |
| ATOM | 393 | HD1  | ARG | 317 | −21.857 | −5.337 | −4.655 | 1.00 | 0.00 |
| ATOM | 394 | HD2  | ARG | 317 | −23.310 | −4.552 | −4.005 | 1.00 | 0.00 |
| ATOM | 395 | NE   | ARG | 317 | −23.634 | −5.757 | −5.720 | 1.00 | 0.00 |
| ATOM | 396 | HE   | ARG | 317 | −23.686 | −6.681 | −6.043 | 1.00 | 0.00 |
| ATOM | 397 | CZ   | ARG | 317 | −24.200 | −4.797 | −6.396 | 1.00 | 0.00 |
| ATOM | 398 | NH1  | ARG | 317 | −25.486 | −4.822 | −6.613 | 1.00 | 0.00 |
| ATOM | 399 | HH11 | ARG | 317 | −26.037 | −5.578 | −6.261 | 1.00 | 0.00 |
| ATOM | 400 | HH12 | ARG | 317 | −25.921 | −4.085 | −7.131 | 1.00 | 0.00 |
| ATOM | 401 | NH2  | ARG | 317 | −23.479 | −3.810 | −6.854 | 1.00 | 0.00 |
| ATOM | 402 | HH21 | ARG | 317 | −22.493 | −3.792 | −6.687 | 1.00 | 0.00 |
| ATOM | 403 | HH22 | ARG | 317 | −23.912 | −3.071 | −7.371 | 1.00 | 0.00 |
| ATOM | 404 | C    | ARG | 317 | −24.978 | −5.293 | −0.649 | 1.00 | 0.00 |
| ATOM | 405 | O    | ARG | 317 | −24.961 | −4.490 | 0.262  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| | | | | | | | | |
|---|---|---|---|---|---|---|---|---|
| ATOM | 406 | N    | GLU | 318 | −25.659 | −6.351  | −0.603 | 1.00 | 0.00 |
| ATOM | 407 | HN   | GLU | 318 | −25.604 | −6.955  | −1.337 | 1.00 | 0.00 |
| ATOM | 408 | CA   | GLU | 318 | −26.484 | −6.684  | 0.581  | 1.00 | 0.00 |
| ATOM | 409 | HA   | GLU | 318 | −26.415 | −5.903  | 1.320  | 1.00 | 0.00 |
| ATOM | 410 | CB   | GLU | 318 | −27.909 | −6.783  | 0.057  | 1.00 | 0.00 |
| ATOM | 411 | HB1  | GLU | 318 | −28.437 | −7.563  | 0.585  | 1.00 | 0.00 |
| ATOM | 412 | HB2  | GLU | 318 | −27.892 | −7.007  | −1.000 | 1.00 | 0.00 |
| ATOM | 413 | CG   | GLU | 318 | −28.610 | −5.452  | 0.288  | 1.00 | 0.00 |
| ATOM | 414 | HG1  | GLU | 318 | −27.921 | −4.647  | 0.083  | 1.00 | 0.00 |
| ATOM | 415 | HG2  | GLU | 318 | −28.935 | −5.394  | 1.316  | 1.00 | 0.00 |
| ATOM | 416 | CD   | GLU | 318 | −29.818 | −5.338  | −0.642 | 1.00 | 0.00 |
| ATOM | 417 | OE1  | GLU | 318 | −29.661 | −5.613  | −1.819 | 1.00 | 0.00 |
| ATOM | 418 | OE2  | GLU | 318 | −30.879 | −4.975  | −0.160 | 1.00 | 0.00 |
| ATOM | 419 | C    | GLU | 318 | −26.021 | −8.012  | 1.164  | 1.00 | 0.00 |
| ATOM | 420 | O    | GLU | 318 | −26.537 | −9.068  | 0.843  | 1.00 | 0.00 |
| ATOM | 421 | N    | ILE | 319 | −25.040 | −7.962  | 2.004  | 1.00 | 0.00 |
| ATOM | 422 | HN   | ILE | 319 | −24.636 | −7.098  | 2.219  | 1.00 | 0.00 |
| ATOM | 423 | CA   | ILE | 319 | −24.515 | −9.211  | 2.627  | 1.00 | 0.00 |
| ATOM | 424 | HA   | ILE | 319 | −24.630 | −10.046 | 1.960  | 1.00 | 0.00 |
| ATOM | 425 | CB   | ILE | 319 | −23.036 | −8.937  | 2.864  | 1.00 | 0.00 |
| ATOM | 426 | HB   | ILE | 319 | −22.940 | −8.157  | 3.594  | 1.00 | 0.00 |
| ATOM | 427 | CG1  | ILE | 319 | −22.377 | −8.502  | 1.558  | 1.00 | 0.00 |
| ATOM | 428 | HG11 | ILE | 319 | −22.924 | −8.912  | 0.723  | 1.00 | 0.00 |
| ATOM | 429 | HG12 | ILE | 319 | −21.357 | −8.860  | 1.533  | 1.00 | 0.00 |
| ATOM | 430 | CG2  | ILE | 319 | −22.350 | −10.198 | 3.392  | 1.00 | 0.00 |
| ATOM | 431 | HG21 | ILE | 319 | −22.771 | −10.460 | 4.352  | 1.00 | 0.00 |
| ATOM | 432 | HG22 | ILE | 319 | −21.290 | −10.011 | 3.504  | 1.00 | 0.00 |
| ATOM | 433 | HG23 | ILE | 319 | −22.501 | −11.009 | 2.698  | 1.00 | 0.00 |
| ATOM | 434 | CD1  | ILE | 319 | −22.385 | −6.976  | 1.470  | 1.00 | 0.00 |
| ATOM | 435 | HD11 | ILE | 319 | −21.464 | −6.635  | 1.021  | 1.00 | 0.00 |
| ATOM | 436 | HD12 | ILE | 319 | −22.478 | −6.559  | 2.462  | 1.00 | 0.00 |
| ATOM | 437 | HD13 | ILE | 319 | −23.221 | −6.655  | 0.866  | 1.00 | 0.00 |
| ATOM | 438 | C    | ILE | 319 | −25.191 | −9.491  | 3.966  | 1.00 | 0.00 |
| ATOM | 439 | O    | ILE | 319 | −25.707 | −8.608  | 4.621  | 1.00 | 0.00 |
| ATOM | 440 | N    | GLU | 320 | −25.183 | −10.721 | 4.366  | 1.00 | 0.00 |
| ATOM | 441 | HN   | GLU | 320 | −24.760 | −11.400 | 3.809  | 1.00 | 0.00 |
| ATOM | 442 | CA   | GLU | 320 | −25.811 | −11.106 | 5.661  | 1.00 | 0.00 |
| ATOM | 443 | HA   | GLU | 320 | −26.273 | −10.254 | 6.123  | 1.00 | 0.00 |
| ATOM | 444 | CB   | GLU | 320 | −26.858 | −12.159 | 5.311  | 1.00 | 0.00 |
| ATOM | 445 | HB1  | GLU | 320 | −26.536 | −13.122 | 5.673  | 1.00 | 0.00 |
| ATOM | 446 | HB2  | GLU | 320 | −26.985 | −12.199 | 4.238  | 1.00 | 0.00 |
| ATOM | 447 | CG   | GLU | 320 | −28.186 | −11.787 | 5.971  | 1.00 | 0.00 |
| ATOM | 448 | HG1  | GLU | 320 | −28.250 | −10.714 | 6.070  | 1.00 | 0.00 |
| ATOM | 449 | HG2  | GLU | 320 | −28.241 | −12.243 | 6.949  | 1.00 | 0.00 |
| ATOM | 450 | CD   | GLU | 320 | −29.344 | −12.286 | 5.108  | 1.00 | 0.00 |
| ATOM | 451 | OE1  | GLU | 320 | −30.474 | −11.938 | 5.410  | 1.00 | 0.00 |
| ATOM | 452 | OE2  | GLU | 320 | −29.082 | −13.007 | 4.160  | 1.00 | 0.00 |
| ATOM | 453 | C    | GLU | 320 | −24.727 | −11.694 | 6.565  | 1.00 | 0.00 |
| ATOM | 454 | O    | GLU | 320 | −24.205 | −12.757 | 6.305  | 1.00 | 0.00 |
| ATOM | 455 | N    | THR | 321 | −24.386 | −11.022 | 7.626  | 1.00 | 0.00 |
| ATOM | 456 | HN   | THR | 321 | −24.811 | −10.168 | 7.826  | 1.00 | 0.00 |
| ATOM | 457 | CA   | THR | 321 | −23.330 | −11.563 | 8.524  | 1.00 | 0.00 |
| ATOM | 458 | HA   | THR | 321 | −22.627 | −12.135 | 7.949  | 1.00 | 0.00 |
| ATOM | 459 | CB   | THR | 321 | −22.631 | −10.345 | 9.084  | 1.00 | 0.00 |
| ATOM | 460 | HB   | THR | 321 | −21.993 | −10.644 | 9.897  | 1.00 | 0.00 |
| ATOM | 461 | OG1  | THR | 321 | −23.597 | −9.411  | 9.550  | 1.00 | 0.00 |
| ATOM | 462 | HG1  | THR | 321 | −23.470 | −9.298  | 10.495 | 1.00 | 0.00 |
| ATOM | 463 | CG2  | THR | 321 | −21.787 | −9.713  | 7.993  | 1.00 | 0.00 |
| ATOM | 464 | HG21 | THR | 321 | −21.535 | −10.461 | 7.255  | 1.00 | 0.00 |
| ATOM | 465 | HG22 | THR | 321 | −20.883 | −9.319  | 8.425  | 1.00 | 0.00 |
| ATOM | 466 | HG23 | THR | 321 | −22.341 | −8.916  | 7.522  | 1.00 | 0.00 |
| ATOM | 467 | C    | THR | 321 | −23.882 | −12.419 | 9.663  | 1.00 | 0.00 |
| ATOM | 468 | O    | THR | 321 | −24.658 | −11.979 | 10.486 | 1.00 | 0.00 |
| ATOM | 469 | N    | ALA | 322 | −23.467 | −13.646 | 9.691  | 1.00 | 0.00 |
| ATOM | 470 | HN   | ALA | 322 | −22.845 | −13.953 | 9.002  | 1.00 | 0.00 |
| ATOM | 471 | CA   | ALA | 322 | −23.910 | −14.600 | 10.742 | 1.00 | 0.00 |
| ATOM | 472 | HA   | ALA | 322 | −24.128 | −14.086 | 11.664 | 1.00 | 0.00 |
| ATOM | 473 | CB   | ALA | 322 | −25.162 | −15.271 | 10.179 | 1.00 | 0.00 |
| ATOM | 474 | HB1  | ALA | 322 | −25.346 | −14.908 | 9.179  | 1.00 | 0.00 |
| ATOM | 475 | HB2  | ALA | 322 | −26.009 | −15.040 | 10.808 | 1.00 | 0.00 |
| ATOM | 476 | HB3  | ALA | 322 | −25.014 | −16.340 | 10.153 | 1.00 | 0.00 |
| ATOM | 477 | C    | ALA | 322 | −22.781 | −15.611 | 10.924 | 1.00 | 0.00 |
| ATOM | 478 | O    | ALA | 322 | −22.859 | −16.725 | 10.462 | 1.00 | 0.00 |

TABLE 2-continued

Coordinates determined by NMR for sub-domain B [EnvZ(C)(290–450), SEQ ID NO: 14]: a representative structure.

REMARK final envZ structures
REMARK DATE:18-Feb-98 13:12:56                              created by user:

| ATOM | 479 | N    | LEU | 323 | −21.739 | −15.230 | 11.617 | 1.00 | 0.00 |
|------|-----|------|-----|-----|---------|---------|--------|------|------|
| ATOM | 480 | HN   | LEU | 323 | −21.710 | −14.327 | 11.999 | 1.00 | 0.00 |
| ATOM | 481 | CA   | LEU | 323 | −20.589 | −16.163 | 11.831 | 1.00 | 0.00 |
| ATOM | 482 | HA   | LEU | 323 | −20.530 | −16.872 | 11.032 | 1.00 | 0.00 |
| ATOM | 483 | CB   | LEU | 323 | −19.365 | −15.253 | 11.796 | 1.00 | 0.00 |
| ATOM | 484 | HB1  | LEU | 323 | −18.522 | −15.774 | 12.224 | 1.00 | 0.00 |
| ATOM | 485 | HB2  | LEU | 323 | −19.571 | −14.370 | 12.377 | 1.00 | 0.00 |
| ATOM | 486 | CG   | LEU | 323 | −19.021 | −14.834 | 10.344 | 1.00 | 0.00 |
| ATOM | 487 | HG   | LEU | 323 | −18.297 | −15.522 | 9.933  | 1.00 | 0.00 |
| ATOM | 488 | CD1  | LEU | 323 | −20.274 | −14.821 | 9.458  | 1.00 | 0.00 |
| ATOM | 489 | HD11 | LEU | 323 | −20.797 | −15.759 | 9.555  | 1.00 | 0.00 |
| ATOM | 490 | HD12 | LEU | 323 | −19.983 | −14.676 | 8.429  | 1.00 | 0.00 |
| ATOM | 491 | HD13 | LEU | 323 | −20.922 | −14.013 | 9.765  | 1..00 | 0.00 |
| ATOM | 492 | CD2  | LEU | 323 | −18.429 | −13.431 | 10.369 | 1.00 | 0.00 |
| ATOM | 493 | HD21 | LEU | 323 | −17.518 | −13.435 | 10.941 | 1.00 | 0.00 |
| ATOM | 494 | HD22 | LEU | 323 | −19.137 | −12.754 | 10.825 | 1.00 | 0.00 |
| ATOM | 495 | HD23 | LEU | 323 | −18.222 | −13.111 | 9.361  | 1.00 | 0.00 |
| ATOM | 496 | C    | LEU | 323 | −20.672 | −16.882 | 13.170 | 1.00 | 0.00 |
| ATOM | 497 | O    | LEU | 323 | −19.937 | −16.584 | 14.087 | 1.00 | 0.00 |
| ATOM | 498 | N    | TYR | 324 | −21.538 | −17.843 | 13.279 | 1.00 | 0.00 |
| ATOM | 499 | HN   | TYR | 324 | −22.098 | −18.082 | 12.514 | 1.00 | 0.00 |
| ATOM | 500 | CA   | TYR | 324 | −21.668 | −18.589 | 14.563 | 1.00 | 0.00 |
| ATOM | 501 | HA   | TYR | 324 | −22.432 | −19.343 | 14.485 | 1.00 | 0.00 |
| ATOM | 502 | CB   | TYR | 324 | −20.304 | −19.250 | 14.762 | 1.00 | 0.00 |
| ATOM | 503 | HB1  | TYR | 324 | −19.688 | −18.621 | 15.388 | 1.00 | 0.00 |
| ATOM | 504 | HB2  | TYR | 324 | −19.826 | −19.382 | 13.803 | 1.00 | 0.00 |
| ATOM | 505 | CG   | TYR | 324 | −20.482 | −20.592 | 15.423 | 1.00 | 0.00 |
| ATOM | 506 | CD1  | TYR | 324 | −19.891 | −20.838 | 16.666 | 1.00 | 0.00 |
| ATOM | 507 | HD1  | TYR | 324 | −19.310 | −20.068 | 17.148 | 1.00 | 0.00 |
| ATOM | 508 | CD2  | TYR | 324 | −21.235 | −21.591 | 14.794 | 1.00 | 0.00 |
| ATOM | 509 | HD2  | TYR | 324 | −21.690 | −21.402 | 3.833  | 1.00 | 0.00 |
| ATOM | 510 | CE1  | TYR | 324 | −20.051 | −22.082 | 17.284 | 1.00 | 0.00 |
| ATOM | 511 | HE1  | TYR | 324 | −19.594 | −22.270 | 18.244 | 1.00 | 0.00 |
| ATOM | 512 | CE2  | TYR | 324 | −21.396 | −22.838 | 15.413 | 1.00 | 0.00 |
| ATOM | 513 | HE2  | TYR | 324 | −21.977 | −23.609 | 14.930 | 1.00 | 0.00 |
| ATOM | 514 | CZ   | TYR | 324 | −20.803 | −23.083 | 16.659 | 1.00 | 0.00 |
| ATOM | 515 | OH   | TYR | 324 | −20.959 | −24.310 | 17.271 | 1.00 | 0.00 |
| ATOM | 516 | HH   | TYR | 324 | −21.779 | −24.696 | 16.957 | 1.00 | 0.00 |
| ATOM | 517 | C    | TYR | 324 | −21.969 | −17.630 | 15.724 | 1.00 | 0.00 |
| ATOM | 518 | O    | TYR | 324 | −21.264 | −16.665 | 15.935 | 1.00 | 0.00 |
| ATOM | 519 | N    | PRO | 325 | −23.008 | −17.930 | 16.447 | 1.00 | 0.00 |
| ATOM | 520 | CA   | PRO | 325 | −23.394 | −17.083 | 17.589 | 1.00 | 0.00 |
| ATOM | 521 | HA   | PRO | 325 | −23.257 | −16.053 | 17.360 | 1.00 | 0.00 |
| ATOM | 522 | CB   | PRO | 325 | −24.858 | −17.402 | 17.793 | 1.00 | 0.00 |
| ATOM | 523 | HB1  | PRO | 325 | −25.475 | −16.708 | 17.246 | 1.00 | 0.00 |
| ATOM | 524 | HB2  | PRO | 325 | −25.104 | −17.378 | 18.850 | 1.00 | 0.00 |
| ATOM | 525 | CG   | PRO | 325 | −25.035 | −18.791 | 17.242 | 1.00 | 0.00 |
| ATOM | 526 | HG1  | PRO | 325 | −25.983 | −18.870 | 16.749 | 1.00 | 0.00 |
| ATOM | 527 | HG2  | PRO | 325 | −24.973 | −19.510 | 18.046 | 1.00 | 0.00 |
| ATOM | 528 | CD   | PRO | 325 | −23.923 | −19.043 | 16.248 | 1.00 | 0.00 |
| ATOM | 529 | HD1  | PRO | 325 | −24.306 | −19.035 | 15.240 | 1.00 | 0.00 |
| ATOM | 530 | HD2  | PRO | 325 | −23.432 | −19.984 | 16.462 | 1.00 | 0.00 |
| ATOM | 531 | C    | PRO | 325 | −22.594 | −17.469 | 18.827 | 1.00 | 0.00 |
| ATOM | 532 | O    | PRO | 325 | −23.107 | −17.506 | 19.927 | 1.00 | 0.00 |
| ATOM | 533 | N    | GLY | 326 | −21.351 | −17.754 | 18.654 | 1.00 | 0.00 |
| ATOM | 534 | HN   | GLY | 326 | −20.978 | −17.720 | 17.765 | 1.00 | 0.00 |
| ATOM | 535 | CA   | GLY | 326 | −20.506 | −18.142 | 19.826 | 1.00 | 0.00 |
| ATOM | 536 | HA1  | GLY | 326 | −20.558 | −19.212 | 19.960 | 1.00 | 0.00 |
| ATOM | 537 | HA2  | GLY | 326 | −20.889 | −17.656 | 20.712 | 1.00 | 0.00 |
| ATOM | 538 | C    | GLY | 326 | −19.030 | −17.730 | 19.620 | 1.00 | 0.00 |
| ATOM | 539 | O    | GLY | 326 | −18.201 | −17.950 | 20.481 | 1.00 | 0.00 |
| ATOM | 540 | N    | SER | 327 | −18.688 | −17.141 | 18.494 | 1.00 | 0.00 |
| ATOM | 541 | HN   | SER | 327 | −19.347 | −16.981 | 17.801 | 1.00 | 0.00 |
| ATOM | 542 | CA   | SER | 327 | −17.270 | −16.732 | 18.266 | 1.00 | 0.00 |
| ATOM | 543 | HA   | SER | 327 | −17.201 | −16.077 | 17.413 | 1.00 | 0.00 |
| ATOM | 544 | CB   | SER | 327 | −16.846 | −15.992 | 19.521 | 1.00 | 0.00 |
| ATOM | 545 | HB1  | SER | 327 | −16.124 | −16.594 | 20.061 | 1.00 | 0.00 |
| ATOM | 546 | HB2  | SER | 327 | −17.701 | −15.819 | 20.139 | 1.00 | 0.00 |
| ATOM | 547 | OG   | SER | 327 | −16.264 | −14.744 | 19.159 | 1.00 | 0.00 |
| ATOM | 548 | HG   | SER | 327 | −15.342 | −14.757 | 19.428 | 1.00 | 0.00 |
| ATOM | 549 | C    | SER | 327 | −16.399 | −17.957 | 18.064 | 1.00 | 0.00 |
| ATOM | 550 | O    | SER | 327 | −16.243 | −18.781 | 18.944 | 1..00 | 0.00 |
| ATOM | 551 | N    | ILE | 328 | −15.837 | −18.081 | 16.917 | 1..00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 552 | HN | ILE | 328 | −15.993 | −17.406 | 16.234 | 1.00 | 0.00 |
|---|---|---|---|---|---|---|---|---|---|
| ATOM | 553 | CA | ILE | 328 | −14.961 | −19.265 | 16.637 | 1.00 | 0.00 |
| ATOM | 554 | HA | ILE | 328 | −15.234 | −20.084 | 17.273 | 1.00 | 0.00 |
| ATOM | 555 | CB | ILE | 328 | −15.187 | −19.665 | 15.175 | 1.00 | 0.00 |
| ATOM | 556 | HB | ILE | 328 | −14.366 | −19.304 | 14.570 | 1.00 | 0.00 |
| ATOM | 557 | CG1 | ILE | 328 | −16.511 | −19.086 | 14.654 | 1.00 | 0.00 |
| ATOM | 558 | HG11 | ILE | 328 | −16.381 | −18.037 | 14.435 | 1.00 | 0.00 |
| ATOM | 559 | HG12 | ILE | 328 | −17.277 | −19.206 | 15.405 | 1.00 | 0.00 |
| ATOM | 560 | CG2 | ILE | 328 | −15.231 | −21.190 | 15.094 | 1.00 | 0.00 |
| ATOM | 561 | HG21 | ILE | 328 | −14.979 | −21.507 | 14.093 | 1.00 | 0.00 |
| ATOM | 562 | HG22 | ILE | 328 | −16.219 | −21.528 | 15.342 | 1.00 | 0.00 |
| ATOM | 563 | HG23 | ILE | 328 | −14.522 | −21.608 | 15.794 | 1.00 | 0.00 |
| ATOM | 564 | CD1 | ILE | 328 | −16.920 | −19.819 | 13.386 | 1.00 | 0.00 |
| ATOM | 565 | HD11 | ILE | 328 | −16.052 | −19.957 | 12.758 | 1.00 | 0.00 |
| ATOM | 566 | HD12 | ILE | 328 | −17.660 | −19.241 | 12.861 | 1.00 | 0.00 |
| ATOM | 567 | HD13 | ILE | 328 | −17.329 | −20.782 | 13.649 | 1.00 | 0.00 |
| ATOM | 568 | C | ILE | 328 | −13.500 | −18.914 | 16.847 | 1.00 | 0.00 |
| ATOM | 569 | O | ILE | 328 | −13.159 | −17.829 | 17.275 | 1.00 | 0.00 |
| ATOM | 570 | N | GLU | 329 | −12.638 | −19.829 | 16.531 | 1.00 | 0.00 |
| ATOM | 571 | HN | GLU | 329 | −12.946 | −20.670 | 16.185 | 1.00 | 0.00 |
| ATOM | 572 | CA | GLU | 329 | −11.193 | −19.594 | 16.695 | 1.00 | 0.00 |
| ATOM | 573 | HA | GLU | 329 | −10.892 | −18.704 | 16.170 | 1.00 | 0.00 |
| ATOM | 574 | CB | GLU | 329 | −11.014 | −19.406 | 18.176 | 1.00 | 0.00 |
| ATOM | 575 | HB1 | GLU | 329 | −11.722 | −18.678 | 18.523 | 1.00 | 0.00 |
| ATOM | 576 | HB2 | GLU | 329 | −10.017 | −19.066 | 18.367 | 1.00 | 0.00 |
| ATOM | 577 | CG | GLU | 329 | −11.255 | −20.730 | 18.903 | 1.00 | 0.00 |
| ATOM | 578 | HG1 | GLU | 329 | −10.334 | −21.289 | 18.947 | 1.00 | 0.00 |
| ATOM | 579 | HG2 | GLU | 329 | −11.999 | −21.303 | 18.367 | 1.00 | 0.00 |
| ATOM | 580 | CD | GLU | 329 | −11.749 | −20.452 | 20.322 | 1.00 | 0.00 |
| ATOM | 581 | OE1 | GLU | 329 | −12.304 | −19.387 | 20.537 | 1.00 | 0.00 |
| ATOM | 582 | OE2 | GLU | 329 | −11.565 | −21.309 | 21.170 | 1.00 | 0.00 |
| ATOM | 583 | C | GLU | 329 | −10.404 | −20.807 | 16.199 | 1.00 | 0.00 |
| ATOM | 584 | O | GLU | 329 | −10.414 | −21.864 | 16.798 | 1.00 | 0.00 |
| ATOM | 585 | N | VAL | 330 | −9.733 | −20.663 | 15.107 | 1.00 | 0.00 |
| ATOM | 586 | HN | VAL | 330 | −9.760 | −19.822 | 14.636 | 1.00 | 0.00 |
| ATOM | 587 | CA | VAL | 330 | −8.944 | −21.797 | 14.564 | 1.00 | 0.00 |
| ATOM | 588 | HA | VAL | 330 | −8.896 | −22.605 | 15.269 | 1.00 | 0.00 |
| ATOM | 589 | CB | VAL | 330 | −9.710 | −22.226 | 13.334 | 1.00 | 0.00 |
| ATOM | 590 | HB | VAL | 330 | −9.307 | −23.145 | 12.972 | 1.00 | 0.00 |
| ATOM | 591 | CG1 | VAL | 330 | −11.170 | −22.423 | 13.691 | 1.00 | 0.00 |
| ATOM | 592 | HG11 | VAL | 330 | −11.504 | −23.366 | 13.302 | 1.00 | 0.00 |
| ATOM | 593 | HG12 | VAL | 330 | −11.756 | −21.625 | 13.264 | 1.00 | 0.00 |
| ATOM | 594 | HG13 | VAL | 330 | −11.281 | −22.418 | 14.763 | 1.00 | 0.00 |
| ATOM | 595 | CG2 | VAL | 330 | −9.575 | −21.142 | 12.243 | 1.00 | 0.00 |
| ATOM | 596 | HG21 | VAL | 330 | −9.952 | −20.201 | 12.618 | 1.00 | 0.00 |
| ATOM | 597 | HG22 | VAL | 330 | −10.137 | −21.434 | 11.369 | 1.00 | 0.00 |
| ATOM | 598 | HG23 | VAL | 330 | −8.532 | −21.028 | 11.977 | 1.00 | 0.00 |
| ATOM | 599 | C | VAL | 330 | −7.556 | −21.357 | 14.142 | 1.00 | 0.00 |
| ATOM | 600 | O | VAL | 330 | −7.260 | −20.190 | 14.057 | 1.00 | 0.00 |
| ATOM | 601 | N | LYS | 331 | −6.707 | −22.292 | 13.866 | 1.00 | 0.00 |
| ATOM | 602 | HN | LYS | 331 | −6.974 | −23.229 | 13.938 | 1.00 | 0.00 |
| ATOM | 603 | CA | LYS | 331 | −5.337 | −21.936 | 13.441 | 1.00 | 0.00 |
| ATOM | 604 | HA | LYS | 331 | −4.969 | −21.105 | 14.009 | 1.00 | 0.00 |
| ATOM | 605 | CB | LYS | 331 | −4.491 | −23.173 | 13.695 | 1.00 | 0.00 |
| ATOM | 606 | HB1 | LYS | 331 | −4.205 | −23.614 | 12.754 | 1.00 | 0.00 |
| ATOM | 607 | HB2 | LYS | 331 | −5.061 | −23.888 | 14.271 | 1.00 | 0.00 |
| ATOM | 608 | CG | LYS | 331 | −3.240 | −22.771 | 14.468 | 1.00 | 0.00 |
| ATOM | 609 | HG1 | LYS | 331 | −3.241 | −21.700 | 14.627 | 1.00 | 0.00 |
| ATOM | 610 | HG2 | LYS | 331 | −2.361 | −23.050 | 13.903 | 1.00 | 0.00 |
| ATOM | 611 | CD | LYS | 331 | −3.235 | −23.485 | 15.817 | 1.00 | 0.00 |
| ATOM | 612 | HD1 | LYS | 331 | −3.104 | −24.544 | 15.662 | 1.00 | 0.00 |
| ATOM | 613 | HD2 | LYS | 331 | −4.178 | −23.308 | 16.319 | 1.00 | 0.00 |
| ATOM | 614 | CE | LYS | 331 | −2.089 | −22.950 | 16.677 | 1.00 | 0.00 |
| ATOM | 615 | HE1 | LYS | 331 | −2.227 | −21.901 | 16.879 | 1.00 | 0.00 |
| ATOM | 616 | HE2 | LYS | 331 | −1.139 | −23.120 | 16.186 | 1.00 | 0.00 |
| ATOM | 617 | NZ | LYS | 331 | −2.169 | −23.728 | 17.943 | 1.00 | 0.00 |
| ATOM | 618 | HZ1 | LYS | 331 | −1.277 | −23.630 | 18.468 | 1.00 | 0.00 |
| ATOM | 619 | HZ2 | LYS | 331 | −2.334 | −24.733 | 17.722 | 1.00 | 0.00 |
| ATOM | 620 | HZ3 | LYS | 331 | −2.951 | −23.367 | 18.523 | 1.00 | 0.00 |
| ATOM | 621 | C | LYS | 331 | −5.383 | −21.609 | 11.958 | 1.00 | 0.00 |
| ATOM | 622 | O | LYS | 331 | −5.164 | −22.459 | 11.117 | 1.00 | 0.00 |
| ATOM | 623 | N | MET | 332 | −5.666 | −20.386 | 11.624 | 1.00 | 0.00 |
| ATOM | 624 | HN | MET | 332 | −5.820 | −19.711 | 12.314 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56           created by user:

| | | | | | | | | |
|---|---|---|---|---|---|---|---|---|
| ATOM | 625 | CA | MET | 332 | −5.731 | −20.013 | 10.194 | 1.00 | 0.00 |
| ATOM | 626 | HA | MET | 332 | −5.145 | −20.692 | 9.599 | 1.00 | 0.00 |
| ATOM | 627 | CB | MET | 332 | −7.224 | −20.178 | 9.852 | 1.00 | 0.00 |
| ATOM | 628 | HB1 | MET | 332 | −7.816 | −19.873 | 10.702 | 1.00 | 0.00 |
| ATOM | 629 | HB2 | MET | 332 | −7.423 | −21.217 | 9.639 | 1.00 | 0.00 |
| ATOM | 630 | CG | MET | 332 | −7.620 | −19.332 | 8.635 | 1.00 | 0.00 |
| ATOM | 631 | HG1 | MET | 332 | −7.688 | −19.966 | 7.765 | 1.00 | 0.00 |
| ATOM | 632 | HG2 | MET | 332 | −6.889 | −18.567 | 8.462 | 1.00 | 0.00 |
| ATOM | 633 | SD | MET | 332 | −9.231 | −18.571 | 8.949 | 1.00 | 0.00 |
| ATOM | 634 | CE | MET | 332 | −8.702 | −17.451 | 10.271 | 1.00 | 0.00 |
| ATOM | 635 | HE1 | MET | 332 | −8.945 | −17.888 | 11.232 | 1.00 | 0.00 |
| ATOM | 636 | HE2 | MET | 332 | −9.210 | −16.509 | 10.169 | 1.00 | 0.00 |
| ATOM | 637 | HE3 | MET | 332 | −7.635 | −17.291 | 10.202 | 1.00 | 0.00 |
| ATOM | 638 | C | MET | 332 | −5.255 | −18.570 | 9.993 | 1.00 | 0.00 |
| ATOM | 639 | O | MET | 332 | −5.635 | −17.666 | 10.710 | 1.00 | 0.00 |
| ATOM | 640 | N | HIS | 333 | −4.421 | −18.366 | 9.019 | 1.00 | 0.00 |
| ATOM | 641 | HN | HIS | 333 | −4.129 | −19.117 | 8.479 | 1.00 | 0.00 |
| ATOM | 642 | CA | HIS | 333 | −3.893 | −16.998 | 8.731 | 1.00 | 0.00 |
| ATOM | 643 | HA | HIS | 333 | −3.265 | −16.653 | 9.534 | 1.00 | 0.00 |
| ATOM | 644 | CB | HIS | 333 | −3.067 | −17.167 | 7.451 | 1.00 | 0.00 |
| ATOM | 645 | HB1 | HIS | 333 | −3.733 | −17.208 | 6.600 | 1.00 | 0.00 |
| ATOM | 646 | HB2 | HIS | 333 | −2.502 | −18.084 | 7.505 | 1.00 | 0.00 |
| ATOM | 647 | CG | HIS | 333 | −2.127 | −16.003 | 7.292 | 1.00 | 0.00 |
| ATOM | 648 | ND1 | HIS | 333 | −1.579 | −15.656 | 6.065 | 1.00 | 0.00 |
| ATOM | 649 | HD1 | HIA | 333 | −1.729 | −16.114 | 5.213 | 1.00 | 0.00 |
| ATOM | 650 | CD2 | HIS | 333 | −1.634 | −15.095 | 8.190 | 1.00 | 0.00 |
| ATOM | 651 | HD2 | HIS | 333 | −1.858 | −15.081 | 9.242 | 1.00 | 0.00 |
| ATOM | 652 | CE1 | HIS | 333 | −0.796 | −14.578 | 6.262 | 1.00 | 0.00 |
| ATOM | 653 | HE1 | HIS | 333 | −0.241 | −14.081 | 5.481 | 1.00 | 0.00 |
| ATOM | 654 | NE2 | HIS | 333 | −0.795 | −14.196 | 7.541 | 1.00 | 0.00 |
| ATOM | 655 | C | HIS | 333 | −5.046 | −16.022 | 8.482 | 1.00 | 0.00 |
| ATOM | 656 | O | HIS | 333 | −5.742 | −16.133 | 7.497 | 1.00 | 0.00 |
| ATOM | 657 | N | PRO | 334 | −5.202 | −15.086 | 9.378 | 1.00 | 0.00 |
| ATOM | 658 | CA | PRO | 334 | −6.283 | −14.086 | 9.240 | 1.00 | 0.00 |
| ATOM | 659 | HA | PRO | 334 | −7.233 | −14.570 | 9.102 | 1.00 | 0.00 |
| ATOM | 660 | CB | PRO | 334 | −6.258 | −13.340 | 10.570 | 1.00 | 0.00 |
| ATOM | 661 | HB1 | PRO | 334 | −6.964 | −13.775 | 11.259 | 1.00 | 0.00 |
| ATOM | 662 | HB2 | PRO | 334 | −6.475 | −12.289 | 10.416 | 1.00 | 0.00 |
| ATOM | 663 | CG | PRO | 334 | −4.863 | −13.522 | 11.081 | 1.00 | 0.00 |
| ATOM | 664 | HG1 | PRO | 334 | −4.858 | −13.517 | 12.158 | 1.00 | 0.00 |
| ATOM | 665 | HG2 | PRO | 334 | −4.224 | −12.733 | 10.701 | 1.00 | 0.00 |
| ATOM | 666 | CD | PRO | 334 | −4.390 | −14.865 | 10.576 | 1.00 | 0.00 |
| ATOM | 667 | HD1 | PRO | 334 | −4.581 | −15.635 | 11.304 | 1.00 | 0.00 |
| ATOM | 668 | HD2 | PRO | 334 | −3.339 | −14.865 | 10.576 | 1.00 | 0.00 |
| ATOM | 669 | C | PRO | 334 | −5.979 | −13.148 | 8.062 | 1.00 | 0.00 |
| ATOM | 670 | O | PRO | 334 | −6.867 | −12.652 | 7.411 | 1.00 | 0.00 |
| ATOM | 671 | N | LEU | 335 | −4.727 | −12.906 | 7.812 | 1.00 | 0.00 |
| ATOM | 672 | HN | LEU | 335 | −4.026 | −13.319 | 8.355 | 1.00 | 0.00 |
| ATOM | 673 | CA | LEU | 335 | −4.355 | −12.007 | 6.694 | 1.00 | 0.00 |
| ATOM | 674 | HA | LEU | 335 | −4.854 | −11.063 | 6.788 | 1.00 | 0.00 |
| ATOM | 675 | CB | LEU | 335 | −2.834 | −11.823 | 6.852 | 1.00 | 0.00 |
| ATOM | 676 | HB1 | LEU | 335 | −2.418 | −12.694 | 7.333 | 1.00 | 0.00 |
| ATOM | 677 | HB2 | LEU | 335 | −2.642 | −10.954 | 7.463 | 1.00 | 0.00 |
| ATOM | 678 | CG | LEU | 335 | −2.170 | −11.635 | 5.488 | 1.00 | 0.00 |
| ATOM | 679 | HG | LEU | 335 | −2.301 | −12.532 | 4.898 | 1.00 | 0.00 |
| ATOM | 680 | CD1 | LEU | 335 | −2.817 | −10.451 | 4.768 | 1.00 | 0.00 |
| ATOM | 681 | HD11 | LEU | 335 | −3.764 | −10.760 | 4.350 | 1.00 | 0.00 |
| ATOM | 682 | HD12 | LEU | 335 | −2.167 | −10.112 | 3.977 | 1.00 | 0.00 |
| ATOM | 683 | HD13 | LEU | 335 | −2.980 | −9.648 | 5.472 | 1.00 | 0.00 |
| ATOM | 684 | CD2 | LEU | 335 | −0.678 | −11.634 | 5.686 | 1.00 | 0.00 |
| ATOM | 685 | HD21 | LEU | 335 | −0.523 | −10.308 | 5.852 | 1.00 | 0.00 |
| ATOM | 686 | HD22 | LEU | 335 | −0.135 | −11.675 | 4.807 | 1.00 | 0.00 |
| ATOM | 687 | HD23 | LEU | 335 | −0.324 | −11.919 | 6.543 | 1.00 | 0.00 |
| ATOM | 688 | C | LEU | 335 | −4.170 | −12.674 | 5.358 | 1.00 | 0.00 |
| ATOM | 689 | O | LEU | 335 | −5.421 | −12.188 | 4.541 | 1.00 | 0.00 |
| ATOM | 690 | N | SER | 336 | −4.223 | −13.858 | 5.138 | 1.00 | 0.00 |
| ATOM | 691 | HN | SER | 336 | −3.660 | −14.286 | 5.813 | 1.00 | 0.00 |
| ATOM | 692 | CA | SER | 336 | −4.527 | −14.563 | 3.863 | 1.00 | 0.00 |
| ATOM | 693 | HA | SER | 336 | −4.172 | −13.990 | 3.002 | 1.00 | 0.00 |
| ATOM | 694 | CB | SER | 336 | −3.769 | −15.883 | 3.951 | 1.00 | 0.00 |
| ATOM | 695 | HB1 | SER | 336 | −4.360 | −16.669 | 3.494 | 1.00 | 0.00 |
| ATOM | 696 | HB2 | SER | 336 | −4.589 | −16.127 | 4.983 | 1.00 | 0.00 |
| ATOM | 697 | OG | SER | 336 | −2.523 | −13.754 | 3.275 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 698 | HG   | SER | 336 | -2.086  | -14.965 | 3.605  | 1.00 | 0.00 |
|------|-----|------|-----|-----|---------|---------|--------|------|------|
| ATOM | 699 | C    | SER | 336 | -6.031  | -14.811 | 3.744  | 1.00 | 0.00 |
| ATOM | 700 | O    | SER | 336 | -6.586  | -14.805 | 2.663  | 1.00 | 0.00 |
| ATOM | 701 | N    | ILE | 337 | -6.699  | -15.028 | 4.846  | 1.00 | 0.00 |
| ATOM | 702 | HN   | LEU | 337 | -6.236  | -15.026 | 5.714  | 1.00 | 0.00 |
| ATOM | 703 | CA   | ILE | 337 | -8.168  | -15.274 | 4.782  | 1.00 | 0.00 |
| ATOM | 704 | HA   | ILE | 337 | -8.387  | -16.030 | 4.047  | 1.00 | 0.00 |
| ATOM | 705 | CB   | ILE | 337 | -8.543  | -15.777 | 6.172  | 1.00 | 0.00 |
| ATOM | 706 | HB   | ILE | 337 | -8.223  | -15.058 | 6.912  | 1.00 | 0.00 |
| ATOM | 707 | CG1  | ILE | 337 | -7.829  | -17.114 | 6.416  | 1.00 | 0.00 |
| ATOM | 708 | HG11 | ILE | 337 | -7.734  | -17.276 | 7.471  | 1.00 | 0.00 |
| ATOM | 709 | HG12 | ILE | 337 | -6.845  | -17.076 | 5.971  | 1.00 | 0.00 |
| ATOM | 710 | CG2  | ILE | 337 | -10.065 | -15.972 | 6.275  | 1.00 | 0.00 |
| ATOM | 711 | HG21 | ILE | 337 | -10.527 | -15.052 | 6.595  | 1.00 | 0.00 |
| ATOM | 712 | HG22 | ILE | 337 | -10.280 | -16.752 | 6.995  | 1.00 | 0.00 |
| ATOM | 713 | HG23 | ILE | 337 | -10.458 | -16.259 | 5.310  | 1.00 | 0.00 |
| ATOM | 714 | CD1  | ILE | 337 | -8.626  | -18.268 | 5.788  | 1.00 | 0.00 |
| ATOM | 715 | HD11 | ILE | 337 | -9.572  | -18.372 | 6.298  | 1.00 | 0.00 |
| ATOM | 716 | HD12 | ILE | 337 | -8.065  | -19.185 | 5.880  | 1.00 | 0.00 |
| ATOM | 717 | HD13 | ILE | 337 | -8.803  | -18.058 | 4.744  | 1.00 | 0.00 |
| ATOM | 718 | C    | ILE | 337 | -8.893  | -13.972 | 4.435  | 1.00 | 0.00 |
| ATOM | 719 | O    | ILE | 337 | -9.898  | -13.978 | 3.755  | 1.00 | 0.00 |
| ATOM | 720 | N    | LYS | 338 | -8.394  | -12.852 | 4.895  | 1.00 | 0.00 |
| ATOM | 721 | HN   | LYS | 338 | -7.581  | -12.860 | 5.444  | 1.00 | 0.00 |
| ATOM | 722 | CA   | LYS | 338 | -9.069  | -11.561 | 4.574  | 1.00 | 0.00 |
| ATOM | 723 | HA   | LYS | 338 | -10.099 | -11.597 | 4.890  | 1.00 | 0.00 |
| ATOM | 724 | CB   | LYS | 338 | -8.291  | -10.491 | 5.340  | 1.00 | 0.00 |
| ATOM | 725 | HB1  | LYS | 338 | -8.487  | -9.523  | 4.905  | 1.00 | 0.00 |
| ATOM | 726 | HB2  | LYS | 338 | -7.233  | -10.704 | 5.283  | 1.00 | 0.00 |
| ATOM | 727 | CG   | LYS | 338 | -8.732  | -10.487 | 6.800  | 1.00 | 0.00 |
| ATOM | 728 | HG1  | LYS | 338 | -7.929  | -10.854 | 7.416  | 1.00 | 0.00 |
| ATOM | 729 | HG2  | LYS | 338 | -9.596  | -11.126 | 6.914  | 1.00 | 0.00 |
| ATOM | 730 | CD   | LYS | 338 | -9.088  | -9.060  | 7.225  | 1.00 | 0.00 |
| ATOM | 731 | HD1  | LYS | 338 | -9.894  | -9.089  | 7.943  | 1.00 | 0.00 |
| ATOM | 732 | HD2  | LYS | 338 | -9.399  | -8.493  | 6.358  | 1.00 | 0.00 |
| ATOM | 733 | CE   | LYS | 338 | -7.864  | -8.393  | 7.862  | 1.00 | 0.00 |
| ATOM | 734 | HE1  | LYS | 338 | -6.957  | -8.868  | 7.523  | 1.00 | 0.00 |
| ATOM | 735 | HE2  | LYS | 338 | -7.933  | -8.435  | 8.942  | 1.00 | 0.00 |
| ATOM | 736 | NZ   | LYS | 338 | -7.906  | -6.979  | 7.392  | 1.00 | 0.00 |
| ATOM | 737 | HZ1  | LYS | 338 | -6.968  | -6.547  | 7.507  | 1.00 | 0.00 |
| ATOM | 738 | HZ2  | LYS | 338 | -8.604  | -6.448  | 7.954  | 1.00 | 0.00 |
| ATOM | 739 | HZ3  | LYS | 338 | -8.176  | -6.955  | 6.390  | 1.00 | 0.00 |
| ATOM | 740 | C    | LYS | 338 | -8.964  | -11.326 | 3.074  | 1.00 | 0.00 |
| ATOM | 741 | O    | LYS | 338 | -9.841  | -10.761 | 2.451  | 1.00 | 0.00 |
| ATOM | 742 | N    | ARG | 339 | -7.882  | -11.764 | 2.496  | 1.00 | 0.00 |
| ATOM | 743 | HN   | ARG | 339 | -7.193  | -12.211 | 3.034  | 1.00 | 0.00 |
| ATOM | 744 | CA   | ARG | 339 | -7.681  | -11.588 | 1.033  | 1.00 | 0.00 |
| ATOM | 745 | HA   | ARG | 339 | -7.926  | -10.582 | 0.735  | 1.00 | 0.00 |
| ATOM | 746 | CB   | ARG | 339 | -6.175  | -11.852 | 0.819  | 1.00 | 0.00 |
| ATOM | 747 | HB1  | ARG | 339 | -5.839  | -12.595 | 1.527  | 1.00 | 0.00 |
| ATOM | 748 | HB2  | ARG | 339 | -5.627  | -10.934 | 0.977  | 1.00 | 0.00 |
| ATOM | 749 | CG   | ARG | 339 | -5.912  | -12.357 | -0.607 | 1.00 | 0.00 |
| ATOM | 750 | HG1  | ARG | 339 | -6.585  | -13.167 | -0.835 | 1.00 | 0.00 |
| ATOM | 751 | HG2  | ARG | 339 | -4.891  | -12.706 | -0.681 | 1.00 | 0.00 |
| ATOM | 752 | CD   | ARG | 339 | -6.132  | -11.218 | -1.599 | 1.00 | 0.00 |
| ATOM | 753 | HD1  | ARG | 339 | -7.049  | -10.700 | -1.378 | 1.00 | 0.00 |
| ATOM | 754 | HD2  | ARG | 339 | -6.147  | -11.602 | -2.611 | 1.00 | 0.00 |
| ATOM | 755 | NE   | ARG | 339 | -4.969  | -10.306 | -1.402 | 1.00 | 0.00 |
| ATOM | 756 | HE   | ARG | 339 | -4.494  | -10.297 | -0.545 | 1.00 | 0.00 |
| ATOM | 757 | CZ   | ARG | 339 | -4.585  | -9.520  | -2.371 | 1.00 | 0.00 |
| ATOM | 758 | NH1  | ARG | 339 | -3.312  | -9.373  | -2.612 | 1.00 | 0.00 |
| ATOM | 759 | HH11 | ARG | 339 | -2.631  | -9.828  | -2.054 | 1.00 | 0.00 |
| ATOM | 760 | HH12 | ARG | 339 | -3.019  | -8.751  | -3.355 | 1.00 | 0.00 |
| ATOM | 761 | NH2  | ARG | 339 | -5.474  | -8.900  | -3.097 | 1.00 | 0.00 |
| ATOM | 762 | HH21 | ARG | 339 | -6.448  | -9.027  | -3.839 | 1.00 | 0.00 |
| ATOM | 763 | HH22 | ARG | 339 | -5.181  | -8.297  | -2.912 | 1.00 | 0.00 |
| ATOM | 764 | C    | ARG | 339 | -8.544  | -12.605 | 0.270  | 1.00 | 0.00 |
| ATOM | 765 | O    | ARG | 339 | -8.950  | -12.375 | -0.852 | 1.00 | 0.00 |
| ATOM | 766 | N    | ALA | 340 | -8.828  | -13.727 | 0.880  | 1.00 | 0.00 |
| ATOM | 767 | HN   | ALA | 340 | -8.488  | -13.892 | 1.783  | 1.00 | 0.00 |
| ATOM | 768 | CA   | ALA | 340 | -9.663  | -14.762 | 0.201  | 1.00 | 0.00 |
| ATOM | 769 | HA   | ALA | 340 | -9.371  | -13.861 | -0.829 | 1.00 | 0.00 |
| ATOM | 770 | CB   | ALA | 340 | -9.369  | -16.060 | 0.952  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                         created by user:

| | | | | | | | | |
|---|---|---|---|---|---|---|---|---|
| ATOM | 771 | HB1 | ALA | 340 | −8.582 | −16.600 | 0.445 | 1.00 | 0.00 |
| ATOM | 772 | HB2 | ALA | 340 | −10.261 | −16.668 | 0.983 | 1.00 | 0.00 |
| ATOM | 773 | HB3 | ALA | 340 | −9.056 | −15.830 | 1.960 | 1.00 | 0.00 |
| ATOM | 774 | C | ALA | 340 | −11.157 | −14.409 | 0.306 | 1.00 | 0.00 |
| ATOM | 775 | O | ALA | 340 | −11.950 | −14.779 | −0.536 | 1.00 | 0.00 |
| ATOM | 776 | N | VAL | 341 | −11.545 | −13.696 | 1.335 | 1.00 | 0.00 |
| ATOM | 777 | HN | VAL | 341 | −10.894 | −13.405 | 2.004 | 1.00 | 0.00 |
| ATOM | 778 | CA | VAL | 341 | −12.986 | −13.325 | 1.487 | 1.00 | 0.00 |
| ATOM | 779 | HA | VAL | 341 | −13.616 | −14.152 | 1.210 | 1.00 | 0.00 |
| ATOM | 780 | CB | VAL | 341 | −13.164 | −13.009 | 2.977 | 1.00 | 0.00 |
| ATOM | 781 | HB | VAL | 341 | −12.420 | −12.287 | 3.283 | 1.00 | 0.00 |
| ATOM | 782 | CG1 | VAL | 341 | −14.559 | −12.431 | 3.210 | 1.00 | 0.00 |
| ATOM | 783 | HG11 | VAL | 341 | −13.823 | −11.782 | 2.389 | 1.00 | 0.00 |
| ATOM | 784 | HG12 | VAL | 341 | −14.564 | −11.867 | 4.131 | 1.00 | 0.00 |
| ATOM | 785 | HG13 | VAL | 341 | −15.275 | −13.236 | 3.277 | 1.00 | 0.00 |
| ATOM | 786 | CG2 | VAL | 341 | −13.004 | −14.292 | 3.802 | 1.00 | 0.00 |
| ATOM | 787 | HG21 | VAL | 341 | −12.174 | −14.866 | 3.420 | 1.00 | 0.00 |
| ATOM | 788 | HG22 | VAL | 341 | −13.909 | −13.878 | 3.737 | 1.00 | 0.00 |
| ATOM | 789 | HG23 | VAL | 341 | −12.817 | −14.034 | 4.836 | 1.00 | 0.00 |
| ATOM | 790 | C | VAL | 341 | −13.314 | −12.090 | 0.633 | 1.00 | 0.00 |
| ATOM | 791 | O | VAL | 341 | −14.437 | −11.894 | 0.212 | 1.00 | 0.00 |
| ATOM | 792 | N | ALA | 342 | −12.341 | −11.257 | 0.380 | 1.00 | 0.00 |
| ATOM | 793 | HN | ALA | 342 | −11.445 | −11.430 | 0.738 | 1.00 | 0.00 |
| ATOM | 794 | CA | ALA | 342 | −12.592 | −10.033 | −0.445 | 1.00 | 0.00 |
| ATOM | 795 | HA | ALA | 342 | −13.372 | −9.436 | −0.003 | 1.00 | 0.00 |
| ATOM | 796 | CB | ALA | 342 | −11.273 | −9.263 | −0.415 | 1.00 | 0.00 |
| ATOM | 797 | HB1 | ALA | 342 | −10.513 | −9.832 | −0.932 | 1.00 | 0.00 |
| ATOM | 798 | HB2 | ALA | 342 | −10.970 | −9.106 | 0.609 | 1.00 | 0.00 |
| ATOM | 799 | HB3 | ALA | 342 | −11.401 | −8.309 | −0.903 | 1.00 | 0.00 |
| ATOM | 800 | C | ALA | 342 | −12.959 | −10.408 | −1.890 | 1.00 | 0.00 |
| ATOM | 801 | O | ALA | 342 | −13.676 | −9.693 | −2.562 | 1.00 | 0.00 |
| ATOM | 802 | N | ASN | 343 | −12.472 | −11.517 | −2.373 | 1.00 | 0.00 |
| ATOM | 803 | HN | ASN | 343 | −11.892 | −12.080 | −1.819 | 1.00 | 0.00 |
| ATOM | 804 | CA | ASN | 343 | −12.797 | −11.928 | −3.776 | 1.00 | 0.00 |
| ATOM | 805 | HA | ASN | 343 | −12.915 | −11.060 | −4.403 | 1.00 | 0.00 |
| ATOM | 806 | CB | ASN | 343 | −11.588 | −12.743 | −4.238 | 1.00 | 0.00 |
| ATOM | 807 | HB1 | ASN | 343 | −11.894 | −13.759 | −4.436 | 1.00 | 0.00 |
| ATOM | 808 | HB2 | ASN | 343 | −10.833 | −12.738 | −3.465 | 1.00 | 0.00 |
| ATOM | 809 | CG | ASN | 343 | −11.016 | −12.129 | −5.516 | 1.00 | 0.00 |
| ATOM | 810 | OD1 | ASN | 343 | −11.745 | −11.842 | −6.445 | 1.00 | 0.00 |
| ATOM | 811 | ND2 | ASN | 343 | −9.732 | −11.913 | −5.603 | 1.00 | 0.00 |
| ATOM | 812 | HD21 | ASN | 343 | −9.144 | −12.146 | −4.855 | 1.00 | 0.00 |
| ATOM | 813 | HD22 | ASN | 343 | −9.357 | −11.516 | −6.417 | 1.00 | 0.00 |
| ATOM | 814 | C | ASN | 343 | −14.068 | −12.788 | −3.809 | 1.00 | 0.00 |
| ATOM | 815 | O | ASN | 343 | −14.700 | −12.939 | −4.835 | 1.00 | 0.00 |
| ATOM | 816 | N | MET | 344 | −14.443 | −13.351 | −2.697 | 1.00 | 0.00 |
| ATOM | 817 | HN | MET | 344 | −13.919 | −13.215 | −1.880 | 1.00 | 0.00 |
| ATOM | 818 | CA | MET | 344 | −15.672 | −14.205 | −2.660 | 1.00 | 0.00 |
| ATOM | 819 | HA | MET | 344 | −15.547 | −15.067 | −3.292 | 1.00 | 0.00 |
| ATOM | 820 | CB | MET | 344 | −15.790 | −14.647 | −1.206 | 1.00 | 0.00 |
| ATOM | 821 | HB1 | MET | 344 | −16.748 | −15.119 | −1.050 | 1.00 | 0.00 |
| ATOM | 822 | HB2 | MET | 344 | −15.072 | −13.786 | −0.559 | 1.00 | 0.00 |
| ATOM | 823 | CG | MET | 344 | −14.677 | −15.642 | −0.888 | 1.00 | 0.00 |
| ATOM | 824 | HG1 | MET | 344 | −14.490 | −15.644 | 0.176 | 1.00 | 0.00 |
| ATOM | 825 | HG2 | MET | 344 | −13.777 | −15.354 | −1.411 | 1.00 | 0.00 |
| ATOM | 826 | SD | MET | 344 | −15.179 | −17.297 | −1.417 | 1.00 | 0.00 |
| ATOM | 827 | CE | MET | 344 | −14.288 | −18.220 | −0.144 | 1.00 | 0.00 |
| ATOM | 828 | HE1 | MET | 344 | −13.228 | −18.025 | −0.236 | 1.00 | 0.00 |
| ATOM | 829 | HE2 | MET | 344 | −14.468 | −19.274 | −0.270 | 1.00 | 0.00 |
| ATOM | 830 | HE3 | MET | 344 | −13.634 | −17.909 | 0.834 | 1.00 | 0.00 |
| ATOM | 831 | C | MET | 344 | −16.921 | −13.412 | −3.077 | 1.00 | 0.00 |
| ATOM | 832 | O | MET | 344 | −17.975 | −13.977 | −3.292 | 1.00 | 0.00 |
| ATOM | 833 | N | VAL | 345 | −16.820 | −12.116 | −3.195 | 1.00 | 0.00 |
| ATOM | 834 | HN | VAL | 345 | −15.967 | −11.669 | −3.019 | 1.00 | 0.00 |
| ATOM | 835 | CA | VAL | 345 | −18.019 | −11.318 | −3.599 | 1.00 | 0.00 |
| ATOM | 836 | HA | VAL | 345 | −18.917 | −11.898 | −3.459 | 1.00 | 0.00 |
| ATOM | 837 | CB | VAL | 345 | −18.030 | −10.114 | −2.662 | 1.00 | 0.00 |
| ATOM | 838 | HB | VAL | 345 | −18.779 | −9.408 | −2.992 | 1.00 | 0.00 |
| ATOM | 839 | CG1 | VAL | 345 | −18.359 | −10.578 | −1.241 | 1.00 | 0.00 |
| ATOM | 840 | HG11 | VAL | 345 | −18.281 | −9,.742 | −0.562 | 1.00 | 0.00 |
| ATOM | 841 | HG12 | VAL | 345 | −17.664 | −11.350 | −0.945 | 1.00 | 0.00 |
| ATOM | 842 | HG13 | VAL | 345 | −19.364 | −10.971 | −1.215 | 1.00 | 0.00 |
| ATOM | 843 | CG2 | VAL | 345 | −16.653 | −9.446 | −2.677 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| | | | | | | | | |
|---|---|---|---|---|---|---|---|---|
| ATOM | 844 | HG21 | VAL | 345 | −16.233 | −9.507 | −3.671 | 1.00 | 0.00 |
| ATOM | 845 | HG22 | VAL | 345 | −16.001 | −9.950 | −1.979 | 1.00 | 0.00 |
| ATOM | 846 | HG23 | VAL | 345 | −16.753 | −8.409 | −2.392 | 1.00 | 0.00 |
| ATOM | 847 | C | VAL | 345 | −17.905 | −10.863 | −5.058 | 1.00 | 0.00 |
| ATOM | 848 | O | VAL | 345 | −18.551 | −9.919 | −5.473 | 1.00 | 0.00 |
| ATOM | 849 | N | VAL | 346 | −17.094 | −11.520 | −5.841 | 1.00 | 0.00 |
| ATOM | 850 | HN | VAL | 346 | −16.581 | −12.279 | −5.493 | 1.00 | 0.00 |
| ATOM | 851 | CA | VAL | 346 | −16.952 | −11.113 | −7.269 | 1.00 | 0.00 |
| ATOM | 852 | HA | VAL | 346 | −17.181 | −10.067 | −7.385 | 1.00 | 0.00 |
| ATOM | 853 | CB | VAL | 346 | −15.489 | −11.369 | −7.620 | 1.00 | 0.00 |
| ATOM | 854 | HB | VAL | 346 | −14.855 | −10.946 | −6.855 | 1.00 | 0.00 |
| ATOM | 855 | CG1 | VAL | 346 | −15.240 | −12.874 | −7.713 | 1.00 | 0.00 |
| ATOM | 856 | HG11 | VAL | 346 | −15.664 | −13.253 | −8.632 | 1.00 | 0.00 |
| ATOM | 857 | HG12 | VAL | 346 | −15.704 | −13.368 | −6.873 | 1.00 | 0.00 |
| ATOM | 858 | HG13 | VAL | 346 | −14.177 | −13.065 | −7.701 | 1.00 | 0.00 |
| ATOM | 859 | CG2 | VAL | 346 | −15.172 | −10.716 | −8.968 | 1.00 | 0.00 |
| ATOM | 860 | HG21 | VAL | 346 | −15.009 | −11.483 | −9.710 | 1.00 | 0.00 |
| ATOM | 861 | HG22 | VAL | 346 | −14.282 | −10.111 | −8.875 | 1.00 | 0.00 |
| ATOM | 862 | HG23 | VAL | 346 | −16.001 | −10.094 | −9.271 | 1.00 | 0.00 |
| ATOM | 863 | C | VAL | 346 | −17.875 | −11.961 | −8.146 | 1.00 | 0.00 |
| ATOM | 864 | O | VAL | 346 | −18.300 | −11.542 | −9.204 | 1.00 | 0.00 |
| ATOM | 865 | N | ASN | 347 | −18.189 | −13.151 | −7.712 | 1.00 | 0.00 |
| ATOM | 866 | HN | ASN | 347 | −17.836 | −13.468 | −6.855 | 1.00 | 0.00 |
| ATOM | 867 | CA | ASN | 347 | −19.086 | −14.026 | −8.520 | 1.00 | 0.00 |
| ATOM | 868 | HA | ASN | 347 | −19.101 | −13.705 | −9.548 | 1.00 | 0.00 |
| ATOM | 869 | CB | ASN | 347 | −18.480 | −15.426 | −8.417 | 1.00 | 0.00 |
| ATOM | 870 | HB1 | ASN | 347 | −17.417 | −15.371 | −8.597 | 1.00 | 0.00 |
| ATOM | 871 | HB2 | ASN | 347 | −18.938 | −16.070 | −9.154 | 1.00 | 0.00 |
| ATOM | 872 | CG | ASN | 347 | −18.729 | −15.991 | −7.017 | 1.00 | 0.00 |
| ATOM | 873 | OD1 | ASN | 347 | −19.860 | −16.199 | −6.616 | 1.00 | 0.00 |
| ATOM | 874 | ND2 | ASN | 347 | −17.713 | −16.249 | −6.241 | 1.00 | 0.00 |
| ATOM | 875 | HD21 | ASN | 347 | −16.801 | −16.081 | −6.555 | 1.00 | 0.00 |
| ATOM | 876 | HD22 | ASN | 347 | −17.863 | −16.611 | −5.342 | 1.00 | 0.00 |
| ATOM | 877 | C | ASN | 347 | −20.496 | −14.005 | −7.930 | 1.00 | 0.00 |
| ATOM | 878 | O | ASN | 347 | −21.343 | −14.798 | −8.288 | 1.00 | 0.00 |
| ATOM | 879 | N | ALA | 348 | −20.750 | −13.101 | −7.025 | 1.00 | 0.00 |
| ATOM | 880 | HN | ALA | 348 | −20.048 | −12.473 | −6.752 | 1.00 | 0.00 |
| ATOM | 881 | CA | ALA | 348 | −22.104 | −13.018 | −6.403 | 1.00 | 0.00 |
| ATOM | 882 | HA | ALA | 348 | −22.843 | −13.466 | −7.047 | 1.00 | 0.00 |
| ATOM | 883 | CB | ALA | 348 | −21.993 | −13.810 | −5.101 | 1.00 | 0.00 |
| ATOM | 884 | HB1 | ALA | 348 | −22.717 | −13.438 | −4.390 | 1.00 | 0.00 |
| ATOM | 885 | HB2 | ALA | 348 | −20.998 | −13.697 | −4.694 | 1.00 | 0.00 |
| ATOM | 886 | HB3 | ALA | 348 | −22.185 | −14.854 | −5.297 | 1.00 | 0.00 |
| ATOM | 887 | C | ALA | 348 | −22.457 | −11.555 | −6.118 | 1.00 | 0.00 |
| ATOM | 888 | O | ALA | 348 | −23.270 | −11.254 | −5.264 | 1.00 | 0.00 |
| ATOM | 889 | N | ALA | 349 | −21.849 | −10.645 | −6.828 | 1.00 | 0.00 |
| ATOM | 890 | HN | ALA | 349 | −21.202 | −10.912 | −7.509 | 1.00 | 0.00 |
| ATOM | 891 | CA | ALA | 349 | −22.139 | −9.202 | −6.609 | 1.00 | 0.00 |
| ATOM | 892 | HA | ALA | 349 | −23.082 | −9.082 | −6.111 | 1.00 | 0.00 |
| ATOM | 893 | CB | ALA | 349 | −21.004 | −8.698 | −5.717 | 1.00 | 0.00 |
| ATOM | 894 | HB1 | ALA | 349 | −20.146 | −8.459 | −6.328 | 1.00 | 0.00 |
| ATOM | 895 | HB2 | ALA | 349 | −20.737 | −9.466 | −5.006 | 1.00 | 0.00 |
| ATOM | 896 | HB3 | ALA | 349 | −21.327 | −7.814 | −5.189 | 1.00 | 0.00 |
| ATOM | 897 | C | ALA | 349 | −22.138 | −8.462 | −7.949 | 1.00 | 0.00 |
| ATOM | 898 | O | ALA | 349 | −21.948 | −7.264 | −8.009 | 1.00 | 0.00 |
| ATOM | 899 | N | ARG | 350 | −22.347 | −9.171 | −9.024 | 1.00 | 0.00 |
| ATOM | 900 | HN | ARG | 350 | −22.496 | −10.137 | −8.951 | 1.00 | 0.00 |
| ATOM | 901 | CA | ARG | 350 | −22.359 | −8.516 | −10.363 | 1.00 | 0.00 |
| ATOM | 902 | HA | ARG | 350 | −21.357 | −8.269 | −10.669 | 1.00 | 0.00 |
| ATOM | 903 | CB | ARG | 350 | −22.947 | −9.563 | −11.307 | 1.00 | 0.00 |
| ATOM | 904 | HB1 | ARG | 350 | −23.220 | −9.094 | −12.241 | 1.00 | 0.00 |
| ATOM | 905 | HB2 | ARG | 350 | −23.824 | −10.005 | −10.854 | 1.00 | 0.00 |
| ATOM | 906 | CG | ARG | 350 | −21.905 | −10.651 | −11.571 | 1.00 | 0.00 |
| ATOM | 907 | HG1 | ARG | 350 | −22.294 | −11.357 | −12.288 | 1.00 | 0.00 |
| ATOM | 908 | HG2 | ARG | 350 | −21.677 | −11.163 | −10.646 | 1.00 | 0.00 |
| ATOM | 909 | CD | ARG | 350 | −20.631 | −10.011 | −12.127 | 1.00 | 0.00 |
| ATOM | 910 | HD1 | ARG | 350 | −20.082 | −9.520 | −11.339 | 1.00 | 0.00 |
| ATOM | 911 | HD2 | ARG | 350 | −20.877 | −9.308 | −12.914 | 1.00 | 0.00 |
| ATOM | 912 | NE | ARG | 350 | −19.838 | −11.147 | −12.670 | 1.00 | 0.00 |
| ATOM | 913 | HE | ARG | 350 | −19.308 | −11.709 | −12.067 | 1.00 | 0.00 |
| ATOM | 914 | CZ | ARG | 350 | −19.847 | −11.393 | −13.952 | 1.00 | 0.00 |
| ATOM | 915 | NH1 | ARG | 350 | −19.846 | −12.625 | −14.378 | 1.00 | 0.00 |
| ATOM | 916 | HH11 | ARG | 350 | −19.838 | −13.379 | −13.723 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                     created by user:

| ATOM | 917 | HH12 | ARG | 350 | −19.852 | −12.816 | −15.360 | 1.00 | 0.00 |
|------|-----|------|-----|-----|---------|---------|---------|------|------|
| ATOM | 918 | NH2  | ARG | 350 | −19.857 | −10.406 | −14.807 | 1.00 | 0.00 |
| ATOM | 919 | HH21 | ARG | 350 | −19.857 | −9.460  | −14.481 | 1.00 | 0.00 |
| ATOM | 920 | HH22 | ARG | 350 | −19.862 | −10.596 | −15.788 | 1.00 | 0.00 |
| ATOM | 921 | C    | ARG | 350 | −23.234 | −7.260  | −10.338 | 1.00 | 0.00 |
| ATOM | 922 | O    | ARG | 350 | −22.756 | −6.165  | −10.115 | 1.00 | 0.00 |
| ATOM | 923 | N    | TYR | 351 | −24.511 | −7.406  | −10.562 | 1.00 | 0.00 |
| ATOM | 924 | HN   | TYR | 351 | −24.879 | −8.297  | −10.736 | 1.00 | 0.00 |
| ATOM | 925 | CA   | TYR | 351 | −25.409 | −6.212  | −10.550 | 1.00 | 0.00 |
| ATOM | 926 | HA   | TYR | 351 | −25.303 | −5.669  | −9.627  | 1.00 | 0.00 |
| ATOM | 927 | CB   | TYR | 351 | −24.929 | −5.354  | −11.719 | 1.00 | 0.00 |
| ATOM | 928 | HB1  | TYR | 351 | −25.294 | −5.772  | −12.646 | 1.00 | 0.00 |
| ATOM | 929 | HB2  | TYR | 351 | −23.849 | −5.337  | −11.733 | 1.00 | 0.00 |
| ATOM | 930 | CG   | TYR | 351 | −25.452 | −3.948  | −11.564 | 1.00 | 0.00 |
| ATOM | 931 | CD1  | TYR | 351 | −26.403 | −3.453  | −12.465 | 1.00 | 0.00 |
| ATOM | 932 | HD1  | TYR | 351 | −26.765 | −4.079  | −13.268 | 1.00 | 0.00 |
| ATOM | 933 | CD2  | TYR | 351 | −24.984 | −3.137  | −10.523 | 1.00 | 0.00 |
| ATOM | 934 | HD2  | TYR | 351 | −24.251 | −3.519  | −9.828  | 1.00 | 0.00 |
| ATOM | 935 | CE1  | TYR | 351 | −26.887 | −2.148  | −12.324 | 1.00 | 0.00 |
| ATOM | 936 | HE1  | TYR | 351 | −27.619 | −1.767  | −13.018 | 1.00 | 0.00 |
| ATOM | 937 | CE2  | TYR | 351 | −25.469 | −1.831  | −10.382 | 1.00 | 0.00 |
| ATOM | 938 | HE2  | TYR | 351 | −25.111 | −1.206  | −9.579  | 1.00 | 0.00 |
| ATOM | 939 | CZ   | TYR | 351 | −26.421 | −1.337  | −11.283 | 1.00 | 0.00 |
| ATOM | 940 | OH   | TYR | 351 | −26.899 | −0.051  | −11.144 | 1.00 | 0.00 |
| ATOM | 941 | HH   | TYR | 351 | −26.987 | 0.328   | −12.021 | 1.00 | 0.00 |
| ATOM | 942 | C    | TYR | 351 | −26.867 | −6.637  | −10.761 | 1.00 | 0.00 |
| ATOM | 943 | O    | TYR | 351 | −27.360 | −6.668  | −11.872 | 1.00 | 0.00 |
| ATOM | 944 | N    | GLY | 352 | −27.563 | −6.962  | −9.704  | 1.00 | 0.00 |
| ATOM | 945 | HN   | GLY | 352 | −27.150 | −6.929  | −8.815  | 1.00 | 0.00 |
| ATOM | 946 | CA   | GLY | 352 | −28.985 | −7.383  | −9.850  | 1.00 | 0.00 |
| ATOM | 947 | HA1  | GLY | 352 | −29.185 | −7.621  | −10.883 | 1.00 | 0.00 |
| ATOM | 948 | HA2  | GLY | 352 | −29.633 | −6.576  | −9.534  | 1.00 | 0.00 |
| ATOM | 949 | C    | GLY | 352 | −29.248 | −8.619  | −8.987  | 1.00 | 0.00 |
| ATOM | 950 | O    | GLY | 352 | −28.580 | −8.854  | −8.000  | 1.00 | 0.00 |
| ATOM | 951 | N    | ASN | 353 | −30.218 | −9.414  | −9.354  | 1.00 | 0.00 |
| ATOM | 952 | HN   | ASN | 353 | −30.741 | −9.209  | −10.156 | 1.00 | 0.00 |
| ATOM | 953 | CA   | ASN | 353 | −30.526 | −10.637 | −8.554  | 1.00 | 0.00 |
| ATOM | 954 | HA   | ASN | 353 | −31.092 | −10.379 | −7.676  | 1.00 | 0.00 |
| ATOM | 955 | CB   | ASN | 353 | −31.368 | −11.516 | −9.479  | 1.00 | 0.00 |
| ATOM | 956 | HB1  | ASN | 353 | −30.805 | −11.744 | −10.370 | 1.00 | 0.00 |
| ATOM | 957 | HB2  | ASN | 353 | −32.274 | −10.991 | −9.748  | 1.00 | 0.00 |
| ATOM | 958 | CG   | ASN | 353 | −31.726 | −12.817 | −8.758  | 1.00 | 0.00 |
| ATOM | 959 | OD1  | ASN | 353 | −31.375 | −13.005 | −7.610  | 1.00 | 0.00 |
| ATOM | 960 | ND2  | ASN | 353 | −32.417 | −13.730 | −9.387  | 1.00 | 0.00 |
| ATOM | 961 | HD21 | ASN | 353 | −32.702 | −13.578 | −10.313 | 1.00 | 0.00 |
| ATOM | 962 | HD22 | ASN | 353 | −32.648 | −14.569 | −8.934  | 1.00 | 0.00 |
| ATOM | 963 | C    | ASN | 353 | −29.232 | −11.354 | −8.164  | 1.00 | 0.00 |
| ATOM | 964 | O    | ASN | 353 | −28.686 | −12.127 | −8.927  | 1.00 | 0.00 |
| ATOM | 965 | N    | GLY | 354 | −28.736 | −11.107 | −6.982  | 1.00 | 0.00 |
| ATOM | 966 | HN   | GLY | 354 | −29.190 | −10.482 | −6.380  | 1.00 | 0.00 |
| ATOM | 967 | CA   | GLY | 354 | −27.478 | −11.778 | −6.551  | 1.00 | 0.00 |
| ATOM | 968 | HA1  | GLY | 354 | −26.676 | −11.501 | −7.217  | 1.00 | 0.00 |
| ATOM | 969 | HA2  | GLY | 354 | −27.617 | −12.847 | −6.581  | 1.00 | 0.00 |
| ATOM | 970 | C    | GLY | 354 | −27.120 | −11.352 | −5.126  | 1.00 | 0.00 |
| ATOM | 971 | O    | GLY | 354 | −26.054 | −10.826 | −4.876  | 1.00 | 0.00 |
| ATOM | 972 | N    | TRP | 355 | −28.001 | −11.573 | −4.188  | 1.00 | 0.00 |
| ATOM | 973 | HN   | TRP | 355 | −28.857 | −11.999 | −4.408  | 1.00 | 0.00 |
| ATOM | 974 | CA   | TRP | 355 | −27.706 | −11.179 | −2.777  | 1.00 | 0.00 |
| ATOM | 975 | HA   | TRP | 355 | −27.415 | −10.142 | −2.734  | 1.00 | 0.00 |
| ATOM | 976 | CB   | TRP | 355 | −29.050 | −11.382 | −2.026  | 1.00 | 0.00 |
| ATOM | 977 | HB1  | TRP | 355 | −29.725 | −11.946 | −2.654  | 1.00 | 0.00 |
| ATOM | 978 | HB2  | TRP | 355 | −29.487 | −10.419 | −1.816  | 1.00 | 0.00 |
| ATOM | 979 | CG   | TRP | 355 | −28.842 | −12.119 | −0.734  | 1.00 | 0.00 |
| ATOM | 980 | CD1  | TRP | 355 | −28.475 | −11.550 | 0.437   | 1.00 | 0.00 |
| ATOM | 981 | HD1  | TRP | 355 | −28.286 | −10.498 | 0.592   | 1.00 | 0.00 |
| ATOM | 982 | CD2  | TRP | 355 | −28.983 | −13.543 | −0.471  | 1.00 | 0.00 |
| ATOM | 983 | NE1  | TRP | 355 | −28.382 | −12.538 | 1.402   | 1.00 | 0.00 |
| ATOM | 984 | HE1  | TRP | 355 | −28.132 | −12.392 | 2.338   | 1.00 | 0.00 |
| ATOM | 985 | CE2  | TRP | 355 | −28.686 | −13.783 | 0.889   | 1.00 | 0.00 |
| ATOM | 986 | CE3  | TRP | 355 | −29.338 | −14.640 | −1.276  | 1.00 | 0.00 |
| ATOM | 987 | HE3  | TRP | 355 | −29.571 | −14.487 | −2.320  | 1.00 | 0.00 |
| ATOM | 988 | CZ2  | TRP | 355 | −28.739 | −15.063 | 1.434   | 1.00 | 0.00 |
| ATOM | 989 | HZ2  | TRP | 355 | −28.507 | −15.219 | 2.476   | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                     created by user:

| | | | | | | | | |
|---|---|---|---|---|---|---|---|---|
| ATOM | 990 | CZ3 | TRP | 355 | −29.392 | −15.934 | −0.730 | 1.00 | 0.00 |
| ATOM | 991 | HZ3 | TRP | 355 | −29.665 | −16.771 | −1.355 | 1.00 | 0.00 |
| ATOM | 992 | CH2 | TRP | 355 | −29.092 | −16.143 | 0.624 | 1.00 | 0.00 |
| ATOM | 993 | HH2 | TRP | 355 | −29.135 | −17.137 | 1.038 | 1.00 | 0.00 |
| ATOM | 994 | C | TRP | 355 | −26.577 | −12.072 | −2.217 | 1.00 | 0.00 |
| ATOM | 995 | O | TRP | 355 | −26.290 | −13.129 | −2.753 | 1.00 | 0.00 |
| ATOM | 996 | N | ILE | 356 | −25.942 | −11.657 | −1.143 | 1.00 | 0.00 |
| ATOM | 997 | HN | ILE | 356 | −26.184 | −10.807 | −0.724 | 1.00 | 0.00 |
| ATOM | 998 | CA | ILE | 356 | −24.843 | −12.483 | −0.564 | 1.00 | 0.00 |
| ATOM | 999 | HA | ILE | 356 | −24.765 | −13.426 | −1.083 | 1.00 | 0.00 |
| ATOM | 1000 | CB | ILE | 356 | −23.576 | −11.665 | −0.780 | 1.00 | 0.00 |
| ATOM | 1001 | HB | ILE | 356 | −23.513 | −10.901 | −0.023 | 1.00 | 0.00 |
| ATOM | 1002 | CG1 | ILE | 356 | −23.603 | −11.015 | −2.170 | 1.00 | 0.00 |
| ATOM | 1003 | HG11 | ILE | 356 | −24.501 | −10.427 | −2.274 | 1.00 | 0.00 |
| ATOM | 1004 | HG12 | ILE | 356 | −23.587 | −11.786 | −2.927 | 1.00 | 0.00 |
| ATOM | 1005 | CG2 | ILE | 356 | −22.368 | −12.579 | −0.676 | 1.00 | 0.00 |
| ATOM | 1006 | HG21 | ILE | 356 | −21.482 | −12.036 | −0.965 | 1.00 | 0.00 |
| ATOM | 1007 | HG22 | ILE | 356 | −22.504 | −13.425 | −1.332 | 1.00 | 0.00 |
| ATOM | 1008 | HG23 | ILE | 356 | −22.266 | −12.922 | 0.341 | 1.00 | 0.00 |
| ATOM | 1009 | CD1 | ILE | 356 | −22.380 | −10.110 | −2.336 | 1.00 | 0.00 |
| ATOM | 1010 | HD11 | ILE | 356 | −21.878 | −10.005 | −1.386 | 1.00 | 0.00 |
| ATOM | 1011 | HD12 | ILE | 356 | −22.697 | −9.139 | −2.686 | 1.00 | 0.00 |
| ATOM | 1012 | HD13 | ILE | 356 | −21.703 | −10.548 | −3.055 | 1.00 | 0.00 |
| ATOM | 1013 | C | ILE | 356 | −25.070 | −12.721 | 0.931 | 1.00 | 0.00 |
| ATOM | 1014 | O | ILE | 356 | −25.722 | −11.950 | 1.613 | 1.00 | 0.00 |
| ATOM | 1015 | N | LYS | 357 | −24.509 | −13.771 | 1.448 | 1.00 | 0.00 |
| ATOM | 1016 | HN | LYS | 357 | −23.958 | −14.352 | 0.889 | 1.00 | 0.00 |
| ATOM | 1017 | CA | LYS | 357 | −24.680 | −14.076 | 2.891 | 1.00 | 0.00 |
| ATOM | 1018 | HA | LYS | 357 | −25.026 | −13.208 | 3.423 | 1.00 | 0.00 |
| ATOM | 1019 | CB | LYS | 357 | −25.742 | −15.175 | 2.935 | 1.00 | 0.00 |
| ATOM | 1020 | HB1 | LYS | 357 | −25.390 | −16.037 | 2.390 | 1.00 | 0.00 |
| ATOM | 1021 | HB2 | LYS | 357 | −26.657 | −14.812 | 2.485 | 1.00 | 0.00 |
| ATOM | 1022 | CG | LYS | 357 | −26.007 | −15.568 | 4.389 | 1.00 | 0.00 |
| ATOM | 1023 | HG1 | LYS | 357 | −26.593 | −14.800 | 4.866 | 1.00 | 0.00 |
| ATOM | 1024 | HG2 | LYS | 357 | −25.006 | −15.679 | 4.909 | 1.00 | 0.00 |
| ATOM | 1025 | CD | LYS | 357 | −26.774 | −16.892 | 4.431 | 1.00 | 0.00 |
| ATOM | 1026 | HD1 | LYS | 357 | −26.078 | −17.716 | 4.370 | 1.00 | 0.00 |
| ATOM | 1027 | HD2 | LYS | 357 | −27.460 | −16.937 | 3.599 | 1.00 | 0.00 |
| ATOM | 1028 | CE | LYS | 357 | −27.556 | −16.987 | 5.744 | 1.00 | 0.00 |
| ATOM | 1029 | HE1 | LYS | 357 | −27.168 | −16.286 | 6.464 | 1.00 | 0.00 |
| ATOM | 1030 | HE2 | LYS | 357 | −27.514 | −17.995 | 6.134 | 1.00 | 0.00 |
| ATOM | 1031 | NZ | LYS | 357 | −28.955 | −16.627 | 5.385 | 1.00 | 0.00 |
| ATOM | 1032 | HZ1 | LYS | 357 | −29.611 | −17.087 | 6.045 | 1.00 | 0.00 |
| ATOM | 1033 | HZ2 | LYS | 357 | −29.156 | −16.947 | 4.415 | 1.00 | 0.00 |
| ATOM | 1034 | HZ3 | LYS | 357 | −29.074 | −15.597 | 5.441 | 1.00 | 0.00 |
| ATOM | 1035 | C | LYS | 357 | −23.369 | −14.587 | 3.484 | 1.00 | 0.00 |
| ATOM | 1036 | O | LYS | 357 | −22.928 | −15.678 | 3.185 | 1.00 | 0.00 |
| ATOM | 1037 | N | VAL | 358 | −22.738 | −13.814 | 4.318 | 1.00 | 0.00 |
| ATOM | 1038 | HN | VAL | 358 | −23.101 | −12.933 | 4.546 | 1.00 | 0.00 |
| ATOM | 1039 | CA | VAL | 358 | −21.460 | −14.275 | 4.919 | 1.00 | 0.00 |
| ATOM | 1040 | HA | VAL | 358 | −20.923 | −14.895 | 4.228 | 1.00 | 0.00 |
| ATOM | 1041 | CB | VAL | 358 | −20.670 | −13.008 | 5.208 | 1.00 | 0.00 |
| ATOM | 1042 | HB | VAL | 358 | −21.330 | −12.258 | 5.601 | 1.00 | 0.00 |
| ATOM | 1043 | CG1 | VAL | 358 | −19.566 | −13.307 | 6.232 | 1.00 | 0.00 |
| ATOM | 1044 | HG11 | VAL | 358 | −19.810 | −12.835 | 7.172 | 1.00 | 0.00 |
| ATOM | 1045 | HG12 | VAL | 358 | −18.625 | −12.921 | 5.869 | 1.00 | 0.00 |
| ATOM | 1046 | HG13 | VAL | 358 | −19.486 | −14.375 | 6.375 | 1.00 | 0.00 |
| ATOM | 1047 | CG2 | VAL | 358 | −20.039 | −12.509 | 3.911 | 1.00 | 0.00 |
| ATOM | 1048 | HG21 | VAL | 358 | −20.650 | −12.816 | 3.074 | 1.00 | 0.00 |
| ATOM | 1049 | HG22 | VAL | 358 | −19.050 | −12.931 | 3.808 | 1.00 | 0.00 |
| ATOM | 1050 | HG23 | VAL | 358 | −19.972 | −11.434 | 3.934 | 1.00 | 0.00 |
| ATOM | 1051 | C | VAL | 358 | −21.760 | −15.035 | 6.198 | 1.00 | 0.00 |
| ATOM | 1052 | O | VAL | 358 | −21.768 | −14.482 | 7.278 | 1.00 | 0.00 |
| ATOM | 1053 | N | SER | 359 | −22.010 | −16.303 | 6.084 | 1.00 | 0.00 |
| ATOM | 1054 | HN | SER | 359 | −21.990 | −16.729 | 5.199 | 1.00 | 0.00 |
| ATOM | 1055 | CA | SER | 359 | −22.313 | −17.109 | 7.291 | 1.00 | 0.00 |
| ATOM | 1056 | HA | SER | 359 | −22.543 | −16.467 | 8.123 | 1.00 | 0.00 |
| ATOM | 1057 | CB | SER | 359 | −23.541 | −17.936 | 6.918 | 1.00 | 0.00 |
| ATOM | 1058 | HB1 | SER | 359 | −23.238 | −18.760 | 6.281 | 1.00 | 0.00 |
| ATOM | 1059 | HB2 | SER | 359 | −24.247 | −17.320 | 6.392 | 1.00 | 0.00 |
| ATOM | 1060 | OG | SER | 359 | −24.147 | −18.436 | 8.104 | 1.00 | 0.00 |
| ATOM | 1061 | HG | SER | 359 | −23.690 | −19.244 | 8.352 | 1.00 | 0.00 |
| ATOM | 1062 | C | SER | 359 | −21.140 | −18.019 | 7.626 | 1.00 | 0.00 |

TABLE 2-continued

Coordinates determined by NMR for sub-domain B [EnvZ(C)(290–450), SEQ ID NO: 14]; a representative structure.

REMARK final envZ structures  
REMARK DATE:18-Feb-98 13:12:56                                created by user:

| ATOM | 1063 | O    | SER | 359 | −20.554 | −18.631 | 6.764  | 1.00 | 0.00 |
|------|------|------|-----|-----|---------|---------|--------|------|------|
| ATOM | 1064 | N    | SER | 360 | −20.793 | −18.102 | 8.871  | 1.00 | 0.00 |
| ATOM | 1065 | HN   | SER | 360 | −21.273 | −17.597 | 9.536  | 1.00 | 0.00 |
| ATOM | 1066 | CA   | SER | 360 | −19.662 | −18.968 | 9.279  | 1.00 | 0.00 |
| ATOM | 1067 | HA   | SER | 360 | −19.308 | −19.539 | 8.441  | 1.00 | 0.00 |
| ATOM | 1068 | CB   | SER | 360 | −18.575 | −18.013 | 9.759  | 1.00 | 0.00 |
| ATOM | 1069 | HB1  | SER | 360 | −18.851 | −17.612 | 10.727 | 1.00 | 0.00 |
| ATOM | 1070 | HB2  | SER | 360 | −18.466 | −17.207 | 9.058  | 1.00 | 0.00 |
| ATOM | 1071 | OG   | SER | 360 | −17.344 | −18.719 | 9.859  | 1.00 | 0.00 |
| ATOM | 1072 | HG   | SER | 360 | −17.296 | −19.108 | 10.737 | 1.00 | 0.00 |
| ATOM | 1073 | C    | SER | 360 | −20.104 | −19.894 | 10.412 | 1.00 | 0.00 |
| ATOM | 1074 | O    | SER | 360 | −21.109 | −19.666 | 11.062 | 1.00 | 0.00 |
| ATOM | 1075 | N    | GLY | 361 | −19.359 | −20.925 | 10.661 | 1.00 | 0.00 |
| ATOM | 1076 | HN   | GLY | 361 | −18.542 | −21.071 | 10.142 | 1.00 | 0.00 |
| ATOM | 1077 | CA   | GLY | 361 | −19.726 | −21.872 | 11.750 | 1.00 | 0.00 |
| ATOM | 1078 | HA1  | GLY | 361 | −20.554 | −22.486 | 11.432 | 1.00 | 0.00 |
| ATOM | 1079 | HA2  | GLY | 361 | −20.005 | −21.315 | 12.635 | 1.00 | 0.00 |
| ATOM | 1080 | C    | GLY | 361 | −18.526 | −22.759 | 12.059 | 1.00 | 0.00 |
| ATOM | 1081 | O    | GLY | 361 | −17.400 | −22.395 | 11.795 | 1.00 | 0.00 |
| ATOM | 1082 | N    | THR | 362 | −18.747 | −23.930 | 12.602 | 1.00 | 0.00 |
| ATOM | 1083 | HN   | THR | 362 | −19.663 | −24.225 | 12.790 | 1.00 | 0.00 |
| ATOM | 1084 | CA   | THR | 362 | −17.593 | −24.817 | 12.916 | 1.00 | 0.00 |
| ATOM | 1085 | HA   | THR | 362 | −17.059 | −25.066 | 12.018 | 1.00 | 0.00 |
| ATOM | 1086 | CB   | THR | 362 | −16.669 | −23.988 | 13.841 | 1.00 | 0.00 |
| ATOM | 1087 | HB   | THR | 362 | −16.202 | −23.220 | 13.276 | 1.00 | 0.00 |
| ATOM | 1088 | OG1  | THR | 362 | −15.729 | −24.833 | 14.443 | 1.00 | 0.00 |
| ATOM | 1089 | HG1  | THR | 362 | −15.573 | −24.518 | 15.337 | 1.00 | 0.00 |
| ATOM | 1090 | CG2  | THR | 362 | −17.557 | −23.342 | 14.927 | 1.00 | 0.00 |
| ATOM | 1091 | HG21 | THR | 362 | −17.825 | −22.340 | 14.626 | 1.00 | 0.00 |
| ATOM | 1092 | HG22 | THR | 362 | −16.998 | −23.303 | 15.851 | 1.00 | 0.00 |
| ATOM | 1093 | HG23 | THR | 362 | −18.453 | −23.926 | 15.074 | 1.00 | 0.00 |
| ATOM | 1094 | C    | THR | 362 | −18.051 | −26.083 | 13.637 | 1.00 | 0.00 |
| ATOM | 1095 | O    | THR | 362 | −19.220 | −26.283 | 13.900 | 1.00 | 0.00 |
| ATOM | 1096 | N    | GLU | 363 | −17.122 | −26.933 | 13.960 | 1.00 | 0.00 |
| ATOM | 1097 | HN   | GLU | 363 | −16.191 | −26.732 | 13.744 | 1.00 | 0.00 |
| ATOM | 1098 | CA   | GLU | 363 | −17.456 | −28.197 | 14.666 | 1.00 | 0.00 |
| ATOM | 1099 | HA   | GLU | 363 | −18.438 | −28.140 | 15.107 | 1.00 | 0.00 |
| ATOM | 1100 | CB   | GLU | 363 | −17.419 | −29.280 | 13.586 | 1.00 | 0.00 |
| ATOM | 1101 | HB1  | GLU | 363 | −16.745 | −30.067 | 13.887 | 1.00 | 0.00 |
| ATOM | 1102 | HB2  | GLU | 363 | −17.078 | −28.849 | 12.655 | 1.00 | 0.00 |
| ATOM | 1103 | CG   | GLU | 363 | −18.824 | −29.860 | 13.395 | 1.00 | 0.00 |
| ATOM | 1104 | HG1  | GLU | 363 | −19.380 | −29.237 | 12.711 | 1.00 | 0.00 |
| ATOM | 1105 | HG2  | GLU | 363 | −19.332 | −29.892 | 14.349 | 1.00 | 0.00 |
| ATOM | 1106 | CD   | GLU | 363 | −18.719 | −31.275 | 12.822 | 1.00 | 0.00 |
| ATOM | 1107 | OE1  | GLU | 363 | −19.088 | −32.205 | 13.522 | 1.00 | 0.00 |
| ATOM | 1108 | OE2  | GLU | 363 | −18.271 | −31.406 | 11.695 | 1.00 | 0.00 |
| ATOM | 1109 | C    | GLU | 363 | −16.394 | −28.452 | 15.738 | 1.00 | 0.00 |
| ATOM | 1110 | O    | GLU | 363 | −15.441 | −27.708 | 15.845 | 1.00 | 0.00 |
| ATOM | 1111 | N    | PRO | 364 | −16.585 | −29.488 | 16.500 | 1.00 | 0.00 |
| ATOM | 1112 | CA   | PRO | 364 | −15.619 | −29.813 | 17.560 | 1.00 | 0.00 |
| ATOM | 1113 | HA   | PRO | 364 | −15.275 | −28.923 | 18.011 | 1.00 | 0.00 |
| ATOM | 1114 | CB   | PRO | 364 | −16.428 | −20.637 | 18.545 | 1.00 | 0.00 |
| ATOM | 1115 | HB1  | PRO | 364 | −16.828 | −30.007 | 19.322 | 1.00 | 0.00 |
| ATOM | 1116 | HB2  | PRO | 364 | −15.812 | −31.418 | 18.973 | 1.00 | 0.00 |
| ATOM | 1117 | CG   | PRO | 364 | −17.556 | −31.237 | 17.736 | 1.00 | 0.00 |
| ATOM | 1118 | HG1  | PRO | 364 | −18.473 | −31.196 | 18.302 | 1.00 | 0.00 |
| ATOM | 1119 | HG2  | PRO | 364 | −17.323 | −32.264 | 17.488 | 1.00 | 0.00 |
| ATOM | 1120 | CD   | PRO | 364 | −17.707 | −30.418 | 16.464 | 1.00 | 0.00 |
| ATOM | 1121 | HD1  | PRO | 364 | −18.640 | −29.876 | 16.470 | 1.00 | 0.00 |
| ATOM | 1122 | HD2  | PRO | 364 | −17.644 | −31.057 | 15.593 | 1.00 | 0.00 |
| ATOM | 1123 | C    | PRO | 364 | −14.434 | −30.594 | 17.015 | 1.00 | 0.00 |
| ATOM | 1124 | O    | PRO | 364 | −13.622 | −31.120 | 17.751 | 1.00 | 0.00 |
| ATOM | 1125 | N    | ASN | 365 | −14.331 | −30.662 | 15.751 | 1.00 | 0.00 |
| ATOM | 1126 | HN   | ASN | 365 | −15.000 | −30.229 | 15.193 | 1.00 | 0.00 |
| ATOM | 1127 | CA   | ASN | 365 | −13.211 | −31.395 | 15.126 | 1.00 | 0.00 |
| ATOM | 1128 | HA   | ASN | 365 | −12.328 | −31.318 | 15.729 | 1.00 | 0.00 |
| ATOM | 1129 | CB   | ASN | 365 | −13.670 | −32.848 | 15.030 | 1.00 | 0.00 |
| ATOM | 1130 | HB1  | ASN | 365 | −13.145 | −33.339 | 14.226 | 1.00 | 0.00 |
| ATOM | 1131 | HB2  | ASN | 365 | −14.733 | −32.877 | 14.838 | 1.00 | 0.00 |
| ATOM | 1132 | CG   | ASN | 365 | −13.368 | −33.566 | 16.348 | 1.00 | 0.00 |
| ATOM | 1133 | OD1  | ASN | 365 | −14.142 | −33.496 | 17.281 | 1.00 | 0.00 |
| ATOM | 1134 | ND2  | ASN | 365 | −12.264 | −34.256 | 16.464 | 1.00 | 0.00 |
| ATOM | 1135 | HD21 | ASN | 365 | −11.637 | −34.308 | 15.713 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56          created by user:

| ATOM | 1136 | HD22 | ASN | 365 | −12.065 | −34.724 | 17.302 | 1.00 | 0.00 |
|------|------|------|-----|-----|---------|---------|--------|------|------|
| ATOM | 1137 | C    | ASN | 365 | −12.971 | −30.807 | 13.756 | 1.00 | 0.00 |
| ATOM | 1138 | O    | ASN | 365 | −12.397 | −31.429 | 12.885 | 1.00 | 0.00 |
| ATOM | 1139 | N    | ARG | 366 | −13.408 | −29.590 | 13.561 | 1.00 | 0.00 |
| ATOM | 1140 | HN   | ARG | 366 | −13.853 | −29.099 | 14.310 | 1.00 | 0.00 |
| ATOM | 1141 | CA   | ARG | 366 | −13.214 | −28.926 | 12.227 | 1.00 | 0.00 |
| ATOM | 1142 | HA   | ARG | 366 | −12.178 | −28.678 | 12.074 | 1.00 | 0.00 |
| ATOM | 1143 | CB   | ARG | 366 | −13.663 | −29.962 | 11.190 | 1.00 | 0.00 |
| ATOM | 1144 | HB1  | ARG | 366 | −14.456 | −29.545 | 10.588 | 1.00 | 0.00 |
| ATOM | 1145 | HB2  | ARG | 366 | −14.024 | −30.846 | 11.692 | 1.00 | 0.00 |
| ATOM | 1146 | CG   | ARG | 366 | −12.490 | −30.331 | 10.287 | 1.00 | 0.00 |
| ATOM | 1147 | HG1  | ARG | 366 | −11.912 | −31.115 | 10.750 | 1.00 | 0.00 |
| ATOM | 1148 | HG2  | ARG | 366 | −11.865 | −29.462 | 10.135 | 1.00 | 0.00 |
| ATOM | 1149 | CD   | ARG | 366 | −13.023 | −30.821 | 8.938  | 1.00 | 0.00 |
| ATOM | 1150 | HD1  | ARG | 366 | −12.379 | −30.498 | 8.137  | 1.00 | 0.00 |
| ATOM | 1151 | HD2  | ARG | 366 | −14.033 | −30.460 | 8.781  | 1.00 | 0.00 |
| ATOM | 1152 | NE   | ARG | 366 | −13.010 | −32.306 | 9.037  | 1.00 | 0.00 |
| ATOM | 1153 | HE   | ARG | 366 | −12.331 | −32.823 | 8.554  | 1.00 | 0.00 |
| ATOM | 1154 | CZ   | ARG | 366 | −13.901 | −32.918 | 9.766  | 1.00 | 0.00 |
| ATOM | 1155 | NH1  | ARG | 366 | −15.172 | −32.755 | 9.518  | 1.00 | 0.00 |
| ATOM | 1156 | HH11 | ARG | 366 | −15.463 | −32.162 | 8.767  | 1.00 | 0.00 |
| ATOM | 1157 | HH12 | ARG | 366 | −15.856 | −33.223 | 10.079 | 1.00 | 0.00 |
| ATOM | 1158 | NH2  | ARG | 366 | −13.520 | −33.696 | 10.743 | 1.00 | 0.00 |
| ATOM | 1159 | HH21 | ARG | 366 | −12.547 | −33.823 | 10.931 | 1.00 | 0.00 |
| ATOM | 1160 | HH22 | ARG | 366 | −14.203 | −34.165 | 11.303 | 1.00 | 0.00 |
| ATOM | 1161 | C    | ARG | 366 | −14.091 | −27.677 | 12.108 | 1.00 | 0.00 |
| ATOM | 1162 | O    | ARG | 366 | −15.299 | −27.751 | 12.184 | 1.00 | 0.00 |
| ATOM | 1163 | N    | ALA | 367 | −13.495 | −26.532 | 11.908 | 1.00 | 0.00 |
| ATOM | 1164 | HN   | ALA | 367 | −12.508 | −26.495 | 11.825 | 1.00 | 0.00 |
| ATOM | 1165 | CA   | ALA | 367 | −14.316 | −25.277 | 11.782 | 1.00 | 0.00 |
| ATOM | 1166 | HA   | ALA | 367 | −15.270 | −25.400 | 12.262 | 1.00 | 0.00 |
| ATOM | 1167 | CB   | ALA | 367 | −13.507 | −24.182 | 12.477 | 1.00 | 0.00 |
| ATOM | 1168 | HB1  | ALA | 367 | −13.297 | −24.478 | 13.494 | 1.00 | 0.00 |
| ATOM | 1169 | HB2  | ALA | 367 | −14.075 | −23.262 | 12.480 | 1.00 | 0.00 |
| ATOM | 1170 | HB3  | ALA | 367 | −12.579 | −24.030 | 11.946 | 1.00 | 0.00 |
| ATOM | 1171 | C    | ALA | 367 | −14.494 | −24.953 | 10.300 | 1.00 | 0.00 |
| ATOM | 1172 | O    | ALA | 367 | −13.830 | −25.516 | 9.474  | 1.00 | 0.00 |
| ATOM | 1173 | N    | TRP | 368 | −15.391 | −24.071 | 9.939  | 1.00 | 0.00 |
| ATOM | 1174 | HN   | TRP | 368 | −15.952 | −23.613 | 10.609 | 1.00 | 0.00 |
| ATOM | 1175 | CA   | TRP | 368 | −15.548 | −23.769 | 8.842  | 1.00 | 0.00 |
| ATOM | 1176 | HA   | TRP | 368 | −14.585 | −23.576 | 8.040  | 1.00 | 0.00 |
| ATOM | 1177 | CB   | TRP | 368 | −16.146 | −25.040 | 7.871  | 1.00 | 0.00 |
| ATOM | 1178 | HB1  | TRP | 368 | −15.464 | −25.865 | 8.023  | 1.00 | 0.00 |
| ATOM | 1179 | HB2  | TRP | 368 | −16.299 | −24.893 | 6.811  | 1.00 | 0.00 |
| ATOM | 1180 | CG   | TRP | 368 | −17.456 | −25.348 | 8.527  | 1.00 | 0.00 |
| ATOM | 1181 | CD1  | TRP | 368 | −17.663 | −26.343 | 9.421  | 1.00 | 0.00 |
| ATOM | 1182 | HD1  | TRP | 368 | −16.915 | −27.039 | 9.770  | 1.00 | 0.00 |
| ATOM | 1183 | CD2  | TRP | 368 | −18.740 | −24.680 | 8.357  | 1.00 | 0.00 |
| ATOM | 1184 | NE1  | TRP | 368 | −18.989 | −26.317 | 9.819  | 1.00 | 0.00 |
| ATOM | 1185 | HE1  | TRP | 368 | −19.398 | −26.927 | 10.468 | 1.00 | 0.00 |
| ATOM | 1186 | CE2  | TRP | 368 | −19.692 | −25.313 | 9.188  | 1.00 | 0.00 |
| ATOM | 1187 | CE3  | TRP | 368 | −19.166 | −23.593 | 7.571  | 1.00 | 0.00 |
| ATOM | 1188 | HE3  | TRP | 368 | −18.463 | −23.088 | 6.925  | 1.00 | 0.00 |
| ATOM | 1189 | CZ2  | TRP | 368 | −21.015 | −24.888 | 9.241  | 1.00 | 0.00 |
| ATOM | 1190 | HZ2  | TRP | 368 | −21.721 | −25.390 | 9.886  | 1.00 | 0.00 |
| ATOM | 1191 | CZ3  | TRP | 368 | −20.504 | −23.161 | 7.623  | 1.00 | 0.00 |
| ATOM | 1192 | HZ3  | TRP | 368 | −20.823 | −22.327 | 7.017  | 1.00 | 0.00 |
| ATOM | 1193 | CH2  | TRP | 368 | −21.425 | −23.810 | 8.458  | 1.00 | 0.00 |
| ATOM | 1194 | HH2  | TRP | 368 | −22.451 | −23.475 | 8.494  | 1.00 | 0.00 |
| ATOM | 1195 | C    | TRP | 368 | −16.472 | −22.575 | 8.256  | 1.00 | 0.00 |
| ATOM | 1196 | O    | TRP | 368 | −17.414 | −22.368 | 8.984  | 1.00 | 0.00 |
| ATOM | 1197 | N    | PHE | 369 | −16.196 | −21.797 | 7.245  | 1.00 | 0.00 |
| ATOM | 1198 | HN   | PHE | 369 | −15.423 | −21.994 | 6.680  | 1.00 | 0.00 |
| ATOM | 1199 | CA   | PHE | 369 | −17.045 | −20.611 | 6.948  | 1.00 | 0.00 |
| ATOM | 1200 | HA   | PHE | 369 | −17.856 | −20.542 | 7.654  | 1.00 | 0.00 |
| ATOM | 1201 | CB   | PHE | 369 | −16.109 | −19.404 | 7.099  | 1.00 | 0.00 |
| ATOM | 1202 | HB1  | PHE | 369 | −15.506 | −19.525 | 7.987  | 1.00 | 0.00 |
| ATOM | 1203 | HB2  | PHE | 369 | −16.696 | −18.501 | 7.183  | 1.00 | 0.00 |
| ATOM | 1204 | CG   | PHE | 369 | −15.208 | −19.303 | 5.893  | 1.00 | 0.00 |
| ATOM | 1205 | CD1  | PHE | 369 | −15.691 | −18.738 | 4.709  | 1.00 | 0.00 |
| ATOM | 1206 | HD1  | PHE | 369 | −16.708 | −18.379 | 4.658  | 1.00 | 0.00 |
| ATOM | 1207 | CD2  | PHE | 369 | −13.889 | −19.768 | 5.962  | 1.00 | 0.00 |
| ATOM | 1208 | HD2  | PHE | 369 | −13.517 | −20.205 | 6.877  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 1209 | CE1  | PHE | 369 | −14.857 | −18.639 | 3.590  | 1.00 | 0.00 |
|------|------|------|-----|-----|---------|---------|--------|------|------|
| ATOM | 1210 | HE1  | PHE | 369 | −15.231 | −18.202 | 2.675  | 1.00 | 0.00 |
| ATOM | 1211 | CE2  | PHE | 369 | −13.054 | −19.670 | 4.843  | 1.00 | 0.00 |
| ATOM | 1212 | HE2  | PHE | 369 | −12.038 | −20.030 | 4.894  | 1.00 | 0.00 |
| ATOM | 1213 | CZ   | PHE | 369 | −13.538 | −19.105 | 3.656  | 1.00 | 0.00 |
| ATOM | 1214 | HZ   | PHE | 369 | −12.894 | −19.027 | 2.792  | 1.00 | 0.00 |
| ATOM | 1215 | C    | PHE | 369 | −17.585 | −20.720 | 5.511  | 1.00 | 0.00 |
| ATOM | 1216 | O    | PHE | 369 | −16.863 | −21.054 | 4.591  | 1.00 | 0.00 |
| ATOM | 1217 | N    | GLN | 370 | −18.844 | −20.450 | 5.314  | 1.00 | 0.00 |
| ATOM | 1218 | HN   | GLN | 370 | −19.411 | −20.196 | 6.062  | 1.00 | 0.00 |
| ATOM | 1219 | CA   | GLN | 370 | −19.416 | −20.543 | 3.938  | 1.00 | 0.00 |
| ATOM | 1220 | HA   | GLN | 370 | −18.636 | −20.721 | 3.220  | 1.00 | 0.00 |
| ATOM | 1221 | CB   | GLN | 370 | −20.352 | −21.754 | 3.998  | 1.00 | 0.00 |
| ATOM | 1222 | HB1  | GLN | 370 | −21.030 | −21.642 | 4.831  | 1.00 | 0.00 |
| ATOM | 1223 | HB2  | GLN | 370 | −19.768 | −22.653 | 4.128  | 1.00 | 0.00 |
| ATOM | 1224 | CG   | GLN | 370 | −21.158 | −21.854 | 2.700  | 1.00 | 0.00 |
| ATOM | 1225 | HG1  | GLN | 370 | −20.612 | −22.443 | 1.983  | 1.00 | 0.00 |
| ATOM | 1226 | HG2  | GLN | 370 | −21.326 | −20.866 | 2.300  | 1.00 | 0.00 |
| ATOM | 1227 | CD   | GLN | 370 | −22.505 | −22.523 | 2.986  | 1.00 | 0.00 |
| ATOM | 1228 | OE1  | GLN | 370 | −22.586 | −23.432 | 3.788  | 1.00 | 0.00 |
| ATOM | 1229 | NE2  | GLN | 370 | −23.574 | −22.108 | 2.360  | 1.00 | 0.00 |
| ATOM | 1230 | HE21 | GLN | 370 | −23.510 | −21.373 | 1.714  | 1.00 | 0.00 |
| ATOM | 1231 | HE22 | GLN | 370 | −24.440 | −22.533 | 2.534  | 1.00 | 0.00 |
| ATOM | 1232 | C    | GLN | 370 | −20.203 | −19.272 | 3.574  | 1.00 | 0.00 |
| ATOM | 1233 | O    | GLN | 370 | −20.744 | −18.591 | 4.427  | 1.00 | 0.00 |
| ATOM | 1234 | N    | VAL | 371 | −20.260 | −18.950 | 2.303  | 1.00 | 0.00 |
| ATOM | 1235 | HN   | VAL | 371 | −19.807 | −19.514 | 1.638  | 1.00 | 0.00 |
| ATOM | 1236 | CA   | VAL | 371 | −21.006 | −17.731 | 1.860  | 1.00 | 0.00 |
| ATOM | 1237 | HA   | VAL | 371 | −21.442 | −17.215 | 2.703  | 1.00 | 0.00 |
| ATOM | 1238 | CB   | VAL | 371 | −19.967 | −16.856 | 1.170  | 1.00 | 0.00 |
| ATOM | 1239 | HB   | VAL | 371 | −19.710 | −17.291 | 0.222  | 1.00 | 0.00 |
| ATOM | 1240 | CG1  | VAL | 371 | −20.542 | −15.453 | 0.949  | 1.00 | 0.00 |
| ATOM | 1241 | HG11 | VAL | 371 | −21.232 | −15.473 | 0.118  | 1.00 | 0.00 |
| ATOM | 1242 | HG12 | VAL | 371 | −19.738 | −14.765 | 0.731  | 1.00 | 0.00 |
| ATOM | 1243 | HG13 | VAL | 371 | −21.060 | −15.130 | 1.840  | 1.00 | 0.00 |
| ATOM | 1244 | CG2  | VAL | 371 | −18.719 | −16.763 | 2.049  | 1.00 | 0.00 |
| ATOM | 1245 | HG21 | VAL | 371 | −18.330 | −17.755 | 2.226  | 1.00 | 0.00 |
| ATOM | 1246 | CG2  | VAL | 371 | −18.977 | −16.305 | 2.992  | 1.00 | 0.00 |
| ATOM | 1247 | HG23 | V1L | 371 | −17.970 | −16.165 | 1.550  | 1.00 | 0.00 |
| ATOM | 1248 | C    | VAL | 371 | −22.112 | −18.135 | 0.875  | 1.00 | 0.00 |
| ATOM | 1249 | O    | VAL | 371 | −21.854 | −18.744 | −0.145 | 1.00 | 0.00 |
| ATOM | 1250 | N    | GLU | 372 | −23.339 | −17.796 | 1.168  | 1.00 | 0.00 |
| ATOM | 1251 | HN   | GLU | 372 | −23.525 | −17.289 | 1.984  | 1.00 | 0.00 |
| ATOM | 1252 | CA   | GLU | 372 | −24.459 | −18.164 | 0.248  | 1.00 | 0.00 |
| ATOM | 1253 | HA   | GLU | 372 | −24.200 | −19.034 | −0.331 | 1.00 | 0.00 |
| ATOM | 1254 | CB   | GLU | 372 | −25.635 | −18.481 | 1.170  | 1.00 | 0.00 |
| ATOM | 1255 | HB1  | GLU | 372 | −26.497 | −17.910 | 0.864  | 1.00 | 0.00 |
| ATOM | 1256 | HB2  | GLU | 372 | −25.374 | −18.223 | 2.187  | 1.00 | 0.00 |
| ATOM | 1257 | CG   | GLU | 372 | −25.960 | −19.972 | 1.089  | 1.00 | 0.00 |
| ATOM | 1258 | HG1  | GLU | 372 | −25.183 | −20.538 | 1.581  | 1.00 | 0.00 |
| ATOM | 1259 | HG2  | GLU | 372 | −26.023 | −20.270 | 0.052  | 1.00 | 0.00 |
| ATOM | 1260 | CD   | GLU | 372 | −27.297 | −20.241 | 1.780  | 1.00 | 0.00 |
| ATOM | 1261 | OE1  | GLU | 372 | −28.301 | −19.747 | 1.295  | 1.00 | 0.00 |
| ATOM | 1262 | OE2  | GLU | 372 | −27.293 | −20.936 | 2.782  | 1.00 | 0.00 |
| ATOM | 1263 | C    | GLU | 372 | −24.804 | −16.994 | −0.670 | 1.00 | 0.00 |
| ATOM | 1264 | O    | GLU | 372 | −24.822 | −15.885 | −0.255 | 1.00 | 0.00 |
| ATOM | 1265 | N    | ASP | 373 | −25.086 | −17.264 | −1.915 | 1.00 | 0.00 |
| ATOM | 1266 | HN   | ASP | 373 | −25.071 | −18.194 | −2.234 | 1.00 | 0.00 |
| ATOM | 1267 | CA   | ASP | 373 | −25.430 | −16.155 | −2.853 | 1.00 | 0.00 |
| ATOM | 1268 | HA   | ASP | 373 | −25.851 | −15.322 | −2.311 | 1.00 | 0.00 |
| ATOM | 1269 | CB   | ASP | 373 | −24.103 | −15.747 | −3.489 | 1.00 | 0.00 |
| ATOM | 1270 | HB1  | ASP | 373 | −23.518 | −15.189 | −2.775 | 1.00 | 0.00 |
| ATOM | 1271 | HB2  | ASP | 373 | −24.295 | −15.133 | −4.358 | 1.00 | 0.00 |
| ATOM | 1272 | CG   | ASP | 373 | −23.332 | −17.000 | −3.909 | 1.00 | 0.00 |
| ATOM | 1273 | OD1  | ASP | 373 | −22.298 | −17.263 | −3.317 | 1.00 | 0.00 |
| ATOM | 1274 | OD2  | ASP | 373 | −23.789 | −17.678 | −4.186 | 1.00 | 0.00 |
| ATOM | 1275 | C    | ASP | 373 | −26.408 | −16.647 | −3.919 | 1.00 | 0.00 |
| ATOM | 1276 | O    | ASP | 373 | −26.502 | −17.827 | −4.191 | 1.00 | 0.00 |
| ATOM | 1277 | N    | ASP | 374 | −27.139 | −15.754 | −4.525 | 1.00 | 0.00 |
| ATOM | 1278 | HN   | ASP | 374 | −27.053 | −14.801 | −4.288 | 1.00 | 0.00 |
| ATOM | 1279 | CA   | ASP | 374 | −28.110 | −16.182 | −5.574 | 1.00 | 0.00 |
| ATOM | 1280 | HA   | ASP | 374 | −28.334 | −17.230 | −5.471 | 1.00 | 0.00 |
| ATOM | 1281 | CB   | ASP | 374 | −29.367 | −15.355 | −5.313 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                              created by user:

| ATOM | 1282 | HB1  | ASP | 374 | −29.793 | −15.041 | −6.253  | 1.00 | 0.00 |
|------|------|------|-----|-----|---------|---------|---------|------|------|
| ATOM | 1283 | HB2  | ASP | 374 | −29.109 | −14.486 | −4.723  | 1.00 | 0.00 |
| ATOM | 1284 | CG   | ASP | 374 | −30.385 | −16.207 | −4.551  | 1.00 | 0.00 |
| ATOM | 1285 | OD1  | ASP | 374 | −31.296 | −15.634 | −3.976  | 1.00 | 0.00 |
| ATOM | 1286 | OD2  | ASP | 374 | −30.237 | −17.419 | −4.555  | 1.00 | 0.00 |
| ATOM | 1287 | C    | ASP | 374 | −27.552 | −15.892 | −6.973  | 1.00 | 0.00 |
| ATOM | 1288 | O    | ASP | 374 | −27.408 | −14.758 | −7.371  | 1.00 | 0.00 |
| ATOM | 1289 | N    | GLY | 375 | −27.236 | −16.915 | −7.719  | 1.00 | 0.00 |
| ATOM | 1290 | HN   | GLY | 375 | −27.357 | −17.826 | −7.377  | 1.00 | 0.00 |
| ATOM | 1291 | CA   | GLY | 375 | −26.687 | −16.699 | −9.092  | 1.00 | 0.00 |
| ATOM | 1292 | HA1  | GLY | 375 | −25.929 | −15.933 | −9.062  | 1.00 | 0.00 |
| ATOM | 1293 | HA2  | GLY | 375 | −27.485 | −16.392 | −9.755  | 1.00 | 0.00 |
| ATOM | 1294 | C    | GLY | 375 | −26.069 | −18.002 | −9.603  | 1.00 | 0.00 |
| ATOM | 1295 | O    | GLY | 375 | −25.988 | −18.973 | −8.800  | 1.00 | 0.00 |
| ATOM | 1296 | N    | PRO | 376 | −25.647 | −17.980 | −10.839 | 1.00 | 0.00 |
| ATOM | 1297 | CA   | PRO | 376 | −25.029 | −19.181 | −11.447 | 1.00 | 0.00 |
| ATOM | 1298 | HA   | PRO | 376 | −25.671 | −20.038 | −11.336 | 1.00 | 0.00 |
| ATOM | 1299 | CB   | PRO | 376 | −24.897 | −18.813 | −12.922 | 1.00 | 0.00 |
| ATOM | 1300 | HB1  | PRO | 376 | −25.750 | −19.169 | −13.476 | 1.00 | 0.00 |
| ATOM | 1301 | HB2  | PRO | 376 | −23.980 | −19.222 | −13.329 | 1.00 | 0.00 |
| ATOM | 1302 | CG   | PRO | 376 | −24.861 | −17.316 | −12.942 | 1.00 | 0.00 |
| ATOM | 1303 | HG1  | PRO | 376 | −25.288 | −16.948 | −13.860 | 1.00 | 0.00 |
| ATOM | 1304 | HG2  | PRO | 376 | −23.840 | −16.969 | −12.839 | 1.00 | 0.00 |
| ATOM | 1305 | CD   | PRO | 376 | −25.693 | −16.848 | −11.769 | 1.00 | 0.00 |
| ATOM | 1306 | HD1  | PRO | 376 | −26.708 | −16.658 | −12.075 | 1.00 | 0.00 |
| ATOM | 1307 | HD2  | PRO | 376 | −25.255 | −15.964 | −11.322 | 1.00 | 0.00 |
| ATOM | 1308 | C    | PRO | 376 | −23.658 | −19.445 | −10.816 | 1.00 | 0.00 |
| ATOM | 1309 | O    | PRO | 376 | −22.916 | −18.531 | −10.517 | 1.00 | 0.00 |
| ATOM | 1310 | N    | GLY | 377 | −23.316 | −20.689 | −10.612 | 1.00 | 0.00 |
| ATOM | 1311 | HN   | GLY | 377 | −23.927 | −21.413 | −10.860 | 1.00 | 0.00 |
| ATOM | 1312 | CA   | GLY | 377 | −21.995 | −21.003 | −10.000 | 1.00 | 0.00 |
| ATOM | 1313 | HA1  | GLY | 377 | −22.144 | −21.394 | −9.007  | 1.00 | 0.00 |
| ATOM | 1314 | HA2  | GLY | 377 | −21.402 | −20.100 | −9.946  | 1.00 | 0.00 |
| ATOM | 1315 | C    | GLY | 377 | −21.261 | −22.044 | −10.847 | 1.00 | 0.00 |
| ATOM | 1316 | O    | GLY | 377 | −20.506 | −21.711 | −11.738 | 1.00 | 0.00 |
| ATOM | 1317 | N    | ILE | 378 | −21.476 | −23.304 | −10.577 | 1.00 | 0.00 |
| ATOM | 1318 | HN   | ILE | 378 | −22.093 | −23.555 | −9.855  | 1.00 | 0.00 |
| ATOM | 1319 | CA   | ILE | 378 | −20.782 | −24.363 | −11.374 | 1.00 | 0.00 |
| ATOM | 1320 | HA   | ILE | 378 | −20.247 | −23.921 | −12.198 | 1.00 | 0.00 |
| ATOM | 1321 | CB   | ILE | 378 | −19.792 | −25.011 | −10.395 | 1.00 | 0.00 |
| ATOM | 1322 | HB   | ILE | 378 | −20.317 | −25.709 | −9.759  | 1.00 | 0.00 |
| ATOM | 1323 | CG1  | ILE | 378 | −19.129 | −23.925 | −9.533  | 1.00 | 0.00 |
| ATOM | 1324 | HG11 | ILE | 378 | −18.990 | −23.033 | −10.125 | 1.00 | 0.00 |
| ATOM | 1325 | HG12 | ILE | 378 | −18.170 | −24.280 | −9.185  | 1.00 | 0.00 |
| ATOM | 1326 | CG2  | ILE | 378 | −18.709 | −25.754 | −11.179 | 1.00 | 0.00 |
| ATOM | 1327 | HG21 | ILE | 378 | −18.381 | −25.143 | −12.007 | 1.00 | 0.00 |
| ATOM | 1328 | HG22 | ILE | 378 | −19.109 | −26.683 | −11.553 | 1.00 | 0.00 |
| ATOM | 1329 | HG23 | ILE | 378 | −17.870 | −25.959 | −10.528 | 1.00 | 0.00 |
| ATOM | 1330 | CD1  | ILE | 378 | −20.022 | −23.604 | −8.332  | 1.00 | 0.00 |
| ATOM | 1331 | HD11 | ILE | 378 | −20.155 | −22.536 | −8.256  | 1.00 | 0.00 |
| ATOM | 1332 | HD12 | ILE | 378 | −19.558 | −23.974 | −7.427  | 1.00 | 0.00 |
| ATOM | 1333 | HD13 | ILE | 378 | −20.984 | −24.078 | −8.461  | 1.00 | 0.00 |
| ATOM | 1334 | C    | ILE | 378 | −21.800 | −25.393 | −11.890 | 1.00 | 0.00 |
| ATOM | 1335 | O    | ILE | 378 | −22.941 | −25.414 | −11.475 | 1.00 | 0.00 |
| ATOM | 1336 | N    | ALA | 379 | −21.391 | −26.247 | −12.792 | 1.00 | 0.00 |
| ATOM | 1337 | HN   | ALA | 379 | −20.465 | −26.215 | −13.111 | 1.00 | 0.00 |
| ATOM | 1338 | CA   | ALA | 379 | −22.334 | −27.275 | −13.338 | 1.00 | 0.00 |
| ATOM | 1339 | HA   | ALA | 379 | −23.297 | −26.836 | −13.532 | 1.00 | 0.00 |
| ATOM | 1340 | CB   | ALA | 379 | −21.699 | −27.739 | −14.647 | 1.00 | 0.00 |
| ATOM | 1341 | HB1  | ALA | 379 | −21.420 | −28.779 | −14.562 | 1.00 | 0.00 |
| ATOM | 1342 | HB2  | ALA | 379 | −20.820 | −27.146 | −14.851 | 1.00 | 0.00 |
| ATOM | 1343 | HB2  | ALA | 379 | −22.408 | −27.621 | −15.452 | 1.00 | 0.00 |
| ATOM | 1344 | C    | ALA | 379 | −22.468 | −28.452 | −12.369 | 1.00 | 0.00 |
| ATOM | 1345 | O    | ALA | 379 | −21.893 | −28.446 | −11.302 | 1.00 | 0.00 |
| ATOM | 1346 | N    | PRO | 379 | −23.237 | −29.426 | −12.783 | 1.00 | 0.00 |
| ATOM | 1347 | CA   | PRO | 380 | −23.456 | −30.626 | −11.950 | 1.00 | 0.00 |
| ATOM | 1348 | HA   | PRO | 380 | −23.639 | −30.351 | −10.926 | 1.00 | 0.00 |
| ATOM | 1349 | CB   | PRO | 380 | −24.701 | −31.260 | −12.550 | 1.00 | 0.00 |
| ATOM | 1350 | HB1  | PRO | 380 | −25.582 | −30.927 | −12.026 | 1.00 | 0.00 |
| ATOM | 1351 | HB2  | PRO | 380 | −24.625 | −32.340 | −12.513 | 1.00 | 0.00 |
| ATOM | 1352 | CG   | PRO | 380 | −24.742 | −30.787 | −13.977 | 1.00 | 0.00 |
| ATOM | 1353 | HG1  | PRO | 380 | −25.763 | −30.620 | −14.278 | 1.00 | 0.00 |
| ATOM | 1354 | HG2  | PRO | 380 | −24.283 | −31.525 | −14.620 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                                created by user:

| ATOM | 1355 | CD   | PRO | 380 | −23.971 | −29.484 | −14.048 | 1.00 | 0.00 |
|------|------|------|-----|-----|---------|---------|---------|------|------|
| ATOM | 1356 | HD1  | PRO | 380 | −24.648 | −28.649 | −14.124 | 1.00 | 0.00 |
| ATOM | 1357 | HD2  | PRO | 380 | −23.287 | −29.499 | −14.887 | 1.00 | 0.00 |
| ATOM | 1358 | C    | PRO | 380 | −22.260 | −31.581 | −12.053 | 1.00 | 0.00 |
| ATOM | 1359 | O    | PRO | 380 | −21.983 | −32.342 | −11.147 | 1.00 | 0.00 |
| ATOM | 1360 | N    | GLU | 381 | −21.551 | −31.549 | −13.149 | 1.00 | 0.00 |
| ATOM | 1361 | HN   | GLU | 381 | −21.788 | −30.930 | −13.871 | 1.00 | 0.00 |
| ATOM | 1362 | CA   | GLU | 381 | −20.377 | −32.459 | −13.298 | 1.00 | 0.00 |
| ATOM | 1363 | HA   | GLU | 381 | −20.554 | −33.380 | −12.778 | 1.00 | 0.00 |
| ATOM | 1364 | CB   | GLU | 381 | −20.262 | −32.723 | −14.798 | 1.00 | 0.00 |
| ATOM | 1365 | HB1  | GLU | 381 | −19.221 | −32.721 | −15.085 | 1.00 | 0.00 |
| ATOM | 1366 | HB2  | GLU | 381 | −20.789 | −31.951 | −15.341 | 1.00 | 0.00 |
| ATOM | 1367 | CG   | GLU | 381 | −20.874 | −34.088 | −15.121 | 1.00 | 0.00 |
| ATOM | 1368 | HG1  | GLU | 381 | −21.951 | −34.011 | −15.113 | 1.00 | 0.00 |
| ATOM | 1369 | HG2  | GLU | 381 | −20.558 | −34.809 | −14.379 | 1.00 | 0.00 |
| ATOM | 1370 | CD   | GLU | 381 | −20.409 | −34.544 | −16.504 | 1.00 | 0.00 |
| ATOM | 1371 | OE1  | GLU | 381 | −19.649 | −35.497 | −16.658 | 1.00 | 0.00 |
| ATOM | 1372 | OE2  | GLU | 381 | −20.820 | −33.933 | −17.476 | 1.00 | 0.00 |
| ATOM | 1373 | C    | GLU | 381 | −19.110 | −31.786 | −12.766 | 1.00 | 0.00 |
| ATOM | 1374 | O    | GLU | 381 | −18.378 | −32.356 | −11.985 | 1.00 | 0.00 |
| ATOM | 1375 | N    | GLU | 382 | −18.846 | −30.581 | −13.183 | 1.00 | 0.00 |
| ATOM | 1376 | HN   | GLU | 382 | −19.452 | −30.139 | −13.813 | 1.00 | 0.00 |
| ATOM | 1377 | CA   | GLN | 382 | −17.621 | −29.873 | −12.698 | 1.00 | 0.00 |
| ATOM | 1378 | HA   | GLN | 382 | −16.734 | −30.404 | −12.997 | 1.00 | 0.00 |
| ATOM | 1379 | CB   | GLN | 382 | −17.662 | −28.503 | −13.372 | 1.00 | 0.00 |
| ATOM | 1380 | HB1  | GLN | 382 | −16.982 | −27.833 | −12.869 | 1.00 | 0.00 |
| ATOM | 1381 | HB2  | GLN | 382 | −18.666 | −28.106 | −13.321 | 1.00 | 0.00 |
| ATOM | 1382 | CG   | GLN | 382 | −17.242 | −28.646 | −14.836 | 1.00 | 0.00 |
| ATOM | 1383 | HG1  | GLN | 382 | −18.036 | −28.289 | −15.474 | 1.00 | 0.00 |
| ATOM | 1384 | HG2  | GLN | 382 | −17.046 | −29.687 | −15.053 | 1.00 | 0.00 |
| ATOM | 1385 | CD   | GLN | 382 | −15.977 | −27.824 | −15.090 | 1.00 | 0.00 |
| ATOM | 1386 | OE1  | GLN | 382 | −15.526 | −27.098 | −14.227 | 1.00 | 0.00 |
| ATOM | 1387 | NE2  | GLN | 382 | −15.382 | −27.909 | −16.248 | 1.00 | 0.00 |
| ATOM | 1388 | HE21 | GLN | 382 | −15.746 | −28.495 | −16.944 | 1.00 | 0.00 |
| ATOM | 1389 | HE22 | GLN | 382 | −14.572 | −27.386 | −16.422 | 1.00 | 0.00 |
| ATOM | 1390 | C    | GLN | 382 | −17.662 | −29.732 | −11.176 | 1.00 | 0.00 |
| ATOM | 1391 | O    | GLN | 382 | −16.642 | −29.740 | −10.516 | 1.00 | 0.00 |
| ATOM | 1392 | N    | ARG | 383 | −18.829 | −29.602 | −10.613 | 1.00 | 0.00 |
| ATOM | 1393 | HN   | ARG | 383 | −19.642 | −29.599 | −11.161 | 1.00 | 0.00 |
| ATOM | 1394 | CA   | ARG | 383 | −18.923 | −29.462 | −9.135  | 1.00 | 0.00 |
| ATOM | 1395 | HA   | ARG | 383 | −18.607 | −28.481 | −8.825  | 1.00 | 0.00 |
| ATOM | 1396 | CB   | ARG | 383 | −20.401 | −29.666 | −8.815  | 1.00 | 0.00 |
| ATOM | 1397 | HB1  | ARG | 383 | −20.621 | −30.723 | −8.791  | 1.00 | 0.00 |
| ATOM | 1398 | HB2  | ARG | 383 | −21.002 | −29.191 | −9.573  | 1.00 | 0.00 |
| ATOM | 1399 | CG   | ARG | 383 | −20.718 | −29.053 | −7.455  | 1.00 | 0.00 |
| ATOM | 1400 | HG1  | ARG | 383 | −21.783 | −28.909 | −7.363  | 1.00 | 0.00 |
| ATOM | 1401 | HG2  | ARG | 383 | −20.214 | −28.100 | −7.363  | 1.00 | 0.00 |
| ATOM | 1402 | CD   | ARG | 383 | −20.236 | −29.995 | −6.352  | 1.00 | 0.00 |
| ATOM | 1403 | HD1  | ARG | 383 | −19.579 | −29.476 | −5.673  | 1.00 | 0.00 |
| ATOM | 1404 | HD2  | ARG | 383 | −19.735 | −30.853 | −6.784  | 1.00 | 0.00 |
| ATOM | 1405 | NE   | ARG | 383 | −21.470 | −30.418 | −5.643  | 1.00 | 0.00 |
| ATOM | 1406 | HE   | ARG | 383 | −22.319 | −30.480 | −6.129  | 1.00 | 0.00 |
| ATOM | 1407 | CZ   | ARG | 383 | −21.421 | −30.707 | −4.374  | 1.00 | 0.00 |
| ATOM | 1408 | NH1  | ARG | 383 | −20.844 | −29.885 | −3.543  | 1.00 | 0.00 |
| ATOM | 1409 | HH11 | ARG | 383 | −20.440 | −29.034 | −3.880  | 1.00 | 0.00 |
| ATOM | 1410 | HH12 | ARG | 383 | −20.805 | −30.104 | −2.569  | 1.00 | 0.00 |
| ATOM | 1411 | NH2  | ARG | 383 | −21.946 | −31.818 | −3.936  | 1.00 | 0.00 |
| ATOM | 1412 | HH21 | ARG | 383 | −22.385 | −32.449 | −4.576  | 1.00 | 0.00 |
| ATOM | 1413 | HH22 | ARG | 383 | −21.907 | −32.040 | −2.962  | 1.00 | 0.00 |
| ATOM | 1414 | C    | ARG | 383 | −18.075 | −30.543 | −8.462  | 1.00 | 0.00 |
| ATOM | 1415 | O    | ARG | 383 | −17.557 | −30.359 | −7.378  | 1.00 | 0.00 |
| ATOM | 1416 | N    | LYS | 384 | −17.933 | −31.671 | −9.102  | 1.00 | 0.00 |
| ATOM | 1417 | HN   | LYS | 384 | −18.362 | −31.795 | −9.973  | 1.00 | 0.00 |
| ATOM | 1418 | CA   | LYS | 384 | −17.121 | −32.771 | −8.512  | 1.00 | 0.00 |
| ATOM | 1419 | HA   | LYS | 384 | −17.191 | −32.753 | −7.437  | 1.00 | 0.00 |
| ATOM | 1420 | CB   | LYS | 384 | −17.745 | −34.057 | −9.052  | 1.00 | 0.00 |
| ATOM | 1421 | HB1  | LYS | 384 | −16.989 | −34.826 | −9.114  | 1.00 | 0.00 |
| ATOM | 1422 | HB2  | LYS | 384 | −18.154 | −33.873 | −10.036 | 1.00 | 0.00 |
| ATOM | 1423 | CG   | LYS | 384 | −18.860 | −34.516 | −8.110  | 1.00 | 0.00 |
| ATOM | 1424 | HG1  | LYS | 384 | −19.808 | −34.460 | −8.621  | 1.00 | 0.00 |
| ATOM | 1425 | HG2  | LYS | 384 | −18.880 | −33.876 | −7.239  | 1.00 | 0.00 |
| ATOM | 1426 | CD   | LYS | 384 | −18.603 | −35.959 | −7.676  | 1.00 | 0.00 |
| ATOM | 1427 | HD1  | LYS | 384 | −18.141 | −35.966 | −6.700  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                created by user:

| | | | | | | | | |
|---|---|---|---|---|---|---|---|---|
| ATOM | 1428 | HD2 | LYS | 384 | −17.947 | −36.439 | −8.389 | 1.00 | 0.00 |
| ATOM | 1429 | CE | LYS | 384 | −19.932 | −36.714 | −7.613 | 1.00 | 0.00 |
| ATOM | 1430 | HE1 | LYS | 384 | −20.757 | −36.021 | −7.580 | 1.00 | 0.00 |
| ATOM | 1431 | HE2 | LYS | 384 | −19.952 | −37.370 | −6.751 | 1.00 | 0.00 |
| ATOM | 1432 | NZ | LYS | 384 | −19.982 | −37.507 | −8.873 | 1.00 | 0.00 |
| ATOM | 1433 | HZ1 | LYS | 384 | −19.551 | −36.961 | −9.644 | 1.00 | 0.00 |
| ATOM | 1434 | HZ2 | LYS | 384 | −20.974 | −37.719 | −9.109 | 1.00 | 0.00 |
| ATOM | 1435 | HZ3 | LYS | 384 | −19.458 | −38.395 | −8.745 | 1.00 | 0.00 |
| ATOM | 1436 | C | LYS | 384 | −15.659 | −32.654 | −8.954 | 1.00 | 0.00 |
| ATOM | 1437 | O | LYS | 384 | −14.751 | −32.914 | −8.190 | 1.00 | 0.00 |
| ATOM | 1438 | N | HIS | 385 | −15.416 | −32.265 | −10.182 | 1.00 | 0.00 |
| ATOM | 1439 | HN | HIS | 385 | −16.157 | −32.062 | −10.791 | 1.00 | 0.00 |
| ATOM | 1440 | CA | HIS | 385 | −14.002 | −32.140 | −10.646 | 1.00 | 0.00 |
| ATOM | 1441 | HA | HIS | 385 | −13.334 | −32.535 | −9.897 | 1.00 | 0.00 |
| ATOM | 1442 | CB | HIS | 385 | −13.908 | −33.000 | −11.916 | 1.00 | 0.00 |
| ATOM | 1443 | HB1 | HIS | 385 | −14.253 | −34.000 | −11.694 | 1.00 | 0.00 |
| ATOM | 1444 | HB2 | HIS | 385 | −12.881 | −33.042 | −12.240 | 1.00 | 0.00 |
| ATOM | 1445 | CG | HIS | 385 | −14.750 | −32.418 | −13.021 | 1.00 | 0.00 |
| ATOM | 1446 | ND1 | HIS | 385 | −14.242 | −31.510 | −13.939 | 1.00 | 0.00 |
| ATOM | 1447 | HD1 | HIS | 385 | −13.332 | −31.148 | −13.953 | 1.00 | 0.00 |
| ATOM | 1448 | CD2 | HIS | 385 | −16.052 | −32.639 | −13.394 | 1.00 | 0.00 |
| ATOM | 1449 | HD2 | HIS | 385 | −16.739 | −33.301 | −12.889 | 1.00 | 0.00 |
| ATOM | 1450 | CE1 | HIS | 385 | −15.227 | −31.224 | −14.812 | 1.00 | 0.00 |
| ATOM | 1451 | HE1 | HIS | 385 | −15.119 | −30.545 | −15.645 | 1.00 | 0.00 |
| ATOM | 1452 | NE2 | HIS | 385 | −16.351 | −31.886 | −14.526 | 1.00 | 0.00 |
| ATOM | 1453 | C | HIS | 385 | −13.642 | −30.676 | −10.941 | 1.00 | 0.00 |
| ATOM | 1454 | O | HIS | 385 | −13.240 | −30.333 | −12.034 | 1.00 | 0.00 |
| ATOM | 1455 | N | LEU | 386 | −13.782 | −29.808 | −9.970 | 1.00 | 0.00 |
| ATOM | 1456 | HN | LEU | 386 | −14.110 | −30.098 | −9.096 | 1.00 | 0.00 |
| ATOM | 1457 | CA | LEU | 386 | −13.444 | −28.372 | −10.199 | 1.00 | 0.00 |
| ATOM | 1458 | HA | LEU | 386 | −13.464 | −28.155 | −11.234 | 1.00 | 0.00 |
| ATOM | 1459 | CB | LEU | 386 | −14.527 | −27.582 | −9.462 | 1.00 | 0.00 |
| ATOM | 1460 | HB1 | LEU | 386 | −14.236 | −27.452 | −8.431 | 1.00 | 0.00 |
| ATOM | 1461 | HB2 | LEU | 386 | −15.460 | −28.127 | −9.506 | 1.00 | 0.00 |
| ATOM | 1462 | CG | LEU | 386 | −14.709 | −26.209 | −10.113 | 1.00 | 0.00 |
| ATOM | 1463 | HG | LEU | 386 | −15.589 | −25.736 | −9.708 | 1.00 | 0.00 |
| ATOM | 1464 | CD1 | LEU | 386 | −13.488 | −25.339 | −9.823 | 1.00 | 0.00 |
| ATOM | 1465 | HD11 | LEU | 386 | −12.992 | −25.702 | −8.935 | 1.00 | 0.00 |
| ATOM | 1466 | HD12 | LEU | 386 | −13.800 | −24.317 | −9.668 | 1.00 | 0.00 |
| ATOM | 1467 | HD13 | LEU | 386 | −12.805 | −25.385 | −10.659 | 1.00 | 0.00 |
| ATOM | 1468 | CD2 | LEU | 386 | −14.871 | −26.373 | −11.626 | 1.00 | 0.00 |
| ATOM | 1469 | HD21 | LEU | 386 | −15.506 | −27.224 | −11.830 | 1.00 | 0.00 |
| ATOM | 1470 | HD22 | LEU | 386 | −13.902 | −26.530 | −12.077 | 1.00 | 0.00 |
| ATOM | 1471 | HD23 | LEU | 386 | −15.320 | −25.483 | −12.039 | 1.00 | 0.00 |
| ATOM | 1472 | C | LEU | 386 | −12.056 | −28.070 | −9.626 | 1.00 | 0.00 |
| ATOM | 1473 | O | LEU | 386 | −11.537 | −26.980 | −9.745 | 1.00 | 0.00 |
| ATOM | 1474 | N | PHE | 387 | −11.460 | −29.039 | −9.025 | 1.00 | 0.00 |
| ATOM | 1475 | HN | PHE | 387 | −11.896 | −29.902 | −8.970 | 1.00 | 0.00 |
| ATOM | 1476 | CA | PHE | 387 | −10.106 | −28.854 | −8.432 | 1.00 | 0.00 |
| ATOM | 1477 | HA | PHE | 387 | −9.506 | −28.219 | −9.054 | 1.00 | 0.00 |
| ATOM | 1478 | CB | PHE | 387 | −10.341 | −28.200 | −7.070 | 1.00 | 0.00 |
| ATOM | 1479 | HB1 | PHE | 387 | −9.441 | −28.273 | −6.476 | 1.00 | 0.00 |
| ATOM | 1480 | HB2 | PHE | 387 | −11.148 | −28.708 | −6.563 | 1.00 | 0.00 |
| ATOM | 1481 | CG | PHE | 387 | −10.702 | −26.744 | −7.255 | 1.00 | 0.00 |
| ATOM | 1482 | CD1 | PHE | 387 | −9.848 | −25.890 | −7.965 | 1.00 | 0.00 |
| ATOM | 1483 | HD1 | PHE | 387 | −8.927 | −26.270 | −8.384 | 1.00 | 0.00 |
| ATOM | 1484 | CD2 | PHE | 387 | −11.894 | −26.249 | −6.173 | 1.00 | 0.00 |
| ATOM | 1485 | HD2 | PHE | 387 | −12.551 | −26.907 | −6.165 | 1.00 | 0.00 |
| ATOM | 1486 | CE1 | PHE | 387 | −10.189 | −24.541 | −8.133 | 1.00 | 0.00 |
| ATOM | 1487 | HE1 | PHE | 387 | −9.531 | −23.881 | −8.678 | 1.00 | 0.00 |
| ATOM | 1488 | CE2 | PHE | 387 | −12.233 | −24.902 | −6.881 | 1.00 | 0.00 |
| ATOM | 1489 | HE2 | PHE | 387 | −13.154 | −24.522 | −6.463 | 1.00 | 0.00 |
| ATOM | 1490 | CZ | PHE | 387 | −11.382 | −24.048 | −7.590 | 1.00 | 0.00 |
| ATOM | 1491 | HZ | PHE | 387 | −11.645 | −23.007 | −7.720 | 1.00 | 0.00 |
| ATOM | 1492 | CZ | PHE | 387 | −9.446 | −30.215 | −8.262 | 1.00 | 0.00 |
| ATOM | 1493 | O | PHE | 387 | −8.629 | −30.420 | −7.388 | 1.00 | 0.00 |
| ATOM | 1494 | N | GLN | 388 | −9.802 | −31.148 | −9.100 | 1.00 | 0.00 |
| ATOM | 1495 | HN | GLN | 388 | −10.454 | −30.946 | −9.798 | 1.00 | 0.00 |
| ATOM | 1496 | CA | GLN | 388 | −9.212 | −32.511 | −9.011 | 1.00 | 0.00 |
| ATOM | 1497 | HA | GLN | 388 | −9.612 | −33.142 | −9.787 | 1.00 | 0.00 |
| ATOM | 1498 | CB | GLN | 388 | −7.721 | −32.308 | −9.230 | 1.00 | 0.00 |
| ATOM | 1499 | HB1 | GLN | 388 | −7.174 | −33.101 | −8.745 | 1.00 | 0.00 |
| ATOM | 1500 | HB2 | GLN | 388 | −7.421 | −31.356 | −8.817 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| | | | | | | | | |
|---|---|---|---|---|---|---|---|---|
| ATOM | 1501 | CG   | GLN | 388 | −7.428  | −32.331 | −10.728 | 1.00 | 0.00 |
| ATOM | 1502 | HG1  | GLN | 388 | −6.592  | −31.685 | −10.941 | 1.00 | 0.00 |
| ATOM | 1503 | HG2  | GLN | 388 | −8.299  | −31.986 | −11.270 | 1.00 | 0.00 |
| ATOM | 1504 | CD   | GLN | 388 | −7.091  | −33.757 | −11.158 | 1.00 | 0.00 |
| ATOM | 1505 | OE1  | GLN | 388 | −7.969  | −24.583 | −11.304 | 1.00 | 0.00 |
| ATOM | 1506 | NE2  | GLN | 388 | −5.847  | −34.083 | −11.368 | 1.00 | 0.00 |
| ATOM | 1507 | HE21 | GLN | 388 | −5.139  | −33.416 | −11.252 | 1.00 | 0.00 |
| ATOM | 1508 | HE22 | GLN | 388 | −5.620  | −34.996 | −11.641 | 1.00 | 0.00 |
| ATOM | 1509 | C    | GLN | 388 | −9.488  | −33.122 | −7.634  | 1.00 | 0.00 |
| ATOM | 1510 | O    | GLN | 388 | −9.519  | −23.428 | −6.637  | 1.00 | 0.00 |
| ATOM | 1511 | N    | PRO | 389 | −9.684  | −34.411 | −7.633  | 1.00 | 0.00 |
| ATOM | 1512 | CA   | PRO | 389 | −9.963  | −35.142 | −6.374  | 1.00 | 0.00 |
| ATOM | 1513 | HA   | PRO | 389 | −10.763 | −34.670 | −5.829  | 1.00 | 0.00 |
| ATOM | 1514 | CB   | PRO | 389 | −10.400 | −36.523 | −6.850  | 1.00 | 0.00 |
| ATOM | 1515 | HB1  | PRO | 389 | −11.473 | −36.573 | −6.929  | 1.00 | 0.00 |
| ATOM | 1516 | HB2  | PRO | 389 | −10.033 | −37.286 | −6.173  | 1.00 | 0.00 |
| ATOM | 1517 | CG   | PRO | 389 | −9.777  | −36.682 | −8.203  | 1.00 | 0.00 |
| ATOM | 1518 | HG1  | PRO | 389 | −10.406 | −37.292 | −8.830  | 1.00 | 0.00 |
| ATOM | 1519 | HG2  | PRO | 389 | −8.797  | −37.133 | −8.108  | 1.00 | 0.00 |
| ATOM | 1520 | CD   | PRO | 389 | −9.656  | −35.299 | −8.797  | 1.00 | 0.00 |
| ATOM | 1521 | HD1  | PRO | 389 | −10.492 | −35.090 | −9.444  | 1.00 | 0.00 |
| ATOM | 1522 | HD2  | PRO | 389 | −8.721  | −35.197 | −9.334  | 1.00 | 0.00 |
| ATOM | 1523 | C    | PRO | 389 | −8.700  | −35.237 | −5.510  | 1.00 | 0.00 |
| ATOM | 1524 | O    | PRO | 389 | −7.603  | −34.971 | −5.962  | 1.00 | 0.00 |
| ATOM | 1525 | N    | PHE | 390 | −8.849  | −35.618 | −4.269  | 1.00 | 0.00 |
| ATOM | 1526 | HN   | PHE | 390 | −9.742  | −35.829 | −3.926  | 1.00 | 0.00 |
| ATOM | 1527 | CA   | PHE | 390 | −7.662  | −35.732 | −3.374  | 1.00 | 0.00 |
| ATOM | 1528 | HA   | PHE | 390 | −7.000  | −34.893 | −3.516  | 1.00 | 0.00 |
| ATOM | 1529 | CB   | PHE | 390 | −8.231  | −35.175 | −1.956  | 1.00 | 0.00 |
| ATOM | 1530 | HB1  | PHE | 390 | −7.479  | −36.057 | −1.261  | 1.00 | 0.00 |
| ATOM | 1531 | HB2  | PHE | 390 | −9.093  | −36.366 | −1.906  | 1.00 | 0.00 |
| ATOM | 1532 | CG   | PHE | 390 | −8.643  | −34.308 | −1.599  | 1.00 | 0.00 |
| ATOM | 1533 | CD1  | PHE | 390 | −9.651  | −33.668 | −2.328  | 1.00 | 0.00 |
| ATOM | 1534 | HD1  | PHE | 390 | −10.135 | −34.181 | −3.145  | 1.00 | 0.00 |
| ATOM | 1535 | CD2  | PHE | 390 | −8.015  | −33.643 | −0.539  | 1.00 | 0.00 |
| ATOM | 1536 | HD2  | PHE | 390 | −7.237  | −34.137 | 0.023   | 1.00 | 0.00 |
| ATOM | 1537 | CE1  | PHE | 390 | −10.032 | −32.364 | −1.999  | 1.00 | 0.00 |
| ATOM | 1538 | HE1  | PHE | 390 | −10.811 | −31.871 | −2.563  | 1.00 | 0.00 |
| ATOM | 1539 | CE1  | PHE | 390 | −8.396  | −32.337 | −0.209  | 1.00 | 0.00 |
| ATOM | 1540 | HE2  | PHE | 390 | −7.911  | −31.824 | 0.608   | 1.00 | 0.00 |
| ATOM | 1541 | CA   | PHE | 390 | −9.404  | −31.698 | −0.939  | 1.00 | 0.00 |
| ATOM | 1542 | HZ   | PHE | 390 | −9.698  | −30.690 | −0.686  | 1.00 | 0.00 |
| ATOM | 1543 | C    | PHE | 390 | −6.927  | −37.047 | −3.641  | 1.00 | 0.00 |
| ATOM | 1544 | O    | PHE | 390 | −7.530  | −38.053 | −3.956  | 1.00 | 0.00 |
| ATOM | 1545 | N    | VAL | 391 | −5.630  | −37.044 | −3.520  | 1.00 | 0.00 |
| ATOM | 1546 | HN   | VAL | 391 | −5.164  | −36.221 | −3.265  | 1.00 | 0.00 |
| ATOM | 1547 | CA   | VAL | 391 | −4.854  | −38.293 | −3.768  | 1.00 | 0.00 |
| ATOM | 1548 | HA   | VAL | 391 | −5.509  | −39.091 | −4.059  | 1.00 | 0.00 |
| ATOM | 1549 | CB   | VAL | 391 | −3.906  | −37.953 | −4.916  | 1.00 | 0.00 |
| ATOM | 1550 | HB   | VAL | 391 | −3.087  | −37.372 | −4.536  | 1.00 | 0.00 |
| ATOM | 1551 | CG1  | VAL | 391 | −3.366  | −39.242 | −5.540  | 1.00 | 0.00 |
| ATOM | 1552 | HG11 | VAL | 391 | −2.431  | −39.035 | −6.039  | 1.00 | 0.00 |
| ATOM | 1553 | HG12 | VAL | 391 | −4.079  | −39.623 | −6.256  | 1.00 | 0.00 |
| ATOM | 1554 | HG13 | VAL | 391 | −3.205  | −39.977 | −4.768  | 1.00 | 0.00 |
| ATOM | 1555 | CG2  | VAL | 391 | −4.657  | −37.150 | −5.984  | 1.00 | 0.00 |
| ATOM | 1556 | HG21 | VAL | 391 | −4.038  | −37.054 | −6.864  | 1.00 | 0.00 |
| ATOM | 1557 | HG22 | VAL | 391 | −4.891  | −36.169 | −5.599  | 1.00 | 0.00 |
| ATOM | 1558 | HG23 | VAL | 391 | −5.572  | −37.663 | −6.242  | 1.00 | 0.00 |
| ATOM | 1559 | C    | VAL | 391 | −4.065  | −38.678 | −2.513  | 1.00 | 0.00 |
| ATOM | 1560 | O    | VAL | 391 | −3.835  | −37.865 | −1.640  | 1.00 | 0.00 |
| ATOM | 1561 | N    | ARG | 392 | −3.652  | −39.909 | −2.417  | 1.00 | 0.00 |
| ATOM | 1562 | HN   | ARG | 392 | −3.848  | −40.546 | −3.132  | 1.00 | 0.00 |
| ATOM | 1563 | CA   | ARG | 392 | −2.879  | −40.348 | −1.221  | 1.00 | 0.00 |
| ATOM | 1564 | HA   | ARG | 392 | −2.887  | −39.583 | −0.463  | 1.00 | 0.00 |
| ATOM | 1565 | CB   | ARG | 392 | −3.604  | −41.593 | −0.717  | 1.00 | 0.00 |
| ATOM | 1566 | HB1  | ARG | 392 | −3.021  | −42.470 | −0.954  | 1.00 | 0.00 |
| ATOM | 1567 | HB2  | ARG | 392 | −4.572  | −41.664 | −1.193  | 1.00 | 0.00 |
| ATOM | 1568 | CG   | ARG | 392 | −3.786  | −41.500 | 0.799   | 1.00 | 0.00 |
| ATOM | 1569 | HG1  | ARG | 392 | −4.713  | −41.974 | 1.079   | 1.00 | 0.00 |
| ATOM | 1570 | HG2  | ARG | 392 | −3.808  | −40.460 | 1.095   | 1.00 | 0.00 |
| ATOM | 1571 | CD   | ARG | 392 | −2.622  | −42.207 | 1.499   | 1.00 | 0.00 |
| ATOM | 1572 | HD1  | ARG | 392 | −1.703  | −42.047 | 0.958   | 1.00 | 0.00 |
| ATOM | 1573 | HD2  | ARG | 392 | −2.827  | −43.266 | 1.592   | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56              created by user:

| | | | | | | | | |
|---|---|---|---|---|---|---|---|---|
| ATOM | 1574 | NE | ARG | 392 | −2.540 | −41.573 | 2.843 | 1.00 | 0.00 |
| ATOM | 1575 | HE | ARG | 392 | −3.192 | −40.889 | 3.103 | 1.00 | 0.00 |
| ATOM | 1576 | CZ | ARG | 392 | −1.600 | −41.929 | 3.676 | 1.00 | 0.00 |
| ATOM | 1577 | NH1 | ARG | 392 | −0.495 | −41.238 | 3.746 | 1.00 | 0.00 |
| ATOM | 1578 | HH11 | ARG | 392 | −0.368 | −40.437 | 3.161 | 1.00 | 0.00 |
| ATOM | 1579 | HH12 | ARG | 392 | 0.226 | −41.511 | 4.384 | 1.00 | 0.00 |
| ATOM | 1580 | NH2 | ARG | 392 | −1.765 | −42.974 | 4.439 | 1.00 | 0.00 |
| ATOM | 1581 | HH21 | ARG | 392 | −2.611 | −43.504 | 4.386 | 1.00 | 0.00 |
| ATOM | 1582 | HH22 | ARG | 392 | −1.044 | −43.246 | −5.077 | 1.00 | 0.00 |
| ATOM | 1583 | C | ARG | 392 | −1.444 | −40.690 | −1.624 | 1.00 | 0.00 |
| ATOM | 1584 | O | ARG | 392 | −0.772 | −41.465 | −0.973 | 1.00 | 0.00 |
| ATOM | 1585 | N | GLY | 393 | −0.972 | −40.121 | −2.698 | 1.00 | 0.00 |
| ATOM | 1586 | HN | GLY | 393 | −1.534 | −39.504 | −3.211 | 1.00 | 0.00 |
| ATOM | 1587 | CA | GLY | 393 | 0.417 | −40.410 | −3.146 | 1.00 | 0.00 |
| ATOM | 1588 | HA1 | GLY | 393 | 0.391 | −40.941 | −4.084 | 1.00 | 0.00 |
| ATOM | 1589 | HA2 | GLY | 393 | 0.917 | −41.015 | −2.401 | 1.00 | 0.00 |
| ATOM | 1590 | C | GLY | 393 | 1.175 | −39.096 | −3.330 | 1.00 | 0.00 |
| ATOM | 1591 | O | GLY | 393 | 0.825 | −38.082 | −2.759 | 1.00 | 0.00 |
| ATOM | 1592 | N | ASP | 394 | 2.209 | −39.102 | −4.123 | 1.00 | 0.00 |
| ATOM | 1593 | HN | ASP | 394 | 2.477 | −39.930 | −4.575 | 1.00 | 0.00 |
| ATOM | 1594 | CA | ASP | 394 | 2.987 | −37.848 | −4.341 | 1.00 | 0.00 |
| ATOM | 1595 | HA | ASP | 394 | 2.342 | −36.988 | −4.274 | 1.00 | 0.00 |
| ATOM | 1596 | CB | ASP | 394 | 4.014 | −37.820 | −3.210 | 1.00 | 0.00 |
| ATOM | 1597 | HB1 | ASP | 394 | 3.505 | −37.734 | −2.261 | 1.00 | 0.00 |
| ATOM | 1598 | HB2 | ASP | 394 | 4.675 | −36.975 | −3.344 | 1.00 | 0.00 |
| ATOM | 1599 | CG | ASP | 394 | 4.830 | −39.114 | −3.231 | 1.00 | 0.00 |
| ATOM | 1600 | OD1 | ASP | 394 | 4.932 | −39.709 | −4.291 | 1.00 | 0.00 |
| ATOM | 1601 | OD2 | ASP | 394 | 5.339 | −39.488 | −2.187 | 1.00 | 0.00 |
| ATOM | 1602 | C | ASP | 394 | 3.686 | −37.890 | −5.701 | 1.00 | 0.00 |
| ATOM | 1603 | O | ASP | 394 | 4.895 | −37.830 | −5.790 | 1.00 | 0.00 |
| ATOM | 1604 | N | SER | 395 | 2.934 | −37.992 | −6.762 | 1.00 | 0.00 |
| ATOM | 1605 | HN | SER | 395 | 1.960 | −38.040 | −6.670 | 1.00 | 0.00 |
| ATOM | 1606 | CA | SER | 395 | 3.559 | −38.038 | −8.114 | 1.00 | 0.00 |
| ATOM | 1607 | HA | SER | 395 | 4.540 | −38.476 | −8.059 | 1.00 | 0.00 |
| ATOM | 1608 | CB | SER | 395 | 2.638 | −38.930 | −8.944 | 1.00 | 0.00 |
| ATOM | 1609 | HB1 | SER | 395 | 1.840 | −38.330 | −9.367 | 1.00 | 0.00 |
| ATOM | 1610 | HB2 | SER | 395 | 2.215 | −39.693 | −8.317 | 1.00 | 0.00 |
| ATOM | 1611 | OG | SER | 395 | 3.390 | −39.544 | −9.985 | 1.00 | 0.00 |
| ATOM | 1612 | HG | SER | 395 | 3.371 | −40.493 | −9.846 | 1.00 | 0.00 |
| ATOM | 1613 | C | SER | 395 | 3.636 | −36.631 | −8.721 | 1.00 | 0.00 |
| ATOM | 1614 | O | SER | 395 | 4.650 | −36.234 | −9.258 | 1.00 | 0.00 |
| ATOM | 1615 | N | ALA | 396 | 2.575 | −35.873 | −8.637 | 1.00 | 0.00 |
| ATOM | 1616 | HN | ALA | 396 | 1.765 | −36.206 | −8.198 | 1.00 | 0.00 |
| ATOM | 1617 | CA | ALA | 396 | 2.602 | −34.495 | −9.214 | 1.00 | 0.00 |
| ATOM | 1618 | HA | ALA | 396 | 3.616 | −34.191 | −9.410 | 1.00 | 0.00 |
| ATOM | 1619 | CB | ALA | 396 | 1.831 | −34.605 | −10.527 | 1.00 | 0.00 |
| ATOM | 1620 | HB1 | ALA | 396 | 1.110 | −35.406 | −10.455 | 1.00 | 0.00 |
| ATOM | 1621 | HB2 | ALA | 396 | 2.520 | −34.814 | −11.332 | 1.00 | 0.00 |
| ATOM | 1622 | HB3 | ALA | 396 | 1.318 | −33.675 | −10.723 | 1.00 | 0.00 |
| ATOM | 1623 | C | ALA | 396 | 1.920 | −33.496 | −8.271 | 1.00 | 0.00 |
| ATOM | 1624 | O | ALA | 396 | 0.821 | −33.043 | −8.520 | 1.00 | 0.00 |
| ATOM | 1625 | N | ARG | 397 | 2.565 | −33.155 | −7.188 | 1.00 | 0.00 |
| ATOM | 1626 | HN | ARG | 397 | 3.437 | −33.546 | −7.002 | 1.00 | 0.00 |
| ATOM | 1627 | CA | ARG | 397 | 1.959 | −32.184 | −6.225 | 1.00 | 0.00 |
| ATOM | 1628 | HA | ARG | 397 | 0.893 | −32.327 | −6.178 | 1.00 | 0.00 |
| ATOM | 1629 | CB | ARG | 397 | 2.591 | −32.522 | −4.855 | 1.00 | 0.00 |
| ATOM | 1630 | HB1 | ARG | 397 | 2.685 | −33.594 | −4.763 | 1.00 | 0.00 |
| ATOM | 1631 | HB2 | ARG | 397 | 1.947 | −32.154 | −4.068 | 1.00 | 0.00 |
| ATOM | 1632 | CG | ARG | 397 | 3.989 | −31.875 | −4.710 | 1.00 | 0.00 |
| ATOM | 1633 | HG1 | ARG | 397 | 4.191 | −31.699 | −3.665 | 1.00 | 0.00 |
| ATOM | 1634 | HG2 | ARG | 397 | 4.020 | −30.938 | −5.237 | 1.00 | 0.00 |
| ATOM | 1635 | CD | ARG | 397 | 5.060 | −32.815 | −5.276 | 1.00 | 0.00 |
| ATOM | 1636 | HD1 | ARG | 397 | 4.957 | −32.906 | −6.341 | 1.00 | 0.00 |
| ATOM | 1637 | HD2 | ARG | 397 | 4.995 | −33.787 | −4.803 | 1.00 | 0.00 |
| ATOM | 1638 | NE | ARG | 397 | 6.356 | −32.162 | −4.948 | 1.00 | 0.00 |
| ATOM | 1639 | HE | ARG | 397 | 6.451 | −31.190 | −5.035 | 1.00 | 0.00 |
| ATOM | 1640 | CZ | ARG | 397 | 7.368 | −32.882 | −4.552 | 1.00 | 0.00 |
| ATOM | 1641 | NH1 | ARG | 397 | 7.865 | −32.705 | −3.359 | 1.00 | 0.00 |
| ATOM | 1642 | HH11 | ARG | 397 | 7.469 | −32.018 | −2.750 | 1.00 | 0.00 |
| ATOM | 1643 | HH12 | ARG | 397 | 8.641 | −33.257 | −3.054 | 1.00 | 0.00 |
| ATOM | 1644 | NH2 | ARG | 397 | 7.886 | −33.778 | −5.348 | 1.00 | 0.00 |
| ATOM | 1645 | HH21 | ARG | 397 | 7.506 | −33.913 | −6.264 | 1.00 | 0.00 |
| ATOM | 1646 | HH22 | ARG | 397 | 8.661 | −34.331 | −5.042 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 1647 | C    | ARG | 397 | 2.280  | −30.740 | −6.648  | 1.00 | 0.00 |
|------|------|------|-----|-----|--------|---------|---------|------|------|
| ATOM | 1648 | O    | ARG | 397 | 2.227  | −29.823 | −5.852  | 1.00 | 0.00 |
| ATOM | 1649 | N    | THR | 398 | 2.616  | −30.536 | −7.894  | 1.00 | 0.00 |
| ATOM | 1650 | HN   | THR | 398 | 2.655  | −31.289 | −8.519  | 1.00 | 0.00 |
| ATOM | 1651 | CA   | THR | 398 | 2.940  | −29.155 | −8.370  | 1.00 | 0.00 |
| ATOM | 1652 | HA   | THR | 398 | 2.548  | −28.419 | −7.688  | 1.00 | 0.00 |
| ATOM | 1653 | CB   | THR | 398 | 4.468  | −29.086 | −8.394  | 1.00 | 0.00 |
| ATOM | 1654 | HB   | THR | 398 | 4.843  | −29.689 | −9.206  | 1.00 | 0.00 |
| ATOM | 1655 | OG1  | THR | 398 | 4.983  | −29.574 | −7.162  | 1.00 | 0.00 |
| ATOM | 1656 | HG1  | THR | 398 | 5.045  | −28.835 | −6.553  | 1.00 | 0.00 |
| ATOM | 1657 | CG2  | THR | 398 | 4.912  | −27.636 | −8.597  | 1.00 | 0.00 |
| ATOM | 1658 | HG21 | THR | 398 | 5.976  | −27.558 | −8.425  | 1.00 | 0.00 |
| ATOM | 1659 | HG22 | THR | 398 | 4.388  | −26.998 | −7.901  | 1.00 | 0.00 |
| ATOM | 1660 | HG23 | THR | 398 | 4.688  | −27.329 | −9.607  | 1.00 | 0.00 |
| ATOM | 1661 | C    | THR | 398 | 2.371  | −28.942 | −9.776  | 1.00 | 0.00 |
| ATOM | 1662 | O    | THR | 398 | 2.785  | −29.577 | −10.725 | 1.00 | 0.00 |
| ATOM | 1663 | N    | ILE | 399 | 1.429  | −28.053 | −9.916  | 1.00 | 0.00 |
| ATOM | 1664 | HN   | ILE | 399 | 1.111  | −27.547 | −9.139  | 1.00 | 0.00 |
| ATOM | 1665 | CA   | ILE | 399 | 0.836  | −27.703 | −11.261 | 1.00 | 0.00 |
| ATOM | 1666 | HA   | ILE | 399 | 0.863  | −28.701 | −11.855 | 1.00 | 0.00 |
| ATOM | 1667 | CB   | ILE | 399 | −0.610 | −27.409 | −10.982 | 1.00 | 0.00 |
| ATOM | 1668 | HB   | ILE | 399 | −1.118 | −28.229 | −10.494 | 1.00 | 0.00 |
| ATOM | 1669 | CG1  | ILE | 399 | −1.311 | −27.086 | −12.302 | 1.00 | 0.00 |
| ATOM | 1670 | HG11 | ILE | 399 | −0.828 | −26.242 | −12.769 | 1.00 | 0.00 |
| ATOM | 1671 | HG12 | ILE | 399 | −2.348 | −26.848 | −12.109 | 1.00 | 0.00 |
| ATOM | 1672 | CG2  | ILE | 399 | −0.638 | −26.179 | −10.074 | 1.00 | 0.00 |
| ATOM | 1673 | HG21 | ILE | 399 | 0.184  | −25.526 | −10.327 | 1.00 | 0.00 |
| ATOM | 1674 | HG22 | ILE | 399 | −0.547 | −26.490 | −9.044  | 1.00 | 0.00 |
| ATOM | 1675 | HG23 | ILE | 399 | −1.571 | −25.653 | −10.210 | 1.00 | 0.00 |
| ATOM | 1676 | CD1  | ILE | 399 | −1.228 | −28.298 | −13.232 | 1.00 | 0.00 |
| ATOM | 1677 | HD11 | ILE | 399 | −0.588 | −28.066 | −14.070 | 1.00 | 0.00 |
| ATOM | 1678 | HD12 | ILE | 399 | −2.216 | −28.545 | −13.592 | 1.00 | 0.00 |
| ATOM | 1679 | HD13 | ILE | 399 | −0.821 | −29.141 | −12.691 | 1.00 | 0.00 |
| ATOM | 1680 | C    | ILE | 399 | 1.577  | −26.667 | −11.975 | 1.00 | 0.00 |
| ATOM | 1681 | O    | ILE | 399 | 2.082  | −25.574 | −11.353 | 1.00 | 0.00 |
| ATOM | 1682 | N    | SER | 400 | 1.642  | −26.717 | −13.279 | 1.00 | 0.00 |
| ATOM | 1683 | HN   | SER | 400 | 1.225  | −27.462 | −13.762 | 1.00 | 0.00 |
| ATOM | 1684 | CA   | SER | 400 | 2.349  | −25.642 | −14.036 | 1.00 | 0.00 |
| ATOM | 1685 | HA   | SER | 400 | 3.207  | −25.294 | −13.486 | 1.00 | 0.00 |
| ATOM | 1686 | CB   | SER | 400 | 2.794  | −26.302 | −15.336 | 1.00 | 0.00 |
| ATOM | 1687 | HB1  | SER | 400 | 1.979  | −26.896 | −15.734 | 1.00 | 0.00 |
| ATOM | 1688 | HB2  | SER | 400 | 3.639  | −26.939 | −15.148 | 1.00 | 0.00 |
| ATOM | 1689 | OG   | SER | 400 | 3.165  | −25.297 | −16.271 | 1.00 | 0.00 |
| ATOM | 1690 | HG   | SER | 400 | 3.899  | −24.802 | −15.900 | 1.00 | 0.00 |
| ATOM | 1691 | C    | SER | 400 | 1.392  | −24.484 | −14.329 | 1.00 | 0.00 |
| ATOM | 1692 | O    | SER | 400 | 1.765  | −23.329 | −14.281 | 1.00 | 0.00 |
| ATOM | 1693 | N    | GLY | 401 | 0.160  | −24.787 | −14.635 | 1.00 | 0.00 |
| ATOM | 1694 | HN   | GLY | 401 | −0.119 | −25.726 | −14.668 | 1.00 | 0.00 |
| ATOM | 1695 | CA   | GLY | 401 | −0.824 | −23.708 | −14.931 | 1.00 | 0.00 |
| ATOM | 1696 | HA1  | GLY | 401 | −0.650 | −23.323 | −15.923 | 1.00 | 0.00 |
| ATOM | 1697 | HA2  | GLY | 401 | −0.713 | −22.911 | −14.208 | 1.00 | 0.00 |
| ATOM | 1698 | C    | GLY | 401 | −2.239 | −24.279 | −14.852 | 1.00 | 0.00 |
| ATOM | 1699 | O    | GLY | 401 | −2.758 | −24.519 | −13.780 | 1.00 | 0.00 |
| ATOM | 1700 | N    | THR | 402 | −2.869 | −24.496 | −15.990 | 1.00 | 0.00 |
| ATOM | 1701 | HN   | THR | 402 | −2.418 | −24.291 | −16.836 | 1.00 | 0.00 |
| ATOM | 1702 | CA   | THR | 402 | −4.270 | −25.058 | −16.013 | 1.00 | 0.00 |
| ATOM | 1703 | HA   | THR | 402 | −4.473 | −25.495 | −16.977 | 1.00 | 0.00 |
| ATOM | 1704 | CB   | THR | 402 | −4.299 | −26.153 | −14.937 | 1.00 | 0.00 |
| ATOM | 1705 | HB   | THR | 402 | −4.560 | −25.717 | −13.986 | 1.00 | 0.00 |
| ATOM | 1706 | OG1  | THR | 402 | −3.016 | −26.758 | −14.848 | 1.00 | 0.00 |
| ATOM | 1707 | HG1  | THR | 402 | −2.770 | −27.063 | −15.725 | 1.00 | 0.00 |
| ATOM | 1708 | CG2  | THR | 402 | −5.338 | −27.211 | −15.310 | 1.00 | 0.00 |
| ATOM | 1709 | HG21 | THR | 402 | −5.995 | −26.819 | −16.072 | 1.00 | 0.00 |
| ATOM | 1710 | HG22 | THR | 402 | −5.916 | −27.471 | −14.436 | 1.00 | 0.00 |
| ATOM | 1711 | HG23 | THR | 402 | −4.836 | −28.091 | −15.685 | 1.00 | 0.00 |
| ATOM | 1712 | C    | THR | 402 | −5.310 | −23.962 | −15.706 | 1.00 | 0.00 |
| ATOM | 1713 | O    | THR | 402 | −6.382 | −23.942 | −16.277 | 1.00 | 0.00 |
| ATOM | 1714 | N    | GLY | 403 | −5.006 | −23.053 | −14.814 | 1.00 | 0.00 |
| ATOM | 1715 | HN   | GLY | 403 | −4.144 | −23.078 | −14.364 | 1.00 | 0.00 |
| ATOM | 1716 | CA   | GLY | 403 | −5.982 | −21.975 | −14.486 | 1.00 | 0.00 |
| ATOM | 1717 | HA1  | GLY | 403 | −6.136 | −21.940 | −13.419 | 1.00 | 0.00 |
| ATOM | 1718 | HA2  | GLY | 403 | −6.922 | −22.179 | −14.981 | 1.00 | 0.00 |
| ATOM | 1719 | C    | GLY | 403 | −5.434 | −20.628 | −14.962 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 1720 | O    | GLY | 403 | −4.258 | −20.486 | −15.232 | 1.00 | 0.00 |
|------|------|------|-----|-----|--------|---------|---------|------|------|
| ATOM | 1721 | N    | LEU | 404 | −6.277 | −19.636 | −15.066 | 1.00 | 0.00 |
| ATOM | 1722 | HN   | LEU | 404 | −7.222 | −19.771 | −14.842 | 1.00 | 0.00 |
| ATOM | 1723 | CA   | LEU | 404 | −5.803 | −18.297 | −15.525 | 1.00 | 0.00 |
| ATOM | 1724 | HA   | LEU | 404 | −4.728 | −18.282 | −15.598 | 1.00 | 0.00 |
| ATOM | 1725 | CB   | LEU | 404 | −6.423 | −18.114 | −16.909 | 1.00 | 0.00 |
| ATOM | 1726 | HB1  | LEU | 404 | −7.493 | −18.015 | −16.813 | 1.00 | 0.00 |
| ATOM | 1727 | HB2  | LEU | 404 | −6.194 | −18.974 | −17.522 | 1.00 | 0.00 |
| ATOM | 1728 | CG   | LEU | 404 | −5.854 | −16.856 | −17.562 | 1.00 | 0.00 |
| ATOM | 1729 | HG   | LEU | 404 | −5.121 | −16.409 | −16.905 | 1.00 | 0.00 |
| ATOM | 1730 | CD1  | LEU | 404 | −5.191 | −17.226 | −18.889 | 1.00 | 0.00 |
| ATOM | 1731 | HD11 | LEU | 404 | −5.227 | −16.381 | −19.559 | 1.00 | 0.00 |
| ATOM | 1732 | HD12 | LEU | 404 | −5.714 | −18.060 | −19.333 | 1.00 | 0.00 |
| ATOM | 1733 | HD13 | LEU | 404 | −4.161 | −17.502 | −18.711 | 1.00 | 0.00 |
| ATOM | 1734 | CD2  | LEU | 404 | −6.989 | −15.861 | −17.819 | 1.00 | 0.00 |
| ATOM | 1735 | HD21 | LEU | 404 | −7.663 | −15.858 | −16.975 | 1.00 | 0.00 |
| ATOM | 1736 | HD22 | LEU | 404 | −7.528 | −16.152 | −18.708 | 1.00 | 0.00 |
| ATOM | 1737 | HD23 | LEU | 404 | −6.577 | −14.872 | −17.955 | 1.00 | 0.00 |
| ATOM | 1738 | C    | LEU | 404 | −6.293 | −17.204 | −14.570 | 1.00 | 0.00 |
| ATOM | 1739 | O    | LEU | 404 | −6.743 | −16.157 | −14.989 | 1.00 | 0.00 |
| ATOM | 1740 | N    | GLY | 405 | −6.207 | −17.440 | −13.289 | 1.00 | 0.00 |
| ATOM | 1741 | HN   | GLY | 405 | −5.840 | −18.291 | −12.972 | 1.00 | 0.00 |
| ATOM | 1742 | CA   | GLY | 405 | −6.668 | −16.415 | −12.309 | 1.00 | 0.00 |
| ATOM | 1743 | HA1  | GLY | 405 | −7.171 | −16.902 | −11.489 | 1.00 | 0.00 |
| ATOM | 1744 | HA2  | GLY | 405 | −7.350 | −15.732 | −12.797 | 1.00 | 0.00 |
| ATOM | 1745 | C    | GLY | 405 | −5.465 | −15.640 | −11.773 | 1.00 | 0.00 |
| ATOM | 1746 | O    | GLY | 405 | −4.354 | −16.132 | −11.756 | 1.00 | 0.00 |
| ATOM | 1747 | N    | LEU | 406 | −5.675 | −14.430 | −11.331 | 1.00 | 0.00 |
| ATOM | 1748 | HN   | LEU | 406 | −6.579 | −14.051 | −11.350 | 1.00 | 0.00 |
| ATOM | 1749 | CA   | LEU | 406 | −4.540 | −13.624 | −10.796 | 1.00 | 0.00 |
| ATOM | 1750 | HA   | LEU | 406 | −3.599 | −14.402 | −11.115 | 1.00 | 0.00 |
| ATOM | 1751 | CB   | LEU | 406 | −4.723 | −12.230 | −11.394 | 1.00 | 0.00 |
| ATOM | 1752 | HB1  | LEU | 406 | −5.618 | −11.781 | −10.992 | 1.00 | 0.00 |
| ATOM | 1753 | HB2  | LEU | 406 | −4.810 | −12.308 | −12.469 | 1.00 | 0.00 |
| ATOM | 1754 | CG   | LEU | 406 | −3.515 | −11.363 | −11.040 | 1.00 | 0.00 |
| ATOM | 1755 | HG   | LEU | 406 | −3.350 | −11.396 | −9.972  | 1.00 | 0.00 |
| ATOM | 1756 | CD1  | LEU | 406 | −2.276 | −11.892 | −11.762 | 1.00 | 0.00 |
| ATOM | 1757 | HD11 | LEU | 406 | −2.532 | −12.787 | −12.309 | 1.00 | 0.00 |
| ATOM | 1758 | HD12 | LEU | 406 | −1.508 | −12.120 | −11.038 | 1.00 | 0.00 |
| ATOM | 1759 | HD13 | LEU | 406 | −1.912 | −11.142 | −12.449 | 1.00 | 0.00 |
| ATOM | 1760 | CD2  | LEU | 406 | −3.779 | −9.919  | −11.473 | 1.00 | 0.00 |
| ATOM | 1761 | HD21 | LEU | 406 | −4.819 | −9.808  | −11.744 | 1.00 | 0.00 |
| ATOM | 1762 | HD22 | LEU | 406 | −3.159 | −9.680  | −12.324 | 1.00 | 0.00 |
| ATOM | 1763 | HD23 | LEU | 406 | −3.546 | −9.250  | −10.658 | 1.00 | 0.00 |
| ATOM | 1764 | C    | LEU | 406 | −4.610 | −13.568 | −9.269  | 1.00 | 0.00 |
| ATOM | 1765 | O    | LEU | 406 | −3.618 | −13.356 | −8.600  | 1.00 | 0.00 |
| ATOM | 1766 | N    | ALA | 407 | −5.776 | −13.754 | −8.711  | 1.00 | 0.00 |
| ATOM | 1767 | HN   | ALA | 407 | −6.565 | −13.922 | −9.268  | 1.00 | 0.00 |
| ATOM | 1768 | CA   | ALA | 407 | −5.907 | −13.711 | −7.227  | 1.00 | 0.00 |
| ATOM | 1769 | HA   | ALA | 407 | −5.529 | −12.778 | −6.841  | 1.00 | 0.00 |
| ATOM | 1770 | CB   | ALA | 407 | −7.407 | −13.819 | −6.957  | 1.00 | 0.00 |
| ATOM | 1771 | HB1  | ALA | 407 | −7.950 | −13.303 | −7.734  | 1.00 | 0.00 |
| ATOM | 1772 | HB2  | ALA | 407 | −7.634 | −13.370 | −6.001  | 1.00 | 0.00 |
| ATOM | 1773 | HB3  | ALA | 407 | −7.696 | −14.859 | −6.945  | 1.00 | 0.00 |
| ATOM | 1774 | C    | ALA | 407 | −5.164 | −14.89  | −6.599  | 1.00 | 0.00 |
| ATOM | 1775 | O    | ALA | 407 | −4.260 | −15.451 | −7.186  | 1.00 | 0.00 |
| ATOM | 1776 | N    | ILE | 408 | −5.536 | −15.277 | −5.410  | 1.00 | 0.00 |
| ATOM | 1777 | HN   | ILE | 408 | −6.264 | −14.809 | −4.950  | 1.00 | 0.00 |
| ATOM | 1778 | CA   | ILE | 408 | −4.846 | −16.424 | −4.749  | 1.00 | 0.00 |
| ATOM | 1779 | HA   | ILE | 408 | −4.449 | −17.099 | −5.489  | 1.00 | 0.00 |
| ATOM | 1780 | CB   | ILE | 408 | −3.702 | −15.786 | −3.963  | 1.00 | 0.00 |
| ATOM | 1781 | HB   | ILE | 408 | −4.107 | −15.125 | −3.211  | 1.00 | 0.00 |
| ATOM | 1782 | CG1  | ILE | 408 | −2.814 | −14.987 | −4.926  | 1.00 | 0.00 |
| ATOM | 1783 | HG11 | ILE | 408 | −3.323 | −14.079 | −5.213  | 1.00 | 0.00 |
| ATOM | 1784 | HG12 | ILE | 408 | −2.615 | −15.581 | −5.807  | 1.00 | 0.00 |
| ATOM | 1785 | CG2  | ILE | 408 | −2.871 | −16.878 | −3.289  | 1.00 | 0.00 |
| ATOM | 1786 | HG21 | ILE | 408 | −3.465 | −17.366 | −2.531  | 1.00 | 0.00 |
| ATOM | 1787 | HG22 | ILE | 408 | −1.999 | −16.435 | −2.832  | 1.00 | 0.00 |
| ATOM | 1788 | HG23 | ILE | 408 | −2.562 | −17.603 | −4.027  | 1.00 | 0.00 |
| ATOM | 1789 | CD1  | ILE | 408 | −1.492 | −14.632 | −4.242  | 1.00 | 0.00 |
| ATOM | 1790 | HD11 | ILE | 408 | −1.686 | −14.295 | −3.234  | 1.00 | 0.00 |
| ATOM | 1791 | HD12 | ILE | 408 | −1.000 | −13.845 | −4.795  | 1.00 | 0.00 |
| ATOM | 1792 | HD13 | ILE | 408 | −0.855 | −15.604 | −4.214  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                          created by user:

| ATOM | 1793 | C    | ILE | 408 | -5.810  | -17.167 | -3.811 | 1.00 | 0.00 |
|------|------|------|-----|-----|---------|---------|--------|------|------|
| ATOM | 1794 | O    | ILE | 408 | -5.404  | -18.00  | -3.026 | 1.00 | 0.00 |
| ATOM | 1795 | N    | VAL | 409 | -7.084  | -16.874 | -3.893 | 1.00 | 0.00 |
| ATOM | 1796 | HN   | VAL | 409 | -7.390  | -16.204 | -4.535 | 1.00 | 0.00 |
| ATOM | 1797 | CA   | VAL | 409 | -8.074  | -17.563 | -3.007 | 1.00 | 0.00 |
| ATOM | 1798 | HA   | VAL | 409 | -8.087  | -17.116 | -2.030 | 1.00 | 0.00 |
| ATOM | 1799 | CB   | VAL | 409 | -9.420  | -17.359 | -3.689 | 1.00 | 0.00 |
| ATOM | 1800 | HB   | VAL | 409 | -9.601  | -16.301 | -3.819 | 1.00 | 0.00 |
| ATOM | 1801 | CG1  | VAL | 409 | -9.407  | -18.047 | -5.056 | 1.00 | 0.00 |
| ATOM | 1802 | HG11 | VAL | 409 | -10.343 | -17.865 | -5.560 | 1.00 | 0.00 |
| ATOM | 1803 | HG12 | VAL | 409 | -9.272  | -19.110 | -4.921 | 1.00 | 0.00 |
| ATOM | 1804 | HG13 | VAL | 409 | -8.595  | -17.653 | -5.650 | 1.00 | 0.00 |
| ATOM | 1805 | CG2  | VAL | 409 | -10.524 | -17.968 | -2.821 | 1.00 | 0.00 |
| ATOM | 1806 | HG21 | VAL | 409 | -11.237 | -18.478 | -3.451 | 1.00 | 0.00 |
| ATOM | 1807 | HG23 | VAL | 409 | -11.025 | -17.184 | -2.272 | 1.00 | 0.00 |
| ATOM | 1808 | HG23 | VAL | 409 | -10.089 | -18.672 | -2.217 | 1.00 | 0.00 |
| ATOM | 1809 | C    | VAL | 409 | -7.748  | -19.050 | -2.907 | 1.00 | 0.00 |
| ATOM | 1810 | O    | VAL | 409 | -7.971  | -19.678 | -1.891 | 1.00 | 0.00 |
| ATOM | 1811 | N    | GLN | 410 | -7.231  | -19.623 | -3.953 | 1.00 | 0.00 |
| ATOM | 1812 | HN   | GLN | 410 | -7.067  | -19.111 | -4.764 | 1.00 | 0.00 |
| ATOM | 1813 | CA   | GLN | 410 | -6.894  | -21.053 | -3.917 | 1.00 | 0.00 |
| ATOM | 1814 | HA   | GLN | 410 | -7.776  | -21.646 | -3.746 | 1.00 | 0.00 |
| ATOM | 1815 | CB   | GLN | 410 | -6.332  | -21.339 | -5.299 | 1.00 | 0.00 |
| ATOM | 1816 | HB1  | GLN | 410 | -5.342  | -20.919 | -5.382 | 1.00 | 0.00 |
| ATOM | 1817 | HB2  | GLN | 410 | -6.976  | -20.900 | -6.049 | 1.00 | 0.00 |
| ATOM | 1818 | CB   | GLN | 410 | -6.265  | -22.833 | -5.502 | 1.00 | 0.00 |
| ATOM | 1819 | HG1  | GFN | 410 | -7.256  | -23.208 | -5.688 | 1.00 | 0.00 |
| ATOM | 1820 | HG2  | GLN | 410 | -5.865  | -23.291 | -4.611 | 1.00 | 0.00 |
| ATOM | 1821 | CD   | GLN | 410 | -5.366  | -23.153 | -6.695 | 1.00 | 0.00 |
| ATOM | 1822 | OE1  | GLN | 410 | -5.058  | -22.286 | -7.489 | 1.00 | 0.00 |
| ATOM | 1823 | NE2  | GLN | 410 | -4.926  | -24.370 | -6.856 | 1.00 | 0.00 |
| ATOM | 1824 | HE21 | GLN | 410 | -5.173  | -25.068 | -6.214 | 1.00 | 0.00 |
| ATOM | 1825 | HE22 | GLN | 410 | -4.352  | -24.587 | -7.620 | 1.00 | 0.00 |
| ATOM | 1826 | C    | GLN | 410 | -5.842  | -21.319 | -2.839 | 1.00 | 0.00 |
| ATOM | 1827 | O    | GLN | 410 | -6.082  | -22.030 | -1.892 | 1.00 | 0.00 |
| ATOM | 1828 | N    | ARG | 411 | -4.681  | -20.743 | -2.981 | 1.00 | 0.00 |
| ATOM | 1829 | HN   | ARG | 411 | -4.516  | -20.171 | -3.757 | 1.00 | 0.00 |
| ATOM | 1830 | CA   | ARG | 411 | -3.599  | -20.956 | -1.968 | 1.00 | 0.00 |
| ATOM | 1831 | HA   | ARG | 411 | -3.200  | -21.954 | -2.047 | 1.00 | 0.00 |
| ATOM | 1832 | CB   | ARG | 411 | -2.520  | -19.933 | -2.325 | 1.00 | 0.00 |
| ATOM | 1833 | HB1  | ARG | 411 | -2.379  | -19.255 | -1.498 | 1.00 | 0.00 |
| ATOM | 1834 | HB2  | ARG | 411 | -2.828  | -19.376 | -3.199 | 1.00 | 0.00 |
| ATOM | 1835 | CG   | ARG | 411 | -1.204  | -20.657 | -2.618 | 1.00 | 0.00 |
| ATOM | 1836 | HG1  | ARG | 411 | -0.906  | -21.229 | -1.753 | 1.00 | 0.00 |
| ATOM | 1837 | HG2  | ARG | 411 | -0.438  | -19.931 | -2.851 | 1.00 | 0.00 |
| ATOM | 1838 | CD   | ARG | 411 | -1.391  | -21.601 | -3.808 | 1.00 | 0.00 |
| ATOM | 1839 | HD1  | ARG | 411 | -1.192  | -21.084 | -4.734 | 1.00 | 0.00 |
| ATOM | 1840 | HD2  | ARG | 411 | -2.394  | -22.009 | -3.809 | 1.00 | 0.00 |
| ATOM | 1841 | NE   | ARG | 411 | -0.389  | -22.681 | -3.602 | 1.00 | 0.00 |
| ATOM | 1842 | HE   | ARG | 411 | -0.088  | -22.905 | -2.696 | 1.00 | 0.00 |
| ATOM | 1843 | CZ   | ARG | 411 | 0.090   | -23.331 | -4.627 | 1.00 | 0.00 |
| ATOM | 1844 | NH1  | ARG | 411 | 0.863   | -22.722 | -5.484 | 1.00 | 0.00 |
| ATOM | 1845 | HH11 | ARG | 411 | 1.089   | -21.756 | -5.355 | 1.00 | 0.00 |
| ATOM | 1846 | HH12 | ARG | 411 | 1.231   | -23.220 | -6.269 | 1.00 | 0.00 |
| ATOM | 1847 | NH2  | ARG | 411 | -0.205  | -24.591 | -4.795 | 1.00 | 0.00 |
| ATOM | 1848 | HH21 | ARG | 411 | -0.797  | -25.058 | -4.139 | 1.00 | 0.00 |
| ATOM | 1849 | HH22 | ARG | 411 | 0.163   | -25.089 | -5.581 | 1.00 | 0.00 |
| ATOM | 1850 | C    | ARG | 411 | -4.123  | -20.712 | -0.551 | 1.00 | 0.00 |
| ATOM | 1851 | O    | ARG | 411 | -3.608  | -21.253 | 0.401  | 1.00 | 0.00 |
| ATOM | 1852 | N    | ILE | 412 | -5.129  | -19.899 | -0.396 | 1.00 | 0.00 |
| ATOM | 1853 | HN   | ILE | 412 | -5.532  | -19.457 | -1.173 | 1.00 | 0.00 |
| ATOM | 1854 | CA   | ILE | 412 | -5.660  | -19.646 | 0.977  | 1.00 | 0.00 |
| ATOM | 1855 | HA   | ILE | 412 | -4.882  | -19.249 | 1.614  | 1.00 | 0.00 |
| ATOM | 1856 | CB   | ILE | 412 | -6.781  | -18.599 | 0.789  | 1.00 | 0.00 |
| ATOM | 1857 | HB   | ILE | 412 | -7.202  | -18.698 | -0.200 | 1.00 | 0.00 |
| ATOM | 1858 | CG1  | ILE | 412 | -6.191  | -17.193 | 0.956  | 1.00 | 0.00 |
| ATOM | 1859 | HG11 | ILE | 412 | -5.260  | -17.256 | 1.495  | 1.00 | 0.00 |
| ATOM | 1860 | HG12 | ILE | 412 | -6.886  | -16.577 | 1.510  | 1.00 | 0.00 |
| ATOM | 1861 | CG2  | ILE | 412 | -7.884  | -18.802 | 1.836  | 1.00 | 0.00 |
| ATOM | 1862 | HG21 | ILE | 412 | -7.458  | -19.236 | 2.727  | 1.00 | 0.00 |
| ATOM | 1863 | HG22 | ILE | 412 | -8.641  | -19.463 | 1.439  | 1.00 | 0.00 |
| ATOM | 1864 | HG23 | ILE | 412 | -8.330  | -17.849 | 2.077  | 1.00 | 0.00 |
| ATOM | 1865 | CD1  | ILE | 412 | -5.941  | -16.566 | -0.418 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| | | | | | | | | |
|---|---|---|---|---|---|---|---|---|
| ATOM | 1866 | HD11 | ILE | 412 | −5.340 | −17.235 | −1.017 | 1.00 | 0.00 |
| ATOM | 1867 | HD12 | ILE | 412 | −5.424 | −15.626 | −0.297 | 1.00 | 0.00 |
| ATOM | 1868 | HD13 | ILE | 412 | −6.882 | −16.392 | −0.907 | 1.00 | 0.00 |
| ATOM | 1869 | C | ILE | 412 | −6.194 | −20.964 | 1.558 | 1.00 | 0.00 |
| ATOM | 1870 | O | ILE | 412 | −5.738 | −21.429 | 2.583 | 1.00 | 0.00 |
| ATOM | 1871 | N | VAL | 413 | −7.147 | −21.570 | 0.909 | 1.00 | 0.00 |
| ATOM | 1872 | HN | VAL | 413 | −7.501 | −21.185 | 0.081 | 1.00 | 0.00 |
| ATOM | 1873 | CA | VAL | 413 | −7.697 | −22.852 | 1.430 | 1.00 | 0.00 |
| ATOM | 1874 | HA | VAL | 413 | −8.019 | −22.741 | 2.451 | 1.00 | 0.00 |
| ATOM | 1875 | CB | VAL | 413 | −8.883 | −23.175 | 0.532 | 1.00 | 0.00 |
| ATOM | 1876 | HB | VAL | 413 | −8.552 | −23.220 | −0.496 | 1.00 | 0.00 |
| ATOM | 1877 | CG1 | VAL | 413 | −9.467 | −24.524 | 0.938 | 1.00 | 0.00 |
| ATOM | 1878 | HG11 | VAL | 413 | −8.751 | −25.059 | 1.544 | 1.00 | 0.00 |
| ATOM | 1879 | HG12 | VAL | 413 | −9.691 | −25.102 | 0.054 | 1.00 | 0.00 |
| ATOM | 1880 | HG13 | VAL | 413 | −10.369 | −24.367 | 1.503 | 1.00 | 0.00 |
| ATOM | 1881 | CG2 | VAL | 413 | −9.949 | −22.086 | 0.683 | 1.00 | 0.00 |
| ATOM | 1882 | HG21 | VAL | 413 | −9.872 | −21.638 | 1.663 | 1.00 | 0.00 |
| ATOM | 1883 | HG22 | VAL | 413 | −10.929 | −22.522 | 0.562 | 1.00 | 0.00 |
| ATOM | 1884 | HG23 | VAL | 413 | −9.798 | −21.327 | −0.072 | 1.00 | 0.00 |
| ATOM | 1885 | C | VAL | 413 | −6.635 | −23.941 | 1.319 | 1.00 | 0.00 |
| ATOM | 1886 | O | VAL | 413 | −6.669 | −23.936 | 2.016 | 1.00 | 0.00 |
| ATOM | 1887 | N | ASP | 414 | −5.692 | −23.757 | 0.443 | 1.00 | 0.00 |
| ATOM | 1888 | HN | ASP | 414 | −5.683 | −22.944 | −0.097 | 1.00 | 0.00 |
| ATOM | 1889 | CA | ASP | 414 | −4.620 | −24.771 | 0.274 | 1.00 | 0.00 |
| ATOM | 1890 | HA | ASP | 414 | −5.029 | −25.766 | 0.307 | 1.00 | 0.00 |
| ATOM | 1891 | CB | ASP | 414 | −4.019 | −24.491 | −1.102 | 1.00 | 0.00 |
| ATOM | 1892 | HB1 | ASP | 414 | −3.293 | −23.697 | −1.023 | 1.00 | 0.00 |
| ATOM | 1893 | HB2 | ASP | 414 | −4.804 | −24.195 | −1.783 | 1.00 | 0.00 |
| ATOM | 1894 | CG | ASP | 414 | −3.336 | −25.754 | −1.629 | 1.00 | 0.00 |
| ATOM | 1895 | OD1 | ASP | 414 | −3.928 | −26.421 | −2.461 | 1.00 | 0.00 |
| ATOM | 1896 | OD2 | ASP | 414 | −2.231 | −26.032 | −1.192 | 1.00 | 0.00 |
| ATOM | 1897 | C | ASP | 414 | −3.577 | −23.417 | 1.956 | 1.00 | 0.00 |
| ATOM | 1898 | O | ASP | 414 | −2.804 | −25.463 | 1.672 | 1.00 | 0.00 |
| ATOM | 1899 | N | ASN | 415 | −3.557 | −23.417 | 1.956 | 1.00 | 0.00 |
| ATOM | 1900 | HN | ASN | 415 | −4.211 | −22.740 | 1.712 | 1.00 | 0.00 |
| ATOM | 1901 | CA | ASN | 415 | −2.574 | −23.142 | 3.032 | 1.00 | 0.00 |
| ATOM | 1902 | HA | ASN | 415 | −1.688 | −23.696 | 2.865 | 1.00 | 0.00 |
| ATOM | 1903 | CB | ASN | 415 | −2.292 | −21.643 | 2.949 | 1.00 | 0.00 |
| ATOM | 1904 | HB1 | ASN | 415 | −1.784 | −21.322 | 3.844 | 1.00 | 0.00 |
| ATOM | 1905 | HB2 | ASN | 415 | −3.226 | −21.108 | 2.852 | 1.00 | 0.00 |
| ATOM | 1906 | CG | ASN | 415 | −1.408 | −21.356 | 1.732 | 1.00 | 0.00 |
| ATOM | 1907 | OD1 | ASN | 415 | −1.366 | −22.136 | 0.801 | 1.00 | 0.00 |
| ATOM | 1908 | ND2 | ASN | 415 | −0.695 | −20.264 | 1.700 | 1.00 | 0.00 |
| ATOM | 1909 | HD21 | ASN | 4125 | −0.726 | −19.636 | 2.451 | 1.00 | 0.00 |
| ATOM | 1910 | HD22 | ASN | 415 | −0.129 | −20.071 | 0.923 | 1.00 | 0.00 |
| ATOM | 1911 | C | ASN | 415 | −3.179 | −23.514 | 4.372 | 1.00 | 0.00 |
| ATOM | 1912 | O | ASN | 415 | −2.555 | −23.409 | 5.409 | 1.00 | 0.00 |
| ATOM | 1913 | N | HIS | 416 | −4.396 | −23.943 | 4.350 | 1.00 | 0.00 |
| ATOM | 1914 | HN | HIS | 416 | −4.865 | −24.013 | 3.501 | 1.00 | 0.00 |
| ATOM | 1915 | CA | HIS | 416 | −5.078 | −24.333 | 5.596 | 1.00 | 0.00 |
| ATOM | 1916 | HA | HIS | 416 | −4.474 | −24.097 | 6.450 | 1.00 | 0.00 |
| ATOM | 1917 | CB | HIS | 416 | −6.368 | −23.518 | 5.613 | 1.00 | 0.00 |
| ATOM | 1918 | HB1 | HIS | 416 | −7.096 | −24.007 | 6.242 | 1.00 | 0.00 |
| ATOM | 1919 | HB2 | HIS | 416 | −6.756 | −23.435 | 4.608 | 1.00 | 0.00 |
| ATOM | 1920 | CG | HIS | 416 | −6.079 | −22.150 | 6.154 | 1.00 | 0.00 |
| ATOM | 1921 | ND1 | HIS | 416 | −6.232 | −21.003 | 5.389 | 1.00 | 0.00 |
| ATOM | 1922 | HD1 | HIS | 416 | −6.547 | −20.961 | 4.462 | 1.00 | 0.00 |
| ATOM | 1923 | CD2 | HIS | 416 | −5.634 | −21.728 | 7.379 | 1.00 | 0.00 |
| ATOM | 1924 | HD2 | HIS | 416 | −5.409 | −22.373 | 8.215 | 1.00 | 0.00 |
| ATOM | 1925 | CE1 | HIS | 416 | −5.883 | −19.957 | 6.160 | 1.00 | 0.00 |
| ATOM | 1926 | HE1 | HIS | 416 | −5.893 | −18.929 | 5.829 | 1.00 | 0.00 |
| ATOM | 1927 | NE2 | HIS | 416 | −5.512 | −20.346 | 7.380 | 1.00 | 0.00 |
| ATOM | 1928 | C | HIS | 416 | −5.379 | −25.819 | 5.536 | 1.00 | 0.00 |
| ATOM | 1929 | O | HIS | 416 | −5.546 | −26.472 | 6.543 | 1.00 | 0.00 |
| ATOM | 1930 | N | ASN | 417 | −5.548 | −26.353 | 4.341 | 1.00 | 0.00 |
| ATOM | 1931 | HN | ASN | 417 | −5.356 | −25.782 | 3.542 | 1.00 | 0.00 |
| ATOM | 1932 | CA | ASN | 417 | −5.749 | −27.806 | 4.179 | 1.00 | 0.00 |
| ATOM | 1933 | HA | ASN | 417 | −5.612 | −28.100 | 3.149 | 1.00 | 0.00 |
| ATOM | 1934 | CB | ASN | 417 | −4.739 | −28.541 | 5.070 | 1.00 | 0.00 |
| ATOM | 1935 | HB1 | ASN | 417 | −4.760 | −29.595 | 4.837 | 1.00 | 0.00 |
| ATOM | 1936 | HB2 | ASN | 417 | −4.998 | −28.399 | 6.108 | 1.00 | 0.00 |
| ATOM | 1937 | CG | ASN | 417 | −3.332 | −27.997 | 4.812 | 1.00 | 0.00 |
| ATOM | 1938 | OD1 | ASN | 417 | −3.118 | −26.802 | 4.823 | 1.00 | 0.00 |

TABLE 2-continued

Coordinates determined by NMR for sub-domain B [EnvZ(C)(290–450), SEQ ID NO: 14]; a representative structure.

REMARK final envZ structures  
REMARK DATE:18-Feb-98 13:12:56                              created by user:

| | | | | | | | | |
|---|---|---|---|---|---|---|---|---|
| ATOM | 1939 | ND2  | ASN | 417 | −2.356  | −28.833 | 4.579  | 1.00 | 0.00 |
| ATOM | 1940 | HD21 | ASN | 417 | −2.528  | −29.798 | 4.572  | 1.00 | 0.00 |
| ATOM | 1941 | HD22 | ASN | 417 | −1.451  | −28.495 | 4.410  | 1.00 | 0.00 |
| ATOM | 1942 | C    | ASN | 417 | −7.174  | −28.091 | 4.624  | 1.00 | 0.00 |
| ATOM | 1943 | O    | ASN | 417 | −7.594  | −29.227 | 4.712  | 1.00 | 0.00 |
| ATOM | 1944 | N    | GLY | 418 | −7.928  | −27.065 | 4.907  | 1.00 | 0.00 |
| ATOM | 1945 | HN   | GLY | 418 | −7.571  | −26.149 | 4.822  | 1.00 | 0.00 |
| ATOM | 1946 | CA   | GLY | 418 | −9.327  | −27.281 | 5.345  | 1.00 | 0.00 |
| ATOM | 1947 | HA1  | GLY | 418 | −9.755  | −26.350 | 5.665  | 1.00 | 0.00 |
| ATOM | 1948 | HA2  | GLY | 418 | −9.346  | −27.991 | 6.162  | 1.00 | 0.00 |
| ATOM | 1949 | C    | GLY | 418 | −10.121 | −27.828 | 4.170  | 1.00 | 0.00 |
| ATOM | 1950 | O    | GLY | 418 | −10.197 | −29.023 | 3.968  | 1.00 | 0.00 |
| ATOM | 1951 | N    | MET | 419 | −10.693 | −26.960 | 3.375  | 1.00 | 0.00 |
| ATOM | 1952 | HN   | MET | 419 | −10.585 | −25.999 | 3.544  | 1.00 | 0.00 |
| ATOM | 1953 | CA   | MET | 419 | −11.490 | −27.434 | 2.196  | 1.00 | 0.00 |
| ATOM | 1954 | HA   | MET | 419 | −10.869 | −28.003 | 1.528  | 1.00 | 0.00 |
| ATOM | 1955 | CB   | MET | 419 | −12.591 | −28.327 | 2.765  | 1.00 | 0.00 |
| ATOM | 1956 | HB1  | MET | 419 | −13.353 | −27.715 | 3.216  | 1.00 | 0.00 |
| ATOM | 1957 | HB2  | MET | 419 | −12.181 | −28.991 | 3.500  | 1.00 | 0.00 |
| ATOM | 1958 | CG   | MET | 419 | −13.209 | −29.132 | 1.629  | 1.00 | 0.00 |
| ATOM | 1959 | HG1  | MET | 419 | −12.444 | −29.766 | 1.156  | 1.00 | 0.00 |
| ATOM | 1960 | HG2  | MET | 419 | −13.636 | −28.453 | 0.906  | 1.00 | 0.00 |
| ATOM | 1961 | SD   | MET | 419 | −14.507 | −30.216 | 2.278  | 1.00 | 0.00 |
| ATOM | 1962 | CE   | MET | 419 | −13.630 | −30.763 | 3.760  | 1.00 | 0.00 |
| ATOM | 1963 | HE1  | MET | 419 | −13.812 | −26.265 | 4.563  | 1.00 | 0.00 |
| ATOM | 1964 | HE2  | MET | 419 | −12.574 | −30.806 | 3.557  | 1.00 | 0.00 |
| ATOM | 1965 | HE3  | MET | 419 | −13.981 | −31.744 | 4.046  | 1.00 | 0.00 |
| ATOM | 1966 | C    | MET | 419 | −12.132 | −26.265 | 1.456  | 1.00 | 0.00 |
| ATOM | 1967 | O    | MET | 419 | −12.229 | −25.164 | 1.958  | 1.00 | 0.00 |
| ATOM | 1968 | N    | LEU | 420 | −12.568 | −26.508 | 0.258  | 1.00 | 0.00 |
| ATOM | 1969 | HN   | LEU | 420 | −12.474 | −27.408 | −0.119 | 1.00 | 0.00 |
| ATOM | 1970 | CA   | LEU | 420 | −13.212 | −25.441 | −0.546 | 1.00 | 0.00 |
| ATOM | 1971 | HA   | LEU | 420 | −13.697 | −24.725 | 0.101  | 1.00 | 0.00 |
| ATOM | 1972 | CB   | LEU | 420 | −12.076 | −24.774 | −1.328 | 1.00 | 0.00 |
| ATOM | 1973 | HB1  | LEU | 420 | −11.675 | −25.473 | −2.048 | 1.00 | 0.00 |
| ATOM | 1974 | HB2  | LEU | 420 | −11.297 | −24.473 | −0.644 | 1.00 | 0.00 |
| ATOM | 1975 | CG   | LEU | 420 | −12.615 | −23.545 | −2.062 | 1.00 | 0.00 |
| ATOM | 1976 | HG   | LEU | 420 | −13.333 | −23.857 | −2.807 | 1.00 | 0.00 |
| ATOM | 1977 | CD1  | LEU | 420 | −13.294 | −22.610 | −1.062 | 1.00 | 0.00 |
| ATOM | 1978 | HD11 | LEU | 420 | −14.358 | −22.606 | −1.239 | 1.00 | 0.00 |
| ATOM | 1979 | HD12 | LEU | 420 | −12.904 | −21.610 | −1.183 | 1.00 | 0.00 |
| ATOM | 1980 | HD13 | LEU | 420 | −13.097 | −22.954 | −0.057 | 1.00 | 0.00 |
| ATOM | 1981 | CD2  | LEU | 420 | −11.458 | −22.806 | −2.742 | 1.00 | 0.00 |
| ATOM | 1982 | HD21 | LEU | 420 | −10.614 | −22.761 | −2.069 | 1.00 | 0.00 |
| ATOM | 1983 | HD22 | LEU | 420 | −11.771 | −21.804 | −2.995 | 1.00 | 0.00 |
| ATOM | 1984 | HD23 | LEU | 420 | −11.174 | −23.333 | −3.641 | 1.00 | 0.00 |
| ATOM | 1985 | C    | LEU | 420 | −14.219 | −26.092 | −1.496 | 1.00 | 0.00 |
| ATOM | 1986 | O    | LEU | 420 | −13.950 | −26.280 | −2.666 | 1.00 | 0.00 |
| ATOM | 1987 | N    | GLU | 421 | −15.377 | −26.439 | −1.002 | 1.00 | 0.00 |
| ATOM | 1988 | HN   | GLU | 421 | −15.576 | −26.276 | −0.055 | 1.00 | 0.00 |
| ATOM | 1989 | CA   | GLU | 421 | −16.399 | −27.083 | −1.883 | 1.00 | 0.00 |
| ATOM | 1990 | HA   | GLU | 421 | −15.925 | −27.523 | −2.743 | 1.00 | 0.00 |
| ATOM | 1991 | CB   | GLU | 421 | −17.022 | −28.180 | −1.023 | 1.00 | 0.00 |
| ATOM | 1992 | HB1  | GLU | 421 | −17.835 | −27.768 | −0.446 | 1.00 | 0.00 |
| ATOM | 1993 | HB2  | GLU | 421 | −16.274 | −28.584 | −0.355 | 1.00 | 0.00 |
| ATOM | 1994 | CG   | GLU | 421 | −17.555 | −29.293 | −1.925 | 1.00 | 0.00 |
| ATOM | 1995 | HG1  | GLU | 421 | −17.887 | −28.870 | −2.861 | 1.00 | 0.00 |
| ATOM | 1996 | HG2  | GLU | 421 | −18.385 | −29.786 | −1.438 | 1.00 | 0.00 |
| ATOM | 1997 | CD   | GLU | 421 | −16.443 | −30.309 | −2.194 | 1.00 | 0.00 |
| ATOM | 1998 | OE1  | GLU | 421 | −15.767 | −30.681 | −1.249 | 1.00 | 0.00 |
| ATOM | 1999 | OE2  | GLU | 421 | −16.286 | −30.696 | −3.340 | 1.00 | 0.00 |
| ATOM | 2000 | C    | GLU | 421 | −17.470 | −26.084 | −2.320 | 1.00 | 0.00 |
| ATOM | 2001 | O    | GLU | 421 | −18.404 | −25.802 | −1.596 | 1.00 | 0.00 |
| ATOM | 2002 | N    | LEU | 422 | −17.344 | −25.551 | −3.502 | 1.00 | 0.00 |
| ATOM | 2003 | HN   | LEU | 422 | −16.582 | −25.792 | −4.069 | 1.00 | 0.00 |
| ATOM | 2004 | CA   | LEU | 422 | −18.355 | −24.572 | −3.992 | 1.00 | 0.00 |
| ATOM | 2005 | HA   | LEU | 422 | −18.923 | −24.168 | −3.169 | 1.00 | 0.00 |
| ATOM | 2006 | CB   | LEU | 422 | −17.547 | −23.468 | −4.671 | 1.00 | 0.00 |
| ATOM | 2007 | HB1  | LEU | 422 | −16.963 | −22.941 | −3.931 | 1.00 | 0.00 |
| ATOM | 2008 | HB2  | LEU | 422 | −18.221 | −22.776 | −5.158 | 1.00 | 0.00 |
| ATOM | 2009 | CG   | LEU | 422 | −16.613 | −24.087 | −5.709 | 1.00 | 0.00 |
| ATOM | 2010 | HG   | LEU | 422 | −16.947 | −25.089 | −5.941 | 1.00 | 0.00 |
| ATOM | 2011 | CD1  | LEU | 422 | −16.629 | −23.239 | −6.982 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 2012 | HD11 | LEU | 422 | −17.651 | −23.034 | −7.265  | 1.00 | 0.00 |
|------|------|------|-----|-----|---------|---------|---------|------|------|
| ATOM | 2013 | HD12 | LEU | 422 | −16.137 | −23.776 | −7.779  | 1.00 | 0.00 |
| ATOM | 2014 | HD13 | LEU | 422 | −16.112 | −22.308 | −6.803  | 1.00 | 0.00 |
| ATOM | 2015 | CD2  | LEU | 422 | −15.189 | −24.138 | −5.146  | 1.00 | 0.00 |
| ATOM | 2016 | HD21 | LEU | 422 | −15.197 | −23.807 | −4.118  | 1.00 | 0.00 |
| ATOM | 2017 | HD22 | LEU | 422 | −14.549 | −23.492 | −5.728  | 1.00 | 0.00 |
| ATOM | 2018 | HD23 | LEU | 422 | −14.819 | −25.152 | −5.195  | 1.00 | 0.00 |
| ATOM | 2019 | C    | LEU | 422 | −19.280 | −25.265 | −4.997  | 1.00 | 0.00 |
| ATOM | 2020 | O    | LEU | 422 | −18.979 | −26.334 | −5.489  | 1.00 | 0.00 |
| ATOM | 2021 | N    | GLY | 423 | −20.400 | −24.676 | −5.312  | 1.00 | 0.00 |
| ATOM | 2022 | HN   | GLY | 423 | −20.634 | −23.812 | −4.911  | 1.00 | 0.00 |
| ATOM | 2023 | CA   | GLY | 423 | −21.320 | −25.327 | −6.286  | 1.00 | 0.00 |
| ATOM | 2024 | HA1  | GLY | 423 | −21.608 | −26.295 | −5.909  | 1.00 | 0.00 |
| ATOM | 2025 | HA2  | GLY | 423 | −20.816 | −25.452 | −7.229  | 1.00 | 0.00 |
| ATOM | 2026 | C    | GLY | 423 | −22.577 | −24.474 | −6.481  | 1.00 | 0.00 |
| ATOM | 2027 | O    | GLY | 423 | −22.664 | −23.354 | −6.001  | 1.00 | 0.00 |
| ATOM | 2028 | N    | THR | 424 | −23.542 | −25.010 | −7.199  | 1.00 | 0.00 |
| ATOM | 2029 | HN   | THR | 424 | −23.418 | −25.908 | −7.571  | 1.00 | 0.00 |
| ATOM | 2030 | CA   | THR | 424 | −24.828 | −24.280 | −7.463  | 1.00 | 0.00 |
| ATOM | 2031 | HA   | THR | 424 | −24.960 | −23.465 | −6.777  | 1.00 | 0.00 |
| ATOM | 2032 | CB   | THR | 424 | −24.711 | −23.749 | −8.894  | 1.00 | 0.00 |
| ATOM | 2033 | HB   | THR | 424 | −24.261 | −24.498 | −9.515  | 1.00 | 0.00 |
| ATOM | 2034 | OG1  | THR | 424 | −23.904 | −22.579 | −8.900  | 1.00 | 0.00 |
| ATOM | 2035 | HG1  | THR | 424 | −24.132 | −22.057 | −8.128  | 1.00 | 0.00 |
| ATOM | 2036 | CG2  | THR | 424 | −26.108 | −23.413 | −9.434  | 1.00 | 0.00 |
| ATOM | 2037 | HG21 | THR | 424 | −26.696 | −22.954 | −8.653  | 1.00 | 0.00 |
| ATOM | 2038 | HG22 | THR | 424 | −26.595 | −24.318 | −9.764  | 1.00 | 0.00 |
| ATOM | 2039 | HG23 | THR | 424 | −26.019 | −22.729 | −10.265 | 1.00 | 0.00 |
| ATOM | 2040 | C    | THR | 424 | −25.990 | −25.274 | −7.356  | 1.00 | 0.00 |
| ATOM | 2041 | O    | THR | 424 | −25.796 | −26.470 | −7.429  | 1.00 | 0.00 |
| ATOM | 2042 | N    | SER | 425 | −27.190 | −24.800 | −7.186  | 1.00 | 0.00 |
| ATOM | 2043 | HN   | SER | 425 | −27.335 | −23.832 | −7.129  | 1.00 | 0.00 |
| ATOM | 2044 | CA   | SER | 425 | −28.344 | −25.741 | −7.078  | 1.00 | 0.00 |
| ATOM | 2045 | HA   | SER | 425 | −28.030 | −26.748 | −7.300  | 1.00 | 0.00 |
| ATOM | 2046 | CB   | SER | 425 | −28.796 | −26.470 | −7.429  | 1.00 | 0.00 |
| ATOM | 2047 | HB1  | SER | 425 | −29.857 | −25.861 | −5.564  | 1.00 | 0.00 |
| ATOM | 2048 | HB2  | SER | 425 | −28.612 | −24.655 | −5.253  | 1.00 | 0.00 |
| ATOM | 2049 | OG   | SER | 425 | −28.065 | −26.584 | −4.843  | 1.00 | 0.00 |
| ATOM | 2050 | HG   | SER | 425 | −28.594 | −27.381 | −4.763  | 1.00 | 0.00 |
| ATOM | 2051 | C    | SER | 425 | −29.469 | −25.315 | −8.019  | 1.00 | 0.00 |
| ATOM | 2052 | O    | SER | 425 | −29.408 | −24.277 | −8.646  | 1.00 | 0.00 |
| ATOM | 2053 | N    | GLU | 426 | −30.497 | −26.113 | −8.126  | 1.00 | 0.00 |
| ATOM | 2054 | HN   | GLU | 426 | −30.523 | −26.948 | −7.614  | 1.00 | 0.00 |
| ATOM | 2055 | CA   | GLU | 426 | −31.631 | −25.756 | −9.027  | 1.00 | 0.00 |
| ATOM | 2056 | HA   | GLU | 426 | −31.292 | −25.669 | −10.046 | 1.00 | 0.00 |
| ATOM | 2057 | CB   | GLU | 426 | −32.615 | −26.916 | −8.897  | 1.00 | 0.00 |
| ATOM | 2058 | HB1  | GLU | 426 | −32.148 | −27.827 | −9.239  | 1.00 | 0.00 |
| ATOM | 2059 | HB2  | GLU | 426 | −33.492 | −26.713 | −9.496  | 1.00 | 0.00 |
| ATOM | 2060 | CG   | GLU | 426 | −33.022 | −27.073 | −7.433  | 1.00 | 0.00 |
| ATOM | 2061 | HG1  | GLU | 426 | −33.109 | −26.098 | −6.977  | 1.00 | 0.00 |
| ATOM | 2062 | HG2  | GLU | 426 | −32.371 | −27.650 | −6.910  | 1.00 | 0.00 |
| ATOM | 2063 | CD   | GLU | 426 | −34.368 | −27.792 | −7.351  | 1.00 | 0.00 |
| ATOM | 2064 | OE1  | GLU | 426 | −35.178 | −27.399 | −6.526  | 1.00 | 0.00 |
| ATOM | 2065 | OE2  | GLU | 426 | −34.568 | −28.724 | −8.113  | 1.00 | 0.00 |
| ATOM | 2066 | C    | GLU | 426 | −32.276 | −24.450 | −8.559  | 1.00 | 0.00 |
| ATOM | 2067 | O    | GLU | 426 | −33.066 | −23.848 | −9.260  | 1.00 | 0.00 |
| ATOM | 2068 | N    | ARG | 427 | −31.945 | −24.009 | −7.374  | 1.00 | 0.00 |
| ATOM | 2069 | HN   | ARG | 427 | −31.310 | −24.514 | −6.825  | 1.00 | 0.00 |
| ATOM | 2070 | CA   | ARG | 427 | −32.534 | −22.741 | −6.852  | 1.00 | 0.00 |
| ATOM | 2071 | HA   | ARG | 427 | −33.608 | −22.766 | −6.924  | 1.00 | 0.00 |
| ATOM | 2072 | CB   | ARG | 427 | −32.108 | −22.682 | −5.381  | 1.00 | 0.00 |
| ATOM | 2073 | HB1  | ARG | 427 | −32.623 | −21.869 | −4.890  | 1.00 | 0.00 |
| ATOM | 2074 | HB2  | ARG | 427 | −31.041 | −22.518 | −5.323  | 1.00 | 0.00 |
| ATOM | 2075 | CG   | ARG | 427 | −32.461 | −24.000 | −4.686  | 1.00 | 0.00 |
| ATOM | 2076 | HG1  | ARG | 427 | −32.650 | −24.760 | −5.428  | 1.00 | 0.00 |
| ATOM | 2077 | HG2  | ARG | 427 | −33.345 | −23.861 | −4.079  | 1.00 | 0.00 |
| ATOM | 2078 | CD   | ARG | 427 | −31.291 | −24.437 | −3.796  | 1.00 | 0.00 |
| ATOM | 2079 | HD1  | ARG | 427 | −31.325 | −23.923 | −2.849  | 1.00 | 0.00 |
| ATOM | 2080 | HD2  | ARG | 427 | −30.349 | −24.247 | −4.295  | 1.00 | 0.00 |
| ATOM | 2081 | NE   | ARG | 427 | −31.488 | −25.898 | −3.591  | 1.00 | 0.00 |
| ATOM | 2082 | HE   | ARG | 427 | −31.389 | −26.516 | −4.345  | 1.00 | 0.00 |
| ATOM | 2083 | CZ   | ARG | 427 | −31.790 | −26.358 | −2.407  | 1.00 | 0.00 |
| ATOM | 2084 | NH1  | ARG | 427 | −31.119 | −25.960 | −1.361  | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                                created by user:

| | | | | | | | | |
|---|---|---|---|---|---|---|---|---|
| ATOM | 2085 | HH11 | ARG | 427 | −30.373 | −25.304 | −1.467 | 1.00 | 0.00 |
| ATOM | 2086 | HH12 | ARG | 427 | −31.351 | −26.311 | −0.454 | 1.00 | 0.00 |
| ATOM | 2087 | NH2 | ARG | 427 | −32.765 | −27.214 | −2.270 | 1.00 | 0.00 |
| ATOM | 2088 | HH21 | ARG | 427 | −33.280 | −27.519 | −3.071 | 1.00 | 0.00 |
| ATOM | 2089 | HH22 | ARG | 427 | −32.996 | −27.566 | −1.363 | 1.00 | 0.00 |
| ATOM | 2090 | C | ARG | 427 | −31.969 | −21.538 | −7.617 | 1.00 | 0.00 |
| ATOM | 2091 | O | ARG | 427 | −32.250 | −20.409 | −7.384 | 1.00 | 0.00 |
| ATOM | 2092 | N | GLY | 428 | −31.063 | −21.771 | −8.527 | 1.00 | 0.00 |
| ATOM | 2093 | HN | GLY | 428 | −30.762 | −22.685 | −8.698 | 1.00 | 0.00 |
| ATOM | 2094 | CA | GLY | 428 | −30.479 | −20.641 | −9.299 | 1.00 | 0.00 |
| ATOM | 2095 | HA1 | GLY | 428 | −31.155 | −19.801 | −9.282 | 1.00 | 0.00 |
| ATOM | 2096 | HA2 | GLY | 428 | −30.307 | −20.950 | −10.322 | 1.00 | 0.00 |
| ATOM | 2097 | C | GLY | 428 | −29.160 | −20.240 | −8.653 | 1.00 | 0.00 |
| ATOM | 2098 | O | GLY | 428 | −28.762 | −22.121 | −8.626 | 1.00 | 0.00 |
| ATOM | 2099 | N | GLY | 429 | −28.443 | −21.195 | −8.131 | 1.00 | 0.00 |
| ATOM | 2100 | HN | GLY | 429 | −28.762 | −22.121 | −8.169 | 1.00 | 0.00 |
| ATOM | 2101 | CA | GLY | 429 | −27.144 | −20.886 | −7.480 | 1.00 | 0.00 |
| ATOM | 2102 | HA1 | GLY | 429 | −27.070 | −19.824 | −7.315 | 1.00 | 0.00 |
| ATOM | 2103 | HA2 | GLY | 429 | −26.333 | −21.213 | −8.115 | 1.00 | 0.00 |
| ATOM | 2104 | C | GLY | 429 | −27.073 | −21.608 | −6.138 | 1.00 | 0.00 |
| ATOM | 2105 | O | GLY | 429 | −28.045 | −22.169 | −5.673 | 1.00 | 0.00 |
| ATOM | 2106 | N | LEU | 430 | −25.933 | −21.608 | −5.511 | 1.00 | 0.00 |
| ATOM | 2107 | HN | LEU | 430 | −25.157 | −21.152 | −5.899 | 1.00 | 0.00 |
| ATOM | 2108 | CA | LEU | 430 | −25.814 | −22.297 | −4.197 | 1.00 | 0.00 |
| ATOM | 2109 | HA | LEU | 430 | −26.780 | −22.390 | −3.746 | 1.00 | 0.00 |
| ATOM | 2110 | CB | LEU | 430 | −25.253 | −23.682 | −4.504 | 1.00 | 0.00 |
| ATOM | 2111 | HB1 | LEU | 430 | −24.371 | −23.582 | −5.082 | 1.00 | 0.00 |
| ATOM | 2112 | HB2 | LEU | 430 | −25.984 | −24.253 | −5.058 | 1.00 | 0.00 |
| ATOM | 2113 | CG | LEU | 430 | −24.918 | −24.410 | −3.205 | 1.00 | 0.00 |
| ATOM | 2114 | HG | LEU | 430 | −24.938 | −23.710 | −2.382 | 1.00 | 0.00 |
| ATOM | 2115 | CD1 | LEU | 430 | −25.944 | −25.516 | −1.963 | 1.00 | 0.00 |
| ATOM | 2116 | HD11 | LEU | 430 | −26.741 | −25.431 | −3.687 | 1.00 | 0.00 |
| ATOM | 2117 | HD12 | LEU | 430 | −26.350 | −25.419 | −1.968 | 1.00 | 0.00 |
| ATOM | 2118 | HD13 | LEU | 430 | −25.466 | −26.478 | −3.066 | 1.00 | 0.00 |
| ATOM | 2119 | CD2 | LEU | 430 | −23.519 | −25.029 | −3.322 | 1.00 | 0.00 |
| ATOM | 2120 | HD21 | LEU | 430 | −22.791 | −24.357 | −2.892 | 1.00 | 0.00 |
| ATOM | 2121 | HD22 | LEU | 430 | −23.285 | −25.194 | −4.364 | 1.00 | 0.00 |
| ATOM | 2122 | HD23 | LEU | 430 | −23.496 | −25.971 | −2.794 | 1.00 | 0.00 |
| ATOM | 2123 | C | LEU | 430 | −24.873 | −21.510 | −3.282 | 1.00 | 0.00 |
| ATOM | 2124 | O | LEU | 430 | −25.255 | −20.507 | −2.703 | 1.00 | 0.00 |
| ATOM | 2125 | N | SER | 431 | −23.642 | −21.936 | −3.145 | 1.00 | 0.00 |
| ATOM | 2126 | HN | SER | 431 | −23.323 | −22.725 | −3.646 | 1.00 | 0.00 |
| ATOM | 2127 | CA | SER | 431 | −22.716 | −21.178 | −2.253 | 1.00 | 0.00 |
| ATOM | 2128 | HA | SER | 431 | −22.741 | −20.129 | −2.491 | 1.00 | 0.00 |
| ATOM | 2129 | CB | SER | 431 | −23.268 | −21.401 | −0.850 | 1.00 | 0.00 |
| ATOM | 2130 | HB1 | SER | 431 | −24.318 | −21.133 | −0.830 | 1.00 | 0.00 |
| ATOM | 2131 | HB2 | SER | 431 | −22.731 | −20.790 | −0.148 | 1.00 | 0.00 |
| ATOM | 2132 | OG | SER | 431 | −23.109 | −22.771 | −0.496 | 1.00 | 0.00 |
| ATOM | 2133 | HG | SER | 431 | −23.944 | −23.084 | −0.140 | 1.00 | 0.00 |
| ATOM | 2134 | C | SER | 431 | −21.285 | −21.172 | −2.351 | 1.00 | 0.00 |
| ATOM | 2135 | O | SER | 431 | −21.001 | −22.647 | −3.071 | 1.00 | 0.00 |
| ATOM | 2136 | N | ILE | 432 | −20.387 | −21.112 | −1.619 | 1.00 | 0.00 |
| ATOM | 2137 | HN | ILE | 432 | −20.647 | −20.361 | −1.055 | 1.00 | 0.00 |
| ATOM | 2138 | CA | ILE | 432 | −18.970 | −21.558 | −1.641 | 1.00 | 0.00 |
| ATOM | 2139 | HA | ILE | 432 | −18.840 | −22.368 | −2.332 | 1.00 | 0.00 |
| ATOM | 2140 | CB | ILE | 432 | −18.172 | −20.335 | −2.094 | 1.00 | 0.00 |
| ATOM | 2141 | HB | ILE | 432 | −18.526 | −20.014 | −3.064 | 1.00 | 0.00 |
| ATOM | 2142 | CG1 | ILE | 432 | −16.684 | −20.698 | −2.185 | 1.00 | 0.00 |
| ATOM | 2143 | HG11 | ILE | 432 | −16.560 | −21.755 | −2.010 | 1.00 | 0.00 |
| ATOM | 2144 | HG12 | ILE | 432 | −16.132 | −20.142 | −1.440 | 1.00 | 0.00 |
| ATOM | 2145 | CG2 | ILE | 432 | −18.358 | −19.203 | −1.083 | 1.00 | 0.00 |
| ATOM | 2146 | HG21 | ILE | 432 | −18.610 | −18.292 | −1.605 | 1.00 | 0.00 |
| ATOM | 2147 | HG22 | ILE | 432 | −17.443 | −19.060 | −0.530 | 1.00 | 0.00 |
| ATOM | 2148 | HG23 | ILE | 432 | −19.154 | −19.458 | −0.401 | 1.00 | 0.00 |
| ATOM | 2149 | CD1 | ILE | 432 | −16.157 | −20.349 | −3.579 | 1.00 | 0.00 |
| ATOM | 2150 | HD11 | ILE | 432 | −16.304 | −19.296 | −3.767 | 1.00 | 0.00 |
| ATOM | 2151 | HD12 | ILE | 432 | −16.690 | −20.925 | −4.321 | 1.00 | 0.00 |
| ATOM | 2152 | HD13 | ILE | 432 | −15.103 | −20.580 | −3.633 | 1.00 | 0.00 |
| ATOM | 2153 | C | ILE | 432 | −18.565 | −21.979 | −0.224 | 1.00 | 0.00 |
| ATOM | 2154 | O | ILE | 432 | −18.445 | −21.158 | 0.666 | 1.00 | 0.00 |
| ATOM | 2155 | N | ARG | 433 | −18.361 | −23.249 | −0.004 | 1.00 | 0.00 |
| ATOM | 2156 | HN | ARG | 433 | −18.465 | −23.895 | −0.731 | 1.00 | 0.00 |
| ATOM | 2157 | CA | ARG | 433 | −17.967 | −23.714 | 1.359 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                     created by user:

| | | | | | | | | |
|---|---|---|---|---|---|---|---|---|
| ATOM | 2158 | HA   | ARG | 433 | −18.402 | −23.078 | 2.109 | 1.00 | 0.00 |
| ATOM | 2159 | CB   | ARG | 433 | −18.545 | −25.121 | 1.477 | 1.00 | 0.00 |
| ATOM | 2160 | HB1  | ARG | 433 | −18.442 | −25.469 | 2.493 | 1.00 | 0.00 |
| ATOM | 2161 | HB2  | ARG | 433 | −18.012 | −25.787 | 0.813 | 1.00 | 0.00 |
| ATOM | 2162 | CG   | ARG | 433 | −20.025 | −25.097 | 1.098 | 1.00 | 0.00 |
| ATOM | 2163 | HG1  | ARG | 433 | −20.147 | −25.491 | 0.101 | 1.00 | 0.00 |
| ATOM | 2164 | HG2  | ARG | 433 | −20.386 | −24.080 | 1.130 | 1.00 | 0.00 |
| ATOM | 2165 | CD   | ARG | 433 | −20.820 | −25.955 | 2.084 | 1.00 | 0.00 |
| ATOM | 2166 | HD1  | ARG | 433 | −21.730 | −25.453 | 2.370 | 1.00 | 0.00 |
| ATOM | 2167 | HD2  | ARG | 433 | −20.219 | −26.179 | 2.957 | 1.00 | 0.00 |
| ATOM | 2168 | HE   | ARG | 433 | −21.139 | −27.201 | 1.336 | 1.00 | 0.00 |
| ATOM | 2169 | HE   | ARG | 433 | −21.436 | −27.149 | 0.403 | 1.00 | 0.00 |
| ATOM | 2170 | CZ   | ARG | 433 | −21.023 | −28.362 | 1.921 | 1.00 | 0.00 |
| ATOM | 2171 | NH1  | ARG | 433 | −21.857 | −28.702 | 2.865 | 1.00 | 0.00 |
| ATOM | 2172 | HH11 | ARG | 433 | −22.583 | −28.073 | 3.141 | 1.00 | 0.00 |
| ATOM | 2173 | HH12 | ARG | 433 | −21.769 | −29.592 | 3.313 | 1.00 | 0.00 |
| ATOM | 2174 | NH2  | ARG | 433 | −20.074 | −29.182 | 1.563 | 1.00 | 0.00 |
| ATOM | 2175 | HH21 | ARG | 433 | −19.433 | −28.921 | 0.840 | 1.00 | 0.00 |
| ATOM | 2176 | HH22 | ARG | 433 | −19.986 | −30.072 | 2.011 | 1.00 | 0.00 |
| ATOM | 2177 | C    | ARG | 433 | −16.448 | −23.749 | 1.509 | 1.00 | 0.00 |
| ATOM | 2178 | O    | ARG | 433 | −15.729 | −24.130 | 0.607 | 1.00 | 0.00 |
| ATOM | 2179 | N    | ALA | 434 | −15.958 | −23.353 | 2.648 | 1.00 | 0.00 |
| ATOM | 2180 | HN   | ALA | 434 | −16.562 | −23.048 | 3.360 | 1.00 | 0.00 |
| ATOM | 2181 | CA   | ALA | 434 | −14.488 | −23.357 | 2.878 | 1.00 | 0.00 |
| ATOM | 2182 | HA   | ALA | 434 | −13.990 | −23.966 | 2.140 | 1.00 | 0.00 |
| ATOM | 2183 | CB   | ALA | 434 | −14.069 | −21.899 | 2.735 | 1.00 | 0.00 |
| ATOM | 2184 | HB1  | ALA | 434 | −13.875 | −21.680 | 1.696 | 1.00 | 0.00 |
| ATOM | 2185 | HB2  | ALA | 434 | −13.176 | −21.723 | 3.314 | 1.00 | 0.00 |
| ATOM | 2186 | HB2  | ALA | 434 | −13.864 | −21.260 | 3.095 | 1.00 | 0.00 |
| ATOM | 2187 | C    | ALA | 434 | −13.203 | −23.866 | 4.290 | 1.00 | 0.00 |
| ATOM | 2188 | O    | ALA | 434 | −14.496 | −23.205 | 5.263 | 1.00 | 0.00 |
| ATOM | 2189 | N    | TRP | 435 | −13.629 | −25.030 | 4.420 | 1.00 | 0.00 |
| ATOM | 2190 | HN   | TRP | 435 | −13.629 | −25.559 | 3.624 | 1.00 | 0.00 |
| ATOM | 2191 | CA   | TRP | 435 | −13.340 | −25.556 | 5.792 | 1.00 | 0.00 |
| ATOM | 2192 | HA   | TRP | 435 | −14.076 | −25.189 | 6.487 | 1.00 | 0.00 |
| ATOM | 2193 | CB   | TRP | 435 | −13.458 | −27.069 | 5.689 | 1.00 | 0.00 |
| ATOM | 2194 | HB1  | TRP | 435 | −13.162 | −27.514 | 6.628 | 1.00 | 0.00 |
| ATOM | 2195 | HB2  | TRP | 435 | −12.813 | −27.426 | 4.909 | 1.00 | 0.00 |
| ATOM | 2196 | CG   | TRP | 435 | −14.863 | −27.444 | 5.390 | 1.00 | 0.00 |
| ATOM | 2197 | CD1  | TRP | 435 | −15.460 | −27.318 | 4.187 | 1.00 | 0.00 |
| ATOM | 2198 | HD1  | TRP | 435 | −14.998 | −26.929 | 3.292 | 1.00 | 0.00 |
| ATOM | 2199 | CD2  | TRP | 435 | −15.860 | −28.004 | 6.289 | 1.00 | 0.00 |
| ATOM | 2200 | NE1  | TRP | 435 | −16.757 | −27.772 | 4.285 | 1.00 | 0.00 |
| ATOM | 2201 | HE1  | TRP | 435 | −17.398 | −27.794 | 3.554 | 1.00 | 0.00 |
| ATOM | 2202 | CE2  | TRP | 435 | −17.054 | −28.204 | 5.566 | 1.00 | 0.00 |
| ATOM | 2203 | CE3  | TRP | 435 | −15.840 | −28.356 | 7.652 | 1.00 | 0.00 |
| ATOM | 2204 | HE3  | TRP | 435 | −14.939 | −28.214 | 8.230 | 1.00 | 0.00 |
| ATOM | 2205 | CZ2  | TRP | 435 | −18.194 | −28.734 | 6.169 | 1.00 | 0.00 |
| ATOM | 2206 | HZ2  | TRP | 435 | −19.095 | −28.875 | 5.595 | 1.00 | 0.00 |
| ATOM | 2207 | CZ3  | TRP | 435 | −16.987 | −28.890 | 8.265 | 1.00 | 0.00 |
| ATOM | 2208 | HZ3  | TRP | 435 | −16.963 | −29.157 | 9.312 | 1.00 | 0.00 |
| ATOM | 2209 | CH2  | TRP | 435 | −18.162 | −29.078 | 7.523 | 1.00 | 0.00 |
| ATOM | 2210 | HH2  | TRP | 435 | −19.041 | −29.489 | 7.997 | 1.00 | 0.00 |
| ATOM | 2211 | C    | TRP | 435 | −11.940 | −25.195 | 6.282 | 1.00 | 0.00 |
| ATOM | 2212 | O    | TRP | 435 | −11.083 | −24.744 | 5.542 | 1.00 | 0.00 |
| ATOM | 2213 | N    | LEU | 436 | −11.737 | −25.419 | 7.548 | 1.00 | 0.00 |
| ATOM | 2214 | HN   | LEU | 436 | −12.458 | −25.808 | 8.069 | 1.00 | 0.00 |
| ATOM | 2215 | CA   | LEU | 436 | −10.444 | −25.139 | 8.224 | 1.00 | 0.00 |
| ATOM | 2216 | HA   | LEU | 436 | −9.620  | −25.204 | 7.529 | 1.00 | 0.00 |
| ATOM | 2217 | CB   | LEU | 436 | −10.571 | −23.720 | 8.798 | 1.00 | 0.00 |
| ATOM | 2218 | HB1  | LEU | 436 | −9.694  | −23.493 | 9.385 | 1.00 | 0.00 |
| ATOM | 2219 | HB2  | LEU | 436 | −11.447 | −23.667 | 9.428 | 1.00 | 0.00 |
| ATOM | 2220 | CG   | LEU | 436 | −10.699 | −22.697 | 7.661 | 1.00 | 0.00 |
| ATOM | 2221 | HG   | LEU | 436 | −11.404 | −23.054 | 6.930 | 1.00 | 0.00 |
| ATOM | 2222 | CD1  | LEU | 436 | −11.192 | −21.365 | 8.228 | 1.00 | 0.00 |
| ATOM | 2223 | HD11 | LEU | 436 | −10.904 | −20.563 | 7.565 | 1.00 | 0.00 |
| ATOM | 2224 | HD12 | LEU | 436 | −10.753 | −21.203 | 9.202 | 1.00 | 0.00 |
| ATOM | 2225 | HD13 | LEU | 436 | −12.268 | −21.388 | 8.318 | 1.00 | 0.00 |
| ATOM | 2226 | CD2  | LEU | 436 | −9.333  | −22.491 | 7.000 | 1.00 | 0.00 |
| ATOM | 2227 | HD21 | LEU | 436 | −9.313  | −21.530 | 6.505 | 1.00 | 0.00 |
| ATOM | 2228 | HD22 | LEU | 436 | −9.162  | −23.272 | 6.274 | 1.00 | 0.00 |
| ATOM | 2229 | HD23 | LEU | 436 | −8.560  | −22.523 | 7.753 | 1.00 | 0.00 |
| ATOM | 2230 | C    | LEU | 436 | −10.301 | −26.172 | 9.357 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56        created by user:

| ATOM | 2231 | O    | LEU | 436 | −11.253 | −26.441 | 10.062 | 1.00 | 0.00 |
|------|------|------|-----|-----|---------|---------|--------|------|------|
| ATOM | 2232 | N    | PRO | 437 | −9.134  | −26.713 | 9.498  | 1.00 | 0.00 |
| ATOM | 2233 | CA   | PRO | 437 | −8.900  | −27.724 | 10.560 | 1.00 | 0.00 |
| ATOM | 2234 | HA   | PRO | 437 | −9.654  | −28.490 | 10.514 | 1.00 | 0.00 |
| ATOM | 2235 | CB   | PRO | 437 | −7.543  | −28.312 | 10.200 | 1.00 | 0.00 |
| ATOM | 2236 | HB1  | PRO | 437 | −7.664  | −29.199 | 9.601  | 1.00 | 0.00 |
| ATOM | 2237 | HB2  | PRO | 437 | −6.980  | −28.536 | 11.099 | 1.00 | 0.00 |
| ATOM | 2238 | CG   | PRO | 437 | −6.855  | −27.243 | 9.402  | 1.00 | 0.00 |
| ATOM | 2239 | HG1  | PRO | 437 | −6.206  | −27.690 | 8.667  | 1.00 | 0.00 |
| ATOM | 2240 | HG2  | PRO | 437 | −6.282  | −26.602 | 10.062 | 1.00 | 0.00 |
| ATOM | 2241 | CD   | PRO | 437 | −7.936  | −26.442 | 8.709  | 1.00 | 0.00 |
| ATOM | 2242 | HD1  | PRO | 437 | −8.072  | −26.784 | 7.697  | 1.00 | 0.00 |
| ATOM | 2243 | HD2  | PRO | 437 | −7.697  | −25.386 | 8.729  | 1.00 | 0.00 |
| ATOM | 2244 | C    | PRO | 437 | −8.873  | −27.099 | 11.961 | 1.00 | 0.00 |
| ATOM | 2245 | O    | PRO | 437 | −8.336  | −26.030 | 12.173 | 1.00 | 0.00 |
| ATOM | 2246 | N    | VAL | 438 | −9.454  | −27.782 | 12.920 | 1.00 | 0.00 |
| ATOM | 2247 | HN   | VAL | 438 | −9.875  | −28.643 | 12.714 | 1.00 | 0.00 |
| ATOM | 2248 | CA   | VAL | 438 | −9.172  | −26.237 | 14.349 | 1.00 | 0.00 |
| ATOM | 2249 | HA   | VAL | 438 | −9.172  | −26.237 | 14.349 | 1.00 | 0.00 |
| ATOM | 2250 | CB   | VAL | 438 | −10.947 | −27.380 | 14.746 | 1.00 | 0.00 |
| ATOM | 2251 | HB   | VAL | 438 | −11.341 | −28.318 | 14.397 | 1.00 | 0.00 |
| ATOM | 2252 | CG1  | VAL | 438 | −11.052 | −27.321 | 16.274 | 1.00 | 0.00 |
| ATOM | 2253 | HG11 | VAL | 438 | −10.164 | −28.860 | 16.679 | 1.00 | 0.00 |
| ATOM | 2254 | HG12 | VAL | 438 | −11.147 | −28.323 | 16.666 | 1.00 | 0.00 |
| ATOM | 2255 | HG13 | VAL | 438 | −11.920 | −26.741 | 16.553 | 1.00 | 0.00 |
| ATOM | 2256 | CG2  | VAL | 438 | −11.752 | −26.230 | 14.135 | 1.00 | 0.00 |
| ATOM | 2257 | HG21 | VAL | 438 | −11.323 | −29.958 | 13.182 | 1.00 | 0.00 |
| ATOM | 2258 | HG22 | VAL | 438 | −11.726 | −25.378 | 14.799 | 1.00 | 0.00 |
| ATOM | 2259 | HG23 | VAL | 438 | −12.777 | −26.543 | 13.993 | 1.00 | 0.00 |
| ATOM | 2260 | C    | VAL | 438 | −8.588  | −28.130 | 15.221 | 1.00 | 0.00 |
| ATOM | 2261 | O    | VAL | 438 | −9.074  | −28.965 | 15.959 | 1.00 | 0.00 |
| ATOM | 2262 | N    | PRO | 439 | −7.305  | −27.898 | 15.128 | 1.00 | 0.00 |
| ATOM | 2263 | CA   | PRO | 439 | −6.330  | −28.665 | 15.941 | 1.00 | 0.00 |
| ATOM | 2264 | HA   | PRO | 439 | −6.449  | −29.772 | 15.851 | 1.00 | 0.00 |
| ATOM | 2265 | CB   | PRO | 439 | −4.985  | −28.291 | 15.338 | 1.00 | 0.00 |
| ATOM | 2266 | HB1  | PRO | 439 | −4.697  | −29.007 | 14.585 | 1.00 | 0.00 |
| ATOM | 2267 | HB2  | PRO | 439 | −4.230  | −28.229 | 16.112 | 1.00 | 0.00 |
| ATOM | 2268 | CG   | PRO | 439 | −5.209  | −26.949 | 14.711 | 1.00 | 0.00 |
| ATOM | 2269 | HG1  | PRO | 439 | −4.567  | −26.828 | 13.859 | 1.00 | 0.00 |
| ATOM | 2270 | HG2  | PRO | 439 | −5.018  | −26.168 | 15.438 | 1.00 | 0.00 |
| ATOM | 2271 | CD   | PRO | 439 | −6.654  | −26.906 | 14.273 | 1.00 | 0.00 |
| ATOM | 2272 | HD1  | PRO | 439 | −6.747  | −27.188 | 13.237 | 1.00 | 0.00 |
| ATOM | 2273 | HD2  | PRO | 439 | −7.071  | −25.920 | 14.443 | 1.00 | 0.00 |
| ATOM | 2274 | C    | PRO | 439 | −6.401  | −28.223 | 17.399 | 1.00 | 0.00 |
| ATOM | 2275 | O    | PRO | 439 | −5.647  | −27.378 | 17.837 | 1.00 | 0.00 |
| ATOM | 2276 | N    | VAL | 440 | −7.294  | −28.785 | 18.156 | 1.00 | 0.00 |
| ATOM | 2277 | HN   | VAL | 440 | −7.895  | −29.458 | 17.789 | 1.00 | 0.00 |
| ATOM | 2278 | CA   | VAL | 440 | −7.403  | −28.388 | 19.576 | 1.00 | 0.00 |
| ATOM | 2279 | HA   | VAL | 440 | −6.470  | −27.981 | 19.919 | 1.00 | 0.00 |
| ATOM | 2280 | CB   | VAL | 440 | −8.480  | −27.280 | 19.558 | 1.00 | 0.00 |
| ATOM | 2281 | HB   | VAL | 440 | −8.837  | −27.160 | 18.545 | 1.00 | 0.00 |
| ATOM | 2282 | CG1  | VAL | 440 | −9.665  | −27.640 | 20.466 | 1.00 | 0.00 |
| ATOM | 2283 | HG11 | VAL | 440 | −9.953  | −28.666 | 20.289 | 1.00 | 0.00 |
| ATOM | 2284 | HG12 | VAL | 440 | −10.498 | −26.990 | 20.245 | 1.00 | 0.00 |
| ATOM | 2285 | HG13 | VAL | 440 | −9.377  | −27.520 | 21.498 | 1.00 | 0.00 |
| ATOM | 2286 | CG2  | VAL | 440 | −7.855  | −25.967 | 20.031 | 1.00 | 0.00 |
| ATOM | 2287 | HG21 | VAL | 440 | −8.591  | −25.179 | 19.979 | 1.00 | 0.00 |
| ATOM | 2288 | HG22 | VAL | 440 | −7.016  | −25.719 | 19.396 | 1.00 | 0.00 |
| ATOM | 2289 | HG23 | VAL | 440 | −7.516  | −26.076 | 21.050 | 1.00 | 0.00 |
| ATOM | 2290 | C    | VAL | 440 | −7.811  | −29.595 | 20.445 | 1.00 | 0.00 |
| ATOM | 2291 | O    | VAL | 440 | −8.379  | −30.557 | 19.966 | 1.00 | 0.00 |
| ATOM | 2292 | N    | THR | 441 | −7.522  | −29.542 | 21.718 | 1.00 | 0.00 |
| ATOM | 2293 | HN   | THR | 441 | −7.063  | −28.757 | 22.083 | 1.00 | 0.00 |
| ATOM | 2294 | CA   | THR | 441 | −7.888  | −30.674 | 22.618 | 1.00 | 0.00 |
| ATOM | 2295 | HA   | THR | 441 | −7.633  | −31.616 | 22.165 | 1.00 | 0.00 |
| ATOM | 2296 | CB   | THR | 441 | −7.057  | −30.459 | 23.879 | 1.00 | 0.00 |
| ATOM | 2297 | HB   | THR | 441 | −7.410  | −31.114 | 24.657 | 1.00 | 0.00 |
| ATOM | 2298 | OG1  | THR | 441 | −7.182  | −29.107 | 24.301 | 1.00 | 0.00 |
| ATOM | 2299 | HG1  | THR | 441 | −8.089  | −28.966 | 24.581 | 1.00 | 0.00 |
| ATOM | 2300 | CG2  | THR | 441 | −5.590  | −30.770 | 23.583 | 1.00 | 0.00 |
| ATOM | 2301 | HG21 | THR | 441 | −5.063  | −30.938 | 23.060 | 1.00 | 0.00 |
| ATOM | 2302 | HG23 | THR | 441 | −5.143  | −29.938 | 23.060 | 1.00 | 0.00 |
| ATOM | 2303 | HG23 | THR | 441 | −5.527  | −31.657 | 22.969 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                          created by user:

| ATOM | 2304 | C    | THR | 441 | −9.383  | −30.621 | 22.943 | 1.00 | 0.00 |
|------|------|------|-----|-----|---------|---------|--------|------|------|
| ATOM | 2305 | O    | THR | 441 | −9.896  | −29.611 | 23.382 | 1.00 | 0.00 |
| ATOM | 2306 | N    | ARG | 442 | −10.086 | −31.700 | 22.734 | 1.00 | 0.00 |
| ATOM | 2307 | CA   | ARG | 442 | −9.655  | −32.507 | 22.384 | 1.00 | 0.00 |
| ATOM | 2308 | CA   | ARG | 442 | −11.549 | −31.705 | 23.033 | 1.00 | 0.00 |
| ATOM | 2309 | HA   | ARG | 442 | −11.770 | −31.034 | 23.847 | 1.00 | 0.00 |
| ATOM | 2310 | CB   | ARG | 442 | −12.214 | −31.208 | 21.750 | 1.00 | 0.00 |
| ATOM | 2311 | HB1  | ARG | 442 | −11.904 | −31.824 | 21.898 | 1.00 | 0.00 |
| ATOM | 2312 | HB2  | ARG | 442 | −11.920 | −30.184 | 21.567 | 1.00 | 0.00 |
| ATOM | 2313 | CG   | ARG | 442 | −13.735 | −31.284 | 21.898 | 1.00 | 0.00 |
| ATOM | 2314 | HG1  | ARG | 442 | −14.007 | −32.218 | 22.364 | 1.00 | 0.00 |
| ATOM | 2315 | HG2  | ARG | 442 | −14.194 | −31.221 | 20.921 | 1.00 | 0.00 |
| ATOM | 2316 | CD   | ARG | 442 | −14.219 | −30.123 | 22.770 | 1.00 | 0.00 |
| ATOM | 2317 | HD1  | ARG | 442 | −13.415 | −20.429 | 22.951 | 1.00 | 0.00 |
| ATOM | 2318 | HD2  | ARG | 442 | −14.614 | −30.497 | 23.706 | 1.00 | 0.00 |
| ATOM | 2319 | NE   | ARG | 442 | −15.291 | −29.463 | 21.977 | 1.00 | 0.00 |
| ATOM | 2320 | HE   | ARG | 442 | −15.377 | −29.648 | 21.017 | 1.00 | 0.00 |
| ATOM | 2321 | CZ   | ARG | 442 | −16.117 | −28.636 | 22.560 | 1.00 | 0.00 |
| ATOM | 2322 | NH1  | ARG | 442 | −16.567 | −28.898 | 23.756 | 1.00 | 0.00 |
| ATOM | 2323 | HH11 | ARG | 442 | −16.280 | −29.732 | 24.227 | 1.00 | 0.00 |
| ATOM | 2324 | HH12 | ARG | 442 | −17.202 | −28.265 | 24.202 | 1.00 | 0.00 |
| ATOM | 2325 | NH2  | ARG | 442 | −16.490 | −27.546 | 21.948 | 1.00 | 0.00 |
| ATOM | 2326 | HH21 | ARG | 442 | −16.144 | −27.343 | 21.032 | 1.00 | 0.00 |
| ATOM | 2327 | HH22 | ARG | 442 | −17.124 | −26.914 | 22.394 | 1.00 | 0.00 |
| ATOM | 2328 | C    | ARG | 442 | −12.018 | −33.123 | 23.368 | 1.00 | 0.00 |
| ATOM | 2329 | O    | ARG | 442 | −12.080 | −33.511 | 24.518 | 1.00 | 0.00 |
| ATOM | 2330 | N    | ALA | 443 | −12.293 | −33.572 | 21.453 | 1.00 | 0.00 |
| ATOM | 2331 | HN   | ALA | 443 | −12.293 | −33.572 | 21.453 | 1.00 | 0.00 |
| ATOM | 2332 | CA   | ALA | 443 | −12.813 | −35.291 | 22.644 | 1.00 | 0.00 |
| ATOM | 2333 | HA   | ALA | 443 | −13.255 | −35.720 | 21.761 | 1.00 | 0.00 |
| ATOM | 2334 | CB   | ALA | 443 | −11.548 | −36.059 | 23.024 | 1.00 | 0.00 |
| ATOM | 2335 | HB1  | ALA | 443 | −11.175 | −35.692 | 23.968 | 1.00 | 0.00 |
| ATOM | 2336 | HB2  | ALA | 443 | −10.797 | −35.916 | 22.260 | 1.00 | 0.00 |
| ATOM | 2337 | HB3  | ALA | 443 | −11.777 | −37.111 | 23.111 | 1.00 | 0.00 |
| ATOM | 2338 | C    | ALA | 443 | −13.814 | −35.291 | 23.804 | 1.00 | 0.00 |
| ATOM | 2339 | O    | ALA | 443 | −14.425 | −34.284 | 24.106 | 1.00 | 0.00 |
| ATOM | 2340 | N    | GLN | 444 | −13.987 | −36.410 | 24.455 | 1.00 | 0.00 |
| ATOM | 2341 | HN   | GLN | 444 | −13.486 | −37.211 | 24.195 | 1.00 | 0.00 |
| ATOM | 2342 | CA   | GLN | 444 | −14.951 | −36.470 | 25.595 | 1.00 | 0.00 |
| ATOM | 2343 | HA   | GLN | 444 | −15.180 | −37.494 | 25.482 | 1.00 | 0.00 |
| ATOM | 2344 | CB   | GLN | 444 | −14.225 | −35.800 | 26.762 | 1.00 | 0.00 |
| ATOM | 2345 | HB1  | GLN | 444 | −14.547 | −34.774 | 26.846 | 1.00 | 0.00 |
| ATOM | 2346 | HB2  | GLN | 444 | −13.159 | −35.830 | 26.587 | 1.00 | 0.00 |
| ATOM | 2347 | CG   | GLN | 444 | −14.551 | −36.541 | 28.060 | 1.00 | 0.00 |
| ATOM | 2348 | HG1  | GLN | 444 | −14.803 | −37.566 | 27.836 | 1.00 | 0.00 |
| ATOM | 2349 | HG2  | GLN | 444 | −15.389 | −36.061 | 28.548 | 1.00 | 0.00 |
| ATOM | 2350 | CD   | GLN | 444 | −13.334 | −36.508 | 28.958 | 1.00 | 0.00 |
| ATOM | 2351 | OE1  | GLN | 444 | −12.945 | −37.521 | 29.534 | 1.00 | 0.00 |
| ATOM | 2352 | NE2  | GLN | 444 | −12.713 | −35.377 | 29.191 | 1.00 | 0.00 |
| ATOM | 2353 | HE22 | GLN | 444 | −13.026 | −34.560 | 28.750 | 1.00 | 0.00 |
| ATOM | 2354 | HE22 | GLN | 444 | −11.934 | −35.346 | 29.785 | 1.00 | 0.00 |
| ATOM | 2355 | C    | GLN | 444 | −16.231 | −35.703 | 25.244 | 1.00 | 0.00 |
| ATOM | 2356 | O    | GLN | 444 | −16.345 | −34.520 | 25.493 | 1.00 | 0.00 |
| ATOM | 2357 | N    | GLY | 445 | −17.192 | −36.369 | 24.664 | 1.00 | 0.00 |
| ATOM | 2358 | HN   | GLY | 445 | −17.078 | −37.322 | 24.470 | 1.00 | 0.00 |
| ATOM | 2359 | CA   | GLY | 445 | −18.463 | −35.680 | 24.296 | 1.00 | 0.00 |
| ATOM | 2360 | HA1  | GLY | 445 | −18.345 | −34.615 | 24.421 | 1.00 | 0.00 |
| ATOM | 2361 | HA2  | GLY | 445 | −19.262 | −36.033 | 24.936 | 1.00 | 0.00 |
| ATOM | 2362 | C    | GLY | 445 | −18.805 | −35.983 | 22.834 | 1.00 | 0.00 |
| ATOM | 2363 | O    | GLY | 445 | −19.793 | −35.512 | 22.308 | 1.00 | 0.00 |
| ATOM | 2364 | N    | THR | 446 | −17.995 | −36.767 | 22.173 | 1.00 | 0.00 |
| ATOM | 2365 | HN   | THR | 446 | −17.203 | −37.137 | 22.614 | 1.00 | 0.00 |
| ATOM | 2366 | CA   | THR | 446 | −18.276 | −37.098 | 20.748 | 1.00 | 0.00 |
| ATOM | 2367 | HA   | THR | 446 | −19.164 | −36.601 | 20.411 | 1.00 | 0.00 |
| ATOM | 2368 | CB   | THR | 446 | −17.062 | −36.578 | 19.974 | 1.00 | 0.00 |
| ATOM | 2369 | HB   | THR | 446 | −16.936 | −37.175 | 19.093 | 1.00 | 0.00 |
| ATOM | 2370 | OG1  | THR | 446 | −15.909 | −36.663 | 20.795 | 1.00 | 0.00 |
| ATOM | 2371 | HG1  | THR | 446 | −15.473 | −35.808 | 20.788 | 1.00 | 0.00 |
| ATOM | 2372 | CG2  | THR | 446 | −17.316 | −35.122 | 19.563 | 1.00 | 0.00 |
| ATOM | 2373 | HG21 | THR | 446 | −17.131 | −35.011 | 18.504 | 1.00 | 0.00 |
| ATOM | 2374 | HG22 | THR | 446 | −16.651 | −34.474 | 20.115 | 1.00 | 0.00 |
| ATOM | 2375 | HG23 | THR | 446 | −18.340 | −34.853 | 19.779 | 1.00 | 0.00 |
| ATOM | 2376 | C    | THR | 446 | −18.414 | −38.614 | 20.572 | 1.00 | 0.00 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                    created by user:

| ATOM | 2377 | O    | THR | 446 | −18.095 | −39.383 | 21.458 | 1.00 | 0.00  |
|------|------|------|-----|-----|---------|---------|--------|------|-------|
| ATOM | 2378 | N    | THR | 447 | −18.885 | −39.046 | 19.436 | 1.00 | 0.00  |
| ATOM | 2379 | HN   | THR | 447 | −19.134 | −38.408 | 18.735 | 1.00 | 0.00  |
| ATOM | 2380 | CA   | THR | 447 | −19.045 | −40.510 | 19.200 | 1.00 | 0.00  |
| ATOM | 2381 | HA   | THR | 447 | −18.125 | −41.030 | 19.413 | 1.00 | 0.00  |
| ATOM | 2382 | CB   | THR | 447 | −20.137 | −40.952 | 20.178 | 1.00 | 0.00  |
| ATOM | 2383 | HB   | THR | 447 | −19.851 | −40.686 | 21.182 | 1.00 | 0.00  |
| ATOM | 2384 | OG1  | THR | 447 | −20.310 | −42.361 | 20.091 | 1.00 | 0.00  |
| ATOM | 2385 | HG1  | THR | 447 | −21.014 | −42.612 | 20.694 | 1.00 | 0.00  |
| ATOM | 2386 | CG2  | THR | 447 | −21.452 | −40.253 | 19.827 | 1.00 | 0.00  |
| ATOM | 2387 | HG21 | THR | 447 | −21.280 | −39.358 | 19.036 | 1.00 | 0.00  |
| ATOM | 2388 | HG22 | THR | 447 | −21.832 | −39.471 | 20.699 | 1.00 | 0.00  |
| ATOM | 2389 | HG23 | THR | 447 | −22.173 | −40.987 | 19.498 | 1.00 | 0.00  |
| ATOM | 2390 | C    | THR | 447 | −19.481 | −40.762 | 17.753 | 1.00 | 0.00  |
| ATOM | 2391 | O    | THR | 447 | −20.509 | −41.357 | 17.499 | 1.00 | 0.00  |
| ATOM | 2392 | N    | LYS | 448 | −18.706 | −40.312 | 16.803 | 1.00 | 0.00  |
| ATOM | 2393 | HN   | LYS | 448 | −17.881 | −39.834 | 17.030 | 1.00 | 0.00  |
| ATOM | 2394 | CA   | LYS | 448 | −19.077 | −40.525 | 15.373 | 1.00 | 0.00  |
| ATOM | 2395 | HA   | LYS | 448 | −19.662 | −41.422 | 15.265 | 1.00 | 0.00  |
| ATOM | 2396 | CB   | LYS | 448 | −19.918 | −39.304 | 15.004 | 1.00 | 0.00  |
| ATOM | 2397 | HB1  | LYS | 448 | −20.855 | −39.336 | 15.539 | 1.00 | 0.00  |
| ATOM | 2398 | HB2  | LYS | 448 | −20.109 | −39.307 | 13.939 | 1.00 | 0.00  |
| ATOM | 2399 | CG   | LYS | 448 | −19.158 | −38.032 | 15.385 | 1.00 | 0.00  |
| ATOM | 2400 | HG1  | LYS | 448 | −18.335 | −37.888 | 14.702 | 1.00 | 0.00  |
| ATOM | 2401 | HG2  | LYS | 448 | −18.779 | −38.129 | 16.392 | 1.00 | 0.00  |
| ATOM | 2402 | CD   | LYS | 448 | −20.098 | −36.828 | 15.307 | 1.00 | 0.00  |
| ATOM | 2403 | HD1  | LYS | 448 | −20.917 | −36.964 | 15.996 | 1.00 | 0.00  |
| ATOM | 2404 | HD2  | LYS | 448 | −20.483 | −36.736 | 14.301 | 1.00 | 0.00  |
| ATOM | 2405 | CE   | LYS | 448 | −19.328 | −35.558 | 15.678 | 1.00 | 0.00  |
| ATOM | 2406 | HE1  | LYS | 448 | −18.864 | −35.668 | 16.644 | 1.00 | 0.00  |
| ATOM | 2407 | HE2  | LYS | 448 | −19.991 | −34.701 | 15.669 | 1.00 | 0.00  |
| ATOM | 2408 | NZ   | LYS | 448 | −18.286 | −35.422 | 16.624 | 1.00 | 0.00  |
| ATOM | 2409 | HZ1  | LYS | 448 | −18.706 | −35.616 | 13.693 | 1.00 | 0.00  |
| ATOM | 2410 | HZ2  | LYS | 448 | −17.518 | −36.102 | 14.807 | 1.00 | 0.00  |
| ATOM | 2411 | HZ3  | LYS | 448 | −17.905 | −34.457 | 14.635 | 1.00 | 0.00  |
| ATOM | 2412 | C    | LYS | 448 | −17.819 | −40.594 | 14.498 | 1.00 | 0.00  |
| ATOM | 2413 | O    | LYS | 448 | −17.080 | −39.636 | 14.379 | 1.00 | 0.00  |
| ATOM | 2414 | N    | GLU | 449 | −17.752 | −41.720 | 13.883 | 1.00 | 0.00  |
| ATOM | 2415 | HN   | GLU | 449 | −18.181 | −42.480 | 13.991 | 1.00 | 0.00  |
| ATOM | 2416 | CA   | GLU | 449 | −16.363 | −41.850 | 13.015 | 1.00 | 0.00  |
| ATOM | 2417 | HA   | GLU | 449 | −16.310 | −42.838 | 12.589 | 1.00 | 0.00  |
| ATOM | 2418 | CB   | GLU | 449 | −16.558 | −40.814 | 11.908 | 1.00 | 0.00  |
| ATOM | 2419 | HB1  | GLU | 449 | −16.511 | −39.822 | 12.330 | 1.00 | 0.00  |
| ATOM | 2420 | HB2  | GLU | 449 | −17.523 | −40.962 | 11.442 | 1.00 | 0.00  |
| ATOM | 2421 | CG   | GLU | 449 | −15.455 | −40.970 | 10.858 | 1.00 | 0.00  |
| ATOM | 2422 | HG1  | GLU | 449 | −15.800 | −41.618 | 10.066 | 1.00 | 0.00  |
| ATOM | 2423 | HG2  | GLU | 449 | −14.577 | −41.400 | 11.320 | 1.00 | 0.00  |
| ATOM | 2424 | CD   | GLU | 449 | −15.108 | −39.598 | 10.276 | 1.00 | 0.00  |
| ATOM | 2425 | OE1  | GLU | 449 | −14.107 | −39.037 | 10.690 | 1.00 | 0.00  |
| ATOM | 2426 | OE2  | GLU | 449 | −15.848 | −39.132 | 9.426  | 1.00 | 0.00  |
| ATOM | 2427 | C    | GLU | 449 | −15.094 | −41.546 | 13.820 | 1.00 | 0.00  |
| ATOM | 2428 | O    | GLU | 449 | −14.857 | −40.425 | 14.233 | 1.00 | 0.00  |
| ATOM | 2429 | N    | GLY | 450 | −14.278 | −42.425 | 14.055 | 1.00 | 0.00  |
| ATOM | 2430 | HN   | GLY | 450 | −14.487 | −42.538 | 13.720 | 1.00 | 0.00  |
| ATOM | 2431 | CA   | GLY | 450 | −13.027 | −42.306 | 14.833 | 1.00 | 0.00  |
| ATOM | 2432 | HA1  | GLY | 450 | −13.137 | −41.418 | 15.435 | 1.00 | 0.00  |
| ATOM | 2433 | HA2  | GLY | 450 | −12.198 | −42.179 | 14.150 | 1.00 | 0.00  |
| ATOM | 2434 | C    | GLY | 450 | −12.761 | −43.506 | 15.744 | 1.00 | 0.00  |
| ATOM | 2435 | OT1  | GLY | 450 | −11.704 | −43.540 | 16.352 | 1.00 | 0.00  |
| ATOM | 2436 | OT2  | GLY | 450 | −13.619 | −44.371 | 15.818 | 1.00 | 0.00  |
| ATOM | 2437 | O3G  | ANP | 451 | −13.242 | −21.284 | −18.267| 1.00 | 14.20 |
| ATOM | 2438 | HO3  | ANP | 451 | −13.780 | −21.257 | −19.060| 1.00 | 0.00  |
| ATOM | 2439 | PG   | ANP | 451 | −11.809 | −21.889 | −18.680| 1.00 | 12.47 |
| ATOM | 2440 | O1G  | ANP | 451 | −11.656 | −21.610 | −20.125| 1.00 | 14.96 |
| ATOM | 2441 | O2G  | ANP | 451 | −11.838 | −23.309 | −18.266| 1.00 | 10.96 |
| ATOM | 2442 | N1B  | ANP | 451 | −10.691 | −21.081 | −17.833| 0.00 | 0.00  |
| ATOM | 2443 | HN1  | ANP | 451 | −11.140 | −20.544 | −17.119| 0.00 | 0.00  |
| ATOM | 2444 | PB   | ANP | 451 | −9.666  | −33.129 | −17.150| 1.00 | 11.61 |
| ATOM | 2445 | O1B  | ANP | 451 | −9.521  | −23.334 | −17.998| 1.00 | 14.01 |
| ATOM | 2446 | O2B  | ANP | 451 | −8.423  | −21.437 | −16.743| 1.00 | 15.08 |
| ATOM | 2447 | O3A  | ANP | 451 | −10.353 | −22.630 | −15.787| 1.00 | 13.84 |
| ATOM | 2448 | PA   | ANP | 451 | −9.971  | −23.830 | −14.790| 1.00 | 14.01 |
| ATOM | 2449 | O1A  | ANP | 451 | −9.031  | −24.733 | −15.489| 1.00 | 15.21 |

TABLE 2-continued

Coordinates determined by NMR for sub-domain B [EnvZ(C)(290–450), SEQ ID NO: 14]; a representative structure.

REMARK final envZ structures
REMARK DATE:18-Feb-98 13:12:56                                created by user:

| ATOM | 2450 | O2A  | ANP | 451 | −9.598  | −23.242 | −13.484 | 1.00 | 13.60 |
| ---- | ---- | ---- | --- | --- | ------- | ------- | ------- | ---- | ----- |
| ATOM | 2451 | O5'  | ANP | 451 | −11.376 | −24.597 | −14.617 | 1.00 | 16.63 |
| ATOM | 2452 | C5'  | ANP | 451 | −12.269 | −24.229 | −13.565 | 1.00 | 15.02 |
| ATOM | 2453 | H5'  | ANP | 451 | −12.378 | −25.064 | −12.879 | 0.00 | 0.00  |
| ATOM | 2454 | H5"  | ANP | 451 | −11.849 | −23.382 | −13.029 | 0.00 | 0.00  |
| ATOM | 2455 | C4'  | ANP | 451 | −13.643 | −23.844 | −14.100 | 1.00 | 16.64 |
| ATOM | 2456 | H4'  | ANP | 451 | −13.983 | −24.611 | −14.799 | 0.00 | 0.00  |
| ATOM | 2457 | O4'  | ANP | 451 | −13.594 | −23.737 | −13.018 | 1.00 | 16.01 |
| ATOM | 2458 | C1'  | ANP | 451 | −15.104 | −22.383 | −12.935 | 1.00 | 17.25 |
| ATOM | 2459 | H1'  | ANP | 451 | −16.191 | −22.405 | −12.997 | 0.00 | 0.00  |
| ATOM | 2460 | N9   | ANP | 451 | −14.706 | −21.757 | −11.658 | 1.00 | 16.89 |
| ATOM | 2461 | C4   | ANP | 451 | −15.424 | −20.825 | −10.937 | 1.00 | 14.99 |
| ATOM | 2462 | N3   | ANP | 451 | −16.614 | −20.303 | −11.272 | 1.00 | 14.98 |
| ATOM | 2463 | C2   | ANP | 451 | −17.035 | −19.427 | −10.358 | 1.00 | 15.41 |
| ATOM | 2464 | H2   | ANP | 451 | −17.996 | −18.949 | −10.549 | 0.00 | 0.00  |
| ATOM | 2465 | N1   | ANP | 451 | −16.402 | −19.070 | −9.229  | 1.00 | 15.41 |
| ATOM | 2466 | C6   | ANP | 451 | −15.207 | −19.615 | −8.920  | 1.00 | 15.56 |
| ATOM | 2467 | N6   | ANP | 451 | −14.594 | −19.253 | −7.794  | 1.00 | 11.16 |
| ATOM | 2468 | H61  | ANP | 451 | −13.699 | −19.657 | −7.554  | 1.00 | 0.00  |
| ATOM | 2469 | H62  | ANP | 451 | −15.027 | −18.581 | −7.176  | 1.00 | 0.00  |
| ATOM | 2470 | C5   | ANP | 451 | −14.675 | −20.544 | −9.815  | 1.00 | 15.66 |
| ATOM | 2471 | N7   | ANP | 451 | −13.487 | −21.290 | −9.819  | 1.00 | 17.45 |
| ATOM | 2472 | C8   | ANP | 451 | −13.599 | −21.952 | −10.916 | 1.00 | 15.92 |
| ATOM | 2473 | H8   | ANP | 451 | −12.822 | −22.645 | −11.238 | 0.00 | 0.00  |
| ATOM | 2474 | C2'  | ANP | 451 | −14.550 | −21.599 | −14.111 | 1.00 | 18.24 |
| ATOM | 2475 | H2'  | ANP | 451 | −14.017 | −20.720 | −13.743 | 0.00 | 0.00  |
| ATOM | 2476 | O2'  | ANP | 451 | −15.600 | −21.189 | −14.993 | 1.00 | 16.32 |
| ATOM | 2477 | H2"  | ANP | 451 | −15.588 | −21.783 | −15.747 | 1.00 | 0.00  |
| ATOM | 2478 | C3'  | ANP | 451 | −13.587 | −22.501 | −14.816 | 1.00 | 18.07 |
| ATOM | 2479 | H3'  | ANP | 451 | −12.578 | −22.084 | −14.733 | 0.00 | 0.00  |
| ATOM | 2480 | O3'  | ANP | 451 | −13.939 | −22.646 | −16.198 | 1.00 | 21.99 |
| ATOM | 2481 | H3"  | ANP | 451 | −13.701 | −23.539 | −16.460 | 0.00 | 0.00  |
| END  |      |      |     |     |         |         |         |      |       |

TABLE 3

Chemical shift coordinates for the $^{1}H$–$^{15}N$ HSQC spectrum of the EnZB domain.

|     |   | res# | HA(i-1) | CA(i-1) | CB(i-1) | CA(i) | CB(i) | CO(i-1) | N(i)   | HN(i) |
| --- | - | ---- | ------- | ------- | ------- | ----- | ----- | ------- | ------ | ----- |
| 25  | G | 291  | 0.00    | 62.10   | 69.96   | 45.32 | 0.00  | 176.31  | 111.56 | 8.70  |
| 97  | Q | 292  | 0.00    | 45.17   | 0.00    | 55.59 | 29.39 | 173.51  | 119.89 | 8.39  |
| 117 | E | 293  | 4.32    | 55.59   | 29.31   | 56.48 | 29.83 | 175.48  | 121.92 | 6.53  |
| 113 | M | 294  | 4.19    | 56.64   | 30.00   | 52.83 | 32.74 | 175.76  | 121.62 | 8.35  |
| 200 | P | 295  | 4.31    | 0.00    | 0.00    | 0.00  | 0.00  | 000.00  | 0.00   | 0.00  |
| 196 | M | 296  | 0.00    | 63.00   | 31.60   | 54.70 | 34.99 | 176.50  | 120.48 | 8.31  |
| 101 | E | 297  | 4.59    | 54.63   | 34.94   | 54.04 | 33.67 | 175.27  | 120.15 | 9.21  |
| 91  | M | 298  | 0.00    | 53.95   | 33.69   | 54.14 | 30.81 | 173.95  | 119.64 | 8.63  |
| 165 | A | 299  | 4.95    | 54.29   | 30.92   | 51.02 | 22.60 | 175.88  | 128.41 | 9.05  |
| 67  | D | 300  | 4.66    | 51.00   | 22.54   | 52.19 | 41.11 | 174.24  | 117.58 | 8.39  |
| 168 | L | 301  | 4.84    | 52.19   | 41.09   | 57.63 | 43.22 | 177.41  | 128.91 | 9.53  |
| 43  | N | 302  | 3.78    | 57.72   | 43.37   | 54.83 | 37.51 | 177.60  | 113.73 | 8.24  |
| 153 | A | 303  | 4.57    | 54.96   | 37.46   | 54.66 | 17.90 | 178.78  | 125.55 | 7.37  |
| 82  | V | 304  | 4.14    | 54.73   | 17.79   | 66.16 | 31.58 | 180.03  | 118.99 | 7.34  |
| 65  | L | 305  | 3.62    | 66.16   | 31.62   | 57.88 | 41.54 | 177.60  | 116.94 | 8.18  |
| 3   | G | 306  | 3.69    | 58.00   | 41.46   | 46.91 | 0.00  | 178.89  | 104.08 | 8.16  |
| 110 | E | 307  | 0.00    | 46.89   | 0.00    | 59.33 | 29.78 | 176.00  | 121.18 | 7.69  |
| 95  | V | 308  | 4.06    | 59.38   | 29.70   | 65.75 | 31.53 | 179.24  | 119.86 | 7.60  |
| 86  | I | 309  | 3.79    | 65.87   | 31.56   | 65.47 | 37.93 | 177.16  | 119.35 | 8.46  |
| 103 | A | 310  | 3.32    | 65.45   | 37.97   | 54.45 | 18.12 | 177.86  | 120.28 | 7.88  |
| 87  | A | 311  | 4.10    | 54.57   | 17.93   | 54.09 | 18.85 | 179.25  | 119.37 | 7.53  |
| 50  | E | 312  | 4.20    | 54.00   | 18.95   | 55.62 | 29.54 | 179.21  | 115.08 | 8.08  |
| 49  | S | 313  | 4.40    | 55.61   | 29.41   | 58.95 | 63.95 | 176.40  | 115.11 | 7.68  |
| 9   | G | 314  | 4.55    | 59.07   | 64.04   | 45.32 | 0.00  | 174.19  | 109.26 | 8.23  |
| 96  | Y | 315  | 0.00    | 45.32   | 0.00    | 58.43 | 37.73 | 176.19  | 119.91 | 8.20  |
| 68  | E | 316  | 4.48    | 58.50   | 37.75   | 57.33 | 28.88 | 175.86  | 117.72 | 8.57  |
| 79  | R | 317  | 4.09    | 57.33   | 28.83   | 55.05 | 31.54 | 175.45  | 118.74 | 7.72  |
| 135 | E | 318  | 4.53    | 55.11   | 31.50   | 55.46 | 30.75 | 174.27  | 123.83 | 8.57  |
| 143 | I | 319  | 4.46    | 55.72   | 30.61   | 60.62 | 39.62 | 175.67  | 124.50 | 8.40  |
| 171 | E | 320  | 4.21    | 60.72   | 39.73   | 55.86 | 30.25 | 175.31  | 129.90 | 8.96  |

TABLE 3-continued

Chemical shift coordinates for the $^1$H–$^{15}$N HSQC spectrum of the EnZB domain.

| | | res# | HA(i-1) | CA(i-1) | CB(i-1) | CA(i) | CB(i) | CO(i-1) | N(i) | HN(i) |
|---|---|---|---|---|---|---|---|---|---|---|
| 52 | T | 321 | 4.48 | 55.94 | 30.27 | 59.67 | 71.03 | 175.20 | 115.37 | 8.72 |
| 169 | A | 322 | 5.27 | 59.71 | 71.23 | 50.95 | 18.99 | 174.00 | 129.40 | 8.65 |
| 126 | L | 323 | 4.68 | 51.04 | 18.90 | 53.94 | 39.88 | 175.98 | 122.58 | 8.65 |
| 160 | Y | 324 | 4.43 | 53.97 | 39.89 | 55.89 | 40.04 | 177.04 | 127.61 | 8.13 |
| 201 | P | 325 | 0.00 | 0.00 | 0.00 | 0.00 | 0.00 | 000.00 | 0.00 | 0.00 |
| 15 | G | 326 | 4.31 | 62.57 | 29.76 | 44.63 | 0.00 | 175.04 | 110.70 | 7.81 |
| 56 | S | 327 | 0.00 | 44.68 | 0.00 | 57.55 | 64.75 | 172.14 | 115.66 | 8.38 |
| 140 | I | 328 | 4.88 | 57.68 | 64.84 | 60.51 | 40.44 | 174.42 | 124.33 | 8.54 |
| 158 | E | 329 | 4.11 | 60.58 | 40.50 | 56.61 | 29.75 | 173.77 | 127.33 | 8.45 |
| 99 | V | 330 | 0.00 | 56.76 | 29.71 | 59.36 | 36.19 | 175.57 | 120.06 | 8.89 |
| 147 | K | 331 | 4.51 | 59.52 | 36.24 | 55.75 | 32.52 | 173.34 | 124.65 | 8.70 |
| 102 | M | 332 | 0.00 | 55.74 | 32.45 | 55.42 | 36.26 | 175.40 | 120.13 | 9.43 |
| 151 | H | 333 | 5.49 | 55.39 | 36.40 | 53.55 | 31.54 | 173.95 | 125.22 | 11.08 |
| 202 | P | 334 | 5.63 | 0.00 | 0.00 | 0.00 | 0.00 | 000.00 | 0.00 | 0.00 |
| 47 | L | 335 | 4.01 | 66.64 | 32.17 | 58.13 | 41.42 | 177.51 | 114.73 | 7.85 |
| 53 | S | 336 | 3.86 | 58.24 | 41.24 | 62.31 | 0.00 | 179.39 | 115.42 | 7.41 |
| 129 | I | 337 | 0.00 | 62.03 | 0.00 | 61.61 | 33.81 | 175.62 | 122.98 | 7.89 |
| 71 | K | 338 | 3.67 | 61.61 | 33.69 | 60.92 | 31.90 | 177.46 | 118.38 | 8.59 |
| 80 | R | 339 | 3.49 | 60.97 | 31.91 | 58.67 | 29.77 | 177.65 | 118.75 | 7.59 |
| 109 | A | 340 | 4.02 | 58.70 | 29.76 | 54.89 | 17.30 | 177.89 | 120.97 | 8.31 |
| 61 | V | 341 | 4.07 | 54.99 | 17.22 | 65.87 | 31.32 | 178.41 | 116.27 | 8.57 |
| 127 | A | 342 | 3.76 | 65.90 | 31.50 | 55.87 | 17.71 | 178.14 | 122.78 | 8.80 |
| 191 | N | 343 | 3.77 | 55.94 | 17.60 | 56.17 | 37.68 | 178.82 | 116.13 | 8.33 |
| 78 | M | 344 | 0.00 | 56.42 | 37.40 | 56.50 | 0.00 | 178.96 | 118.65 | 7.93 |
| 84 | V | 346 | 3.51 | 67.24 | 31.30 | 66.55 | 31.19 | 176.54 | 119.24 | 9.00 |
| 131 | A | 348 | 4.67 | 53.65 | 38.59 | 54.76 | 19.1O | 175.14 | 123.59 | 7.93 |
| 186 | A | 349 | 4.29 | 54.62 | 19.12 | 54.16 | 18.30 | 180.25 | 120.48 | 8.31 |
| 66 | R | 350 | 3.96 | 53.96 | 18.22 | 57.85 | 30.67 | 178.23 | 117.13 | 8.11 |
| 178 | Y | 351 | 3.87 | 57.91 | 30.59 | 61.39 | 37.54 | 177.72 | 114.36 | 8.25 |
| 4 | G | 352 | 0.00 | 0.00 | 0.00 | 43.58 | 0.00 | 176.54 | 105.25 | 7.14 |
| 11 | G | 354 | 5.17 | 52.98 | 40.22 | 45.29 | 0.00 | 175.21 | 110.01 | 8.95 |
| 137 | W | 355 | 0.00 | 45.44 | 0.00 | 57.83 | 29.15 | 173.68 | 124.16 | 8.68 |
| 163 | I | 356 | 5.01 | 57.92 | 29.10 | 59.91 | 42.14 | 175.68 | 128.23 | 7.86 |
| 149 | K | 357 | 4.50 | 59.96 | 42.30 | 53.11 | 36.86 | 172.63 | 124.83 | 7.90 |
| 170 | V | 358 | 5.29 | 53.22 | 36.90 | 60.39 | 33.85 | 176.06 | 129.60 | 8.74 |
| 88 | S | 359 | 5.29 | 60.28 | 33.66 | 56.28 | 67.18 | 173.34 | 119.40 | 9.21 |
| 34 | S | 360 | 0.00 | 56.37 | 67.32 | 55.49 | 66.86 | 171.60 | 112.09 | 7.57 |
| 1 | G | 361 | 0.00 | 55.38 | 66.80 | 44.83 | 0.00 | 171.21 | 102.89 | 6.74 |
| 6 | T | 362 | 0.00 | 44.84 | 0.00 | 60.04 | 71.11 | 169.19 | 107.54 | 7.81 |
| 148 | E | 363 | 4.90 | 60.11 | 71.13 | 54.34 | 30.99 | 171.58 | 124.71 | 9.04 |
| 203 | P | 364 | 0.00 | 0.00 | 0.00 | 0.00 | 0.00 | 000.00 | 0.00 | 0.00 |
| 17 | N | 365 | 0.00 | 66.13 | 31.22 | 54.02 | 39.08 | 176.20 | 110.84 | 8.56 |
| 77 | R | 366 | 0.00 | 54.06 | 39.09 | 56.24 | 34.89 | 175.45 | 118.71 | 7.97 |
| 144 | A | 367 | 5.31 | 56.31 | 34.93 | 50.22 | 23.35 | 172.33 | 124.48 | 9.54 |
| 46 | W | 368 | 5.11 | 50.22 | 23.34 | 54.41 | 31.55 | 174.85 | 114.36 | 8.26 |
| 14 | F | 369 | 0.00 | 54.40 | 31.59 | 55.74 | 43.44 | 174.26 | 110.38 | 8.33 |
| 119 | Q | 370 | 5.45 | 55.82 | 43.33 | 54.16 | 29.80 | 172.76 | 122.28 | 9.20 |
| 136 | V | 371 | 5.68 | 54.36 | 0.00 | 61.44 | 34.37 | 173.01 | 124.13 | 8.81 |
| 157 | E | 372 | 4.97 | 61.41 | 34.45 | 54.16 | 37.22 | 174.14 | 126.41 | 8.91 |
| 42 | D | 373 | 5.78 | 54.22 | 37.25 | 53.80 | 46.42 | 174.01 | 113.49 | 7.88 |
| 76 | D | 374 | 5.81 | 53.63 | 46.36 | 52.14 | 41.44 | 175.60 | 118.59 | 9.00 |
| 8 | G | 375 | 0.00 | 52.11 | 41.44 | 45.47 | 0.00 | 177.13 | 108.18 | 9.99 |
| 204 | P | 376 | 0.00 | 0.00 | 0.00 | 0.00 | 0.00 | 000.00 | 0.00 | 0.00 |
| 26 | G | 377 | 4.61 | 63.11 | 32.44 | 43.58 | 0.00 | 178.52 | 111.55 | 9.67 |
| 57 | I | 378 | 0.00 | 43.88 | 0.00 | 60.51 | 39.63 | 171.56 | 115.76 | 7.82 |
| 175 | A | 379 | 4.10 | 60.40 | 39.61 | 51.17 | 17.25 | 174.91 | 132.49 | 8.85 |
| 205 | P | 380 | 4.49 | 0.00 | 0.00 | 0.00 | 0.00 | 000.00 | 0.00 | 0.00 |
| 60 | E | 381 | 3.87 | 66.35 | 32.04 | 59.17 | 28.58 | 178.68 | 116.22 | 9.35 |
| 64 | Q | 382 | 4.05 | 59.21 | 28.52 | 56.86 | 28.69 | 177.61 | 116.89 | 7.54 |
| 73 | R | 383 | 4.29 | 56.93 | 28.73 | 59.29 | 30.04 | 177.74 | 118.47 | 7.85 |
| 54 | K | 384 | 3.72 | 59.33 | 30.09 | 58.33 | 32.10 | 177.31 | 115.44 | 7.53 |
| 51 | H | 385 | 0.00 | 58.24 | 32.04 | 55.73 | 29.90 | 177.31 | 115.27 | 7.48 |
| 81 | L | 386 | 4.71 | 55.72 | 29.64 | 56.24 | 42.81 | 175.30 | 118.83 | 7.37 |
| 44 | F | 367 | 3.97 | 56.32 | 42.78 | 56.64 | 38.45 | 176.44 | 114.14 | 7.82 |
| 104 | Q | 388 | 4.59 | 56.80 | 38.52 | 53.68 | 28.93 | 175.03 | 120.41 | 7.93 |
| 206 | P | 389 | 4.64 | 0.00 | 0.00 | 0.00 | 0.00 | 000.00 | 0.00 | 0.00 |
| 89 | F | 390 | 0.00 | 63.24 | 31.88 | 57.47 | 39.40 | 177.42 | 119.46 | 8.21 |
| 120 | V | 391 | 4.64 | 57.50 | 39.44 | 61.92 | 32.85 | 175.21 | 122.37 | 8.07 |
| 142 | R | 392 | 4.04 | 61.95 | 32.85 | 56.42 | 30.64 | 175.28 | 124.49 | 8.37 |
| 13 | G | 393 | 4.22 | 56.20 | 30.50 | 45.36 | 0.00 | 176.49 | 110.29 | 8.50 |
| 105 | D | 394 | 0.00 | 45.29 | 0.00 | 54.19 | 41.15 | 173.69 | 120.30 | 8.25 |
| 59 | S | 395 | 4.64 | 54.23 | 41.15 | 58.69 | 63.48 | 176.39 | 116.00 | 8.31 |
| 146 | A | 396 | 4.36 | 58.78 | 63.54 | 52.66 | 19.08 | 174.16 | 124.57 | 8.33 |
| 74 | R | 397 | 0.00 | 52.74 | 18.98 | 56.03 | 30.83 | 177.39 | 118.52 | 8.08 |
| 45 | T | 398 | 4.37 | 56.06 | 30.82 | 61.63 | 69.62 | 176.08 | 114.35 | 8.13 |

TABLE 3-continued

Chemical shift coordinates for the $^1H$–$^{15}N$ HSQC spectrum of the EnZB domain.

| res# | | HA(i-1) | CA(i-1) | CB(i-1) | CA(i) | CB(i) | CO(i-1) | N(i) | HN(i) |
|---|---|---|---|---|---|---|---|---|---|
| 118 | I | 399 | 0.00 | 61.75 | 69.71 | 61.35 | 38.64 | 174.44 | 121.98 | 8.17 |
| 75 | S | 400 | 4.20 | 61.64 | 38.66 | 58.25 | 63.77 | 175.83 | 118.51 | 8.31 |
| 16 | G | 401 | 4.47 | 58.31 | 63.86 | 45.33 | 0.00 | 174.60 | 110.64 | 8.42 |
| 37 | T | 402 | 0.00 | 45.36 | 0.00 | 61.58 | 69.79 | 173.85 | 112.22 | 8.08 |
| 177 | G | 403 | 0.00 | 61.71 | 69.96 | 45.58 | 0.00 | 174.53 | 110.84 | 8.53 |
| 107 | A | 407 | 0.00 | 54.40 | 41.29 | 54.16 | 18.30 | 176.51 | 120.63 | 8.33 |
| 83 | R | 411 | 3.78 | 59.31 | 28.73 | 59.16 | 29.70 | 177.15 | 118.94 | 7.91 |
| 98 | I | 412 | 4.17 | 58.99 | 29.77 | 65.58 | 39.03 | 178.37 | 120.03 | 8.42 |
| 121 | V | 413 | 3.91 | 65.72 | 38.85 | 68.29 | 31.07 | 179.51 | 122.46 | 8.91 |
| 133 | D | 414 | 3.43 | 68.32 | 30.61 | 58.09 | 40.55 | 178.69 | 123.59 | 9.02 |
| 90 | N | 415 | 4.54 | 58.12 | 40.53 | 54.76 | 38.34 | 180.46 | 119.47 | 8.60 |
| 55 | H | 416 | 4.60 | 55.18 | 38.35 | 57.88 | 29.12 | 175.51 | 115.66 | 7.72 |
| 48 | N | 417 | 4.35 | 58.00 | 29.19 | 54.49 | 36.95 | 173.44 | 114.74 | 8.41 |
| 2 | G | 418 | 4.63 | 54.54 | 36.94 | 44.41 | 0.00 | 174.23 | 102.89 | 8.19 |
| 180 | M | 419 | 0.00 | 44.42 | 0.00 | 54.85 | 36.32 | 173.25 | 116.62 | 8.27 |
| 138 | L | 420 | 4.69 | 54.94 | 36.32 | 53.43 | 45.59 | 173.13 | 124.24 | 8.93 |
| 128 | E | 421 | 5.40 | 53.40 | 45.58 | 55.26 | 34.05 | 175.79 | 122.90 | 9.50 |
| 159 | L | 422 | 4.70 | 55.32 | 34.05 | 54.31 | 43.53 | 174.11 | 127.46 | 8.92 |
| 12 | G | 423 | 5.15 | 54.26 | 43.46 | 45.29 | 0.00 | 176.04 | 110.27 | 8.93 |
| 116 | T | 424 | 0.00 | 45.10 | 0.00 | 61.13 | 70.49 | 173.23 | 121.53 | 8.81 |
| 123 | S | 425 | 5.09 | 61.27 | 70.56 | 56.78 | 66.99 | 174.20 | 122.49 | 9.03 |
| 100 | E | 426 | 0.00 | 56.72 | 67.19 | 58.53 | 30.20 | 175.80 | 120.12 | 9.01 |
| 40 | R | 427 | 4.19 | 58.58 | 30.15 | 54.90 | 30.31 | 176.41 | 113.04 | 7.29 |
| 7 | G | 428 | 4.53 | 55.00 | 30.23 | 46.18 | 0.00 | 175.61 | 107.71 | 7.73 |
| 5 | G | 429 | 0.00 | 46.20 | 0.00 | 44.39 | 0.00 | 173.26 | 107.48 | 7.31 |
| 139 | L | 430 | 0.00 | 44.43 | 0.00 | 0.00 | 42.93 | 174.53 | 124.30 | 8.48 |
| 92 | S | 431 | 0.00 | 55.68 | 42.63 | 55.65 | 64.44 | 177.08 | 119.73 | 7.94 |
| 155 | I | 432 | 5.02 | 55.81 | 64.47 | 59.23 | 40.81 | 172.72 | 125.74 | 8.87 |
| 164 | R | 433 | 0.00 | 59.17 | 40.93 | 53.28 | 33.96 | 171.43 | 128.33 | 8.82 |
| 162 | A | 434 | 0.00 | 53.33 | 0.00 | 49.42 | 21.03 | 172.89 | 127.97 | 8.50 |
| 108 | W | 435 | 5.00 | 49.38 | 20.98 | 54.93 | 31.91 | 174.18 | 120.67 | 9.05 |
| 94 | L | 436 | 5.47 | 55.04 | 31.68 | 51.00 | 44.83 | 175.95 | 119.78 | 9.58 |
| 207 | P | 437 | 5.16 | 0.00 | 0.00 | 0.00 | 0.00 | 000.00 | 0.00 | 0.00 |
| 70 | V | 438 | 0.00 | 63.17 | 32.31 | 59.03 | 32.86 | 176.39 | 118.25 | 7.49 |
| 208 | P | 439 | 0.00 | 0.00 | 0.00 | 0.00 | 0.00 | 000.00 | 0.00 | 0.00 |
| 106 | V | 440 | 4.55 | 62.93 | 31.96 | 62.41 | 32.55 | 176.34 | 120.52 | 8.28 |
| 72 | T | 441 | 4.20 | 62.28 | 32.70 | 61.61 | 69.65 | 176.12 | 116.40 | 8.29 |
| 179 | R | 442 | 4.37 | 61.62 | 69.81 | 55.69 | 30.90 | 173.91 | 123.88 | 8.41 |
| 152 | A | 443 | 4.37 | 55.67 | 30.86 | 52.38 | 19.11 | 175.48 | 125.50 | 8.42 |
| 93 | Q | 444 | 4.31 | 52.42 | 19.02 | 55.85 | 29.54 | 177.39 | 119.80 | 8.46 |
| 10 | G | 445 | 4.32 | 55.86 | 29.51 | 45.21 | 0.00 | 176.22 | 109.97 | 8.51 |
| 41 | T | 446 | 0.00 | 45.22 | 0.00 | 61.56 | 69.68 | 173.99 | 113.17 | 8.16 |
| 62 | T | 447 | 4.44 | 61.64 | 69.78 | 61.56 | 69.69 | 174.54 | 116.52 | 8.27 |
| 134 | K | 448 | 4.39 | 61.62 | 69.81 | 56.17 | 33.01 | 174.01 | 123.77 | 8.43 |
| 125 | E | 449 | 4.34 | 56.30 | 32.98 | 56.31 | 30.41 | 175.94 | 122.60 | 8.48 |
| 58 | G | 450 | 4.33 | 56.37 | 30.39 | 45.98 | 0.00 | 175.50 | 116.01 | 8.02 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference herein in their entireties.

What is claimed is:

1. The purified form of an N-terminal truncated transmembrane sensor histidine kinase fragment ($N_t$TSHK) obtained by purifying the $N_t$TSHK after expressing a nucleic acid encoding the $N_t$TSHK in a host cell; wherein said $N_t$TSHK is capable of phosphorylating a TSHK but lacks the autophosphorylatable histidine of the TSHK; and wherein the $N_t$TSHK comprises the amino acid sequence of SEQ ID NO:14 or SEQ ID NO:14 with a conservative amino acid substitution.

2. An N-terminal truncated transmembrane sensor histidine kinase fragment ($N_t$TSHK) comprising an amino acid sequence that is at least 80% identical to SEQ ID NO:12 over the length of the $N_t$TSHK; wherein said $N_t$TSHK is incapable of phosphorylating a transmembrane sensor histidine kinase (TSHK) but contains a histidine that can be phosphorylated by a protein histidine kinase selected from the group consisting of the TSHK and a fragment of the TSHK having protein histidine kinase activity.

3. The N$_t$TSHK of claim 2 that consists of the amino acid sequence of SEQ ID NO:12, or SEQ ID NO:12 with a conservative amino acid substitution.

4. A fusion protein or peptide comprising the N$_t$TSHK of claim 2 as part of the fusion protein or peptide.

5. The N$_t$TSHK of claim 2 comprising the amino acid sequence of SEQ ID NO:10, or SEQ ID NO:10 with a conservative amino acid substitution.

6. An N-terminal truncated transmembrane sensor histidine kinase Fragment (N$_t$TSHK) consisting of the amino acid sequence of SEQ ID NO:8, or SEQ ID NO:8 with a conservative amino acid substitution.

7. An N-terminal truncated transmembrane sensor histidine kinase fragment (N$_t$TSHK) that comprises an amino acid sequence that is at least 80% identical to SEQ ID NO:14 over the length of the N$_t$TSHK; wherein said N$_t$TSHK is capable of phosphorylating a transmembrane sensor histidine kinase (TSHK) but lacks the autophosphorylatable histidine of the TSHK.

8. The N$_t$TSHK of claim 7 which consists of the amino acid sequence of SEQ ID NO: 14, or SEQ ID NO: 14 with a conservative amino acid substitution.

9. A fusion protein or peptide comprising the N$_t$TSHK of claim 8 as part of the fusion protein or peptide.

10. A fusion protein or peptide comprising the N$_t$TSHK of claim 7 as part of the fusion protein or peptide.

11. The N$_t$TSHK of claim 7 that comprises the amino acid sequence of SEQ ID NO:6, or SEQ ID NO:6 with a conservative amino acid substitution.

12. An N-terminal truncated transmembrane sensor histidine kinase fragment (N$_t$TSHK) comprising a catalytic core that has a single globular fold containing four glycines analogous to G375, G403, G405, and G429 of SEQ ID NO:2 and two asparagines analogous to N343 and N347 of SEQ ID NO:2; wherein said N$_t$TSHK is capable of phosphorylating a transmembrane sensor histidine kinase (TSHK) but lacks the autophosphorylatable histidine of the TSHK; and wherein the single globular fold comprises an α/β sandwich fold with one layer consisting of a five stranded β-sheet and the other layer comprising three helices wherein the two layers enclose an extensive hydrophobic core, augmented by a small anti-parallel β-sheet which seals the sandwich at one end.

13. The N$_t$TSHK of claim 12 that comprises amino acids 380 to 417 of SEQ ID NO:2, or 380 to 417 of SEQ ID NO:2 with a conservative amino acid substitution.

14. The N$_t$TSHK of claim 13 that comprises amino acids 366 to 425 of SEQ ID NO:2, or 366 to 425 of SEQ ID NO:2 with a conservative amino acid substitution.

15. The N$_t$TSHK of claim 14 that comprises amino acids 334 to 437 of SEQ ID NO:2, or 334 to 437 of SEQ ID NO:2 with a conservative amino acid substitution.

16. A fusion protein or peptide comprising the N$_t$TSHK of claim 12 as part of the fusion protein or peptide.

17. The purified form of an N-terminal truncated transmembrane sensor histidine kinase (N$_t$TSHK) fragment; wherein said N$_t$TSHK is obtained by purifying the N$_t$TSHK after expressing a nucleic acid encoding the N$_t$TSHK in a host cell; wherein said N$_t$TSHK is incapable of phosphorylating a transmembrane sensor histidine kinase (TSHK) but contains a histidine that can be phosphorylated by a protein histidine kinase selected from the group consisting of the TSHK and a fragment of the TSHK having protein histidine kinase activity; and wherein the N$_t$TSHK comprises the amino acid sequence of SEQ ID 12 or SEQ ID NO:12 with a conservative amino acid substitution.

18. An N-terminal truncated transmembrane sensor histidine kinase fragment (N$_t$TSHK); wherein said N$_t$TSHK comprises the amino acid sequence of SEQ ID NO:12, or SEQ ID NO:12 with a conservative amino acid substitution; and wherein said N$_t$TSHK is incapable of phosphorylating a transmembrane sensor histidine kinase (TSHK) but contains a histidine that can be phosphorylated by a protein histidine kinase selected from the group consisting of the TSHK and a fragment of the TSHK having protein histidine kinase activity.

19. An N-terminal truncated transmembrane sensor histidine kinase fragment (N$_t$TSHK) that comprises the amino acid sequence of SEQ ID NO:14 or SEQ ID NO:14 with a conservative amino acid substitution; wherein said N$_t$TSHK is capable of phosphorylating a transmembrane sensor histidine kinase (TSHK) but lacks the autophosphorylatable histidine of the TSHK.

20. A fusion protein or peptide comprising the N$_t$TSHK of claim 19 as part of the fusion protein or peptide.

21. A fusion protein or peptide comprising the N$_t$TSHK of claim 18 as part of the fusion protein or peptide.

22. A fusion protein or peptide comprising the N$_t$TSHK of claim 15 as part of the fusion protein or peptide.

23. A fusion protein or peptide comprising the N$_t$TSHK of claim 14 as part of the fusion protein or peptide.

24. A fusion protein or peptide comprising the N$_t$TSHK of claim 13 as part of the fusion protein or peptide.

25. A fusion protein or peptide comprising the N$_t$TSHK of claim 12 as part of the fusion protein or peptide.

26. A fusion protein or peptide consisting of the N$_t$TSHK of claim 6 as part of the fusion protein or peptide.

27. A fusion protein or peptide comprising the N$_t$TSHK of claim 5 as part of the fusion protein or peptide.

28. A fusion protein or peptide consisting of the N$_t$TSHK of claim 3 as part of the fusion protein or peptide.

* * * * *